United States Patent [19]

Kawamoto et al.

[11] Patent Number: 5,712,267
[45] Date of Patent: Jan. 27, 1998

[54] CARBAPENEM DERIVATIVES, THEIR PREPARATION AND THEIR USE AS ANTIBIOTICS

[75] Inventors: Isao Kawamoto; Rokuro Endo; Masao Miyauchi; Katsuya Ishikawa; Eiji Nakayama; Hiroshi Yasuda; Satoshi Ohya; Yukio Utsui; Katsuhiko Watanabe, all of Tokyo, Japan

[73] Assignee: Sankyo Company, Limited, Tokyo, Japan

[21] Appl. No.: 472,850

[22] Filed: Jun. 6, 1995

Related U.S. Application Data

[63] Continuation-in-part of Ser. No. 288,987, Aug. 11, 1994, abandoned, and Ser. No. 293,378, Aug. 19, 1994, abandoned, which is a continuation of Ser. No. 81,848, Jun. 22, 1993, abandoned, which is a continuation of Ser. No. 894,004, Jun. 3, 1992, abandoned, said Ser. No. 288,987, is a continuation of Ser. No. 29,779, Mar. 11, 1993, abandoned.

[30] Foreign Application Priority Data

| Jun. 4, 1991 | [JP] | Japan | 131545/1991 |
| Dec. 27, 1991 | [JP] | Japan | 345737/1991 |
| Feb. 18, 1992 | [JP] | Japan | 30521/1992 |
| Mar. 11, 1992 | [JP] | Japan | 52163/1992 |
| Apr. 10, 1992 | [JP] | Japan | 91283/1992 |
| Sep. 14, 1992 | [JP] | Japan | 244953/1992 |
| Sep. 16, 1992 | [JP] | Japan | 246578/1992 |

[51] Int. Cl.$^6$ .................... C07D 487/04; A61K 31/40
[52] U.S. Cl. ............................ 514/210; 540/350
[58] Field of Search ..................... 540/350; 514/210

[56] References Cited

U.S. PATENT DOCUMENTS

| 3,950,357 | 4/1976 | Kahan et al. |
| 4,194,047 | 3/1980 | Christensen et al. |
| 4,552,873 | 11/1985 | Miyadera et al. |
| 4,771,046 | 9/1988 | Kawamoto et al. |
| 5,122,604 | 6/1992 | Sunagawa et al. |
| 5,310,735 | 5/1994 | Kawamoto et al. |
| 5,420,119 | 5/1995 | Kawamoto. |

FOREIGN PATENT DOCUMENTS

| 0 126 587 | 11/1984 | European Pat. Off. |
| 0 242 134 | 10/1987 | European Pat. Off. |
| 0 243 686 | 11/1987 | European Pat. Off. |
| 0 333 175 | 9/1989 | European Pat. Off. |
| 0 442 497 | 8/1991 | European Pat. Off. |
| 0 443 883 | 8/1991 | European Pat. Off. |
| 0 472 062 | 2/1992 | European Pat. Off. |
| 0 518 558 | 12/1992 | European Pat. Off. |
| 658 248 | 10/1986 | Switzerland. |

OTHER PUBLICATIONS

Chemical Abstracts, vol. 117, 1992, Columbus, Ohio, US, "Preparation of carbapenem derivatives and their salts as antibiotics," abstract No. 69658X of JP-A-92 36,282.

*Primary Examiner*—Rebecca Cook
*Attorney, Agent, or Firm*—Frishauf, Holtz, Goodman, Langer & Chick, P.C.

[57] ABSTRACT

Compounds of formula (I):

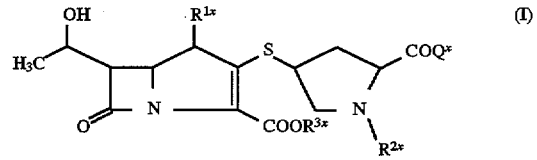

wherein $R^{1x}$ is hydrogen or methyl, $R^{2x}$ is hydrogen optionally substituted aliphatic hydrocarbon or acylimidoyl, $R^{3x}$ is hydrogen or an ester group, and $Q^x$ is cyclic or acyclic nitrogen-containing group. The compounds are potent antibiotics which are resistant to dehydropeptidase I, and are thus useful for the treatment of many microbial infections.

37 Claims, No Drawings

CARBAPENEM DERIVATIVES, THEIR PREPARATION AND THEIR USE AS ANTIBIOTICS

This application is a continuation-in-part application of (i) application Ser. No. 08/293,378 filed Aug. 19, 1994, (abandoned) which is a continuation of application Ser. No. 08/081,848 filed Jun. 22, 1993 (abandoned), which is a continuation of application Ser. No. 07/894,004 filed Jun. 3, 1992 (abandoned) and (ii) application Ser. No. 08/288,987 filed Aug. 11, 1994, (abandoned) which is a continuation of application Ser. No. 08/029,779 filed Mar. 11, 1993 (abandoned).

BACKGROUND OF THE INVENTION

The present invention relates to a series of new carbapenem derivatives which have excellent antibiotic activity and outstanding stability in vivo. By virtue of their enhanced resistance to inactivation by dehydropeptidase I, the compounds of the present invention have improved value in the therapy and prophylaxis of infectious diseases.

The invention also provides methods and compositions using these derivatives for the treatment and prophylaxis of infections, as well as processes for their preparation.

The carbapenem compounds are a well known series of compounds, related to the penicillins, which have been used or have been proposed for use as antibiotics. They have in common a basic structure which may be represented by the formula (A):

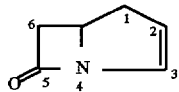

(A)

In this formula, we have indicated the numbering of those positions of importance to the carbapenem compounds, using the numbering scheme commonly used in the art and as employed in the nomenclature of the compounds of the present invention. In accordance with the recommendations of the International Union of Pure and Applied Chemistry (IUPAC), Commission on Nomenclature of Organic Chemistry, the compounds referred to herein are named semi-systematically, using the above carbapenem structure as the parent name.

Those carbapenem antibiotics having no substituent at the 1-position are potentially a very useful series of compounds which have extraordinarily potent antibacterial activity. Unfortunately, however, they are chemically unstable and, moreover, are sensitive to dehydropeptidase I in vivo. Dehydropeptidase I is an enzyme which hydrolyses the β-lactam ring in carbapenem antibiotics and which exists in mammalian tissue, for example in the renal cortex. It is responsible for the extensive metabolisation of many otherwise valuable β-lactam antibiotics in animals, including humans, thus greatly reducing their value. Despite these disadvantages, these carbapenem antibiotics are finding increasing use in the treatment of bacterial infections. A typical and common antibiotic of this type is thienamycin, which has the formula (B):

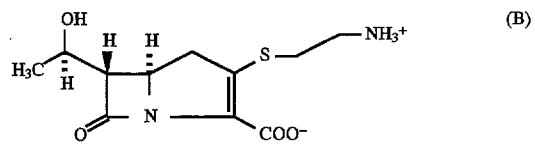

Metabolism of the antibiotic in vivo may be demonstrated by a low recovery of the compound itself (as opposed to its metabolic products) in the urine, and this has been demonstrated for thienamycin [H. Kropp et al., Antimicrob. Agents, Chemother., 22, 62 (1982); and S. R. Norrby et al., ibid., 23, 300 (1983)].

Although it has been found that carbapenem compounds having a substituent an the 1-position (commonly a 1-methyl group) do non have this susceptibility to dehydropepnidase I in vivo, many of the compounds of this type discovered no date lack sufficient activity. It is, therefore, considered highly desirable to find a carbapenem antibiotic which combines the good activity of thienamycin with a resistance to dehydropeptidase I in vivo.

Many carbapenem compounds are now known. Some are described, for example, in European Patent Publications No. 126 587, 182 213, 333 175, 442 497, 443 883 and 508 602. EP 182 213 and EP 333 175 disclose compounds in which a thio-pyrrolidinyl group and its ring carbon atom substituent are linked by an alkylene group, and thus differ from the compound of the present invention in that there is no linking carbonyl group. The compounds disclosed in EP 126 587, on the other hand, are carboxylic thio-pyrrolidinyl beta-lactam compounds. EP 126 587 and EP 508 682 are thought to represent the closest prior art to the compounds of the present invention. However, the present compounds have demonstrated significantly better activity than the prior art compounds.

BRIEF SUMMARY OF INVENTION

It is therefore an object of the present invention to provide a series of new carbapenem compounds, including 1-methylcarbapenem compounds.

It is a further object to provide such compounds which have antibiotic activity.

It is a still further object of the present invention to provide such compounds which have useful antibiotic activity and a good resistance to dehydropeptidase I in vivo.

Other objects and advantages will become apparent as the description proceeds.

Thus, compounds of the present invention include compounds of formula (I):

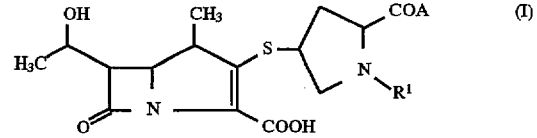

wherein:

$R^1$ represents:

a hydrogen atom, an unsubstituted alkyl group having from 1 to 6 carbon atoms, a substituted alkyl group which has from 1 to 6 carbon atoms and which is substituted by at least one substituent selected from the group consisting of substituents (a), defined below, an alkenyl group having from 2 to 6 carbon atoms, an alkynyl group having from 2 to 6 carbon atoms, or
a group of formula —C(=NH)R°, where R° represents a hydrogen atom or an alkyl group having from 1 to 6 carbon atoms; and A represents a group of formula (A1), (A2), (A3), (A4), (A5), (A6), (A7) or (A8):

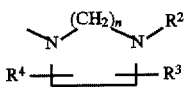  (A1)

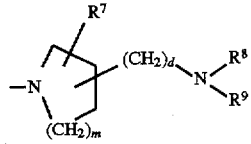  (A2)

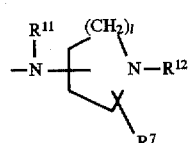  (A3)

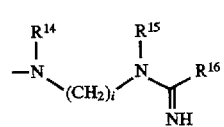  (A4)

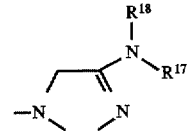  (A5)

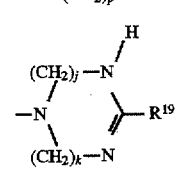  (A6)

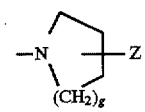  (A7)

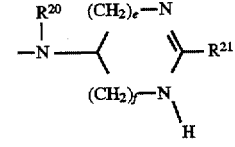  (A8)

wherein:
$R^2$ represents:
a hydrogen atom,
an unsubstituted alkyl group having from 1 to 6 carbon atoms,
a substituted alkyl group which has from 1 to 6 carbon atoms and which is substituted by an least one substituent selected from the group consisting of substituents (b), defined below,
an alkenyl group having from 2 to 6 carbon atoms,
an alkynyl group having from 2 to 6 carbon atoms, or
a group of formula —C(=NH)R⁶,
where $R^6$ represents a hydrogen atom, an unsubstituted alkyl group having from 1 to 6 carbon atoms, a substituted alkyl group which has from 1 to 6 carbon atoms and which is substituted by at least one substituent selected from the group consisting of substituents (c), defined below, or a cycloalkyl group having from 3 to 7 ring carbon atoms;

$R^3$, $R^4$ and $R^7$ are independently selected from the group consisting of:
hydrogen atoms,
unsubstituted alkyl groups having from 1 to 6 carbon atoms,
substituted alkyl groups which have from 1 to 6 carbon atoms and which are substituted by at least one substituent selected from the group consisting of substituents (d), defined below,
halogen atoms,
hydroxy groups,
carboxy groups,
groups of formula —CO.NR$^a$R$^b$, —OCO.NR$^a$R$^b$ and —NR$^a$R$^b$,
wherein $R^a$ and $R^b$ are independently selected from the group consisting of hydrogen atoms and
alkyl groups having from i to 4 carbon atoms, and cyano groups;

$R^8$ represents:
a hydrogen atom,
an unsubstituted alkyl group having from 1 to 6 carbon atoms,
a substituted alkyl group which has from 1 to 6 carbon atoms and which is substituted by at least one substituent selected from the group consisting of substituents (a), defined below,
an alkenyl group having from 2 to 6 carbon atoms, or
an alkynyl group having from 2 to 6 carbon atoms;

$R^9$ represents:
a hydrogen atom,
an unsubstituted alkyl group having from 1 to 6 carbon atoms,
a substituted alkyl group which has from 1 to 6 carbon atoms and which is substituted by at least one substituent selected from the group consisting of substituents (a), defined below, or
a group of formula —C(=NH)R¹⁰,
where $R^{10}$ represents a hydrogen atom, an unsubstituted alkyl group having from 1 to 6 carbon atoms, a substituted alkyl group which has from 1 to 6 carbon atoms and which is substituted by at least one substituent selected from the group consisting of substituents (c), defined below, or a cycloalkyl group having from 3 to 7 ring carbon atoms;

or $R^8$ and $R^9$ together represent a group of formula —(CH$_2$)$_s$—w—(CH$_2$)$_t$—
wherein w represents a carbon—carbon single bond, an oxygen atom, a sulfur atom or a group of formula >NR²² wherein $R^{22}$ represents a hydrogen atom or an alkyl group having from 1 to 6 carbon atoms, and
s and t are independently 1, 2 or 3;

$R^{11}$ represents a hydrogen atom or an alkyl group having from 1 to 6 carbon atoms;

$R^{12}$ represents:
a hydrogen atom,
an unsubstituted alkyl group having from 1 to 6 carbon atoms,
a substituted alkyl group which has from 1 to 6 carbon atoms and which is substituted by at least one substituent selected from the group consisting of substituents (a), defined below,
an alkenyl group having from 2 to 6 carbon atoms,
an alkynyl group having from 2 to 6 carbon atoms, or
a group of formula —C(=NH)$R^{13}$,
where $R^{13}$ represents a hydrogen atom, an unsubstituted alkyl group having from 1 to 6 carbon atoms, a substituted alkyl group which has from 1 to 6 carbon atoms and which is substituted by at least one substituent selected from the group consisting of substituents (c), defined below, or a cycloalkyl group having from 3 to 7 ring carbon atoms;

$R^{14}$ and $R^{15}$ are independently selected from the group consisting of hydrogen atoms and alkyl groups having from 1 to 6 carbon atoms;

$R^{16}$ represents a hydrogen atom, an unsubstituted alkyl group having from 1 to 6 carbon atoms, a substituted alkyl group which has from 1 to 6 carbon atoms and which is substituted by at least one substituent selected from the group consisting of substituents (c), defined below, or a cycloalkyl group having from 3 to 7 ring carbon atoms;

$R^{17}$ and $R^{18}$ are independently selected from the group consisting of:
hydrogen atoms,
unsubstituted alkyl groups having from 1 to 6 carbon atoms, and
substituted alkyl groups which have from 1 to 6 carbon atoms and which are substituted by at least one substituent selected from the group consisting of substituents (a), defined below;
or
$R^{17}$ and $R^{18}$ together represent a group of formula

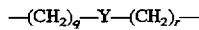
—(CH$_2$)$_q$—Y—(CH$_2$)$_r$— wherein Y represents a carbon—carbon single bond, an oxygen atom, a sulfur atom or a group of formula >$NR^{23}$ wherein $R^{23}$ represents a hydrogen atom or an alkyl group having from 1 to 6 carbon atoms, and
q and r are independently 1, 2 or 3;

$R^{19}$, $R^{20}$ and $R^{21}$ are independently selected from the group consisting of hydrogen atoms and alkyl groups having from 1 to 6 carbon atoms;

Z represents an imidazolyl, triazolyl or tetrazolyl group;
d is 0 or 1;
e, f, i, j and k are independently 1 or 2;
g, l and m are independently 0, 1 or 2; and
n and p are independently 1, 2 or 3;
PROVIDED THAT, where A represents a group of formula (A1):
$R^2$, $R^3$ and $R^4$ do not all represent hydrogen atoms when $R^1$ represents a hydrogen atom; and
$R^1$, $R^3$ and $R^4$ do not all represent hydrogen atoms when $R^2$ represents an alkyl group;

said substituents (a) are selected from the group consisting of hydroxy groups, carboxy groups, cyano groups, halogen atoms, oxygen atoms (to form an oxo group), alkoxy groups having from 1 to 6 carbon atoms, and groups of formula —CO.NR$^a$R$^b$, —OCO.NR$^a$R$^b$ and —NR$^a$R$^b$, wherein R$^a$ and R$^b$ are as defined above;

said substituents (b) are selected from the group consisting of:
hydroxy groups,
carboxy groups,
cyano groups,
halogen atoms,
alkoxy groups having from 1 to 6 carbon atoms,
groups of formula —CO.NR$^a$R$^b$, —OCO.NR$^a$R$^b$ and —NR$^a$R$^b$, wherein R$^a$ and R$^b$ are as defined above,
sulfamoyl groups,
ureido groups,
sulfo groups,
alkanoyl groups having from 1 to 6 carbon atoms,
alkanoylamino groups having from 1 to 6 carbon atoms,
alkanoyloxy groups having from 1 to 6 carbon atoms,
alkylthio groups having from 1 to 6 carbon atoms,
alkylsulfinyl groups having from 1 to 6 carbon atoms, and
alkylsulfonyl groups having from 1 to 6 carbon atoms;
said substituents (c) are selected from the group consisting of:
halogen atoms,
alkoxy groups having from 1 to 6 carbon atoms,
cycloalkyl groups having from 3 to 7 ring carbon atoms; and
said substituents (d) are selected from the group consisting of:
hydroxy groups,
cyano groups,
groups of formula —CO.NR$^a$R$^b$, —OCO.NR$^a$R$^b$ and —NR$^a$R$^b$, wherein R$^a$ and R$^b$ are as defined above,
carboxy groups,
halogen atoms, and
alkoxy groups having from 1 to 6 carbon atoms;
and pharmaceutically acceptable salts and esters thereof.

The compounds of the present invention also include compounds of formula (I)" and pharmaceutically acceptable salts and esters thereof:

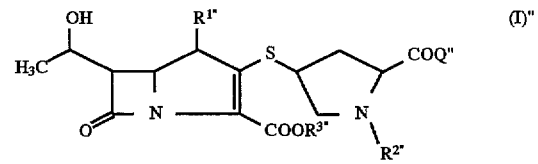

in which:
$R^{1''}$ represents a hydrogen atom or a methyl group;
$R^{2''}$ represents a hydrogen atom, an unsubstituted alkyl group having from 1 to 6 carbon atoms, a substituted alkyl group which has from 1 to 6 carbon atoms and which is substituted by at least one substituent selected from the group consisting of substituents A", defined below, an alkenyl group having from 2 to 6 carbon atoms, an alkynyl group having from 2 to 6 carbon atoms, or, provided that Q" does not contain a quaternary nitrogen atom, a group of formula —C(=NH)$R^{0''}$,
where $R^{0''}$ represents a hydrogen atom or an alkyl group having from 1 to 6 carbon atoms;
$R^{3''}$ represents a hydrogen atom, a negative ion or a carboxy-protecting group; and
Q" represents a group of formula (Q-I)", (Q-II)", (Q-III)", (Q-IV)", (Q-V)", (Q-VI)", (Q-VII)",(Q-VIII)", (Q-IX)", (Q-X)", (Q-XI)", (Q-XII)" and (Q-XIII)":

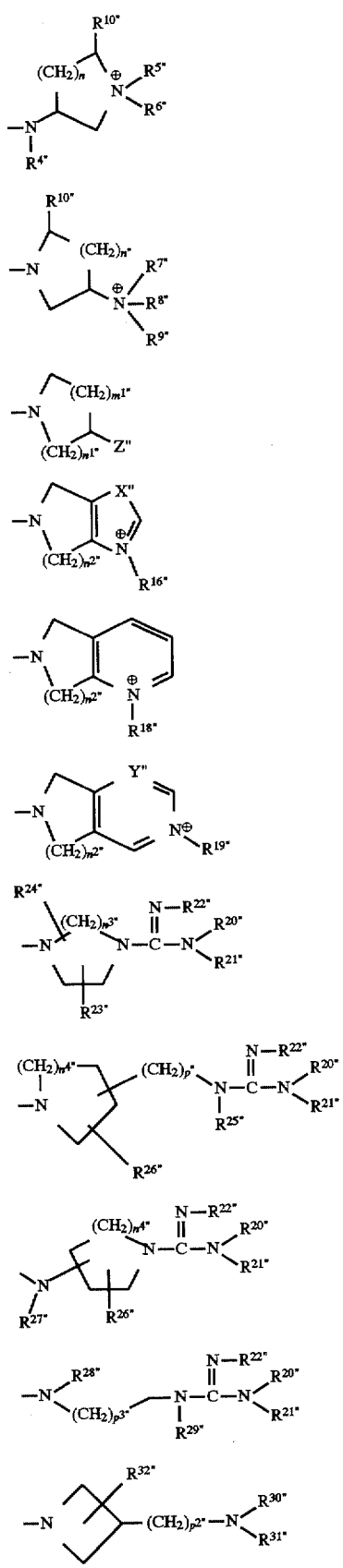

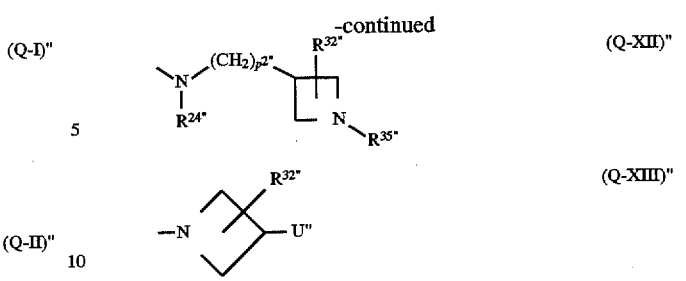

wherein:

$R^{4''}$ represents a hydrogen atom, an unsubstituted alkyl group having from 1 to 6 carbon atoms, or a substituted alkyl group which has from 1 to 6 carbon atoms and which is substituted by at least one substituent selected from the group consisting of substituents B'', defined below;

$R^{5''}$ and $R^{6''}$ are independently selected from the group consisting of unsubstituted alkyl groups having from 1 to 6 carbon atoms, and substituted alkyl groups which have from 1 to 6 carbon atoms and which are substituted by at least one substituent selected from the group consisting of substituents B'', defined below;

or $R^{4''}$ and $R^{5''}$ together represent a group of formula $-(CH_2)_{m''}-$, where m'' is 2 or 3;

$R^{7''}$, $R^{8''}$, and $R^{9''}$ are independently selected from the group consisting of unsubstituted alkyl groups having from 1 to 6 carbon atoms, and substituted alkyl groups which have from 1 to 6 carbon atoms and which are substituted by at least one substituent selected from the group consisting of substituents B'', defined below;

$R^{10''}$ represents a hydrogen atom, a carbamoyl group, an unsubstituted alkyl group having from 1 to 6 carbon atoms, or a substituted alkyl group which has from 1 to 6 carbon atoms and which is substituted by at least one substituent selected from the group consisting of substituents B'', defined below;

or $R^{7''}$ and $R^{8''}$ and together represent a group of formula $-(CH_2)_{p''}-(W)_{w''}-(CH_2)_{q''}-$, where p'' is 0, 1, 2 or 3, q'' is 0, 1, 2 or 3, W represents an oxygen or sulfur atom and w'' is 0 or 1, provided that (p''+q''+w'')is an integer from 2 to 6;

or $R^{7''}$ and $R^{10''}$ together represent a group of formula $-(CH_2)_{p'''}-,(W)''-(CH_2)_{q'''}-$, where p''' is 0, 1, 2 or 3, q''' is 0, 1, 2 or 3, w'' represents an oxygen or sulfur atom and w''' is 0 or 1;

n'' is 0 or 1;

Z'' represents a group of formula (Z-I)'', (Z-II)'', (Z-III)'', (Z-IV)'', (Z-V)'', (Z-VI)'', (Z-VII)'' or (Z-VIII)'':

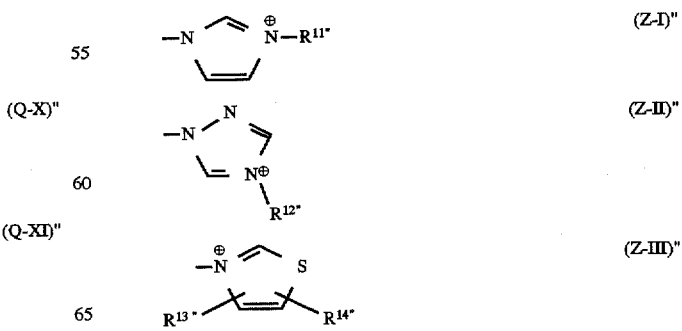

-continued

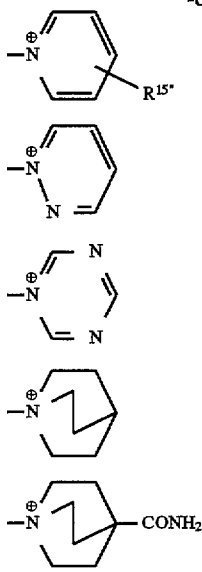

(Z-IV)"

(Z-V)"

(Z-VI)"

(Z-VII)"

(Z-VIII)"

wherein:

$R^{11"}$ and $R^{12"}$ are independently selected from the group consisting of unsubstituted alkyl groups having from 1 to 6 carbon atoms, and substituted alkyl groups which have from 1 to 6 carbon atoms and which are substituted by at least one substituent selected from the group consisting of substituents B", defined below; and $R^{13"}$, $R^{14"}$ and $R^{15"}$ are independently selected from the group consisting of carbamoyl groups, unsubstituted alkyl groups having from 1 to 6 carbon atoms, and substituted alkyl groups which have from 1 to 6 carbon atoms and which are substituted by at least one substituent selected from the group consisting of substituents B", defined below;, $m^{1"}$ is 0 or 1 and $n^{1"}$ is 0, 1 or 2, provided that $(m^{1"}+n^{1"})$ is greater than 0;

$R^{16"}$ represents an unsubstituted alkyl group having from 1 to 6 carbon atoms, or a substituted alkyl group which has from 1 to 6 carbon atoms and which is substituted by at least one substituent selected from the group consisting of substituents B", defined below;

$R^{18"}$ represents an unsubstituted alkyl group having from 1 to 6 carbon atoms, or a substituted alkyl group which has from 1 to 6 carbon atoms and which is substituted by at least one substituent selected from the group consisting of substituents B", defined below;

x" represents a sulfur atom or a group of formula >NR$^{17"}$, where $R^{17"}$ represents an unsubstituted alkyl group having from 1 to 6 carbon atoms;

$n^{2"}$ is 1 or 2;

$R^{19"}$ represents an unsubstituted alkyl group having from 1 to 6 carbon atoms, or a substituted alkyl group which has from 1 to 6 carbon atoms and which is substituted by at least one substituent selected from the group consisting of substituents B", defined below;

Y" represents a group of formula

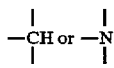

$R^{20"}$, $R^{21"}$ and $R^{22"}$ are independently selected from the group consisting of hydrogen atoms and unsubstituted alkyl groups having from 1 to 6 carbon atoms;

or $R^{20"}$, $R^{21"}$ and $R^{22"}$ together represent a group of formula —$(CH_2)_{s"}$(w)$_{w"}$'"—$(CH_2)_{t"}$, where s" is 0, 1, 2 or 3, t" is 0, 1, 2 or 3, w" represents an oxygen or sulfur atom and w'" is 0 or 1;

$R^{22"}$ and $R^{24"}$ are independently selected from the group consisting of hydrogen atoms, halogen atoms, unsubstituted alkyl groups having from 1 to 6 carbon atoms, and substituted alkyl groups which have from 1 to 6 carbon atoms and which are substituted by at least one substituent selected from the group consisting of substituents C, defined below, hydroxy groups, carboxy groups, carbamoyl groups, amino groups, cyano groups and carbamoyloxy groups;

$n^{3"}$ is 1, 2 or 3;

$R^{25"}$ represents a hydrogen atom, an unsubstituted alkyl group having from 1 to 6 carbon atoms, a substituted alkyl group which has from 1 to 6 carbon atoms and which is substituted by at least one substituent selected from the group consisting of substituents C, defined below, an alkenyl group having from 2 to 6 carbon atoms, or an alkynyl group having from 2 to 6 carbon atoms;

$R^{26"}$ represents a hydrogen atom, a halogen atom, an unsubstituted alkyl group having from 1 to 6 carbon atoms, a substituted alkyl group which has from 1 to 6 carbon atoms and which is substituted by at least one substituent selected from the group consisting of substituents C, defined below, a hydroxy group, a carboxy group, a carbamoyl group, an amino group, a cyano group or a carbamoyloxy group;

$n^{4"}$ is 0, 1 or 2;

$p^{2"}$ is 0 or 1;

$R^{27"}$ represents a hydrogen atom or an unsubstituted alkyl group having from 1 to 6 carbon atoms;

$R^{28"}$ and $R^{29"}$ are independently selected from the group consisting of hydrogen atoms, unsubstituted alkyl groups having from 1 to 6 carbon atoms, and substituted alkyl groups which have from 1 to 6 carbon atoms and which are substituted by at least one substituent selected from the group consisting of substituents C, defined below;

$p^{3"}$ is 1 or 2;

$R^{30"}$ represents a hydrogen atom, an unsubstituted alkyl group having from 1 to 6 carbon atoms, a substituted alkyl group which has from 1 to 6 carbon atoms and which is substituted by at least one substituent selected from the group consisting of substituents D", defined below, an alkenyl group having from 2 to 6 carbon atoms, an alkynyl group having from 2 to 6 carbon atoms, or a group of formula where $R^{33"}$ represents a hydrogen atom, an unsubstituted alkyl group having from 1 to 6 carbon atoms, a substituted alkyl group which has from 1 to 6 carbon atoms and which is substituted by at least one substituent selected from the group consisting of substituents E", defined below, a cycloalkyl group having from 3 to 6 ring carbon atoms or a cycloalkylalkyl group in which the cycloalkyl part has from 3 to 6 ring carbon atoms and the alkyl part has from 1 to 6 ring carbon atoms;

$R^{31"}$ represents a hydrogen atom, an unsubstituted alkyl group having from 1 to 6 carbon atoms, a substituted alkyl group which has from 1 to 6 carbon atoms and which is substituted by at least one substituent selected from the group consisting of substituents F", defined below, an alkenyl group having from 2 to 6 carbon atoms, or an alkynyl group having from 2 to 6 carbon atoms;

$R^{32"}$ represents a hydrogen atom, a halogen atom, an unsubstituted alkyl group having from 1 to 6 carbon atoms, a substituted alkyl group which has from 1 to 6 carbon atoms and which is substituted by at least one substituent selected from the group consisting of substituents F", defined below, a hydroxy group, a carboxy group, a carbamoyl group, an amino group, a cyano group or a carbamoyloxy group;

$R^{34}$" represents a hydrogen atom or an unsubstituted alkyl group having from 1 to 6 carbon atoms;

$R^{35}$" represents a hydrogen atom, an unsubstituted alkyl group having from 1 to 6 carbon atoms, a substituted alkyl group which has from 1 to 6 carbon atoms and which is substituted by at least one substituent selected from the group consisting of substituents G", defined below, an alkenyl group having from 2 to 6 carbon atoms, an alkynyl group having from 2 to 6 carbon atoms, or a group of formula —C(=NH)$R^{33}$" where $R^{33}$" is as defined above; and U" represents an imidazolyl group, a triazolyl group or a tetrazolyl group;

substituents A" are selected from the group consisting of hydroxy groups, carboxy groups, carbamoyl groups, carbamoyloxy groups, cyano groups, halogen atoms, oxygen atoms (to form an oxo group), alkoxy groups having from 1 to 6 carbon atoms, amino groups, alkylamino groups having from 1 to 6 carbon atoms and dialkylamino groups in which each alkyl part has from 1 to 6 carbon atoms;

substituents B" are selected from the group consisting of cyano groups, hydroxy groups, carboxy groups, sulfo groups, halogen atoms, alkoxy groups having from 1 to 6 carbon atoms, alkylthio groups having from 1 to 6 carbon atoms, alkylsulfinyl groups having from 1 to 6 carbon atoms, alkylsulfonyl groups having from 1 to 6 carbon atoms, alkanoylamino groups having from 1 to 6 carbon atoms, alkanoyloxy groups having from 1 to 6 carbon atoms, alkanoyl groups having from 1 to 6 carbon atoms, alkoxycarbonyl groups having from 2 to 7 carbon atoms, ureido groups, carbamoyl groups, alkylcarbamoyl groups having from 2 to 7 carbon atoms, dialkylcarbamoyl groups in which each alkyl part has from 1 to 6 carbon atoms, carbamoyloxy groups, alkylcarbamoyloxy groups having from 2 to 7 carbon atoms, dialkylcarbamoyloxy groups in which each alkyl part has from 1 to 6 carbon atoms, amino groups, alkylamino groups having from 1 to 6 carbon atoms, dialkylamino groups in which each alkyl part has from 1 to 6 carbon atoms, sulfamoyl groups and oxygen atoms (to form an oxo group);

substituents C" are selected from the group consisting of hydroxy groups, carboxy groups, carbamoyl groups, cyano groups, halogen atoms, alkoxy groups having from 1 to 6 carbon atoms and amino groups;

substituents D" are selected from the group consisting of hydroxy groups, carboxy groups, carbamoyl groups, carbamoyloxy groups, cyano groups, sulfamoyl groups, ureido groups, sulfo groups, alkoxy groups having from 1 to 6 carbon atoms, alkoxycarbonyl groups having from 2 to 7 carbon atoms, alkanoyl groups having from 1 to 6 carbon atoms, alkanoylamino groups having from 1 to 6 carbon atoms, alkanoyloxy groups having from 1 to 6 carbon atoms, halogen atoms, amino groups, alkylamino groups having from 1 to 6 carbon atoms, alkylthio groups having from 1 to 6 carbon atoms, alkylsulfinyl groups having from 1 to 6 carbon atoms, alkylsulfonyl groups having from 1 to 6 carbon atoms, dialkylamino groups in which each alkyl part has from 1 to 6 carbon atoms; alkylcarbamoyl groups having from 2 to 7 carbon atoms, dialkylcarbamoyl groups in which each alkyl part has from 1 to 6 carbon atoms, alkylcarbamoyloxy groups having from 2 to 7 carbon atoms and dialkylcarbamoyloxy groups in which each alkyl part has from 1 to 6 carbon atoms;

substituents E" are selected from the group consisting of halogen atoms and alkoxy groups having from 1 to 6 carbon atoms;

substituents F" are selected from the group consisting of hydroxy groups, carboxy groups, carbamoyl groups, halogen atoms, alkoxy groups having from 1 to 6 carbon atoms and amino groups; and substituents G" are selected from the group consisting of hydroxy groups, carboxy groups, carbamoyl groups, carbamoyloxy groups, cyano groups, halogen atoms, alkoxy groups having from 1 to 6 carbon atoms and amino groups.

The present invention also provides a pharmaceutical composition comprising a pharmaceutically acceptable carrier, diluent or adjuvant in admixture with an effective amount of an antibiotic, wherein the antibiotic is selected from the group consisting of compounds of formula (I) or formula (I)" and pharmaceutically acceptable salts and esters thereof.

The present invention further provides a method for the treatment or prophylaxis of microbial, generally bacterial, infections in an animal, for example a mammal, such as a human being, which comprises administering to said animal an effective amount of an antibiotic, wherein the antibiotic is selected from the group consisting of the compounds of formula (I), the compounds of formula (I)" and pharmaceutically acceptable salts and esters thereof.

The present invention also provides processes for preparing these compounds, which are described in greater detail hereafter.

DETAILED DESCRIPTION OF INVENTION

In the compounds of the present invention, where $R^1$, $R^2$, $R^3$, $R^4$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ or $R^{23}$ represents an alkyl group having from 1 to 6 carbon atoms, this may be a straight or branched chain group having from 1 to 6, preferably from 1 to 4, carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methyl- pentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alky groups having from 1 to 4 carbon atoms, preferably the methyl, ethyl, propyl, isopropyl, butyl, isobutyl and t-butyl groups, and most preferably the methyl group.

Where $R°$ represents an alkyl group having from 1 to 6 carbon atoms, this may likewise be a straight or branched chain group having from 1 to 6, preferably from 1 to 4, carbon atoms, and examples include the methyl, ethyl, propyl, isopropyl, butyl, isobutyl, sec-butyl, n-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4, more preferably from 1 to 3, carbon atoms, preferably the methyl, ethyl, propyl, isopropyl, butyl, isobutyl and t-butyl groups, more preferably the methyl, ethyl and propyl groups, and most preferably the methyl group.

Where $R^1$, $R^2$, $R^3$, $R^4$, $R^6$, $R^7$, $R^8$, $R^9$, $R^{10}$, $R^{12}$, $R^{13}$, $R^{16}$, $R^{17}$ or $R^{18}$, represents a substituted alkyl group having from 1 to 6 carbon atoms, this may be a straight or branched chain group, preferably a straight chain group, having from 1 to 6, preferably from 1 to 4, carbon atoms, and examples include the methyl, ethyl, propyl, isopropyl, butyl, isobutyl, sec-butyl, t-butyl, pentyl, isopentyl, neopentyl, hexyl and isohexyl groups. Of these, we prefer those alkyl groups having from 1 to 3 carbon atoms, preferably the methyl, ethyl and propyl groups, and most preferably the methyl and ethyl groups. The substituents may be selected from the appropriate one of substituents (a), (b), (c) and (d), as defined above and exemplified below. There is no particular limitation on the number of substituents, except such as may be imposed by the number of substitutable positions, and possibly by steric constraints. However, in general, from 1 to 3 substituents are preferred, a single substituent being normally most preferred.

Where $R^1$, $R^2$, $R^8$ or $R^{12}$ represents an alkenyl group having from 2 to 6 carbon atoms, this may be a straight or branched chain group having from 2 to 6, preferably 3 or 4, carbon atoms, and examples include the vinyl, allyl, 2-methylallyl, 1-propenyl, isopropenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl and 5-hexenyl groups, of which the vinyl, allyl, 2-methylallyl, 1-propenyl, isopropenyl and butenyl groups are preferred, the allyl and 2-methylallyl groups being most preferred.

Where $R^1$, $R^2$, $R^8$ or $R^{12}$ represents an alkynyl group having from 2 to 6 carbon atoms, this may be a straight or branched chain group having from 2 to 6, preferably 3 or 4, carbon atoms, and examples include the ethynyl, propargyl (2-propynyl), 1-propynyl, 1-butynyl, 2-butynyl, 3-butynyl, 2-methyl-2-propynyl, 1-pentynyl, 2-pentynyl, 3-pentynyl and 4-pentynyl groups, of which the propynyl and butynyl groups are preferred, the propargyl and 2-methyl-2-propynyl groups being most preferred.

Where $R^6$, $R^{10}$, $R^{13}$, $R^{16}$ or substituent (c) represents a cycloalkyl group, this may have from 3 to 7 ring carbon atoms, and examples include the cyclopropyl, cyclobutyl, cyclopentyl, cyclohexyl and cycloheptyl groups, of which the cyclopropyl, cyclobutyl and cyclopentyl groups are preferred, the cyclopropyl group being most preferred.

Where $R^3$, $R^4$, $R^7$, substituent (a), substituent (b), substituent (c) or substituent (d) represents a halogen atom, this may be a fluorine, chlorine, bromine or iodine atom, more preferably a fluorine, chlorine or bromine atom, and most preferably a fluorine or chlorine atom.

Where $R^a$ or $R^b$ represents an alkyl group, this may be a straight or branched chain alkyl group having from 1 to 4 carbon atoms, and examples include the methyl, ethyl, propyl, isopropyl, butyl, isobutyl, sec-butyl and t-butyl groups. Of these, we prefer those alkyl groups having 1 or 2 carbon atoms, most preferably the methyl group. However $R^a$ and $R^b$ preferably both represent hydrogen atoms. Preferred groups of formula —CO.NR$^a$R$^b$, —OCO.NR$^a$R$^b$ and —NR$^a$R$^b$ are the amino, methylamino, ethylamino, propylamino, butylamino, dimethylamino, diethylamino, methylethylamino, methylbutylamino, carbamoyl, methylcarbamoyl, ethylcarbamoyl, propylcarbamoyl, butylcarbamoyl, dimethylcarbamoyl, diethylcarbamoyl, methylethylcarbamoyl, methylbutylcarbamoyl, carbamoyloxy, methylcarbamoyloxy, ethylcarbamoyloxy, propylcarbamoyloxy, butylcarbamoyloxy, dimethylcarbamoyloxy, diethylcarbamoyloxy, methylethylcarbamoyloxy and methylbutylcarbamoyloxy groups, of which the amino, carbamoyl and carbamoyloxy groups are preferred.

Where $R^8$ and $R^9$ together represent a group of formula —(CH$_2$)$_s$—W—(CH$_2$)$_t$—, W represents a carbon-carbon single bond, an oxygen atom, a sulfur atom or a group of formula >NR$^{22}$, wherein $R^{22}$ represents a hydrogen atom or an alkyl group having from 1 to 6 carbon atoms, and s and t are independently 1, 2 or 3. In this case, $R^8$ and $R^9$ together with the nitrogen atom to which they are attached form a nitrogen-containing heterocyclic group. Preferably, where W represents a carbon-carbon single bond, (s+t) is an integer from 3 to 6, more preferably from 3 to 5 and most preferably 4 or 5. Where W represents an oxygen atom, a sulfur atom or a group of formula >NR$^{22}$ (s+t) is preferably an integer from 2 to 5 more preferably from 2 to 4 and most preferably 3 or 4. Within these preferred constraints, s and t are preferably each 1 or 2. Examples of such groups of formula —(CH$_2$)$_s$—W—(CH$_2$)$_t$— include:

—(CH$_2$)$_4$—;
—(CH$_2$)$_5$—;
—(CH$_2$)—O—(CH$_2$)$_2$—;
—(CH$_2$)$_2$—O—(CH$_2$)$_2$—;
—(CH$_2$)—S—(CH$_2$)$_2$—;
—(CH$_2$)$_2$—S—(CH$_2$)$_2$—;
—(CH$_2$)—NH—(CH$_2$)$_2$—;
—(CH$_2$)$_2$—NH—(CH$_2$)$_2$—;
—(CH$_2$)—NMe—(CH$_2$)$_2$—; and
—(CH$_2$)$_2$—NMe—(CH$_2$)$_2$—;

where Me represents a methyl group.

Where $R^{17}$ and $R^{18}$ together represent a group of formula —(CH$_2$)$_q$—Y—(CH$_2$)$_r$— Y represents a carbon-carbon single bond, an oxygen atom, a sulfur atom or a group of formula >NR$^{23}$ wherein $R^{23}$ represents a hydrogen atom or an alkyl group having from 1 to 6 carbon atoms, and q and r are independently 1, 2 or 3. In this case, $R^{17}$ and $R^{18}$ together with the nitrogen atom to which they are attached form a nitrogen-containing heterocyclic group. Preferably, where Y represents a carbon-carbon single bond, (q+r) is an integer from 3 to 6, more preferably from 3 to 5 and most preferably 4 or 5. Where Y represents an oxygen atom, a sulfur atom or a group of formula NR$^{23}$ (q+r) is preferably an integer from 2 to 5, more preferably from 2 to 4 and most preferably 3 or 4. Within these preferred constraints, q and r are preferably each 1 or 2. Examples of such groups of formula —(CH$_2$)$_q$—Y—(CH$_2$)$_r$— includes:

—(CH$_2$)$_4$—;
—(CH$_2$)$_5$—;
—(CH$_2$)—O—(CH$_2$)$_2$—;
—(CH$_2$)$_2$—O—(CH$_2$)$_2$—;
—(CH$_2$)—S—(CH$_2$)$_2$—;
—(CH$_2$)$_2$—S—(CH$_2$)$_2$—;
—(CH$_2$)—NH—(CH$_2$)$_2$—;
—(CH$_2$)$_2$—NH—(CH$_2$)$_2$—;
—(CH$_2$)—NMe—(CH$_2$)$_2$—; and
—(CH$_2$)$_2$—NMe—(CH$_2$)$_2$—;

where Me represents a methyl group.

Where substituent (a), substituent (b), substituent (c) or substituent (d) represents an alkoxy group having from 1 to 6 carbon atoms, this may likewise be a straight or branched chain group having from 1 to 6, preferably from 1 to 4, carbon atoms, and examples include the methoxy, ethoxy, propoxy, isopropoxy, butoxy, isobutoxy, sec-butoxy, t-butoxy, pentyloxy, isopentyloxy, neopentyloxy, 2-methylbutoxy, 1-ethylpropoxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy, 2-ethylbutoxy, hexyloxy and isohexyloxy groups. Of these, we prefer those alkoxy groups having from 1 to 3 carbon atoms, preferably the methoxy, ethoxy, propoxy, isopropoxy, butoxy, isobutoxy and t-butoxy groups, more preferably the methoxy, ethoxy and propoxy groups, and most preferably the methoxy group.

Where substituent (b) represents an alkanoyl group, this has from 1 to 6 carbon atoms, preferably from 1 to 4 carbon atoms, and examples include the formyl, acetyl, propionyl, butyryl, isobutyryl, pivaloyl, valeryl, isovaleryl and hexanoyl groups, of which the acetyl and propionyl groups are more preferred, the acetyl group being most preferred.

Where substituent (b) represents an alkanoylamino group, this has from 1 to 6 carbon atoms, preferably from 1 to 4 carbon atoms, and examples include the formylamino, acetylamino, propionylamino, butyrylamino, isobutyrylamino, pivaloylamino, valerylamino, isovalerylamino and hexanoylamino groups, of which the acetylamino and propionylamino groups are more preferred, the acetylamino group being most preferred.

Where substituent (b) represents an alkanoyloxy group, this has from 1 to 6 carbon atoms, preferably from 1 to 4 carbon atoms, and examples include the formyloxy, acetyloxy, propionyloxy, butyryloxy, isobutyryloxy, pivaloyloxy, valeryloxy, isovaleryloxy and hexanoyloxy groups, of which the acetyloxy and propionyloxy groups are more preferred, the acetyloxy group being most preferred.

Where substituent (b) represents an alkylthio group having from 1 to 6 carbon atoms, this may likewise be a straight or branched chain group having from 1 to 6, preferably from 1 to 4, carbon atoms, and examples include the methylthio, ethylthio, propylthio, isopropylthio, butylthio, isobutylthio, sec-butylthio, t-butylthio, pentylthio, isopentylthio, neopentylthio, 2-methylbutylthio, 1-ethylpropylthio, 4-methylpentylthio, 3-methylpentylthio, 2-methylpentylthio, 1-methylpentylthio, 3,3-dimethylbutylthio, 2,2-dimethylbutylthio, 1,1-dimethylbutylthio, 1,2-dimethylbutylthio, 1,3-dimethylbutylthio, 2,3-dimethylbutylthio, 2-ethylbutylthio, hexylthio and isohexylthio groups. Of these, we prefer those alkylthio groups having from 1 to 4, more preferably from 1 to 3, carbon atoms, preferably the methylthio, ethylthio, propylthio, isopropylthio, butylthio, isobutylthio and t-butylthio groups, more preferably the methylthio, ethylthio and propylthio groups, and most preferably the methylthio group.

Where substituent (b) represents an alkylsulfinyl group having from 1 to 6 carbon atoms, this may likewise be a straight or branched chain group having from 1 to 6, preferably from 1 to 4, carbon atoms, and examples include the methylsulfinyl, ethylsulfinyl, propylsulfinyl, isopropylsulfinyl, butylsulfinyl, isobutylsulfinyl, sec-butylsulfinyl, t-butylsulfinyl, pentylsulfinyl, isopentylsulfinyl, neopentylsulfinyl, 2-methylpentylsulfinyl, 1-ethylpropylsulfinyl, 4-methylpentylsulfinyl, 3-methylpentylsulfinyl, 2-methylpentylsulfinyl, 1-methylpentylsulfinyl, 3,3-dimethylbutylsulfinyl, 2,2-dimethylbutylsulfinyl, 1,1-dimethylbutylsulfinyl, 1,2-dimethylbutylsulfinyl, 1,3-dimethylbutylsulfinyl, 2,3-dimethylbutylsulfinyl, 2-ethylbutylsulfinyl, hexylsulfinyl and isohexylsulfinyl groups. Of these, preferred are alkylsulfinyl groups having from 1 to 4, more preferably from 1 to 3, carbon atoms, preferably the methylsulfinyl, ethylsulfinyl, propylsulfinyl, isopropylsulfinyl, butylsulfinyl, isobutylsulfinyl and t-butylsulfinyl groups, more preferably the methylsulfinyl, ethylsulfinyl and propylsulfinyl groups, and most preferably the methylsulfinyl group.

Where substituent (b) represents an alkylsulfonyl group having from 1 to 6 carbon atoms, this may likewise be a straight or branched chain group having from 1 to 6, preferably from 1 to 4, carbon atoms, and examples include the methylsulfonyl, ethylsulfonyl, propylsulfonyl, isopropylsulfonyl, butylsulfonyl, isobutylsulfonyl, sec-butylsulfonyl, t-butylsulfonyl, pentylsulfonyl, isopentylsulfonyl, neopentylsulfonyl, 2-methylbutylsulfonyl, 1-ethylpropylsulfonyl, 4-methylpentylsulfonyl, 3-methylpentylsulfonyl, 2-methylpentylsulfonyl, 1-methylpentylsulfonyl, 3,3-dimethylbutylsulfonyl, 2,2-dimethylbutylsulfonyl, 1,1-dimethylbutylsulfonyl, 1,2-dimethylbutylsulfonyl, 1,3-dimethylbutylsulfonyl, 2,3-dimethylbutylsulfonyl, 2-ethylbutylsulfonyl, hexylsulfonyl and isohexylsulfonyl groups. Of these, we prefer those alkylsulfonyl groups having from 1 to 4, more preferably from 1 to 3, carbon atoms, preferably the methylsulfonyl, ethylsulfonyl, propylsulfonyl, isopropylsulfonyl, butylsulfonyl, isobutylsulfonyl, propylsulfonyl and t-butylsulfonyl groups, more preferably the methylsulfonyl, ethylsulfonyl and propylsulfonyl groups, and most preferably the methylsulfonyl group.

The compounds of formula (I) have a carboxy group at the carbapenem 3-position, and the compounds may also contain one or more additional carboxy groups depending upon the meanings of $R^3$, $R^4$, $R^7$, substituent (a), substituent (b) and substituent (d). Such carboxy groups can, of course form salts and esters, and such salts and esters also form part of the present invention. There is no particular restriction on the nature of these salts and esters, provided that, where they are intended for therapeutic use, they are pharmaceutically acceptable. Where they are intended for non-therapeutic uses, e.g. as intermediates in the preparation of other, and possibly more active, compounds, even this restriction does not apply. In the case of the esters, we prefer, in general, an ester residue which is capable of hydrolysis in the mammalian body, as is well known in the art. However, any ester residue can be used, provided that, as explained above, if the compound is intended for therapeutic use, it is pharmaceutically acceptable. Examples of suitable ester groups include:

$C_1$—$C_{20}$ alky groups, more preferably $C_1$–$C_6$ alkyl groups, such as those exemplified in relation to $R^1$ etc. and higher alkyl groups as are well known in the art, such as the heptyl, octyl, nonyl, decyl, dodecyl, tridecyl, pentadecyl, octadecyl, nonadecyl and icosyl groups, but most preferably the methyl, ethyl and t-butyl groups; $C_3$–$C_7$ cycloalkyl groups, for example as illustrated herein in relation to $R^6$ etc.;

aralkyl groups, in which the alkyl part is a $C_1$–$C_3$ alkyl group and the aryl part is a $C_6$–$C_{14}$ carbocyclic aromatic group which may be substituted or unsubstituted and, if substituted, has at least one substituent selected from the group consisting of substituents (e) defined and exemplified below, although the unsubstituted groups are preferred; examples of such aralkyl groups include the benzyl, phenethyl, 1-phenylethyl, 3-phenylpropyl, 2-phenylpropyl, 1-naphthylmethyl, 2-naphthylmethyl, 2-(1-naphthyl)ethyl, 2-(2-naphthyl)ethyl, benzhydryl (i.e. diphenylmethyl), triphenylmethyl, bis(o-nitrophenyl)methyl, 9-anthrylmethyl, 2,4,6-trimethylbenzyl, 4-bromobenzyl, 2-nitrobenzyl, 4-nitrobenzyl, 3-nitrobenzyl, 4-methoxybenzyl and piperonyl groups;

alkenyl groups such as those defined and exemplified above in relation to $R^1$ etc., but which may be substituted or unsubstituted and, if substituted have at least one substituent selected from the group consisting of substituents (a) defined above; examples of the unsubstituted groups are given above in relation to $R^1$ etc., and preferred groups include the allyl, 2-chloroallyl and 2-methylallyl groups;

halogenated $C_1$–$C_6$, preferably $C_1$–$C_4$, alkyl groups in which the alkyl part is as defined and exemplified in relation to the alkyl groups which may be represented by $R^1$ etc., and the halogen atom is chlorine, fluorine, bromine or iodine, such as the 2,2,2-trichloroethyl, 2-haloethyl (e.g. 2-chloroethyl, 2-fluoroethyl, 2-bromoethyl or 2-iodoethyl), 2,2-dibromoethyl and 2,2,2-tribromoethyl group;

substituted silylalkyl groups, in which the alkyl part is as defined and exemplified in relation the alkyl groups which may be represented by $R^1$ etc., and the silyl group has up to 3 substituents selected from the group consisting of $C_1$–$C_6$ alkyl groups and phenyl groups which are unsubstituted or have at least one substituent selected from the group consisting of substituents (e) defined and exemplified below, for example 2-trimethylsilylethyl group;

phenyl groups, in which the phenyl group is unsubstituted or substituted, preferably with at least one $C_1$–$C_4$ alkyl or acylamino group, for example the phenyl, tolyl and benzamidophenyl groups;

phenacyl groups, which may be unsubstituted or have at least one substituent selected from the group consisting of substituents (e) defined and exemplified below, for example the phenacyl group itself or the p-bromophenacyl group;

cyclic and acyclic terpenyl groups, for example the geranyl, neryl, linalyl, phytyl, menthyl (especially m- and p-menthyl), thujyl, caryl, pinanyl, bornyl, notcaryl, norpinanyl, norbornyl, menthenyl, camphenyl and norbornenyl groups;

alkoxymethyl groups, in which the alkoxy park is $C_1$ $C_6$, preferably $C_1$–$C_4$, and may itself be substituted by a single unsubstituted alkoxy group, such as the methoxymethyl, ethoxymethyl, propoxymethyl, isopropoxymethyl, butoxymethyl and methoxyethoxymethyl groups; aliphatic acyloxyalkyl groups, in which the acyl group is preferably an alkanoyl group and is more preferably a $C_2$–$C_6$ alkanoyl group, and the alkyl part is a $C_2$–$C_6$, and preferably $C_2$–$C_4$, alkyl group, such as the acetoxymethyl, propionyloxymethyl, butyryloxymethyl, isobutyryloxymethyl, pivaloyloxymethyl, 1-pivaloyloxyethyl, 1-acetoxyethyl, 1-isobutyryloxyethyl, 1-pivaloyloxypropyl, 2-methyl-1-pivaloyloxypropyl, 2-pivaloyloxypropyl, 1-isobutyryloxyethyl, 1-isobutyryloxypropyl, 1-acetoxypropyl, 1-acetoxy-2-methylpropyl, 1-propionyloxyethyl, 1-propionyloxypropyl, 2-acetoxypropyl and 1-butyryloxyethyl groups;

cycloalkyl-substituted aliphatic acyloxyalkyl groups, in which the acyl group is preferably an alkanoyl group and is more preferably a $C_2$–$C_6$ alkanoyl group, the cycloalkyl substituent is $C_3$–$C_7$, and the alkyl part is a $C_1$–$C_6$ alkyl group, preferably a $C_1$–$C_4$ alkyl group, such as the (cyclohexylacetoxy)methyl, 1-(cyclohexylacetoxy)ethyl, 1-(cyclohexylacetoxy) propyl, 2-methyl-1-(cyclohexylacetoxy)propyl, (cyclopenylacetoxy)methyl, 1-(cyclopentylacetoxy)ethyl, 1-(cyclopentylacetoxy) propyl and 2-methyl-1-(cyclopentylacetoxy)propyl, groups;

alkoxycarbonyloxyalkyl groups, especially 1-(alkoxycarbonyloxy) ethyl groups, in which the alkoxy part is $C_1$–$C_{10}$, preferably $C_1$–$C_6$, and more preferably $C_1$ $C_4$, and the alkyl part is $C_1$–$C_6$, preferably $C_1$–$C_4$, such as the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-sec-butoxycarbonyloxyethyl, 1-t-butoxycarbonyloxyethyl, 1-(1-ethylpropoxycarbonyloxy)ethyl and 1-(1,1-dipropylbutoxycarbonyloxy)ethyl groups, and other alkoxycarbonylalkyl groups, in which both the alkoxy and alkyl groups are $C_1$–$C_6$, preferably $C_1$–$C_4$, such as the 2-methyl-1-(isopropoxycarbonyloxy) propyl, 2-(isopropoxycarbonyloxy) propyl, isopropoxycarbonyloxymethyl, t-butoxycarbonyloxymethyl, methoxycarbonyloxymethyl and ethoxycarbonyloxymethyl groups;

cycloalkylcarbonyloxyalkyl and cycloalkyloxycarbonyloxyalkyl groups, in which the cycloalkyl group is $C_3$–$C_{10}$, preferably $C_3$–$C_7$, is mono- or poly- cyclic and is optionally substituted by at least one (and preferably only one) $C_1$–$C_4$ alkyl group (e.g. selected from those alkyl groups exemplified above) and the alkyl group is a $C_1$–$C_6$, more preferably $C_1$–$C_4$, alkyl group (e.g. selected from those alkyl groups exemplified above) and is most preferably methyl, ethyl or propyl, for example the 1-methylcyclohexylcarbonyloxymethyl, 1-methylcyclohexyloxycarbonyloxymethyl, cyclopentyloxycarbonyloxymethyl, cyclopentylcarbonyloxymethyl, 1-cyclohexyloxycarbonyloxyethyl, 1-cyclohexylcarbonyloxyethyl, 1-cyclopentyloxycarbonyloxyethyl, 1-cyclopentylcarbonyloxyethyl, 1-cycloheptyloxycarbonyloxyethyl, 1-cycloheptylcarbonyloxyethyl, 1-methylcyclopentylcarbonyloxymethyl, 1-methylcyclopentyloxycarbonyloxymethyl, 2-methyl-1-(1-methylcyclohexylcarbonyloxy)propyl, 1-(1-methylcyclohexylcarbonyloxy)propyl, 2-(1-methylcyclohexylcarbonyloxy)propyl, 1-(cyclohexylcarbonyloxy)propyl, 2-(cyclohexylcarbonyloxy)propyl, 2-methyl-1-(1-methylcyclopentylcarbonyloxy)propyl, 1-(1-methylcyclopentylcarbonyloxy)propyl, 2-(1-methylcyclopentylcarbonyloxy)propyl-(cyclopentylcarbonyloxypropyl, 2-(cyclopentylcarbonyloxy)propyl, 1-(1-methylcylopentylcarbonyloxy)ethyl, 1-(1-methylcyclopennylcarbonyloxy)propyl, adamantyloxycarbonyloxymethyl, adamantyloxycarbonyloxymethyl, 1-adamantyloxycarbonyloxyethyl and 1-adamantylcarbonyloxyethyl groups;

cycloalkylalkoxycarbonyloxyalkyl groups in which the alkoxy group has a single cycloalkyl substituent, the cycloalkyl substituent being $C_3$–$C_{10}$, preferably $C_3$–$C_7$, and mono- or poly- cyclic, for example the cyclopropylmethoxycarbonyloxymethyl, cyclobutylmethoxycarbonyloxymethyl, cyclopentylmethoxycarbonyloxymethyl, cyclohexylmethoxycarbonyloxymethyl, 1-(cyclopropylmethoxycarbonyloxy)ethyl, 1-(cyclobutylmethoxycarbonyloxy)ethyl, 1-(cyclopentylmethoxycarbonyloxy)ethyl and 1-(cyclohexylmethoxycarbonyloxy)ethyl groups;

terpenylcarbonyloxyalkyl and terpenyloxycarbonyloxyalkyl groups, in which the terpenyl group is as exemplified above, and is preferably a cyclic terpenyl group, for example the 1-(menthyloxycarbonyloxy)ethyl, 1-(menthylcarbonyloxy) ethyl, menthyloxycarbonyloxymethyl, menthylcarbonyloxymethyl, 1-(3-pinanyloxycarbonyloxy) ethyl, 1-(3-pinanylcarbonyloxy)ethyl, 3-pinanytoxycarbonyloxymethyl and 3-pinanylcarbonyloxymethyl groups;

5-alkyl or 5-phenyl [which may be substituted by at least one substituent selected from the group consisting of substituents (e)](2-oxo-1,3-dioxolen-4-yl)alkyl groups in which each alkyl group (which may be the same or different) is $C_1-C_6$, preferably $C_1-C_4$, for example the (5-methyl-2-oxo-1,3-dioxolen-4-yl)methyl, (5-phenyl-2-oxo-1,3-dioxolen-4-yl)methyl, (5-isopropyl-2-oxo-1,3-dioxolen-4-yl)methyl, (5-t-butyl-2-oxo-1,3-dioxolen-4-yl)methyl and 1-(5-methyl-2-oxo-1,3-dioxolen-4-yl)ethyl groups; and other groups, especially groups which are easily removed in vivo such as the phthalidyl, indanyl and 2-oxo-4,5,6,7-tetrahydro-1,3-benzodioxolen-4-yl groups.

Of the above groups, we especially prefer those groups which can be removed easily in vivo, and most preferably the aliphatic acyloxyalkyl groups, alkoxycarbonyloxyalkyl groups, cycloalkylcarbonyloxyalkyl groups, phthalidyl groups and (5-substituted 2-oxo-1,3-dioxolen-4-yl)methyl groups.

In the case of the carboxy groups represented by $R^3$, $R^4$, $R^7$, substituent (a), substituent (b) and substituent (d), preferred ester groups are the alkyl groups, i.e. the carboxy group is replaced by an alkoxycarbonyl group, such as a methoxycarbonyl, ethoxycarbonyl or propoxycarbonyl group.

The substituents (e), referred to above include:

$C_1-C_4$ alkyl groups, such as those exemplified above in relation to $R^a$ and $R^b$;

$C_1-C_4$ alkoxy groups, such as the methoxy, ethoxy, propoxy, isopropoxy, butoxy, isobutoxy, sec-butoxy and t-butoxy groups;

$C_1$ $C_4$ haloalkyl groups, in which the alkyl part is as exemplified above in relation to $R^a$ and $R^b$ and the halogen atom is as exemplified above in relation to $R^3$ etc., such as the chloromethyl, fluoromethyl, bromomethyl, iodomethyl, 2-chloroethyl, 2-fluoroethyl, 2-bromoethyl, 2-iodoethyl, trifluoromethyl, 2,2,2-trifluoroethyl, 2,2,2-trichloroethyl, 3-fluoropropyl and 4-chlorobutyl groups;

$C_1-C_3$ alkylenedioxy groups, such as the methylenedioxy, ethylenedioxy, propylenedioxy and trimethylenedioxy groups;

halogen atoms, such as those exemplified above in relation to $R^3$ etc.;

cyano groups and nitro groups.

Thus, preferred compounds of formula (I) of the present invention are those compounds of formula (Ia):

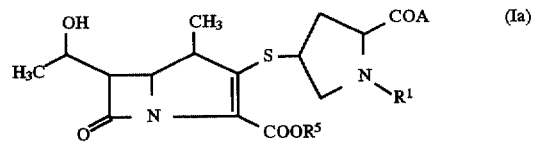

(Ia)

wherein $R^1$ and A are as defined above, and $R^5$ represents a hydrogen atom or an ester group, preferably an ester group capable of hydrolysis in vivo, and more preferably an aliphatic acyloxyalkyl group, an alkoxycarbonyloxyalkyl group, a cycloalkylcarbonyloxyalkyl group, a phthalidyl group or a (5-substituted 2-oxo-1,3-dioxolen-4-yl)methyl group.

In particular, we prefer that $R^5$ should represent a hydrogen atom, a (5-substituted 2-oxo-1,3-dioxolen-4-yl)methyl group, a 1-methylcyclohexylcarbonyloxymethyl group, a 1-isopropoxycarbonyloxyethyl group or a 1-cyclohexylcarbonyloxyethyl group.

The compounds of formuls (I)" of the present invention may contain ammonium group) in the groups of formula (Q-I)", (Q-II)", (Q-IV)", (Q-V)" and (Q-VI)". In this case, it is preferred that $R^{3"}$ should represent a negative ion (i.e. there should be a group of formula $-COO^-$ at the carbapenem 3-position), to balance the positively charged onium However, if $R^{3"}$ represents, for example, an ester group, then it is necessary that the compound should contain a negative ion to balance the positive onium ion. Such a negative ion may be provided by the anionic part of any of the acids referred to hereafter.

In the compounds of the present invention, where $R^{4"}$, $R^{5"}$, $R^{6"}$, $R^{7"}$, $R^{8"}$, $R^{9"}$, $R^{10"}$, $R^{11"}$, $R^{12"}$, $R^{13"}$, $R^{14"}$, $R^{15"}$, $R^{16"}$, $R^{18"}$, $R^{19"}$, $R^{20"}$, $R^{21"}$, $R^{22"}$, $R^{23"}$, $R^{24"}$, $R^{25"}$, $R^{26"}$, $R^{27"}$, $R^{28"}$, $R^{29"}$, $R^{30"}$, $R^{31"}$, $R^{32"}$, $R^{33"}$, $R^{34"}$ or $R^{35"}$ represents an alkyl group having from 1 to 6 carbon atoms, this may be a straight or branched chain group having from 1 to 6, preferably from 1 to 4, carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl, ethyl, propyl, isopropyl, butyl, isobutyl, sec-butyl and t-butyl groups, and most preferably the methyl and ethyl groups.

Where $R^{0"}$ or $R^{2"}$ represents an alkyl group having from 1 to 6 carbon atoms, this may be a straight or branched chain group having from 1 to 6, preferably from 1 to 4, carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, preferred are alkyl groups having from 1 to 3 carbon atoms, preferably the methyl, ethyl and propyl groups, and most preferably the methyl group.

Where $R^{2"}$, $R^{25"}$, $R^{30"}$, $R^{31"}$ or $R^{35"}$ represents an alkenyl group, this may be a straight or branched chain group having from 2 to 6, preferably 3 or 4, carbon atoms, and examples include the vinyl, allyl, 2-methylallyl, 1-propenyl, isopropenyl, 1-butenyl, 2-butenyl, 3-butenyl, 1-pentenyl, 2-pentenyl, 3-pentenyl, 4-pentenyl and 3-hexenyl groups, of which the vinyl, allyl, 2-methylallyl, 1-propenyl, isopropenyl and butenyl groups are preferred, the allyl and 2-methylallyl groups being most preferred.

Where $R^{2"}$, $R^{25"}$, $R^{30"}$, $R^{31"}$ or $R^{35"}$ represents an alkenyl group, this may be a straight or branched chain group having from 2 to 6, preferably 3 or 4, carbon atoms, and examples include the ethynyl, propargyl (2-propynyl), 1-propynyl, 2-methylpropargyl, 1-butynyl, 2-butynyl, 3-butynyl, 1-pentynyl, 2-pentynyl, 3-pentynyl, 4-pentynyl and 3-hexynyl groups, of which the propynyl and 2-methylpropargyl groups are preferred.

Where $R^{33"}$ represents a cycloalkyl group, this has from 3 to 6 ring carbon atoms, and may be a cyclopropyl, cyclobutyl, cyclopentyl or cyclohexyl group, of which the cyclopropyl, cyclobutyl and cyclopentyl groups are preferred.

Where $R^{33"}$ represents a cycloalkylalkyl group, the cycloalkyl part has from 3 to 6 ring carbon atoms and the alkyl part has from 1 to 6 ring carbon atoms. Examples of the alkyl part, which may be a straight or branched chain group, are as given above in relation to $R^{4"}$ etc., and examples of the cycloalkyl part are as given above in relation to $R^{33"}$. Specific examples of such cycloalkylalkyl groups include the cyclopropylmethyl, 1- and 2-cyclopropylethyl, cyclobutylmethyl, cyclopentylmethyl, 3-cyclopropylpropyl, 4-cyclopentylbutyl, 5-cyclopropylpentyl, 6-cyclobutylhexyl, 2-cyclopropylpropyl and 2-cyclopropylbutyl groups, of which the cyclopropylmethyl, cyclopropylethyl, cyclobutylmethyl and cyclopentylmethyl groups are preferred.

Where $R^{2"}$ represents a substituted alkyl group, the alkyl part itself may be any of the alkyl groups exemplified above in relation to the unsubstituted alkyl groups, and the substituents are selected from the group consisting of substituents A", for example:

hydroxy groups, carboxy groups, carbamoyl groups, carbamoyloxy groups, cyano groups;

halogen atoms, such as the fluorine, chlorine, bromine or iodine atoms, preferably the fluorine, chlorine or bromine atoms;

oxygen atoms (to form an oxo group);

alkoxy groups having from 1 to 6 carbon atoms, which may be straight or branched chain alkoxy groups, and examples include the methoxy, ethoxy, propoxy, isopropoxy, butoxy, isobutoxy, sec-butoxy, t-butoxy, pentyloxy, neopentyloxy, isopentyloxy and hexyloxygroups, of which preferred are alkoxy groups having from 1 to 3 carbon atoms, more preferably the methoxy, ethoxy or propoxy group;

amino groups;

alkylamino groups having from 1 to 6 carbon atoms, in which the alkyl part may be as exemplified above in relation to $R^2$ etc., and examples include the methylamino, ethylamino, propylamino, isopropylamino, butylamino, isobutylamino, sec-butylamino, t-butylamino, pentylamino, isopentylamino, neopentylamino, and hexylamino groups, of which we prefer the methylamino, ethylamino and propylamino groups; and dialkylamino groups in which each alkyl part has from 1 to 6 carbon atoms and may be as exemplified above in relation to $R^{2"}$ etc.; examples include the dimethylamino, diethylamino, dipropylamino, diisopropylamino, dibutylamino, dipentylamino, dihexylamino, methylethylamino and methylpropylamino, of which preferred are the dimethylamino, diethylamino and dipropylamino groups.

Where $R^{4"}$, $R^{5"}$, $R^{6"}$, $R^{7"}$, $R^{8"}$, $R^{9"}$, $R^{10"}$, $R^{11"}$, $R^{12"}$, $R^{13"}$, $R^{14"}$, $R^{15"}$, $R^{16"}$, or $R^{18"}$, or $R^{19"}$ represents a substituted alkyl group, this has from 1 to 6 carbon atoms and may be any of the alkyl groups exemplified above in relation to the unsubstituted groups represented by these symbols. The substituents may be selected from the group consisting of substituents B", for example:

cyano groups, hydroxy groups, carboxy groups, sulfo groups, ureido groups, carbamoyl groups, carbamoyloxy groups, amino groups, sulfamoyl groups and oxygen atoms (to form an oxo group);

halogen atoms, alkoxy groups, alkylamino groups and dialkylamino groups, all as exemplified above in relation to substituents A";

alkylthio groups having from 1 to 6 carbon atoms, in which the alkyl part may be as exemplified above in relation to $R^{2"}$ etc., preferably the methylthio, ethylthio or propylthio groups;

alkylsulfinyl groups having from 1 to 6 carbon atoms, in which the alkyl part may be as exemplified above in relation to $R^{2"}$ etc., preferably the methylsulfinyl, ethylsulfinyl or propylsulfinyl groups;

alkylsulfonyl groups having from 1 to 6 carbon atoms, in which the alkyl part may be as exemplified above in relation to $R^{2"}$ etc., preferably the methylsulfonyl, ethylsulfonyl or propylsulfonyl groups;

alkanoylamino groups having from 1 to 6 carbon atoms, which may be a straight or branched chain group; examples of such groups include the formamido, acetamido, propionamido, butyramido, isobutyramido, valerylamino, isovalerylamtno, pivaloylamino and hexanoylamino groups, of which the acetamido and propionamido groups are preferred;

alkanoyloxy groups having from 1 to 6 carbon atoms, which may be a straight or branched chain group; examples of such groups include the formyloxy, acetoxy, propionyloxy, butyryloxy, isobutyryloxy, valeryloxy, isovaleryloxy, pivaloyloxy and hexanoyloxy groups, of which the acetoxy and propionyloxy groups are preferred;

alkanoyl groups having from 1 to 6 carbon atoms, which may be a straight or branched chain group; examples of such groups include the formyl, acetyl, propionyl, butyryl, isobutyryl, valeryl, isovaleryl, pivaloyl and hexanoyl groups, of which the acetyl and propionyl groups are preferred;

alkoxycarbonyl groups having from 2 to 7 carbon atoms, that is the alkoxy part has from 1 to 6 carbon atoms, and examples include the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl and hexyloxycarbonyl groups; of these, we prefer those alkoxycarbonyl groups having from 1 to 3 carbon atoms, more preferably the methoxycarbonyl, ethoxycarbonyl and propoxycarbonyl groups;

alkylcarbamoyl groups having from 2 to 7 carbon atoms, that is the alkyl part has from 1 to 6 carbon atoms, and examples include the methylcarbamoyl, ethylcarbamoyl, propylcarbamoyl, isopropylcarbamoyl, butylcarbamoyl, isobutylcarbamoyl, sec-butylcarbamoyl, t-butylcarbamoyl, pentylcarbamoyl, isopentylcarbamoyl, neopentylcarbamoyl, and hexylcarbamoyl groups, of which we prefer the methyl carbamoyl, ethyl carbamoyl and propyl carbamoyl groups;

dialkylcarbamoyl groups in which each alkyl part has from 1 to 6 carbon atoms; examples include the dimethylcarbamoyl, diethylcarbamoyl, dipropylcarbamoyl, diisopropylcarbamoyl, dibutylcarbamoyl, dipentylcarbamoyl, dihexylcarbamoyl, methylethylcarbamoyl and methylpropylcarbamoyl groups, of which we prefer the dimethylcarbamoyl, diethylcarbamoyl and dipropylcarbamoyl groups;

alkylcarbamoyloxy groups having from 2 to 7 carbon atoms, that is the alkyl part has from 1 to 6 carbon atoms, end examples include the methylcarbamoyloxy, ethylcarbamoyloxy, propylcarbamoyloxy, isopropylcarbamoyloxy, butylcarbamoyloxy, isobutylcarbamoyloxy, sec-butylcarbamoyloxy, t-butylcarbamoyloxy, pentylcarbamoyloxy, isopentylcarbamoyloxy, neopentylcarbamoyloxy, and hexylcarbamoyloxy groups, of which we prefer the methylcarbamoyloxy, ethylcarbamoyloxy and propylcarbamoyloxy groups; and dialkylcarbamoyloxy groups in which each alkyl part has from 1 to 6 carbon atoms; examples include the dimethylcarbamoyloxy, diethylcarbamoyloxy, dipropylcarbamoyloxy, diisopropylcarbamoyloxy, dibutylcarbamoyloxy, dipentylcarbamoyloxy, dihexylcarbamoyloxy, methylethylcarbamoyloxy and methylpropylcarbamoyloxy groups, of which we prefer the dimethylcarbamoyloxy, diethylcarbamoyloxy and dipropylcarbamoyloxy groups.

In the case of substituents C", D", E", F" and G", examples of the groups and atoms which may be included in these are as given in relation to the equivalent groups and atoms of substituents B".

Where $R^{3"}$ represents a carboxy-protecting group, this is preferably a group capable of forming an ester with a carboxylic acid. Examples of ester groups include:

alkyl groups having from 1 to 20 carbon atoms, more preferably from 1 to 6 carbon atoms, such as those exemplified in relation to substituents $R^{4"}$ and higher alkyl groups as are well known in the art, such as the heptyl, octyl, nonyl, decyl, dodecyl, tridecyl, pentadecyl, octadecyl, nonadecyl and icosyl groups, but preferably groups having from 1 to 4 carbon atoms and most preferably the methyl, ethyl and t-butyl groups;

cycloalkyl groups having from 3 to 7 carbon atoms, for example the cyclopropyl, cyclobutyl, cyclopentyl, cyclohexyl and cycloheptyl groups; aralkyl groups, in which the alkyl part has from 1 to 3 carbon atoms and the aryl part is a carbocyclic aromatic group having from 6 to 14 carbon atoms, which may be substituted or unsubstituted and, if substituted, has at least one of substituents H defined and exemplified below, although the unsubstituted groups are preferred; examples of such aralkyl groups include the benzyl, phenethyl, 1-phenylethyl, 3-phenylpropyl, 2-phenylpropyl, 1-naphthylmethyl, 2-naphthylmethyl, 2-(1-naphthyl)ethyl, 2-(2-naphthyl)ethyl, benzhydryl (i.e. diphenylmethyl), triphenylmethyl, bis(o-nitrophenyl) methyl, 9-anthrylmethyl, 2,4,6-trimethylbenzyl, 4-bromobenzyl, 2-nitrobenzyl, 4-nitrobenzyl, 3-nitrobenzyl, 4-methoxybenzyl and piperonyl groups, of which the benzyl, benzhydryl, 4-nitrobenzyl and 2-nitrobenzyl groups are preferred;

alkenyl groups having from 2 to 6 carbon atoms, and halogenated alkenyl groups having from 2 to 6 carbon atoms, such as the the vinyl, allyl, 2-methylallyl, 2-chloroallyl, 1-propenyl, isopropenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl and 5-hexenyl groups, of which the vinyl, allyl, 2-methylallyl, 1-propenyl, isopropenyl and butenyl groups are preferred, the allyl, 2-chloroallyl and 2-methylallyl groups being most preferred.

halogenated alkyl groups having from 1 to 6, preferably from 1 to 4, carbon atoms, in which the alkyl part is as defined and exemplified in relation to the alkyl groups above, and the halogen atom is chlorine, fluorine, bromine or iodine (preferably chlorine or bromine), such as the 2,2,2-trichloroethyl, 2-haloethyl (e.g. 2-chloroethyl, 2-fluoroethyl, 2-bromoethyl or 2-iodoethyl), 2,2-dibromoethyl and 2,2,2-tribromoethyl groups, preferably the 2,2,2-trichloroethyl, 2,2-dibromoethyl and 2,2,2-tribromoethyl groups;

substituted silylalkyl groups, in which the alkyl part is as defined and exemplified above, and the silyl group has up to 3 substituents selected from alkyl groups having from 1 to 6 carbon atoms and phenyl groups which are unsubstituted or have at least one substituent selected from substituents H defined and exemplified below, for example a 2-trimethylsilylethyl group;

phenyl groups, in which the phenyl group is unsubstituted or substituted, preferably with at least one alkyl group having from 1 to 4 carbon atoms or acylamino group, for example the phenyl, tolyl and benzamidophenyl groups;

phenacyl groups, which may be unsubstituted or have at least one of substituents H defined and exemplified below, for example the phenacyl group itself or the p-bromophenacyl group;

cyclic and acyclic terpenyl groups, for example the geranyl, neryl, linalyl, phytyl, menthyl (especially m- and p-menthyl), thujyl, caryl, pinanyl, bornyl, notcaryl, norpinanyl, norbornyl, menthenyl, camphenyl and norbornenyl groups;

alkoxymethyl groups, in which the alkoxy part has from 1 to 6, preferably from 1 to 4, carbon atoms and may itself be substituted by a single unsubstituted alkoxy group, such as the methoxymethyl, ethoxymethyl, propoxymethyl, isopropoxymethyl, butoxymethyl and methoxyethoxymethyl groups;

aliphatic acyloxyalkyl groups, in which the acyl group is preferably an alkanoyl group and is more preferably an alkanoyl group having from 2 to 6 carbon atoms, and the alkyl part has from 1 to 6, and preferably from 1 to 4, carbon atoms such as the acetoxymethyl, propionyloxymethyl, butyryloxymethyl, 1-isobutyryloxymethyl, pivaloyloxymethyl, 1-pivaloyloxyethyl, 1-acetoxyethyl, 1-isobutyryloxyethyl, 1-pivaloyloxypropyl, 2-methyl-1-pivaloyloxypropyl, 2-pivaloyloxypropyl, 1-isobutyryloxyethyl, 1-isobutyryloxypropyl, 1-acetoxypropyl, 1-acetoxy-2-methylpropyl, 1-propionyloxyethyl, 1-propionyloxypropyl, 2-acetoxypropyl and 1-butyryloxyethyl groups, preferably a pivaloyloxymethyl, isobutyryloxymethyl, 1-isobutyryloxyethyl, acetoxymethyl or 1-acetoxyethyl group;

cycloalkyl-substituted aliphatic acyloxyalkyl groups, in which the acyl group is preferably an alkanoyl group and is more preferably an alkanoyl group having from 2 to 6 carbon atoms, the cycloalkyl substituent has from 3 to 7 carbon atoms, and the alkyl part has from 1 to 6, preferably from 1 to 4, carbon atoms, such as the (cyclohexylacetoxy) methyl, 1-(cyclohexylacetoxy)ethyl, 1-(cyclohexylacetoxy) propyl, 2-methyl-1-(cyclohexylacetoxy)propyl, (cyclopentylacetoxy)methyl, 1-(cyclopentylacetoxy)ethyl, 1-(cyclopentylacetoxy)propyl and 2-methyl-1-(cyclopentylacetoxy)propyl, groups;

alkoxycarbonyloxyalkyl groups, especially 1-(alkoxycarbonyloxy)ethyl groups, in which the alkoxy part has from 1 to 10, preferably from 1 to 6, and more preferably from 1 to 4, carbon atoms, and the alkyl part has from 1 to 6, preferably from 1 to 4, carbon atoms, such as the t-butoxycarbonyloxyethyl, 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-sec-butoxycarbonyloxyethyl, 1-t-butoxycarbonyloxyethyl, 1-(1-ethylpropoxycarbonyloxy)ethyl and 1-(1,1-dipropylbutoxycarbonyloxy)ethyl groups, and other alkoxycarbonylalkyl groups, in which both the alkoxy and alkyl groups have from 1 to 6, preferably from 1 to 4, carbon atoms, such as the 2-methyl-1-(isopropoxycarbonyloxy) propyl, 2-1isopropoxycarbonyloxy)propyl, isopropoxycarbonyloxymethyl, t-butoxycarbonyloxymethyl, methoxycarbonyloxymethyl and ethoxycarbonyloxymethyl groups; of these, the t-butoxycarbonyloxyethyl, 1-methoxycarbonyloxyethyl, 1-ethoxycarbonyloxyethyl, 1-isopropoxycarbonyloxyethyl and 1-t-butoxycarbonyloxyethyl groups are preferred;

cycloalkylcarbonyloxyalkyl and cycloalkyloxycarbonyloxyalkyl groups, in which the cycloalkyl group has from 3 to 10, preferably from 3 to 7, carbon atoms, is mono- or poly- cyclic and is optionally substituted by at least one (and preferably only one) alkyl group having from 1 to 4 carbon atoms (e.g. selected from those alkyl groups exemplified above) and the alkyl part has from 1 to 6, more preferably from 1 to 4, carbon atoms (e.g. selected from those alkyl groups exemplified above) and is most preferably methyl, ethyl or propyl, for example the 1-methylcyclohexylcarbonyloxymethyl, 1-methylcyclohexyloxycarbonyloxymethyl, cyclopentyloxycarbonyloxymethyl, cyclopentylcarbonyloxymethyl, 1-cyclohexyloxycarbonyloxyethyl,
1-cyclohexylcarbonyloxyethyl,
1-cyclopentyloxycarbonyloxyethyl,
1-cyclopentylcarbonyloxyethyl,
1-cycloheptyloxycarbonyloxyethyl,
1-cycloheptylcarbonyloxyethyl,
1-methylcyclopentylcarbonyloxymethyl,
1-methylcyclopentyloxycarbonyloxymethyl, 2-methyl-1-(1-methylcyclohexylcarbonyloxy)propyl, 1-(1-methylcyclohexylcarbonyloxy)propyl, 2-(1-methylcyclohexylcarbonyloxy)propyl, 1-(cyclohexylcarbonyloxy)propyl, 2-(cyclohexylcarbonyloxy)propyl, 2-methyl-1-(1-methylcyclopentylcarbonyloxy)propyl, 1-(1-methylcyclopentylcarbonyloxy)propyl, 2-(1-methylcyclopentylcarbonyloxy)propyl, 1-(cyclopentylcarbonyloxy)propyl, 2-(cyclopentylcarbonyloxy)propyl, 1-(1-methylcyclopentylcarbonyloxy)ethyl, 1-(1-methylcyclopentylcarbonyloxy)propyl, adamantyloxycarbonyloxymethyl, adamantylcarbonyloxymethyl, 1-adamantyloxycarbonyloxyethyl and 1-adamantylcarbonyloxyethyl groups, preferably the 1-cyclohexylcarbonyloxyethyl or 1-cyclopentylcarbonyloxyethyl group;

cycloalkylalkoxycarbonyloxyalkyl groups in which the alkoxy group has a single cycloalkyl substituent, the cycloalkyl substituent having from 3 to 10, preferably from 3 to 7, carbon atoms and mono- or poly- cyclic, for example the cyclopropylmethoxycarbonyloxymethyl, cyclobutylmethoxycarbonyloxymethyl, cyclopentylmethoxycarbonyloxymethyl, cyclohexylmethoxycarbonyloxymethyl, 1-(cyclopropylmethoxycarbonyloxy)ethyl, 1-(cyclobutylmethoxycarbonyloxy)ethyl, 1-(cyclopentylmethoxycarbonyloxy)ethyl and 1-(cyclohexylmethoxycarbonyloxy)ethyl groups;

terpenylcarbonyloxyalkyl and terpenyloxycarbonyloxy-alkyl groups, in which the terpenyl group is as exemplified above, and is preferably a cyclic terpenyl group, for example the 1-menthyloxycarbonyloxy)ethyl, 1-(menthylcarbonyloxy) ethyl, menthyloxycarbonyloxymethyl, menthylcarbonyloxymethyl, 1-(3-pinanyloxycarbonyloxy) ethyl, 1-(3-pinanylcarbonyloxy)ethyl, 3-pinanyloxycarbonyloxymethyl and 3-pinanylcarbonyloxymethyl groups;

5-alkyl or 5-phenyl [which may be substituted by at least one of substituents C", defined and exemplified above] (2-oxo-1,3-dioxolen- 4-yl)alkyl groups in which each alkyl group (which may be the same or different) has from 1 to 6, preferably from 1 to 4, carbon atoms, for example the (5-methyl-2-oxo-1,3-dioxolen-4-yl)methyl, (5-phenyl-2-oxo-1,3-dioxolen-4-yl)methyl, (5-isopropyl-2-oxo-1,3-dioxolen-4-yl)methyl, (5-t-butyl-2-oxo-1,3-dioxolen-4-yl) methyl and 1-(5-methyl-2-oxo-1,3-dioxolen-4-yl)ethyl groups; and other groups, especially groups which are easily removed in vivo such as the phthalidyl, indanyl 2-oxo-4,5,6,7-tetrahydro-1,3-benzodioxolen-4-yl groups.

Of the above groups, especially preferred are groups which can be removed easily in vivo, and most preferably the aliphatic acyloxyalkyl groups (especially the pivaloyloxymethyl group), alkoxycarbonyloxyalkyl groups (especially the 1-isopropoxycarbonyloxyethyl group); cycloalkylcarbonyloxyalkyl groups (especially the 1-methylcyclohexylcarbonyloxymethyl and 1-cyclohexylcarbonyloxyethyl groups), phthalidyl groups and (5-substituted 2-oxo-1,3-dioxolen-4-yl)methyl groups [especially the (5-methyl-2-oxo-1,3-dioxolen-4-yl)methyl] group].

In general, in the compounds of the present invention, $R^{1'''}$ may represent a hydrogen atom or a methyl group, preferably a methyl group.

The compounds of the present invention can also form salts with bases. Examples of such salts include: salts with an alkali metal, such as sodium, potassium or lithium; salts with an alkaline earth metal, such as barium or calcium; salts with another metal, such as magnesium or aluminum; organic base salts, such as a salt with triethylamine, diisopropylamine, cyclohexylamine or dicyclohexylamine; and salts with a basic amino acid, such as lysine or arginine. Also, where the compound of the present invention contains a basic group in its molecule, it can form acid addition salts. Examples of such acid addition salts include: salts with mineral acids, especially hydrohalic acids (such as hydrofluoric acid, hydrobromic acid, hydroiodic acid or hydrochloric acid), nitric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid; and salts with amino acids, such as glutamic acid or aspartic acid.

For formula (I), preferred groups and atoms which may be represented by $R^1$ include: the hydrogen atom; alkyl groups having from 1 to 3 carbon atoms (such as the methyl, ethyl and propyl groups); substituted alkyl groups having from 1 to 3 carbon atoms, in which the substituent is selected from the group consisting of substituents (a'), defined below; alkenyl groups having 3 or 4 carbon atoms (such as the allyl group); alkynyl groups having 3 or 4 carbon atoms (such as the propargyl group); and the formimidoyl and acetimidoyl groups.

Substituents (a') are selected from the group consisting of hydroxy groups, carboxy groups, carbamoyl groups, carbamoyloxy groups, cyano groups, halogen atoms (such as fluorine atoms), alkoxy groups having from 1 to 3 carbon atoms (such as methoxy groups or ethoxy groups), amino groups, and mono- and di- alkylamino groups in which the or each alkyl group has from 1 to 3 carbon atoms (such as methylamino groups or dimethylamino groups).

In the compounds of formula (I) and (Ia) and pharmaceutically acceptable salts and esters thereof, where A represents a group of formula (A1), we prefer that n should be 2 or 3.

Also, in this case, $R^2$ preferably represents:

a hydrogen atom;

an alkyl group having from 1 to 3 carbon atoms, such as a methyl, ethyl or propyl group;

a substituted alkyl group having from 1 to 3 carbon atoms, in which the substituent is selected from the group consisting of substituents (b'), defined below, such as a substituted methyl, ethyl or propyl group;

an alkenyl group having 3 or 4 carbon atoms (such as the allyl group);

an alkynyl group having 3 or 4 carbon atoms (such as the propargyl group); or a group of formula —C(=NH)R$^6$, where R$^6$ represents a hydrogen atom, an unsubstituted alkyl group having from 1 to 3 carbon atoms, such as a methyl or ethyl group, a substituted alkyl group which has from 1 to 3 carbon atoms and which is substituted by at least one substituent selected from the group consisting of halogen atoms, alkoxy groups having from 1 to 3 carbon atoms and cycloalkyl groups having from 3 to 6 carbon atoms, such as a chloromethyl group, a methoxymethyl group or a cyclopropylmethyl group, or cycloalkyl group having from 3 to 6 ring carbon atoms, such as a cyclopropyl group.

Substituents (b'), as mentioned above, include:

hydroxy groups;
carboxy groups;
carbamoyl groups;
carbamoyloxy groups;
cyano groups;
sulfamoyl groups;
ureido groups;
sulfo groups;
alkoxy groups having from 1 to 3 carbon atoms, such as the methoxy group;
alkoxycarbonyl groups having from 2 to 4 carbon atoms, such as the methoxycarbonyl group; alkanoyl groups having from 2 to 4 carbon atoms, such as the acetyl group;
alkanoylamino groups having from 2 to 4 carbon atoms, such as the acetamido group;
alkanoyloxy groups having from 2 to 4 carbon atoms, such as the acetoxy group;
amino groups;
mono- and di- alkylamino groups in which the or each alkyl group has from 1 to 3 carbon atoms, such as the methylamino and dimethylamino groups;
alkylthio groups having from 1 to 3 carbon atoms, such as the methylthio group;
alkylsulfinyl groups having from 1 to 3 carbon atoms, such as the methylsulfinyl group;
alkylsulfonyl groups having from 1 to 3 carbon atoms, such as the methylsulfonyl group;
mono- and di- alkylcarbamoyl groups in which the or each alkyl group has from 1 to 3 carbon atoms, such as the methylcarbamoyl and dimethylcarbamoyl groups; and
mono- and di- alkylcarbamoyloxy groups in which the or each alkyl group has from 1 to 3 carbon atoms, such as the methylcarbamoyloxy and dimethylcarbamoyloxy groups.

In addition, where A represents a group of formula (A1), $R^3$ and $R^4$, which may be the same or different from each other, each represents a hydrogen atom, an alkyl group having from 1 to 3 carbon atoms (such as a methyl or ethyl group), a hydroxy group, a carboxy group, a carbamoyl group or a substituted alkyl group which has from 1 to 3 carbon atoms and which is substituted by at least one substituent selected from the group consisting of hydroxy groups, alkoxy groups having from 1 to 3 carbon atoms, amino groups, carbamoyl groups and halogen atoms (such as the hydroxymethyl, methoxymethyl, aminomethyl, carbamoylmethyl and fluoromethyl groups).

More preferred compounds of formula (I) and (Ia) and pharmaceutically acceptable salts and esters thereof, in which A represents a group of formula (A1) are those in which:

n is 2;

$R^1$ represents a hydrogen atom, a methyl group, a fluoromethyl group, a formimidoyl group or an acetimidoyl group;

$R^2$ represents a hydrogen atom, a 2-hydroxyethyl group, a 2-carbamoylethyl group, a carboxymethyl group, a carbamoylmethyl group, a 2-fluoroethyl group, a formimidoyl group or an acetimidoyl group; and $R^3$ and $R^4$ are the same or different and each represents a hydrogen atom, a methyl group, a carbamoyl group, a cyano group, a carboxy group, a hydroxymethyl group, a fluoromethyl group or an aminomethyl group.

An alternative preferred class of compounds of formula (I) and (Ia) and pharmaceutically acceptable salts and esters thereof, in which A represents a group of formula (A1) are those in which:

n is 3;

$R^1$ represents a hydrogen atom, a methyl group, a fluoromethyl group, a formimidoyl group or an acetimidoyl group;

$R^2$ represents a hydrogen atom, a methyl group, a formimidoyl group, an acetimidoyl group, a carboxymethyl group, a carbamoylmethyl group, a 2-hydroxyethyl group or a 2-fluoroethyl group; and $R^3$ and $R^4$ are the same or different and each represents a hydrogen atom, a methyl group, a hydroxy group, an amino group, a cyano group, a carboxy group, a carbamoyl group, a carbamoyloxy group, a hydroxymethyl group, a fluoromethyl group or an aminomethyl group.

A most preferred class of compounds of formula and (Ia) and pharmaceutically acceptable salts, and esters thereof, in which A represents a group of formula (A1) are those in which:

n is 2;

$R^1$ represents a hydrogen atom, a methyl group, a formimidoyl group or an acetimidoyl group;

$R^2$ represents a hydrogen atom, a 2-hydroxyethyl group, a carboxymethyl group, a formimidoyl group or an acetimidoyl group;

$R^3$ represents a hydrogen atom; and $R^4$ represents a methyl group, a carbamoyl group, a cyano group, a hydroxymethyl group, a fluoromethyl group or an aminomethyl group.

An alternative most preferred class of compounds of formula (I) and (Ia) and pharmaceutically acceptable salts and esters thereof, in which A represents a group of formula (A1), are those in which:

n is 3;

$R^1$ represents a hydrogen atom, a methyl group, a formimidoyl group or an acetimidoyl group;

$R^2$ represents a formimidoyl group, an acetimidoyl group, a carboxymethyl group, a 2-hydroxyethyl group or a 2-fluoroethyl group; and $R^3$ and $R^4$ are the same or different and each represents a hydrogen atom, a hydroxy group, an amino group or a cyano group.

Where A in the compound of formula (I) or,(Ia) and pharmaceutically acceptable salts and esters thereof represents a group of formula (A2), d is 0 or 1. and m is 0, 1 or 2. In this case, it is preferred that $R^7$ should represent:

a hydrogen atom;

a carboxy group;

a carbamoyl group;

an alkyl group having from 1 to 3 carbon atoms, such as a methyl, ethyl or propyl group; or a substituted alkyl group having from 1 to 3 carbon atoms, in which the substituent is selected from the group consisting of hydroxy groups, alkoxy groups having from 1 to 3 carbon atoms (such as the methoxy or ethoxy groups), carbamoyl groups, carboxy groups and cyano groups, such as a substituted methyl, ethyl or propyl group.

Where A represents a group of formula (A2), it is preferred that $R^8$ should represent:

a hydrogen atom;

an alkyl group having from 1 to 3 carbon atoms, such as a methyl, ethyl or propyl group;

a substituted alkyl group having from 1 to 3 carbon atoms, such as a substituted methyl, ethyl or propyl group, in which the substituent is selected from the group consisting of hydroxy groups, alkoxy groups having from 1 to 3 carbon atoms (such as the methoxy or ethoxy groups), carbamoyl groups, carbamoyloxy groups, carboxy groups, cyano groups, amino groups and halogen atoms (such as the fluorine and chlorine atoms);

an alkenyl group having 3 or 4 carbon atoms (such as the allyl group); or an alkynyl group having 3 or 4 carbon atoms (such as the propargyl group).

In such a case, $R^9$ preferably represents:

a hydrogen atom;

an alkyl group having from 1 to 3 carbon atoms, such as a methyl, ethyl or propyl group;

a substituted alkyl group having from 1 to 3 carbon atoms, such as a substituted methyl, ethyl or propyl group, in which the substituent is selected from the group consisting of hydroxy groups, alkoxy groups having from 1 to 3 carbon atoms (such as the methoxy or ethoxy groups), carbamoyl groups, carbamoyloxy groups, carboxy groups, cyano groups, amino groups and halogen atoms (such as the fluorine and chlorine atoms); or a group of formula —C(=NH)$R^{10}$ in which $R^{10}$ represents:

a hydrogen atom;

an alkyl group having from 1 to 3 carbon atoms, such as a methyl, ethyl or propyl group;

a substituted alkyl group having from 1 to 3 carbon atoms, such as a substituted methyl, ethyl or propyl group, in which the substituent is selected from the group consisting of alkoxy groups having from 1 to 3 carbon atoms (such as the methoxy or ethoxy groups) and halogen atoms (such as the fluorine and chlorine atoms);

a cycloalkyl group having from 3 to 6 carbon atoms, such as a cyclopropyl group or a cyclobutyl group; or an alkyl group having from 1 to 3 carbon atoms, such as a methyl or ethyl group, which is substituted by a single cycloalkyl group having from 3 to 6 carbon atoms, such as a cyclopropylmethyl group, a cyclopropylethyl group or a cyclobutylmethyl group.

Alternatively, $R^8$ and $R^9$ my together represent a group of formula —(CH$_2$)$_s$—W—(CH$_2$)$_t$—, wherein W represents a carbon—carbon single bond, an oxygen atom, a sulfur atom or a group of formula >N$R^{22}$, wherein $R^{22}$ represents a hydrogen atom or an alkyl group having from 1 to 3 carbon atoms (such as a methyl or ethyl group), s is 1, 2 or 3 and t is 2.

In particular, a preferred class of compounds of the formula (I) in which A represents a group of formula (A2), are those compounds of formula (I) or (Ia), and pharmaceutically acceptable salts and esters thereof, in which:

d is 0 or 1;

m is 0, 1 or 2;

$R^1$ represents a hydrogen atom, a methyl group, a fluoromethyl group, a formimidoyl group or an acetimidoyl group;

$R^7$ represents a hydrogen atom, an alkyl group having from 1 to 3 carbon atoms (such as a methyl group or an ethyl group), a hydroxy group, an amino group, a cyano group, a halogen atom (such as a fluorine atom or a chlorine atom), a carboxy group, a carbamoyl group or a hydroxymethyl group;

$R^8$ represents a hydrogen atom, an alkyl group having from 1 to 3 carbon atoms (such as a methyl group or an ethyl group), a fluoromethyl group, a carbamoylmethyl group, a carboxymethyl group, an alkenyl group having 3 or 4 carbon atoms (such as an allyl group), an alkynyl group having 3 or 4 carbon atoms (such as a propargyl group), a 2-haloethyl group (such as a 2-fluoroethyl group), a 2-hydroxyethyl group, a 2-alkoxyethyl group, in which the alkoxy part has from 1 to 3 carbon atoms (such as a 2-methoxyethyl group) or a 2-aminoethyl group;

$R^9$ represents a hydrogen atom, an alkyl group having from 1 to 3 carbon atoms (such as a methyl group or an ethyl group), a fluoromethyl group, a carbamoylmethyl group, a carboxymethyl group, a formimidoyl group, an acetimidoyl group, a 2-haloethyl group (such as a 2-fluoroethyl group), a 2-hydroxyethyl group, a 2-alkoxyethyl group, in which the alkoxy part has from to 3 carbon atoms (such as a 2-methoxyethyl group) or a 2-aminoethyl group;

or $R^8$ and $R^9$ together represent a group of formula (CH$_2$)$_4$—, (CH$_2$)$_5$—, (CH$_2$)$_2$O(CH$_2$)$_2$—, (CH$_2$)$_2$S(CH$_2$)$_2$—, (CH$_2$)$_2$NH(CH$_2$)$_2$— or (CH$_2$)$_2$NCH$_3$(CH$_2$)$_2$—.

The most preferred class of compounds of the formula (I) and formula (Ia) in which A represents a group of formula (A2), are those compounds of formula (I) and (Ia) and pharmaceutically acceptable salts and esters thereof, in which:

d is 0;

m is 1 or 2;

$R^1$ represents a hydrogen atom, a methyl group, a fluoromethyl group, a formimidoyl group or an acetimidoyl group;

$R^7$ represents a hydrogen atom;

$R^8$ represents a hydrogen atom, an alkyl group having from 1 to 3 carbon atoms (such as a methyl group or an ethyl group), a carbamoylmethyl group, a carboxymethyl group, a 2-fluoroethyl group or a 2-hydroxyethyl group; and $R^9$ represents a hydrogen atom, an alkyl group having from 1 to 3 carbon atoms (such as a methyl group or an ethyl group), a formimidoyl group, an acetimidoyl group or a 2-fluoroethyl group.

In the case of those compounds of the present invention in which A represents a group of formula (A3), is 0, 1 or 2. $R^7$ preferably represents a hydrogen atom or an alkyl group having from 1 to 3 carbon atoms, such as a methyl, ethyl or propyl group.

$R^{11}$ preferably represents a hydrogen atom or an alkyl group having from 1 to 3 carbon atoms, such as a methyl, ethyl or propyl group.

$R^{12}$ also preferably represents:

a hydrogen atom;

an alkyl group having from 1 to 3 carbon atoms, such as a methyl, ethyl or propyl group;

a substituted alkyl group having from 1 to 3 carbon atoms, such as a substituted methyl, ethyl or propyl group, in which the substituent is selected from the group consisting of hydroxy groups, alkoxy groups having from 1 to 3 carbon atoms (such as the methoxy or ethoxy groups), carbamoyl groups, carbamoyloxy groups, carboxy groups, cyano groups, amino groups and halogen atoms (such as the fluorine and chlorine atoms);

an alkenyl group having 3 or 4 carbon atoms (such as the allyl group);

an alkynyl group having 3 or 4 carbon atoms (such as the propargyl group) or;

a group of formula —C(=NH)$R^{13}$ in which $R^{13}$ represents:

a hydrogen atom;

an alkyl group having from 1 to 3 carbon atoms, such as a methyl, ethyl or propyl group;

a substituted alkyl group having from 1 to 3 carbon atoms, such as a substituted methyl, ethyl or propyl group, in which the substituent is selected from the group consisting of alkoxy groups having from 1 to 3 carbon atoms (such as the methoxy or ethoxy groups) and halogen atoms (such as the fluorine and chlorine atoms); a cycloalkyl group having from 3 to 6 carbon atoms, such as a cyclopropyl group or a cyclobutyl group; or an alkyl group having from 1 to 3 carbon atoms, such as a methyl or ethyl group, which is substituted by a single cycloalkyl group having from 3 to 6 carbon atoms, such as a cyclopropylmethyl group, a cyclopropylethyl group or a cyclobutylmethyl group.

In particular, a preferred class of compounds of the formula (I) and formula (Ia) in which A represents a group of formula (A3) are those compounds of formula (I) or (Ia), and pharmaceutically acceptable salts and esters thereof, in which:

e is 0, 1 or 2;

$R^1$ represents a hydrogen atom, a methyl group, a fluoromethyl group, a formimidoyl group or an acetimidoyl group;

$R^7$ represents a hydrogen atom;

$R^{11}$ represents a hydrogen atom or an alkyl group having from 1 to 3 carbon atoms, such as a methyl group or an ethyl group; and $R^{12}$ represents a hydrogen atom, an alkyl group having from 1 to 3 carbon atoms (such as a methyl group or an ethyl group), a fluoromethyl group, a carbamoylmethyl group, a carboxymethyl group, an alkenyl group having 3 or 4 carbon atoms (such as the allyl group), an alkynyl group having 3 or 4 carbon atoms (such as the propargyl group), a formimidoyl group, an acetimidoyl group, a 2-haloethyl group (such as a 2-fluoroethyl group), a 2-hydroxyethyl group, a 2-alkoxyethyl group, in which the alkoxy part has from 1 to 3 carbon atoms (such as a 2-methoxyethyl group) or a 2-aminoethyl group.

The most preferred class of compounds of the present invention in which A represents a group of formula (A3) are those compounds of formula (I) and (Ia) and pharmaceutically acceptable salts and esters thereof, in which:

l is 1 or 2;

$R^1$ represents a hydrogen atom, a methyl group, a fluoromethyl group, a formimidoyl group or an acetimidoyl group;

$R^7$ represents a hydrogen atom;

$R^{11}$ represents a hydrogen atom or a methyl group; and $R^{12}$ represents a hydrogen atom, an alkyl group having from 1 to 3 carbon atoms (such as a methyl group or an ethyl group), a fluoromethyl group, a carbamoylmethyl group, a carboxymethyl group, a formimidoyl group, an acetimidoyl group, a 2-fluoroethyl group or a 2-hydroxyethyl group.

In the case of those compounds of the present invention in which A represents a group of formula (A4), i is 1 or 2. $R^{14}$ and $R^{15}$ which may be the same or different, preferably each represents a hydrogen atom or an alkyl group having from 1 to 3 carbon atoms, such as a methyl, ethyl or propyl group.

Additionally, it is preferred that $R^{16}$ should represent:

a hydrogen atom;

an alkyl group having from 1 to 3 carbon atoms, such as a methyl, ethyl or propyl group;

a substituted alkyl group having from 1 to 3 carbon atoms, such as a substituted methyl, ethyl or propyl group, in which the substituent is selected from the group consisting of alkoxy groups having from 1 to 3 carbon atoms (such as the methoxy or ethoxy, groups) and halogen atoms (such as the fluorine and chlorine atoms);

a cycloalkyl group having from 3 to 6 carbon atoms, such as a cyclopropyl group or a cyclobutyl group; or an alkyl group having from 1 to 3 carbon atoms, such as a methyl or ethyl group, which is substituted by a single cycloalkyl group having from 3 to 6 carbon atoms, such as a cyclopropylmethyl group, a cyclopropylethyl group or a cyclobutylmethyl group.

In particular, a preferred class of compounds of formula (I) and formula (Ia) in which A represents a group of formula (A4) are those compounds of formula (I) or (Ia), in which:

i is 1 or 2; and $R^1$, $R^{14}$, $R^{15}$ and $R^{16}$ are independently selected from the group consisting of hydrogen atoms and alkyl groups having from 1 to 3 carbon atoms (such as the methyl group or the ethyl group, especially the methyl group).

The most preferred class of compounds of the formula (I) and formula (Ia) in which A represents a group of formula (A4) are those compounds of formula (I) and (Ia) and pharmaceutically acceptable salts and esters thereof, in which:

i is 1; and $R^1$, $R^{14}$, $R^{15}$ and $R^{16}$ are independently selected from the group consisting of hydrogen atoms and methyl groups.

In the case of those compounds of the present invention in which A represents a group of formula (A5), p is 1, 2 or 3, preferably 2. $R^{17}$ and $R^{18}$ which may be the same or different, preferably each represents:

a hydrogen atom;

an alkyl group having from 1 to 3 carbon atoms, such as a methyl, ethyl or propyl group;

a substituted alkyl group having from 1 to 3 carbon atoms, such as a substituted methyl, ethyl or propyl group, in which the substituent is selected from the group consisting of hydroxy groups, alkoxy groups having from 1 to 3 carbon atoms (such as the methoxy or ethoxy groups) and halogen atoms (such as the fluorine and chlorine atoms).

Alternatively, $R^{17}$ and $R^{18}$ may together preferably represent a group of formula —$(CH_2)_q$—Y—$(CH_2)_r$—, wherein Y represents a carbon—carbon single bond, an oxygen atom or a group of formula $>NR^{23}$, wherein $R^{23}$ represents a hydrogen atom or an alkyl group having from 1 to 3 carbon atoms (such as a methyl or ethyl group), and q and r are each 2 or 3.

In particular, a preferred class of compounds of the formula (I) and formula (Ia) in which A represents a group of formula (A5) are those compounds of formula (I) or (Ia), and pharmaceutically acceptable salts and esters thereof, in which:

p is 2;

$R^1$ represents a hydrogen atom, a methyl group, a fluoromethyl group, a formimidoyl group or an, acetimidoyl group;

$R^{17}$ and $R^{18}$ are the same or different and each represents a hydrogen atom, an alkyl group having from 1 to 3 carbon atoms (such as a methyl group or an ethyl group), a 2-haloethyl group (such as a 2-fluoroethyl group) or a 2-hydroxyethyl group;

or $R^{17}$ and $R^{18}$ together represent a group of formula

—$(CH_2)_4$—,

—$(CH_2)_5$—,

—$(CH_2)_2O(CH_2)_2$—,

—$(CH_2)_2S(CH_2)_2$—,

—$(CH_2)_2NH(CH_2)_2$— or

—$(CH_2)_2NCH_3(CH_2)_2$—,

The most preferred class of compounds of the formula (I) and formula (Ia) in which A represents a group of formula (A5) are those compounds of formula (I) and (Ia) and pharmaceutically acceptable salts and esters thereof, in which:

p is 2;

$R^1$ represents a hydrogen atom, a methyl group, a fluoromethyl group, a formimidoyl group or an acetimidoyl group; and $R^{17}$ and $R^{18}$ are the same or different and each represents a hydrogen atom or a methyl group.

In the case of those compounds of the formula (I) in which A represents a group of formula (A6), J and k are independently 1 or 2, and preferably each is 2.

$R^{19}$ preferably represents a hydrogen atom or an alkyl group having from 1 to 3 carbon atoms (such as a methyl group or an ethyl group).

In particular, a preferred class of compounds of the formula (I) and formula (Ia) in which A represents a group of formula (A6) are those compounds of formula (I) or (Ia), and pharmaceutically acceptable salts and esters hereof, in which:

j and k are both 2;

$R^1$ represents a hydrogen atom, a methyl group, a fluoromethyl group, a formimidoyl group or an acetimidoyl group; and $R^{19}$ preferably represents a hydrogen atom or an alkyl group having from 1 to 3 carbon atoms (such as a methyl group or an ethyl group).

The most preferred class of compounds of the formula (I) and formula (Ia) in which A represents a group of formula (A6) are those compounds of formula (I) and (Ia) and pharmaceutically acceptable salts and esters thereof, in which:

j and k are both 2; and $R^1$ and $R^{19}$ are independently selected from the group consisting of hydrogen atoms and methyl groups.

In the case of those compounds of the present invention in which A represents a group of formula (A7), g is 0, 1 or 2, and preferably 1 or 2.

In these compounds, Z preferably represents a 1-imidazolyl group, a 1,2,4-triazol-1-yl group or a 1,2,3-triazol-1-yl group.

In particular, a preferred class of compounds of the formula (I) and formula (Ia) in which A represents a group of formula (A7) are those compounds of formula (I) or (Ia), and pharmaceutically acceptable salts and esters thereof, in which:

S is 0, 1 or 2;

$R^1$ represents a hydrogen atom or a methyl group; and

Z represents a 1-imidazolyl group, a 1,2,4-triazol-1-yl group or a 1,2,3-triazol-1-yl group.

The most preferred class of compounds of the formula (I) and formula (Ia) in which A represents a group of formula (A7) are those compounds of formula (I) and (Ia) and pharmaceutically acceptable sails and esters thereof, in which:

g is, 1 or 2;

$R^1$ represents a hydrogen atom or a methyl group; and

Z represents a 1-imidazolyl group, a 1,2,4-triazol-1-yl group or a 1,2,3-triazol-1-yl group.

In the case of those compounds of the present invention in which A represents a group of formula (AS), e and f are independently 1 or 2, and preferably each is 1.

$R^{20}$ and $R^{21}$ which may be the same or different preferably each represents a hydrogen atom or an alkyl group having from 1 to 3 carbon atoms, such as a methyl, ethyl or propyl group.

In particular, a preferred class of compounds of the formula (I) and formula (Ia) in which A represents a group of formula (A8) are those compounds of formula (I) or (Ia). and pharmaceutically acceptable salts and esters thereof, in which:

e and f are both 1;

$R^1$ represents a hydrogen atom, a methyl group, a fluoromethyl group, a formimidoyl group or an acetimidoyl group; and $R^{20}$ and $R^{21}$ which may be the same or different, each represents a hydrogen atom or an alkyl group having from 1 to 3 carbon atoms, such as a methyl, ethyl or propyl group.

The most preferred class of compounds of the formula (I) in which A represents a group of formula (AS). are those compounds of formula (I) and (Ia) and pharmaceutically acceptable salts and esters thereof, in which:

e and f are both 1;

$R^1$ represents a hydrogen atom or a methyl group;

$R^{20}$ represents a hydrogen atom; and $R^{21}$ represents a hydrogen atom or a methyl group.

In the case of all of the compounds of the formula (I) and formula (Ia), including the preferred compounds and most preferred compounds, referred to above, those compounds in which $R^5$ represents a hydrogen atom are preferred, that is to say compounds of formula (I).

A preferred class of compounds of the formula (I)", including pharmaceutically acceptable salts and esters thereof, are those in which:

$R^{1"}$ represents a hydrogen atom or a methyl group;

$R^{2"}$ represents a hydrogen atom, an unsubstituted alkyl group having from 1 to 3 carbon atoms, a substituted alkyl group which has from 1 to 3 carbon atoms and which is substituted by at least one substituent selected from the group consisting of substituents $A^{1"}$, defined below, an alkenyl group having 3 or 4 carbon atoms, an alkynyl group having 3 or 4 carbon atoms, or, provided that Q" does not contain a quaternary nitrogen atom, a group of formula —C(=NH)R⁰", where $R^{0"}$ represents a hydrogen atom or an alkyl group having from 1 to 3 carbon atoms;

$R^{3"}$ represents a hydrogen atom or a negative ion; and

Q" represents a group of formula (Q-I)", (Q-II)", (Q-III)", (Q-IV)", (Q-V)", (Q-VI)", (Q-VII)", (Q-VIII)", (Q-IX)", (Q-X)", (Q-XI)", (Q-XII)" and (Q-XIII)", defined above, wherein:

$R^{4"}$ represents a hydrogen atom, an unsubstituted alkyl group having from 1 to 3 carbon atoms, or a substituted alkyl group which has from 1 to 3 carbon atoms and which is substituted by at least one substituent selected from the group consisting of substituents $B^{1"}$, defined below;

$R^{5"}$ and $R^{6"}$ are independently selected from the group consisting of unsubstituted alkyl groups having from 1 to 3 carbon atoms, and substituted alkyl, groups which have from 1 to 3 carbon atoms and which are substituted by at least one substituent selected from the group consisting of substituents $B^{1"}$, defined below:

or $R^{4"}$ and $R^{5"}$ together represent a group of formula —(CH$_2$)$_m"$—, where m" is 2 or 3;

$R^{7"}$, $R^{8"}$ and $R^{8'"}$ are independently selected from the group consisting of unsubstituted alkyl groups having from 1 to 3 carbon atoms, and substituted alkyl groups which have from 1 to 3 carbon atoms and which are substituted by at least one substituent selected from the group consisting of substituents $B^{1"}$, defined below;

or $R^{10"}$ represents a hydrogen atom, a carbamoyl group, an unsubstituted alkyl group having from 1 to 3 carbon atoms, or a substituted alkyl group which has from 1 to 3 carbon atoms and which is substituted by at least one substituent selected from the group consisting of substituents $B^{1"}$, defined below;

or $R^{7"}$ and $R^{8"}$ together represent a group of formula —(CH$_2$)$_p"$(w")$_w"$—(CH$_2$)$_q"$, where p" is 0, 1, 2 or 3 q" is 0, 1, 2 or 3, w" represents an oxygen or sulfur atom and w" is 0 or 1, provided that (p"+q"+w")is an integer from 2 to 6;

or $R^{7"}$ and $R^{10"}$ together represent a group of formula —(CH$_2$)$_p'"$—(w'")—(CH$_2$)$_q'"$, where p'" is 0, 1, 2 or 3, q'" is 0, 1, 2 or 3, w'" represents an oxygen or sulfur atom and w'" is 0 or 1;

n" is 0 or 1;

Z" represents a group of formula (Z-I)", (Z-II)", (Z-III)", (Z-IV)", (Z-V)", (Z-VI)", (Z-VII)" or (Z-VIII)", defined above, wherein:

$R^{11"}$ and $R^{12"}$ are independently selected from the group consisting of unsubstituted alkyl groups having from 1 to 3 carbon atoms, and substituted alkyl groups which have from 1 to 3 carbon atoms and which are substituted by at least one substituent selected from the group consisting of substituents $B^{1"}$, defined below; and $R^{13"}$, $R^{14"}$ and $R^{15"}$ are independently selected from the group consisting of carbamoyl groups, unsubstituted alkyl groups having from 1 to 3 carbon atoms, and substituted alkyl groups which have from 1 to 3 carbon atoms and which are substituted by at least one substituent selected from the group consisting of substituents $B^1$, defined below;

m¹" is 0 or 1 and n¹" is 0, 1 or 2, provided that (m¹"+n¹") is greater than 0;

$R^{16"}$ represents an unsubstituted alkyl group having from 1 to 3 carbon atoms, or a substituted alkyl group which has from 1 to 3 carbon atoms and which is substituted by at least one substituent selected from the group consisting of substituents $B^{1"}$, defined below;

$R^{18"}$ represents an unsubstituted alkyl group having from 1 to 3 carbon atoms, or a substituted alkyl group which has from 1 to 3 carbon atoms and which is substituted by at least one substituent selected from the group consisting of substituents $B^{1"}$, defined below;

X" represents a sulfur atom or a group of formula >NR¹⁷", where $R^{17"}$ represents an unsubstituted alkyl group having from 1 to 3 carbon atoms or a substituted alkyl group which has from 1 to 3 carbon atoms and which is substituted by at least one substituent selected from the group consisting of carbamoyl groups and hydroxy groups;

n²" is 1 or 2;

$R^{19"}$ represents an unsubstituted alkyl group having from 1 to 3 carbon atoms or a substituted alkyl group which has from 1 to 3 carbon atoms and which is substituted by at least one substituent selected from the group consisting of carbamoyl groups and hydroxy groups;

Y" represents a group of formula

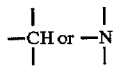

$R^{20"}$, $R^{21"}$ and $R^{22"}$ are independently selected from the group consisting of hydrogen atoms and unsubstituted alkyl groups having from 1 to 3 carbon atoms;

or $R^{20"}$ and $R^{21"}$ or $R^{20"}$ and $R^{22"}$ together represent a group of formula —(CH$_2$)$_s"$—(W)$_w'"$—(CH$_2$)$_t"$, where s" is 1 or 2, w" is 1 or 2, w" represents an oxygen or sulfur atom and w'" is 0 or 1, provided that (s"+w"+t) is 2, 3 or 4;

$R^{23"}$ and $R^{24"}$ are independently selected from the group consisting of hydrogen atoms, halogen atoms, unsubstituted alkyl groups having from 1 to 3 carbon atoms, substituted alkyl groups which have from 1 to 3 carbon atoms and which are substituted by at least one substituent selected from the group consisting of substituents $C^{1"}$ defined below, hydroxy groups, carboxy groups, carbamoyl groups, amino groups, cyano groups and carbamoyloxy groups;

n³" is 1, 2 or 3;

$R^{25"}$ represents a hydrogen atom, an unsubstituted alkyl group having from 1 to 3 carbon atoms, a substituted alkyl group which has from 1 to 3 carbon atoms and which is substituted by at least one substituent selected from the group consisting of substituents $C^{1"}$, defined below, an alkenyl group having 3 or 4 carbon atoms, or an alkynyl group having 3 or 4 carbon atoms;

$R^{26"}$ represents a hydrogen atom, a halogen atom, an unsubstituted alkyl group having from 1 to 3 carbon atoms, a substituted alkyl group which has from 1 to 3 carbon atoms and which is substituted by at least one substituent selected from the group consisting of substituents $C^{1"}$, defined below, a hydroxy group, a carboxy group, a carbamoyl group, an amino group, a cyano group or a carbamoyloxy group;

n⁴" is 0, 1 or 2;

p²" is 0 or 1;

$R^{27"}$ represents a hydrogen atom or an unsubstituted alkyl group having from 1 to 3 carbon atoms;

$R^{28"}$ and $R^{29"}$ are independently selected from the group consisting of hydrogen atoms, unsubstituted alkyl groups having from 1 to 3 carbon atoms, and substituted alkyl groups which have from 1 to 3 carbon atoms and which are substituted by at least one substituent selected from the group consisting of substituents $C^{1''}$, defined below;

$p^{3''}$ is 1 or 2;

$R^{30''}$ represents a hydrogen atom, an unsubstituted alkyl group having from 1 to 3 carbon atoms, a substituted alkyl group which has from 1 to 3 carbon atoms and which is substituted by at least one substituent selected from the group consisting of substituents $D^{1''}$, defined below, an alkenyl group having 3 or 4 carbon atoms, an alkynyl group having 3 or 4 carbon atoms, or a group of formula —C(=NH)$R^{33''}$, where $R^{33''}$ represents a hydrogen atom, an unsubstituted alkyl group having from 1 to 3 carbon atoms, a substituted alkyl group which has from 1 to 3 carbon atoms and which is substituted by at least one substituent selected from the group consisting of halogen atoms and alkoxy groups having from 1 to 3 carbon atoms, a cycloalkyl group having from 3 to 6 ring carbon atoms or a cycloalkylalkyl group in which the cycloalkyl part has from 3 to 6 ring carbon atoms and the alkyl part has 1 or 2 carbon atoms;

$R^{31''}$ represents a hydrogen atom, an unsubstituted alkyl group having from 1 to 3 carbon atoms, a substituted alkyl group which has from 1 to 3 carbon atoms and which is substituted by at least one substituents selected from the group consisting of substituents $F^{1''}$, defined below, an alkenyl group having 3 or 4 carbon atoms, or an alkynyl group having 3 or 4 carbon atoms;

$R^{32''}$ represents a hydrogen atom, a halogen atom or an unsubstituted alkyl group having from 1 to 3 carbon atoms;

$R^{34''}$ represents a hydrogen atom or an unsubstituted alkyl group having from 1 to 3 carbon atoms;

$R^{35''}$ represents a hydrogen atom, an unsubstituted alkyl group having from 1 to 3 carbon atoms, a substituted alkyl group which has from 1 to 3 carbon atoms and which is substituted by at least one substituent selected from the group consisting of substituents $G^{1''}$, defined below, an alkenyl group having 3 or 4 carbon atoms, an alkynyl group having 3 or 4 carbon atoms, or a group of formula —C(=NH)$R^{33''}$, where $R^{33''}$ is as defined above; and $U''$ represents an imidazolyl group, a triazolyl group or a tetrazolyl group;

substituents $A^{1''}$ are selected from the group consisting of hydroxy groups, carboxy groups, carbamoyl groups, carbamoyloxy groups, cyano groups, halogen atoms and amino groups;

substituents $B^{1''}$ are selected from the group consisting of cyano groups, hydroxy groups, carboxy groups, halogen atoms, alkoxy groups having from 1 to 3 carbon atoms, alkylthio groups having from 1 to 3 carbon atoms, alkylsulfinyl groups having from 1 to 3 carbon atoms, alkylsulfonyl groups having from 1 to 3 carbon atoms, alkanoylamino groups having from 1 to 5 carbon atoms, alkanoyloxy groups having from 1 to 5 carbon atoms, alkanoyl groups having from 1 to 5 carbon atoms, alkoxycarbonyl groups having from 2 to 5 carbon atoms, ureido groups, carbamoyl groups, alkylcarbamoyl groups having from 2 to 5 carbon atoms, dialkylcarbamoyl groups in which each alkyl part has from 1 to 3 carbon atoms, carbamoyloxy groups, alkylcarbamoyloxy groups having from 2 to 5 carbon atoms, dialkylcarbamoyloxy groups in which each alkyl part has from 1 to 4 carbon atoms, amino groups, alkylamino groups having from 1 to 4 carbon atoms, dialkylamino groups in which each alkyl part has from 1 to 4 carbon atoms, oxygen atoms (to form an oxo group) and cycloalkyl groups having from 3 to 6 ring carbon atoms;

substituents $C^{1''}$ are selected from the group consisting of hydroxy groups, carboxy groups, carbamoyl groups, halogen atoms and amino groups;

substituents $D^{1''}$ are selected from the group consisting of hydroxy groups, carboxy groups, carbamoyl groups, carbamoyloxy groups, cyano groups, ureido groups, alkoxy groups having from 1 to 3 carbon atoms, alkoxycarbonyl groups having from 2 to 5 carbon atoms, alkanoyl groups having from 1 to 5 carbon atoms, alkanoylamino groups having from 1 to 5 carbon atoms, alkanoyloxy groups having from 1 to 5 carbon atoms, halogen atoms, amino groups, alkylamino groups having from 1 to 3 carbon atoms, dialkylamino groups in which each alkyl part has from 1 to 3 carbon atoms, alkylcarbamoyl groups having from 2 to 5 carbon atoms, dialkylcarbamoyl groups in which each alkyl part has from 1 to 3 carbon atoms, alkylcarbamoyloxy groups having from 2 to 5 carbon atoms and dialkylcarbamoyloxy groups in which each alkyl part has from 1 to 3 carbon atoms;

substituents $F^{1''}$ are selected from the group consisting of hydroxy groups, carboxy groups, carbamoyl groups, halogen atoms, alkoxy groups having from 1 to 3 carbon atoms and amino groups: and substituents $G^{1''}$ are selected from the group consisting of hydroxy groups, carboxy groups, carbamoyl groups, carbamoyloxy groups, halogen atoms, alkoxy groups having from 1 to 3 carbon atoms and amino groups.

A more preferred class of compounds are those compound of formula (I)" and pharmaceutically acceptable salts and esters thereof, in which:

$R^{1''}$ represents a hydrogen atom or a methyl group;

$R^{2''}$ represents a hydrogen atom, an unsubstituted alkyl group having from 1 to 3 carbon atoms, a substituted alkyl group which has from 1 to 3 carbon atoms and which is substituted by at least one substituent selected from the group consisting of substituents $A^{2''}$, defined below, or, provided that Q" does not contain a quaternary nitrogen atom, a group of formula —C(=NH)$R^{6''}$, where $R^{0''}$ represents a hydrogen atom or an alkyl group having from 1 to 3 carbon atoms;

$R^{3''}$ represents a hydrogen atom or a negative ion; and

Q" represents a group of formula (Q-I)", (Q-II)", (Q-III)", (Q-IV)", (Q-V)", (Q-VI)", (Q-VII)", (Q-VIII)", (Q-IX)", (Q-X)", (Q-XI)", (Q-XII)" and (Q-XIII)", defined above, wherein:

$R^{4''}$ represents a hydrogen atom, an unsubstituted alkyl group having from 1 to 3 carbon atoms, or a substituted alkyl group which has from 1 to 3 carbon atoms and which is substituted by at least one substituent selected from the group consisting of substituents $B^{2''}$, defined below;

$R^{5''}$ and $R^{6''}$ are independently selected from the group consisting of unsubstituted alkyl groups having from 1 to 3 carbon atoms, and substituted alkyl groups which have from 1 to 3 carbon atoms and which are substituted by at least one substituent selected from the group consisting of substituents B , defined below;

or $R^{4''}$ and $R^{5''}$ together represent a group of formula —(CH$_2$)$_{m''}$, where m" is 2 or 3;

$R^{7''}$, $R^{8''}$ and $R^{9''}$ are independently selected from the group consisting of unsubstituted alkyl groups having from 1 to 3 carbon atoms, and substituted alkyl groups which have from 1 to 3 carbon atoms and which are substituted by at least one substituent selected from the group consisting of substituents $B^{2''}$, defined below;

$R^{10''}$ represents a hydrogen atom, a carbamoyl group, an unsubstituted alkyl group having from 1 to 3 carbon atoms, or a substituted alkyl group which has from 1 to 3 carbon atoms and which is substituted by at least one substituent selected from the group consisting of hydroxy groups, amino groups and halogen atoms;

$R^{7"}$ and $R^{8"}$ together represent a group of formula —$(CH_2)_{p"}$—$(W)_{w"}$—$(CH_2)_{q"}$, where p" is 1 or 2, q" is 1, 2 or 3, w" represents an oxygen or sulfur atom and w" is 0 or 1, provided that (p"+q"+w") is an integer from 4 to 6;

or $R^{7"}$ and $R^{8"}$ together represent a group of formula —$(CH_2)_{p'''}$— where p''' is 1, 2 or 3;

n" is 0 or 1;

Z" represents a group of formula (Z-I)", (Z-II)", (Z-III)", (Z-IV)", (Z-V)", (Z-VI)", (Z-VII)" or (Z-VIII)" defined above, wherein:

$R^{11"}$ and $R^{12"}$ are independently selected from the group consisting of unsubstituted alkyl groups having from 1 to 3 carbon atoms, and substituted alkyl groups which have from 1 to 3 carbon atoms and which are substituted by at least one substituent selected from the group consisting of substituents $B^{2"}$, defined below; and $R^{13"}$, $R^{14"}$ and $R^{15"}$ are independently selected from the group consisting of carbamoyl groups, unsubstituted alkyl groups having from 1 to 3 carbon atoms, and substituted alkyl groups which have from 1 to 3 carbon atoms and which are substituted by at least one substituent selected from the group consisting of substituents $B^{2"}$, defined below;

$m^{1"}$ is 0 or 1 and $n^{1"}$ is 0, 1 or 2, provided that ($m^{1"}+n^{1"}$) is an integer from 1 to 3;

$R^{16"}$ represents an unsubstituted alkyl group having from 1 to 3 carbon atoms, or a substituted alkyl group which has from 1 to 3 carbon atoms and which is substituted by at least one substituent selected from the group consisting of substituents $B^{2"}$, defined below;

$R^{18"}$ represents an unsubstituted alkyl group having from 1 to 3 carbon atoms, or a substituted alkyl group which has from 1 to 3 carbon atoms and which is substituted by at least one substituent selected from the group consisting of substituents $B^{2"}$, defined below;

X" represents a sulfur atom or a group of formula >$N^{17"}$ where $R^{17"}$ represents an unsubstituted alkyl group having from 1 to 3 carbon atoms or a substituted alkyl group which has from 1 to 3 carbon atoms and which is substituted by at least one substituent selected from the group consisting of carbamoyl groups and hydroxy groups;

$n^{2"}$ is 1 or 2;

$R^{19"}$ represents an unsubstituted alkyl group having from 1 to 3 carbon atoms or a substituted alkyl group which has from 1 to 3 carbon atoms and which is substituted by at least one substituent selected from the group consisting of carbamoyl groups and hydroxy groups;

Y" represents a group of formula

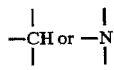

$R^{20"}$, $R^{21"}$ and $R^{22"}$ are independently selected from the group consisting of hydrogen atoms and unsubstituted alkyl groups having from 1 to 3 carbon atoms;

or $R^{20"}$ and $R^{21"}$ or $R^{20"}$ and $R^{22"}$ together represent a group of formula —$(CH_2)_{s"}$—$(w")_{w'''}$—$(CH_2)_{t"}$, where s" is 1 or 2, t" is 1 or 2, w" represents an oxygen or sulfur atom and w''' is 0 or 1, provided that (s"+w'''+t") is 2, 3 or 4;

$R^{23"}$ and $R^{24"}$ are independently selected from the group consisting of hydrogen atoms, halogen atoms, hydroxy groups, carbamoyl groups, carboxy groups, unsubstituted alkyl groups having from 1 to 3 carbon atoms and substituted alkyl groups which have from 1 to 3 carbon atoms and which are substituted by at least one substituent selected from the group consisting of hydroxy groups, amino groups and carbamoyl groups;

$n^{3"}$ is 1, 2 or 3;

$R^{25"}$ represents a hydrogen atom or a methyl group;

$R^{26"}$ represents a hydrogen atom;

$n^{4"}$ is 0, 1 or 2;

$p^{2"}$ is 0 or 1;

$R^{27"}$ represents a hydrogen atom or a methyl group;

$R^{28"}$ and $R^{29"}$ are independently selected from the group consisting of hydrogen atoms and methyl groups;

$p^{3"}$ is 1 or 2;

$R^{30"}$ represents a hydrogen atom, an unsubstituted alkyl group having from 1 to 3 carbon atoms, a substituted alkyl group which has from 1 to 3 carbon atoms and which is substituted by at least one substituent selected from the group consisting of substituents $D^{2"}$, defined below, an alkenyl group having 3 carbon atoms, an alkynyl group having 3 carbon atoms, or a group of formula —C(=NH)$R^{33"}$, where $R^{33"}$ represents a hydrogen atom, a methyl group, a substituted alkyl group which has 1 or 2 carbon atoms and which is substituted by at least one substituent selected from the group consisting of halogen atoms and methoxy groups, a cyclopropyl group or a cyclopropylmethyl group;

$R^{31"}$ represents a hydrogen atom or an unsubstituted alkyl group having from 1 to 3 carbon atoms;

$R^{32"}$ represents a hydrogen atom;

$R^{34"}$ represents a hydrogen atom or a methyl group;

$R^{35"}$ represents a hydrogen atom, an unsubstituted alkyl group having from 1 to 3 carbon atoms, a substituted alkyl group which has from 1 to 3 carbon atoms and which is substituted by at least one substituent selected from the group consisting of substituents $G^{2"}$, defined below, or a group of formula —C(—NH)$R^{33"}$ where $R^{33"}$ is as defined above; and U" represents an imidazolyl group, a triazolyl group or a tetrazolyl group;

substituents $A^{2"}$ are selected from the group consisting of hydroxy groups, carboxy groups, carbamoyl groups, carbamoyloxy groups, halogen atoms and amino groups;

substituents $B^{2"}$ are selected from the group consisting of cyano groups, hydroxy groups, carboxy groups, halogen atoms, alkoxy groups having from 1 to 3 carbon atoms, alkanoylamino groups having from 1 to 5 carbon atoms, alkanoyloxy groups having from 1 to 5 carbon atoms, alkanoyl groups having from 1 to 5 carbon atoms, alkoxycarbonyl groups having from 2 to 5 carbon atoms, ureido groups, carbamoyl groups, alkylcarbamoyl groups having from 2 to 5 carbon atoms, dialkylcarbamoyl groups in which each alkyl part has from 1 to 3 carbon atoms, carbamoyloxy groups, alkylcarbamoyloxy groups having from 2 to 5 carbon atoms, dialkylcarbamoyloxy groups in which each alkyl part has from 1 to 4 carbon atoms, amino groups, alkylamino groups having from 1 to 4 carbon atoms, dialkylamino groups in which each alkyl part has from 1 to 4 carbon atoms and cycloalkyl groups having from 3 to 6 ring carbon atoms;

substituents $D^{2"}$ are selected from the group consisting of hydroxy groups, carboxy groups, carbamoyl groups, carbamoyloxy groups, halogen atoms, amino groups, alkylamino groups having from 1 to 3 carbon atoms and dialkylamino groups in which each alkyl part has from 1 to 3 carbon atoms;

substituents $G^{2"}$ are selected from the group consisting Of hydroxy groups, carboxy groups, carbamoyl groups, carbamoyloxy groups, halogen atoms, methoxy groups and amino groups.

Of these, we still more prefer those in which Q'" represents a group of formula (Q-I)", (Q-II)", (Q-III)", (Q-VII)", (Q-VIII)" and (Q-XI)", more especially a group of formula (Q-II)", (Q-III)", (Q-VII)" and (Q-XI)".

Of all of the compounds of formula (I)", the most preferred are those in which $R^{1''}$ represents a methyl group.

The compounds of the present invention necessarily contain several asymmetric carbon atoms in their molecules, and can thus form optical isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

Of the isomers, especially preferred are those in which the carbon atoms are in the same configurations as those of thienamycin, that is: in the R configuration at position 1, in the (5S, 6S) configuration at positions 5 and 6, and in the E configuration at the hydroxy-substituted α-position of the side chain at position 6.

Specific examples of compounds of the present invention are those compounds of formula (I), in which the various substituent groups are as defined in Tables 1 to 8. In the Tables, the following abbreviations are used:

| | |
|---|---|
| Ac | acetyl |
| Acim | acetimidoyl |
| All | allyl |
| Azp | perhydroazepinyl (= homopiperazinyl) |
| Azt | azetidinyl |
| Car | carbamoyl |
| Et | ethyl |
| Foim | formimidoyl |
| Imaz | imidazolidinyl |
| Imid | imidazolyl |
| Me | methyl |
| Mec | methoxycarbonyl |
| Mor | morpholino |
| Pip | piperidyl |
| Piz | piperazinyl |
| Prg | propargyl (= 2-propynyl) |
| Pyrd | pyrrolidinyl |
| Sam | sulfamoyl |
| Thz | perhydro-1,4-thiazin-4-yl (= thiomorpholino) |
| Ur | ureido |

TABLE 1

| Cpd. No. | $R^1$ | A |
|---|---|---|
| 1-1 | Me | 1-Azp |
| 1-2 | H | 4-(HOOC.CH$_2$)-1-Azp |
| 1-3 | Et | 1-Azp |
| 1-4 | 2-FEt | 1-Azp |
| 1-5 | 2-HOEt | 1-Azp |
| 1-6 | All | 1-Azp |
| 1-7 | H | 4-(2-HOEt)-1-Azp |
| 1-8 | H | 4-(CarCH$_2$)-1-Azp |
| 1-9 | H | 4-(2-CarOEt)-1-Azp |
| 1-10 | H | 4-(3-sulfoPr)-1-Azp |
| 1-11 | H | 4-Acim-1-Azp |
| 1-12 | H | 4-Foim-1-Azp |
| 1-13 | HOOC.CH$_2$— | 1-Azp |
| 1-14 | CarCH$_2$— | 1-Azp |

TABLE 1-continued

| Cpd. No. | $R^1$ | A |
|---|---|---|
| 1-15 | 2-CarOEt | 1-Azp |
| 1-16 | Me | 4-(HOOC.CH$_2$)-1-Azp |
| 1-17 | Me | 4-(CarCH$_2$)-1-Azp |
| 1-18 | Me | 4-(2-CarOEt)-1-Azp |
| 1-19 | Me | 4-Me-1-Azp |
| 1-20 | H | 4-(2-FEt)-1-Azp |
| 1-21 | Me | 4-(2-FEt)-1-Azp |
| 1-22 | Me | 4-(3-sulfoPr)-1-Azp |
| 1-23 | Me | 4-All-1-Azp |
| 1-24 | Me | 4-Et-1-Azp |
| 1-25 | Prg | 1-Azp |
| 1-26 | H | 4-Prg-1-Azp |
| 1-27 | NC.CH$_2$— | 1-Azp |
| 1-28 | H | 4-(NC.CH$_2$)-1-Azp |
| 1-29 | Et | 4-(HOOC.CH$_2$)-1-Azp |
| 1-30 | 2-FEt | 4-(HOOC.CH$_2$)-1-Azp |
| 1-31 | 2-HOEt | 4-(HOOC.CH$_2$)-1-Azp |
| 1-32 | Car.CH$_2$— | 4-(HOOC.CH$_2$)-1-Azp |
| 1-33 | All | 4-(HOOC.CH$_2$)-1-Azp |
| 1-34 | HOOC.CH$_2$— | 4-(HOOC.CH$_2$)-1-Azp |
| 1-35 | H | 4-(SamCH$_2$)-1-Azp |
| 1-36 | 2-NH$_2$Et | 1-Azp |
| 1-37 | 2-NH$_2$Et | 4-(HOOC.CH$_2$)-1-Azp |
| 1-38 | H | 4-(2-NH$_2$Et)-1-Azp |
| 1-39 | H | 4-[2-NH(Me)Et]-1-Azp |
| 1-40 | H | 4-(2-NMe$_2$Et)-1-Azp |
| 1-41 | H | 4-(AcCH$_2$)-1-Azp |
| 1-42 | H | 4-(2-AcOEt)-1-Azp |
| 1-43 | 2-MeOEt | 1-Azp |
| 1-44 | H | 4-(2-MeOEt)-1-Azp |
| 1-45 | 2-NMe$_2$Et | 1-Azp |
| 1-46 | 2-NH(Me)Et | 1-Azp |
| 1-47 | H | 4-(2-UrEt)-1-Azp |
| 1-48 | H | 4-[2-NH(Ac)Et]-1-Azp |
| 1-49 | H | 4-(MecCH$_2$)-1-Azp |
| 1-50 | H | 4-(MeS.CH$_2$)-1-Azp |
| 1-51 | H | 4-(MeSO.CH$_2$)-1-Azp |
| 1-52 | H | 4-(MeSO$_2$.CH$_2$)-1-Azp |
| 1-53 | Me | 4-((MeCar).CH$_2$)-1-Azp |
| 1-54 | Me | 4-[2-(diMeCar)Et]-1-Azp |
| 1-55 | Me | 4-[2-(MeCarO)Et]-1-Azp |
| 1-56 | Me | 4-[2-(diMeCarO)Et]-1-Azp |
| 1-57 | Me | 4-Foim-1-Azp |
| 1-58 | Me | 4-Acim-1-Azp |
| 1-59 | Et | 4-Acim-1-Azp |
| 1-60 | Me | 1-Piz |
| 1-61 | Me | 4-Me-1-Piz |
| 1-62 | H | 4-(HOOC.CH$_2$)-1-Piz |
| 1-63 | H | 4-(CarCH$_2$)-1-Piz |
| 1-64 | H | 4-(2-CarOEt)-1-Piz |
| 1-65 | H | 4-(2-HOEt)-1-Piz |
| 1-66 | H | 3-Me-1-Piz |
| 1-67 | H | 3,5-diMe-1-Piz |
| 1-68 | H | 2,5-diMe-1-Piz |
| 1-69 | Me | 3-Me-1-Piz |
| 1-70 | H | 4-(HOOC.CH$_2$)-3-Me-1-Piz |
| 1-71 | H | 4-(3-sulfoPr)-1-Piz |
| 1-72 | Me | 4-(HOOC.CH$_2$)-1-Piz |
| 1-73 | Me | 3-Me-4-(HOOC.CH$_2$)-1-Piz |
| 1-74 | H | 4-Foim-1-Piz |
| 1-75 | H | 4-Acim-1-Piz |
| 1-76 | Me | 4-Foim-1-Piz |
| 1-77 | Me | 4-Acim-1-Piz |
| 1-78 | H | 3-Me-4-Foim-1-Piz |
| 1-79 | H | 3-Me-4-Acim-1-Piz |
| 1-80 | Me | 3,5-diMe-1-Piz |
| 1-81 | Me | 2,5-diMe-1-Piz |
| 1-82 | Et | 1-Piz |
| 1-83 | Et | 3-Me-1-Piz |
| 1-84 | 2-HOEt | 1-Piz |
| 1-85 | 2-HOEt | 3-Me-1-Piz |
| 1-86 | HOOC.CH$_2$— | 1-Piz |
| 1-87 | HOOC.CH$_2$— | 3-Me-1-Piz |
| 1-88 | CarCH$_2$— | 1-Piz |
| 1-89 | CarCH$_2$— | 3-Me-1-Piz |
| 1-90 | Me | 3-Me-4-Foim-1-Piz |

TABLE 1-continued

| Cpd. No. | R¹ | A |
|---|---|---|
| 1-91 | Me | 3-Me-4-Acim-1-Piz |
| 1-92 | H | 3-CH₂F-1-Piz |
| 1-93 | Me | 3-CH₂F-1-Piz |
| 1-94 | 2-FEt | 1-Piz |
| 1-95 | 2-FEt | 3-Me-1-Piz |
| 1-96 | All | 1-Piz |
| 1-97 | All | 3-Me-1-Piz |
| 1-98 | 2-NH₂Et | 1-Piz |
| 1-99 | 2-NH₂Et | 3-Me-1-Piz |
| 1-100 | H | 4-(2-NH₂Et)-1-Piz |
| 1-101 | Me | 4-(2-NH₂Et)-1-Piz |
| 1-102 | H | 2-Me-1-Piz |
| 1-103 | H | 2-Me-4-Foim-1-Piz |
| 1-104 | H | 2-Me-4-Acim-1-Piz |
| 1-105 | H | 2,5-diMe-4-Foim-1-Piz |
| 1-106 | H | 2,5-diMe-4-Acim-1-Piz |
| 1-107 | H | 3,5-diMe-4-Foim-1-Piz |
| 1-108 | H | 3-Car-1-Piz |
| 1-109 | H | 2-Car-1-Piz |
| 1-110 | H | 3-HOOC-1-Piz |
| 1-111 | H | 3-HOMe-1-Piz |
| 1-112 | H | 3-Car-4-Foim-1-Piz |
| 1-113 | H | 3-Car-4-Acim-1-Piz |
| 1-114 | H | 3-(MeO.CH₂)-4-Foim-1-Piz |
| 1-115 | H | 3-(MeO.CH₂)-4-Acim-1-Piz |
| 1-116 | H | 3-(NH₂.CH₂)-1-Piz |
| 1-117 | H | 3-(CarCH₂)-1-Piz |
| 1-118 | H | 3-(CarCH₂)-4-Foim-1-Piz |
| 1-119 | H | 4-[Et.C(=NH)-]-1-Piz |
| 1-120 | H | 4-[CH₂Cl.C(=NH)-]-1-Piz |
| 1-121 | H | 4-[MeO.CH.C(=NH)-]-1-Piz |
| 1-122 | H | 4-[Et.C(=NH)-]-1-Azp |
| 1-123 | H | 4-[CH₂Cl.C(=NH)-]-1-Azp |
| 1-124 | H | 4-[MeO.CH₂.C(=NH)-]-1-Azp |
| 1-125 | H | 4-[cPr.CH₂.C(=NH)-]-1-Piz |
| 1-126 | H | 4-[cPr.C(αNH)-]-1-Piz |
| 1-127 | H | 4-[cPr.CH₂.C(=NH)-]-1-Azp |
| 1-128 | H | 4-[cPr.C(=NH)-]-1-Azp |
| 1-129 | H | 3-Acim-1-Imaz |
| 1-130 | H | 3-Foim-1-Imaz |
| 1-131 | H | 3,3-diMe-1-Piz |
| 1-132 | H | 6-HO-1-Azp |
| 1-133 | H | 4-Foim-6-HO-1-Azp |
| 1-134 | H | 4-Acim-6-HO-1-Azp |
| 1-135 | H | 3-HOMe-4-Foim-1-Piz |
| 1-136 | H | 3-HOMe-4-Acim-1-Piz |
| 1-137 | H | 4-Acim-6-F-1-Azp |
| 1-138 | H | 4-Foim-6-F-1-Azp |
| 1-139 | H | 6-NH₂-1-Azp |
| 1-140 | H | 3-CH₂F-4-Acim-1-Piz |
| 1-141 | H | 3-CH₂F-4-Foim-1-Piz |
| 1-142 | H | 3-CN-4-Acim-1-Piz |
| 1-143 | H | 3-CN-4-Foim-1-Piz |
| 1-144 | H | 4-Foim-6-CN-1-Azp |
| 1-145 | H | 4-Acim-6-CN-1-Azp |
| 1-146 | H | 4-Foim-6-CarO-1-Azp |
| 1-147 | H | 6-CarO-1-Azp |
| 1-148 | Me | 3-Acim-1-Imaz |
| 1-149 | CH₂F— | 4-Acim-1-Piz |
| 1-150 | CH₂F— | 4-Foim-1-Piz |
| 1-151 | CH₂F— | 4-Acim-1-Azp |
| 1-152 | CH₂F— | 4-Foim-1-Azp |
| 1-153 | CH₂F— | 3-Me-4-Acim-1-Piz |
| 1-154 | CH₂F— | 3-Me-4-Foim-1-Piz |
| 1-155 | CH₂F— | 2-Me-4-Acim-1-Piz |
| 1-156 | CH₂F— | 2-Me-4-Foim-1-Piz |
| 1-157 | CH₂F— | 1-Azp |
| 1-158 | CH₂F— | 6-HO-1-Azp |
| 1-159 | CH₂F— | 1-Imaz |
| 1-160 | CH₂F— | 3-HOMe-1-Piz |
| 1-161 | CH₂F— | 1-Piz |
| 1-162 | CH₂F— | 3-Me-1-Piz |
| 1-163 | CH₂F— | 3,3-diMe-1-Piz |
| 1-164 | CH₂F— | 2-Me-1-Piz |
| 1-165 | CH₂F— | 2,5-diMe-1-Piz |
| 1-166 | Foim | 1-Piz |
| 1-167 | Acim | 1-Piz |
| 1-168 | Foim | 4-Foim-1-Piz |
| 1-169 | Foim | 4-Acim-1-Piz |
| 1-170 | Acim | 4-Foim-1-Piz |
| 1-171 | Acim | 4-Acim-1-Piz |
| 1-172 | Foim | 1-Azp |
| 1-173 | Acim | 1-Azp |
| 1-174 | Foim | 4-Foim-1-Azp |
| 1-175 | Foim | 4-Acim-1-Azp |
| 1-176 | Acim | 4-Foim-1-Azp |
| 1-177 | Acim | 4-Acim-1-Azp |
| 1-178 | Foim | 3-Me-1-Piz |
| 1-179 | Foim | 2-Me-1-Piz |
| 1-180 | Acim | 3-Me-1-Piz |
| 1-181 | Acim | 2-Me-1-Piz |
| 1-182 | Foim | 3-HOMe-1-Piz |
| 1-183 | Acim | 3-HOMe-1-Piz |
| 1-184 | CH₂F— | 3-HOMe-1-Piz |
| 1-185 | H | 2-HOMe-4-Acim-1-Piz |
| 1-186 | H | 2-HOMe-4-Foim-1-Piz |
| 1-187 | Foim | 2-HOMe-4-Foim-1-Piz |
| 1-188 | Me | 2-Me-4-Acim-1-Piz |
| 1-189 | Me | 2-Me-4-Foim-1-Piz |

TABLE 2

| Cpd. No. | R¹ | A |
|---|---|---|
| 2-1 | H | 3-(Acim-NH)-1-Pyrd |
| 2-2 | H | 3-(Foim-NH)-1-Pyrd |
| 2-3 | H | 3-(Acim-NMe)-1-Pyrd |
| 2-4 | H | 3-(Foim-NMe)-1-Pyrd |
| 2-5 | H | 3-NH(Et)-1-Pyrd |
| 2-6 | H | 3-NH(Me)-1-Pyrd |
| 2-7 | H | 3-NEt₂-1-Pyrd |
| 2-8 | H | 3-NH(2-FEt)-1-Pyrd |
| 2-9 | H | 3-NH₂-1-Pyrd |
| 2-10 | H | 3-NMe₂-1-Pyrd |
| 2-11 | H | 3-(1-Pydr)-1-Pyrd |
| 2-12 | H | 3-Mor-1-Pyrd |
| 2-13 | H | 3-Thz-1-Pyrd |
| 2-14 | H | 3-[N(Acim)(2-FEt)]-1-Pyrd |
| 2-15 | H | 3-[N(Foim)(2-FEt)]-1-Pyrd |
| 2-16 | H | 3-[Et-C(=NH)—NH-]-1-Pyrd |
| 2-17 | H | 3-[ClCH₂-C(=NH)—NH-]-1-Pyrd |
| 2-18 | H | 3-[MeO—CH₂—C(=NH)—NH-]-1-Pyrd |
| 2-19 | H | 4-(Acim-NH-)-1-Pip |
| 2-20 | H | 4-(Foim-NH-)-1-Pip |
| 2-21 | H | 4-[Acim-N(Me)-]-1-Pip |
| 2-22 | H | 4-[Foim-N(Me)-]-1-Pip |
| 2-23 | H | 3-(Acim-NH-)-1-Pip |
| 2-24 | H | 3-(Foim-NH-)-1-Pip |
| 2-25 | H | 4-(Acim-NH—CH₂-)-1-Pip |
| 2-26 | H | 4-(Foim-NH—CH₂-)-1-Pip |
| 2-27 | H | 4-(Acim-NMe—CH₂-)-1-Pip |
| 2-28 | H | 4-(Foim-NMe—CH₂-)-1-Pip |
| 2-29 | H | 3-[N(Foim)(2-FEt)]-1-Pyrd |
| 2-30 | H | 3-[N(Foim)(All)]-1-Pyrd |
| 2-31 | H | 3-[N(Foim)(Prg)]-1-Pyrd |
| 2-32 | H | 3-[cPr-CH₂—C(=NH)—NH-]-1-Pyrd |
| 2-33 | H | 3-[cPr—C(=NH)—NH-]-1-Pyrd |
| 2-34 | H | 4-[cPr—CH₂—C(=NH)—NH-]-1-Pip |
| 2-35 | H | 4-[cPr—C(=NH)—NH-]-1-Pip |
| 2-36 | H | 4-[MeO—CH₂—C(=NH)—NH-]-1-Pip |
| 2-37 | Me | 3-NH₂-1-Pyrd |
| 2-38 | Me | 3-(Acim-NH-)-1-Pyrd |
| 2-39 | Me | 3-(Foim-NH-)-1-Pyrd |
| 2-40 | H | 3-[(CarCH₂)(Acim)N-]-1-Pyrd |
| 2-41 | H | 3-[(CarCH₂)(Foim)N-]-1-Pyrd |
| 2-42 | H | 3-[(2-FEt)(Acim)N-]-1-Pyrd |
| 2-43 | H | 3-[(2-FEt)(Foim)N-]-1-Pyrd |
| 2-44 | H | 3-[(2-HOEt)(Acim)N-]-1-Pyrd |

TABLE 2-continued

| Cpd. No. | R¹ | A |
|---|---|---|
| 2-45 | H | 3-[(2-HOEt)(Foim)N-]-1-Pyrd |
| 2-46 | H | 3-(1-Piz)-1-Pyrd |
| 2-47 | H | 3-(4-Me-1-Piz)-1-Pyrd |
| 2-48 | H | 4-[(2-FEt)(Acim)N-]-1-Pip |
| 2-49 | H | 4-[(2-FEt)(Foim)N-]-1-Pip |
| 2-50 | H | 4-[(CarCH₂)(Foim)N-]-1-Pip |
| 2-51 | H | 4-[(2-HOEt)(Foim)N-]-1-Pip |
| 2-52 | H | 3-[(2-FEt)(Foim)N-]-1-Pip |
| 2-53 | H | 3-[(2-HOEt)(Foim)N-]-1-Pip |
| 2-54 | H | 3-[(CarCH₂)(Foim)N-]-1-Pip |
| 2-55 | H | 3-NH₂-1-Azt |
| 2-56 | H | 3-(Foim-NH-)-Azt |
| 2-57 | H | 3-(Acim-NH-)-Azt |
| 2-58 | H | 3-(NH₂—CH₂)-1-Pyrd |
| 2-59 | H | 3-[(Acim-NH-)CH₂]-1-Pyrd |
| 2-60 | H | 3-[(Foim-NH—)CH₂]-1-Pyrd |
| 2-61 | H | 3-(NH₂—CH₂)-1-Azt |
| 2-62 | H | 3-[(Acim-NH-)CH₂]-1-Azt |
| 2-63 | H | 3-[(Foim-NH-)CH₂]-1-Azt |
| 2-64 | Me | 3-NH₂-1-Azt |
| 2-65 | Me | 3-(Acim-NH-)-1-Azt |
| 2-66 | Me | 3-(Foim-NH-)-1-Azt |
| 2-67 | Me | 4-(Acim-NH-)-1-Pip |
| 2-68 | Me | 4-(Foim-NH-)-1-Pip |
| 2-69 | Me | 3-(Acim-NH-)-1-Pip |
| 2-70 | Me | 3-(Foim-NH-)-1-Pip |
| 2-71 | H | 3-NH₂-4-HO-1-Pyrd |
| 2-72 | Me | 3-NH₂-4-HO-1-Pyrd |
| 2-73 | H | 3-(Acim-NH-)-4-HO-1-Pyrd |
| 2-74 | H | 3-(Foim-NH-)-4-HO-1-Pyrd |
| 2-75 | H | 4-NH₂-3-HO-1-Pip |
| 2-76 | H | 3-NH₂-4-HO-1-Pip |
| 2-77 | H | 4-(Acim-NH-)-3-HO-1-Pip |
| 2-78 | H | 4-(Foim-NH-)-3-HO-1-Pip |
| 2-79 | H | 3-(Acim-NH-)-4-HO-1-Pip |
| 2-80 | H | 4-(Acim-NH-)-2-Car-1-Pyrd |
| 2-81 | H | 4-(Acim-NH-)-2-HOMe-1-Pyrd |
| 2-82 | H | 4-(Acim-NH-)-2-Me-1-Pyrd |
| 2-83 | H | 4-(Acim-NH-)-2-CH₂F-1-Pyrd |
| 2-84 | H | 4-(Acim-NH-)-2-CN-1-Pyrd |
| 2-85 | H | 4-(Acim-NH-)-2-CH₂CN-1-Pyrd |
| 2-86 | H | 3-CarO-4-NMe₂-1-Pyrd |
| 2-87 | CH₂F— | 3-NH₂-1-Pyrd |
| 2-88 | CH₂F— | 3-NH₂-4-HO-1-Pyrd |
| 2-89 | CH₂F— | 3-(Acim-NH-)-1-Pyrd |
| 2-90 | CH₂F— | 3-(Foim-NH-)-1-Pyrd |
| 2-91 | CH₂F— | 3-(Acim-NH-)-1-Azt |
| 2-92 | CH₂F— | 3-(Foim-NH-)-1-Azt |
| 2-93 | CH₂F— | 3-NH₂-1-Azt |
| 2-94 | CH₂F— | 4-NH₂-1-Pip |
| 2-95 | CH₂F— | 3-NH₂-1-Pip |
| 2-96 | CH₂F— | 3-NH₂-4-HO-1-Pip |
| 2-97 | CH₂F— | 4-NH₂-3-HO-1-Pip |
| 2-98 | CH₂F— | 3-NH(Me)-1-Pyrd |
| 2-99 | Foim | 3-NH₂-1-Pyrd |
| 2-100 | Acim | 3-NH₂-1-Pyrd |
| 2-101 | Foim | 3-(Foim-NH-)-1-Pyrd |
| 2-102 | Foim | 3-(Acim-NH-)-1-Pyrd |
| 2-103 | Acim | 3-(Foim-NH-)-1-Pyrd |
| 2-104 | Acim | 3-(Acim-NH-)-1-Pyrd |
| 2-105 | Foim | 3-NH₂-1-Azt |
| 2-106 | Acim | 3-NH₂-1-Azt |
| 2-107 | Foim | 3-(Foim-NH-)-1-Azt |
| 2-108 | Foim | 3-(Acim-NH-)-1-Azt |
| 2-109 | Acim | 3-(Foim-NH-)-1-Azt |
| 2-110 | Acim | 3-(Acim-NH-)-1-Azt |
| 2-111 | Foim | 3-NH(Me)-1-Azt |
| 2-112 | Acim | 3-NH(Me)-1-Azt |
| 2-113 | Foim | 3-(Foim-NMe)-1-Pyrd |
| 2-114 | Foim | 3-(Acim-NMe)-1-Pyrd |
| 2-115 | Acim | 3-(Foim-NMe)-1-Pyrd |
| 2-116 | Acim | 3-(Acim-NMe)-1-Pyrd |
| 2-117 | Foim | 4-(Acim-NH)-1-Pip |
| 2-118 | Foim | 4-(Foim-NH)-1-Pip |
| 2-119 | Acim | 4-(Acim-NH)-1-Pip |
| 2-120 | Acim | 4-(Foim-NH)-1-Pip |
| 2-121 | CH₂F— | 4-(Acim-NH)-1-Pip |
| 2-122 | CH₂F— | 4-(Foim-NH)-1-Pip |
| 2-123 | Foim | 4-NH₂-1-Pip |
| 2-124 | Acim | 4-NH₂-1-Pip |
| 2-125 | Foim | 3-NH₂-1-Pip |
| 2-126 | Acim | 3-NH₂-1-Pip |
| 2-127 | Foim | 3-(Acim-NH)-1-Pip |
| 2-128 | Acim | 3-(Acim-NH)-1-Pip |
| 2-129 | Foim | 3-(Foim-NH)-1-Pip |
| 2-130 | Acim | 3-(Foim-NH)-1-Pip |

TABLE 3

| Cpd. No. | R¹ | A |
|---|---|---|
| 3-1 | H | —N(3-Pyrd)Me |
| 3-2 | H | —NH(1-Foim-3-Pyrd) |
| 3-3 | H | —NH(1-Acim-3-Pyrd) |
| 3-4 | H | —N(1-Foim-3-Pyrd)Me |
| 3-5 | H | —N(1-Acim-3-Pyrd)Me |
| 3-6 | H | —NH(3-Pyrd) |
| 3-7 | H | —NH(1-Acim-4-Pip) |
| 3-8 | H | —NH(1-Foim-4-Pip) |
| 3-9 | H | —N(1-Acim-4-Pip)Me |
| 3-10 | H | —N(1-Foim-4-Pip)Me |
| 3-11 | H | —NH(1-Acim-3-Pip) |
| 3-12 | H | —NH(1-Foim-3-Pip) |
| 3-13 | H | —N(1-Acim-3-Pip)Me |
| 3-14 | H | —N(1-Foim-3-Pip)Me |
| 3-15 | H | —NH(1-Me-3-Pyrd) |
| 3-16 | H | —NH[1-(2-FEt)-3-Pyrd] |
| 3-17 | H | —NH[1-(2-HoEt)-3-Pyrd] |
| 3-18 | H | —NH[1-(Car.CH₂)-3-Pyrd] |
| 3-19 | H | —NH{1-[cPr.C(=NH)-]-3-Pyrd} |
| 3-20 | H | —NH{1-[cPr.CH₂.C(=NH)-]-3-Pyrd} |
| 3-21 | H | —NH{1-[MeO.CH₂.C(=NH)-]-3-Pyrd} |
| 3-22 | H | —NH(1-All-3-Pyrd) |
| 3-23 | H | —NH(1-Prg-3-Pyrd) |
| 3-24 | Me | —NH(3-Pyrd) |
| 3-25 | Me | —NH(1-Foim-3-Pyrd) |
| 3-26 | Me | —NH(1-Acim-3-Pyrd) |
| 3-27 | H | —NH(3-Azt) |
| 3-28 | H | —NH(1-Foim-3-Azt) |
| 3-29 | H | —(1-Acim-3-Azt) |
| 3-30 | Me | —NH(3-Azt) |
| 3-31 | Me | —NH(1-Acim-3-Azt) |
| 3-32 | Me | —NH(1-Foim-3-Azt) |
| 3-33 | Me | —NH(1-Acim-4-Pip) |
| 3-34 | Me | —NH(1-Foim-4-Pip) |
| 3-35 | CH₂F— | —NH(3-Pyrd) |
| 3-36 | CH₂F— | —NH(3-Azt) |
| 3-37 | Foim | —NH(3-Pyrd) |
| 3-38 | Acim | —NH(3-Pyrd) |
| 3-39 | Foim | —NH(1-Foim-3-Pyrd) |
| 3-40 | Foim | —NH(1-Acim-3-Pyrd) |
| 3-41 | Acim | —NH(i-Foim-3-Pyrd) |
| 3-42 | Acim | —NH(1-Acim-3-Pyrd) |
| 3-43 | Foim | —NH(3-Azt) |
| 3-44 | Acim | —NH(3-Azt) |
| 3-45 | Foim | —NH(1-Foim-3-Azt) |
| 3-46 | Acim | —NH(1-Foim-3-Azt) |
| 3-47 | Acim | —NH(1-Acim-3-Azt) |
| 3-48 | Foim | —NH(1-Acim-3-Azt) |

TABLE 4

| Cpd. No. | R¹ | A |
|---|---|---|
| 4-1 | H | —NH—CH₂CH₂—NH—CH=NH |
| 4-2 | H | —NH—CH₂CH₂—NH—C(=NH)-Me |
| 4-3 | H | —NH—CH₂CH₂—NMe—CH=NH |
| 4-4 | H | —NH—CH₂CH₂—NMe—C(=NH)-Me |
| 4-5 | H | —NMe—CH₂CH₂—NMe—CH=NH |
| 4-6 | H | —NMe—CH₂CH₂—NMe—C(=NH)-Me |
| 4-7 | Me | —NH—CH₂CH₂—NH—CH=NH |
| 4-8 | Me | —NH—CH₂CH₂—NH—C(=NH)-Me |

TABLE 5

| Cpd. No. | R¹ | A |
|---|---|---|
| 5-1 | H | (piperazine with NMe₂ substituent) |
| 5-2 | H | (piperazine with NHMe substituent) |
| 5-3 | H | (piperazine with pyrrolidine substituent) |
| 5-4 | H | (piperazine with morpholine substituent) |
| 5-5 | H | (piperazine with NH-CH₂CH₂F substituent) |
| 5-6 | H | (imidazoline with NMe, NMe₂) |
| 5-7 | H | (diazepane with NMe₂) |
| 5-8 | H | (piperazine with NH₂) |
| 5-9 | Me | (piperazine with NH₂) |
| 5-10 | Me | (piperazine with NMe₂) |
| 5-11 | Me | (piperazine with NHMe) |
| 5-12 | Me | (piperazine with piperazine NH) |
| 5-13 | CH₂F | (piperazine with NMe₂) |
| 5-14 | CH₂F | (piperazine with NHMe) |
| 5-15 | Foim | (piperazine with NMe₂) |
| 5-16 | Foim | (piperazine with NH₂) |
| 5-17 | Acim | (piperazine with NMe₂) |
| 5-18 | Acim | (piperazine with NH₂) |

TABLE 5-continued

| Cpd. No. | R¹ | A |
|---|---|---|
| 5-19 | Foim | (ring: -N-CH₂-CH₂-N=C(NHMe)-CH₂-, 6-membered with NHMe substituent) |
| 5-20 | Acim | (ring: -N-CH₂-CH₂-N=C(NHMe)-CH₂-, 6-membered with NHMe substituent) |

TABLE 6

| Cpd. No. | R¹ | A |
|---|---|---|
| 6-1 | H | 7-membered ring -N-(CH₂)₂-N=CH-(CH₂)₂- with NH |
| 6-2 | H | 7-membered ring with NH, CH₃ substituent on C=N |
| 6-3 | Me | 7-membered ring with NH |
| 6-4 | Me | 7-membered ring with NH, CH₃ |
| 6-5 | CH₂F | 7-membered ring with NH |
| 6-6 | CH₂F | 7-membered ring with NH, CH₃ |
| 6-7 | Foim | 7-membered ring with NH |
| 6-8 | Acim | 8-membered ring with NH, CH₃ |
| 6-9 | Foim | 8-membered ring with NH |
| 6-10 | Acim | 8-membered ring with NH, CH₃ |

TABLE 7

| Cpd. No. | R¹ | A |
|---|---|---|
| 7-1 | H | 3-(1-Imid)-1-Pyrd |
| 7-2 | H | 3-(1,2,4-triazol-1-yl)-1-Pyrd |
| 7-3 | H | 3-(1,2,3-triazol-1-yl)-1-Pyrd |
| 7-4 | H | 4-(1-Imid)-1-Pip |
| 7-5 | H | 4-(1,2,4-triazol-1-yl)-1-Pip |
| 7-6 | H | 4-(1,2,3-triazol-1-yl)-1-Pip |
| 7-7 | Me | 3-(1-Imid)-1-Pyrd |
| 7-8 | Me | 4-(1-Imid)-1-Pip |
| 7-9 | Me | 4-(1,2,4-triazol-1-yl)-1-Pip |
| 7-10 | Me | 3-(1,2,4-triazol-1-yl)-1-Pyrd |
| 7-11 | H | 3-(1-Imid)-1-Azt |
| 7-12 | H | 3-(1,2,4-triazol-1-yl)-1-Azt |
| 7-13 | H | 3-(1-Imid)-1-Pip |
| 7-14 | H | 3-(1,2,4-triazol-1-yl)-1-Pip |

TABLE 8

| Cpd. No. | R¹ | A |
|---|---|---|
| 8-1 | H | (structure with -NH- linked to ring containing N, CH=N-NH) |
| 8-2 | H | (structure with -NH- linked to ring containing N, C(CH₃)=N-NH) |
| 8-3 | Me | (structure with -NH- linked to ring containing N, CH=N-NH) |

TABLE 8-continued

| Cpd. No. | R¹ | A |
|---|---|---|
| 8-4 | Me | -N(H)-CH(-N=C(CH₃)-NH-) (piperazine-like ring with =N-CH₃) |
| 8-5 | CH₂F | -N(H)-CH(-N=CH-NH-) |
| 8-6 | CH₂F | -N(H)-CH(-N=C(CH₃)-NH-) |
| 8-7 | Foim | -N(H)-CH(-N=CH-NH-) |
| 8-8 | Foim | -N(H)-CH(-N=C(CH₃)-NH-) |
| 8-9 | Acim | -N(H)-CH(-N=CH-NH-) |
| 8-10 | Acim | -N(H)-CH(-N=C(CH₃)-NH-) |

Of the compounds of formula (I) listed above, the following are preferred, that is to say Compounds No. 1-1, 1-2, 1-7, 1-8, 1-11, 1-12, 1-20, 1-57, 1-58, 1-60, 1-62, 1-64, 1-65, 1-66, 1-68, 1-69, 1-74, 1-75, 1-76, 1-77, 1-78, 1-79, 1-82, 1-90, 1-102, 1-103, 1-104, 1-111, 1-132, 1-166, 1-168, 1-172, 2-1, 2-2, 2-3, 2-4, 2-9, 2-10, 2-19, 2-20, 2-23, 2-37, 2-38, 2-39, 2-67, 2-99, 2-102, 3-2, 3-6, 4-1, 4-2, 5-1, 6-1, 7-1, 7-2 and 8-1, and the following are more preferred, that is to say Compounds No. 1-1, 1-2, 1-7, 1-11, 1-12, 1-20, 1-57, 1-60, 1-65, 1-66, 1-74, 1-75, 1-76, 1-77, 1-78, 1-79, 1-102, 1-103, 1-104, 1-111, 1-132, 1-168, 2-1, 2-2, 2-3, 2-4, 2-9, 2-10, 2-19, 2-20, 2-23, 2-37, 2-38, 2-39, 2-67, 2-99, 3-2, 3-6, 4-1, 5-1, 7-1 and 7-2. The most preferred specific compounds of formula (I) are Compounds No.

1-1. 2-[2-(1-Homopiperazinylcarbonyl)-1-methylpyrrolidin-4-ylthio]-6-(1-hydroxyethyl)-1-methyl-1-carbapen-2-em-3-carboxylic acid;

1-2. 2-[2-(4-Carboxymethylhomopiperazin-1-ylcarbonyl) pyrrolidin-4-ylthio]-6-(1-hydroxyethyl)-1-methyl-1-carbapen-2-em-3-carboxylic acid;

1-7. 2-{2-[4-(2-Hydroxyethyl)homopiperazin-1-ylcarbonyl]pyrrolidin-4-ylthio}-6-(1-hydroxyethyl)-1-methyl-1-carbapen-2-em-3-carboxylic acid;

1-11. 2-[2-(4-Acetimidoylhomopiperazin-1-ylcarbonyl) pyrrolidin-4-ylthio]-6-(1-hydroxyethyl)-1-methyl-1-carbapen-2-em-3-carboxylic acid;

1-12. 2-[2-(4-Formimidoylhomopiperazin-1-ylcarbonyl) pyrrolidin-4-ylthio]-6-(1-hydroxyethyl)-1-methyl-1-carbapen-2-em-3-carboxylic acid;

1-57. 2-[2-(4-Formimidoylhomopiperazin-1-ylcarbonyl)-1-methylpyrrolidin-4-ylthio]-6-(1-hydroxyethyl)-1-methyl-1-carbapen-2-em-3-carboxylic acid:

1-60. 2-[1-Methyl-2-(piperazin-1-ylcarbonyl)pyrrolidin-4-ylthio]-6-(1-hydroxyethyl)-1-methyl-1-carbapen-2-em-3-carboxylic acid:

1-65. 2-{2-[4-(2-Hydroxyethyl)piperazin-1-ylcarbonyl] pyrrolidin-4-ylthio}-6-(1-hydroxyethyl)-1-methyl-1-carbapen-2-em-3-carboxylic acid:

1-66. 2-[2-(3-Methylpiperazin-1-ylcarbonyl)pyrrolidin-4-ylthio]-6-(1-hydroxyethyl)-1-methyl-1-carbapen-2-em-3-carboxylic acid:

1-74. 2-[2-(4-Formimidoylpiperazin-1-ylcarbonyl) pyrrolidin-4-ylthio]-6-(1-hydroxyethyl)-1-methyl-1-carbapen-2-em-3-carboxylic acid:

1-75. 2-[2-(4-Acetimidoylpiperazin-1-ylcarbonyl) pyrrolidin-4-ylthio]-6-(1-hydroxyethyl)-1-methyl-1-carbapen-2-em-3-carboxylic acid;

1-76. 2-[2-(4-Formimidoylpiperazin-1-ylcarbonyl)-1-methylpyrrolidin-4-ylthio]-6-(1-hydroxyethyl)-1-methyl-1-carbapen-2-em-3-carboxylic acid:

1-77. 2-[2-(4-Acetimidoylpiperazin-1-ylcarbonyl)-1-methylpyrrolidin-4-ylthio]-6-(1-hydroxyethyl)-1-methyl-1-carbapen-2-em-3-carboxylic acid;

1-78. 2-[2-(4-Formimidoyl-3-methylpiperazin-1-ylcarbonyl)pyrrolidin-4-ylthio]-6-(1-hydroxyethyl)-1-methyl-1-carbapen-2-em-3-carboxylic acid:

1-79. 2-[2-(4-Acetimidoyl-3-methylpiperazin-1-ylcarbonyl)pyrrolidin-4-ylthio]-6-(1-hydroxyethyl)-1-methyl-1-carbapen-2-em-3-carboxylic acid;

1-102. 2-[2-(2-Methylpiperazin-1-ylcarbonyl)pyrrolidin-4-ylthio]-6-(1-hydroxyethyl)-1-methyl-1-carbapen-2-era-3-carboxylic acid;

1-103. 2-[2-(4-Formimidoyl-2-methylpiperazin-1-ylcarbonyl)pyrrolidin-4- ylthio]-6-(1- hydroxyethyl)-1-methyl-1-carbapen-2- em-3-carboxylic acid;

1-104. 2-[2-(4-Acetimidoyl-2-methylpiperazin-1-ylcarbonyl)pyrrolidin-4-ylthio]-6-(1- hydroxyethyl)-1-methyl-1-carbapen-2-em-3-carboxylic acid;

1-111. 2-[2-(3-Hydroxymethylpiperazin-1-ylcarbonyl) pyrrolidin-4-ylthio]-6-(1-hydroxyethyl)-1-methyl-1-carbapen-2-em-3-carboxylic acid;

1-168. 2-[1-Formimidoyl-2-(4-formimidoylpiperazin-1-ylcarbonyl)pyrrolidin-4-ylthio]-6-(1-hydroxyethyl methyl-1-carbapen-2-em-3-carboxylic acid 2-1. 2-[2-(3-Acetimidoylaminopyrrolidin-1-ylcarbonyl) pyrrolidin-4-ylthio]-6-(1-hydroxyethyl)-1-methyl-1-carbapen-2-em-3-carboxylic acid;

2-2. 2-[2-(3-Formimidoylaminopyrrolidin-1-ylcarbonyl) pyrrolidin-4-ylthio]-6-(1-hydroxyethyl)-1-methyl-1-carbapen-2-em-3-carboxylic acid;

2-9. 2-[2-(3-Aminopyrrolidin-1-ylcarbonyl)pyrrolidin-4-ylthio]-6-(1-hydroxyethyl)-1-methyl-1-carbapen-2-em-3-carboxylic acid;

2-19. 2-[2-(4-Acetimidoylaminopiperidin-1-ylcarbonyl) pyrrolidin-4-ylthio]-6-(1-hydroxyethyl)-1-methyl-1-carbapen-2-em-3-carboxylic acid;

2-37. 2-[2-(3-Aminopyrrolidin-1-ylcarbonyl)-1-methylpyrrolidin-4-ylthio]-6-(1-hydroxyethyl)-1-methyl-1-carbapen-2-em-3-carboxylic acid;

2-38. 2-[2-(3-Acetimidoylaminopyrrolidin-1-ylcarbonyl)-1-methylpyrrolidin-4-ylthio]-6-(1-hydroxyethyl)-1-methyl-1-carbapen-2-em-3-carboxylic acid;

2-39. 2-[2-(3-Formimidoylaminopyrrolidin-1-ylcarbonyl)-1-methylpyrrolidin-4-ylthio]-6-(1-hydroxyethyl)-1-methyl-1-carbapen-2-em-3-carboxylic acid;

2-67. 2-[2-(4-Acetimidoylaminopiperidin-1-ylcarbonyl)-1-methylpyrrolidin-4-ylthio]-6-(1-hydroxyethyl)-1-methyl-1-carbapen-2-em-3-carboxylic acid:

3-2. 2-[2-(1-Formimidoylpyrrolidin-3-ylcarbamoyl)pyrrolidin-4-ylthio]-6-(1-hydroxyethyl)-1-methyl-1-carbapen-2-em-3-carboxylic acid;

5-1. 2-[2-(3-Dimethylamino-1,2,5,6-tetrahydropyrazin-1-ylcarbonyl)pyrrolidin-4-ylthio]-6-(1-hydroxyethyl)-1-methyl-1-carbapen-2-em-3-carboxylic acid.

Specific examples of the compounds of formula (I)" are shown in the following formulae (I-1)" and (I-2)". In these formulae, Q" is as defined in Tables 1 to 21; Tables 9 to 14 relate to formula (I-1)", and Tables 15 to 21 relate to formula (I-2)". In each of the examples given in Tables 9 to 14, each of R and $R^{1"}$ and $R^{2"}$ can be a hydrogen atom or a methyl group, i.e. each of the options shown represents 4 possibilities, that is:

(a) $R^{1"}$=hydrogen, $R^{2"}$=hydrogen;
(b) $R^{1"}$=methyl, $R^{2"}$=hydrogen;
(c) $R^{1"}$=hydrogen, $R^{2"}$=methyl;
(d) $R^{1"}$=methyl, $R^{2"}$=methyl.

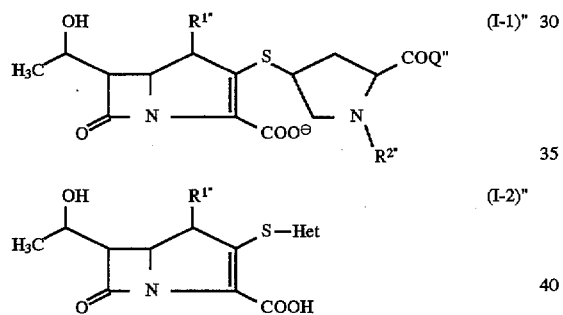

TABLE 9

| Compound No. | Q" |
|---|---|
| 1-1" | |
| 1-2" | |
| 1-3" | |
| 1-4" | |
| 1-5" | |
| 1-6" | |
| 1-7" | |
| 1-8" | |
| 1-9" | |
| 1-10" | |
| 1-11" | |

TABLE 9-continued
| Compound No. | Q" |
|---|---|
| 1-12" | 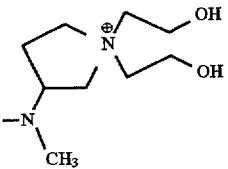 |
| 1-13" | 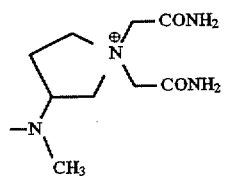 |
| 1-14" | 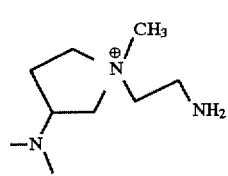 |
| 1-15" | 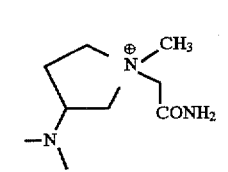 |
| 1-16" | 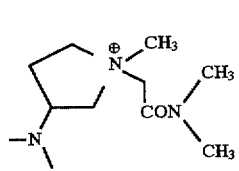 |
| 1-17" | 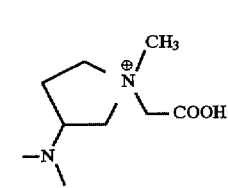 |
| 1-18" | 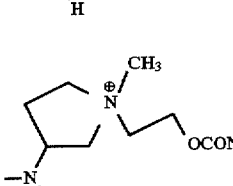 |
| 1-19" | 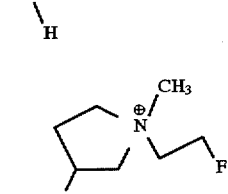 |
| 1-20" | 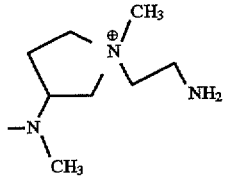 |
| 1-21" | 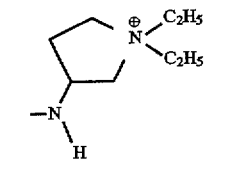 |
| 1-22" | 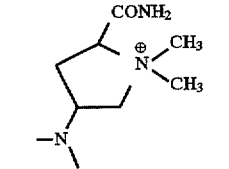 |
| 1-23" | 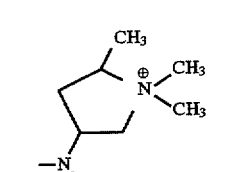 |
| 1-24" | 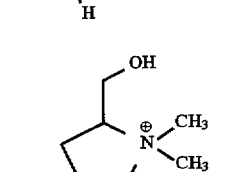 |
| 1-25" | 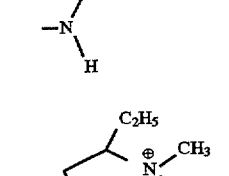 |
| 1-26" | 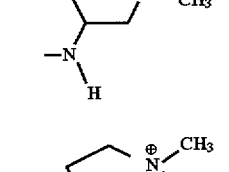 |
| 1-27" | 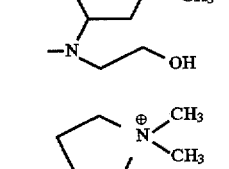 |

TABLE 9-continued

| Compound No. | Q" |
|---|---|
| 1-28" | (structure: pyrrolidinium with N⁺(CH₃)₂ and N-CH₂CONH₂) |
| 1-29" | (structure: pyrrolidinium with N⁺(CH₃)₂ and N-CH₂CH₂F) |
| 1-30" | (structure: pyrrolidinium with N⁺(CH₃)(CONH₂) and N-CH₂CH₂OH) |
| 1-31" | (structure: pyrrolidinium with N⁺(CH₃)(CH₂CH₂OH) and N-CH₂CH₂OH) |
| 1-32" | (structure: pyrrolidinium with N⁺(CH₃)(CH₂CONH₂) and N-CH₂CH₂OH) |
| 1-33" | (structure: pyrrolidinium with N⁺-COOH and -N) |
| 1-34" | (structure: pyrrolidinium with N⁺-CH₂CH₂F and -N) |
| 1-35" | (structure: pyrrolidinium with N⁺-CH₂CH₂NH₂ and -N) |
| 1-36" | (structure: pyrrolidinium with N⁺-CH₂CH₂NH₂ and -N) |
| 1-37" | (structure: pyrrolidinium with N⁺-CH₃ and -N) |
| 1-38" | (structure: pyrrolidinium with N⁺-CH₂CONH₂ and -N) |
| 1-39" | (structure: pyrrolidinium with N⁺-CH₂CH₂OH and -N) |
| 1-40" | (structure: pyrrolidinium with N⁺-CH₂COOH and -N) |
| 1-41" | (structure: pyrrolidinium with N⁺-CH₂CH₂F and -N) |
| 1-42" | (structure: pyrrolidinium with N⁺-CH₃ and -N) |
| 1-43" | (structure: pyrrolidinium with N⁺-CH₂CONH₂ and -N) |
| 1-44" | (structure: pyrrolidinium with N⁺-CH₂CH₂OH and -N) |
| 1-45" | (structure: azetidine with -NH- and N⁺(CH₃)₂) |
| 1-46" | (structure: azetidine with -NH- and N⁺(CH₃)(CH₂CONH₂)) |
| 1-47" | (structure: azetidine with -NH- and N⁺(CH₃)(CH₂CH₂F)) |
| 1-48" | (structure: azetidine with -NH- and N⁺(CH₃)(CH₂CH₂OH)) |

TABLE 9-continued

| Compound No. | Q" |
|---|---|
| 1-49" | -N(CH₃)-CH(azetidine)-N⁺(CH₃)₂CH₃ |
| 1-50" | -NH-CH(azetidine)-N⁺(CH₃)(CH₂COOH) |

TABLE 10

| Compound No. | Q" |
|---|---|
| 2-1" | pyrrolidine-N⁺(CH₃)₃ |
| 2-2" | pyrrolidine-N⁺(CH₃)₂CH₂OCH₃ |
| 2-3" | pyrrolidine-N⁺(CH₃)₂CH₂CH₂OH |
| 2-4" | pyrrolidine-N⁺(CH₃)₂CH₂CONH₂ |
| 2-5" | pyrrolidine-N⁺(CH₃)₂CH₂CONHCH₃ |
| 2-6" | pyrrolidine-N⁺(CH₃)₂CH₂CON(CH₃)₂ |
| 2-7" | pyrrolidine-N⁺(CH₃)₂CH₂CH₂OCONH₂ |
| 2-8" | pyrrolidine-N⁺(CH₃)₂CH₂CH₂F |
| 2-9" | pyrrolidine-N⁺(CH₃)₂C₂H₅ |
| 2-10" | pyrrolidine-N⁺(CH₃)₂CH₂CH₂CONH₂ |
| 2-11" | pyrrolidine-N⁺(CH₃)₂CH₂CH₂CH₂OH |
| 2-12" | pyrrolidine-N⁺(C₂H₅)₂CH₃ with C₂H₅ |
| 2-13" | pyrrolidine-N⁺(CH₃)₂CH₂COOH |
| 2-14" | pyrrolidine-N⁺(CH₃)₂CH₂CH₂SO₃H |
| 2-15" | pyrrolidine-N⁺(pyrrolidine-CH₃) |
| 2-16" | pyrrolidine-N⁺(piperidine-CH₃) |

TABLE 10-continued
| Compound No. | Q" |
|---|---|
| 2-17" | 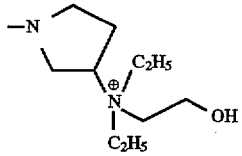 |
| 2-18" | 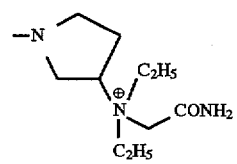 |
| 2-19" | 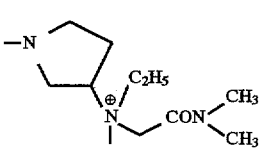 |
| 2-20" | 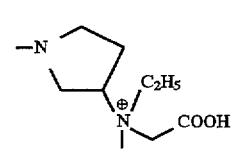 |
| 2-21" | 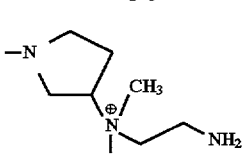 |
| 2-22" | 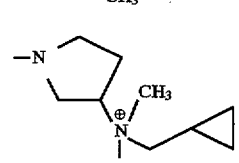 |
| 2-23" | 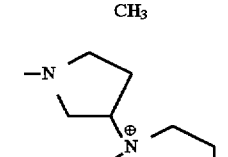 |
| 2-24" | 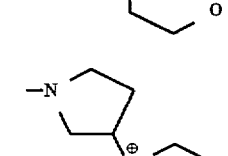 |
| 2-25" | 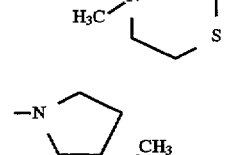 |
| 2-26" | 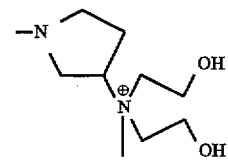 |
| 2-27" | 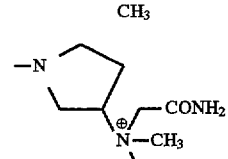 |
| 2-28" | 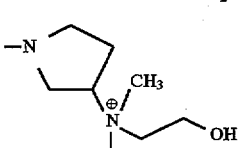 |
| 2-29" | 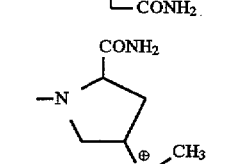 |
| 2-30" | 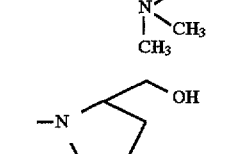 |
| 2-31" | 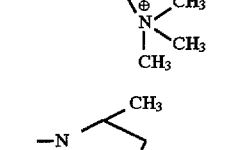 |
| 2-32" | 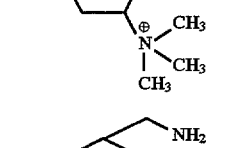 |
| 2-33" | 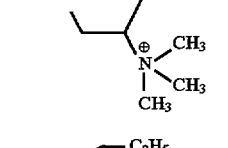 |
| 2-34" | 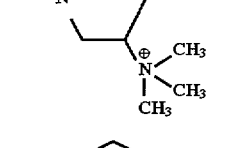 |

TABLE 10-continued

| Compound No. | Q" |
|---|---|
| 2-35" | pyrrolidine-N,N-dimethyl ammonium |
| 2-36" | pyrrolidine-N-methyl-N-(2-hydroxyethyl) ammonium |
| 2-37" | pyrrolidine-N-methyl-N-(CH₂CONH₂) ammonium |
| 2-38" | pyrrolidine-N,N-bis(CH₂CONH₂) ammonium |
| 2-39" | pyrrolidine (3-position) N,N-dimethyl ammonium |
| 2-40" | pyrrolidine (3-position) N-methyl-N-(2-hydroxyethyl) ammonium |
| 2-41" | pyrrolidine (3-position) N-methyl-N-(CH₂CONH₂) ammonium |
| 2-42" | pyrrolidine (3-position) N,N-bis(CH₂CONH₂) ammonium |
| 2-43" | azetidine-N,N,N-trimethyl ammonium |

TABLE 10-continued

| Compound No. | Q" |
|---|---|
| 2-44" | azetidine-N,N-dimethyl-N-(CH₂CH₂F) ammonium |
| 2-45" | azetidine-N,N-dimethyl-N-(CH₂CH₂OH) ammonium |
| 2-46" | azetidine-N,N-dimethyl-N-(CH₂CONH₂) ammonium |
| 2-47" | azetidine-N,N-dimethyl-N-(CH₂CONHCH₃) ammonium |
| 2-48" | azetidine-N,N-dimethyl-N-(CH₂CON(CH₃)₂) ammonium |
| 2-49" | azetidine-N,N-dimethyl-N-C₂H₅ ammonium |
| 2-50" | azetidine-N,N-dimethyl-N-(CH₂CH₂OCONH₂) ammonium |
| 2-51" | azetidine-N,N-dimethyl-N-(CH₂CH₂CONH₂) ammonium |
| 2-52" | azetidine-N-methylpyrrolidinium |
| 2-53" | azetidine-N,N,N-triethyl ammonium |
| 2-54" | azetidine-N-(fluoropyrrolidinium) |
| 2-55" | azetidine-N,N-dimethyl-N-(CH₂COOH) ammonium |

TABLE 10-continued

| Compound No. | Q" |
|---|---|
| 2-56" | -N[azetidine]-N⁺(CH₃)(CH₃)CH₂CH₂OCH₃ |
| 2-57" | -N[azetidine](CH₃)-N⁺[piperidine] |
| 2-58" | -N[azetidine](CH₃)-N⁺[morpholine] |

TABLE 11

| Compound No. | Q" |
|---|---|
| 3-1" | -N[pyrrolidine]-[imidazolium]-CH₃ |
| 3-2" | -N[pyrrolidine]-[imidazolium]-CH₂CONH₂ |
| 3-3" | -N[pyrrolidine]-[thiazolium] |
| 3-4" | -N[pyrrolidine]-[imidazolium]-CH₂CH₂OH |
| 3-5" | -N[pyrrolidine]-[imidazolium]-CH₂CH₂F |
| 3-6" | -N[pyrrolidine]-[imidazolium]-CH₂CON(CH₃)₂ |
| 3-7" | -N[pyrrolidine]-[imidazolium]-CH₂CH₂OCONH₂ |
| 3-8" | -N[pyrrolidine]-[imidazolium]-C₂H₅ |
| 3-9" | -N[pyrrolidine]-[imidazolium]-CH₂CONHCH₃ |
| 3-10" | -N[pyrrolidine]-[thiazolium substituted with CH₃ and CH₂CH₂OH] |
| 3-11" | -N[pyrrolidine]-[thiazolium substituted with CH₃ and CH₂OH] |
| 3-12" | -N[pyrrolidine]-[thiazolium substituted with CH₃ and CH₃] |
| 3-13" | -N[pyrrolidine]-[pyridinium] |
| 3-14" | -N[pyrrolidine]-[pyridinium-CONH₂] |
| 3-15" | -N[piperidine]-[imidazolium]-CH₃ |

TABLE 11-continued
| Compound No. | Q" |
|---|---|
| 3-16" | 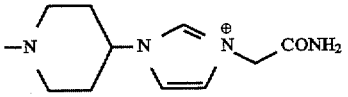 |
| 3-17" | 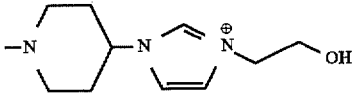 |
| 3-18" | 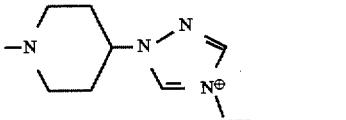 |
| 3-19" | 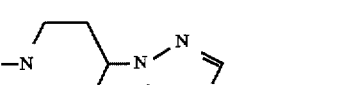 |
| 3-20" | 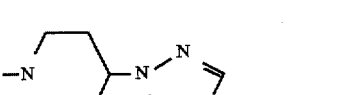 |
| 3-21" |  |
| 3-22" | 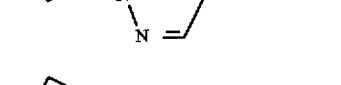 |
| 3-23" | 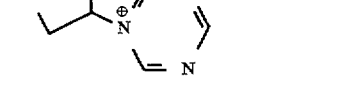 |
| 3-24" |  |
| 3-25" |  |
| 3-26" | 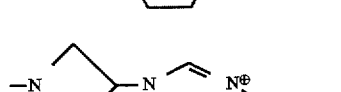 |
| 3-27" | 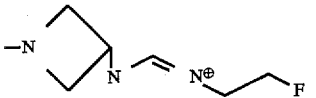 |
| 3-28" | 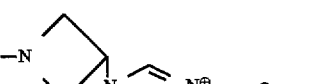 |
| 3-29" | 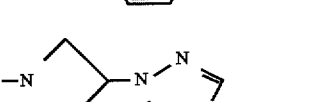 |
| 3-30" |  |
| 3-31" | 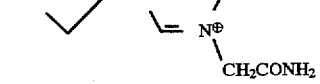 |
| 3-32" | 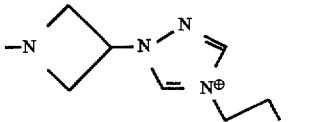 |
| 3-33" | 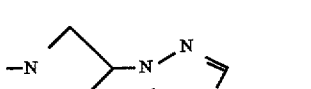 |
| 3-34" |  |
| 3-35" | 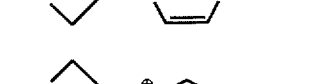 |
| 3-36" | 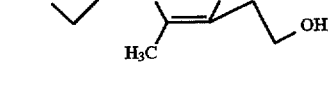 |
| 3-37" | 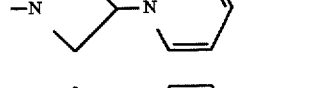 |

TABLE 11-continued

| Compound No. | Q" |
|---|---|
| 3-38" | (azetidinyl-pyrazolium-CH₂COOH) |
| 3-39" | (azetidinyl-imidazolium-CH₂COOH) |
| 3-40" | (azetidinyl-imidazolium-CH₂CH₂OCONH₂) |

TABLE 12

| Compound No. | Q" |
|---|---|
| 4-1" | (pyrrolidinyl-thiazolium-CH₃) |
| 4-2" | (pyrrolidinyl-thiazolium-CH₂CONH₂) |
| 4-3" | (pyrrolidinyl-thiazolium-CH₂CH₂OH) |
| 4-4" | (pyrrolidinyl-imidazolium-N,N'-diCH₃) |
| 4-5" | (piperidinyl-thiazolium-CH₃) |
| 4-6" | (piperidinyl-thiazolium-CH₂CONH₂) |

TABLE 12-continued

| Compound No. | Q" |
|---|---|
| 4-7" | (piperidinyl-thiazolium-CH₂CH₂OH) |
| 4-8" | (piperidinyl-imidazolium-N,N'-diCH₃) |

TABLE 13

| Compound No. | Q" |
|---|---|
| 5-1" | (pyrrolo-pyridinium-CH₃) |
| 5-2" | (pyrrolo-pyridinium-CH₂CONH₂) |
| 5-3" | (pyrrolo-pyridinium-CH₂CH₂OH) |

TABLE 14

| Compound No. | Q" |
|---|---|
| 6-1" | (pyrrolo-pyridinium-CH₃) |
| 6-2" | (pyrrolo-pyridinium-CH₂CONH₂) |
| 6-3" | (pyrrolo-pyridinium-CH₂CH₂OH) |
| 6-4" | (pyrrolo-pyrimidinium-CH₃) |

TABLE 14-continued
| Compound No. | Q" |
|---|---|
| 6-5" | 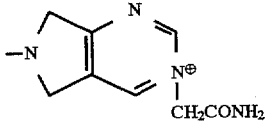 |
| 6-6" | 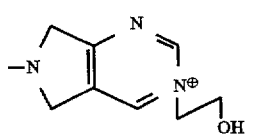 |
TABLE 15
| Cpd. No. | R¹" | Het |
|---|---|---|
| 7-1" | CH₃ | 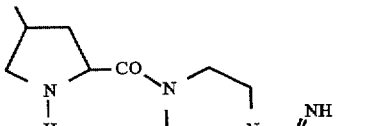 |
| 7-2" | CH₃ | 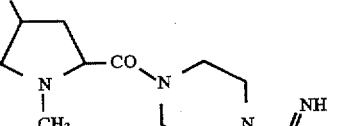 |
| 7-3" | CH₃ | 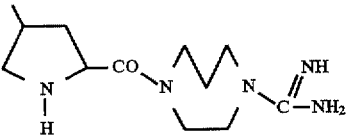 |
| 7-4" | CH₃ | 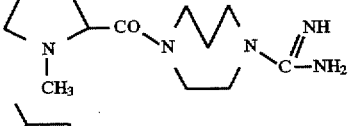 |
| 7-5" | CH₃ | 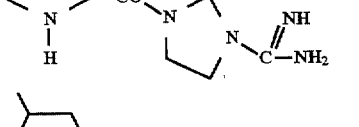 |
| 7-6" | CH₃ | 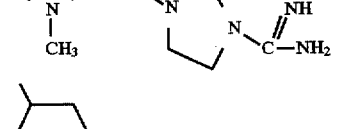 |
| 7-7" | CH₃ | 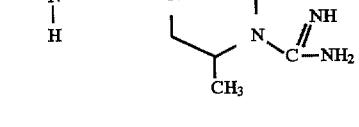 |
TABLE 15-continued
| Cpd. No. | R¹" | Het |
|---|---|---|
| 7-8" | CH₃ | 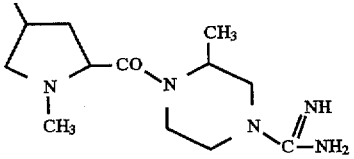 |
| 7-9" | CH₃ | 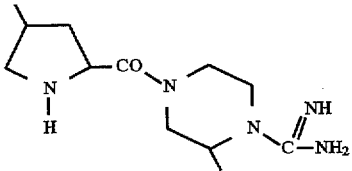 |
| 7-10" | CH₃ | 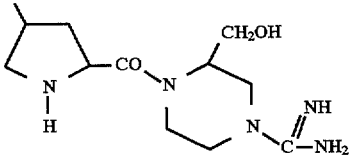 |
| 7-11" | CH₃ | 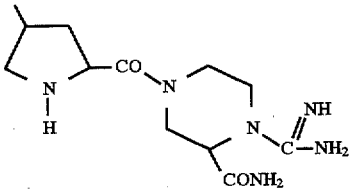 |
| 7-12" | CH₃ | 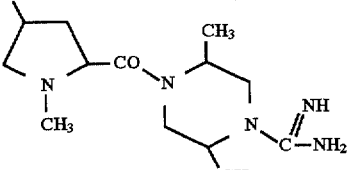 |
| 7-13" | CH₃ | 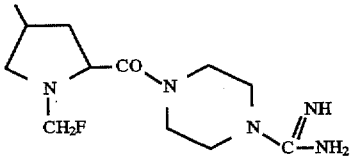 |
| 7-14" | CH₃ | 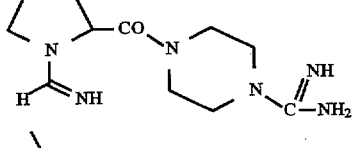 |
| 7-15" | CH₃ | 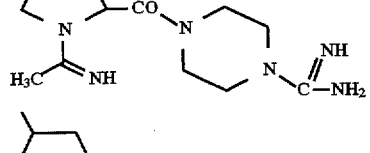 |
| 7-16" | CH₃ | 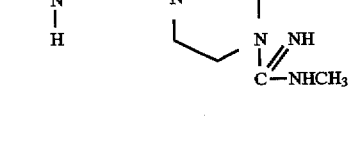 |

TABLE 15-continued

| Cpd. No. | R¹" | Het |
|---|---|---|
| 7-17" | CH₃ | (structure) |
| 7-18" | CH₃ | (structure) |
| 7-19" | CH₃ | (structure) |
| 7-20" | CH₃ | (structure) |
| 7-21" | CH₃ | (structure) |
| 7-22" | CH₃ | (structure) |
| 7-23" | CH₃ | (structure) |
| 7-24" | CH₃ | (structure) |
| 7-25" | H | (structure) |
| 7-26" | H | (structure) |
| 7-27" | H | (structure) |
| 7-28" | H | (structure) |
| 7-29" | H | (structure) |
| 7-30" | H | (structure) |
| 7-31" | H | (structure) |
| 7-32" | CH₃ | (structure) |
| 7-33" | CH₃ | (structure) |

TABLE 15-continued
| Cpd. No. | R¹" | Het |
|---|---|---|
| 7-34" | CH₃ | 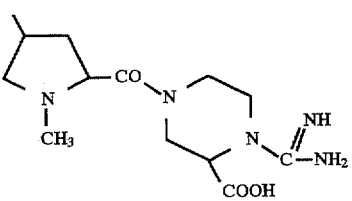 |
| 7-35" | CH₃ | 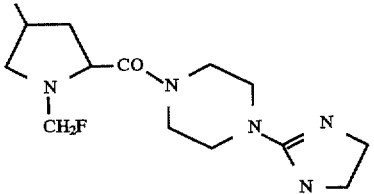 |
| 7-36" | CH₃ | 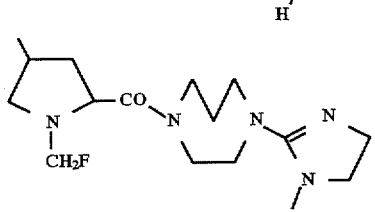 |
| 7-37" | H | 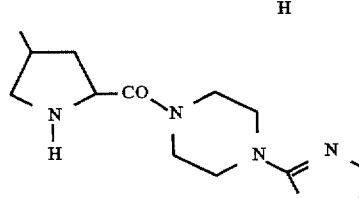 |
| 7-38" | H | 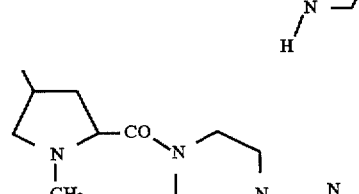 |
| 7-39" | H | 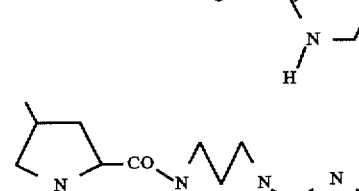 |
| 7-40" | H | 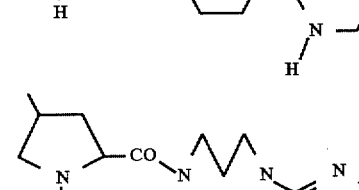 |
| 7-41" | CH₃ | 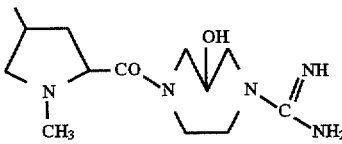 |
TABLE 16
| Cpd. No. | R¹" | Het |
|---|---|---|
| 8-1" | CH₃ | 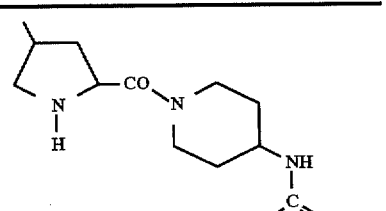 |
| 8-2" | CH₃ | 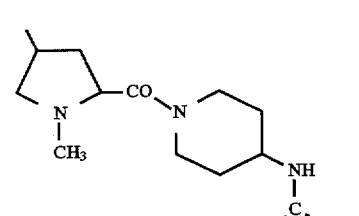 |
| 8-3" | CH₃ | 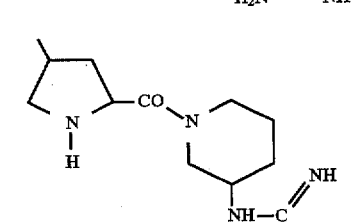 |
| 8-4" | CH₃ | 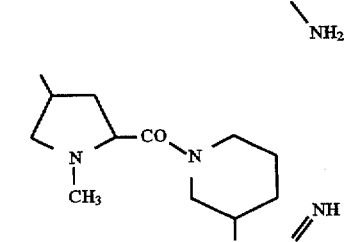 |
| 8-5" | CH₃ | 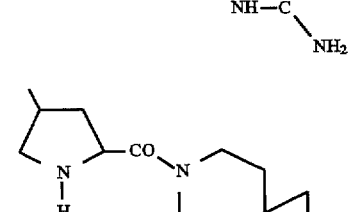 |

TABLE 16-continued
| Cpd. No. | R[1"] | Het |
|---|---|---|
| 8-6" | CH₃ | 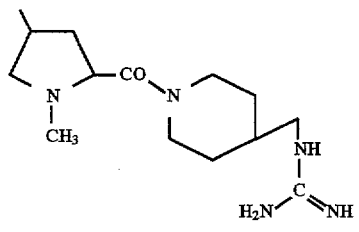 |
| 8-7" | CH₃ | 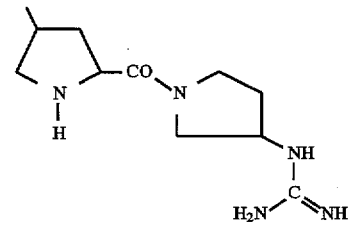 |
| 8-8" | CH₃ | 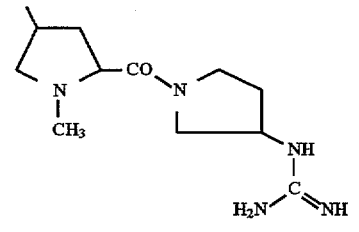 |
| 8-9" | CH₃ | 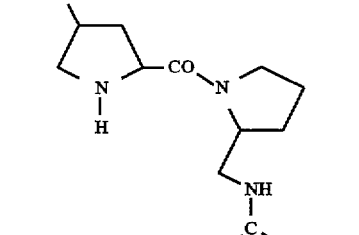 |
| 8-10" | CH₃ | 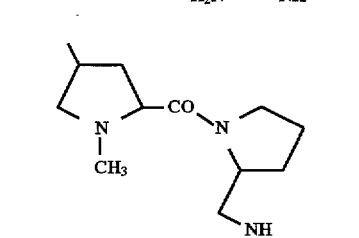 |
| 8-11" | CH₃ | 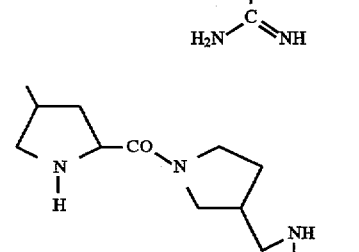 |// |
| 8-12" | CH₃ | 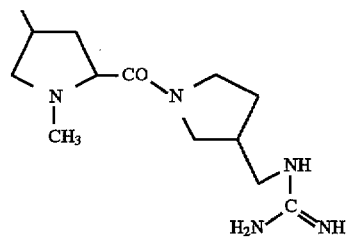 |
| 8-13" | CH₃ | 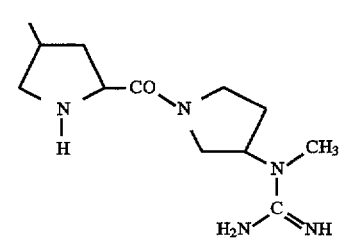 |
| 8-14" | CH₃ | 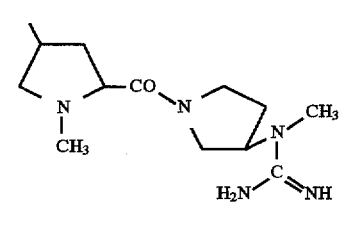 |
| 8-15" | CH₃ | 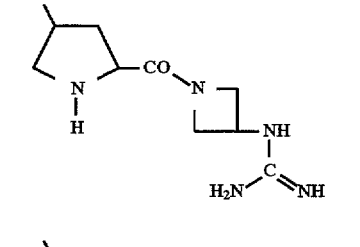 |
| 8-16" | CH₃ | 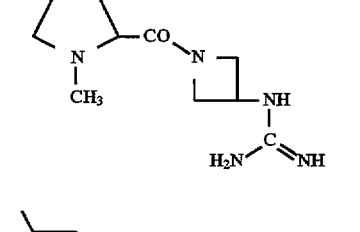 |
| 8-17" | H | 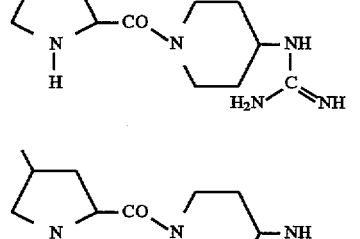 |
| 8-18" | H | 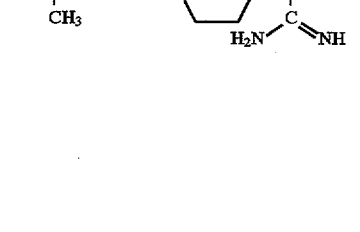 |

TABLE 16-continued

| Cpd. No. | R[1]″ | Het |
|---|---|---|
| 8-19″ | H | (4-methylpyrrolidine-2-carbonyl)-pyrrolidin-3-yl-guanidine |
| 8-20″ | H | (1,4-dimethylpyrrolidine-2-carbonyl)-pyrrolidin-3-yl-guanidine |
| 8-21″ | H | (4-methylpyrrolidine-2-carbonyl)-(3-methylpyrrolidin-3-yl)-guanidine |
| 8-22″ | H | (1,4-dimethylpyrrolidine-2-carbonyl)-(3-methylpyrrolidin-3-yl)-guanidine |
| 8-23″ | H | (4-methylpyrrolidine-2-carbonyl)-azetidin-3-yl-guanidine |
| 8-24″ | H | (1,4-dimethylpyrrolidine-2-carbonyl)-azetidin-3-yl-guanidine |
| 8-25″ | CH₃ | (4-methylpyrrolidine-2-carbonyl)-piperidin-4-yl-(4,5-dihydroimidazol-2-yl) |
| 8-26″ | CH₃ | (1,4-dimethylpyrrolidine-2-carbonyl)-piperidin-4-yl-(4,5-dihydroimidazol-2-yl) |
| 8-27″ | CH₃ | (4-methylpyrrolidine-2-carbonyl)-pyrrolidin-3-yl-(4,5-dihydroimidazol-2-yl) |
| 8-28″ | CH₃ | (1,4-dimethylpyrrolidine-2-carbonyl)-pyrrolidin-3-yl-(4,5-dihydroimidazol-2-yl) |
| 8-29″ | CH₃ | (4-methylpyrrolidine-2-carbonyl)-azetidin-3-yl-(4,5-dihydroimidazol-2-yl) |
| 8-30″ | CH₃ | (1,4-dimethylpyrrolidine-2-carbonyl)-azetidin-3-yl-(4,5-dihydroimidazol-2-yl) |
| 8-31″ | CH₃ | (1-fluoromethyl-4-methylpyrrolidine-2-carbonyl)-piperidin-4-yl-guanidine |
| 8-32″ | CH₃ | (1-fluoromethyl-4-methylpyrrolidine-2-carbonyl)-pyrrolidin-3-yl-guanidine |
| 8-33″ | CH₃ | (1-fluoromethyl-4-methylpyrrolidine-2-carbonyl)-azetidin-3-yl-guanidine |
| 8-34″ | CH₃ | (4-methylpyrrolidine-2-carbonyl)-(3-fluoropiperidin-4-yl)-guanidine |
| 8-35″ | CH₃ | (4-methylpyrrolidine-2-carbonyl)-(4-fluoropyrrolidin-3-yl)-guanidine |

TABLE 16-continued
| Cpd. No. | R[1]″ | Het |
|---|---|---|
| 8-36″ | H | 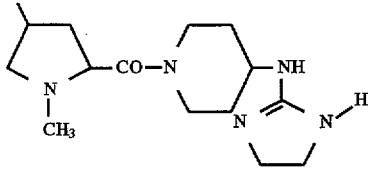 |
| 8-37″ | H | 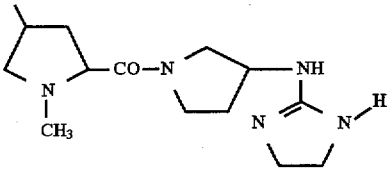 |
| 8-38″ | H | 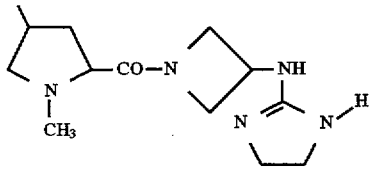 |
TABLE 17
| Cpd. No. | R[1]″ | Het |
|---|---|---|
| 9-1″ | CH$_3$ | 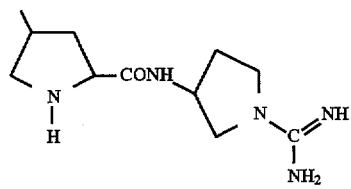 |
| 9-2″ | CH$_3$ | 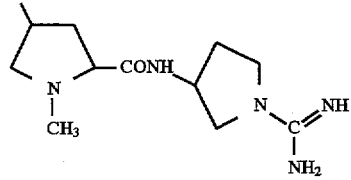 |
| 9-3″ | CH$_3$ | 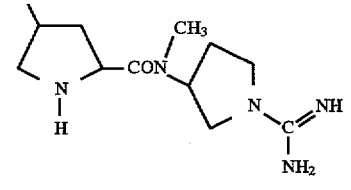 |
| 9-4″ | CH$_3$ | 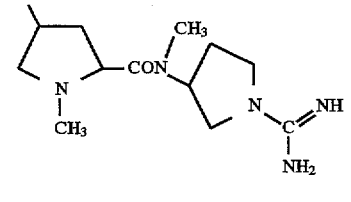 |
TABLE 17-continued
| Cpd. No. | R[1]″ | Het |
|---|---|---|
| 9-5″ | CH$_3$ | 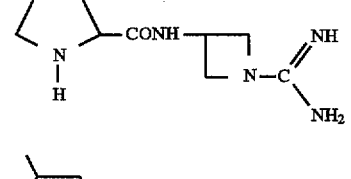 |
| 9-6″ | CH$_3$ | 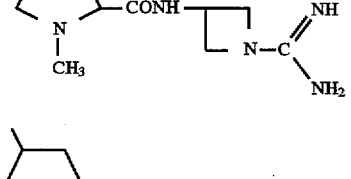 |
| 9-7″ | CH$_3$ | 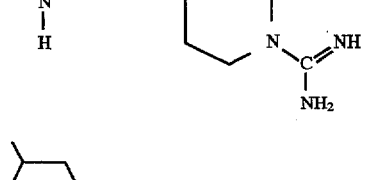 |
| 9-8″ | CH$_3$ | 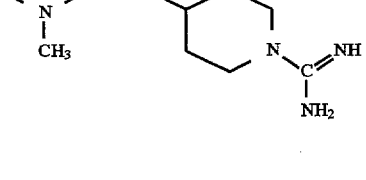 |
| 9-9″ | CH$_3$ | 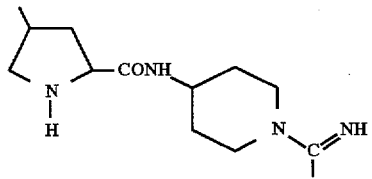 |
| 9-10″ | CH$_3$ | 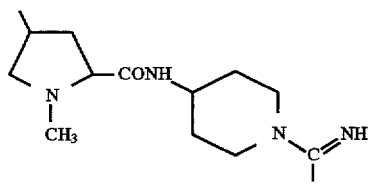 |
| 9-11″ | H | 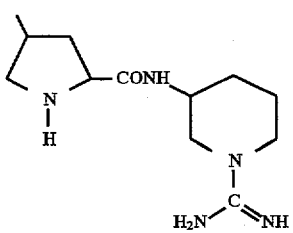 |
| 9-12″ | H | 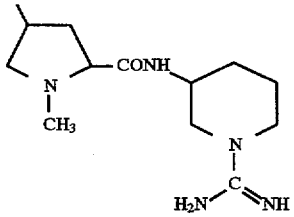 |

TABLE 17-continued

| Cpd. No. | R[1"] | Het |
|---|---|---|
| 9-13" | H | (pyrrolidine-NH)-CONH-(pyrrolidine-N-C(=NH)NH2) |
| 9-14" | H | (N-methyl pyrrolidine)-CONH-(pyrrolidine-N-C(=NH)NH2) |
| 9-15" | H | (pyrrolidine-NH)-CON(CH3)-(pyrrolidine-N-C(=NH)NH2) |
| 9-16" | H | (N-methyl pyrrolidine)-CON(CH3)-(pyrrolidine-N-C(=NH)NH2) |
| 9-17" | H | (pyrrolidine-NH)-CONH-(azetidine-N-C(=NH)NH2) |
| 9-18" | H | (N-methyl pyrrolidine)-CONH-(azetidine-N-C(=NH)NH2) |
| 9-19" | H | (pyrrolidine-NH)-CONH-(piperidine-N-C(=NH)NH2) |
| 9-20" | H | (N-methyl pyrrolidine)-CONH-(piperidine-N-C(=NH)NH2) |

TABLE 18

| Cpd. No. | R[1"] | Het |
|---|---|---|
| 10-1" | CH3 | (pyrrolidine-NH)-CONH-CH2CH2-NH-C(=NH)NH2 |
| 10-2" | CH3 | (N-methyl pyrrolidine)-CONH-CH2CH2-NH-C(=NH)NH2 |
| 10-3" | CH3 | (pyrrolidine-NH)-CON(CH3)-CH2CH2-NH-C(=NH)NH2 |
| 10-4" | CH3 | (N-methyl pyrrolidine)-CON(CH3)-CH2CH2-NH-C(=NH)NH2 |
| 10-5" | CH3 | (N-methyl pyrrolidine)-CON(CH3)-CH2CH2-N(CH3)-C(=NH)NH2 |
| 10-6" | CH3 | (N-methyl pyrrolidine)-CONH-CH2CH2-N(CH3)-C(=NH)NH2 |
| 10-7" | CH3 | (pyrrolidine-NH)-CONH-CH2CH2-N(CH3)-C(=NH)NH2 |
| 10-8" | CH3 | (N-methyl pyrrolidine)-CONH-CH2CH2-N(CH3)-C(=NH)NH2 |
| 10-9" | CH3 | (pyrrolidine-NH)-CONH-CH2CH2CH2-NH-C(=NH)NH2 |
| 10-10" | CH3 | (N-methyl pyrrolidine)-CONH-CH2CH2CH2-NH-C(=NH)NH2 |

TABLE 18-continued

| Cpd. No. | R¹" | Het |
|---|---|---|
| 10-11" | H | pyrrolidine-CONH-CH₂CH₂-NH-C(=NH)-NH₂ (N-H on pyrrolidine) |
| 10-12" | H | pyrrolidine-CONH-CH₂CH₂-NH-C(=NH)-NH₂ (N-CH₃ on pyrrolidine) |
| 10-13" | H | pyrrolidine-CON(CH₃)-CH₂CH₂-NH-C(=NH)-NH₂ (N-H on pyrrolidine) |
| 10-14" | H | pyrrolidine-CON(CH₃)-CH₂CH₂-NH-C(=NH)-NH₂ (N-CH₃ on pyrrolidine) |

TABLE 19

| Cpd. No. | R¹" | Het |
|---|---|---|
| 11-1" | CH₃ | pyrrolidine-CO-N(azetidine)-NH₂ |
| 11-2" | CH₃ | pyrrolidine-CO-N(azetidine)-NHCH₃ |
| 11-3" | CH₃ | pyrrolidine-CO-N(azetidine)-N(CH₃)₂ |
| 11-4" | CH₃ | pyrrolidine-CO-N(azetidine)-NHC₂H₅ |
| 11-5" | CH₃ | pyrrolidine-CO-N(azetidine)-NH-CH₂CH₂F |
| 11-6" | CH₃ | pyrrolidine-CO-N(azetidine)-NH-CH₂CH₂OH |
| 11-7" | CH₃ | pyrrolidine-CO-N(azetidine)-NH-CH₂CONH₂ |
| 11-8" | CH₃ | pyrrolidine-CO-N(azetidine)-NH-CH₂COOH |
| 11-9" | CH₃ | pyrrolidine-CO-N(azetidine)-NH-CH₂CH₂OH |
| 11-10" | CH₃ | pyrrolidine-CO-N(azetidine)-N(CH₃)-CH₂CONH₂ |
| 11-11" | CH₃ | pyrrolidine-CO-N(azetidine)-N(CH₃)-CH₂COOH |
| 11-12" | CH₃ | pyrrolidine-CO-N(azetidine)-N(CH₃)-CH₂CH₂-OCONH |
| 11-13" | CH₃ | pyrrolidine-CO-N(azetidine)-N(CH₃)-CH₂CH₂NH₂ |
| 11-14" | CH₃ | pyrrolidine-CO-N(azetidine)-N(CH₃)-CH₂CH₂F |
| 11-15" | CH₃ | pyrrolidine-CO-N(azetidine)-NH-C(CH₃)=NH |

TABLE 19-continued

| Cpd. No. | R¹" | Het |
|---|---|---|
| 11-16" | CH₃ | (structure) |
| 11-17" | CH₃ | (structure) |
| 11-18" | CH₃ | (structure) |
| 11-19" | CH₃ | (structure) |
| 11-20" | CH₃ | (structure) |
| 11-21" | CH₃ | (structure) |
| 11-22" | CH₃ | (structure) |
| 11-23" | CH₃ | (structure) |
| 11-24" | CH₃ | (structure) |
| 11-25" | CH₃ | (structure) |
| 11-26" | CH₃ | (structure) |
| 11-27" | CH₃ | (structure) |
| 11-28" | CH₃ | (structure) |
| 11-29" | CH₃ | (structure) |
| 11-30" | CH₃ | (structure) |
| 11-31" | CH₃ | (structure) |
| 11-32" | H | (structure) |
| 11-33" | H | (structure) |
| 11-34" | H | (structure) |
| 11-35" | H | (structure) |

TABLE 19-continued

| Cpd. No. | R[1"] | Het |
|---|---|---|
| 11-36" | H | (4-methylpyrrolidine N-CH3, CO-N-azetidine-NH-C(=NH)CH3) |
| 11-37" | H | (4-methylpyrrolidine N-CH3, CO-N-azetidine-NH-CH=NH) |
| 11-38" | H | (4-methylpyrrolidine N-C(CH3)=NH, CO-N-azetidine-NH2) |
| 11-39" | H | (4-methylpyrrolidine N-CH=NH, CO-N-azetidine-NH2) |
| 11-40" | H | (4-methylpyrrolidine N-C(CH3)=NH, CO-N-azetidine-NH-C(=NH)CH3) |
| 11-41" | H | (4-methylpyrrolidine N-CH=NH, CO-N-azetidine-NH-C(=NH)CH3) |
| 11-42" | H | (4-methylpyrrolidine N-CH=NH, CO-N-azetidine-NH-CH=NH) |
| 11-43" | H | (4-methylpyrrolidine N-CH2F, CO-N-azetidine-CH(CH3)-NH... ) |
| 11-44" | H | (4-methylpyrrolidine NH, CO-N-azetidine-CH2NH2) |
| 11-45" | H | (4-methylpyrrolidine N-CH3, CO-N-azetidine-CH2-NH-C(=NH)CH3) |
| 11-46" | CH3 | (4-methylpyrrolidine NH, CO-N-azetidine-CH2-NH-C(=NH)CH3) |
| 11-47" | CH3 | (4-methylpyrrolidine NH, CO-N-azetidine-CH2-NH-CH=NH) |
| 11-48" | CH3 | (4-methylpyrrolidine NH, CO-N-azetidine-CH2NH2) |
| 11-49" | CH3 | (4-methylpyrrolidine N-CH3, CO-N-azetidine-CH2NH2) |
| 11-50" | CH3 | (4-methylpyrrolidine N-CH3, CO-N-azetidine-CH2-NH-C(=NH)CH3) |
| 11-51" | CH3 | (4-methylpyrrolidine N-CH3, CO-N-azetidine-CH2-NH-CH=NH) |
| 11-52" | CH3 | (4-methylpyrrolidine N-C(CH3)=NH, CO-N-azetidine-CH2NH2) |
| 11-53" | CH3 | (4-methylpyrrolidine N-CH=NH, CO-N-azetidine-CH2-NH-C(=NH)CH3) |

TABLE 19-continued

| Cpd. No. | R¹" | Het |
|---|---|---|
| 11-54" | CH₃ | (structure) |
| 11-55" | CH₃ | (structure) |
| 11-56" | CH₃ | (structure) |
| 11-57" | CH₃ | (structure) |
| 11-58" | CH₃ | (structure) |

TABLE 20

| Cpd. No. | R¹" | Het |
|---|---|---|
| 12-1" | CH₃ | (structure) |
| 12-2" | CH₃ | (structure) |
| 12-3" | CH₃ | (structure) |

TABLE 20-continued

| Cpd. No. | R¹" | Het |
|---|---|---|
| 12-4" | CH₃ | (structure) |
| 12-5" | CH₃ | (structure) |
| 12-6" | CH₃ | (structure) |
| 12-7" | CH₃ | (structure) |
| 12-8" | CH₃ | (structure) |
| 12-9" | CH₃ | (structure) |
| 12-10" | CH₃ | (structure) |
| 12-11" | CH₃ | (structure) |
| 12-12" | CH₃ | (structure) |
| 12-13" | CH₃ | (structure) |

TABLE 20-continued

| Cpd. No. | R[1]″ | Het |
|---|---|---|
| 12-14″ | CH₃ | pyrrolidine(NH)-CONH-azetidine-N-CH₂CH₂-OCONH₂ |
| 12-15″ | CH₃ | pyrrolidine(NH)-CONH-azetidine-N-CH₂CH₂F |
| 12-16″ | CH₃ | pyrrolidine(N-CH₃)-CONH-azetidine-N-CH₃ |
| 12-17″ | CH₃ | pyrrolidine(N-CH₃)-CONH-azetidine-N-CH₂CH₂OH |
| 12-18″ | CH₃ | pyrrolidine(N-CH₃)-CONH-azetidine-N-CH₂CONH₂ |
| 12-19″ | CH₃ | pyrrolidine(N-CH₃)-CONH-azetidine-N-CH₂CH₂F |
| 12-20″ | CH₃ | pyrrolidine(N-CH₃)-CONH-azetidine-N-CH₂COOH |
| 12-21″ | CH₃ | pyrrolidine(NH)-CON(CH₃)-azetidine-NH |
| 12-22″ | CH₃ | pyrrolidine(NH)-CON(CH₃)-azetidine-N-C(CH₃)=NH |
| 12-23″ | H | pyrrolidine(NH)-CONH-azetidine-NH |
| 12-24″ | H | pyrrolidine(NH)-CONH-azetidine-N-C(CH₃)=NH |
| 12-25″ | H | pyrrolidine(NH)-CONH-azetidine-N-CH=NH |
| 12-26″ | H | pyrrolidine(N-CH₃)-CONH-azetidine-NH |
| 12-27″ | H | pyrrolidine(N-CH₃)-CONH-azetidine-N-C(CH₃)=NH |
| 12-28″ | H | pyrrolidine(N-CH₃)-CONH-azetidine-N-CH=NH |
| 12-29″ | CH₃ | pyrrolidine(N-CH₂F)-CONH-azetidine-NH |
| 12-30″ | CH₃ | pyrrolidine(N-CH₂F)-CONH-azetidine-N-C(CH₃)=NH |
| 12-31″ | CH₃ | pyrrolidine(N-CH₂F)-CONH-azetidine-N-CH=NH |
| 12-32″ | H | pyrrolidine(N-CH₂F)-CONH-azetidine-NH |
| 12-33″ | H | pyrrolidine(N-CH₂F)-CONH-azetidine-N-C(CH₃)=NH |

TABLE 20-continued

| Cpd. No. | R¹" | Het |
|---|---|---|
| 12-34" | CH₃ | pyrrolidin-2-CONH-azetidin-N=C(OCH₃)(NH) |
| 12-35" | CH₃ | pyrrolidin-2-CONH-azetidin-N=C(Cl)(NH) |
| 12-36" | CH₃ | pyrrolidin-2-CONH-azetidin-N=C(cyclopropyl)(NH) |
| 12-37" | CH₃ | pyrrolidin-2-CONH-azetidin-N-C(cyclopropyl)=NH |
| 12-38" | CH₃ | pyrrolidin-2-CONH-CH₂-azetidin-NH |

TABLE 21

| Cpd. No. | R¹" | Het |
|---|---|---|
| 13-1" | CH₃ | pyrrolidin-2-CO-N-azetidin-N(imidazol-1-yl) |
| 13-2" | CH₃ | pyrrolidin-2-CO-N-azetidin-N(1,2,3-triazol-1-yl) |
| 13-3" | CH₃ | pyrrolidin-2-CO-N-azetidin-N(1,2,3-triazol-2-yl) |
| 13-4" | H | pyrrolidin-2-CO-N-azetidin-N(imidazol-1-yl) |
| 13-5" | H | pyrrolidin-2-CO-N-azetidin-N(1,2,3-triazol-1-yl) |
| 13-6" | CH₃ | pyrrolidin-2-CO-N-azetidin-N(tetrazol-1-yl) |

Of the specific compounds of the formula (I)', preferred compounds are as follows:

6-(1-Hydroxyethyl)-1-methyl-2-[2-(3-trimethylammoniopyrrolidin-1-ylcarbonyl)pyrrolidin-4-ylthio]-1-carbapen-2-em-3-carboxylate;

2-[2-(1,1-Dimethyl-3-pyrrolidinioaminocarbonyl)pyrrolidin-4-ylthio]-6-(1-hydroxyethyl)-1-methyl-1-carbapen-2-em-3-carboxylate;

2-{2-[3-(Carbamoylmethyldimethylammonio)pyrrolidin-1-ylcarbonyl]pyrrolidin-4-ylthio}-6-(1-hydroxyethyl)-1-methyl-1-carbapen-2-em-3-carboxylate;

2-[2-{3-[(2-Hydroxyethyl)dimethylammonio]pyrrolidin-1-ylcarbonyl}pyrrolidin-4-ylthio]-6-(1-hydroxyethyl)-1-methyl-1-carbapen-2-em-3-carboxylate;

2-[2-(3-[N-(2-Fluoroethyl)-N,N-dimethylammonio]-pyrrolidin-1-ylcarbonyl)pyrrolidin-4-ylthio]-6-(1-hydroxyethyl)-1-methyl-1-carbapen-2-em-3-carboxylate;

6-(1-Hydroxyethyl)-1-methyl-2-(2-[4-(3-methylimidazolio)piperadin-1-ylcarbonyl]pyrrolidin-4-ylthio)-1-carbapen-2-em-3-carboxylate;

6-(1-Hydroxyethyl)-1-methyl-2-{2-[3-(3-methylimidazolio)pyrrolidin-1-ylcarbonyl]pyrrolidin-4-ylthio}-1-carbapen-2-em-3-carboxylate;

2-[2-(4-Amidinopiperazin-1-ylcarbonyl)pyrrolidin-4-ylthio]-6-(1-hydroxyethyl)-1-methyl-1-carbapen-2-em-3-carboxylic acid;

2-[2-(4-Amidinopiperazin-1-ylcarbonyl)-1-methylpyrrolidin-4-ylthio]-6-(1-hydroxyethyl)-1-methyl-1-carbapen-2-em-3-carboxylic acid;

2-[2-(4-Amidinohomopiperazin-1-ylcarbonyl)pyrrolidin-4-ylthio]-6-(1-hydroxyethyl)-1-methyl-1-carbapen-2-em-3-carboxylic acid;

2-[2-(4-Amidinohomopiperazin-1-ylcarbonyl)-1-methylpyrrolidin-4-ylthio]-6-(1-hydroxyethyl)-1-methyl-1-carbapen-2-em-3-carboxylic acid;

2-[2-(3-Aminoazetidin-1-ylcarbonyl)pyrrolidin-4-ylthio]-6-(1-hydroxyethyl)-1-methyl-1-carbapen-2-em-3-carboxylic acid;

2-[2-(3-Acetimidoylaminoazetidin-1-ylcarbonyl)pyrrolidin-4-ylthio]-6-(1- hydroxyethyl)-1-methyl-1- carbapen-2-em-3-carboxylic acid;

2-[2-(3-Formimidoylaminoazetidin-1-ylcarbonyl)pyrrolidin-4-ylthio]-6-(1-hydroxyethyl)-1-methyl-1-carbapen-2-em-3-carboxylic acid;

2-[2-(3-Aminoazetidin-1-ylcarbonyl)-1-methylpyrrolidin-4-ylthio]-6-(1-hydroxyethyl)-1-methyl-1-carbapen-2-em-3-carboxylic acid;

6-(1-Hydroxyethyl)-1-methyl-2-{2-[3-(4-methyl-1-1,2,4-triazolio)pyrrolidin-1-ylcarbonyl]pyrrolidin-4-ylthio}-1-carbapen-2-em-3-carboxylate;

6-(1-Hydroxyethyl)-1-methyl-2-{2-[3-(4-methyl-1-1,2,4-triazolio)azetidin-1-ylcarbonyl]pyrrolidin-4-ylthio}-1-carbapen-2-em-3-carboxylate;

6-(1-Hydroxyethyl)-1-methyl-2-[2-(3-trimethylammonioazetidin-1-ylcarbonyl)pyrrolidin-4-ylthio]-1-carbapen-2-em-3-carboxylate;

6-(1-Hydroxyethyl)-1-methyl-2-{2-[3-(3-methyl-1-imidazolio)azetidin-1-ylcarbonyl]pyrrolidin-4-ylthio}-1-carbapen-2-em-3-carboxylate;

2-[2-{3-[3-(2-Fluoroethyl)-1-imidazolio]azetidin-1-ylcarbonyl}pyrrolidin-4-ylthio]-6-(1-hydroxyethyl)-1-methyl-1-carbapen-2-em-3-carboxylate;

2-{2-[3-[(2-Fluoroethyl)dimethylammonio]azetidin-1-ylcarbonyl}pyrrolidin-4-ylthio)-6-(1-hydroxyethyl)-1-methyl-1-carbapen-2-em-3-carboxylate;

2-[2-(3-Acetimidoylaminoazetidin-1-ylcarbonyl)pyrrolidin-4-ylthio]-6-(1-hydroxyethyl)-1-methyl-1-carbapen-2-em-3-carboxylic acid;

and pharmaceutically acceptable salts thereof.

The most preferred compounds are:

6-(1-Hydroxyethyl)-1-methyl-2-[2-(3-trimethylammoniopyrrolidin-1-ylcarbonyl)pyrrolidin-4-ylthio]-1-carbapen-2-em-3-carboxylate;

2-{2-[3-(Carbamoylmethyldimethylammonio)pyrrolidin-1-ylcarbonyl]pyrrolidin-4-ylthio}-6-(1-hydroxyethyl)-1-methyl-carbapen-2-em-3-carboxylate;

2-[2-{3-[(2-Hydroxyethyl)dimethylammonio]pyrrolidin-1-ylcarbonyl}pyrrolidin-4-ylthio]-6-(1-hydroxyethyl)-1-methyl-1- carbapen[-2-em-3-carboxylate;

2-[2-{3-[N-[2-Fluoroethyl)-N,N-dimethylammonio]-pyrrolidin-1-ylcarbonyl}pyrrolidin-4-ylthio]-6-(1-hydroxyethyl)-1-methyl-1-carbapen-2-em-3-carboxylate;

6-(1-Hydroxyethyl)-1-methyl-2-{2-[3-(3-methylimidazolio)pyrrolidin-1-ylcarbonyl]pyrrolidin-4-ylthio}-1-carbapen-2-em-3-carboxylate;

2-[2-(4-Amidinopiperazin-1-ylcarbonyl)pyrrolidin-4-ylthio]-6-(1-hydroxyethyl)-1-methyl-1-carbapen-2-em-3-carboxylic acid;

2-[2-(4-Amidinopiperazin-1-ylcarbonyl)-1-methylpyrrolidin-4-ylthio]-6-(1-hydroxyethyl)-1-methyl-1-carbapen-2-em-3-carboxylic acid;

2-[2-(4-Amidinohomopiperazin-1-ylcarbonyl)pyrrolidin-4-ylthio]-6-(1-hydroxyethyl)-1-methyl-1-carbapen-2-em-3-carboxylic acid;

2-[2-(4-Amidinohomopiperazin-1-ylcarbonyl)-1-methylpyrrolidin-4-ylthio]-6-(1-hydroxyethyl)-1-methyl-1-carbapen-2-em-3-carboxylic acid;

2-[2-(3-Aminoazetidin-1-ylcarbonyl)pyrrolidin-4-ylthio]-6-(1-hydroxyethyl)-1-methyl-1-carbapen-2-em-3-carboxylic acid;

2-[2-(3-Acetimidoylaminoazetidin-1-ylcarbonyl)pyrrolidin-4-ylthio]-6-(1-hydroxyethyl)-1-methyl-1-carbapen-2-em-3-carboxylic acid;

2-[2-(3-Formimidoylaminoazetidin-1-ylcarbonyl)pyrrolidin-4-ylthio]-6-(1-hydroxyethyl)-1-methyl-1-carbapen-2-em-3-carboxylic acid;

2-[2-(3-Aminoazetidin-1-ylcarbonyl)-1-methylpyrrolidin-4-ylthio]-6-(1-hydroxyethyl)-1-methyl-1-carbapen-2-em-3-carboxylic acid;

6-(1-Hydroxyethyl)-1-methyl-2-{2-[3-(4-methyl-1-1,2,4-triazolio)pyrrolidin-1-ylcarbonyl]pyrrolidin-4-ylthio}-1-carbapen-2-em-3-carboxylate;

6-(1-Hydroxyethyl)-1-methyl-2-{2-[3-(4-methyl-1-1,2,4-triazolio)azetidin-1-ylcarbonyl]pyrrolidin-4-ylthio}-1-carbapen-2-em-3-carboxylate;

6-(1-Hydroxyethyl)-1-methyl-2-[2-(3-trimethylammonioazetidin-1-ylcarbonyl)pyrrolidin-4-ylthio]-1-carbapen-2-em-3-carboxylate;

6-(1-Hydroxyethyl)-1-methyl-2-{2-[3-(3-methyl-1-imidazolio)azetidin-1-ylcarbonyl]pyrrolidin-4-ylthio}-1-carbapen-2-em-3-carboxylate;

and pharmaceutically acceptable salts thereof.

The compounds of the formula (I) can be prepared by a variety of methods, whose general techniques are known in the art for the preparation of compounds of this type. For example, they may be prepared by reacting a compound of formula (II):

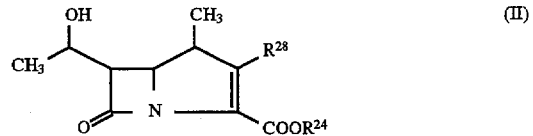

[in which $R^{24}$ represents a carboxy-protecting group, as exemplified below, and $R^{28}$ represents an alkanesulfonyloxy group, an arylsulfonyloxy group, a dialkylphosphoryloxy group, a diarylphosphoryloxy group (as exemplified hereafter in relation to $R^{25}$) or a group of formula —S(—O)$R^{27}$, where $R^{27}$ represents an alkyl group, a haloalkyl group, an acetamidoalkyl group, an acetamidoalkenyl group, an aryl group, or an aromatic heterocyclic group] with a compound of formula (III):

(in which $R^{26}$ represents any of the groups or atoms represented by $R^1$ or any such group or atom in which any active group is protected, and A' represents any of the groups or atoms represented by A or any such group or atom in which any active group is protected) and then, if necessary removing any protecting group.

In the above formulae, $R^{24}$ represents a carboxy-protecting group. Examples of such groups include: alkyl groups, such as the methyl, ethyl and t-butyl groups; aralkyl groups, such as the benzyl, benzhydryl (diphenylmethyl), 4-nitrobenzyl and 2-nitrobenzyl groups; alkenyl groups, such as the allyl, 2-chloroallyl and 2-methylallyl group; halogenated alkyl groups, such as the 2,2,2-trichloroethyl, 2,2-dibromoethyl and 2,2,2-tribromoethyl groups; and the 2-trimethylsilylethyl group.

A' and $R^{26}$ have the same meaning as defined for A and $R^1$, respectively, or, if A' or $R^{26}$ requires a protecting group, A' or $R^{26}$ includes such a protecting group. Examples of such protecting groups include: normal hydroxy-, imino-, amino- and carboxy-protecting group; and examples include: the p-nitrobenzyloxycarbonyl and p-nitrobenzyl groups. However, many such groups are well known to those skilled in the art and any group capable of protecting an active group in this type of compound may equally be used here.

$R^{27}$ represents:

an alkyl group, preferably having from 1 to 4 carbon atoms, such as a methyl, ethyl, propyl or isopropyl group; a halogenated alkyl group, preferably having from 1 no 4 carbon atoms, such as a fluoromethyl, chloromethyl, fluoroethyl, chloroethyl, fluoropropyl, difluoromethyl, difluoroethyl, dichloroethyl, trifluoromethyl or trifluoroethyl group;

an acetamidoalkyl group, such as a 2-acetamidoethyl group;

an acetamidoalkenyl group, such as a 2-acetamidovinyl group;

an aryl group, such as an optionally substituted phenyl or naphthyl group, which may optionally have from one to three of the following substituents, which may be the same or different: fluorine, chlorine and bromine atoms, methyl, ethyl, propyl, isoproyl, methoxy, ethoxy, propoxy, isopropoxy, methoxycarbonyl, ethoxycarbonyl, t-butoxycarbonyl, carbamoyl, mono- and di- alkylcarbamoyl (wherein examples of alkyl groups include, for example, the methyl, ethyl and propyl groups), nitro, hydroxy and cyano groups; or an aromatic heterocyclic group, such as an optionally substituted pyridyl or pyrimidinyl group, which may optionally have from one to three of the following substituents, which may be the same or different: fluorine, chlorine and bromine atoms, methyl, ethyl, propyl and isopropyl groups.

In more detail, the compounds of the formula (I) invention may preferably be prepared as illustrated the following Reaction Schemes A and B:

Reaction Scheme A:

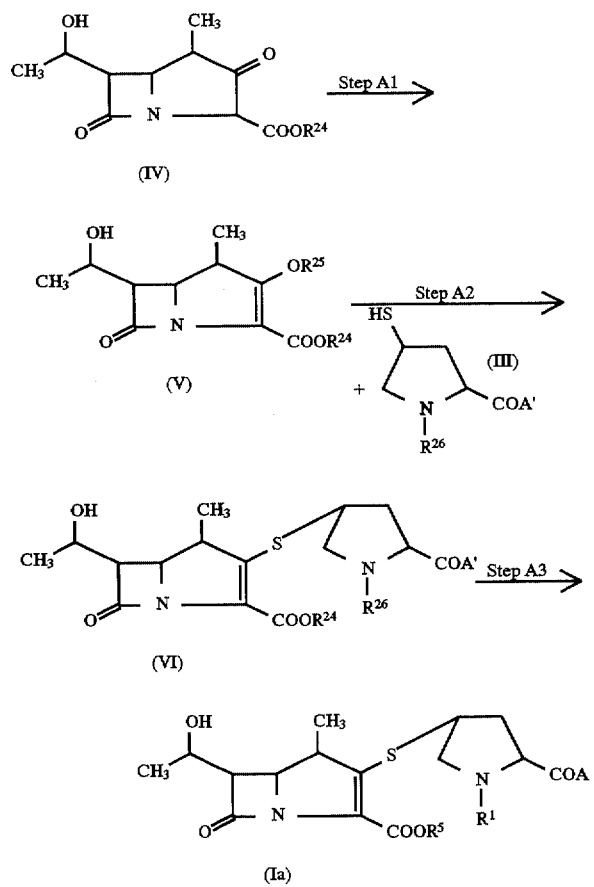

Reaction Scheme B:

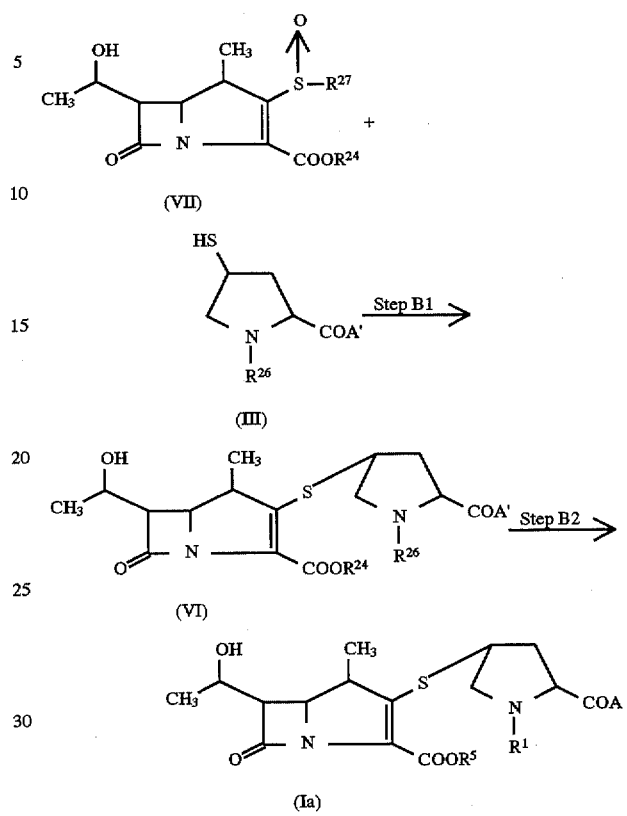

In the above formulae, A', $R^1$, $R^5$, $R^{24}$, $R^{26}$ and $R^{27}$ are as defined above and $R^{25}$ is defined below.

$R^{25}$ represents a sulfonyl or phosphoryl group, for example: an alkanesulfonyl group, such as a methanesulfonyl, trifluoromethanesulfonyl, ethanesulfonyl, propanesulfonyl, isopropanesulfonyl or butanesulfonyl group; an arylsulfonyl group, such as a phenylsulfonyl, tolylsulfonyl or naphthylsulfonyl group; a dialkylphosphoryl group, such as a dimethylphosphoryl, diethylphosphoryl, dipropylphosphoryl, diisopropylphosphoryl, dibutylphosphoryl or dipentylphosphoryl group; or a diarylphosphoryl group, such as a diphenylphosphoryl or ditolylphosphoryl group.

In Step A1 of Reaction Scheme A, a compound of formula (V) is prepared by reacting a compound of formula (IV) with an alkanesulfonic acid anhydride, an arylsulfonic acid anhydride, a dialkylphosphoryl halide or a diarylphosphoryl halide in the presence of a base to produce a compound of formula (V).

Examples of reagents which may be used in this Step include: alkanesulfonic acid anhydrides, such as methanesulfonic acid anhydride, trifluoromethanesulfonic acid anhydride or ethanesulfonic acid anhydride; anhydrous arylsulfonic acid anhydrides, such as anhydrous benzenesulfonic acid anhydride or p-toluenesulfonic acid anhydride; dialkylphosphoryl halides, such as dimethylphosphoryl chloride or diethylphosphoryl chloride; and diarylphosphoryl chlorides, such as diphenylphosphoryl chloride or diphenylphosphoryl bromide. Of these, we especially prefer p-toluenesulfonic acid anhydride or diphenylphosphoryl chloride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, especially halogenated aliphatic hydrocarbons, such as methylene chloride, 1,2-dichloroethane or chloroform; nitriles, such as acetonitrile; and amides, especially fatty acid amides, such as N,N-dimethylformamide or N,N-dimethylacetamide.

There is likewise no particular limitation on the nature of the base used for the reaction, provided that it has no adverse effect on other parts of the molecule, especially the β-lactam ring. Preferred examples of such bases include: organic bases, especially tertiary amines, such as triethylamine, diisopropylethylamine or 4-dimethylaminopyridine.

The reaction can take place over a wide range of temperatures, and the precise reaction temperature is not critical to the invention. In general, we find it convenient to carry out the reaction at a relatively low temperature in order to control side reactions, for example at a temperature of from −20° C. to about 40° C. The time required for the reaction may also vary widely, depending on many factors, notably the reaction temperature and the nature of the reagents and solvent employed. However, provided that the reaction is effected under the preferred conditions outlined above, a period of from 10 minutes to 5 hours will usually suffice.

The reaction mixture thus obtained can be treated, in Step A2 of the Reaction Scheme, with a compound of formula (III) in the presence of a base and without any intermediate isolation or purification of the compound of formula (V). There is no particular limitation on the nature of the base used for this step and preferred examples include: organic bases, especially tertiary amines, such as triethylamine or diisopropylethylamine; and inorganic bases, such as potassium carbonate or sodium carbonate.

The reaction can take place over a wide range of temperatures, and the precise reaction temperature is not critical to the invention. In general, we find it convenient to carry out the reaction at a temperature of from −20° C. to room temperature. The time required for the reaction may also vary widely, depending on many factors, notably the reaction temperature and the nature of the reagents and solvent employed. However, provided that the reaction is effected under the preferred conditions outlined above, a period of from 30 minutes to 108 hours will usually suffice.

After completion of the reaction, the desired compound of formula (VI) can be recovered from the reaction mixture by conventional means. An example of one such technique comprises: concentrating the reaction mixture by distilling off the solvent, preferably under reduced pressure; adding a water-immiscible organic solvent to the residue; washing the organic phase water; and finally distilling off the organic solvent. If necessary, the desired compound thus obtained can be further purified by conventional means, for example, by recrystallization, reprecipitation or the various chromatography techniques, notably column chromatography or preparative thin layer chromatography. Alternatively, if desired, the reaction mixture obtained in this Step can also be used as a starting material for subsequent Steps without isolation of the compound of formula (VI).

In Step A3, if necessary, the compound of formula (VI) obtained in Step A2 can be converted to a free carboxylic acid derivative by eliminating the carboxy-protecting group represented by $R^{24}$ according to conventional means. The reaction used to remove the protecting group represented by $R^{24}$ will, of course, vary depending upon the nature of the protecting group, but any reaction known in the art for the deprotection of compounds of this type may equally be used here.

For example, where the substituent on the compound of formula (VI) represented by $R^{24}$ is a protecting group capable of removal by reduction, for example, a halogenated alkyl, aralkyl or benzhydryl group, the reaction can preferably be carried out by contacting the compound of formula (VI) with a reducing reagent. Preferred examples of reducing reagents which may be used for this reaction include: where the carboxy-protecting is, for example, a halogenated alkyl group (such as a 2,2-dibromoethyl or 2,2,2-trichloroethyl group), zinc and acetic acid; and where it is, for example, an aralkyl group (such as a benzyl, 4-nitrobenzyl group or a benzhydryl group), hydrogen and a catalyst for use in catalytic reduction, such as palladium on charcoal or an alkali metal sulfide, such as sodium sulfide or potassium sulfide. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as tetrahydrofuran or dioxane; aliphatic acids, such as acetic acid; and mixtures of water with one or more of these organic solvents.

The reaction can take place over a wide range of temperatures, and the precise reaction temperature is not critical to the invention. In general, we find it convenient to carry out the reaction at a temperature of from 0° C. to about room temperature. The time required for the reaction may also vary widely, depending on many factors, notably the reaction temperature and the nature of the reagents and solvent employed. However, provided that the reaction is effected under the preferred conditions outlined above, a period of from 5 minutes to 12 hours will usually suffice.

After completion of the reaction, the desired compound can be recovered from the reaction mixture by conventional means. An example of one such technique comprises: filtering off insoluble materials deposited in the reaction mixture and distilling off the solvent from the filtrate.

The compound thus obtained can, if necessary, be further purified by conventional means, for example, by recrystallization, or the various chromatography techniques, notably column chromatography or preparative thin layer chromatography.

If necessary, the carboxy group deprotected as described above can be converted to an ester group capable of hydrolyzing in vivo and the ester compound can be purified as a pharmacologically acceptable salt by conventional means.

When A' or $R^{26}$ contains a hydroxy-, imino-, amino- or carboxy-protecting group (for example, a p-nitrobenzyloxycarbonyl group or a p-nitrobenzyl group), the protecting group can be removed at the same time as the aforementioned removal of the carboxy-protecting group (when $R^{24}$ is a p-nitrobenzyl group.).

Alternatively compounds of formula (Ia) can also be prepared by Reaction Scheme B, as shown above.

The compound of formula (VII) used as a starting compound in this reaction scheme is disclosed, for example, in Japanese Patent Kokai Publication No. Sho 62-30781.

In Step B1 of this Reaction Scheme, a compound of formula (VI) is prepared by reacting the compound of formula (VII) with a mercaptan of formula (III) in the presence of a base. The reaction is also normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: esters, such as ethyl acetate; ethers, such as tetrahydrofuran; nitriles, such as acetonitrile; amides, especially fatty acid amides, such as N,N-dimethylformamide; sulfoxides, such as dimethyl sulfoxide; water; and mixtures of any two or more of these solvents. There is also no particular limitation on the nature of the base employed for the reaction, provided that it has no adverse effect on other parts of the molecule, especially the β-lactam ring. Examples of such bases include: organic bases, especially tertiary amines, such as diisopropylethylamine, triethylamine, N-methylpiperidine or 4-dimethylaminopyridine; and inorganic bases, especially alkali metal carbonates and hydrogencarbonates, such as potassium carbonate or sodium hydrogencarbonate.

The reaction can take place over a wide range of temperatures, and the precise reaction temperature is not critical to the invention. In general, we find it convenient to carry out the reaction at a relatively low temperature in order to reduce side reactions, for example at a temperature of from −20° C. to 40° C. The time required for the reaction may also vary widely, depending on many factors, notably the reaction temperature and the nature of the reagents and solvent employed. However, provided that the reaction is effected under the preferred conditions outlined above, a period of from 15 minutes to 75 hours will usually suffice.

After completion of the reaction, the desired compound of formula (VI) of the reaction can be recovered from the reaction mixture by conventional means.

Compounds of formula (Ia) can then be prepared from this compound of formula (VI) by removing the protecting groups which may be present in the groups represented by A' and $R^{26}$ as described in Reaction Scheme A, if any, and by removing any other protecting group or, if necessary, by converting a deprotected carboxy group to an ester group capable of hydrolyzing in vivo.

Compounds of formula (Ia) prepared as described above can be converted to a pharmacologically acceptable salt using procedures and techniques well known in the field of β-lactam antibiotics.

The mercaptan of formula (III) used as a starting material in both of the above Reaction Schemes can be prepared following the procedure described in Japanese Patent Kokai Application No. Hei 2-28180 and No. Hei 2-3687, and Japanese Patent Application No. Hei 3-27059 and No. Hei 3-13145.

The compounds of the formula (I)" may be prepared by a variety of processes well known in the art for the preparation of compounds of this type. For example, in general terms, they may be prepared by reacting a carbapenem compound of formula (II)":

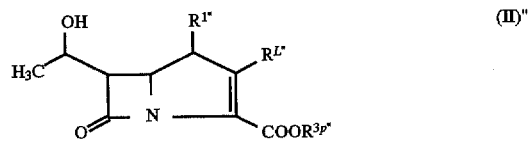

(in which $R^{1"}$ is as defined above, $R^{L"}$ represents a sulfonyloxy or phosphoryloxy group or a group of formula —S(O)$R^{L1"}$, $R^{L1"}$ represents an alkyl group, a haloalkyl group, an alkanoylaminoalkyl group, an alkenoylaminoalkyl group, an aryl group or an aromatic heterocyclic group, and $R^{3p"}$ represents a carboxy-protecting group) with a pyrrolidine derivative of formula (III)":

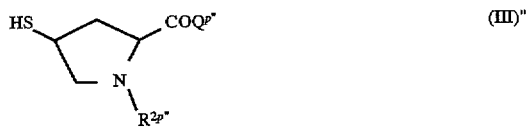

(in which $R^{2p"}$ represents any of the groups or atoms represented by $R^{2"}$ or any such group or atom which has been protected, and $Q^{p"}$ represents any of the groups or atoms represented by Q" or any such group or atom which has been protected or any such group in which a quaternary nitrogen atom is replaced by a corresponding tertiary nitrogen atom, and, where the group $Q^{p"}$ contains a quaternary nitrogen atom, the compound is accompanied by a balancing anion), and, if necessary, converting any non-quaternized nitrogen atom to the corresponding quaternary nitrogen in the group of formula (Q-I)", (Q-II)", (Q-IV)", (Q-V)" or (Q-VI)" or in the group represented by Z", and, if necessary, removing any protecting groups, and optionally salifying and/or esterifying the product.

In more detail, the reactions involved may be as illustrated in the following Reaction Schemes A" and B".

Reaction Scheme A":

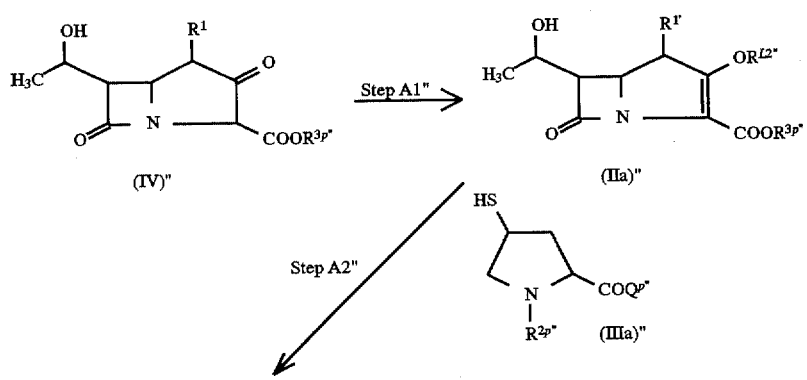

Reaction Scheme A":

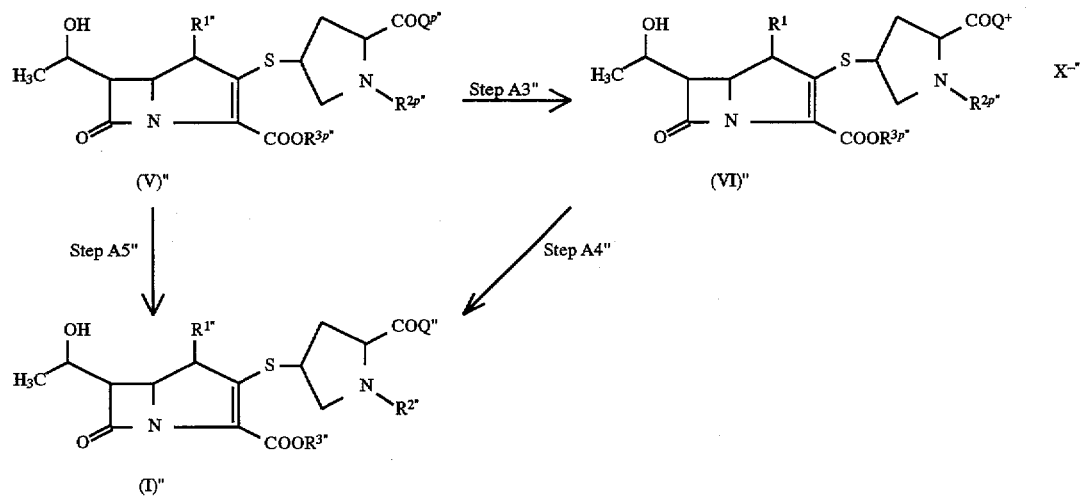

Reaction Scheme B":

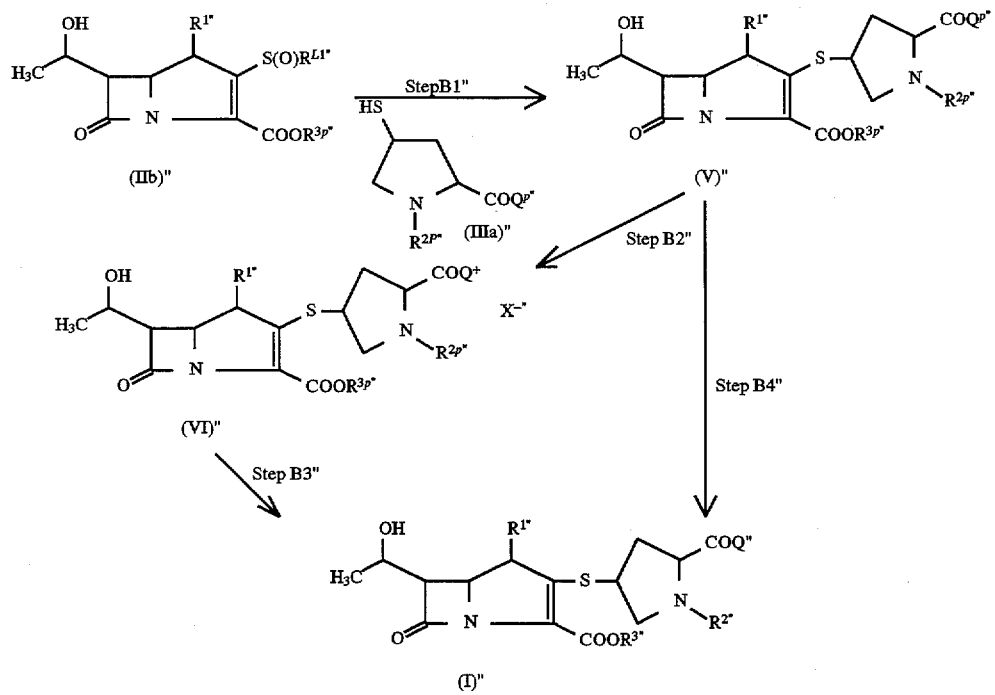

In the above formulae, $R^{1"}$, $R^{2"}$, $R^{3"}$, $R^{2p"}$, $R^{3p"}$, $Q^{p"}$ and $Q"$ as defined above.

$R^{L1"}$ represents:

an alkyl group, such as a methyl, ethyl, propyl or isopropyl group;

a haloalkyl group, such as a fluoromethyl, chloromethyl, fluoroethyl, chloroethyl, fluoropropyl, difluoromethyl, difluoroethyl, dichloroethyl, trifluoromethyl or trifluoroethyl group;

a 2-acetamidoethyl group;

a 2- acetamidovinyl group;

an optionally substituted aryl group, such as a phenyl or naphthyl group which may be unsubstituted or may have from 1 to 3 substituents which may be the same or different from one another, for example: fluorine, chlorine, bromine, methyl, ethyl, propyl, isopropyl, methoxy, ethoxy, propoxy, isopropoxy, methoxycarbonyl, ethoxycarbonyl, t -butoxycarbonyl, nitro, carbamoyl, mono- and di-substituted alkylcarbamoyl (where the alkyl group is, for example, methyl, ethyl or propyl), hydroxy or cyano;

or an optionally substituted aromatic heterocyclic group, such as a pyridyl and pyrimidyl group, which may be unsubstituted or may have from 1 to 3 substituents which may be the same or different from one another, for example: fluorine, chlorine, bromine, methyl, ethyl, propyl and isopropyl.

$R^{L2"}$ represents:

- an alkanesulfonyl group, such as a methanesulfonyl, trifluoromethanesulfonyl, ethanesulfonyl, propanesulfonyl, isopropanesulfonyl or butanesulfonyl group;
- an arylsulfonyl group, such as a phenylsulfonyl, tolylsulfonyl, e.g. p-tolylsulfonyl, or 1- or 2-naphthylsulfonyl group;
- a dialkylphosphoryl group, such as a dimethylphosphoryl, diethylphosphoryl, dipropylphosphoryl, diisopropylphosphoryl, dibutylphosphoryl or dipentylphosphoryl group;
- or a diarylphosphoryl group, such as a diphenylphosphoryl or ditolylphosphoryl group.

$Q^{+"}$ represents any of the groups represented by $Q"$ which includes a quaternary nitrogen atom.

$X^{-"}$ represents an anjou, for example a chlorine atom, a bromine atom, an iodine atom, a monomethyl sulfate group, a sulfate group, a methanesulfonyloxy group, a toluenesulfonyloxy group, a trifluoromethanesulfonyloxy group or a fluorosulfonyloxy group.

If $Q^{p"}$ or $R^{3p"}$ includes a protecting group, this may be selected from the many such groups well known to those skilled in the art and commonly used for the protection of hydroxy groups, imino groups, amino groups or carboxy groups. Such groups are described fully in many standard texts, for example T. W. Greene, "Protective Groups in Organic Synthesis", published by John Wiley & Son, the disclosure of which is incorporated herein by reference. Examples of such groups typically include the p-nitrobenzyloxycarbonyl and p-nitrobenzyl groups.

As defined above, $R^{3p"}$ represents a protecting group for the carboxy group, such as an alkyl group, e.g. a methyl, ethyl or t-butyl group; an aralkyl group, e.g. a benzyl, diphenylmethyl, 4-nitrobenzyl or 2-nitrobenzyl group; an alkenyl group, e.g. an allyl, 2-chloroallyl or 2-methylallyl group; a haloalkyl group, e.g. a 2,2,2-trichloroethyl, 2,2-dibromoethyl or 2,2,2-tribromoethyl group; or a 2-trimethylsilylethyl group.

In Step A1 of Reaction Scheme A", a carbapenam compound of formula (IV) is converted to a carbapenem compound of formula (IIa) by reaction with an active sulfonyl or phosphoryl compound containing a group corresponding to the group $R^{L2"}$, for example an alkanesulfonic anhydride, an arylsulfonic anhydride, a dialkylphosphoryl halide or a diarylphosphoryl halide.

This reaction is normally and preferably effected in the presence of a base. There is no particular restriction on the nature of the base employed, provided that it has no adverse effect on other parts of the molecule, notably the β-lactam ring, and preferred examples include organic bases such as triethylamine, diisopropylethylamine and 4-dimethylaminopyridine.

Examples of sulfonyl or phosphoryl compounds which may be employed in this reaction include: alkanesulfonic anhydrides, such as methanesulfonic anhydride, trifluoromethanesulfonic anhydride and ethanesulfonic anhydride; arylsulfonic anhydrides, such as benzenesulfonic anhydride and p-toluenesulfonic anhydride; dialkylphosphoryl halides, such as dimethylphosphoryl chloride and diethylphosphoryl chloride; and diarylphosphoryl halides, such as diphenylphosphoryl chloride and diphenylphosphoryl bromide. Of these reagents, we particularly prefer p-toluenesulfonic anhydride and diphenylphosphoryl chloride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride, 1,2-dichloroethane and chloroform; nitriles, such as acetonitrile; and amides, such as dimethylformamide and dimethylacetamide.

The reaction can take place over a wide range of temperatures, and the precise reaction temperature is not critical to the invention. In general, we find it convenient to carry out the reaction at a relatively low temperature, for example from −20° C. to 40° C., in order to suppress any side reactions. The time required for the reaction may also vary widely, depending on many factors, notably the reaction temperature and the nature of the reagents and solvent employed. However, provided that the reaction is effected under the preferred conditions outlined above, a period of from 10 minutes to 5 hours will usually suffice.

The compound of formula (IIa)" thus obtained is not normally isolated; instead, in Step A2", the reaction mixture is reacted, without any isolation, with a mercaptan of formula (IIIa)" in the presence of a base to obtain a compound of formula (V)". The resulting compound may then, if necessary, be subjected, in Step A5", to a deprotection reaction to eliminate any protecting group in the groups represented by $R^{3p"}$ or $Q^{p"}$ and thus to prepare the desired compound of formula (I)".

There is no particular limitation on the nature of the base which may be employed in Step A2, provided that it has no adverse effect on other parts of the molecule, notably the β-lactam ring, and preferred examples include: organic bases, such as triethylamine and diisopropylethylamine; and inorganic bases, such as potassium carbonate and sodium carbonate. The reaction can take place over a wide range of temperatures and the precise reaction temperature is not critical to the invention. In general, we find it convenient to carry out the reaction at a temperature of from −20° C. to room temperature. The time required for the reaction may also vary widely, depending on many factors, notably the reaction temperature and the nature of the reagents and solvent employed. However, provided that the reaction is effected under the preferred conditions outlined above, a period of from 30 minutes to 5 days will usually suffice.

After completion of the reaction, the desired compound of formula (V)" can be collected from the reaction mixture by any conventional procedure. For example, in one suitable recovery procedure, the solvent is removed from the reaction mixture by distillation to obtain the desired compound. Alternatively, in the case of the non-quaternary compounds, the solvent is removed, preferably by evaporation, the residue is extracted with an organic solvent, and the extract is washed with water and dried, after which the solvent is removed by evaporation. The compound thus obtained can be further purified, if necessary, by conventional procedures, such as recrystallization, reprecipitation or the various chromatography techniques, notably column chromatography. If desired, the compound can be purified by subjecting the reaction mixture directly to reprecipitation. Alternatively, if desired, the compound of formula (V)" can be subjected to the subsequent carboxy deprotection reaction in Step A5 without isolation.

If necessary, in Step A5", the compound of formula (V)" obtained in Step A2" can be converted to a carboxylic acid derivative of formula (I)" by eliminating the protecting group $R^{3p''}$ for the carboxy group by conventional means. The nature of the reaction employed for the elimination of the protecting group will, of course, vary, depending upon the nature of the protecting group, as is well known in the art. For example, where the protecting group can be eliminated by reduction (as can the haloalkyl groups, the aralkyl groups, and the benzyhydryl group), this can be achieved by bringing the compound of formula (V)" into contact with a reducing agent. Examples of preferred reducing agents which may be employed in this reaction include: zinc and acetic acid when the carboxy-protecting group is, for example, a haloalkyl group (such as a 2,2-dibromoethyl or 2,2,2,-trichloroethyl group); or, when the protecting group is for example, an aralkyl group (such as a benzyl or 4-nitrobenzyl group) or a benzhydryl group, it is possible to use as the reducing agent either an alkali metal sulfide (such as sodium sulfide or potassium sulfide) or hydrogen in the presence of a reducing catalyst (such as palladium-on-carbon). The reducing reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as tetrahydrofuran or dioxan; fatty acids, such as acetic acid; and mixtures of any one or more of such organic solvents with water. The reaction can take place over a wide range of temperatures, and the precise reaction temperature is not critical to the invention. In general, we find it convenient to carry out the reaction at a temperature of from 0° C. to approximately room temperature. The time required for the reaction may also vary widely, depending on many factors, notably the reaction temperature and the nature of the reagents and solvent employed. However, provided that the reaction is effected under the preferred conditions outlined above, a period of from 5 minutes to 12 hours will usually suffice.

If $Q^{p''}$ and/or $R^{2p''}$ includes a protecting group for a hydroxy group, an imino group, an amino group or a carboxy group (for example a p-nitrobenzyloxycarbonyl group or a p-nitrobenzyl group), such a protecting group can be eliminated simultaneously with the elimination of the above-mentioned carboxy-protecting group (in the case where $R^{3p''}$ is a p-nitrobenzyl group).

After completion of the reaction, the desired compound of the present invention can be collected from the reaction mixture by conventional means. For example, one suitable recovery procedure comprises: removing insolubles precipitated from the reaction mixture by filtration; and then removing the solvent by distillation. The compound thus obtained can be further purified, if necessary, by conventional procedures, such as recrystallization, reprecipitation or the various chromatography techniques, notably column chromatography.

Alternatively, where Q" represents one of the groups containing a quaternary nitrogen atom, it may be prepared from a mercaptan of formula (IIIa)" in which $Q^{p''}$ represents a corresponding tertiary nitrogen atom. In this case, in Step A2", the compound of formula (IIa)" is reacted with such a mercaptan of formula (IIIa)", to give a compound of formula (V)". This is then converted to a corresponding quaternary ammonium compound in Step A3", and then, if necessary, deprotected in Step A4", to give the desired compound of formula (I)".

Quaternization in Step A3" can be carried out using methods well known in the art, for example by reacting the compound of formula (V)" with a compound of formula R"X", in which R" represents an optionally substituted alkyl group, which may be as defined above in relation to any of the groups attached to a quaternary nitrogen atom in the groups represented by Q" or Z". X" represents a halogen atom (for example a chlorine atom, a bromine atom or an iodine atom), a monomethyl sulfate group, a sulfate group, or a sulfonyloxy group (for example a methanesulfonyloxy, toluenesulfonyloxy, trifluoromethanesulfonyloxy or fluorosulfonyloxy group). In the reaction for converting the nitrogen atom into a quaternary atom, the compounds of formulae (V)" and R"X" may be reacted directly, or a solvent may be used. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride, 1,2-dichloroethane or chloroform; nitriles, such as acetonitrile; ethers, such as tetrahydrofuran; esters, such as ethyl acetate; and amides, such as dimethylformamide or dimethylacetamide. The reaction can take place over a wide range of temperatures, and the precise reaction temperature is not critical to the invention. In general, we find it convenient to carry out the reaction at a temperature of from −20° C. to 100° C.

After completion of the reaction, the desired compound of formula (VI)" can be collected from the reaction mixture by conventional means. For example, the solvent in the reaction mixture is simply evaporated off. The compound thus obtained can be further purified, if necessary, by conventional procedures, such as recrystallization, reprecipitation or the various chromatography techniques, notably column chromatography. Alternatively, the desired compound can be purified by subjecting the reaction mixture to precipitation. If required, the compound of formula (VI)" can be subjected, in Step A4", to the subsequent step of carboxy deprotection without isolation, which may be carried out as described above in relation to Step A5.

The carboxy group of the compound thus obtained can be converted to an ester group, particularly to such a group which undergoes hydrolysis under physiological conditions, by conventional means. When $R^{3''}$ is an ester which undergoes hydrolysis under physiological conditions [such as an alkanoyloxyalkyl group, e.g. a pivaloyloxymethyl or acetoxymethyl group, an alkoxycarbonyloxyalkyl group, e.g. a 1-(ethoxycarbonyloxy)ethyl or 1-(isopropoxycarbonyloxy)ethyl group, or a phthalidyl, indanyl, methoxymethyl or 2-oxo-5-methyl-1,3-dioxolen-4-ylmethyl group], the compound of formula (I)" need not be deprotected and can be administered directly to a patient, since such a compound can be hydrolyzed in a living body under physiological conditions.

Alternatively, the compound (V)" can be prepared, as shown in Reaction Scheme B", from a compound (IIb)". This compound of formula (IIb)" can be synthesized by the method disclosed in Japanese Unexamined Patent Publication No. Sho-62-30781 (Kokai). The reaction of the compound of formula (IIb)" with a mercaptan of formula (IIIa)" in the presence of a base to give a compound of formula (V)" is normally and preferably carried out in an inert solvent. There is no particular restriction on the nature of the solvent to be employed, provided that it has no adverse effect on the reaction or on the reagents involved and that it can dissolve the reagents, at least to some extent. Examples of suitable solvents include: tetrahydrofuran, acetonitrile, dimethylformamide, dimethyl sulfoxide, water and mixtures of any two or more of these solvents. There is also no particular limitation on the nature of the base employed, provided that it does not affect other portions of the compound, particularly the β-lactam ring, and examples include: organic bases, such as diisopropylethylamine, triethylamine, N-methylpiperidine or 4-dimethylaminopyridine; and inorganic bases, such as potassium carbonate or sodium hydrogencarbonate. The reaction can take place over a wide range of temperatures, and the precise reaction temperature is not critical to the invention. In general, we find it convenient to carry out the reaction at a relatively low temperature in order to suppress any side reaction, usually at a temperature of from −20° C. to 40° C. The time required for the reaction may also vary widely, depending on many factors, notably the reaction temperature and the nature of the reagents and solvent employed. However, provided that the reaction is effected under the preferred conditions outlined above, a period of from 5 minutes to 5 days will usually suffice.

After completion of the reaction, the desired compound of formula (V)" can be collected from the reaction mixture by conventional means, as described in relation to Reaction Scheme A". It may then be subjected to Step B2" and B3" or Step B4", which correspond to Steps A3" and A4" or A5" of Reaction Scheme A".

The compounds prepared as described above may be salified and/or esterified by conventional means well known in the art.

The compounds of the present invention exhibit excellent antibacterial activity with a broad antibacterial spectrum and have the ability to inhibit the activity of β-lactamase, unlike most thienamycin-type compounds, which are liable to be metabolized in the mammalian body. The derivatives of the present invention, in addition, exhibit excellent stability against dehydropeptidase I, which is also known to catalyze the inactivation of compounds of the thienamycin type. The derivatives of the present invention showed a strong antibacterial activity against a wide range of pathogenic bacteria including Gram-positive bacteria such as *Staphylococcus aureus*, and *Bacillus subtilis*, Gram-negative bacteria such as *Escherichia coli*, *Shigella* species, *Proteus* species, *Serratin* species, *Enterobacter* species, *Klebsiella* species and *Pseudomonas* species, and anaerobic bacteria such as *Bacteroides fragilis*.

The antibacterial activity was determined by the agar plate dilution method, and the minimal inhibitory concentrations of the compounds of the present invention against a variety of common pathogenic bacteria were determined and the results for some of the compounds are shown in the following Table 23. The compounds of the invention are identified by reference to the one of the following Examples which illustrates their preparation. The compounds of Examples 1, 4, 5, 6, 11, 15, 23, 37, 42, 43, 44, 45, 50, 54, 55, 61 and 66 were all found to be more active than imipenem against strains of *Escherichia coli* NIHJ, *Klebsiella pneumoniae* 846 and *Pseudomonas aeruginosa* 1001. The compounds also had a generally superior activity against *Staphylococcus aureus* 209P, similar to that of imipenem.

In Table 23, the compounds of the present invention are identified by reference to the one of the following Examples which illustrates its preparation.

The microorganisms used in Table 23 are identified as follows:

A:*Staphylococcus aureus* 209P;

B:*Escherichia coli* NIHJ;

C:*Pseudomonas aeruginosa* 1001.

TABLE 23

| Compound of Example No. | Microorganism | | |
|---|---|---|---|
| | A | B | C |
| 99 | 0.02 | 0.02 | 0.2 |
| 100 | ≦0.01 | ≦0.01 | 0.1 |
| 123 | ≦0.01 | ≦0.01 | 0.1 |
| 124 | ≦0.01 | ≦0.01 | 0.1 |
| 131 | ≦0.01 | ≦0.01 | 0.1 |
| imipenem | ≦0.01 | 0.05 | 3.1 |

These results demonstrate that the compounds of the present invention have activities which are, in general, better than that of imipenem: moreover, they are, unlike imipenem, resistant to dehydropeptidase I and β-lactamase.

The carbapenem-3-carboxylic acid derivatives of the present invention, therefore, are useful as therapeutic agents for the treatment and prophylaxis of infections caused by these pathogenic bacteria. The compounds may be administered in any conventional form for this purpose, and the exact formulation used will depend on the disease to be treated, the age and condition of the patient and other factors, which are well known in the art. For example, for oral administration, the compounds may be formulated as tablets, capsules, granules, powders or syrups; and for parenteral administration, they may be formulated for intravenous injection or intramuscular injection. The dosage will vary widely, depending upon the age, body weight, symptoms and condition of the patient, as well as the mode of administration and times and routine of administration; however, for an adult human patient, a daily dosage of from about 100 mg to 3000 mg is recommended, and this may be administered as a single dose or in divided doses.

In the following Examples (which illustrate the preparation of compounds according to the present invention) and preparations (which illustrate the preparation of certain starting materials), unless otherwise indicated, nuclear magnetic resonance spectrum measurements in deuterium oxide were carried out using tetramethylsilane as an external standard and those in other solvents were carried out using tetramethylsilane as an internal standard. Also, in measurement of partial sizes, the mesh sizes used are in accordance with the Tyler standard.

EXAMPLE 1

(1R,5S,6S)-2-[(2S,4S)-2-(4-Acetimidoylpiperazin-1-ylcarbonyl)pyrrolidin-4-ylthio]-6-[(1R)-1-hydroxyethyl]-1-methyl-1-carbapen-2-em-3-carboxylic acid

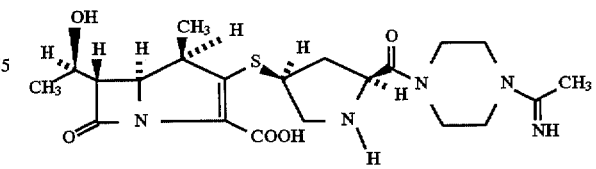

1(a) 4-Nitrobenzyl (1R,5S,6S) -2-[(2S,4S)-2-[4-(N-4-nitrobenzyloxycarbonylacetimidoyl)piperazin-1-ylcarbonyl]-1-(4-nitrobenzyloxycarbonyl)pyrrolidin-4-ylthio]-6-[(1R)-1-hydroxyethyl]-1-methyl-1-carbapen-2-em-3-carboxylate 127 μl of diphenylphosphoryl chloride and 108 μl of diisopropylethylamine were added dropwise, whilst ice-cooling, to a solution of 210 mg of 4-nitrobenzyl (1R,5R,6S)-6-[(1R)-1-hydroxyethyl]-1-methyl-2-oxo-1-carbapenam-3-carboxylate in 2.6 ml of dry acetonitrile, and the resulting mixture was stirred at the same temperature for 1 hour. At the end of this time, a solution of 450 mg of (2S,4S)-4-mercapto-2-[4-(N-4-nitrobenzyloxycarbonylacetimidoyl)piperazin-1-ylcarbonyl]-1-(4-nitrobenzyloxycarbonyl)pyrrolidine trifluoromethanesulfonate (prepared as described in Preparation 1) in 2.4 ml of dry acetonitrile and 274 µl of diisopropylethylamine were simultaneously added dropwise to the mixture, whilst ice-cooling, and the mixture was allowed to stand overnight at the same temperature. The reaction mixture was then concentrated by evaporation under reduced pressure, and the concentrate was diluted with ethyl acetate. The diluted solution was washed, in turn, with water and with an aqueous solution of sodium chloride, after which it was dried over anhydrous magnesium sulfate. The solvent was then removed by distillation under reduced pressure, and the resulting residue was purified by column chromatography through 100 ml of silica gel 60 (Merck Art No. 9385), using a 10:5:2 by volume mixture of ethyl acetate, methylene chloride and methanol as the eluent. Those fractions containing the title compound were combined and concentrated by evaporation under reduced pressure, to give 120 mg of the title compound, as an amorphous solid.

Infrared Absorption Spectrum (KBr), $v_{max}$ cm$^{-1}$: 1772, 1709, 1663, 1607, 1562, 1521, 1495, 1431, 1405, 1346, 1291, 1261, 1210.

Nuclear Magnetic Resonance Spectrum (CDCl$_3$, 270 MHz), δ ppm:

1.27 & 1.28 (together 3H, two doublets, J=7.33 & 6.84 Hz);
1.37 (3H, doublet, J=5.86 Hz);
1.60 (1H, broad singlet);
1.86–2.08 (1H, multiplet);
2.26 & 2.31 (together 3H, two singlets);
2.60–2.78 (1H, multiplet);
3.25–4.28 (15H, multiplet);
4.65–4.80 (1H, multiplet);
5.04–5.52 (6H, multiplet);
7.41–7.67 (6H, multiplet);
8.17–8.24 (6H, multiplet).

1(b) (1R,5S,6S) -2-[(2S,4S) -2-(4-Acetimidoylpiperazin-1-ylcarbonyl)pyrrolidin-4-ylthio]-6-[(1R)-1-hydroxyethyl]-1-methyl-1-carbapen-2-em-3-carboxylic acid 114 mg of 4-nitrobenzyl (1R,5S,6S)-2-[(2S,4S)-2-[4-(N-4-nitrobenzyloxycarbonylacetimidoyl)piperazin-1-ylcarbonyl]-1-(4-nitrobenzyloxycarbonyl)pyrrolidin-4-ylthio]-6-[(1R)-1-hydroxyethyl]-1-methyl-1-carbapen-2-em-3-carboxylate [prepared as described in step (a) above] were dissolved in 6 ml of a 2:1 by volume mixture of tetrahydrofuran and water, and were hydrogenated by bubbling hydrogen through it at room temperature for 2 hours in the presence of 300 mg of 10% w/w palladium-on-charcoal. At the end of this time, the catalyst was filtered off and the filtrate was washed with diethyl ether. The resulting solution was concentrated by evaporation under reduced pressure, and the residue was purified by reverse phase column chromatography through 5 ml of Cosmo Sil 75C$_{18}$-PREP (a trade mark for a product of Nacalai Tesque), using 20% v/v aqueous methanol as the eluent. Those fractions containing the title compound were combined, concentrated by evaporation under reduced pressure, and lyophilized, to give 13 mg of the title compound as a powder.

Ultraviolet absorption spectrum (H$_2$O) $\lambda_{max}$ nm: 300.

Infrared Absorption Spectrum (KBr), $v_{max}$ cm$^{-1}$: 1753, 1603, 1447, 1385, 1284, 1251.

Nuclear Magnetic Resonance Spectrum (270 MHz, D$_2$O, using sodium tetradeuteratad trimethylsilylpropionate as an internal standard), δ ppm:

1.22 (3H, doublet, J=6.84 Hz);
1.30 (3H, doublet, J=6.35 Hz);
1.58–1.68 (1H, multiplet);
2.36 (3H, singlet);
2.66–2.78 (1H, multiplet);
3.02–3.18 (2H, multiplet);
3.34–3.45 (2H, multiplet);
3.65–3.93 (9H, multiplet);
4.10 (1H, triplet, J=8.06 Hz);
4.19–4.30 (2H, multiplet).

EXAMPLE 2

(1R,5S,6S)-2-[(2S,4S)-2-(4-Acetimidoylhomopiperazin-1-ylcarbonyl)pyrrolidin-4-ylthio]-6-[(1R)-1-hydroxyethyl]-1-methyl-1-carbapen-2-em-3-carboxylic acid

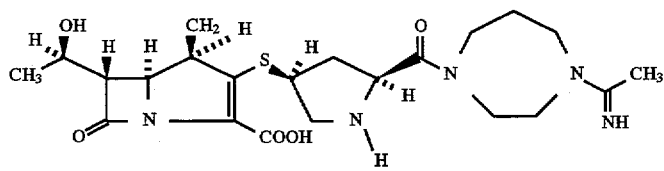

2(a) 4-Nitrobenzyl (1R,5S,6S)-2-[(2S,4S)-2-[4-(N-4-nitrobenzyloxycarbonylacetimidoyl)homopiperazin-1-ylcarbonyl]-1-(4- nitrobenzyloxycarbonyl)pyrrolidin-4-yl-thio]-5-[(1R)-1-hydroxyethyl]-1-methyl-1-carbapen-2-em-3- carboxylate 82 µl of diphenylphosphoryl chloride and 70 µl of diisopropylethylamine were added dropwise, whilst ice-cooling, to a solution of 136 mg of 4-nitrobenzy (1R,5R,6S)-6-[(1R)-1-hydroxyethyl]-1-methyl-2-oxo-1-carbapenam-3-carboxylate in 1.7 ml of dry acetonitrile, and the resulting mixture was stirred at the same temperature for 1 hour. At the end of this time, a solution of 296 mg of (2S,4S)-4-mercapto-2-[4-(N-4-nitrobenzyloxycarbonylacetimidoyl)homopiperazin-1-yl-carbonyl]-1-(4-nitrobenzyloxycarbonyl)pyrrolidine trifluoromethanesulfonate (prepared as described in Preparation 2) in 1.5 ml of dry acetonitrile and 179 µl of diisopropylethylamine were simultaneously added dropwise to the mixture, whilst ice-cooling, and the mixture thus obtained was stirred at the same temperature for 3 hours. The reaction mixture was then concentrated by evaporation under reduced pressure, and the resulting residue was worked up and purified in the same manner as described in Example 1(a), to give 148 mg of the title compound, as a powder.

Infrared Absorption Spectrum (KBr), $v_{max}$ cm$^{-1}$: 1773, 1709, 1657, 1607, 1561, 1521, 1496, 1429, 1405, 1346, 1305, 1278, 1210.

Nuclear Magnetic Resonance Spectrum (CDCl$_3$, 270 MHz), δ ppm:

1.27 (3H, doublet, J=7.33 Hz);
1.37 (3H, doublet, J=6.35 Hz);
1.42–2.20 (4H, multiplet);
1.28 & 2.39 (together 3H, two singlets);
2.60–2.79 (1H, multiplet);
3.25–4.35 (15H, multiplet);
4.62–4.83 (1H, multiplet);
5.05–5.52 (6H, multiplet);
7.42–7.67 (6H, multiplet);
8.15–8.24 (6H, multiplet).

2(b) (1R,5S,6S)-2-[(2S,4S)-2-(4-Acetimidoylhomopiperazin-1-ylcarbonyl)pyrrolidin-4-ylthio]-6-[(1R)-1-hydroxyethyl]-1-methyl-1-carbapen-2-em-3-carboxylic acid 144 mg of 4-nitrobenzyl (1R,5S,6S)-2-[(2S,4S)-2-(4-(N-4-nitrobenzyloxycarbonylacetimidoyl)homopiperazin-1-ylcarbonyl]-1-(4-nitrobenzyloxycarbonyl)pyrrolidin-4-ylthio]-6-[(1R)-1-hydroxyethyl]-1-methyl-1-carbapen-2-em-3-carboxylate [prepared as described in step (a) above] were dissolved in 7.5 ml of a 2:1 by volume mixture of tetrahydrofuran and water, and were hydrogenated by bubbling hydrogen through the solution at room temperature for 1.5 hours in the presence of 375 mg of 10% w/w palladium-on-charcoal. At the end of this time, the reaction mixture was worked up and purified by the same procedure as described in Example 1(b), to give 24 mg of the title compound as a powder.

Ultraviolet absorption spectrum (H$_2$O) $\lambda_{max}$ nm: 298.

Infrared Absorption Spectrum (KBr), $v_{max}$ cm$^{-1}$: 1754, 1597, 1450, 1383, 1288, 1259.

Nuclear Magnetic Resonance Spectrum (270 MHz, D$_2$O, using tetradeuterated sodium trimethylsilylpropionate as an internal standard), δ ppm:

1.22 (3H, doublet, J=6.84 Hz);
1.30 (3H, doublet, J=6.35 Hz);
1.38–1.63 (1H, multiplet);
1.85–2.04 (2H, multiplet);
2.31 & 2.36 (together 3H, two singlets);
2.67–2.82 (1H, multiplet);
3.03–3.18 (2H, multiplet);
3.34–3.47 (2H, multiplet);
3.64–3.96 (9H, multiplet);
4.09 (1H, triplet, J=8.06 Hz);
4.19–4.30 (2H, multiplet).

EXAMPLE 3

(1R,5S,6S)-2-[(2S,4S)-2-[3S)-4-Acetimidoyl-3-methylpiperazin-1-ylcarbonyl]pyrrolidin-4-ylthio]-6-[(1R)-1-hydroxyethyl]-1-methyl-1-carbapen-2-em-3-carboxylic acid

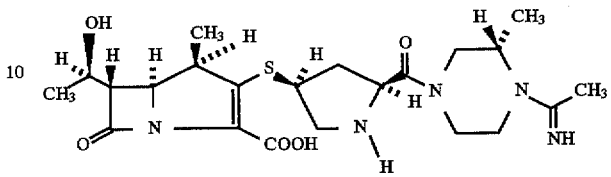

3(a) 4-Nitrobenzyl (1R,5S,6S)-2-[(2S,4S)-2-[(3S)-4-(N-4-nitrobenzyloxycarbonylacetimidoyl)-3-methylpiperazin-1-ylcarbonyl]-1-(4-nitrobenzyloxycarbonyl)pyrrolidin-4-ylthio]-6-[(1R)-1-hydroxyethyl]-1-methyl-1-carbapen-2-em-3-carboxylate 85 μl of diphenylphosphoryl chloride and 72 μl of diisopropylethylamine were added dropwise, whilst ice-cooling, to a solution of 140 mg of 4-nitrobenzyl (1R,5R,6S)-6-[(1R)-1-hydroxyethyl]-1-methyl-2-oxo-1-carbapenam-3-carboxylate in 1.8 ml of dry acetonitrile, and the resulting mixture was stirred an the same temperature for 1 hour. A solution of 290 mg of (2S,4S)-4-mercapto-2-[(3S)-4-(N-4-nitrobenzyloxycarbonylacetimidoyl)-3-methylpiperazin-1-ylcarbonyl]-1-(4-nitrobenzyloxycarbonyl)pyrrolidine trifluoromethanesulfonate (prepared as described in Preparation 3) in 1.6 ml of dry acetonitrile and 182 μl of diisopropylethylamine were simultaneously added dropwise to the mixture, whilst ice-cooling, and the mixture thus obtained was allowed to stand overnight at the same temperature. At the end of this time, the reaction mixture was worked up and purified by the same procedure as described in Example 1(a), to give 118 mg of the title compound, as a powder.

3(b) (1R,5S,6S)-2-[(2S,4S)-2-[(3S)-4-Acetimidoyl-3-methylpiperazin-1-ylcarbonyl]pyrrolidin-4-ylthio]-6-[(1R)-1-hydroxyethyl]-1-methyl-1-carbapen-2-em-3-carboxylic acid 85 mg of 4-nitrobenzyl (1R,5S,6S)-2-[(2S,4S)-2-[(3S)-4-(N-4- nitrobenzyloxycarbonylacetimidoyl)-3-methylpiperazin-1-ylcarbonyl]-1-(4-nitrobenzyloxycarbonyl)pyrrolidin-4-ylthio]-6-[(1R)-1-hydroxyethyl]-1-methyl-1-carbapen-2-em-3-carboxylate [prepared as described in step (a) above] were dissolved in 4.1 ml of a 2:1 by volume mixture of tetrahydrofuran and water, and were hydrogenated by bubbling hydrogen through the solution at room temperature for 2 hours in the presence of 210 mg of 10% w/w palladium-on-charcoal. At the end of this time, the reaction mixture was worked up and purified by the same procedure as described in Example 1(b), to give 14 mg of the title compound as a powder.

Ultraviolet absorption spectrum (H$_2$O) $\lambda_{max}$ nm: 299.

Infrared Absorption Spectrum (KBr), $v_{max}$ cm$^{-1}$: 1755, 1642, 1607, 1448, 1385, 1283, 1249.

Nuclear Magnetic Resonance Spectrum (270 MHz, D$_2$O, using tetradeuterated sodium trimethylsilylpropionate as an internal standard), δ ppm:

1.20–1.35 (9H, multiplet);
1.51–1.72 (1H, multiplet);
2.34 (3H, broad singlet);
2.66–2.86 (1H, multiplet);
3.02–3.20 (2H, multiplet);

3.25–3.47 (2H, multiplet);
3.48–4.38 (11H, multiplet).

EXAMPLE 4

(1R,5S,6S)-2-[(2S,4S)-2-(4-Formimidoylpiperazin-1-ylcarbonyl)pyrrolidin-4-ylthio]-6-[(1R)-1-hydroxyethyl]-1-methyl-1-carbapen-2-em-3-carboxylic acid

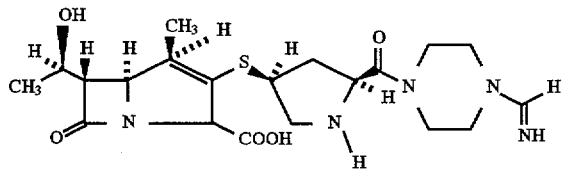

4(a) 4-Nitrobenzyl (1R,5S,6S)-2-(2-[4-(N-4-nitrobenzyloxycarbonylformimidoyl)piperazin-1-ylcarbonyl]-1-(4-nitrobenzyloxycarbonyl)pyrrolidin-4-ylthio]-6-[(1R)-1-hydroxyethyl]-1-methyl-1-carbapen-2-em-3-carboxylate 98 µl of diphenylphosphoryl chloride and 84 µl of diisopropylethylamine were added dropwise, whilst ice-cooling, to a solution of 162 mg of 4-nitrobenzyl (1R, 5R, 6S)-6-[(1R)-1-hydroxyethyl]-1-methyl-2-oxo-1-carbapenam-3-carboxylate in 2 ml of dry acetonitrile, and the resulting mixture was stirred at the same temperature for 1 hour. A solution of 337 mg of (2S,4S)-4-mercapto-2-[4-(N-4-nitrobenzyloxycarbonylformimidoyl)piperazin-1-ylcarbonyl]-1-(4-nitrobenzyloxycarbonyl)pyrrolidine trifluoromethanesulfonate [prepared as described in Preparation 4(2)] in 1.8 ml of dry acetonitrile and 212 µl of diisopropylethylamine were then simultaneously added dropwise to the mixture, whilst ice-cooling, and the mixture was allowed to stand overnight at the same temperature. The reaction mixture was then worked up and purified by the same procedure as described in Example 1(a), to give 110 mg of the title compound, as a powder.

Infrared Absorption Spectrum (KBr), $v_{max}$ cm$^{-1}$: 1774, 1709, 1660, 1604, 1520, 1345.

Nuclear Magnetic Resonance Spectrum (CDCl$_3$, 270 MHz), δ ppm:

1.26 & 1.28 (together 3H, two doublets, J=7.3 Hz);
1.36 (3H, doublet, J=6.4 Hz);
1.80–2.10 (1H, multiplet);
2.60–2.80 (1H, multiplet);
3.25–4.30 (15H, multiplet);
4.70–4.85 (1H, multiplet);
5.15–5.53 (6H, multiplet);
7.40–7.70 (6H, multiplet);
8.15–8.26 (6H, multiplet);
8.48 & 8.53 (together 1H, two singlets).

4(b) (1R,5S,6S)-2-[(2S,4S)-2-(4-Formimidoylpiperazin-1-ylcarbonyl)pyrrolidin-4-ylthio]-6-[(1R)-1-hydroxyethyl]-1-methyl-1-carbapen-2-em-3-carboxylic acid 98 mg of 4-nitrobenzyl (1R,5S,6S)-2-(2-[4-(N-4-nitrobenzyloxycarbonylformimidoyl)piperazin-1-ylcarbonyl]-1-(4-nitrobenzyloxycarbonyl)pyrrolidin-4-ylthio)-6-[(1R)-1-hydroxyethyl]-1-methyl-1-carbapen-2-em-3-carboxylate [prepared as described in step (a) above] were dissolved in 5 ml of a 2:1 by volume mixture of tetrahydrofuran and water, and were hydrogenated by bubbling hydrogen through it at room temperature for 2 hours in the presence of 250 mg of 10% w/w palladium-on-charcoal. At the end of this time, the reaction mixture was worked up and purified by the same procedure as described in Example 1(b), to give 12 mg of the title compound as a powder.

Ultraviolet absorption spectrum (H$_2$O) $\lambda_{max}$ nm: 299,

Infrared Absorption Spectrum (KBr), $v_{max}$ cm$^{-1}$: 1756, 1711, 1647, 1589, 1448, 1383, 1248.

Nuclear Magnetic Resonance Spectrum (270 MHz, D$_2$O, using tetradeuterated sodium trimethylsilylpropionate as an internal standard), δ ppm:

1.2 (3H, doublet, J=7.3 Hz);
1.30 (3H, doublet, J=6.44 Hz);
1.63–1.74 (1, multiplet);
2.70–2.82 (1H, multiplet);
3.06–3.26 (2H, mulniplet);
3.34–3.46 (2H, multiplet);
3.55–3.90 (9H, multiplet);
4.14–4.31 (3H, multiplet);
7.92 (1H, singlet).

EXAMPLE 5

(1R,5S,6S)-2-[(2S,4S)-2-(4-Formimidoylhomopiperazin-1-ylcarbonyl)pyrrolidin-4-ylthio]-6-[(1R)-1-hydroxyethyl]-1-methyl-1-carbapen-2-em-3-carboxylic acid

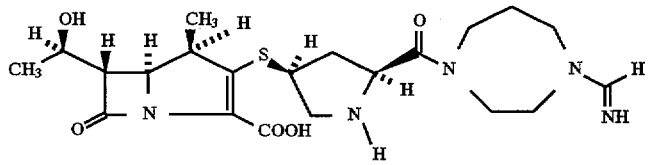

5(a) 4-Nitrobenzyl (1R,5S,6S)-2-[(2S,4S)-2-[4-(N-4-nitrobenzyloxycarbonylformimidoyl)homopiperazin-1-ylcarbonyl]-1-(4-nitrobenzyloxycarbonyl)pyrrolidin-4-ylthio]-6-[(1R)-1-hydroxyethyl]-1-methyl-1-carbapen-2-em-3-carboxylate 90 µl of diphenylphosphoryl chloride and 77 µl of diisopropylethylamine were added dropwise, whilst ice-cooling, to a solution of 150 mg of 4-nitrobenzyl (1R, 5R,6S)-6-[(1R)-1-hydroxyethyl]-1-methyl-2-oxo-1-carbapenam-3-carboxylate in 1.9 ml of dry acetonitrile, and the resulting mixture was shirred at the same temperature for 1 hour. A solution of 316 mg of (2S,4S)-4-mercapto-2-[4-(N-4-nitrobenzyloxycarbonylformimidoyl)homopiperazin-1-ylcarbonyl]-1-(4-nitrobenzyloxycarbonyl)pyrrolidine trifluoromethanesulfonate [prepared as described in Preparation 5(1)] in 1.7 ml of dry acetonitrile and 195 µl of diisopropylethylamine were then simultaneously added dropwise to the mixture, whilst ice-cooling and the mixture was allowed to stand overnight at the same temperature. At the end of this time, the reaction mixture was worked up and purified by the same procedure as described in Example 1(b), to give 105 mg of the title compound, as a powder.

Infrared Absorption Spectrum (Far), $v_{max}$ cm$^{-1}$: 1773, 1709, 1657, 1601, 1521, 1346, 1209, 1161.

Nuclear Magnetic Resonance Spectrum (CDCl$_3$, 270 MHz), δ ppm:

1.22–1.38 (6H, multiplet);
1.80–2.18 (3H, multiplet);
2.60–2.81 (1H, multiplet);
3.22–4.30 (15H, multiplet);
4.60–4.72 (1H, multiplet);
5.10–5.53 (6H, multiplet);
7.39–7.68 (6H, multiplet);
8.14–8.25 (6H, multiplet);
8.32–8.57 (1H, multiplet).

5(b) (1R,5S,6S)-2-[(2S,4S)-2-(4-Formimidoylhomopiperazin-1-ylcarbonyl)pyrrolidin-4-ylthio]-6-[(1R)-1-hydroxyethyl]-1-methyl-1-carbapen-1-em-3-carboxylic acid 89 mg of 4-nitrobenzyl (1R,5S,6S)-2-[(2S,4S)-2-[4-(N-4-nitrobenzyloxycarbonylformimidoyl)homopiperazin-1-ylcarbonyl]-1-(4-nitrobenzyloxycarbonyl)pyrrolidin-4-ylthio]-6-[(1R)-1-hydroxyethyl]-1-methyl-1-carbapen-2-em-3-carboxylate [prepared as described in step (a) above] were dissolved in 4.5 ml of a 2:1 by volume mixture of tetrahydrofuran and water, and were hydrogenated by bubbling hydrogen through the solution at room temperature for 2 hours in the presence of 230 mg of 10% w/w palladium-on-charcoal. At the end of this time, the reaction mixture was worked up and purified by the same procedure as described in Example 1(b), to give 13 mg of the title compound as a powder.

Ultraviolet absorption spectrum (H$_2$O) $\lambda_{max}$ nm: 298.

Infrared Absorption Spectrum (KBr), $v_{max}$ cm$^{-1}$: 1754, 1706, 1638, 1588, 1383.

Nuclear Magnetic Resonance Spectrum (270 MHz, D$_2$O, using tetradeuterated sodium trimethylsilylpropionate as an internal standard), δ ppm:

1.21 (3H, doublet, J=7.3 Hz);
1.30 (3H, doublet, J=6.4 Hz);
1.45–1.62 (1H, multiplet);
1.90–2.02 (2H, multiplet);
2.67–2.83 (1H, multiplet);
3.03–3.20 (2H, multiplet);
3.30–3.47 (2H, multiplet);
3.60–3.97 (9H, multiplet);
4.02–4.16 (1H, multiplet);
4.20–4.31 (2H, multiplet);
7.84, 7.93 & 7.96 (together 1H, three singlets).

EXAMPLE 6

(1R,5S,6S)-2-{(2S,4S)-2-[(3S)-4-Formimidoyl-3-methylpiperazin-1-ylcarbonyl]pyrrolidin-4-ylthio}-6-[(1R)-1-hydroxyethyl]-1-methyl-1-carbapen-2-em-3-carboxylic acid

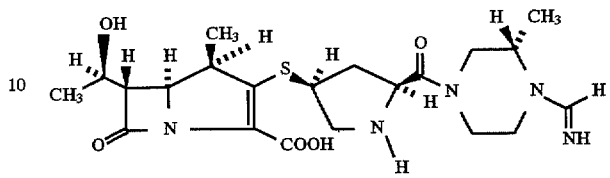

6(a) 4-Nitrobenzyl (1R,5S,6S)-2-{(2S,4S)-2-[(3S)-4-(N-4-nitrobenzyloxycarbonylformimidoyl)-3-methylpiperazin-1-ylcarbonyl]-1-(4-nitrobenzyloxycarbonyl)pyrrolidin-4-ylthio}-6-[(1R)-1- hydroxyethyl]-1-methyl-1-carbapen-2-em -3- carboxylate 83 μl of diphenylphosphoryl chloride and 17 μl of diisopropylethylamine were added dropwise, whilst ice-cooling, to a solution of 138 mg of 4-nitrobenzyl (1R,5R,6S)-6-[(1R)-1-hydroxyethyl]-1-methyl-2-oxo-1-carbapenam-3-carboxylate in 1.7 ml of dry acetonitrile, and the resulting mixture was stirred at the same temperature for 1 hour. A solution of 290 mg of (2S,4S)-4-mercapto-2-[(3S)-4-(N-4-nitrobenzyloxycarbonylformimidoyl)-3-methylpiperazin-1-ylcarbonyl]-1-(4-nitrobenzyloxycarbonyl)pyrrolidine trifluoromethanesulfonate (prepared as described in Preparation 6) in 1.5 ml of dry acetonitrile and 179 μl of diisopropylethylamine were then simultaneously added dropwise to the resulting solution, whilst ice-cooling, and the mixture thus obtained was allowed to stand overnight at the same temperature. At the end of this time, the reaction mixture was worked up and purified by the same procedure as described in Example 1(a), to give 108 mg of the title compound, as a powder.

6(b) (1R,5S,6S)-2-{(2S,4S)-2-[(3S)-4-Formimidoyl-3-methylpiperazin-1-ylcarbonyl]pyrrolidin-4-ylthio}-6-[(1R)-1-hydroxyethyl]-1-methyl-1-carbapen-2-em-3-carboxylic acid 87 mg of 4-nitrobenzyl (1R,5S,6S)-2-{(2S,4S)-2-[(3S)-4-(N-4-nitrobenzyloxycarbonylformimidoyl)-3-methylpiperazin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 4.5 ml of a 2:1 by volume mixture of tetrahydrofuran and water, and were hydrogenated by bubbling hydrogen through the solution at room temperature for 2 hours in the presence of 220 mg of 10% w/w palladium-on-charcoal. The reaction mixture was then worked up and purified by the same procedure as that described in Example 1(b), to give 16 mg of the title compound, as a powder.

Ultraviolet absorption spectrum (H$_2$O) $\lambda_{max}$ nm: 299.

Infrared Absorption Spectrum (KBr), $v_{max}$ cm$^{-1}$: 1754, 1705, 1645, 1591, 1447, 1386, 1258.

Nuclear Magnetic Resonance Spectrum (270 MHz, D$_2$O, using tetradeuterated sodium trimethylsilylpropionate as an internal standard), δ ppm:

1.17–1.43 (9H, multiplet);
1.52–1.73 (1H, multiplet);
2.66–2.87 (1H, multiplet);
3.01–3.26 (2H, multiplet);
3.33–3.48 (2H, multiplet);
3.48–4.43 (11H, multiplet);
7.84 & 7.95 (together 1H, two singlets).

EXAMPLE 7

(1R,5S,6S)-2-[(2S,4S)-2-(2-Methyl-1-piperazinylcarbonyl)pyrrolidin-4-ylthio]-6-[(1R)-1-hydroxyethyl]-1-methyl-1-carbapen-2-em-3-carboxylic acid hydrochloride

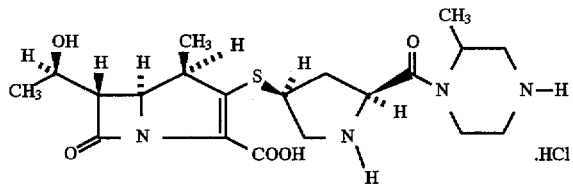

7(a) 4-Nitrobenzyl (1R, 5S,6S)-2-{(2S,4S)-2-[2-methyl-4-(4-nitrobenzyloxcarbonyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 0.67 ml of diphenylphosphoryl chloride and 0.56 ml of diisopropylethylamine were added dropwise, whilst ice-cooling, to a solution of 1.05 g of 4-nitrobenzyl (1R,5R,6S)-6-[(1R)-1-hydroxyethyl]-1-methyl-2-oxo-1-carbapenam-3-carboxylate in 10 ml of dry acetonitrile, and the resulting mixture was stirred at the same temperature for 1 hour. A solution of 1.98 g of (2S,4S)-4-mercapto-2-[2-methyl-4-(4-nitrobenzyloxycarbonyl)-1-piperazinylcarbonyl]-1-(4-nitrobenzyloxycarbonyl)pyrrolidine (prepared as described in Preparation 7) in 10 ml of dry acetonitrile and 0.56 ml of diisopropylethylamine were then simultaneously added dropwise to the mixture at a temperature of between 2° C. and 10° C., and the mixture thus obtained was stirred for 90 minutes, whilst ice-cooling; it was then allowed to stand overnight at the same temperature. At the end of this time, the reaction mixture was concentrated by evaporation under reduced pressure, and the residue was diluted with ethyl acetate. The diluted solution was washed, in turn, with water and with an aqueous solution of sodium chloride. The ethyl acetate solution was then dried over anhydrous magnesium sulfate, and the solvent was removed by distillation under reduced pressure. The resulting residue was purified by column chromatography through 250 ml of silica gel 60 (Merck Art No. 9385), using a 95:5 by volume mixture of ethyl acetate and methanol as the eluent, to give 2.48 g of the title compound, as an amorphous solid.

Infrared Absorption Spectrum (KBr), $v_{max}$ cm$^{-1}$: 1775, 1708, 1655, 1606, 1522, 1434, 1346.

Nuclear Magnetic Resonance Spectrum (CDCl$_3$, 270 MHz), δ ppm:

1.28 (3H, doublet, J=7.32 Hz);

1.36 (3H, doublet, J=6.35 Hz);

1.06–1.47 (3H, multiplet);

1.66–2.06 (1H, multiplet);

2.47–5.15 (17H, multiplet);

5.20–5.52 (6H, multiplet);

7.43–7.52 (4H, multiplet);

7.65 (2H, doublet, J=8.79 Hz)

8.23 (4H, two doublets, J=8.29 Hz);

8.17–8.25 (2H, multiplet).

7(b) (1R,5S,6S)-2-[(2S,4S)-2-(2-Methyl-1-piperazinylcarbonyl)pyrrolidin-4-ylthio]-6-[(1R)-1-hydroxyethyl]-1-methyl-1-carbapen-2-em-3-carboxylic acid hydrochloride 2.48 g of 4-nitrobenzyl (1R,5S,6S)-2-{(2S,4S)-2-[2-methyl-4-(4-nitrobenzyloxycarbonyl)-1-piperazinylcarbonyl]-1-(4-ninrobenzyloxycarbonyl)pyrrolidin-4-yl-thio}-6-[(1R)-1-hydroxyethyl]-1-methyl-1-carbapen-2-em-3-carboxylate [prepared as described in step (a) above] were dissolved in 30 ml of a 1:1 by volume mixture of tetrahydrofuran and water, and then 2.9 ml of 1N aqueous hydrochloric acid were added, and the mixture was hydrogenated by bubbling hydrogen through it at room temperature for 2.5 hours in the presence of 2.5 g of 10% w/w palladium-on-charcoal. The catalyst was filtered off, and the filtrate was washed with diethyl ether. The resulting aqueous solution was concentrated by evaporation under reduced pressure, and the residue was purified by reverse phase column chromanography through 125 ml of Cosmo Sil 75C$_{18}$-PREP (a trade mark for a product of Nacalai Tesque), using water as the eluent. Those fractions containing the title compound were combined, concentrated by evaporation under reduced pressure and lyophilized, to give 440 mg of the title compound as a powder.

Infrared Absorption Spectrum (KBr), $v_{max}$ cm$^{-1}$: 1760, 1655, 1593, 1447, 1384, 1287.

Nuclear Magnetic Resonance Spectrum (270 MHz, D$_2$O, using tetradeuterated sodium trimethylsilylpropionate as an internal standard), δ ppm:

1.21 (3H, doublet, J=7.32 Hz);

1.28 (3H, doublet, J=6.35 Hz);

1.34–1.51 (3H, multiplet);

1.92–2.07 (1H, multiplet);

2.99–3.55 (9H, multiplet);

3.69–4.65 (6H, multiplet);

4.72–4.95 (1H, multiplet).

Ultraviolet absorption spectrum (H$_2$O) $\lambda_{max}$ nm: 296.

EXAMPLE 8

(1R,5S,6S)-2-[(2S,4S)-2-(3-Methyl-1-piperazinylcarbonyl)pyrrolidin-4-ylthio]-6-[(1R)-1-hydroxyethyl]-1-methyl-1-carbapen-2-em-3-carboxylic acid hydrochloride

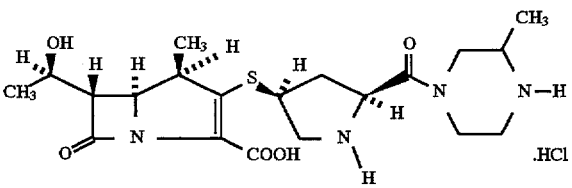

8(a) 4-Nitrobenzyl (1R,5S,6S)-2-{(2S,4S)-2-[3-methyl-4-(4-nitrobenzyloxycarbonyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 0.60 ml of diphenylphosphoyl chloride and 0.51 ml of diisopropylethylamine were added dropwise, whilst ice-cooling, to a solution of 0.96 g of 4-nitrobenzyl (1R,5R,6S)-6-[(1R)-1-hydroxyethyl]-1-methyl-2-oxo-1-carbapenam-3-carboxylate in 10 ml of dry acetonitrile, and the resulting mixture was stirred at the same temperature for 40 minutes. A solution of 1.55 g of (2S,4S)-4-mercapto-2-[3-methyl-4-(4-nitrobenzyloxycarbonyl)-1-piperazinylcarbonyl]-1-(4-nitrobenzyloxycarbonyl)pyrrolidine (prepared as described in Preparation 8) in 20 ml of dry acetonitrile and 0.46 ml of diisopropylethylamine were then simultaneously added dropwise to the mixture at a temperature of between 2° C. and 7° C. and the mixture was allowed to stand overnight at the same temperature. At the end of this time, the reaction mixture was concentrated by evaporation under reduced pressure, and the residue was diluted with ethyl acetate. The diluted solution was ,washed, in turn, with water and with an aqueous solution of sodium chloride, after which in was dried over anhydrous magnesium sulfate, and the solvent was removed by distillation under reduced pressure. The resulting residue was purified by column chromanography through 250 ml of silica gel 60 (Merck Art No. 9385), using a 95:5 by volume mixture of ethyl acetane and methanol as the eluent, to give 1.98 g of the title compound, as an amorphous solid.

Infrared Absorption Spectrum (KBr), $v_{max}$ cm$^{-1}$: 1775, 1706, 1659, 1607, 1522, 1430, 1406, 1346.

Nuclear Magnetic Resonance Spectrum (CDCl$_3$, 270 MHz), δ ppm:

1.16–1.38 (6H, multiplet);
1.36 (3H, doublet, J=6.35 Hz);
1.80–2.07 (1H, multiplet);
2.63–4.81 (17H, multiplet);
5.09–5.52 (6H, multiplet);
7.27–7.52 (4H, multiplet);
7.65 (2H, doublet, J=8.30 Hz);
8.22 (4H, doublet, J=8.79 Hz);
8.16–8.25 (2H, multiplet).

8(b) (1R,5S,6S)-2-[(2S,4S)-2-(3-Methyl-1-piperazinylcarbonyl]pyrrolidin-4-ylthio]-6-[(1R)-1-hydroxyethyl]-1-methyl-1-carbapen-2-em-3-carboxylic acid hydrochloride 1.97 g of 4-nitrobenzyl (1R,5S,6S)-2-{(2S,4S)-2-[3-methyl-4-(4-nitrobenzyloxycarbonyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] was dissolved in 40 ml of a 1:1 by volume mixture of tetrahydrofuran and water, and then 2.3 ml of 1N aqueous hydrochloric acid were added, and the mixture was hydrogenated by bubbling hydrogen through it at room temperature for 2 hours in the presence of 2.0 g of w/w palladium-on-charcoal. The catalyst was filtered off, and the filtrate was washed with diethyl ether was then concentrated by evaporation under reduced pressure, and the resulting residue was purified by reverse phase column chromatography through 100 ml of Cosmo Sil 75C$_{18}$-PREP (a trademark for a product of Nacalai Tesque), using water as the eluent. Those fractions containing the title compound were combined, concentrated by evaporation under reduced pressure and lyophilized, to give 320 mg of the title compound as a powder.

Infrared Absorption Spectrum (KBr), $v_{max}$ cm$^{-1}$: 1760, 1660, 1594, 1453, 1386, 1263.

Nuclear Magnetic Resonance Spectrum (270 MHz, D$_2$O, using tetradeuterated sodium trimethylsilylpropionate as an internal standard), δ ppm:

1.21 (3H, doublet, J=7.33 Hz);
1.28 (3H, doublet, J=6.35 Hz);
1.36–1.40 (3H, multiplet);
1.97–2.07 (1H, multiplet);
3.01–3.67 (9H, multiplet);
3.77–4.53 (6H, multiplet);
4.72–4.95 (1H, multiplet).

Ultraviolet absorption spectrum (H$_2$O) $\lambda_{max}$ nm: 296.

EXAMPLE 9

(1R,5S,6S)-2-{(2S,4S)-2-[(2S)-2-Methyl-1-piperazinylcarbonyl]pyrrolidin-4-ylthio}-6-[(1R)-1-hydroxyethyl]-1-methyl-1-carbapen-2-em-3-carboxylic acid hydrochloride

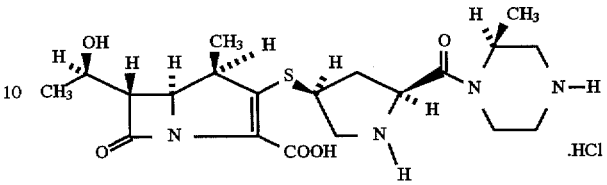

9(a) 4-Nitrobenzyl (1R, 5S, 6S)-2-{(2S, 4S)-2-[(2S)-2-methyl-4-(4-nitrobenzyloxycarbonyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 57 µl of diphenylphosphoryl chloride and 48 µl of diisopropylethylamine were added dropwise, whilst ice-cooling, to a solution of 89 mg of 4-nitrobenzyl (1R, 5R, 6S)-6-[(1R)-1-hydroxyethyl]-1-methyl-2-oxo-1-carbapenam-3-carboxylate in 1.0 ml of dry acetonitrile, and the resulting mixture was stirred at the same temperature for 1 hour. A solution of 168 mg of (2S, 4S)-4-mercapto-2-[(2S)-2-methyl-4-(4-nitrobenzyloxycarbonyl)-1-piperazinylcarbonyl]-1-(4-nitrobenzyloxycarbonyl) pyrrolidine (prepared as described in Preparation 9) in 0.5 ml of dry acetonitrile and 48 µl of diisopropylethylamine were simultaneously added dropwise to the mixture, whilst ice-cooling. The mixture was then stirred at the same temperature for 1 hour, after which it was allowed to stand overnight at the same temperature. At the end of this time, the reaction mixture was worked up and purified by the same procedure as described in Example 7(a) to give 205 mg of the title compound, as a powder.

9(b) (1R, 5S, 6S)-2-{(2S, 4S)-2-[(2S)-2-Methyl-1-piperazinylcarbonyl]pyrrolidin-4-ylthio}-6-[(1R)-1-hydroxyethyl]-1-methyl-1-carbapen-2-em-3-carboxylic acid hydrochloride 205 mg of 4-nitrobenzyl (1R, 5S, 6S)-2-{(2S, 4S)-2-[(2S)-2-methyl-4-(4-nitrobenzyloxycarbonyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 3 ml of a 1:1 by volume mixture of tetrahydrofuran and water, after which 240 µl of 1N aqueous hydrochloric acid were added, and the mixture was hydrogenated by bubbling hydrogen through it at room temperature for 2 hours in the presence of 250 mg of 10% w/w palladium-on-charcoal. The reaction mixture was then worked up and purified by the same procedure as described in Example 7(b), to give 30 mg of the title compound as a powder.

Ultraviolet absorption spectrum (H$_2$O) $\lambda_{max}$ nm: 296.
Infrared Absorption Spectrum (KBr), $v_{max}$ cm$^{-1}$: 1759, 1653, 1591, 1447, 1384, 1287.

Nuclear Magnetic Resonance Spectrum (270 MHz, D$_2$O, using tetradeuterated sodium trimethylsilylpropionate as an internal standard), δ ppm:

1.21 (3H, doublet, J=6.83 Hz);
1.28 (3H, doublet, J=6.35 Hz);
1.35 & 1.50 (together 3H, two doublets, J=6.83 Hz);
1.88–2.11 (1H, multiplet);
2.97–3.60 (8H, multiplet);

3.47 (1H, doublet of doublets, J=6.35 & 2.93 Hz);
3.63–3.90 (2H, multiplet);
4.03–4.13 (1H, multiplet);
4.20–4.29 (2H, multiplet);
4.33–4.98 (2H, multiplet).

EXAMPLE 10

(1R, 5S, 6S)-2-{(2S, 4S)-2-[(2R)-2-Methyl-1-piperazinylcarbonyl]pyrrolidin-4-ylthio}-6-[(1R)-1-hydroxyethyl]-1-methyl-1-carbapen-2-em-3-carboxylic acid hydrochloride

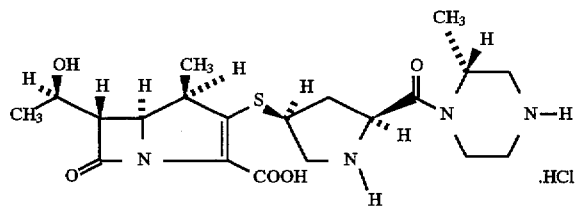

10(a) 4-Nitrobenzyl (1R, 5S, 6S)-2-{(2S, 4S)-2-[(2R)-2-methyl-4-(4-nitrobenzyloxycarbonyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 37 μl of diphenylphosphoryl chloride and 31 μl of diisopropylethylamine were added dropwise, whilst ice-cooling, to a solution of 58 mg of 4-nitrobenzyl (1R, 5R, 6S)-6-[(1R)-1-hydroxyethyl]-1-methyl-2-oxo-1-carbapenam-3-carboxylate in 1.0 ml of dry acetonitrile, and the resulting mixture was stirred at the same temperature for 1 hour. A solution of 109 mg of (2S, 4S)-4-mercapto-2-[(2R)-2-methyl-4-(4-nitrobenzyloxycarbonyl)-1-piperazinylcarbonyl]-1-(4-nitrobenzyloxycarbonyl)pyrrolidine (prepared as described in Preparation 10) in 0.5 ml of dry acetonitrile and 31 μl of diisopropylethylamine were then simultaneously added dropwise to the mixture at a temperature of 5° C. to 10° C. and the mixture thus obtained was stirred for 30 minutes, whilst ice-cooling, after which it was allowed to stand overnight at the same temperature. At the end of this time, the reaction mixture was worked up and purified by the same procedure as described in Example 7(a), to give 132 mg of the title compound, as a powder.

10(b) (1R, 5S, 6S)-2-{(2S, 4S)-2-[(2R)-2-Methyl-1-piperazinylcarbonyl]pyrrolidin-4-ylthio}-6-[(1R)-1-hydroxyethyl]-1-methyl-1-carbapen-2-em-3-carboxylic acid hydrochloride 132 mg of 4-nitrobenzyl (1R, 5S, 6S)-2-{(2S, 4S)-2-[(2R)-2-methyl-4-(4-nitrobenzyloxycarbonyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] was dissolved in 3 ml of a 1:1 by volume mixture of tetrahydrofuran and water, after which 160 μl of 1N aqueous hydrochloric acid were added, and the mixture was hydrogenated by bubbling hydrogen through it at room temperature for 2 hours in the presence of 150 mg of 10% w/w palladium-on-charcoal. At the end of this time, the reaction mixture was worked up and purified by the same procedure as described in Example 7(b), to give 23 mg of the title compound as a powder.

Ultraviolet absorption spectrum (H$_2$O) λ$_{max}$ nm: 296.

EXAMPLE 11

(1R, 5S, 6S)-2-{(2S, 4S)-2-[(3S)-3-Methyl-1-piperazinylcarbonyl]pyrrolidin-4-ylthio}-6-[(1R)-1-hydroxyethyl]-1-methyl-1-carbapen-2-em-3-carboxylic acid hydrochloride

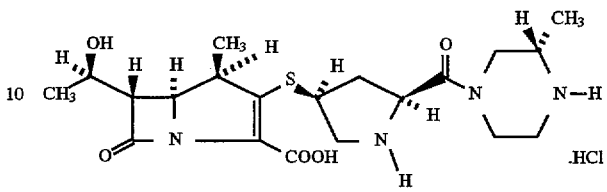

11(a) 4-Nitrobenzyl (1R, 5S, 6S)-2-{(2S, 4S)-2-[(3S)-3-methyl-4-(4-nitrobenzyloxycarbonyl)-1-piperazinylcarbonyl]-1-(4-nitrobenzyloxycarbonyl)pyrrolidin-4-ylthio]-6-[(1R)-1-hydroxyethyl]-1-methyl-1-carbapen-2-em-3-carboxylate 50 μl of diphenylphosphoryl chloride and 43 μl of diisopropylethylamine were added dropwise, whilst ice-cooling, to a solution of 80 mg of 4-nitrobenzyl (1R, 5R, 6S)-6-[(1R)-1-hydroxyethyl]-1-methyl-2-oxo-1-carbapenam-3-carboxylate in 1.0 ml of dry acetonitrile, and the resulting mixture was stirred at the same temperature for 50 minutes. A solution of 130 mg of (2S, 4S)-4-mercapto-2-[(3S)-3-methyl-4-(4-nitrobenzyloxycarbonyl)-1-piperazinylcarbonyl]-1-(4-nitrobenzyloxycarbonyl)pyrrolidine (prepared as described in Preparation 11) in 1.5 ml of dry acetonitrile and 38 μl of diisopropylethylamine were then simultaneously added dropwise to the mixture, whilst ice-cooling, and the mixture was stirred at the same temperature for 2 hours, after which it was allowed to stand overnight at the same temperature. At the end of this time, the reaction mixture was worked up and purified by the same procedure as described in Example 8(b), to give 170 mg of the title compound, as a powder.

11(b) (1R, 5S, 6S)-2-{(2S, 4S)-2-[(3S)-3-Methyl-1-piperazinylcarbonyl]pyrrolidin-4-ylthio}-6-[(1R)-1-hydroxyethyl]-1-methyl-1-carbapen-2-em-3-carboxylic acid hydrochloride 170 mg of 4-nitrobenzyl (1R, 5S, 6S)-2-{(2S, 4S)-2-[(3S)-3-methyl-4-(4-nitrobenzyloxycarbonyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 3.5 ml of a 1:1 by volume mixture of tetrahydrofuran and water, after which 0.19 ml of 1N aqueous hydrochloric acid was added, and the mixture was hydrogenated by bubbling hydrogen through it at room temperature for 2.5 hours in the presence of 170 mg of 10% w/w palladium-on-charcoal. At the end of this time, the reaction mixture was worked up and purified by the same procedure as described in Example 8(b), to give 25.0 mg of the title compound as a powder.

Ultraviolet absorption spectrum (H$_2$O) λ$_{max}$ nm: 296.

Infrared Absorption Spectrum (KBr), ν$_{max}$ cm$^{-1}$: 1761, 1660, 1594, 1453, 1385, 1262.

Nuclear Magnetic Resonance Spectrum (270 MHz, D$_2$O, using tetradeuterated sodium trimethylsilylpropionate as an internal standard), δ ppm:

1.20 (3H, doublet, J=7.32 Hz);
1.28 (3H, doublet, J=6.35 Hz);
1.36–1.40 (3H, multiplet);
1.99–2.07 (1H, multiplet);
3.04–3.63 (9H, multiplet);

3.76–4.50 (6H, multiplet);
4.72–4.93 (1H, multiplet).

EXAMPLE 12

(1R, 5S, 6S)-2-{(2S, 4S)-2-[(3R)-3-Methyl-1-piperazinylcarbonyl]pyrrolidin-4-ylthio}-6-[(1R)-1-hydroxyethyl]-1-methyl-1-carbapen-2-em-3-carboxylic acid hydrochloride

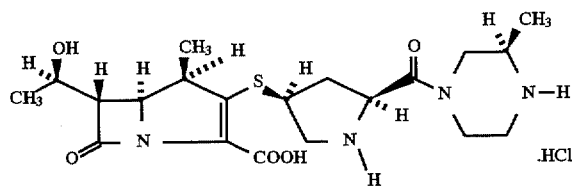

12(a) 4-Nitrobenzyl (1R, 5S, 6S)-2-{(2S, 4S)-2-[(3R)-3-methyl-4-(4-nitrobenzyloxycarbonyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 55 μl of diphenylphosphoryl chloride and 47 μl of diisopropylethylamine were added dropwise, whilst ice-cooling, to a solution of 87 mg of 4-nitrobenzyl (1R, 5R, 6S)-6-[(1R)-1-hydroxyethyl]-1-methyl-2-oxo-1-carbapenam-3-carboxylate in 1.0 ml of dry acetonitrile, and the resulting mixture was stirred at the same temperature for 1 hour. A solution of 145 mg of (2S, 4S)-4-mercapto-2-[(3R)-3-methyl-4-(4-nitrobenzyloxycarbonyl)-1-piperazinylcarbonyl]-1-(4-nitrobenzyloxycarbonyl)pyrrolidine (prepared as described in Preparation 12) in 2.0 ml of dry acetonitrile and 42 μl of diisopropylethylamine were then simultaneously added dropwise to the mixture, whilst ice-cooling, and the mixture was stirred at the same temperature for 1 hour, after which it was allowed to stand overnight at the same temperature. At the end of this time, the reaction mixture was worked up and purified by the same procedure as described in Example 8(a), to give 175 mg of the title compound, as an amorphous solid.

12(b) (1R, 5S, 6S)-2-{(2S, 4S)-2-[(3R)-3-Methyl-1-piperazinylcarbonyl]pyrrolidin-4-ylthio}-6-[(1R)-1-hydroxyethyl]-1-methyl-1-carbapen-2-em-3-carboxylic acid hydrochloride 175 mg of 4-nitrobenzyl (1R, 5S, 6S)-2-{(2S, 4S)-2-[(3R)-3-methyl-4-(4-nitrobenzyloxycarbonyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 35 ml of a 1:1 by volume mixture of tetrahydrofuran and water, after which 0.20 ml of 1N aqueous hydrochloric acid was added, and the mixture was hydrogenated by bubbling hydrogen through it at room temperature for 2 hours in the presence of 175 mg of 10% w/w palladium-on-charcoal. At the end of this time, the reaction mixture was worked up and purified by the same procedure as described in Example 8(b), to give 28.0 mg of the title compound as a powder.

Ultraviolet absorption spectrum (H$_2$O) λ$_{max}$ nm: 296.

EXAMPLE 13

(1R, 5S, 6S)-2-[(2S, 4S)-2-(trans-2,5-Dimethyl-1-piperazinylcarbonyl)pyrrolidin-4-ylthio]-6-[(1R)-1-hydroxyethyl]-1-methyl-1-carbapen-2-em-3-carboxylic acid hydrochloride

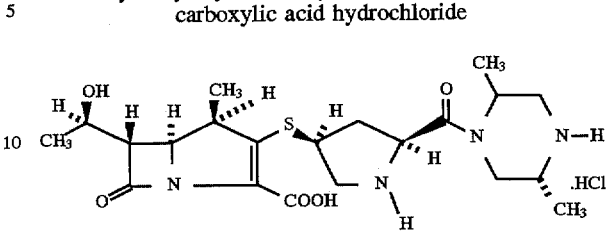

13(a) 4-Nitrobenzyl (1R, 5S, 6S)-2-{(2S, 4S)-2-[trans-2,5-dimethyl-4-(4-nitrobenzyloxycarbonyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 150 μl of diphenylphosphoryl chloride and 127 μl of diisopropylethylamine were added dropwise, whilst ice-cooling, to a solution of 248 mg of (1R, 5R, 6S)-6-[(1R)-1-hydroxyethyl]-1-methyl-2-oxo-1-carbapenam-3-carboxylic acid in 3 ml of dry acetonitrile, and the resulting mixture was stirred at the same temperature for 1 hour. A solution of 533 mg of (2S, 4S)-4-mercapto-2-[trans-2,5-dimethyl-4-(4-nitrobenzyloxycarbonyl)-1-piperazinylcarbonyl]-1-(4-nitrobenzyloxycarbonyl)pyrrolidine (prepared as described in Preparation 13) in 2.5 ml of dry acetonitrile and 132 μl of diisopropylethylamine were then simultaneously added dropwise to the mixture at a temperature of between 0° and 5° C., and the mixture was stirred for 2 hours, whilst ice-cooling, after which it was allowed to stand overnight in a refrigerator. At the end of this time, the reaction mixture was worked up and purified by the same procedure as described in Example 7(a), to give 281 mg of the title compound, as a powder.

13(b) (1R, 5S, 6S)-2-[(2S, 4S)-2-(trans-2,5-Dimethyl-1-piperazinylcarbonyl)pyrrolidin-4-ylthio]-6-[(1R)-1-hydroxyethyl]-1-methyl-1-carbapen-2-em-3-carboxylic acid hydrochloride 281 mg of 4-nitrobenzyl (1R, 5S, 6S)-2-{(2S, 4S)-2-[trans-2,5-dimethyl-4-(4-nitrobenzyloxycarbonyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 6 ml of a 1:1 by volume mixture of tetrahydrofuran and water, after which 328 μl of 1N aqueous hydrochloric acid were added, and the mixture was hydrogenated by bubbling hydrogen through it at room temperature for 2 hours in the presence of 0.3 g of 10% w/w palladium-on-charcoal. At the end of this time, the reaction mixture was worked up and purified by the same procedure as described in Example 7(b), to give 29 mg of the title compound as a powder.

Ultraviolet absorption spectrum (H$_2$O) λ$_{max}$ nm: 296.5.

Infrared Absorption Spectrum (KBr), ν$_{max}$ cm$^{-1}$: 1762, 1656, 1592, 1455, 1386, 1139.

Nuclear Magnetic Resonance Spectrum (270 MHz, D$_2$O, using tetradeuterated sodium trimethylsilylpropionate as an internal standard), δ ppm:

1.20 (3H, doublet, J=7.32 Hz);
1.28 (3H, doublet, J=6.35 Hz);
1.35 (3H, doublet, J=7.32 Hz);
1.41 & 1.46 (together 3H, two doublets, J=6.84 Hz);
1.92–2.08 (1H, multiplet);

2.96–3.65 (6H, multiplet);

3.47 (1H, doublet of doublets, J=6.35 & 2.93 Hz);

3.76–3.90 (3H, multiplet);

4.00–4.15 (1H, multiplet);

4.20–4.41 (3H, multiplet);

4.75–4.88 (1H, multiplet).

EXAMPLE 14

(1R, 5S, 6S)-2-[(2S, 4S)-2-(cis-3,5-Dimethyl-1-piperazinylcarbonyl)pyrrolidin-4-ylthio]-6-[(1R)-1-hydroxyethyl]-1-methyl-1-carbapen-2-em-3-carboxylic acid hydrochloride

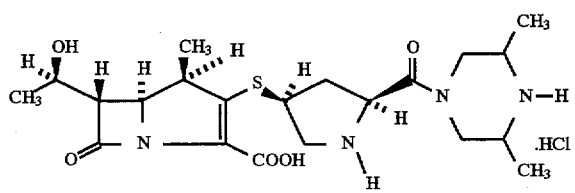

14(a) 4-Nitrobenzyl (1R, 5S, 6S)-2-[(2S, 4S)-2-(cis-3,5-dimethyl-1-piperazinylcarbonyl)-1-(4-nitrobenzyloxycarbonyl)pyrrolidin-4-ylthio]-6-[(1R)-1-hydroxyethyl]-1-methyl-1-carbapen-2-em-3-carboxylate 92 µl of diphenylphosphoryl chloride and 78 µl of diisopropylethylamine were added dropwise, whilst ice-cooling, to a solution of 152 mg of 4-nitrobenzyl (1R, 5R, 6S)-6-[(1R)-1-hydroxyethyl]-1-methyl-2-oxo-1-carbapenam-3-carboxylate in 2 ml of dry acetonitrile, and the resulting mixture was stirred at the same temperature for 1 hour. At the end of this time, 176 µl of diisopropylethylamine and a solution of 230 mg of (2S, 4S)-4-mercapto-2-(cis-3,5-dimethyl-1-piperazinylcarbonyl)-1-(4-nitrobenzyloxycarbonyl)pyrrolidine (prepared as described in Preparation 14) in 1.8 ml of dry acetonitrile were simultaneously added dropwise to the mixture, whilst ice-cooling, and the mixture was stirred at the same temperature for 5 hours, after which it was allowed to stand overnight in a refrigerator. The reaction mixture was then freed from the solvent by distillation under reduced pressure, and the resulting residue was mixed with an aqueous solution of sodium hydrogencarbonate and then extracted with ethyl acetate. The extract was dried over anhydrous magnesium sulfate and the solvent was removed by distillation under reduced pressure. The resulting residue was worked up and purified by the same procedure as described in Example 8(a), to give 224 mg of the title compound, as a powder.

14(b) (1R, 5S, 6S)-2-[(2S, 4S)-2-(cis-3,5-Dimethyl-1-piperazinylcarbonyl)pyrrolidin-4-ylthio]-6-[(1R)-1-hydroxyethyl]-1-methyl-1-carbapen-2-em-3-carboxylic acid hydrochloride The whole of the 4-nitrobenzyl (1R, 5S, 6S)-2-[(2S, 4S)-2-(cis-3,5-dimethyl-1-piperazinylcarbonyl]-1-(4-nitrobenzyloxycarbonyl)pyrrolidin-4-ylthio]-6-[(1R)-1-hydroxyethyl]-1-methyl-1-carbapen-2-em-3-carboxylate prepared as described in step (a) above was dissolved in 4 ml of a 1:1 by volume mixture of tetrahydrofuran and water, after which 261 µl of 1N aqueous hydrochloric acid were added, and the mixture was hydrogenated by bubbling hydrogen through it at room temperature for 2 hours in the presence of 0.2 g of 10% w/w palladium-on-charcoal. At the end of this time, the reaction mixture was worked up and purified by the same procedure as described in Example 8(b), to give 27 mg of the title compound as a powder.

Ultraviolet absorption spectrum (H₂O) $\lambda_{max}$ nm: 296.5.

Infrared Absorption Spectrum (KBr), $\nu_{max}$ cm⁻¹: 1761, 1661, 1599, 1459, 1386, 1268.

Nuclear Magnetic Resonance Spectrum (270 MHz, D₂O, using tetradeuterated sodium trimethylsilylpropionate as an internal standard), δ ppm:

1.20 (3H; doublet, J=7.32 Hz);

1.28 (3H, doublet, J=6.35 Hz);

1.35–1.39 (6H, multiplet);

1.96–2.06 (1H, multiplet);

2.72–3.53 (9H, multiplet);

3.75–4.29 (5H, multiplet);

4.53–4.94 (1H, multiplet).

EXAMPLE 15

(1R, 5S, 6S)-2-{(2S, 4S)-2-[4-(2-Hydroxyethyl)-1-homopiperazinylcarbonyl]pyrrolidin-4-ylthio}-6-[(1R)-1-hydroxyethyl]-1-methyl-1-carbapen-2-em-3-carboxylic acid hydrochloride

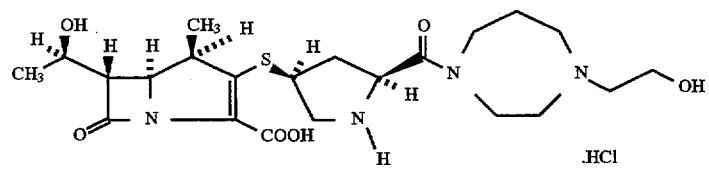

15(a) 4-Nitrobenzyl (1R, 5S, 6S)-2-{(2S, 4S)-2-[4-(2-4'-nitrobenzyloxycarbonyloxyethyl)-1-homopiperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 460 µl of diphenylphosphoryl chloride and 390 µl of diisopropylethylamine were added dropwise, whilst ice-cooling, to a solution of 761 mg of 4-nitrobenzyl (1R, 5R, 6S)-6-[(1R)-1-hydroxyethyl]-1-methyl-2-oxo-1-carbapenam-3-carboxylate in 10 ml of dry acetonitrile, and the resulting mixture was stirred at the same temperature for 1 hour. At the end of this time, 780 µl of diisopropylethylamine and a solution of 2.2 g of (2S, 4S)-4-mercapto-2-{4-[2-(4-nitrobenzyloxycarbonyl)oxyethyl]-1-homopiperazinylcarbonyl}-1-(4-nitrobenzyloxycarbonyl) pyrrolidine trifluoromethanesulfonate (prepared as described in Preparation 15) in 5 ml of dry acetonitrile were simultaneously added dropwise to the mixture, whilst ice-cooling, and the mixture was stirred overnight at the same temperature. The solvent was then removed by distillation under reduced pressure, and the resulting residue was mixed with an aqueous solution of sodium hydrogencarbonate. The mixture was then extracted with ethyl acetate. The extract was dried over anhydrous sodium sulfate and the solvent was removed by distillation under reduced pressure. The resulting residue was purified by column chromatography through 50 g of silica gel (a product of Merck, 230 to 400 mesh), using a 9:1 by volume mixture of ethyl acetate and methanol as the eluent. Those fractions containing the title compound were combined and concentrated by evaporation under reduced pressure, to give 857 mg of the title compound, as a powder.

Infrared Absorption Spectrum (KBr), $v_{max}$ cm$^{-1}$: 1768, 1750, 1710, 1649, 1522, 1347, 1260.

Nuclear Magnetic Resonance Spectrum (CDCl$_3$, 270 MHz), δ ppm:

1.27 (3H, doublet, J=7.3 Hz);
1.36 (3H, doublet, J=6.0 Hz);
1.80–2.05 (3H, multiplet);
2.40–3.00 (7H, multiplet);
3.23–3.78 (7H, multiplet);
4.00–4.29 (5H, multiplet);
3.66–3.84 (7H, multiplet);
3.91–3.96 (2H, multiplet);
4.04–4.13 (1H, multiplet);
4.20–4.29 (2H, multiplet);
4.81–4.91 (1H, multiplet).

EXAMPLE 16

(1R, 5S, 6S)-2-[(2S, 4S)-2-(4-Carbamoylmethyl-1-homopiperazinylcarbonyl)pyrrolidin-4-ylthio]-6-[(1R)-1-hydroxyethyl]-1-methyl-1-carbapen-2-em-3-carboxylic acid hydrochloride

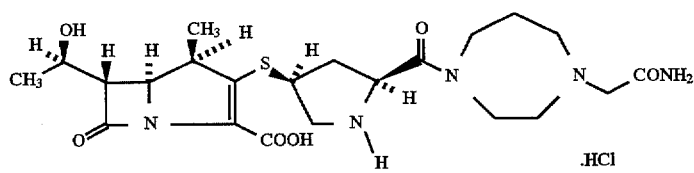

16(a) 4-Nitrobenzyl (1R, 5S, 6S)-2-[(2S, 4S)-2-(4-carbamoylmethyl-1-homopiperazinylcarbonyl)-1-(4-nitrobenzyloxycarbonyl)pyrrolidin-4-ylthio]-6-[(1R)-1-hydroxyethyl]-1-methyl-1-carbapen-2-em-3-carboxylate 2.45 ml of diphenylphosphoryl chloride and 2.05 ml of diisopropylethylamine were added dropwise, whilst ice-cooling, to a solution of 3.98 g of 4-nitrobenzyl (1R, 5R, 6S)-6-[(1R)-1-hydroxyethyl]-1-methyl-2-oxo-1-carbapenam-3-carboxylate in 40 ml of dry acetonitrile, and the resulting mixture was stirred at the same temperature for 1 hour. At the end of this time, 1.85 ml of diisopropylethylamine and a solution of 4.88 g of (2S, 4S)-4-mercapto-2-(4-carbamoylmethyl-1-homopiperazinylcarbonyl)-1-(4-nitrobenzyloxycarbonyl)pyrrolidine (prepared as described in Preparation 16) in 30 ml of dry acetonitrile were simultaneously added dropwise to the mixture, whilst ice-cooling, and the mixture was stirred at the same temperature for 1 hour. The reaction mixture was then diluted with 130 ml of acetonitrile and 200 ml of water, after which 1.85 g of sodium hydrogencarbonate was added. The mixture thus obtained was purified by reverse phase column chromatography through 500 g of Cosmo Sil 75C$_{18}$-PREP (a trade mark for a product of Nacalai Tesque), using 50% v/v aqueous acetonitrile as the eluent. Those fractions containing the title compound were combined and concentrated to give 6.05 g of the title compound, as a powder.

Infrared Absorption Spectrum (KBr), $v_{max}$ cm$^{-1}$: 1772, 1708, 1521, 1346.

Nuclear Magnetic Resonance Spectrum (hexadeuterated dimethyl sulfoxide, 270 MHz), δ ppm:

1.14–1.20 (6H, multiplet);
1.59–1.75 (3H, multiplet);
2.30–3.02 (6H, multiplet);
3.13–3.38 (2H, multiplet);
3.42–3.70 (5H, multiplet);
3.75–4.00 (2H, multiplet);
4.10–4.28 (2H, multiplet);
4.68–4.83 (1H, multiplet);
5.05–5.49 (6H, multiplet);

4.61–4.77 (1H, multiplet);
5.03–5.53 (6H, multiplet);
7.42–7.67 (6H, multiplet);
8.16–8.25 (6H, multiplet).

15(b) (1R, 5S, 6S)-2-{(2S, 4S)-2-[4-(2-Hydroxyethyl)-1-homopiperazinylcarbonyl]pyrrolidin-4-ylthio}-6-[(1R)-1-hydroxyethyl]-1-methyl-1-carbapen-2-em-3-carboxylic acid hydrochloride 350 mg of 4-nitrobenzyl (1R, 5S, 6S)-2-{(2S, 4S)-2-[4-(2-4'-nitrobenzyloxycarbonyloxyethyl)-1-homopiperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 20 ml of a 3:2 by volume mixture of tetrahydrofuran and water, after which 0.33 ml of 1N aqueous hydrochloric acid was added, and the mixture was hydrogenated by bubbling hydrogen through it at room temperature for 2 hours in the presence of 0.5 g of 10% w/w palladium-on-charcoal. At the end of this time, the catalyst was filtered off, and the filtrate was extracted with diethyl ether. The remaining aqueous layer was concentrated by evaporation under reduced pressure, and the resulting residue was purified by Lobar column chromatography (a product of Merck, LiChroprep RP-8, size B), using water as the eluent. Those fractions containing the title compound were combined, concentrated by evaporation under reduced pressure and lyophilized, to give 105 mg of the title compound as a colorless powder.

Infrared Absorption Spectrum (KBr), $v_{max}$ cm$^{-1}$: 1759, 1652, 1595, 1460, 1378, 1286.

Nuclear Magnetic Resonance Spectrum (270 MHz, D$_2$O, using tetradeuterated sodium trimethylsilylpropionate as an internal standard), δ ppm:

1.21 (3H, doublet, J=7.3 Hz);
1.28 (3H, doublet, J=6.4 Hz);
1.96–2.10 (1H, multiplet);
2.25–2.34 (2H, multiplet);
3.00–3.15 (1H, multiplet);
3.33–3.54 (6H, multiplet);

7.08–7.22 (2H, multiplet);
7.54–7.74 (4H, multiplet);
8.20–8.25 (4H, multiplet).

16(b) (1R, 5S, 6S)-2-[(2S, 4S)-2-(4-Carbamoylmethyl-1-homopiperazinylcarbonyl)pyrrolidin-4-ylthio]-6-[(1R)-1-hydroxyethyl]-1-methyl-1-carbapen-2-em-3-carboxylic acid hydrochloride 200 mg of 4-nitrobenzyl (1R, 5S, 6S)-2-[(2S, 4S)-2-(4-carbamoylmethyl-1-homopiperazinylcarbonyl)-1-(4-nitrobenzyloxycarbonyl)pyrrolidin-4-ylthio]-6-[(1R)-1-hydroxyethyl]-1-methyl-1-carbapen-2-em-3-carboxylate [prepared as described in step (a) above] were dissolved in 20 ml of a 1:1 by volume mixture of tetrahydrofuran and water, after which 0.18 ml of 1N aqueous hydrochloric acid were added to the mixture, which was then hydrogenated by bubbling hydrogen through it at room temperature for 2 hours in the presence of 0.3 g of 10% w/w palladium-on-charcoal. The catalyst was then filtered off, and the filtrate was extracted with diethyl ether. The aqueous layer was concentrated by evaporation under reduced pressure, and the resulting residue was purified by column chromatography through a Lobar column (a product of Merck, LiChroprep RP-8, size B), using water as the eluent. Those fractions containing the title compound were combined, concentrated by evaporation under reduced pressure and lyophilized, to give 30 mg of the title compound as a colorless powder.

Ultraviolet absorption spectrum (H$_2$O) $\lambda_{max}$ nm: 297.

EXAMPLE 17

(1R, 5S, 6S)-2-[(2S, 4S)-2-(4-Acetimidoylpiperazin-1-ylcarbonyl)pyrrolidin-4-ylthio]-6-[(1R)-1-hydroxyethyl]-1-methyl-1-carbapen-2-em-3-carboxylic acid hydrochloride an aqueous solution of sodium chloride. The ethyl acetate layer was then dried over anhydrous sodium sulfate, and the solvent was removed by distillation under reduced pressure. The residue was purified by column chromatography through silica gel, using a 6:4 by volume mixture of ethyl acetate and acetonitrile as the eluent. Those fractions containing the title compound were combined and concentrated to give 5.17 g of the title compound, as a powder.

The spectral data of this compound are identical with those of the compound prepared as described in Example 1(a).

17(b) (1R, 5S, 6S)-2-[(2S, 4S)-2-(4-Acetimidoylpiperazin-1-ylcarbonyl)pyrrolidin-4-ylthio]-6-[(1R)-1-hydroxyethyl]-1-methyl-1-carbapen-2-em-3-carboxylic acid 5.10 g of 4-nitrobenzyl (1R, 5S, 6S)-2-{(2S, 4S)-2-[4-(N-4-nitrobenzyloxycarbonylacetimidoyl)piperazin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 100 ml of a 6:4 by volume mixture of tetrahydrofuran and water, and the mixture was hydrogenated by bubbling hydrogen through it at room temperature for 2.5 hours in the presence of 5.0 g of 10% w/w palladium-on-charcoal. The catalyst was filtered off, and the filtrate was washed with diethyl ether and then concentrated by evaporation under reduced pressure. The resulting residue was purified by reverse phase column chromatography through 250 ml of Cosmo Sil 75C$_{18}$-PREP (a trade mark for a product of Nacalai Tesque), using water, 5% v/v aqueous acetonitrile and 7% v/v aqueous acetonitrile, in that order, as the eluent. Those fractions containing the title compound were combined, concentrated by evaporation under reduced pressure and lyophilized to give 940 mg of the title compound, as a powder.

The spectral data of this compound are identical with those of the compound prepared as described in Example 1(b).

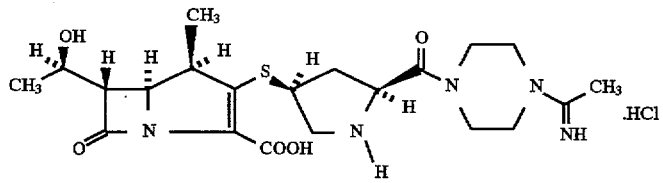

17(a) 4-Nitrobenzyl (1R, 5S, 6S)-2-{(2S, 4S)-2-[4-(N-4-nitrobenzyloxycarbonylacetimidoyl)piperazin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 1.45 ml of diphenylphosphoryl chloride and 1.22 ml of diisopropylethylamine were added dropwise, whilst ice-cooling, to a solution of 2.43 g of 4-nitrobenzyl (1R, 5R, 6S)-6-[(1R)-1-hydroxyethyl]-1-methyl-2-oxo-1-carbapenam-3-carboxylate in 25 ml of dry acetonitrile and the resulting mixture was stirred at the same temperature for 30 minutes. A solution of 3.99 g of (2S, 4S)-4-mercapto-2-[4-(N-4-nitrobenzyloxycarbonylacetimidoyl)piperazin-1-ylcarbonyl]-1-(4-nitrobenzyloxycarbonyl)pyrrolidine (prepared as described in Preparation 17) in 15 ml of dry acetonitrile and 1.22 ml of diisopropylethylamine were then simultaneously added dropwise to the mixture, whilst ice-cooling, and the mixture was stirred overnight at the same temperature. At the end of this time, the reaction mixture was concentrated by evaporation under reduced pressure, and the resulting residue was diluted with ethyl acetate. The diluted solution was washed, in turn, with an aqueous solution of sodium hydrogencarbonate, with water and with 17(c) (1R, 5S, 6S)-2-[(2S, 4S)-2-(4-Acetimidoylpiperazin-1-ylcarbonyl)pyrrolidin-4-ylthio]-6-[(1R)-1-hydroxyethyl]-1-methyl-1-carbapen-2-em-3-carboxylic acid hydrochloride 200 mg of (1R, 5S, 6S)-2-[(2S, 4S)-2-(4-acetimidoylpiperazin-1-ylcarbonyl)pyrrolidin-4-ylthio]-6-[(1R)-1-hydroxyethyl]-1-methyl-1-carbapen-2-em-3- carboxylic acid [prepared as described in step (b) above] were dissolved in 5 ml of water, after which 0.43 ml of 1N aqueous hydrochloric acid was added. The resulting mixture was worked up and purified by reverse phase column chromatography through 30 ml of Cosmo Sil 75C$_{18}$-PREP (a trade mark for a product of Nacalai Tesque), using water as the eluent. Those fractions containing the title compound were combined and lyophilized to give 149 mg of the title compound as a powder.

Infrared Absorption Spectrum (KBr), $v_{max}$ cm$^{-1}$: 1756, 1656, 1620, 1450, 1382, 1252.

Ultraviolet absorption spectrum (H$_2$O) $\lambda_{max}$ nm: 297.

Nuclear Magnetic Resonance Spectrum (D$_2$O, 270 MHz), δ ppm:

1.21 (3H, doublet, J=7.3 Hz);
1.29 (3H, doublet, J=6.4 Hz);

1.97–2.07 (1H, multiplet);
2.35 & 2.36 (together 3H, two singlets);
3.02–3.14 (1H, multiplet);
3.31–3.43 (1H, multiplet);
3.45–3.53 (2H, multiplet);
3.68–3.88 (9H, multiplet);
4.03–4.12 (1H, multiplet);
4.20–4.30 (2H, multiplet);
4.82–4.90 (1H, multiplet).

EXAMPLE 18

(1R, 5S, 6S)-2-{(2S, 4S)-2-[(3S)-3-Aminopyrrolidin-1-ylcarbonyl]pyrrolidin-4-ylthio}-6-[(1R)-1-hydroxyethyl]-1-methyl-1-carbapen-2-em-3-carboxylic acid hydrochloride 5.05–5.49 (7H, multiplet);
7.48–7.82 (6H, multiplet);
8.17–8.25 (6H, multiplet).

18(b) (1R, 5S, 6S)-2-{(2S, 4S)-2-[(3S)-3-Aminopyrrolidin-1-ylcarbonyl]pyrrolidin-4-ylthio}-6-[(1R)-1-hydroxyethyl]-1-methyl-1-carbapen-2-em-3-carboxylic acid hydrochloride 1.0 g of 4-nitrobenzyl (1R, 5S, 6S)-2-{(2S, 4S)-2-[(3S)-3-(4-nitrobenzyloxycarbonyl)aminopyrrolidin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 30 ml of a 2:1 by volume mixture of tetrahydrofuran and water, after which 1.0 ml of 1N aqueous hydrochloric acid was added, and the mixture was hydrogenated by bubbling hydrogen through in at room temperature for 2 hours in the presence of 1.5 g of 10% w/w palladium-on-charcoal. The catalyst was filtered off, and the

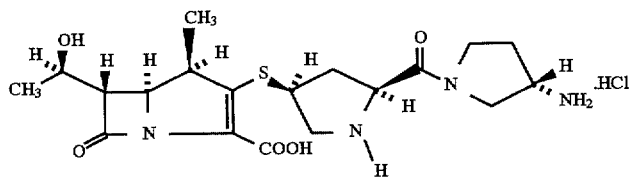

18(a) 4-Nitrobenzyl (1R, 5S, 6S)-2-{(2S, 4S)-2-[(3S)-3-(4-nitrobenzyloxycarbonyl)aminopyrrolidin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 453 μl of diphenylphosphoryl chloride and 381 μl of diisopropylethylamine were added dropwise, whilst ice-cooling, to a solution of 760 mg of 4-nitrobenzyl (1R, 5R, 6S)-6-[(1R)-1-hydroxyethyl]-1-methyl-2-oxo-1-carbapenam-3-carboxylate in 6 ml of dry acetonitrile, and the resulting mixture was stirred at the same temperature for 1 hour. A solution of 1.26 g of (2S, 4S)-4-mercapto-2-[(3S)-3-(4-nitrobenzyloxycarbonyl)aminopyrrolidin-1-ylcarbonyl]-1-(4-nitrobenzyloxycarbonyl)pyrrolidine (prepared as described in Preparation 18) in 5 ml of dry acetonitrile and 364 μl of diisopropylethylamine were then simultaneously added dropwise to the mixture, whilst ice-cooling and the mixture was stirred at the same temperature for 3 hours. At the end of this time, the solvent was removed by distillation under reduced pressure, and the resulting residue was diluted with 70 ml of ethyl acetate. The diluted solution was then washed, in turn, with water, with a saturated aqueous solution of sodium hydrogencarbonate, with water and with a saturated aqueous solution of sodium chloride, in that order. The washed organic solution was then dried over anhydrous magnesium sulfate, and the solvent was removed by distillation under reduced pressure. The resulting residue was purified by column chromatography through silica gel, using a 4:96 by volume mixture of methanol and ethyl acetate as the eluent, to give 1.01 g of the title compound, as a powder.

Infrared Absorption Spectrum (KBr), $v_{max}$ cm$^{-1}$: 3377, 1774, 1713, 1648, 1607, 1521, 1346, 852, 736.

Nuclear Magnetic Resonance Spectrum (hexadeuterated dimethyl sulfoxide, 270 MHz), δ ppm:

1.15–1.18 (6H, multiplet);
1.70–2.20 (2H, multiplet);
2.77–2.85 (1H, multiplet);
3.12–4.27 (14H, multiplet);
4.49–4.64 (1H, multiplet);

filtrate was washed with diethyl ether. The washed aqueous solution was concentrated by evaporation under reduced pressure, and the residue was purified by reverse phase column chromatography through 19 ml of Cosmo Sil 75C$_{18}$-PREP (a trade mark for a product of Nacalai Tesque), using water as the eluent. Those fractions containing the title compound were combined, concentrated by evaporation under reduced pressure and lyophilized to give 169 mg of the title compound as a powder.

Infrared Absorption Spectrum (KBr), $v_{max}$ cm$^{-1}$: 3397, 1758, 1653, 1587, 1465, 1386.

Nuclear Magnetic Resonance Spectrum (270 Hz, D$_2$O, using tetradeuterated sodium trimethylsilylpropionate as an internal standard), δ ppm:

1.21 (3H, doublet, J=7.32 Hz);
1.29 (3H, doublet, J=6.35 Hz);
1.97–2.19 (1H, multiplet);
2.21–2.29 (1H, multiplet);
2.36–2.60 (1H, multiplet);
3.02–3.14 (1H, multiplet);
3.32–3.43 (1H, multiplet);
3.45–3.53 (2H, multiplet);
3.57–3.90 (5H, multiplet);
3.98–4.17 (2H, multiplet);
4.20–4.29 (2H, multiplet);
4.63–4.82 (1H, multiplet).

EXAMPLE 19

(1R, 5S, 6S)-2-{(2S, 4S)-2-[(3S)-Pyrrolidin-3-ylaminocarbonyl]pyrrolidin-4-ylthio}-6-[(1R)-1-hydroxyethyl]-1-methyl-1-carbapen-2-em-3-carboxylic acid hydrochloride

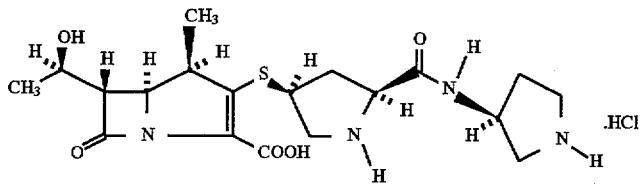

19(a) 4-Nitrobenzyl (1R, 5S, 6S)-2-{(2S, 4S)-2-[(3S)-1-(4-nitrobenzyloxycarbonyl)pyrrolidin-3-ylaminocarbonyl]-1-(4-nitrobenzyloxycarbonyl)pyrrolidin-4-ylthio}-6-[(1R)-1-hydroxyethyl]-1-methyl-1-carbapen-2-em-3-carboxylate 253 μl of diphenylphosphoryl chloride and 212 μl of diisopropylethylamine were added dropwise, whilst ice-cooling, to a solution of 420 mg of 4-nitrobenzyl (1R, 5R, 6S)-6-[(1R)-1-hydroxyethyl]-1-methyl-2-oxo-1-carbapenam-3-carboxylate in 4.2 ml of dry acetonitrile, and the resulting mixture was stirred at the same temperature for 1 hour. A solution of 913 mg of (2S, 4S)-4-mercapto-2-[(3S)-1-(4-nitrobenzyloxycarbonyl)pyrrolidin-3-ylaminocarbonyl]-1-(4-nitrobenzyloxycarbonyl)pyrrolidine (prepared as described in Preparation 19) in 5 ml of dry acetonitrile and 404 μl of diisopropylethylamine were then simultaneously added dropwise to the mixture, whilst ice-cooling, and the mixture was stirred at the same temperature for 7 hours and then allowed to stand overnight at the same temperature. At the end of this time, 101 μl of diisopropylethylamine were added, and the mixture was stirred at the same temperature for 1 hour. The reaction mixture was then worked up and purified by the same procedure as described in Example 18(a), to give 504 mg of the title compound, as a powder.

Infrared Absorption Spectrum (KBr), $v_{max}$ cm$^{-1}$: 3385, 1775, 1709, 1607, 1522, 1346, 853, 737.

Nuclear Magnetic Resonance Spectrum (hexadeuterated dimethyl sulfoxide, 270 MHz), δ ppm:

1.15–1.18 (6H, multiplet);
1.69–2.07 (3H, multiplet);
2.60–2.80 (1H, multiplet);
3.10–3.70 (9H, multiplet);
3.80–4.35 (6H, multiplet);
5.15–5.48 (6H, multiplet);
7.57–7.73 (6H, multiplet);
8.21–8.33 (6H, multiplet).

19(b) (1R, 5S, 6S)-2-{(2S, 4S)-2-[(3S)-Pyrrolidin-3-ylaminocarbonyl]pyrrolidin-4-ylthio}-6-[(1R)-1-hydroxyethyl]-1-methyl-1-carbapen-2-em-3-carboxylic acid hydrochloride 475 mg of 4-nitrobenzyl (1R, 5S, 6S)-2-{(2S, 4S)-2-[(3S)-1-(4-nitrobenzyloxycarbonyl)pyrrolidin-3-ylaminocarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 15 ml of a 2:1 by volume mixture of tetrahydrofuran and water, after which 0.45 ml of 1N aqueous hydrochloric acid was added, and the mixture hydrogenated by bubbling hydrogen through it at room temperature for 2 hours in the presence of 1 g of 10% w/w palladium-on-charcoal. At the end of this time, the reaction mixture was worked up and purified by the same procedure as described in Example 18(b), to give 46 mg of the title compound as a powder.

Infrared Absorption Spectrum (KBr), $v_{max}$ cm$^{-1}$: 3367, 1760, 1683, 1558, 1390, 1281.

Nuclear Magnetic Resonance Spectrum (270 MHz, D$_2$O, using tetradeuterated sodium trimethylsilylpropionate as an internal standard), δ ppm:

1.21 (3H, doublet, J=7.33 Hz);
1.28 (3H, doublet, J=6.35 Hz);
2.04–2.24 (2H, multiplet);
2.33–2.46 (1H, multiplet);
2.88–3.00 (1H, multiplet);
3.31–3.56 (6H, multiplet);
3.59–3.67 (1H, multiplet);
3.77–3.84 (1H, multiplet);
4.04–4.13 (1H, multiplet);
4.20–4.29 (2H, multiplet);
4.47–4.56 (2H, multiplet).

EXAMPLE 20

(1R, 5S, 6S)-2-{(2S, 4S)-2-[(3R)-Pyrrolidin-3-ylaminocarbonyl]pyrrolidin-4-ylthio}-6-[(1R)-1-hydroxyethyl]-1-methyl-1-carbapen-2-em-3-carboxylic acid hydrochloride

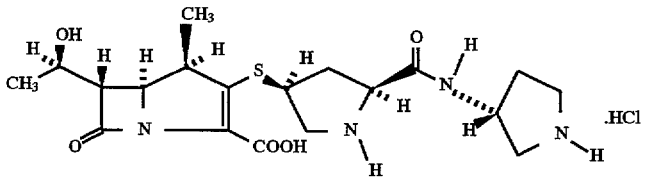

20(a) 4-Nitrobenzyl (1R, 5S, 6S)-2-{(2S, 4S)-2-[(3R)-1-(4-nitrobenzyloxycarbonyl)pyrrolidin-3-ylaminocarbonyl]-1-(4-nitrobenzyloxycarbonyl)pyrrolidin-4-ylthio}-6-[(1R)-1-hydroxyethyl]-1-methyl-1-carbapen-2-em-3-carboxylate Following a procedure similar to than described in Example 19(a), but using 1.06 g of (2S, 4S)-4-mercapto-2-[(3R)-1-(4-nitrobenzyloxycarbonyl)pyrrolidin-3-ylaminocarbonyl]-1-(4-nitrobenzyloxycarbonyl)pyrrolidine (prepared as described in Preparation 20) instead of the (2S, 4S)-4-mercapto-2-[(3S)-1-(4-nitrobenzyloxycarbonyl)pyrrolidin-3-ylaminocarbonyl]-1-(4-nitrobenzyloxycarbonyl)pyrrolidine, 540 mg of the title compound were obtained as a powder.

20(b) (1R, 5S, 6S)-2-{(2S, 4S)-2-[(3R)-Pyrrolidin-3-ylaminocarbonyl]pyrrolidin-4-ylthio}-6-[(1R)-1-hydroxyethyl]-1-methyl-1-carbapen-2-em-3-carboxylic acid hydrochloride 500 mg of 4-nitrobenzyl (1R, 5S, 6S)-2-{(2S, 4S)-2-[(3R)-1-(4-nitrobenzyloxycarbonyl)pyrrolidin-3-ylaminocarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 20 ml of a 1:1 by volume mixture of tetrahydrofuran and water, after which 0.47 ml of 1N aqueous hydrochloric acid was added, and the mixture was hydrogenated by bubbling hydrogen through it at room temperature for 2 hours in the presence of 1 g of 10% w/w palladium-on-charcoal. The reaction mixture was then worked up and purified by the same procedure as described in Example 18(b), to give 43 mg of the title compound as a powder.

Ultraviolet absorption spectrum ($H_2O$) $\lambda_{max}$ nm: 297.

EXAMPLE 21

(1R, 5S, 6S)-2-{(2S, 4S)-2-[(3S)-3-Dimethylaminopyrrolidin-1-ylcarbonyl]pyrrolidin-4-ylthio}-6-[(1R)-1-hydroxyethyl]-1-methyl-1-carbapen-2-em-3-carboxylic acid hydrochloride

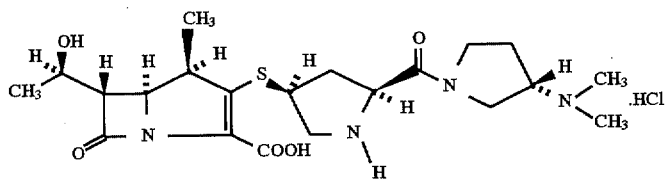

21(a) 4-Nitrobenzyl (1R, 5S, 6S)-2-{(2S, 4S)-2-[(3S)-3-dimethylaminopyrrolidin-1-ylcarbonyl]-1-(4-nitrobenzyloxycarbonyl)pyrrolidin-4-ylthio]-6-[(1R)-1-hydroxyethyl]-1-methyl-1-carbapen-2-em-3-carboxylate 880 µl of diphenylphosphoryl chloride and 740 µl of diisopropylethylamine, whilst ice-cooling, were added dropwise to a solution of 1.46 g of 4-nitrobenzyl (1R, 5R, 6S)-6-[(1R)-1-hydroxyethyl]-1-methyl-2-oxo-1-carbapenam-3-carboxylate in 12 ml of dry acetonitrile, and the resulting mixture was stirred at the same temperature for 0.5 hours. A solution of 1.70 g of (2S, 4S)-4-mercapto-2-[(3H)-3-dimethylaminopyrrolidin-1-ylcarbonyl]-1-(4-nitrobenzyloxycarbonyl)pyrrolidine trifluorosulfonate (prepared as described in Preparation 21) in 8 ml of dry acetonitrile and 700 µl of diisopropylethylamine were then simultaneously added dropwise to the mixture, whilst ice-cooling, and the mixture was stirred at the same temperature for 2.5 hours. At the end of this time, the reaction mixture was worked up and purified by the same procedure as described in Example 18(a), to give 1.65 g of the title compound, as a powder.

Infrared Absorption Spectrum (KBr), $\nu_{max}$ cm$^{-1}$: 1773, 1711, 1650, 1607, 1522, 1346, 854, 738.

Nuclear Magnetic Resonance Spectrum (hexadeuterated dimethyl sulfoxide, 270 MHz), δ ppm:

1.15 (3H, doublet, J=3.42 Hz);
1.18 (3H, doublet, J=3.90 Hz);
2.09 (2H, doublet, J=8.3 Hz);
2.17 (1H, singlet);
2.70–3.93 (17H, multiplet);
3.95–4.08 (1H, multiplet);
4.11–4.20 (1H, multiplet);
4.23–4.29 (1H, multiplet);
4.55–4.66 (1H, multiplet);
5.06–5.75 (4H, multiplet);
7.53–7.74 (4H, multiplet);
8.21–8.25 (4H, multiplet).

21(b) (1R, 5S, 6S)-2-{(2S, 4S)-2-[(3S)-3-Dimethylaminopyrrolidin-1-ylcarbonyl]pyrrolidin-4-ylthio}-6-[(1R)-1-hydroxyethyl]-1-methyl-1-carbapen-2-em-3-carboxylic acid hydrochloride 306 mg of 4-nitrobenzyl (1R, 5S, 6S)-2-{(2S, 4S)-2-[(3S)-3-dimethylaminopyrrolidin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 12 ml of a 2:1 by volume mixture of tetrahydrofuran and water, after which 0.38 ml of 1N aqueous hydrochloric acid was added, and the mixture was hydrogenated by bubbling hydrogen through it at room temperature for 2 hours in the presence of 600 mg of 10% w/w palladium-on-charcoal. The reaction mixture was then worked up and purified by the same procedure as described in Example 18(b), to give 19 mg of the title compound as a powder.

Infrared Absorption Spectrum (KBr), $\nu_{max}$ cm$^{-1}$: 3385, 1764, 1656, 1553, 1466, 1375.

Nuclear Magnetic Resonance Spectrum (270 MHz, $D_2O$, using tetradeuterated sodium trimethylsilylpropionate as an internal standard), δ ppm:

1.22 (3H, doublet, J=7.32 Hz);
1.28 (3H, doublet, J=6.35 Hz);
1.95–2.10 (1H, multiplet);
2.15–2.35 (3H, multiplet);
2.5–2.7 (1H, multiplet);
2.96–2.97 (6H, multiplet);
3.00–3.15 (1H, multiplet);
3.37–3.43 (1H, multiplet);
3.46–3.52 (2H, multiplet);
3.56–3.70 (2H, multiplet);
3.73–4.11 (6H, multiplet);
4.15–4.30 (2H, multiplet).

EXAMPLE 22

(1R, 5S, 6S)-2-{(2S, 4S)-2-[(3S)-3-Methylaminopyrrolidin-1-ylcarbonyl]pyrrolidin-4-ylthio}-6-[(1R)-1-hydroxyethyl]-1-methyl-1-carbapen-2-em-3-carboxylic acid hydrochloride

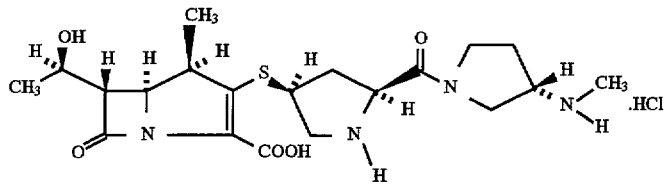

22(a) 4-Nitrobenzyl (1R, 5S, 6S)-2-{(2S, 4S)-2-[(3S)-3-N-methyl-N-(4-nitrobenzyloxycarbonyl)aminopyrrolidin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate Following a procedure similar to that described in Example 18(a), but using 820 mg of (2S, 4S)-4-mercapto-2-[(3S)-3-N-methyl-N-(4-nitrobenzyloxycarbonyl)aminopyrrolidin-1-ylcarbonyl]-1-(4-nitrobenzyloxycarbonyl)pyrrolidine (prepared as described in Preparation 22) instead of the (2S, 4S)-4-mercapto-2-[(3S)-3-(4-nitrobenzyloxycarbonyl)aminopyrrolidin-1-ylcarbonyl]-1-(4-nitrobenzyloxycarbonyl)pyrrolidine, 630 mg of the title compound were obtained.

22(b) (1R, 5S, 6S)-2-{(2S, 4S)-2-[(3S)-3-Methylaminopyrrolidin-1-ylcarbonyl]pyrrolidin-4-ylthio}-6-[(1R)-1-hydroxyethyl]-1-methyl-1-carbapen-2-em-3-carboxylic acid hydrochloride 580 mg of 4-nitrobenzyl (1R, 5S, 6S)-2-{(2S, 4S)-2-[(3S)-3-N-methyl-N-(4-nitrobenzyloxycarbonyl)aminopyrrolidin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 12 ml of a 1:1 by volume mixture of tetrahydrofuran and water, after which 0.55 ml of 1N aqueous hydrochloric acid was added, and the mixture was hydrogenated by bubbling hydrogen through it at room temperature for 2 hours in the presence of 700 mg of 10% w/w palladium-on-charcoal. At the end of this time, the reaction mixture was worked up and purified by the same procedure as described in Example 18(b), to give 53 mg of the title compound as a powder.

Ultraviolet absorption spectrum (H$_2$O) $\lambda_{max}$ nm: 297.

EXAMPLE 23

(1R, 5S, 6S)-1-{(2S, 4S)-2-[(3S)-Acetimidoylaminopyrrolidin-1-ylcarbonyl]pyrrolidin-4-ylthio}-6-[(1R)-1-hydroxyethyl]-1-methyl-1-carbapen-2-em-3-carboxylic acid wise to a solution of 384 mg of 4-nitrobenzyl (1R, 5R, 6S)-6-[(1R)-1-hydroxyethyl]-1-methyl-2-oxo-1-carbapenam-3-carboxylate in 6 ml of dry acetonitrile, and the resulting mixture was stirred an the same temperature for 45 minutes. A solution of 652 mg of (2S, 4S)-4-mercapto-2-[(3S)-3-(N-4-nitrobenzyloxycarbonylacetimidoylamino)pyrrolidin-1-ylcarbonyl]-1-(4-nitrobenzyloxycarbonyl)pyrrolidine (prepared as described in Preparation 23) in 4 ml of acetonitrile and 185 µl of diisopropylethylamine were then simultaneously added dropwise to the mixture, and the mixture was stirred at the same temperature for 3 hours. At the end of this time, the reaction mixture was concentrated by evaporation under reduced pressure. The resulting residue was diluted with ethyl acetate and the diluted solution was washed with water and with an aqueous solution of sodium chloride. The ethyl acetate solution was dried over anhydrous magnesium sulfate and the solvent was removed by distillation under reduced pressure. The resulting residue was purified by column chromatography through silica gel, using a 9:9:1 by volume mixture of methylene chloride, ethyl acetate and methanol as the eluent. Those fractions containing the title compound were combined and concentrated to give 510 mg of the title compound, as a powder.

Infrared Absorption Spectrum (KBr), $v_{max}$ cm$^{-1}$: 1774, 1709, 1654, 1607, 1551, 1521, 1441, 1404, 1346.

Nuclear Magnetic Resonance Spectrum (hexadeuterated dimethyl sulfoxide+D$_2$O, 270 MHz), δ ppm:

1.15 (3H, doublet, J=6.35 Hz);

1.16 (3H, doublet, J=7.32 Hz);

1.60–2.28 (2H, multiplet);

2.10 (3H, singlet);

2.69–2.93 (1H, multiplet);

3.10–4.72 (14H, multiplet);

5.04–5.51 (6H, multiplet);

7.46–7.76 (6S, multiplet);

8.14–8.28 (6H, multiplet).

23(b) (1R, 5S, 6S)-1-{(2S, 4S)-2-[(3S)-Acetimidoylaminopyrrolidin-1-ylcarbonyl]pyrrolidin-4-

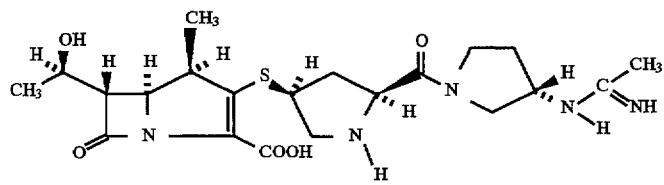

23(a) 4-Nitrobenzyl (1R, 5S, 6S)-2-{(2S, 4S)-2-[(3S)-3-(N-4-nitrobenzyloxycarbonylacetimidoylamino)pyrrolidin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 231 µl of diphenylphosphoryl chloride and 194 µl of diisopropylethylamine, whilst ice-cooling, were added dropylthio}-6-[(1R)-1-hydroxyethyl]-1-methyl-1-carbapen-2-em-3-carboxylic acid 500 mg of 4-nitrobenzyl (1R, 5S, 6S)-2-{(2S, 4S)-2-[(3S)-3-(N-4-nitrobenzyloxycarbonylacetimidoylamino)pyrrolidin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 16 ml of a 1:1 by volume mixture of tetrahydrofuran and water, and the mixture was hydrogenated by bubbling hydrogen through it at room temperature for 2 hours in the presence of 400 mg of 10% w/w palladium-on-charcoal. The catalyst was then filtered off, and the filtrate was washed with diethyl ether. The aqueous layer was concentrated by evaporation under reduced pressure, and the concentrate was purified by reverse phase column chromatography through 20 ml of Cosmo Sil 75$C_{18}$-PREP (a product of Nacalai Tesque), using 6% v/v aqueous acetonitrile as the eluent. Those fractions containing the title compound were combined, concentrated by evaporation under reduced pressure and lyophilized, to give 136 mg of the title compound as a powder.

Ultraviolet absorption spectrum ($H_2O$) $\lambda_{max}$ nm: 298.

Infrared Absorption Spectrum (KBr), $v_{max}$ $cm^{-1}$: 1756, 1632, 1590, 1451, 1386, 1283, 1259.

Nuclear Magnetic Resonance Spectrum (270 MHz, $D_2O$, using tetradeuterated sodium trimethylsilylpropionate as an internal standard), δ ppm:

1.22 (3H, doublet, J=7.32 Hz);
1.30 (3H, doublet, J=6.35 Hz);
1.57–1.71 (1H, multiplet);
1.97–2.51 (2H, multiplet);
2.23 & 2.25 (together 3H, two singlets);
2.64–2.81 (1H, multiplet);
3.05 (1H, doublet of doublets, J=12.21 & 3.91 Hz);
3.18 (1H, doublet of doublets, J=12.21 & 5.86 Hz);
3.43 (1H, doublet of doublets, J=6.35 & 2.24 Hz);
3.32–4.06 (7H, multiplet);
4.22 (1H, doublet of doublets, J=9.28 & 2.44 Hz);
4.18–4.43 (2H, multiplet).

EXAMPLE 24

(1R, 5S, 6S)-2-{(2S, 4S)-2-[(3S)-Formimidoylaminopyrrolidin-1-ylcarbonyl]pyrrolidin-4-ylthio}-6-[(1R)-1-hydroxyethyl]-1-methyl-1-carbapen-2-em-3-carboxylic acid 24(a) 4-Nitrobenzyl (1R, 5S, 6S)-2-{(2S, 4S)-2-[(3S)-3-(N-4-nitrobenzyloxycarbonylformimidoylamino)pyrrolidin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 250 μl of diphenylphosphoryl chloride and 210 μl of diisopropylethylamine were added dropwise, whilst ice-cooling, to a solution of 417 mg of 4-nitrobenzyl (1R, 5R, 6S)-6-[(1R)-1-hydroxyethyl]-1-methyl-2-oxo-1-carbapenam-3-carboxylate in 8 ml of dry acetonitrile, and the resulting mixture was stirred at the same temperature for 1 hour. A solution of 659 mg of (2S, 4S)-4-mercapto-2-[(3S)-3-(N-4-nitrobenzyloxycarbonylformimidoylamino)pyrrolidin-1-ylcarbonyl]-1-(4-nitrobenzyloxycarbonyl)pyrrolidine (prepared as described in Preparation 24) in 7 ml of dry acetonitrile and 210 μl of diisopropylethylamine were then simultaneously added dropwise to the mixture, whilst ice-cooling, and the mixture was stirred an the same temperature for 1 hour and then allowed to stand overnight at the same temperature. At the end of this time, the reaction mixture was worked up and purified by the same procedure as described in Example 23(a), to give 593 mg of the title compound, as a powder.

Infrared Absorption Spectrum (KBr), $v_{max}$ $cm^{-1}$: 1772, 1707, 1655, 1605, 1521, 1444, 1346, 1210, 1136, 1111.

Nuclear Magnetic Resonance Spectrum ($CDCl_3+D_2O$, 270 MHz), δ ppm:

1.25 (3H, doublet, J=7.32 Hz);
1.36 (3H, doublet, J=6.35 Hz);
1.75–2.80 (4H, multiplet);
3.22–4.32 (12H, multiplet);
4.40–4.65 (1H, multiplet);
5.12–5.55 (6H, multiplet);
7.38–7.69 (6H, multiplet);
8.06–8.31 (6H, multiplet);
8.42 (1H, singlet).

24(b) (1R, 5S, 6S)-2-{(2S, 4S)-2-[(3S)-Formimidoylaminopyrrolidin-1-ylcarbonyl]pyrrolidin-4-ylthio}-6-[(1R)-1-hydroxyethyl]-1-methyl-1-carbapen-2-em-3-carboxylic acid 570 mg of 4-nitrobenzyl (1R, 5S, 6S)-2-{(2S, 4S)-2-[(3S)-3-(N-4-nitrobenzyloxycarbonylformimidoylamino)pyrrolidin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 20 ml of a 1:1 by volume mixture of tetrahydrofuran and water, and the mixture was hydrogenated by bubbling hydrogen through it at room temperature for 2 hours in the presence of 450 mg of 10% w/w palladium-on-charcoal. At the end of this time, the reaction mixture was worked up and purified by the same procedure as described in Example 23(b) to give 125 mg of the title compound as a powder.

Ultraviolet absorption spectrum ($H_2O$) $\lambda_{max}$ nm: 300.

Infrared Absorption Spectrum (KBr), $v_{max}$ $cm^{-1}$: 1755, 1634, 1592, 1455, 1388, 1286, 1260, 1182, 1148.

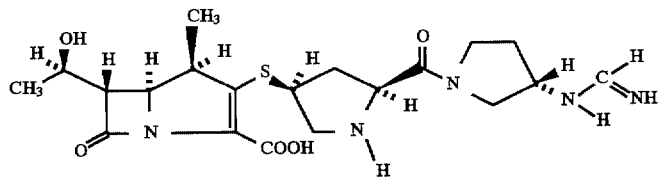

Nuclear Magnetic Resonance Spectrum (270 MHz, $D_2O$, using sodium tetradeuterated trimethylsilylpropionate as an internal standard), δ ppm:

1.22 (3H, doublet, J=7.32 Hz);
1.30 (3H, doublet, J=6.35 Hz);
1.58–1.75 (1H, multiplet);
1.98–2.53 (2H, multiplet);
2.64–2.86 (1H, multiplet);
3.07 (1H, doublet of doublets, J=12.21 & 3.91 Hz);
3.21 (1H, doublet of doublets, J=12.21 & 5.86 Hz);
3.32–4.12 (8H, multiplet);
4.17–4.53 (3H, multiplet);
7.80, 7.82, 7.95 & 7.96 (together 1H, four singlets).

EXAMPLE 25

(1R, 5S, 6S)-2-{(2S, 4S)-2-[(3R)-1-Formimidoylpyrrolidin-3-ylaminocarbonyl]pyrrolidin-4-ylthio}-6-[(1R)-1-hydroxyethyl]-1-methyl-1-carbapen-2-em-3-carboxylic acid

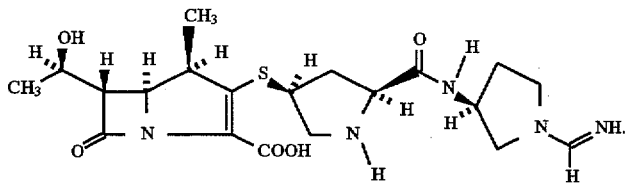

25(a) 4-Nitrobenzyl (1R, 5S, 6S)-2-{(2S, 4S)-2-[(3S)-1-(N-4-nitrobenzyloxycarbonylformimidoyl)pyrrolidin-3-ylaminocarbonyl]-1-(4-nitrobenzyloxycarbonyl)pyrrolidin-4-ylthio}-6-[(1R)-1-hydroxyethyl]-1-methyl-1-carbapen-2-em-3-carboxylate 225 µl of diphenylphosphoryl chloride and 189 µl of diisopropylethylamine were added dropwise, whilst ice-cooling, to a solution of 374 mg of 4-nitrobenzyl (1R, 5R, 6S)-6-[(1R)-1-hydroxyethyl]-1-methyl-2-oxo-1-carbapenam-3-carboxylate in 5 ml of dry acetonitrile, and the resulting mixture was stirred at the same temperature for 1 hour. A solution of 620 mg of (2S, 4S)-4-mercapto-2-[(3S)-1-(N-4-nitrobenzyloxycarbonylformimidoyl)pyrrolidin-3-ylaminocarbonyl]-1-(4-nitrobenzyloxycarbonyl)pyrrolidine (prepared as described in Preparation 25) in 5 ml of dry acetonitrile and 189 µl of diisopropylethylamine were then simultaneously added dropwise to the mixture, whilst ice-cooling, and the mixture was stirred an the same temperature for 1 hour, after which it was allowed to stand overnight at the same temperature. At the end of this time, the reaction mixture was worked up and purified by the same procedure as described in Example 23(a), to give 250 mg of the title compound, as a powder.

Infrared Absorption Spectrum (KBr), $v_{max}$ cm$^{-1}$: 1774, 1710, 1605, 1520, 1450, 1346, 1220, 1157, 1108.

Nuclear Magnetic Resonance Spectrum (CDCl$_3$+D$_2$O, 270 MHz), δ ppm:

1.27 (3H, doublet, J=7.32 Hz);
1.36 (3H, doublet, J=6.35 Hz);
2.01–2.38 (2H, multiplet);
3.23–4.62 (14H, multiplet);
5.10–5.36 (6H, multiplet);
5.37–5.52 (1H, multiplet);
7.42–7.68 (6H, multiplet);
8.11–8.28 (6H, multiplet);
8.63 (1H, singlet).

25(b) (1R, 5S, 6S)-2-{(2S, 4S)-2-[(3R)-1-Formimidoylpyrrolidin-3-ylaminocarbonyl]pyrrolidin-4-ylthio}-6-[(1R)-1-hydroxyethyl]-1-methyl-1-carbapen-2-em-3-carboxylic acid 205 mg of 4-nitrobenzyl (1R, 5S, 6S)-2-{(2S, 4S)-2-[(3S)-1-(N-4-nitrobenzyloxycarbonylformimidoyl)pyrrolidin-3-ylaminocarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 12 ml of 1:1 by volume mixture of tetrahydrofuran and water, and the mixture was hydrogenated by bubbling hydrogen through it at room temperature for 2 hours in the presence of 160 mg of 10% w/w palladium-on-charcoal. At the end of this time, the reaction mixture was worked up and purified by the same procedure as described in Example 23(b), to give 50 mg of the title compound as a powder.

Ultraviolet absorption spectrum (H$_2$O) $\lambda_{max}$ nm: 299.

Infrared Absorption Spectrum (KBr), $v_{max}$ cm$^{-1}$: 1754, 1710, 1657, 1586, 1449, 1427, 1386, 1285, 1262, 1182, 1146.

Nuclear Magnetic Resonance Spectrum (270 Hz, D$_2$O, using sodium tetradeuterated trimethylsilylpropionate as an internal standard), δ ppm:

1.21 (3H, doublet, J=7.32 Hz);
1.30 (3H, doublet, J=6.35 Hz);
1.75–3.04 (5H, multiplet);
3.31–4.95 (12H, multiplet);
8.01 & 8.03 (together 1H, two singlets).

EXAMPLE 26

(1R, 5S, 6S)-2-{(2S, 4S)-2[(3S)-1-Acetimidoylpyrrolidin-3-ylaminocarbonyl]pyrrolidin-4-ylthio}-6-[(1R)-1-hydroxyethyl]-1-methyl-1-carbapen-2-em-3-carboxylic acid

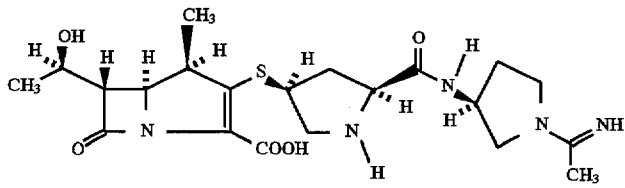

26(a) 4-Nitrobenzyl (1R, 5S, 6S)-2-{(2S, 4S)-2-[(3S)-1-(N-4-nitrobenzyloxycarbonylacetimidoyl)pyrrolidin-3-ylaminocarbonyl]-1-(4-nitrobenzyloxycarbonyl)pyrrolidin-4-ylthio}-6-[(1R)-1-hydroxyethyl]-1-methyl-1-carbapen-2-em-3-carboxylate Following a procedure similar to that described in Example 23(a), but using 422 mg of 4-nitrobenzyl (1R, 5R, 6S)-6-[(1R)-1-hydroxyethyl]-1-methyl-2-oxo-1-carbapenam-3-carboxylate and 717 mg of (2S, 4S)-4-mercapto-2-[(3S)-1-(N-4-nitrobenzyloxycarbonylacetimidoyl)pyrrolidin-3- ylaminocarbonyl]-1-(4-nitrobenzyloxycarbonyl)pyrrolidine (prepared as described in Preparation 26), 535 mg of the title compound were obtained as a powder.

26(b) (1R, 5S, 6S)-2-{(2S, 4S)-2-[(3S)-1-Acetimidoylpyrrolidin-3-ylaminocarbonyl]pyrrolidin-4-ylthio}-6-[(1R)-1-hydroxyethyl]-1-methyl-1-carbapen-2-em-3-carboxylic acid Following a procedure similar to that described in Example 23(b), but using 523 mg of 4-nitrobenzyl (1R, 5S, 6S)-2-{(2S, 4S)-2-[(3S)-1-(N-4-nitrobenzyloxycarbonylacetimidoyl)pyrrolidin-3-ylaminocarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above], 128 mg of the title compound were obtained as a powder.

Ultraviolet absorption spectrum ($H_2O$) $\lambda_{max}$ nm: 299.

EXAMPLE 27

(1R, 5S, 6S)-2-{(2S, 4S)-2-[(3R)-1-Formimidoylpyrrolidin-3-ylaminocarbonyl]pyrrolidin-4-ylthio}-6-[(1R)-1-hydroxyethyl]-1-methyl-1-carbapen-2-em-3-carboxylic acid

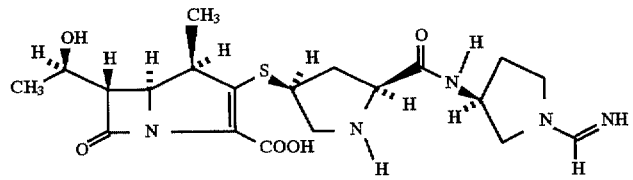

27(a) 4-Nitrobenzyl (1R, 5S, 6S)-2-{(2S, 4S)-2-[(3R)-1-N-4-nitrobenzyloxycarbonylformimidoyl)pyrrolidin-3-ylaminocarbonyl]-1-(4-nitrobenzyloxycarbonyl)pyrrolidin-4-ylthio}-6-[(1R)-1-hydroxyethyl]-1-methyl-1-carbapen-2-em-3-carboxylate Following a procedure similar to that described in Example 23(a), but using 464 mg of 4-nitrobenzyl (1R, 5R, 6S)-6-[(1R)-1-hydroxyethyl]-1-methyl-2-oxo-1-carbapenam-3-carboxylate and 788 mg of (2S, 4S)-4-mercapto-2-[(3R)-1-(N-4-nitrobenzyloxycarbonylformimidoyl)pyrrolidin-3-ylaminocarbonyl]-1-(4-nitrobenzyloxycarbonyl)pyrrolidine (prepared as described in Preparation 27), 548 mg of the title compound were obtained, as a powder.

27(b) (1R, 5S, 6S)-2-{(2S, 4S)-2-[(3R)-1-Formimidoylpyrrolidin-3-ylaminocarbonyl]pyrrolidin-4-ylthio}-6-[(1R)-1-hydroxyethyl]-1-methyl-1-carbapen-2-em-3-carboxylic acid Following a procedure similar to that described in Example 23(b), but using 530 mg of 4-nitrobenzyl (1R, 5S, 6S)-2-[(2S, 4S)-2-[(3R)-1-(N-4-nitrobenzyloxycarbonylformimidoyl)pyrrolidin-3-ylaminocarbonyl]-1-(4-nitrobenzyloxycarbonyl)pyrrolidin-4-ylthio]-6-[(1R)-1-hydroxyethyl]-1-methyl-1-carbapen-2-em-3-carboxylate [prepared as described in step (a) above], 133 mg of the title compound were obtained as a powder.

Ultraviolet absorption spectrum ($H_2O$) $\lambda_{max}$ nm: 300.

EXAMPLE 28

(1R, 5S, 6S)-2-{(2S, 4S)-2-[N-Methyl-N-((3S)-3-pyrrolidinyl)carbamoyl]pyrrolidin-4-ylthio}-6-[(1R)-1-hydroxyethyl]-1-methyl-1-carbapen-2-em-3-carboxylic acid hydrochloride

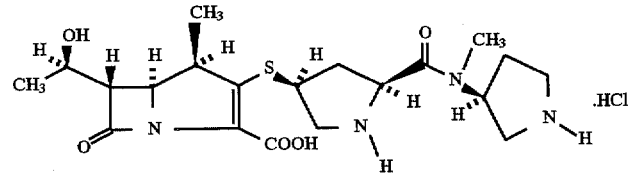

28(a) 4-Nitrobenzyl (1R, 5S, 6S)-2{(2S, 4S)-2-{N-methyl-N-[(3S)-1-(4-nitrobenzyloxycarbonyl)pyrrolidin-3-yl]carbamoyl}-1-(4-nitrobenzyloxycarbonyl)pyrrolidin-4-ylthio}-6-[(1R)-1-hydroxyethyl]-1-methyl-1-carbapen-2-em-3-carboxylate Following a procedure similar to than described in Example 19(b), but using 1.09 g of (2S, 4S)-4-mercapto-2-{(N-methyl-N-[(3S)-1-(4-nitrobenzyloxycarbonyl)pyrrolidin-3-yl]carbamoyl}-1-(4-nitrobenzyloxycarbonyl)pyrrolidine instead of the (2S, 4S)-4-mercapto-2-[(3S)-1-(4-nitrobenzyloxycarbonyl)pyrrolidin-3-ylaminocarbonyl]-1-(4-nitrobenzyloxycarbonyl)pyrrolidine, 550 mg of the title compound were obtained as a powder.

28(b) (1R, 5S, 6S)-2-{(2S, 4S)-2-[N-Methyl-N-((3S)-3-pyrrolidinyl)carbamoyl]pyrrolidin-4-ylthio}-6-[(1R)-1-hydroxyethyl]-1-methyl-1-carbapen-2-em-3-carboxylic acid hydrochloride 500 mg of 4-nitrobenzyl (1R, 5S, 6S)-2-{(2S, 4S)-2-{N-methyl-N-[(3S)-1-(4-nitrobenzyloxycarbonyl)-pyrrolidin-3-yl]carbamoyl}-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 20 ml of a 1:1 by volume mixture of tetrahydrofuran and water, after which 0.45 ml of 1N aqueous hydrochloric acid was added, and the mixture was hydrogenated by bubbling hydrogen through it at room temperature for 2 hours in the presence of 700 mg of 10% w/w palladium-on-charcoal. At the end of this time, the reaction mixture was worked up and purified by the same procedure as described in Example 18(b), to give 30 mg of the title compound as a powder.

Ultraviolet absorption spectrum (H$_2$O) $\lambda_{max}$ nm: 297.

EXAMPLE 29

(1R, 5S, 6S)-2-{(2S, 4S)-2-[N-Methyl-N-((3S)-1-formimidoylpyrrolidin-3-yl)carbamoyl]pyrrolidin-4-ylthio}-6-[(1R)-1-hydroxyethyl]-1-methyl-1-carbapen-2-em-3-carboxylic acid

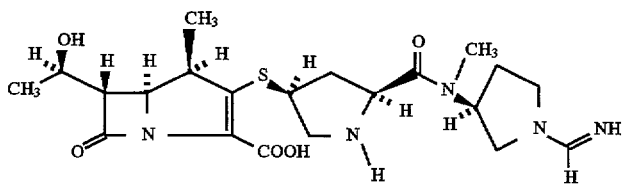

29(a) 4-Nitrobenzyl (1R, 5S, 6S)-2-{(2S, 4S)-2-{N-methyl-N-[(3S)-1-(N-4-nitrobenzyloxycarbonylformimidoyl)pyrrolidin-3-yl]carbamoyl}pyrrolidin-4-ylthio}-6-[(1R)-1-hydroxyethyl]-1-methyl-1-carbapen-2-em-3-carboxylate Following a procedure similar to that described in Example 23(a), but using 400 mg of 4-nitrobenzyl (1R, 5R, 6S)-6-[(1R)-1-hydroxyethyl]-1-methyl-2-oxo-1-carbapenam-3-carboxylate and 679 mg of (2S, 4S)-4-mercapto-2-(N-methyl-N-[(3S)-(N-4-nitrobenzyloxycarbonylformimidoyl)pyrrolidin-3-yl]carbamoyl}-1-(4-nitrobenzyloxycarbonyl)pyrrolidine (prepared as described in Preparation 29), 420 mg of the title compound were obtained as a powder.

29(b) (1R, 5S, 6S)-2-{(2S, 4S)-2-[N-Methyl-N-((3S)-1-formimidoylpyrrolidin-3-yl)carbamoyl]pyrrolidin-4-ylthio}-6-[(1R)-1-hydroxyethyl]-1-methyl-1-carbapen-2-em-3-carboxylic acid Following a procedure similar to that described in Example 23(b), but using 410 mg of 4-nitrobenzyl (1R, 5S, 6S)-2-{(2S, 4S)-2-{N-methyl-N-[(3S)-1-(N-4-nitrobenzyloxycarbonylformimidoyl)pyrrolidin-3-yl]carbamoyl}pyrrolidin-4-ylthio}-6-[(1R)-1-hydroxyethyl]-1-methyl-1-carbapen-2-em-3-carboxylate [prepared as described in step (a) above], 104 mg of the title compound were obtained as a powder.

Ultraviolet absorption spectrum (H$_2$O) $\lambda_{max}$ nm: 299.

EXAMPLE 30

(1R, 5S, 6S)-2-[(2S, 4S)-2-(3-Carbamoyl-1-piperazinylcarbonyl)pyrrolidin-4-ylthio]-6-[(1R)-1-hydroxyethyl]-1-methyl-1-carbapen-2-em-3-carboxylic acid hydrochloride

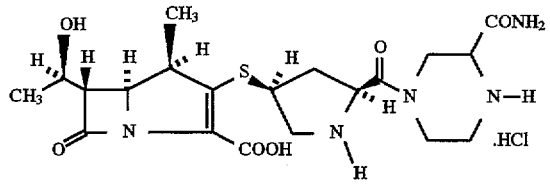

30(a) 4-Nitrobenzyl (1R, 5S, 6S)-2-{(2S, 4S)-2-[3-carbamoyl-4-(4-nitrobenzyloxycarbonyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 0.78 ml of diphenylphosphoryl chloride and 0.65 ml of diisopropylethylamine were added dropwise, whilst ice-cooling, to a solution of 1.23 g of 4-nitrobenzyl (1R, 5S, 6S)-6-[(1R)-1-hydroxyethyl]-1-methyl-2-oxo-1-carbapenam-3-carboxylate in 20 ml of dry acetonitrile, and the resulting mixture was stirred at the same temperature for 1 hour. A solution of 2.11 g of (2S, 4S)-4-mercapto-2-[3-carbamoyl-4-(4-nitrobenzyloxycarbonyl)-1-piperazinylcarbonyl]-1-(4-nitrobenzyloxycarbonyl)pyrrolidine (prepared as described in Preparation 30) in 20 ml of dry acetonitrile and 0.59 ml of diisopropylethylamine were then simultaneously added to the mixture, whilst ice-cooling, and the mixture was stirred at the temperature of ice-cooling for 90 minutes and then stirred at room temperature for 90 minutes. At the end of this time, the reaction mixture was worked up and purified by the same procedure as described in Example 7(a), to give 2.38 g of the title compound, as a powder.

30(b) (1R, 5S, 6S)-2-[(2S, 4)-2-(3-Carbamoyl-1-piperazinylcarbonyl)pyrrolidin-4-ylthio]-6-[(1R)-1-hydroxyethyl]-1-methyl-1-carbapen-2-em-3-carboxylic acid hydrochloride 2.33 g of 4-nitrobenzyl (1R, 5S, 6S)-2-{(2S, 4S)-2-[3-carbamoyl-4-(4-nitrobenzyloxycarbonyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 25 ml of a 1:1 by volume mixture of tetrahydrofuran and water, after which 2.7 ml of 1N aqueous hydrochloric acid were added, at the mixture was hydrogenated by bubbling hydrogen through it at room temperature for 2 hours in the presence of 2.33 g of 10% w/w palladium-on-charcoal. At the end of this time, the reaction mixture was worked up and purified by the same procedure as described in Example 7(b), to give 160 mg of the title compound, as a powder.

Infrared Absorption Spectrum (KBr), $v_{max}$ cm$^{-1}$: 1759, 1698, 1662, 1450, 1383, 1266.

Nuclear Magnetic Resonance Spectrum (270 MHz, D$_2$O, using sodium tetradeuterated trimethylsilylpropionate as an internal standard), δ ppm:

1.21 (3H, doublet, J=7.32 Hz);
1.28 (3H, doublet, J=6.35 Hz);
2.04–2.10 (1H, multiplet);
3.01–5.08 (16H, multiplet).

Ultraviolet absorption spectrum (H$_2$O) λ$_{max}$ nm: 297.

EXAMPLE 31

(1R, 5S, 6S)-2-{(2S, 4S)-2-[4-(2-Fluoroethyl)-1-homopiperazinylcarbonyl]pyrrolidin-4-ylthio}-6-[(1R)-1-hydroxyethyl]-1-methyl-1-carbapen-2-em-3-carboxylic acid hydrochloride

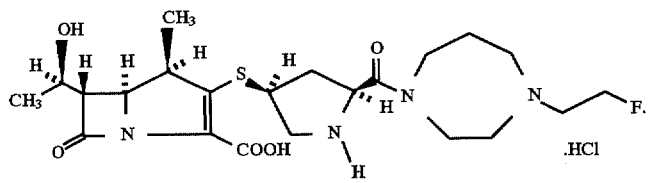

31(a) 4-Nitrobenzyl (1R, 5S, 6S)-2-{(2S, 4S)-2-[4-(2-fluoroethyl)-1-homopiperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 1.37 ml of diphenylphosphoryl chloride and 1.15 ml of diisopropylethylamine were added dropwise, whilst ice-cooling, to a solution of 2.23 g of 4-nitrobenzyl (1R, 5R, 6S)-6-[(1R)-1-hydroxyethyl]-1-methyl-2-oxo-1-carbapenam-3-carboxylate in 23 ml of dry acetonitrile, and the resulting mixture was stirred at the same temperature for 1 hour. A solution of 3.99 g of (2S, 4S)-4-mercapto-2-[4-(2-fluoroethyl)-1-homopiperazinylcarbonyl]-1-(4-nitrobenzyloxycarbonyl)pyrrolidine trifluoromethansulfonate (prepared as described in Preparation 31) in 57 ml of dry acetonitrile and 3.40 ml of diisopropylethylamine were then simultaneously added dropwise to the mixture, whilst ice-cooling, and the mixture was stirred at the same temperature for 1 hour, after which it was allowed to stand overnight at the same temperature. At the end of this time, the reaction mixture was worked up and purified by the same procedure as described in Example 15(a), to give 2.96 g of the title compound, as a powder.

Infrared Absorption Spectrum (KBr), ν$_{max}$ cm$^{-1}$: 1773, 1710, 1647, 1522, 1346, 1206.

Nuclear Magnetic Resonance Spectrum (CDCl$_3$, 270 MHz), δ ppm:

1.25–1.40 (6H, multiplet);
1.73–2.02 (3H, multiplet);
2.45–3.05 (7H, multiplet);
3.24–3.88 (8H, multiplet);
4.01–4.78 (6H, multiplet);
5.03–5.54 (4H, multiplet);
7.42–7.67 (4H, multiplet);
8.17–8.25 (4H, multiplet).

31(b) (1R, 5S, 6S)-2-{(2S, 4S)-2-[4-(2-Fluoroethyl)-1-homopiperazinylcarbonyl]pyrrolidin-4-ylthio}-6-[(1R)-1-hydroxyethyl]-1-methyl-1-carbapen-2-em-3-carboxylic acid hydrochloride 500 mg of 4-nitrobenzyl (1R, 5S, 6S)-2-{(2S, 4S)-2-[4-(2-fluoroethyl)-1-homopiperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 12 ml of a 1:1 by volume mixture of tetrahydrofuran and water, after which 0.62 ml of 1N aqueous hydrochloric acid was added, and the mixture was hydrogenated by bubbling hydrogen through it at room temperature for 2 hours in the presence of 500 mg of 10% w/w palladium-on-charcoal. At the end of this time, the reaction mixture was worked up and purified by the same procedure as described in Example 15(b), to give 96 mg of the title compound, as a powder.

Infrared Absorption Spectrum (KBr), ν$_{max}$ cm$^{-1}$: 1763, 1653, 1460, 1384, 1284.

Ultraviolet absorption spectrum (H$_2$O) λ$_{max}$ nm: 297.

Nuclear Magnetic Resonance Spectrum (D$_2$O, 270 MHz), δ ppm:

1.22 (3H, doublet, J=7.3 Hz);
1.28 (3H, doublet, J=6.4 Hz);
2.00–2.12 (1H, multiplet);
2.22–2.38 (2H, multiplet);
3.02–3.16 (1H, multiplet);
3.36–4.16 (15H, multiplet);
4.20–4.30 (2H, multiplet);
4.76–4.98 (3H, multiplet).

EXAMPLE 32

(1R, 5S, 6S)-2-{(2S, 4S)-2-[(3S)-3-(Imidazol-1-yl)pyrrolidin-1-ylcarbonyl]pyrrolidin-4-ylthio}-6-[(1R)-1-hydroxyethyl]-1-methyl-1-carbapen-2-em-3-carboxylic acid hydrochloride

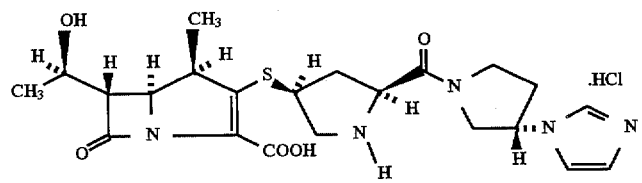

32(a) 4-Nitrobenzyl (1R, 5S, 6S)-2-[(2S, 4S)-2-[(3S)-3-(imidazol-1-yl)pyrrolidin-1-ylcarbonyl]-1-(4- nitrobenzyloxycarbonyl)pyrrolidin-4-ylthio]-6-[(1R)-1-hydroxyethyl]-1-methyl-1-carbapen-2-em-3-carboxylate 970 μl of diphenylphosphoryl chloride and 810 μl of diisopropylethylamine were added dropwise, whilst ice-cooling, to a solution of 1.60 g of 4-nitrobenzyl (1R, 5R, 6S)-6-[(1R)-1-hydroxyethyl]-1-methyl-2-oxo-1-carbapenam-3-carboxylate in 16 ml of dry acetonitrile, and the resulting mixture was stirred for 30 minutes under the same conditions. A solution of 1.9 g of (2S, 4S)-4-mercapto-2-[(3S)-3-(imidazol-1-yl)pyrrolidin-1-ylcarbonyl]-1-(4-nitrobenzyloxycarbonyl)pyrrolidine (prepared as described in Preparation 32) in 22 ml of dry acetonitrile and 770 μl of diisopropylethylamine were then simultaneously added dropwise to the mixture, and the mixture was stirred for 2 hours, whilst ice-cooling, and then allowed to stand overnight at 4° C. At the end of this time, the reaction mixture was diluted with an equivalent amount of water and mixed with 800 mg of sodium hydrogencarbonate. The mixture thus obtained was purified by reverse phase column chromatography through 300 g of Cosmo Sil 75C$_{18}$-PREP (a trade mark for a product of Nacalai Tesque), using a 1:1 by volume mixture of acetonitrile and water as the eluent. Those fractions containing the title compound were combined and concentrated by evaporation under reduced pressure, to give 2.31 g of the title compound, as a powder.

Infrared Absorption Spectrum (KBr), $v_{max}$ cm$^{-1}$: 1773, 1709, 1656, 1521, 1346.

Nuclear Magnetic Resonance Spectrum (CDCl$_3$, 270 MHz), δ ppm:

1.25–1.39 (6H, multiplet);
2.00–2.80 (4H, multiplet);
3.25–4.96 (13H, multiplet);
5.05–5.53 (4H, multiplet);
6.82–8.29 (11H, multiplet).

32(b) (1R, 5S, 6S)-2-{(2S, 4S)-2-[(3S)-3-(Imidazol-1-yl)pyrrolidin-1-ylcarbonyl]pyrrolidin-4-ylthio}-6-[(1R)-1-hydroxyethyl]-1-methyl-1-carbapen-2-em-3-carboxylic acid hydrochloride 200 mg of 4-nitrobenzyl (1R, 5S, 6S)-2-{(2S, 4S)-2-[(3S)-3-(imidazol-1-yl)pyrrolidin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in a mixture of 15 ml of tetrahydrofuran and 10 ml of water, and the solution was vigorously stirred for 1.7 hours at a temperature of between 28° C. and 30° C. in an atmosphere of hydrogen and in the presence of 0.3 g of 10% w/w palladium-on-charcoal. At the end of this time, the catalyst was removed by filtration, and the filtrate was washed three times, each time with 20 ml of diethyl ether. The resulting aqueous solution was concentrated by evaporation under reduced pressure, and the residue was purified by reverse phase column chromatography through 20 ml of Cosmo Sil 75C$_{18}$-PREP, using water as the eluent. Those fractions containing the title compound were combined and lyophilized, to give 17 mg of the title compound, as a colorless powder.

Ultraviolet absorption spectrum (H$_2$O) λ$_{max}$ nm: 297.

EXAMPLE 33

(1R, 5S, 6S)-2-{(2S, 4S)-2-[(3S)-3-(1,2,4-Triazol-1-yl)pyrrolidin-1-ylcarbonyl]pyrrolidin-4-ylthio]-6-[(1R)-1-hydroxyethyl]-1-methyl-1-carbapen-2-em-3-carboxylic acid hydrochloride

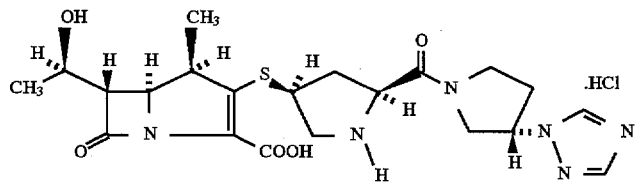

(33a) 4-Nitrobenzyl (1R, 5S, 6S)-2-{(2S, 4S)-2-[(3S)-3-(1,2,4-triazol-1-yl)pyrrolidin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 290 μl of diphenylphosphoryl chloride and 250 μl of diisopropylethylamine were added dropwise, whilst ice-cooling, to a solution of 486 mg of 4-nitrobenzyl (1R, 5R, 6S)-6-[(1R)-1-hydroxyethyl]-1-methyl-2-oxo-1-carbapenam-3-carboxylate in 5 ml of dry acetonitrile, and the resulting mixture was stirred at the same temperature for 1 hour. A solution of 690 mg of (2S, 4S)-4-mercapto-2-[(3S)-3-(1,2,4-triazol-1-yl)pyrrolidin-1-ylcarbonyl]-1-(4-nitrobenzyloxycarbonyl)pyrrolidine (prepared as described in Preparation 33) in 4 ml of dry acetonitrile and 230 μl of diisopropylethylamine were then simultaneously added dropwise to the mixture, and the mixture was stirred at the same temperature for 4 hours. An the end of this time, the reaction mixture was worked up and purified by the same procedure as described in Example 18(a), to give 744 mg of the title compound, as a powder.

Infrared Absorption Spectrum (KBr), $v_{max}$ cm$^{-1}$: 3401, 1772, 1709, 1655, 1607, 1522, 1346, 854, 738.

Nuclear Magnetic Resonance Spectrum (hexadeuterated dimethyl sulfoxide, 270 MHz), δ ppm:

1.14–1.20 (6H, multiplet);
1.50–1.70 (1H, multiplet);
2.30–2.50 (1H, multiplet);
2.70–2.95 (1H, multiplet);
3.10–4.30 (14H, multiplet);
4.51–4.70 (1H, multiplet);
5.05–5.49 (5H, multiplet);
7.48–7.74 (4H, multiplet);
8.15–8.27 (4H, multiplet);
8.52–8.63 (1H, multiplet).

33(b) (1R, 5S, 6S)-2-{(2S, 4S)-2-[(3S)-3-(1,2,4-Triazol-1-yl)pyrrolidin-1-ylcarbonyl]pyrrolidin-4-ylthio]-6-[(1R)-1-hydroxyethyl]-1-methyl-1-carbapen-2-em-3-carboxylic acid hydrochloride 528 mg of 4-nitrobenzyl (1R, 5S, 6S)-2-{(2S, 4S)-2-[(3S)-3-(1,2,4-triazol-1-yl)pyrrolidin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 10 ml of a 1:1 by volume mixture of tetrahydrofuran and water, after which 0.63 ml of 1N aqueous hydrochloric acid was added, and the mixture was hydrogenated by bubbling hydrogen through it at room temperature for 2 hours in the presence of 1 g of 10% w/w palladium-on-charcoal. At the end of this time, the reaction mixture was worked up and purified by the same procedure as described in Example 18(b), to give 85 mg of the title compound, as a powder.

Ultraviolet absorption spectrum (H$_2$O) $\lambda_{max}$ nm: 297.

EXAMPLE 34

(1R, 5S, 6S)-2-{(2S, 4S)-2-[(3R)-3-Aminopyrrolidin-1-ylcarbonyl]pyrrolidin-4-ylthio}-6-[(1R)-1-hydroxyethyl]-1-methyl-1-carbapen-2-em-3-carboxylic acid hydrochloride

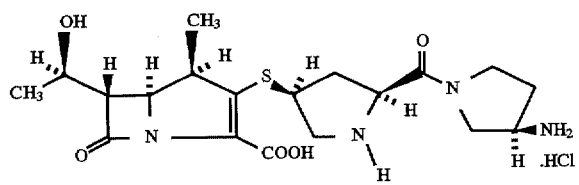

34(a) 4-Nitrobenzyl (1R, 5S, 6S)-2-{(2S, 4S)-2-[(3R)-3-(4-nitrobenzyloxycarbonyl)aminopyrrolidin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate Following a procedure similar to than described in Example 18(a), but using 950 mg of (2S, 4S)-4-mercapto-2-[(3R)-3-(4-nitrobenzyloxycarbonyl)aminopyrrolidin-1-ylcarbonyl]-1-(4-nitrobenzyloxycarbonyl)pyrrolidine (prepared as described in Preparation 34) instead of the (2S, 4S)-4-mercapto-2-[(3S)-3-(4-nitrobenzyloxycarbonyl)aminopyrrolidin-1-ylcarbonyl]-1-(4-nitrobenzyloxycarbonyl)pyrrolidine, 760 ml of the title compound were obtained, as a powder.

34(b) (1R, 5S, 6S)-2-{(2S, 4S)-2-[(3R)-3-Aminopyrrolidin-1-ylcarbonyl]pyrrolidin-4-ylthio}-6-[(1R)-1-hydroxyethyl]-1-methyl-1-carbapen-2-em-3-carboxylic acid hydrochloride 730 mg of 4-nitrobenzyl (1R, 5S, 6S)-2-{(2S, 4S)-2-[(3R)-3-(4-nitrobenzyloxycarbonyl)aminopyrrolidin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 20 ml of a 1:1 by volume mixture of tetrahydrofuran and water, after which 0.75 ml of 1N aqueous hydrochloric acid was added, and the mixture was hydrogenated by bubbling hydrogen through it at room temperature for 2 hours in the presence of 1.0 g of 10% w/w palladium-on-charcoal. At the end of this time, the reaction mixture was worked up and purified by the same procedure as described in Example 18(b), to give 120 mg of the title compound, as a powder.

Ultraviolet absorption spectrum (H$_2$O) $\lambda_{max}$ nm: 297.

EXAMPLE 35

(1R, 5S, 6S)-2-{(2S, 4S)-2-[(3R)-3-Acetimidoylpyrrolidin-1-ylcarbonyl]pyrrolidin-4-ylthio}-6-[(1R)-1-hydroxyethyl]-1-methyl-1-carbapen-2-em-3-carboxylic acid

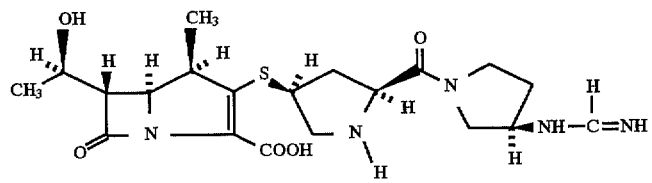

35(a) 4-Nitrobenzyl (1R, 5S, 6S)-2-{(2S, 4S)-2-[(3R)-3-(N-4-nitrobenzyloxycarbonylacetimidoylamino)pyrrolidin-1-ylcarbonyl]-1-(4-nitrobenzyloxycarbonyl)pyrrolidin-4ylthio}-6-[(1R)-1-hydroxyethyl]-1-methyl-1-carbapen-2-em-3-carboxylate Following a procedure similar to that described in Example 23(a), but using 92 mg of 4-nitrobenzyl (1R, 5R, 6S)-6-[(1R)-1-hydroxyethyl]-1-methyl-2-oxo-1-carbapenam-3-carboxylate and 156 mg of (2S, 4S)-4-mercapto-2-[(3R)-3-(N-4-nitrobenzyloxycarbonylacetimidoylamino)pyrrolidin-1-ylcarbonyl]-1-(4-nitrobenzyloxycarbonyl)pyrrolidine (prepared as described in Preparation 35), were obtained 125 mg of the title compound, as a powder.

35(b) (1R, 5S, 6S)-2-{(2S, 4S)-2-[(3R)-3-Acetimidoylpyrrolidin-1-ylcarbonyl]pyrrolidin-4-ylthio}-6-[(1R)-1-hydroxyethyl]-1-methyl-1-carbapen-2-em-3-carboxylic acid Following a procedure similar to that described in Example 23(b), but using 120 mg of 4-nitrobenzyl (1R, 5S, 6S)-2-{(2S, 4S)-2-[(3R)-3-(N-4-nitrobenzyloxycarbonylacetimidoylamino)pyrrolidin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above], 31 mg of the title compound were obtained as a powder.

Ultraviolet absorption spectrum (H$_2$O) $\lambda_{max}$ nm: 299.

Infrared Absorption Spectrum (KBr), $v_{max}$ cm$^{-1}$: 1755, 1631, 1590, 1452, 1386, 1284, 1260.

Nuclear Magnetic Resonance Spectrum (270 MHz, D$_2$O, using sodium tetradeuterated trimethylsilylpropionate as an internal standard), δ ppm:

1.22 (3H, doublet, J=7.33 Hz);

1.30 (3H, doublet, J=6.35 Hz);

1.57–1.73 (1H, multiplet);

2.06–2.46 (2H, multiplet);

2.24 (3H, singlet);

2.64–2.84 (1H, multiplet);

3.00–3.25 (2H, multiplet);

3.33–3.90 (7H, multiplet);

3.95–4.09 (1H, multiplet);

4.17–4.42 (3H, multiplet).

EXAMPLE 36

(1R, 5S, 6S)-2-{(2S, 4S)-2-[(3R)-3-Formimidoylaminopyrrolidin-1-ylcarbonyl]pyrrolidin-4-ylthio}-6-[(1R)-hydroxyethyl]-1-methyl-1-carbapen-2-em-3-carboxylic acid

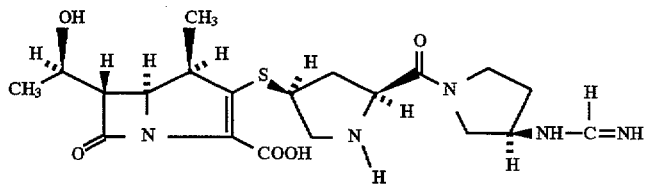

36(a) 4-Nitrobenzyl (1R, 5S, 6S)-2-{(2S, 4S)-2-[(3R)-3-(N-4-nitrobenzyloxycarbonylformimidoylamino)pyrrolidin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate Following a procedure similar to that described in Example 23(a), but using 120 mg of 4-nitrobenzyl (1R, 5R, 6S)-6-[(1R)-1-hydroxyethyl]-1-methyl-2-oxo-1-carbapenam-3-carboxylate and 192 mg of (2S, 4S)-4-mercapto-2-[(3R)-3-(N-4-nitrobenzyloxycarbonylformimidoylamino)pyrrolidin-1-ylcarbonyl]-1-(4-nitrobenzyloxycarbonyl)pyrrolidine (prepared as described in Preparation 36), were obtained 172 mg of the title compound, as a powder.

36(b) (1R, 5S, 6S)-2-{(2S, 4S)-2-[(3R)-3-Formimidoylaminopyrrolidin-1-ylcarbonyl]pyrrolidin-4-ylthio}-6-[(1R)-1-hydroxyethyl]-1-methyl-1-carbapen-2-em-3-carboxylic acid Following a procedure similar to that described in Example 23(b), but using 165 mg of 4-nitrobenzyl (1R, 5S, 6S)-2-{(2S, 4S)-2-[(3R)-3-(N-4-nitrobenzyloxycarbonylformimidoylamino)pyrrolidin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above], 38 mg of the title compound were obtained as a powder.

Ultraviolet absorption spectrum (H$_2$O) $\lambda_{max}$ nm: 300.

EXAMPLE 37

(1R, 5S, 6S)-2-[2S, 4S)-2-(3-Hydroxymethyl-1-piperazinylcarbonyl)pyrrolidin-4-ylthio]-6-[(1R)-hydroxyethyl]-1-methyl-1-carbapen-2-em-3-carboxylic acid hydrochloride

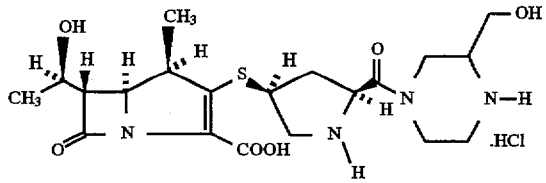

37(a) 4-Nitrobenzyl (1R, 5S, 6S)-2{(2S, 4S)-2-[3-(4-nitrobenzylcarbonyloxymethyl)-4-(4-nitrobenzyloxycarbonyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 46 µl of diphenylphosphoryl chloride and 38 λl of diisopropylethylamine were added dropwise, whilst ice-cooling, to a solution of 73 mg of 4-nitrobenzyl (1R, 5R, 6S)-6-[(1R)-1-hydroxyethyl]-1-methyl-2-oxo-1-carbapenam-3-carboxylate in 1.0 ml of dry acetonitrile, and the resulting mixture was stirred at the same temperature for 1 hour. A solution of 157 mg of (2S, 4S)-4-mercapto-2-[3-(4-nitrobenzylcarbonyloxymethyl)-4-(4-nitrobenzyloxycarbonyl)-1-piperazinylcarbonyl]-1-(4-nitrobenzyloxycarbonyl)pyrrolidine (prepared as described in Preparation 37) in 1.0 ml of dry acetonitrile and 35 µl of diisopropylethylamine were then simultaneously added to the mixture, whilst ice-cooling, and the mixture was stirred at the same temperature for 1 hour, after which it was allowed to stand overnight at the same temperature. At the end of this time, the reaction mixture was worked up and purified by the same procedure as described in Example 7(a) to give 147 mg of the title compound, as a powder.

Infrared Absorption Spectrum (KBr), $v_{max}$ cm$^{-1}$: 1758, 1706, 1660, 1608, 1522, 1432, 1347, 1268.

Nuclear Magnetic Resonance Spectrum (CDCl$_3$, 270 MHz), δ ppm:
1.27 (3H, doublet, J=7.33 Hz);
1.37 (3H, doublet, J=5.86 Hz);
2.53–3.02 (2H, multiplet);
3.10–3.78 (7H, multiplet);
3.81–4.37 (8H, multiplet);
4.47–4.85 (3H, multiplet);
5.09–5.52 (8H, multiplet);
7.47 (6H, doublet, J=8.30 Hz);
7.65 (2H, doublet, J=8.79 Hz);
8.15–8.23 (8H, multiplet).

37(b) (1R, 5S, 6S)-2-[(2S, 4S)-2-(3-Hydroxymethyl-1-piperazinylcarbonyl)pyrrolidin-4-ylthio]-6-[(1R)-1-hydroxyethyl]-1-methyl-1-carbapen-2-em-3-carboxylic acid hydrochloride 140 mg of 4-nitrobenzyl (1R, 5S, 6S)-2-{(2S, 4S)-2-[3-(4-nitrobenzylcarbonyloxymethyl)-4-(4-nitrobenzyloxycarbonyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 2 ml of a 1:1 by volume mixture of tetrahydrofuran and water, after which 0.13 ml of 1N aqueous hydrochloric acid was added, and the mixture was hydrogenated by bubbling hydrogen through it at room temperature for 2 hours in the presence of 140 mg of 10% w/w palladium-on-charcoal. At the end of this time, the reaction mixture was worked up and purified by the same procedure as described in Example 7(b), to give 20 mg of the title compound, as a powder.

Ultraviolet absorption spectrum (H$_2$O) $\lambda_{max}$ nm: 297.

Infrared Absorption Spectrum (KBr), $v_{max}$ cm$^{-1}$: 1759, 1660, 1594, 1451, 1387, 1266.

Nuclear Magnetic Resonance Spectrum (270 MHz, D$_2$O, using sodium tetradeuterated trimethylsilylpropionate as an internal standard), δ ppm:
1.21 (3H, doublet, J=7.32 Hz);
1.28 (3H, doublet, J=6.35 Hz);

1.97–2.08 (1H, multiplet);
3.01–3.15 (1H, multiplet);
3.19–3.41 (3H, multiplet);
3.44–3.68 (4H, multiplet);
3.48 (1H, doublet of doublets, J=6.35 & 2.93 Hz);
3.73–4.15 (5H, multiplet);
4.20–4.29 (2H, multiplet);
4.42–4.60 (1H, multiplet);
4.75–4.96 (1H, multiplet).

EXAMPLE 38

(1R, 5S, 6S)-2-[(2S, 4S)-2-(3-Carboxy-1-piperazinylcarbonyl)pyrrolidin-4-ylthio]-6-[(1R)-1-hydroxyethyl]-1-methyl-1-carbapen-2-em-3-carboxylic acid

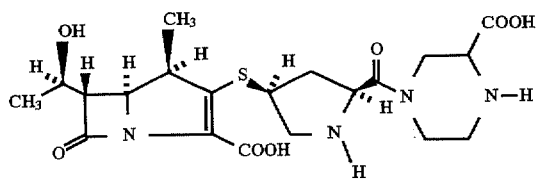

38(a) 4-Nitrobenzyl (1R, 5S, 6S)-2-{(2S, 4S)-2-[3-(4-nitrobenzyloxycarbonyl)-4-(4-nitrobenzyloxycarbonyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 55 µl of diphenylphosphoryl chloride and 46 µl of diisopropylethylamine were added dropwise, whilst ice-cooling, to a solution of 88 mg of 4-nitrobenzyl (1R, 5R, 6S)-6-[(1R)-1-hydroxyethyl]-1-methyl-2-oxo-1-carbapenam-3-carboxylate in 1.5 ml of dry acetonitrile, and the resulting mixture was stirred at the same temperature for 1 hour. A solution of 184 mg of (2S, 4S)-4-mercapto-2-[3-(4-nitrobenzyloxycarbonyl)-4-(4-nitrobenzyloxycarbonyl)-1-piperazinylcarbonyl]-1-(4-nitrobenzyloxycarbonyl)pyrrolidine (prepared as described in Preparation 38) in 1.5 ml of dry acetonitrile and 42 µl of diisopropylethylamine were then simultaneously added dropwise to the mixture, whilst ice-cooling, and the mixture was allowed to stand overnight at the same temperature. At the end of this time, the reaction mixture was worked up and purified by the same procedure as described in Example 7(a) to give 160 mg of the title compound, as a powder.

38(b) (1R, 5S, 6S)-2-[(2S, 4S)-2-(3-Carboxy-1-piperazinylcarbonyl)pyrrolidin-4-ylthio]-6-[(1R)-1-hydroxyethyl]-1-methyl-1-carbapen-2-em-3-carboxylic acid 160 mg of 4-nitrobenzyl (1R, 5S, 6S)-2-{(2S, 4S)-2-[3-(4-nitrobenzyloxycarbonyl)-4-(4-nitrobenzyloxycarbonyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 3 ml of a 1:1 by volume mixture of tetrahydrofuran and water, and the mixture was hydrogenated by bubbling hydrogen through it at room temperature for 2 hours in the presence of 160 ml of 10% w/w palladium-on-charcoal. At the end of this time, the reaction mixture was worked up and purified by the same procedure as described in Example 7(b), to give 35 ml of the title compound, as a powder.

Ultraviolet absorption spectrum (H$_2$O) $\lambda_{max}$ nm: 297.

EXAMPLE 39

(1R, 5S, 6S)-2-{(2S, 4S)-2-[(3R)-1-Acetimidoylpyrrolidin-3-ylaminocarbonyl]pyrrolidin-4-ylthio}-6-[(1R)-1-hydroxyethyl]-1-methyl-1-carbapen-2-em-3-carboxylic acid

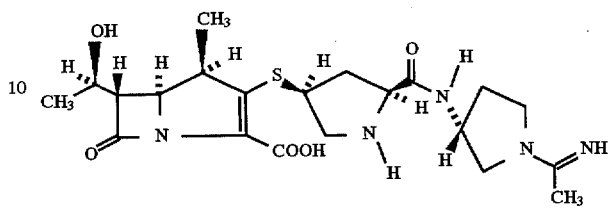

39(a) 4-Nitrobenzyl (1R, 5S, 6S)-2-{(2S, 4S)-2-[(3R)-1-(N-4-nitrobenzyloxycarbonylacetimidoyl)pyrrolidin-3-ylaminocarbonyl]-1-(4-nitrobenzyloxycarbonyl)pyrrolidin-4-ylthio}-6-[(1R)-1-hydroxyethyl]-1-methyl-1-carbapen-2-em-3-carboxylate Following a procedure similar to that described in Example 23(a), but using 300 mg of 4-nitrobenzyl (1R, 5R, 6S)-6-[(1R)-1-hydroxyethyl]-1-methyl-2-oxo-1-carbapenam-3-carboxylate and 510 mg of (2S, 4S)-4-mercapto-2-[(3R)-1-(N-4-nitrobenzyloxycarbonylacetimidoyl)pyrrolidin-3-ylaminocarbonyl]-1-(4-nitrobenzyloxycarbonyl)pyrrolidine (prepared as described in Preparation 39), 206 mg of the title compound were obtained as a powder.

39(b) (1R, 5S, 6S)-2-{(2S, 4S)-2-[(3R)-1-Acetimidoylpyrrolidin-3-ylaminocarbonyl]pyrrolidin-4-ylthio}-6-[(1R)-1-hydroxyethyl]-1-methyl-1-carbapen-2-em-3-carboxylic acid Following a procedure similar to that described in Example 23(b), but using 198 mg of 4-nitrobenzyl (1R, 5S, 6S)-2-[(2S, 4S)-2-[(3R)-1-(N-4-nitrobenzyloxycarbonylacetimidoyl)pyrrolidin-3-ylaminocarbonyl]-1-(4-nitrobenzyloxycarbonyl)pyrrolidin-4-ylthio]-6-[(1R)-1-hydroxyethyl]-1-methyl-1-carbapen-2-em-3-carboxylate [prepared as described in step (a) above], 48 mg of the title compound were obtained as a powder.

Ultraviolet absorption spectrum (H$_2$O) $\lambda_{max}$ nm: 298.

EXAMPLE 40

(1R, 5S, 6S)-2-{(2S, 4S)-2-[N-(2-Acetimidoylaminoethyl)carbamoyl]pyrrolidin-4-ylthio}-6-[(1R)-1-hydroxyethyl]-1-methyl-1-carbapen-2-em-3-carboxylic acid

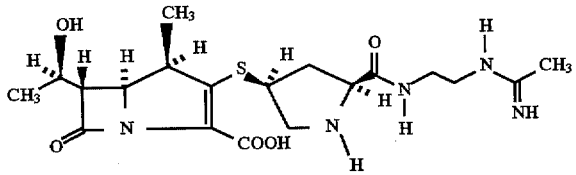

40(a) 4-Nitrobenzyl (1R, 5S, 6S)-2-{(2-N-[2-(N-4-nitrobenzyloxycarbonylacetimidoyl)aminoethyl]carbamoyl-1-(4-nitrobenzyloxycarbonyl)pyrrolidin-4-ylthio}-6-[(1R)-1-hydroxyethyl]-1-methyl-1-carbapen-2-em-3-carboxylate 105 µl of diphenylphosphoryl chloride and 88 µl of diisopropylethylamine were added dropwise, whilst ice-cooling, to a solution of 170 mg of 4-nitrobenzyl (1R, 5R, 6S)-6-[(1R)-1-hydroxyethyl]-1-methyl-2-oxo-1-carbapenam-3-carboxylate in 2 ml of dry acetonitrile, and the resulting mixture was stirred at the same temperature for 1 hour. A solution of 290 mg of (2S, 4S)-4-mercapto-2-{N-[2-(N-4-nitrobenzyloxycarbonylacetimidoyl)aminoethyl]carbamoyl}-1-(4-nitrobenzyloxycarbonyl)pyrrolidine (prepared as described in Preparation 40) in 10 ml of dry acetonitrile and 92 µl of diisopropylethylamine were then simultaneously added dropwise to the mixture, and the mixture was allowed to stand overnight at the same temperature. At the end of this time, the reaction mixture was worked up and purified by the same procedure as described in Example 1(a) to give 270 mg of the title compound, as a powder.

40(b) (1R, 5S, 6S)-2-{(2S, 4S)-2-[N-(2-Acetimidoylaminoethyl)carbamoyl]pyrrolidin-4-ylthio}-6-[(1R)-1-hydroxyethyl]-1-methyl-1-carbapen-2-em-3-carboxylic acid 265 mg of 4-nitrobenzyl (1R, 5S, 6S)-2-{N-[2-(N-4-nitrobenzyloxycarbonylacetimidoyl)aminoethyl]carbamoyl-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 15 ml of a 2:1 by volume mixture of tetrahydrofuran and water, and the mixture was hydrogenated by bubbling hydrogen through it at room temperature for 2 hours in the presence of 270 ml of 10% w/w palladium-on-charcoal. At the end of this time, the reaction mixture was worked up and purified by the same procedure as described in Example 1(b), to give 60 mg of the title compound, as a powder.

Ultraviolet absorption spectrum (H$_2$O) $\lambda_{max}$ nm: 299.

Nuclear Magnetic Resonance Spectrum (D$_2$O, 270 MHz), δ ppm:

1.21 (3H, doublet, J=7.3 Hz);
1.30 (3H, doublet, J=6.6 Hz);
1.68–1.70 (1H, multiplet);
2.23 (3H, singlet);
2.60–2.73 (1H, multiplet);
2.89 (1H, doublet of doublets, J=11.2 & 4.0 Hz);
3.32–3.66 (7H, multiplet);
3.69–3.80 (1H, multiplet);
3.85 (1H, doublet of doublets, J=9.2 & 5.3 Hz);
4.18–4.32 (2H, multiplet).

EXAMPLE 41

(1R, 5S, 6S)-2-{(2S, 4S)-2-[N-(2-Formimidoylaminoethyl)carbamoyl]pyrrolidin-4-ylthio}-6-[(1R)-1-hydroxyethyl]-1-methyl-1-carbapen-2-em-3-carboxylic acid

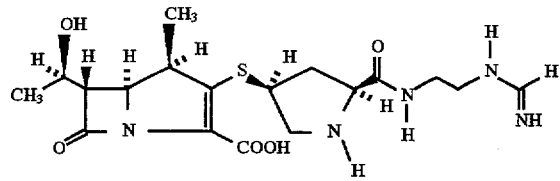

41(a) 4-Nitrobenzyl (1R, 5S, 6S)-2-{2-N-[2-(4-nitrobenzyloxycarbonylformimidoyl)aminoethyl]carbamoyl-1-(4-nitrobenzyloxycarbonyl)pyrrolidin-4-ylthio}-6-[(1R)-1-hydroxyethyl]-1-methyl-1-carbapen-2-em-3-carboxylate 53 µl of diphenylphosphoryl chloride and 44 µl of diisopropylethylamine were added dropwise, whilst ice-cooling, to a solution of 90 mg of 4-nitrobenzyl (1R, 5R, 6S)-6-[(1R)-1-hydroxyethyl]-1-methyl-2-oxo-1-carbapenam-3-carboxylate in 1 ml of dry acetonitrile, and the resulting mixture was stirred at the same temperature for 1 hour. A solution of 150 mg of (2S, 4S)-4-mercapto-2-{N-[2-(N-4-nitrobenzyloxycarbonylformimidoyl)aminoethyl]carbamoyl}-1-(4-nitrobenzyloxycarbonyl)pyrrolidine (prepared as described in Preparation 41) in 10 ml of dry acetonitrile and 50 µl of diisopropylethylamine were then simultaneously added dropwise to the mixture, and the mixture was allowed to stand overnight an the same temperature. At the end of this time, the reaction mixture was worked up and purified by the same procedure as described in Example 1(a), to give 155 mg of the title compound, as a powder.

41(b) (1R, 5S, 6S)-2-{(2S, 4S)-2-[N-(2-Formimidoylaminoethyl)carbamoyl]pyrrolidin-4-ylthio}-6-[(1R)-1-hydroxyethyl]-1-methyl-1-carbapen-2-em-3-carboxylic acid 150 mg of 4-nitrobenzyl (1R, 5S, 6S)-2-{N-[2-(4-nitrobenzyloxycarbonylformimidoyl)aminoethyl]carbamoyl-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 10 ml of a 2:1 by volume mixture of tetrahydrofuran and water, and the mixture was hydrogenated by bubbling hydrogen through it at room temperature for 2 hours in the presence of 150 mg of 10% w/w palladium-on-charcoal. At the end of this time, the reaction mixture was worked up and purified by the same procedure as described in Example 1(b), to give 20 mg of the title compound as a powder.

Ultraviolet absorption spectrum (H$_2$O) $\lambda_{max}$ nm: 299.

Nuclear Magnetic Resonance Spectrum (270 MHz, D$_2$O, using sodium tetradeuterated trimethylsilylpropionate as an internal standard), δ ppm:

1.21 (3H, doublet, J=7.3 Hz);
1.30 (3H, doublet, J=6.4 Hz);
1.70–1.84 (1H, multiplet);
2.60–2.76 (1H, multiplet);
2.89–2.97 (1H, multiplet);
3.32–3.62 (7H, multiplet);
3.70–3.81 (1H, multiplet);
3.85–3.92 (1H, multiplet);
4.19–4.29 (2H, multiplet);
7.84 & 7.85 (1H, two singlets).

Infrared Absorption Spectrum (KBr), $v_{max}$ cm$^{-1}$: 1755, 1717, 1660, 1590, 1388.

EXAMPLE 42

(1R, 5S, 6S)-2-[(2S, 4S)-2-(3-Dimethylamino-1,2,5,6-tetrahydropyrazin-1-ylcarbonyl)pyrrolidin-4-ylthio]-6-[(1R)-1-hydroxyethyl]-1-methyl-1-carbapen-2-em-3-carboxylic acid

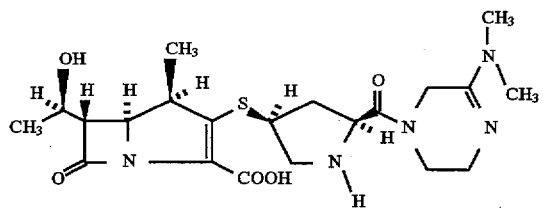

42(a) 4-Nitrobenzyl (1R, 5S, 6S)-2-[2S, 4S)-2-(3-dimethylamino-1,2,5,6-tetrahydropyrazin-1-ylcarbonyl)-1-

(4-nitrobenzyloxycarbonyl)pyrrolidin-4-ylthio]-6-[(1R)-1-hydroxyethyl]-1-methyl-1-carbapen-2-em-3-carboxylate 126 μl of diphenylphosphoryl chloride and 106 μl of diisopropylethylamine were added dropwise, whilst ice-cooling, to a solution of 208 mg of 4-nitrobenzyl (1R, 5R, 6S)-6-[(1R)-1-hydroxyethyl]-1-methyl-2-oxo-1-carbapenam-3-carboxylate in 2.6 ml of dry acetonitrile, and the resulting mixture was stirred at the same temperature for 1 hour. A solution of 445 mg of (2S, 4S)-4-mercapto-2-(3-dimethylamino-1,2,5,6-tetrahydropyrazin-1-ylcarbonyl)-1-(4-nitrobenzyloxycarbonyl)pyrrolidine trifluoromethanesulfonate (prepared as described in Preparation 42) in 2.4 ml of dry acetonitrile and 271 μl of diisopropylethylamine were then simultaneously added dropwise to the mixture, and the mixture was allowed to stand overnight at the same temperature. At the end of this time, the reaction mixture was worked up and purified by the same procesure as described in Example 1(a), to give 98 mg of the title compound, as a powder.

Infrared Absorption Spectrum (KBr), $v_{max}$ cm$^{-1}$: 1771, 1709, 1659, 1608, 1522, 1495, 1441, 1405, 1346, 1277, 1209.

Nuclear Magnetic Resonance Spectrum (CDCl$_3$+ hexadeuterated dimethyl sulfoxide, 270 MHz), δ ppm:

1.28 (3H, doublet, J=7.32 Hz);
1.34 (3H, doublet, J=6.34 Hz);
1.85–2.08 (1H, multiplet);
2.71–2.86 (1H, multiplet);
3.08–4.85 (20H, multiplet);
5.05–5.53 (4H, multiplet);
7.42–7.58 (2H, multiplet);
7.66 (2H, doublet, J=8.79 Hz);
8.16–8.26 (4H, multiplet).

42(b) (1R, 5S, 6S)-2-[(2S, 4S)-2-(3-Dimethylamino-1,2,5,6-tetrahydropyrazin-1-ylcarbonyl)pyrrolidin-4-ylthio]-6-[(1R)-1-hydroxyethyl]-1-methyl-1-carbapen-2-em-3- carboxylic acid 95 mg of 4-nitrobenzyl (1R, 5S, 6S)-2-[(2S, 4S)-2-(3-dimethylamino-1,2,5,6-tetrahydropyrazin-1-ylcarbonyl)-1-(4-nitrobenzyloxycarbonyl)pyrrolidin-4-ylthio]-6-(1R)-1-hydroxyethyl]-1-methyl-1-carbapen-2-em-3-carboxylate [prepared as described in step (a) above] were dissolved in 5 ml of a 2:1 by volume mixture of tetrahydrofuran and water, and the mixture was hydrogenated by bubbling hydrogen through it at room temperature for 2 hours in the presence of 250 mg of 10% w/w palladium-on-charcoal. At the end of this time, the reaction mixture was worked up and purified by the same procedure as described in Example 1(b), to give 8 mg of the title compound as a powder.

Ultraviolet absorption spectrum (H$_2$O) $\lambda_{max}$ nm: 299.

Infrared Absorption Spectrum (KBr), $v_{max}$ cm$^{-1}$: 1751, 1659, 1598, 1455, 1391, 1346, 1247.

Nuclear Magnetic Resonance Spectrum (270 MHz, D$_2$O, using sodium tetradeuterated trimethylsilylpropionate as an internal standard), δ ppm:

1.22 (3H, doublet, J=7.33 Hz);
1.30 (3H, doublet, J=6.35 Hz);
1.60–1.83 (1H, multiplet);
2.68–2.92 (1H, multiplet);
3.03–4.43 (20H, multiplet).

EXAMPLE 43

(1R, 5S, 6S)-2-[(2S, 4S)-2-(4-Acetimidoylaminopiperidin-1-ylcarbonyl)pyrrolidin-4-ylthio]-6-[(1R)-1-hydroxyethyl]-1-methyl-1-carbapen-2-em-3-carboxylic acid

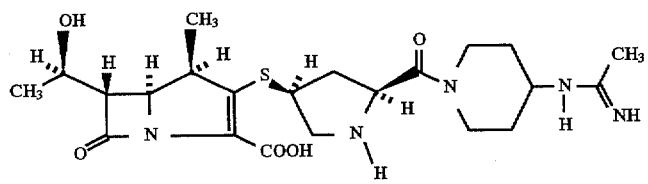

Following a procedure similar to that described in Example 1, but using 181 mg of 4-nitrobenzyl (1R, 5R, 6S)-6-[(1R)-1-hydroxyethyl]-1-methyl-2-oxo-1-carbapenam-3-carboxylate and 300 mg of (2S, 4S)-4-mercapto-2-(4-nitrobenzyloxycarbonylacetimidoyl)aminopiperidin-1-ylcarbonyl]-1-(4-nitrobenzyloxycarbonyl)pyrrolidine (prepared as described in Preparation 43), 21 mg of the title compound were obtained, as a powder.

Ultraviolet absorption spectrum (H$_2$O) $\lambda_{max}$ nm: 299.

Nuclear Magnetic Resonance Spectrum (270 MHz, D$_2$O, using sodium tetradeuterated trimethylsilylpropionate as an internal standard), δ ppm:

1.21 (3H, doublet, J=7.3 Hz);
1.30 (3H, doublet, J=6.4 Hz);
1.46–1.70 (3H, multiplet);
2.02–2.18 (2H, multiplet);
2.22 (3H, singlet);
2.69–2.83 (1H, multiplet);
2.90–3.04 (1H, multiplet);
3.06–3.46 (5H, multiplet);
3.78–3.99 (3H, multiplet);
4.12–4.44 (4H, multiplet).

EXAMPLE 44

(1R, 5S, 6S)-2-[(2S, 4S)-2-(4-Acetimidoylpiperazin-1-ylcarbonyl)-1-methylpyrrolidin-4-ylthio]-6-[(1R)-1-hydroxyethyl]-1-methyl-1-carbapen-2-em-3-carboxylic acid

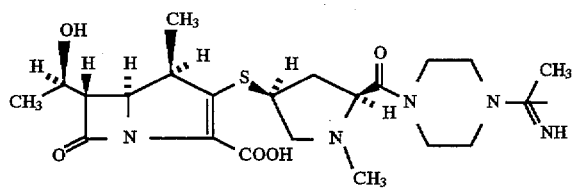

Following a procedure similar to that described in Example 1, but using 181 mg of 4-nitrobenzyl (1R, 5R, 6S)-6-[(1R)-1-hydroxyethyl]-1-methyl-2-oxo-1-carbapenam-3 -carboxylate and 220 mg of (2S, 4S)-4-mercapto-2-[4-(N-4-nitrobenzyloxycarbonylacetimidoyl) piperazin-1-ylcarbonyl]-1-methylpyrrolidine (prepared as described in Preparation 44), 20 mg of the title compound were obtained, as a powder.

Ultraviolet absorption spectrum (H$_2$O) $\lambda_{max}$ nm: 299.

Nuclear Magnetic Resonance Spectrum (270 MHz, D$_2$O, using sodium tetradeuterated trimethylsilylpropionate as an internal standard), δ ppm:

1.21 (3H, doublet, J=7.3 Hz);

1.30 (3H, doublet, J=6.4 Hz);

1.66 (1H, doubled doublet of doublets, J=13.7, 8.8 & 5.4 Hz);

2.29 (3H, singlet);

2.35 (3H, singlet);

2.75–2.88 (2H, multiplet);

3.10 (1H, doublet of doublets, J=12.2 & 1.4 Hz);

3.31–3.43 (2H, multiplet);

3.52 (1H, triplet, J=8.3 Hz);

3.60–4.00 (9H, multiplet);

4.18–4.30 (2H, multiplet).

Infrared Absorption Spectrum (KBr), v$_{max}$ cm$^{-1}$: 1754, 1608, 1594, 1448, 1384, 1285.

EXAMPLE 45

(1R, 5S, 6S)-2-[(2S, 4S)-2-[(3S)-3-Aminopyrrolidin-1-ylcarbonyl]-1-methylpyrrolidin-4-ylthio]-6-[(1R)-1-hydroxyethyl]-1-methyl-1-carbapen-2-em-3-carboxylic acid hydrochloride 45(a) 4-Nitrobenzyl (1R, 5S, 6S)-2-{(2S, 4S)-2-[(3S)-3-(4-nitrobenzyloxycarbonyl)aminopyrrolidin-1-ylcarbonyl]-1-methylpyrrolidin-4-ylthio}-6-[(1R)-1-hydroxyethyl]-1-methyl-1-carbapen-2-em-3-carboxylate Following a procedure similar to that described in Example 18(a), but using 1.05 g of (2S, 4S)-4-mercapto-2- [(3S)-3-(4-nitrobenzyloxycarbonyl)aminopyrrolidin-1-ylcarbonyl]-1-methylpyrrolidine instead of the (2S, 4S)-4-mercapto-2-[(3S)-3-(4-nitrobenzyloxycarbonyl) aminopyrrolidin-1-ylcarbonyl]-1-(4-nitrobenzyloxycarbonyl)pyrrolidine, 1.20 g of the title compound was obtained as a powder.

45(b) (1R, 5S, 6S)-2-[(2S, 4S)-2-[(3S)-3-Aminopyrrolidin-1-ylcarbonyl]-1-methylpyrrolidin-4-ylthio]-6-[(1R)-1-hydroxyethyl]-1-methyl-1-carbapen-2-em-3-carboxylic acid hydrochloride 1.0 g of 4-nitrobenzyl (1R, 5S, 6S)-2-{(2S, 4S)-2-[(3S)-3-(4-nitrobenzyloxycarbonyl)aminopyrrolidin-1-ylcarbonyl]-1-methylpyrrolidin-4-ylthio}-6-[(1R)-1-hydroxyethyl]-1-methyl-1-carbapen-2-em-3-carboxylate [prepared as described in step (a) above] was dissolved in 30 ml of a 2:1 by volume mixture of tetrahydrofuran and water, after which 1.04 ml of 1N aqueous hydrochloric acid was added, and the mixture was hydrogenated by bubbling hydrogen through it at room temperature for 2 hours in the presence of 1.5 g of 10% w/w palladium-on-charcoal. At the end of this time, the reaction mixture was worked up and purified by the same procedure as described in Example 18(b), to give 175 mg of the title compound as a powder.

Ultraviolet absorption spectrum (H$_2$O) $\lambda_{max}$ nm: 297.

Infrared Absorption Spectrum (KBr), v$_{max}$ cm$^{-1}$: 3390, 1760, 1655, 1599, 1467, 1374.

Nuclear Magnetic Resonance Spectrum (270 MHz, D$_2$O, using sodium tetradeuterated trimethylsilylpropionate as an internal standard), δ ppm:

1.21 (3H, doublet, J=7.32 Hz);

1.29 (3H, doublet, J=6.35 Hz);

1.95–2.30 (1H, multiplet);

2.30–2.70 (2H, multiplet);

2.96 (3H, doublet, J=2.93 Hz);

3.15–3.27 (1H, multiplet);

3.27–3.40 (1H, multiplet);

3.46–3.49 (1H, multiplet);

3.50–4.35 (10H, multiplet);

4.45–4.65 (1H, multiplet).

EXAMPLE 46

(1R, 5S, 6S)-2-{(2S, 4S)-2-[(3S)-3-Formimidoylaminopyrrolidin-1-ylcarbonyl]-1-methylpyrrolidin-4-ylthio}-6-[(1R)-1-hydroxyethyl]-1-methyl-1-carbapen-2-em-3-carboxylic acid

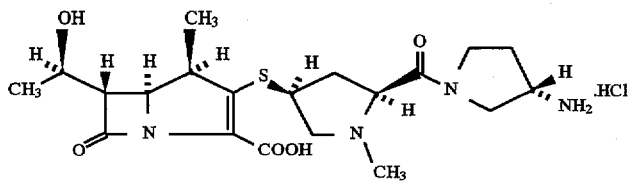

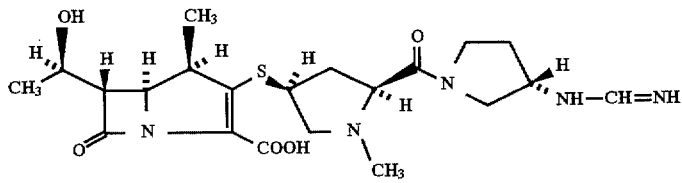

46(a) 4-Nitrobenzyl (1R, 5S, 6S)-2-{(2S, 4S)-2-[(3S)-3-(N-4-nitrobenzyloxycarbonylformimidoylamino)pyrrolidin-1-ylcarbonyl]-1-methylpyrrolidin-4-ylthio}-6-[(1R)-1-hydroxyethyl]-1-methyl-1-carbapen-2-em-3-carboxylate Following a procedure similar to than described in Example 23(a), but using 124 mg of 4-nitrobenzyl (1R, 5R, 6S)-6-[(1R)-1-hydroxyethyl]-1-methyl-2-oxo-1-carbapenam-3-carboxylate and 190 mg of (2S, 4S)-4-mercapto-2-[(3S)-3-(N-4-nitrobenzyloxycarbonylformimidoylamino)pyrrolidin-1-ylcarbonyl]-1-methylpyrrolidine (prepared as described in Preparation 46), 178 mg of the title compound were obtained as a powder.

46(b) (1R, 5S, 6S)-2-{(2S, 4S)-2-[(3S)-3-Formimidoylaminopyrrolidin-1-ylcarbonyl]-1-methylpyrrolidin-4-ylthio}-6-[(1R)-1-hydroxyethyl]-1-methyl-1-carbapen-2-em-3-carboxylic acid Following a procedure similar to that described in Example 23(b), but using 170 mg of 4-nitrobenzyl (1R, 5S, 6S)-2-{(2S, 4S)-2-[(3S)-3-(N-4-nitrobenzyloxycarbonylformimidoylamino)pyrrolidin-1-ylcarbonyl]-1-methylpyrrolidin-4-ylthio}-6-[(1R)-1-hydroxyethyl]-1-methyl-1-carbapen-2-em-3-carboxylate [prepared as described in step (a) above], 35 mg of the title compound were obtained as a powder.

Ultraviolet absorption spectrum (H₂O) λ_max nm: 298

Infrared Absorption Spectrum (KBr), ν_max cm⁻¹: 3255, 1755, 1634, 1595, 1455, 1386.

Nuclear Magnetic Resonance Spectrum (400 MHz, D₂O, using sodium tetradeuterated trimethylsilylpropionate as an internal standard), δ ppm:

1.21 (3H, doublet, J=7.32 Hz);
1.31 (3H, doublet, J=6.60 Hz);
1.60–1.75 (1H, multiplet);
2.30 (3H, doublet, J=5.86 Hz);
2.05–2.50 (2H, multiplet);
2.75–2.95 (2H, multiplet);
3.05–3.15 (1H, multiplet);
3.30–3.50 (3H, multiplet);
3.50–3.95 (4H, multiplet);
3.96–4.05 (1H, multiplet);
4.20 (1H, doublet of doublets, J=2.57 & 9.17 Hz);
4.26 (1H, quartet, J=6.40 Hz);
4.30–4.47 (1H, multiplet);
7.80, 7.81 & 7.94 (together 1H, three singlets).

EXAMPLE 47

(1R, 5S, 6S)-2-{(2S, 4S)-2-[4-(Imidazol-1-yl)piperidin-1-ylcarbonyl]pyrrolidin-4-ylthio}-6-[(1R)-1-hydroxyethyl]-1-methyl-1-carbapen-2-em-3-carboxylic acid hydrochloride

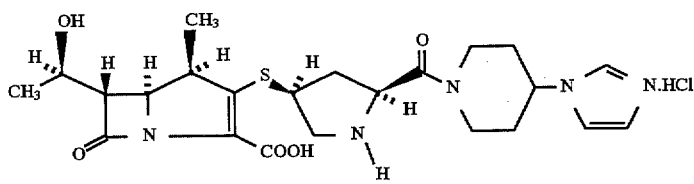

47(a) 4-Nitrobenzyl (1R, 5S, 6S)-2-{(2S, 4S)-2-[4-(imidazol-1-yl)piperidin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 560 μl of diphenylphosphoryl chloride and 470 μl of diisopropylethylamine were added dropwise, whilst ice-cooling, to a solution of 910 mg of 4-nitrobenzyl (1R, 5R, 6S)-6-[(1R)-1-hydroxyethyl]-1-methyl-2-oxo-1-carbapenam-3-carboxylate in 10 ml of dry acetonitrile, and the resulting mixture was stirred for 30 minutes under the same conditions. A solution of 1140 mg of (2S, 4S)-4-mercapto-2-[4-(imidazol-1-yl)piperidin-1-ylcarbonyl]-1-(4-nitrobenzyloxycarbonyl)pyrrolidine (prepared as described in Preparation 47) in 10 ml of dry acetonitrile and 435 μl of diisopropylethylamine were then simultaneously added dropwise to the mixture, and the mixture was stirred for 2 hours, whilst ice-cooling, after which it was allowed to stand overnight at 4° C. At the end of this time, the reaction mixture was diluted with an equivalent amount of water and mixed with 800 mg of sodium hydrogencarbonate. The mixture thus obtained was purified by reverse phase column chromatography through 200 ml of Cosmo Sil 75C₁₈-PREP (a trade mark for a product of Nacalai Tesque) using a 1:1 by volume mixture of acetonitrile and water as the eluent. Those fractions containing the title compound were combined and concentrated to give 1.40 g of the title compound, as a powder.

Nuclear Magnetic Resonance Spectrum (hexadeuterated dimethyl sulfoxide, 270 MHz), δ ppm:

1.12–1.20 (6H, multiplet);
1.58–1.90 (3H, multiplet);
1.91–2.06 (2H, multiplet);
2.62–2.79 (1H, multiplet);
2.80–2.97 (1H, multiplet);
3.06–3.37 (4H, multiplet);
3.55–3.70 (1H, multiplet);

3.71–3.93 (1H, multiplet);
3.94–4.56 (5H, multiplet);
4.74–4.97 (1H, multiplet);
5.04–5.49 (5H, multiplet);
6.81–8.28 (11H, multiplet).

Infrared Absorption Spectrum (KBr), $\nu_{max}$ cm$^{-1}$: 1773, 1710, 1656, 1522, 1346, 1208.

47(b) (1R, 5S, 6S)-2-{(2S, 4S)-2-[4-(Imidazol-1-yl)piperidin-1-ylcarbonyl]pyrrolidin-4-ylthio}-6-[(1R)-1-hydroxyethyl]-1-methyl-1-carbapen-2-em-3-carboxylic acid hydrochloride 200 mg of 4-nitrobenzyl (1R, 5S, 6S)-2-{(2S, 4S)-2-[4-(imidazol-1-yl)piperidin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in a mixture of 15 ml of tetrahydrofuran and 10 ml of water, and the solution was vigorously stirred at a temperature of between 28° C. and 30° C. for 1.7 hours in an atmosphere of hydrogen and in the presence of 0.3 g of 10% w/w palladium-on-charcoal. At the end of this time, the catalyst was removed by filtration, and the filtrate was washed three times, each time with 20 ml of diethyl ether. The resulting aqueous solution was concentrated by evaporation under reduced pressure. The concentrate was purified by reverse phase column chromatography through 20 ml of Cosmo Sil 75C$_{18}$-PREP (a trade mark for a product of Nacalai Tesque), using water as the eluent. Those fractions containing the title compound were combined and lyophilized, to give 18 mg of the title compound as a colorless powder.

Ultraviolet absorption spectrum (H$_2$O) $\lambda_{max}$ nm: 297.

EXAMPLE 48

(1R, 5S, 6S)-2-[(2S, 4S)-2-(3,3-Dimethyl-1-piperazinylcarbonyl)pyrrolidin-4-ylthio]-6-[(1R)-1-hydroxyethyl]-1-methyl-1-carbapen-2-em-3-carboxylic acid hydrochloride

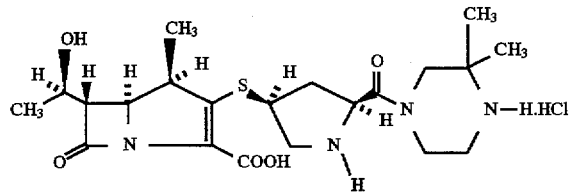

48(a) 4-Nitrobenzyl (1R, 5S, 6S)-2-{(2S, 4S)-2-[3,3-dimethyl-4-(4-nitrobenzyloxycarbonyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 67 µl of diphenylphosphoryl chloride and 56 µl of diisopropylethylamine were added dropwise, whilst ice-cooling, to a solution of 100 mg of 4-nitrobenzyl (1R, 5R, 6S)-6-[(1R)-1-hydroxyethyl]-1-methyl-2-oxo-1-carbapenam-3-carboxylate in 1.5 ml of dry acetonitrile, and the resulting mixture was stirred at the same temperature for 1 hour. A solution of 200 mg of (2S, 4S)-4-mercapto-2-[3,3-dimethyl-4-(4-nitrobenzyloxycarbonyl)-1-piperazinylcarbonyl]-1-(4-nitrobenzyloxycarbonyl)pyrrolidine (prepared as described in Preparation 48) in 1.5 ml of dry acetonitrile and 56 µl of diisopropylethylamine were then simultaneously added dropwise to the mixture, and the mixture was stirred at the same temperature for 1 hour, after which it was allowed to stand overnight at the same temperature. At the end of this time, the reaction mixture was worked up and purified by the same procedure as described in Example 7(a), to give 205 mg of the title compound, as a powder.

48(b) (1R, 5S, 6S)-2-[(2S, 4S)-2-(3,3-Dimethyl-1-piperazinylcarbonyl)pyrrolidin-4-ylthio]-6-[(1R)-1-hydroxyethyl]-1-methyl-1-carbapen-2-em-3-carboxylic acid hydrochloride 205 mg of 4-nitrobenzyl (1R, 5S, 6S)-2-{(2S, 4S)-2-[3,3-dimethyl-4-(4-nitrobenzyloxycarbonyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] were dissolved in 5 ml of a 1:1 by volume mixture of tetrahydrofuran and water, after which 0.23 ml of 1N aqueous hydrochloric acid was added, and the mixture was hydrogenated by bubbling hydrogen through it at room temperature for 2 hours in the presence of 200 mg of 10% w/w palladium-on-charcoal. At the end of this time, the reaction mixture was worked up and purified by the same procedure as described in Example 7(b), to give 35 mg of the title compound as a powder.

Ultraviolet absorption spectrum (H$_2$O) $\lambda_{max}$ nm: 296.

EXAMPLE 49

(1R, 5S, 6S)-2-[(2S, 4S)-2-(1-Homopiperazinylcarbonyl)-1-methylpyrrolidin-4-ylthio]-6-[(1R)-1-hydroxyethyl]-1-methyl-1carbapen-2-em-3-carboxylic acid hydrochloride 49(a) 4-Nitrobenzyl (1R, 5S, 6S)-2-[(2S, 4S)-2-[4-(4-nitrobenzyloxycarbonyl)-1-homopiperazinylcarbonyl]-1-methylpyrrolidin-4-ylthio]-6-[(1R)-1-hydroxyethyl]-1-methyl-1-carbapen-2-em-3-carboxylate 0.89 ml of diphenylphosphoryl chloride and 0.75 ml of diisopropylethylamine were simultaneously added dropwise, whilst ice-cooling, to a solution of 1.4 g of 4-nitrobenzyl (1R, 5R, 6S)-6-[(1R)-1-hydroxyethyl]-1-methyl-2-oxo-1-carbapenam-3-carboxylate in 14 ml of dry acetonitrile, and the resulting mixture was stirred at the same temperature for 40 minutes. A solution of 2.68 g of (2S, 4S)-4-mercapto-1-methyl-2-[4-(4-nitrobenzyloxycarbonyl)-1-homopiperazinylcarbonyl]pyrrolidine trifluoromethanesulfonate (prepared as described in Preparation 49) in 14 ml of dry acetonitrile and 1.64 ml of diisopropylethylamine were then simultaneously added dropwise to the mixture, whilst ice-cooling, and the resulting mixture was stirred at the same temperature for 5 hours, after which it was allowed to stand overnight at room temperature. At the end of this time, the reaction mixture was concentrated by evaporation under reduced pressure, and the residue was diluted with ethyl acetate. The dilute solution was then washed with an aqueous solution of sodium hydrogencarbonate, with a phosphate buffer solution (pH 6.86), with water and with an aqueous solution of sodium chloride, in that order, after which it was dried over anhydrous magnesium sulfate. The solvent was then removed by distillation under reduced pressure, and the resulting residue was purified by column chromatography through silica gel (Merck Art No. 7734), using a gradient elution method with mixtures of ethyl acetate and methanol ranging from 85:15 to 80:20 by volume as the eluent, to give 1.7 g of the title compound, as a powder.

Infrared Absorption Spectrum (KBr), $\nu_{max}$ cm$^{-1}$: 1769, 1702, 1642, 1521, 1346.

Nuclear Magnetic Resonance Spectrum (CDCl$_3$, 270 MHz), δ ppm:

1.27 (3H, doublet, J=7.32 Hz);

1.35 (3H, doublet, J=6.35 Hz);
1.40–2.05 (6H, multiplet);
2.32–2.85 (3H, multiplet);
3.15–4.05 (13H, multiplet);
4.20–4.37 (2H, multiplet);
5.20–5.52 (4H, multiplet);
7.47–7.53 (2H, multiplet);
7.67 (2H, doublet, J=8.79 Hz);
8.23 (4H, doublet, J=8.79 Hz).

49(b) (1R, 5S, 6S)-2-[(2S, 4S)-2-(1-Homopiperazinylcarbonyl)-1-methylpyrrolidin-4-ylthio]-6-[(1R)-1-hydroxyethyl]-1-methyl-1-carbapen-2-em-3-carboxylic acid hydrochloride A solution of 1.3 g of 4-nitrobenzyl (1R, 5S, 6S)-2-[(2S, 4S)-2-[4-(4-nitrobenzyloxycarbonyl)-1-homopiperazinylcarbonyl]-1-methylpyrrolidin-4-ylthio]-6-[(1R)-1-hydroxyethyl]-1-methyl-1-carbapen-2-em-3- carboxylate [prepared as described in step (a) above] in 20 ml of a 1:1 by volume mixture of tetrahydrofuran and water was mixed with 2.6 ml of 1N aqueous hydrochloric acid, and the mixture was hydrogenated by bubbling hydrogen through it at room temperature for 2 hours in the presence of 10% w/w palladium-on-charcoal. The catalyst was then removed by filtration, and the filtrate was washed with diethyl ether. The aqueous solution was concentrated by evaporation under reduced pressure, after which the residue was purified by reverse phase column chromatography through a Lobar column (Merck, LiChroprep RP-8, size B), using water as the eluent. Those fractions containing the title compound were collected, concentrated by evaporation under reduced pressure and lyophilized, to give 260 mg of the title compound as a powder.

Infrared Absorption Spectrum (KBr), $v_{max}$ cm$^{-1}$: 1759, 1650, 1598, 1458, 1389.

Ultraviolet Absorption Spectrum (H$_2$O) $\lambda_{max}$ nm: 297.6

Nuclear Magnetic Resonance Spectrum (270 MHz, D$_2$O, using tetradeuterated sodium trimethylsilylpropionate as an internal standard) δ ppm:

1.21 (3H, doublet, J=7.32 Hz);
1.29 (3H, doublet, J=6.35 Hz);
1.99–2.32 (3H, multiplet);
2.97 (3H, singlet);
3.18–4.05 (13H, multiplet);
4.12–4.35 (3H, multiplet);
4.66–4.82 (1H, multiplet).

EXAMPLE 50

(1R, 5S, 6S)-2-[(2S, 4S)-2-(4-Carboxymethyl-1-homopiperazinylcarbonyl)pyrrolidin-4-ylthio]-6-[(1R)-1-hydroxyethyl]-1-methyl-1-carbapen-2-em-3-carboxylic acid 50(a) 4-Nitrobenzyl (1R, 5S, 6S)-2-[(2S, 4S)-2-[4-(4-nitrobenzyloxycarbonylmethyl)-1-homopiperazinylcarbonyl]-1-(4-nitrobenzyloxycarbonyl)pyrrolidin-4-ylthio]-6-[(1R)-1-hydroxyethyl]-1-methyl-1-carbapen-2-em-3-carboxylate 0.37 ml of diphenylphosphoryl chloride and 0.31 ml of diisopropylethylamine were added dropwise, whilst ice-cooling, to a solution of 580 mg of 4-nitrobenzyl (1R, 5R, 6S)-6-[(1R)-1-hydroxyethyl]-1-methyl-2-oxo-1-carbapenam-3-carboxylate in 10 ml of dry acetonitrile, and the resulting mixture was stirred at the same temperature for 1 hour. 0.99 ml of diisopropylethylamine and a solution of 1.43 g of (2S, 4S)-4-mercapto-2-[4-(4-nitrobenzyloxycarbonylmethyl)-1-homopiperazinylcarbonyl]-1-(4-nitrobenzyloxycarbonyl) pyrrolidine bis(trifluoromethanesulfonate) (prepared as described in Preparation 50) in 10 ml of dry acetonitrile were then simultaneously added dropwise to the mixture, whilst ice-cooling, and the resulting mixture was stirred overnight at the same temperature. At the end of this time, the solvent was removed by distillation under reduced pressure, and the residue was mixed with an aqueous solution of sodium hydrogencarbonate. It was then extracted with ethyl acetate. The extract was dried over anhydrous magnesium sulfate and the solvent was removed by distillation under reduced pressure. The residue was subjected to column chromatography through a Lobar column (Merck, LiChroprep Si60, size B), using a 5:1 by volume mixture of ethyl acetate and methanol as the eluent to give 1.1 g of the title compound, as a powder.

Infrared Absorption Spectrum (KBr), $v_{max}$ cm$^{-1}$: 1771, 1709, 1647, 1606, 1521, 1346.

Nuclear Magnetic Resonance Spectrum (270 MHz, CDCl$_3$), δ ppm:

1.28 (3H, doublet, J=6.84 Hz);
1.37 (3H, doublet, J=6.35 Hz);
1.74–2.04 (4H, multiplet);
2.62–2.96 (6H, multiplet);
3.27 (1H, doublet of doublets, J=6.83 & 2.44 Hz);
3.34–3.79 (9H, multiplet);
4.19–4.27 (2H, multiplet);
4.66–4.77 (1H, multiplet);
5.06–5.52 (6H, multiplet);
7.45–7.52 (4H, multiplet);
7.65 (2H, doublet, J=8.79 Hz);
8.23 (6H, doublet, J=8.79 Hz).

50(b) (1R, 5S, 6S)-2-[(2S, 4S)-2-(4-Carboxymethyl-1-homopiperazinylcarbonyl)pyrrolidin-4-ylthio]-6-[(1R)-1-hydroxyethyl]-1-methyl-1-carbapen-2-em-3-carboxylic acid A solution of 0.5 g of 4-nitrobenzyl (1R, 5S, 6S)-2-[(2S, 4S)-2-[4-(4-nitrobenzyloxycarbonylmethyl)-1-homopiperazinylcarbonyl]-1-(4-nitrobenzyloxycarbonyl) pyrrolidin-4-ylthio]-6-[(1R)-1-hydroxyethyl]-1-methyl-1-carbapen-2-em-3-carboxylate [prepared as described in step (a) above] in 15 ml of a 1:1 by volume mixture of tetrahydrofuran and water was mixed with 0.26 ml of 1N aqueous hydrochloric acid, and the mixture was hydrogenated by bubbling hydrogen through it at room temperature for 90 minutes in the presence of 0.5 g of 10% w/w palladium-on-charcoal. The catalyst was then removed by filtration, and the filtrate was washed with diethyl ether. The washed aqueous solution was then concentrated by evaporation under reduced pressure, and the concentrate was purified by reverse phase column chromatography through a Lobar column (Merck, LiChroprep RP-8, size B), using 1% v/v aqueous methanol as the eluent. Those fractions containing the title compound were collected, concentrated by evaporation under reduced pressure and lyophilized, to give 170 mg of the title compound as a powder.

Infrared Absorption Spectrum (KBr), $v_{max}$ cm$^{-1}$: 1754, 1638, 1460, 1374.

Ultraviolet Absorption Spectrum (H$_2$O) $\lambda_{max}$ nm: 296.6.

Nuclear Magnetic Resonance Spectrum (270 MHz, D$_2$O, using tetradeuterated sodium trimethylsilylpropionate as an internal standard) δ ppm:

1.22 (3H, doublet, J=7.33 Hz);

1.30 (3H, doublet, J=6.34 Hz);
1.93–2.10 (1H, multiplet);
2.13–2.42 (2H, multiplet);
2.95–3.17 (1H, multiplet);
3.27–3.98 (13H, multiplet;
3.99–4.15 (2H, multiplet);
4.18–4.35 (2H, multiplet);
4.43–4.65 (1H, multiplet).

EXAMPLE 51

(1R,5S,6S)-2-[(2S,4S)-2-(4-Methyl-1-piperazinylcarbonyl)-1-methylpyrrolidin-4-ylthio]-6-[(1R)-1-hydroxyethyl]-1-methyl-1-carbapen-2-em-3-carboxylic Acid Hydrochloride 51(a) 4-Nitrobenzyl (1R,5S,6S)-2-[(2S,4S)-2-(4-methyl-1-piperazinylcarbonyl)-1-methylpyrrolidin-4-ylthio]-6-[(1R)-1-hydroxyethyl]-1-methyl-1-carbapen-2-em-3-carboxylate 540 μl of diphenylphosophoryl chloride and 470 μl of diisopropylethylamine were added dropwise, whilst ice-cooling, to a solution of 920 mg of 4-nitrobenzyl (1R,5 R,6S)-6-[(1 R)-1-hydroxyethyl]-1-methyl-2-oxo-1-carbapenam-3- carboxylate in 10 ml of dry acetonitrile, and the resulting mixture was stirred at the same temperature for 1 hour. 1400 μl of diisopropylethylamine and a solution of 1350 mg of (2 S,4S)-4-mercapto-2-(4-methyl-1-piperazinylcarbonyl)-1-methylpyrrolidine bis(trifluoromethanesulfonate) (prepared as described in Preparation 51) in 5 ml of dry acetonitrile were then simultaneously added dropwise to the mixture, whilst ice-cooling, and the resulting mixture was stirred at the same temperature for 2 hours, after which it was allowed to stand overnight in a refrigerator. At the end of this time, the solvent was removed by distillation under reduced pressure, and the residue was purified by chromatography through a Lobar column (Merck, LiChroprep RP-8, size B). The column was successively eluted with 65% by volume aqueous methanol and with 70% by volume aqueous methanol. Those fractions containing the title compound were combined and concentrated by evaporation under reduced pressure, to give 730 mg of the title compound, as a powder.

Nuclear Magnetic Resonance Spectrum (CDCl$_3$, 270 MHz), δ ppm: 1.27 (3H, doublet, J=7.3 Hz); 1.37 (3H, doublet, J=6.3 Hz); 1.83–1.93 (1H, multiplet); 2.30 (3H, singlet); 2.35 (3H, singlet); 2.35–2.48 (4H, multiplet); 2.57–2.73 (2H, multiplet); 3.13–3.36 (4H, multiplet); 3.55–3.95 (5H, multiplet); 4.21–4.28 (2H, multiplet); 5.25 (1H, doublet, J=14.2 Hz); 5.48 (1H, doublet, J=14.2 Hz); 7.66 (2H, doublet, J=8.8 Hz); 8.23 (2H, doublet, J=8.8 Hz).

Infrared Absorption Spectrum (KBr), ν$_{max}$ cm$^{-1}$: 1769, 1706, 1639, 1606, 1521, 1450, 1346, 1208, 1137.

51(b) (1R,5S,6S)-2-[(2S,4S)-2-(4-Methyl-1-piperazinylcarbonyl)-1-methylpyrrolidin-4-ylthio]-6-[(1R)-1-hydroxyethyl]-1-methyl-1-carbapen-2-em-3-carboxylic Acid Hydrochloride A solution of 720 mg of 4-nitrobenzyl (1R, 5S,6 S)-2-[(2S,4 S)-2-(4-methyl-1-piperazinylcarbonyl)-1-methylpyrrolidin-4-ylthio]-6-[(1R)-1-hydroxyethyl]- 1-methyl-1-carbapen-2-em-3-carboxylate [prepared as described in step (a) above] in 60 ml of a 1:1 by volume mixture of tetrahydrofuran and water was mixed with 1.2 ml of 1N aqueous hydrochloric acid, and the mixture was hydrogenated by bubbling hydrogen through it at room temperature for 2 hours in the presence of 800 mg of 10% w/w palladium-on-charcoal. The catalyst was then removed by filtration and the filtrate was washed with diethyl ether. The aqueous solution was concentrated by evaporation under reduced pressure, the residue was subjected to column chromatography using a Lobar column (Merck, LiChroprep RP-8, size B) and the column was eluted with 3% by volume aqueous methanol. Those fractions containing the title compound were combined and concentrated by evaporation under reduced pressure, to give 326 mg of the title compound as a colorless powder.

Nuclear Magnetic Resonance Spectrum (270 MHz, D$_2$O, using tetradeuterated sodium trimethylsilylpropionate as an internal standard) δ ppm: 1.21 (3H, doublet, J=6.8 Hz); 1.29 (3H, doublet, J=6.3 Hz); 1.97–2.07 (1H, multiplet); 2.96 (3H, singlet); 2.97 (3H, singlet); 3.18–3.50 (8H, multiplet); 3.67–3.84 (5H, multiplet); 4.17–4.30 (3H, multiplet); 4.70–4.77 (1H, multiplet).

Infrared Absorption Spectrum (KBr), ν$_{max}$ cm$^{-1}$: 1754, 1658, 1600, 1456, 1385, 1261.

Ultraviolet Absorption Spectrum (H$_2$O) λ$_{max}$ nm (ε): 297 (8660).

EXAMPLE 52

(1R,5S,6S)-2-{(2S,4S)-2-[4-(2-Hydroxyethyl)-1-piperazinylcarbonyl]-1-methylpyrrolidin-4-ylthio}-6-[(1R)-1-hydroxyethyl]-1-methyl-1-carbapen-2-em-3-carboxylic Acid Hydrochloride 52(a) 4-Nitrobenzyl (1R,5S,6S)-2-{(2S,4S)-2-[4-(2-hydroxyethyl)-1-piperazinylcarbonyl]-1-methylpyrrolidin-4-ylthio}-6-[(1R)-1-hydroxyethyl]-1-methyl-1-carbapen-2-em-3-carboxylate 600 μl of diphenylphosphoryl chloride and 510 μl of diisopropylethylamine were added dropwise, whilst ice-cooling, to a solution of 1000 mg of 4-nitrobenzyl (1R,5 S,6S)-6-[(1 R)-1-hydroxyethyl]-1-methyl-2-oxo-1-carbapenam-3- carboxylate in 10 ml of dry acetonitrile, and the resulting mixture was stirred at the same temperature for 1 hour. 1800 μl of diisopropylethylamine and a solution of 1680 mg of (2 S,4S)-4-mercapto-2-[4-(2-hydroxyethyl)-1-piperazinylcarbonyl]-1-methylpyrrolidine bis (trifluoromethanesulfonate) (prepared as described in Preparation 52) in 5 ml of dry acetonitrile were then simultaneously added dropwise to the mixture, whilst ice-cooling, and the resulting mixture was stirred at the same temperature for 2 hours, after which it was allowed to stand overnight in a refrigerator. At the end of this time, the solvent was removed by distillation under reduced pressure, and the residue was subjected to column chromatography through a Lobar column (Merck, LiChroprep RP-8, size B). The column was eluted first with 55% v/v aqueous methanol and then with 60% v/v aqueous methanol. Those fractions containing the title compound were collected, concentrated by evaporation under reduced pressure and lyophilized, to give 710 mg of the title compound, as a powder.

Nuclear Magnetic Resonance Spectrum (CDCl$_3$, 270 MHz), δ ppm: 1.27 (3H, doublet, J=7.3 Hz); 1.36 (3H, doublet, J=5.9 Hz); 1.83–1.93 (1H, multiplet); 2.34 (3H, singlet); 2.40–2.76 (8H, multiplet); 3.10–3.38 (4H, multiplet); 3.55–4.04 (7H, multiplet); 4.18–4.31 (2H, multiplet); 5.24 (1H, doublet, J=13.8 Hz); 5.48 (1H, doublet, J=13.8 Hz); 7.66 (2H, doublet, J=8.6 Hz); 8.22 (2H, doublet, J=8.6 Hz).

Infrared Absorption Spectrum (KBr), $v_{max}$ cm$^{-1}$: 1756, 1651, 1596, 1464, 1390, 1373, 1286, 1261.

52(b) (1R,5S,6S)-2-{(2S,4S)-2-[4-(2-Hydroxyethyl)-1-piperazinylcarbonyl]-1-methylpyrrolidin-4-ylthio}-6-[(1R)-1-hydroxyethyl]-1-methyl-1-carbapen-2-em-3-carboxylic Acid Hydrochloride A solution of 700 mg of 4-nitrobenzyl (1R,5S,6S)-2-{(2S,4S)-2-[4-(2-hydroxyethyl)-1-piperazinylcarbonyl]-1-methylpyrrolidin-4-ylthio}-6-[(1R)-1-hydroxyethyl]-1-methyl-1-carbapen-2-em-3-carboxylate [prepared as described in step (a) above] in 60 ml of a 1:1 by volume mixture of tetrahydrofuran and water was mixed with 1.15 ml of 1N aqueous hydrochloric acid, and the mixture was hydrogented by bubbling hydrogen through it at room temperature for 2 hours in the presence of 1000 mg of 10% w/w palladium-on-charcoal. At the end of this time, the catalyst was removed by filtration, and the filtrate was extracted with diethyl ether. The remaining aqueous layer was concentrated by evaporation under reduced pressure, and the residue was subjected to column chromatography through a Lobar column (Merck, LiChroprep RP-8, size B). The column was eluted with 1.5% v/v aqueous methanol and those fractions containing the title compound were combined, concentrated by evaporation under reduced pressure and lyophilized, to give 300 mg of the title compound as a colorless powder.

Nuclear Magnetic Resonance Spectrum (270 MHz, D$_2$O, using tetradeuterated sodium trimethylsilylpropionate as an internal standard), δ ppm: 1.21 (3H, doublet, J=7.3 Hz); 1.29 (3H, doublet, J=6.3 Hz); 1.98–2.07 (1H, multiplet); 2.95 (3H, singlet); 3.17–3.45 (9H, multiplet); 3.45–3.52 (1H, multiplet); 3.64–3.86 (5H, multiplet); 3.86–3.95 (2H, multiplet); 4.13–4.30 (3H, multiplet); 4.68–4.77 (1H, multiplet).

Infrared Absorption Spectrum (KBr), $v_{max}$ cm$^{-1}$: 1757, 1658, 1596, 1450, 1391, 1374, 1260.

Ultraviolet Absorption Spectrum (H$_2$O)) $\lambda_{max}$ nm (ε): 297 (9252).

EXAMPLE 53

(1R,5S,6S)-2-{(2S,4S)-2-[4-(2-Carbamoyloxyethyl)-1-piperazinylcarbonyl]pyrrolidin-4-ylthio}-6-[(1R)-1-hydroxyethyl]-1-methyl-1-carbapen-2-em-3-carboxylic Acid Hydrochloride

53(a) 4-Nitrobenzyl (1R,5S,6S)-2-{(2S,4S)-2-[4-(2-carbamoyloxyethyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 91 µl of diphenylphosphoryl chloride and 77 µl of diisopropylethylamine were added dropwise, whilst ice-cooling, to a solution of 152 mg of 4-nitrobenzyl (1R,5R,6S)-6-[(1R)-1-hydroxyethyl]-1-methyl-2-oxo-1-carbapenam-3-carboxylate in 2.0 ml of dry, acenonitrile, and the resulting mixture was stirred at the same temperature for 1 hour. 176 µl of diisopropylethylamine and a solution of 318 mg of (2S,4S)-4-mercapto-2-[4-(2-carbamoyloxyethyl)-1-piperazinylcarbonyl]-1-(4-nitrobenzyloxycarbonyl) pyrrolidine trifluoromethanesulfonate (prepared as described in Preparation 53) in 2.0 ml of dry acetonitrile were then simultaneously added dropwise to the mixture, whilst ice-cooling, and the resulting mixture was stirred at the same temperature for 2 hours, after which in was allowed to stand overnight in a refrigerator. At the end of this time, the solvent was removed by distillation under reduced pressure, and the residue was mixed with an aqueous solution of sodium hydrogencarbonate. The mixture was then extracted with ethyl acetate, and the extract was dried over anhydrous magnesium sulfate. The solvent was Then removed from the extract by distillation under reduced pressure, and the resulting residue was purified by chromatography through a Lobar column (Merck, LiChroprep Si60, size B), using a 5:1 by volume mixture of ethyl acetate and methanol as the eluent to give 99 mg of the title compound, as a powder.

Infrared Absorption Spectrum (KBr), $v_{max}$ cm$^{-1}$: 1773, 1711, 1650, 1521, 1345.

Nuclear Magnetic Resonance Spectrum (270 MHz, hexadeuterated dimethyl sulfoxide) δ ppm: 1.15 (3H, doublet, J=6.35 Hz); 1.16 (3H, doublet, J=7.32 Hz); 1.51–1.72 (1H, multiplet); 2.10–2.57 (6H, multiplet); 2.72–2.93 (1H, multiplet); 3.06–4.30 (13H, multiplet); 4.76 & 4.85 (together 1H, two triplets, J=7.81 Hz); 5.03–5.27 (3H, multiplet); 5.30 & 5.46 (2H, AB-quartet, J=14.16 Hz); 6.46 (2H, broad singlet); 7.55 & 7.65 (2H, two doublets, J=8.79 Hz); 7.72 (2H, doublet, J=8.79 Hz); 8.22 & 8.23 (4H, two doublets, J=8.79 Hz).

53(b) (1R,5S,6S)-2-{(2S,4S)-2-[4-(2-Carbamoyloxyethyl)-1-piperazinylcarbonyl]pyrrolidin-4-ylthio}-6-[(1R)-1-hydroxyethyl]-1-methyl-1-carbapen-2-em-3-carboxylic Acid Hydrochloride 1.0 g of 4-nitrobenzyl (1R,5S,6S)-2-{(2S,4S)-2-[4-(2-carbamoyloxyethyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (a) above] was dissolved in 60 ml of a 1:1 by volume mixture of tetrahydrofuran and water, and the mixture was hydrogenated by bubbling hydrogen through it at room temperature for 3 hours in the presence of 1.1 g of 10% w/w palladium-on-charcoal. At the end of this time, the catalyst was removed by filtration, and the filtrate was extracted with diethyl ether. The remaining aqueous layer was concentrated by evaporation under reduced pressure, and the resulting residue was subjected to column chromatography through a Lobar column (Merck, LiChroprep RP-8, size B). The column was eluted with 20% v/v aqueous methanol. Those fractions containing the title compound were combined and the pH was adjusted to a value of 4 by the addition of 1N aqueous hydrochloric acid. The solution was then concentrated by evaporation under reduced pressure, and the concentrate was lyophilized, to give 327 mg of the title compound as a colorless powder.

Infrared Absorption Spectrum (KBr), $v_{max}$ cm$^{-1}$: 1728, 1654, 1597, 1392.

Ultraviolet Absorption Spectrum (H$_2$O) $\lambda_{max}$ nm (ε): 297 (9706).

Nuclear Magnetic Resonance Spectrum (270 MHz, D$_2$O, using tetradeuterated sodium trimethylsilylpropionate as an internal standard), δ ppm: 1.21 (3H, doublet, J=7.3 Hz); 1.29 (3H, doublet, J=6.3 Hz); 1.95–2.06 (1H, multiplet); 3.01–3.25 (7H, multiplet); 3.31–3.43 (1H, multiplet); 3.46–3.52 (2H, multiplet); 3.72–3.90 (5H, multiplet); 4.02–4.11 (1H, multiplet); 4.21–4.30 (2H, multiplet); 4.32–4.36 (2H, multiplet); 4.82–4.89 (1H, multiplet).

EXAMPLE 54

(1R,5S,6S)-2-{(2S,4S)-2-[4-(2-Hydroxyethyl)-1-piperazinylcarbonyl]pyrrolidin-4-ylthio}-6-[(1R)-1-hydroxyethyl]-1-methyl-1-carbapen-2-em-3-carboxylic Acid Hydrochloride

54(a)(i) 4-Nitrobenzyl (1R,5S,6S)-2-[(2S,4S)-2-[4-(2-hydroxyethyl)-1-piperazinylcarbonyl]-1-(4-nitrobenzyloxycarbonyl)pyrrolidin-4-ylthio]-6-[(1R)-1-hydroxyethyl]-1-methyl-1-carbapen-2-em-3-carboxylate 90 μl of diphenylphosphoryl chloride and 76 μl of diisopropylethylamine were added dropwise, whilst ice-cooling, to a solution of 148 mg of 4-nitrobenzyl (1R,5R,6S)-6-[(1R)-1-hydroxyethyl]-1-methyl-2-oxo-1-carbapenam-3-carboxylate in 1.9 ml of dry acetonitrile, and the resulting mixture was stirred at the same temperature for 1 hour. 257 μl of diisopropylethylamine and 361 mg of (2S,4S)-2-[4-(2-hydroxyethyl)-1-piperazinylcarbonyl]-4-mercapto-1-(4-nitrobenzyloxycarbonyl)pyrrolidine bis (trifluoromethanesulfonate) (prepared as described in Preparation 54) were then simultaneously added dropwise to the mixture, whilst ice-cooling, and the resulting mixture was stirred at the same temperature for 6 hours, after which it was allowed to stand overnight in a refrigerator. At the end of this time, the reaction mixture was worked up in a similar manner to that described in Example 49(b). The crude product thus obtained was purified by chromatography through a Lobar column (Merck, LiChroprep Si60), using a 5:1 by volume mixture of acetonitrile and methanol as the eluent, to give 220 mg of the title compound, as a powder.

Ultraviolet Absorption Spectrum (MeOH) $\lambda_{max}$ nm: 268, 315.

Infrared Absorption Spectrum (KBr), $v_{max}$ cm$^{-1}$: 1772, 1710, 1652, 1606, 1521, 1489, 1440, 1405, 1345, 1280, 1207.

Nuclear Magnetic Resonance Spectrum (CDCl$_3$, 270 MHz), δ ppm: 1.27 & 1.28 (3H, two doublets, J=7.33 Hz); 1.37 (3H, doublet, J=6.35 Hz); 1.82–2.00 (1H, multiplet); 2.33–2.78 (8H, multiplet); 3.25–3.29 (1H, multiplet); 3.32–3.82 (9H, multiplet); 4.00–4.30 (3H, multiplet); 4.69 & 4.74 (1H, two triplets, J=7.81 Hz); 5.05–5.52 (5H, multiplet); 7.44 & 7.51 (2H, two doublets, J=8.79 Hz); 7.64 (2H, doublet, J=8.79 Hz); 8.23 (4H, doublet, J=8.79 Hz).

54(a)(i') 4-Nitrobenzyl (1R,5S,6S)-2-[(2S,4S)-2-[4-(2-hydroxyethyl)-1-piperazinylcarbonyl]-1-(4-nitrobenzyloxycarbonyl)pyrrolidin-4-ylthio]-6-[(1R)-1-hydroxyethyl]-1-methyl-1-carbapen-2-em-3-carboxylate 1.82 ml of diphenylphosphoryl chloride and 1.54 ml of diisopropylethylamine were added dropwise, whilst ice-cooling, to a solution of 3.0 g of 4-nitrobenzyl (1R,5R,6S)-6-[(1R)-1-hydroxyethyl]-1-methyl-2-oxo-1-carbapenam-3-carboxylate in 38 ml of dry acetonitrile, and the resulting mixture was stirred at the same temperature for 1 hour. 1.54 ml of diisopropylethylamine and a solution of 3.63 g of (2S,4S)-2-[4-(2-hydroxyethyl)-1-piperazinylcarbonyl]-4-mercapto-1-(4-nitrobenzyloxycarbonyl)pyrrolidine (prepared as described in Preparation 54) in 30 ml of dry acetonitrile were then simultaneously added dropwise to the mixture, whilst ice-cooling, and the resulting mixture was stirred at the same temperature for 3 hours, after which it was allowed to stand overnight in a refrigerator. At the end of this time, the reaction mixture was worked up in a similar manner to that described in Example 49(b). The crude product was then purified by column chromatography through silica gel, using a 2:1 by volume mixture of ethyl acetate and methanol as the eluent, to give 3.4 g of the title compound, as a powder. The infrared absorption spectrum and nuclear magnetic resonance spectrum of the product were identical with those of the compound prepared as described in step 54(i), above.

54(a)(ii) (1R,5S,6S)-2-{(2S,4S)-2-[4-(2-Hydroxyethyl)-1-piperazinylcarbonyl]pyrrolidin-4-ylthio}-6-[(1R)-1-hydroxyethyl]-1-methyl-1-carbapen-2-em-3-carboxylic Acid Hydrochloride 1.38 g of 4-nitrobenzyl (1R,5S,6S)-2-[(2S,4S)-2-[4-(2-hydroxyethyl)-1-piperazinylcarbonyl]-1-(4-nitrobenzyloxycarbonyl)pyrrolidin-4-ylthio]-6-[(1R)-1-hydroxyethyl]-1-methyl-1-carbapen-2-em-3-carboxylate [prepared as described in step 54(a)(i) or step 54(a)(i') above] was dissolved in 40 ml of a 1:1 by volume mixture of tetrahydrofuran and water, and the mixture was hydrogenated by bubbling hydrogen through it at room temperature for 2 hours in the presence of 1.2 g of 10% w/w palladium-on-charcoal. At the end of this time, the catalyst was removed by filtration, and the filtrate was extracted with diethyl ether. The pH of the remaining aqueous layer was adjusted to a value of 4 by the addition of 1N aqueous hydrochloric acid, and then the solution was concentrated by evaporation under reduced pressure. The resulting residue was subjected to column chromatography through a Lobar column (Merck, LiChroprep RP-8, size B) and the column was eluted with 3% v/v aqueous methanol. Those fractions containing the title compound were combined, concentrated by evaporation and lyophilized, to give 314 mg of the title compound as a colorless powder.

Nuclear Magnetic Resonance Spectrum (270 MHz, D$_2$O, using sodium tetradeuterated trimethylsilylpropionate as an internal standard), δ ppm: 1.21 (3H, doublet, J=7.3 Hz); 1.28 (3H, doublet, J=6.4 Hz); 1.97–2.07 (1H, multiplet); 3.02–3.13 (1H, multiplet); 3.32–3.70 (10H, multiplet); 3.70–4.00 (6H, multiplet); 4.00–4.16 (1H, multiplet); 4.18–4.29 (2H, multiplet); 4.86–4.92 (1H, multiplet).

Ultraviolet Absorption Spectrum (H$_2$O) $\lambda_{max}$ nm (ε): 297 (8124).

Infrared Absorption Spectrum (KBr), $v_{max}$ cm$^{-1}$: 1757, 1659, 1595, 1393, 1376, 1277.

54(b)(i) 4-Nitrobenzyl (1R,5S,6S)-2-{(2S,4S)-[4-(2-4'-nitrobenzyloxycarbonyloxyethyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 6.38 g of diphenylphosphoryl chloride and 5.37 ml of diisopropylethylamine were added dropwise, whilst ice-cooling, to a solution of 10.63 g of 4-nitrobenzyl (1R,5R,6S)-6-[(1R)-1-hydroxyethyl]-1-methyl-2-oxo-1-carbapenam-3-carboxylate in 75 ml of dry acetonitrile, and the resulting mixture was stirred at the same temperature for 1 hour. 16.26 ml of diisopropylethylamine and a solution of 32.5 g of (2S,4S)-4-mercapto-2-{4-[2-(4-nitrobenzyloxycarbonyl)oxyethyl]-1-piperazinylcarbonyl}-1-(4-nitrobenzyloxycarbonyl)pyrrolidine bis (trifluoromethanesulfonate) in 65 ml of dry acetonitrile were then simultaneously added dropwise to the mixture, whilst ice-cooling. The resulting mixture was then stirred at the same temperature for 1 hour, after which it was allowed to stand overnight, whilst ice-cooling. At the end of this time, the solvent was removed by distillation under reduced pressure, and the resulting residue was mixed with an aqueous solution of sodium hydrogencarbonate; it was then extracted with ethyl acetate. The extract was dried over anhydrous magnesium sulfate, and the solvent was removed by distillation under reduced pressure. The residue was purified by column chromatography through silica gel, using a 18:1 by volume mixture of ethyl acetate and methanol as the eluent, to give 19.75 g of the title compound, as a powder.

Infrared Absorption Spectrum (KBr), $v_{max}$ cm$^{-1}$: 1769, 1751, 1710, 1653, 1607, 1521, 1443, 1347.

Nuclear Magnetic Resonance Spectrum (CDCl$_3$, 270 MHz), δ ppm: 1.27 & 1.28 (3H, two doublets, J=7.33 Hz); 1.37 (3H, doublet, J=6.35 Hz); 1.78–1.98 (1H, multiplet); 2.31–2.80 (7H, multiplet); 3.27 (1H, doublet of doublets, J=6.83 & 2.44 Hz); 3.31–3.76 (8H, multiplet); 4.01–4.33 (8H, multiplet); 4.68 & 4.74 (1H, two triplets, J=7.81 Hz); 5.04–5.52 (6H, multiplet); 7.44 & 7.51 (2H, two doublets, J=8.79 Hz); 7.55 & 7.65 (4H, two doublets, J=8.79 Hz); 8.17–8.25 (6H, multiplet).

54(b)(i') 4-Nitrobenzyl (1R,5S,6S)-2-{(2S,4S)-[4-(2-4'-nitrobenzyloxycarbonyloxyethyl)-1-piperazinylcarbonyl]-1-(4-nitrobenzyloxycarbonyl) pyrrolidin-4-ylthio}-6-[(1R)-1-hydroxyethyl]-1-methyl-1-carbapen-2-em-3-carboxylate 675 μl of diphenylphosphoryl chloride and 567 μl of diisopropylethylamine were added dropwise, whilst ice-cooling, to a solution of 1.12 g of 4-nitrobenzyl (1 R,5R,6S)-6-[(1R)-1-hydroxyethyl]-1-methyl-2-oxo-1-carbapenam-3-carboxylate in 10 ml of dry acetonitrile, and the resulting mixture was stirred at the same temperature for 1 hour. A solution of 2.30 g of (2S,4S)-4- mercapto-2-{4-[2-(4-nitrobenzyloxycarbonyl)oxyethyl]-1-piperazinylcarbonyl}-1-(4-nitrobenzyloxycarbonyl) pyrrolidine in 5 ml of dry acetonitrile was then added dropwise to the mixture, whilst ice-cooling, and the resulting mixture was stirred at the same temperature for 1 hour. At the end of this time, the reaction mixture was worked up and purified in a similar manner to that described in step 54(b)(i) above, to give 2.70 g of the title compound, as a powder. The infrared absorption spectrum and nuclear magnetic resonance spectrum of the compound thus obtained were identical with those of the compound prepared as described in step 54(b)(i) above.

54(b)(i") 4-Nitrobenzyl (1R,5S,6S)-2-{(2S,4S)-[4-(2-4'-nitrobenzyloxycarbonyloxyethyl)-1-piperazinylcarbonyl]-1-(4-nitrobenzyloxycarbonyl) pyrrolidin-4-ylthio}-6-[(1R)-1-hydroxyethyl]-1-methyl-1-carbapen-2-em-3-carboxylate A solution of 28.3 mg of 4-nitrobenzyl (1R,5S,6 S)-2-phenylsulfinyl-6-[(1R)-1-hydroxyethyl]- 1-methyl-1-carbapen- 2-em-3-carboxylate in 1 ml of dry acetonitrile was added dropwise to a solution of 112 mg of (2S,4S)-{4-[2-(4-nitrobenzyloxycarbonyl)oxyethyl]-1-piperazinylcarbonyl}-4-mercapto-1-(4-nitrobenzyloxycarbonyl)pyrrolidine in 0.5 ml of dry acetonitrile, whilst ice-cooling, and the resulting mixture was stirred at the same temperature for 1 hour. At the end of this time, the reaction mixture was freed from the solvent by distillation under reduced pressure. The resulting residue was purified by column chromatography through silica gel, using a 20:1 by volume mixture of ethyl acetate and methanol as the eluent, to give 14 mg of the title compound, as a powder. The infrared absorption spectrum and nuclear magnetic resonance spectrum of the compound thus obtained were identical with those of the compound prepared as described in step 54(b)(i) above.

54(b)(i''') 4-Nitrobenzyl (1R,5S,6S)-2-{(2S,4S)-[4-(2-4'-nitrobenzyloxycarbonyloxyethyl)-1-piperazinylcarbonyl]-1-(4-nitrobenzyloxycarbonyl) pyrrolidin-4-ylthio}-6-[(1R)-1-hydroxyethyl]-1-methyl-1-carbapen-2-em-3-carboxylate A solution of 50 mg of 4-nitrobenzyl (1R,5S,6 S)-2-(4-chlorophenyl)sulfinyl-6-[(1R)-1-hydroxyethyl]-1-methyl-1-carbapen-2-em-3-carboxylate and 19.4 mg of diisopropylethylamine in 0.5 ml of dry acetonitrile was added dropwise to a solution of 93 mg of (2S,4 S)-{4-[2-(4-nitrobenzyloxycarbonyl)oxyethyl]-1-piperazinylcarbonyl}-4-mercapto-1-(4-nitrobenzyloxycarbonyl)pyrrolidine in 0.5 ml of dry acetonitrile, whilst ice-cooling, and the resulting mixture was stirred at the same temperature for 1 hour. At the end of this time, the reaction mixture was freed from the solvent by distillation under reduced pressure. The residue was worked up in a similar manner to that described in step 54(a)(i), to give 13 mg of 4-nitrobenzyl (1R,5S,6S)-2-[(2S,4 S)-[4-(2-4'-nitrobenzyloxycarbonyloxyethyl)-1-piperazinylcarbonyl]-1-(4-nitrobenzyloxycarbonyl) pyrrolidin-4 -ylthio}-6-[(1R)-1-hydroxyethyl]-1- methyl-1-carbapen-2-em-3-carboxylate as a powder. The infrared absorption spectrum and nuclear magnetic resonance spectrum of the compound thus obtained were identical with those of the compound prepared as described in step 54(b)(i) above.

54(b)(ii) (1R,5S,6S)-2-{(2S,4S)-2-[4-(2-Hydroxyethyl)-1-piperazinylcarbonyl]pyrrolidin-4-ylthio}-6-[(1R)-1-hydroxyethyl]-1-methyl-1-carbapen-2-em-3-carboxylic Acid Hydrochloride 0.962 g of 4-nitrobenzyl (1R,5S,6S)-2-{(2S,4S)-[4-(2-4'-nitrobenzyloxycarbonyloxyethyl)-1-piperazinylcarbonyl]-1-(4-nitrobenzyloxycarbonyl)pyrrolidin-4-ylthio}-6-[(1 R)-1-hydroxyethyl]-1-methyl-1-carbapen-2-em-3- carboxylate [prepared as described in steps 54(b)(i) to 54(b)(i''')) above] was dissolved in 30 ml of a 1:1 by volume mixture of tetrahydrofuran and water, to which 1.2 ml of 1N aqueous hydrochloric acid had been added, and the mixture was hydrogenated by bubbling hydrogen through it in the presence of 1 g of 10% w/w palladium-on-charcoal. At the end of this time, the catalyst was removed by filtration and the filtrate was extracted with ethyl acetate. The aqueous layer was concentrated by evaporation under reduced pressure, and the resulting residue was subjected to column chromatography through a Lobar column (Merck, LiChroprep RP-8, size B), using 3% v/v aqueous methanol as the eluent. Those fractions containing the title compound were combined, concentrated by evaporation under reduced pressure and lyophilized, to give 181 mg of the title compound as a colorless powder.

The infrared absorption spectrum and nuclear magnetic resonance spectrum of the compound thus obtained were identical with those of the compound prepared as described in step 54(a)(ii) above.

EXAMPLE 55

(1R,5S,6S)-2-[(2S,4S)-2-(1-Piperazinylcarbonyl)-1-methylpyrrolidin-4-ylthio]-6-[(1R)-1-hydroxyethyl]-1-methyl-1-carbapen-2-em-3-carboxylic Acid Hydrochloride 55(a) 4-Nitrobenzyl (1R,5S,6S)-2-[(2S,4S)-2-[4-(4-nitrobenzyloxycarbonyl)-1-piperazinylcarbonyl]-1methylpyrrolidin-4-ylthio]-6-[(1R)-1-hydroxyethyl]-1-methyl-1-carbapen-2-em-3-carboxylate 7.0 g of diphenylphosphoryl chloride and 3.4 g of diisopropylethylamine were added dropwise, whilst ice-cooling, to a solution of 8.6 g of 4-nitrobenzyl (1R,5R,6S)-6-[(1R)-1-hydroxyethyl]-1-methyl-2-oxo-1-carbapenam-3-carboxylate in 120 ml of dry acetonitrile, and the resulting mixture was stirred at the same temperature for 1 hour. 6.7 g of diisopropylethylamine and a solution of 13.8 g of (2S,4S)-4-mercapto-2-[4-(4-nitrobenzyloxycarbonyl)-1-piperazinylcarbonyl]-1-methylpyrrolidine trifluoromethanesulfonate in dry acetonitrile were then simultaneously added dropwise to the mixture, whilst ice-cooling, and the resulting mixture was allowed to stand overnight, whilst ice-cooling. At the end of this time, the reaction mixture was worked up and purified in a similar manner to that described in Example 49(a), to give 7.0 g of the title compound, as a powder.

Infrared Absorption Spectrum (KBr), $v_{max}$ cm$^{-1}$: 1771, 1706, 1647, 1521, 1436, 1346.

Nuclear Magnetic Resonance Spectrum (CDCl$_3$, 270 MHz), δ ppm: 1.27 (3H, doublet, J=6.84 Hz); 1.37 (3H, doublet, J=6.35 Hz); 1.79–1.95 (1H, multiplet); 2.37 (3H, singlet); 2.60–2.81 (2H, multiplet); 3.10–3.92 (13H, multiplet); 3.97–4.33 (3H, multiplet); 5.21–5.52 (4H, multiplet); 7.53 (2H, doublet, J=8.79 Hz); 7.66 (2H, doublet, J=8.79 Hz); 8.22 & 8.24 (4H, two doublets, J=8.79 Hz).

55(b) (1R,5S,6S)-2-[(2S,4S)-2-(1-Piperazinylcarbonyl)-1-methylpyrrolidin-4-ylthiol-6-[(1R)-1-hydroxyethyl]-1-methyl-1-carbapen-2-em-3-carboxylic Acid Hydrochloride 0.22 g of 4-nitrobenzyl (1R,5S,6S)-2-[(2S,4S)-2-[4-(4-nitrobenzyloxycarbonyl)-1-piperazinylcarbonyl]-1-methylpyrrolidin-4-ylthio]-6-[(1R)-1-hydroxyethyl]-1-methyl-1-carbapen-2-em-3-carboxylate [prepared as described in step (a) above] was dissolved in a 1:1 by volume mixture of tetrahydrofuran and water, and the mixture was hydrogenated by bubbling hydrogen through it at room temperature for 2 hours in the presence of 0.22 g of 10% w/w palladium-on-charcoal. At the end of this time, the catalyst was removed by filtration, and the filtrate was washed with diethyl ether. The remaining aqueous layer was concentrated by evaporation under reduced pressure, and the resulting residue was mixed with 0.35 ml of 1N aqueous hydrochloric acid. The mixture was purified by reverse phase column chromatography through a Lobar column (Merck, LiChroprep RP-8, size B), using 2% v/v aqueous methanol as the eluent. Those fractions containing the title compound were combined, concentrated by evaporation under reduced pressure and lyophilized, to give 98 mg of the title compound as a powder.

Infrared Absorption Spectrum (KBr), $v_{max}$ cm$^{-1}$: 1759, 1657, 1600, 1451, 1383, 1266.

Ultraviolet Absorption Spectrum (H$_2$O) $\lambda_{max}$ nm: 296.6.

Nuclear Magnetic Resonance Spectrum (270 MHz, D$_2$O, using sodium tetradeuterated trimethylsilylpropionate as an internal standard), δ ppm: 1.21 (3H, doublet, J=7.32 Hz); 1.29 (3H, doublet, J=6.35 Hz); 1.91–2.19 (1H, multiplet); 2.96 (3H, singlet); 3.15–3.43 (6H, multiplet); 3.48 (1H, doublet of doublets, J=6.11 & 2.69 Hz); 3.66–3.82 (4H, multiplet); 3.89–3.93 (2H, multiplet); 4.13–4.31 (3H, multiplet); 4.64–4.83 (1H, multiplet).

EXAMPLE 56

(1R,5S,6S)-2-[(2S,4S)-2-(4-Carboxymethyl-1-piperazinylcarbonyl)pyrrolidin-4-ylthio]-1-[(1R)-1-hydroxyethyl]-1-methyl-1-carbapen-2-em-3-carboxylic Acid 56(a) 4-Nitrobenzyl (1R,5S,6S)-2-{(2S,4S)-2-[4-(4-nitrobenzyloxycarbonylmethyl)-1-piperazinylcarbonyl]pyrrolidin-4-ylthio}-6-[(1R)-1-hydroxyethyl]-1-methyl-1-carbapen-2-em-3-carboxylate 290 µl of diphenylphosphoryl chloride and 245 µl of diisopropylethylamine were added dropwise, whilst ice-cooling, to a solution of 500 mg of 4-nitrobenzyl (1R,5R,6S)-6-[(1R)-1-hydroxyethyl]-1-methyl-2-oxo-1-carbapenam-3-carboxylate in 5 ml of dry acetonitrile, and the resulting mixture was stirred at the same temperature for 1 hour. 520 µl of diisopropylethylamine and a solution of 1.57 g of (2S,4S)-4-mercapto-2-[4-(4-nitrobenzyloxycarbonylmethyl)-1-piperazinylcarbonyl]-1-(4-nitrobenzyloxycarbonyl)pyrrolidine bis(trifluoromethanesulfonate) (prepared as described in Preparation 56) in 5 ml of dry acetonitrile were then simultaneously added dropwise to the mixture, whilst ice-cooling, and the resulting mixture was allowed to stand overnight at the same temperature. At the end of this time, the solvent was removed by distillation under reduced pressure, and the resulting residue was subjected to column chromatography through a Lobar column (Merck, LiChroprep Si60, size B), using with a 5:1 by volume mixture of ethyl acetate and methanol as the eluent. Those fractions containing the title compound were combined and concentrated by evaporation under reduced pressure, to give 706 mg of the title compound, as a powder.

Infrared Absorption Spectrum (KBr), $v_{max}$ cm$^{-1}$: 1772, 1710, 1654, 1521, 1346.

Nuclear Magnetic Resonance Spectrum (CDCl$_3$, 270 MHz), δ ppm: 1.27 (3H, doublet, J=7.3 Hz); 1.37 (3H, doublet, J=5.9 Hz); 1.85–2.06 (2H, multiplet); 2.53–2.77 (5H, multiplet); 3.25–3.76 (10H, multiplet); 4.03–4.28 (3H, multiplet); 4.67–4.79 (1H, multiplet); 5.06–5.52 (6H, multiplet); 7.43–7.66 (6H, multiplet); 8.20 & 8.25 (6H, multiplet).

56(b) (1R,5S,6S)-2-[(2S,4S)-2-(4-Carboxymethyl-1-piperazinylcarbonyl)pyrrolidine-4-ylthio]-1-[(1R)-1-hydroxyethyl]-1-methyl-1-carbapen-2-em-3-carboxylic Acid 200 mg of 4-nitrobenzyl (1R,5S,6S)-2-{(2S,4S)-2-[4-(4-nitrobenzyloxycarbonylmethyl)-1-piperazinylcarbonyl]pyrrolidin-4-ylthio}-6-[(1R)-1-hydroxyethyl]-1-methyl-1carbapen-2-em-3-carboxylate (prepared as described in step (a) above] were dissolved in 20 ml of a 1:1 by volume mixture of tetrahydrofuran and water, and the mixture was hydrogenated by bubbling hydrogen through it at room temperature for 2 hours in the presence of 0.3 g of 10% w/w palladium-on-charcoal. At the end of this time, the catalyst was removed by filtration, and the filtrate was extracted with 30 ml of ether. The remaining aqueous layer was separated and concentrated by evaporation under reduced pressure. The resulting residue was subjected to column chromatography through a Lobar column (Merck, LiChroprep RP-8, size B), using water as the eluent. Those fractions containing the title compound were combined, concentrated by evaporation under reduced pressure and lyophilized, to give 20 mg of the title compound as a colorless powder.

Infrared Absorption Spectrum (KBr), $v_{max}$ cm$^{-1}$: 1755, 1639, 1603, 1386.

Ultraviolet Absorption Spectrum (H$_2$O) $\lambda_{max}$ nm (ε): 297 (7753).

Nuclear Magnetic Resonance Spectrum (270 MHz, D$_2$O) δ ppm: 1.02 (3H, doublet, J=7.3 Hz); 1.10 (3H, doublet, J=6.3 Hz); 1.72–1.82 (1H, multiplet); 2.77–2.88 (1H, multiplet); 2.95–3.10 (4H, multiplet); 3.10–3.32 (3H, multiplet); 3.39 (2H, singlet); 3.44–3.75 (6H, multiplet); 3.79–3.88 (1H, multiplet); 4.01–4.10 (2H, multiplet).

EXAMPLE 57

(1R,5S,6S)-2-{(2R,4S)-2-[4-(2-Hydroxyethyl)-1-piperazinylcarbonyl]pyrrolidin-4-ylthio)-5-[(1R)-1-hydroxyethyl]-1-methyl-1-carbapen-2-em-3-carboxylic Acid Hydrochloride

57(a) 4-Nitrobenzyl (1R,5S,6S)-2-?(2R,4S)-2-[4-(2-4'-nitrobenzyloxycarbonyloxyethyl)-1-piperazinylcarbonyl]-1-(4-nitrobenzyloxycarbonyl)pyrrolidin-4-ylthio/-6-[(1R)-1-hydroxyethyl]-1-methyl-1-carbapen-2-em-3-carboxylate 109 µl of diphenylphosphoryl chloride and 92 µl of diisopropylethylamine were added dropwise, whilst ice-cooling, to a solution of 181 mg of 4-nitrobenzyl (1R,5R,6S)-6-[(1R)-1-hydroxyethyl]-1-methyl-2-oxo-1-carbapenam-3-carboxylate in 2 ml of dry acetonitrile, and the resulting mixture was stirred at the same temperature for 50 minutes. 87.1 µl of diisopropylethylamine and a solution of 308 mg of (2R,4S)-4-mercapto- 2-{4-[2-(4-nitrobenzyloxycarbonyl)oxyethyl]-1-piperazinylcarbonyl}-1-(4-nitrobenzyloxycarbonyl)pyrrolidine (prepared as described in Preparation 57) in 1 ml of dry acetonitrile were added dropwise to the mixture, whilst ice-cooling, and the resulting mixture was stirred at the same temperature for 5 hours. At the end of this time, the solvent was removed by distillation under reduced pressure, and the resulting residue was purified by chromatography through silica gel, using a 5:1 by volume mixture of ethyl acetate and methanol as the eluent. Those fractions containing the title compound were combined and concentrated by evaporation under reduced pressure, to give 277 mg of the title compound, as a powder.

Infrared Absorption Spectrum (KBr), $v_{max}$ cm$^{-1}$: 1771, 1750, 1710, 1650, 1607, 1522, 1443, 1347.

Nuclear Magnetic Resonance Spectrum (CDCl$_3$, 270 MHz), δ ppm: 1.28 (3H, doublet, J=6.84 Hz); 1.36 (3H, doublet, J=6.34 Hz); 3.31–3.96 (8H, multiplet); 4.01–4.33 (5H, multiplet); 4.77–4.90 (1H, multiplet); 5.02–5.55 (6H, multiplet); 7.41–7.66 (4H, multiplet); 8.19–8.25 (4H, multiplet).

57(b) (1R,5S,6S)-2-{(2R,4S)-2-[4-(2-Hydroxyethyl)-1-piperazinylcarbonyl]pyrrolidin-4-ylthio{-5-[(1R)-1-hydroxyethyl]-1-methyl-1-carbapen-2-em-3-carboxylic Acid Hydrochloride 240 mg of 4-nitrobenzyl (1R,5S,6S)-2-{(2R,4S)-2-[4-(2-4'-nitrobenzyloxycarbonyloxyethyl)-1-piperazinylcarbonyl]-1-(4-nitrobenzyloxycarbonyl)pyrrolidin-4-ylthio}-6-[(1R)-1- hydroxyethyl]-1-methyl-1-carbapen-2-em-3-carboxylate [prepared as described in step (a) above] were dissolved in 8 ml of a 1:1 by volume mixture of tetrahydrofuran and water and mixed with 0.3 ml of 1N aqueous hydrochloric acid. The mixture was then hydrogenated by bubbling hydrogen through it at room temperature for 2 hours in the presence of 0.3 g of 10% w/w palladium-on-charcoal. At the end of this time, the catalyst was removed by filtration, and the filtrate was extracted with diethyl ether. The remaining aqueous layer was concentrated by evaporation under reduced pressure. The resulting residue was subjected to column chromatography through a Lobar column (Merck, LiChroprep RP-8, size A), using 3% v/v aqueous methanol as the eluent. Those fractions containing the title compound were combined, concentrated by evaporation under reduced pressure and lyophilized, to give 35 mg of the title compound as a colorless powder.

Ultraviolet Absorption Spectrum (H$_2$O) $\lambda_{max}$ nm: 297.

EXAMPLE 58

(1R,5S,6S)-2-{(2R,4R)-2-[4-(2-Hydroxyethyl)-1-piperazinylcarbonyl]pyrrolidin-4-ylthio}-6-[(1R)-1-hydroxyethyl]-1-methyl-1-carbapen-2-em-3-carboxylic Acid Hydrochloride

58(a) 4-Nitrobenzyl (1R,5S,6S)-2-{(2R,4R)-2-[4-(2-4'-nitrobenzyloxycarbonyloxyethyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 164 µl of diphenylphosphoryl chloride and 138 µl of diisopropylethylamine were added dropwise, whilst ice-cooling, to a solution of 272 mg of 4-nitrobenzyl (1 R,5R,6S)-6-[(1R)-1-hydroxyethyl]-1-methyl-2-oxo-1-carbapenam-3-carboxylate in 3 ml of dry acetonitrile, and the resulting mixture was stirred at the same temperature for 1 hour. 131 µl of diisopropylethylamine and a solution of 463 mg of (2R,4R)-4-mercapto-2-{4-[2-(4-nitrobenzyloxycarbonyl)oxyethyl]-1-piperazinylcarbonyl}-1-(4-nitrobenzyloxycarbonyl)pyrrolidine in 2 ml of dry acetonitrile were then simultaneously added dropwise to the mixture, whilst ice-cooling, and the resulting mixture was stirred at the same temperature for 1.5 hours. At the end of this time, the solvent was removed by distillation under reduced pressure, and the resulting residue was purified by chromatography through silica gel, using a 9:1 by volume mixture of ethyl acetate and methanol as the eluent. Those fractions containing the title compound were combined and concentrated by evaporation under reduced pressure, to give 490 mg of the title compound, as a powder.

Infrared Absorption Spectrum (KBr), $v_{max}$ cm$^{-1}$: 1770, 1751, 1711, 1654, 1606, 1522, 1496, 1444, 1404, 1347, 1263, 1208.

Nuclear Magnetic Resonance Spectrum (CDCl$_3$ , 270 MHz), δ ppm: 1.27 (3H, doublet, J=7.33 Hz); 1.36 (3H, doublet, J=5.86 Hz); 1.82–2.05 (1H, multiplet); 2.25–3.10 (7H, multiplet); 3.25–3.85 (9H, multiplet); 4.05–4.86 (6H, multiplet); 5.05–5.51 (6H, multiplet); 7.43–7.67 (6H, multiplet); 8.18–8.25 (6H, multiplet).

58(b) (1R,5S,6S)-2-{(2R,4S)-2-[4-(2-Hydroxyethyl)-1-piperazinylcarbonyl]pyrrolidin-4-ylthio}-6-[(1R)-1-hydroxyethyl]-1-methyl-1-carbapen-2-em-3-carboxylic Acid Hydrochloride 191 mg of 4-nitrobenzyl (1R,5S,6S)-2-{(2R,4R)-2- [4-(2-4'-nitrobenzyloxycarbonyl)oxyethyl]-1-piperazinylcarbonyl]-1-(4-nitrobenzyloxycarbonyl)pyrrolidin-4-ylthio}-6-[(1R)-1- hydroxyethyl]-1-methyl-1-carbapen-2-em-3-carboxylate [prepared as described in step (a) above] were dissolved in 8 ml of a 1:1 by volume mixture of tetrahydrofuran and water, and the mixture was hydrogenated by bubbling hydrogen through it at room temperature for 1 hour in the presence of 218 µl of 1N aqueous hydrochloric acid and 0.3 g of 10% w/w palladium-on-charcoal. At the end of this time, the catalyst was removed by filtration, and the filtrate was extracted with diethyl ether. The remaining aqueous layer was concentrated by evaporation under reduced pressure, and the resulting residue was subjected to column chromatography through a Lobar column (Merck, LiChroprep RP-8, size A), using 3% v/v aqueous methanol as the eluent. Those fractions containing the title compound were combined, concentrated by evaporation under reduced pressure and lyophilized, to give 26 mg of the title compound as a colorless powder.

Ultraviolet Absorption Spectrum (H$_2$O) $\lambda_{max}$ nm: 297.

Infrared Absorption Spectrum (KBr), $v_{max}$ cm$^{-1}$: 1758, 1659, 1595, 1451, 1385, 1261, 1181, 1145.

Nuclear Magnetic Resonance Spectrum (270 MHz, D$_2$O, using tetradeuterated sodium trimethylsilylpropionate as an internal standard), δ ppm: 1.20 (3H, doublet, J=7.33 Hz); 1.28 (3H, doublet, J=6.35 Hz); 2.13–2.22 (1H, multiplet); 2.91–3.03 (1H, multiplet); 3.26–3.63 (9H, multiplet); 3.75–4.11 (8H, multiplet); 4.21–4.30 (2H, multiplet); 4.83–4.93 (1H, multiplet).

EXAMPLES 59 TO 88

Following a procedure similar to that described in Example 1 or Example 49, the following compounds were obtained by using the mercaptan shown in the corresponding one of Preparations 59 to 88.

EXAMPLE 59

(1R,5S,6S)-2-{(2S,4S)-2-[(2S)-4-Acetimidoyl-2-methylpiperazin-1-ylcarbonyl]pyrrolidin-4-ylthio}-6-[(1R)-1-hydroxyethyl]-1-methyl-1-carbapen-2-em-3-carboxylic Acid Ultraviolet Absorption Spectrum (H$_2$O), $\lambda_{max}$ nm: 300.

Infrared Absorption Spectrum (KBr), $v_{max}$ cm$^{-1}$: 1755, 1629, 1591, 1448, 1384, 1281.

Nuclear Magnetic Resonance Spectrum (270 MHz, D$_2$O, using sodium tetradeuterated trimethylsilylpropionate as an internal standard), δ ppm: 1.21–1.36 (6H, multiplet); 1.30 (3H, doublet, J=6.35 Hz); 1.58–1.75 (1H, multiplet); 2.35 & 2.39 (together 3H, two singlets); 2.63–2.85 (1H, multiplet); 3.06 (1H, doublet of doublets, J=12.21 & 3.42 Hz); 3.18 (1H, doublet of doublets, J=12.21 & 5.86 Hz); 3.26–3.62 (4H, multiplet); 3.65–4.67 (9H, multiplet).

EXAMPLE 60

(1R,5S,6S)-2-{(2S,4S)-2-[(2S)-4-Formimidoyl-2-methylpiperazin-1-ylcarbonyl]pyrrolidin-4-ylthio}-6-[(1R)-1-hydroxyethyl]1-methyl-1-carbapen-2-em-3-carboxylic Acid Ultraviolet Absorption Spectrum (H$_2$O), $\lambda_{max}$ nm: 296.

Infrared Absorption Spectrum (KBr), $v_{max}$ cm$^{-1}$: 1755, 1711, 1641, 1592, 1452, 1384.

Nuclear Magnetic Resonance Spectrum (270 MHz, D$_2$O, using sodium tetradeuterated trimethylsilylpropionate as an internal standard), δ ppm: 1.22 (3H, doublet, J=7.3 Hz); 1.58 (3H, doublet, J=6.3 Hz); 1.24 & 1.35 (together 3H, two doublets, J=6.8 Hz); 1.62–1.77 (1H, multiplet); 2.68–2.89 (1H, multiplet); 3.06–4.50 (15H, multiplet); 7.93, 7.96, 8.03 & 8.19 (together 1H, four singlets).

EXAMPLE 61

(1R,5S,6S)-2-{2S,4S)-1-Methyl-2-[(3S)-3-acetimidoylaminopyrrolidin-1-ylcarbonyl]pyrrolidin-4-ylthio}-6-[(1R)-1-hydroxyethyl]-1-methylcarbapen-2-em-3-carboxylic Acid Ultraviolet Absorption Spectrum (H$_2$O), $v_{max}$ nm: 301.

Infrared Absorption Spectrum (KBr), $v_{max}$ cm$^{-1}$: 1756, 1682, 1632, 1593, 1453, 1385.

Nuclear Magnetic Resonance Spectrum (270 MHz, D$_2$O, using sodium tetradeuterated trimethylsilylpropionate as an internal standard), δ ppm: 1.21 (3H, doublet, J=7.32 Hz); 1.30 (3H, doublet, J=6.35 Hz); 1.60–1.75 (1H, multiplet); 2.24 (3H, doublet, J=2.93 Hz); 2.28 (3H, doublet, J=4.88 Hz); 2.70–2.90 (2H, multiplet); 3.05–3.15 (1H, multiplet); 3.25–3.50 (3H, multiplet); 3.50–4.05 (7H, multiplet); 4.15–4.40 (3H, multiplet).

EXAMPLE 62

(1R,5S,6S)-2-[(2S,4S)-2-(3-Acetimidoylaminopiperidin-1-ylcarbonyl)pyrrolidin-4-ylthio]-6-[(1R)-1-hydroxyethyl]-1-methyl-1-carbapen-2-em-3-carboxylic Acid Ultraviolet Absorption Spectrum (H$_2$O), $\lambda_{max}$ nm: 300.

EXAMPLE 63

(1R,5S,6S)-2-[(2S,4S)-1-Methyl-2-(4-acetimidoylaminopiperidin-1-ylcarbonyl)pyrrolidin-4-ylthio]-6-[(1R)-1-hydroxyethyl]-1-methyl-1-carbapen-2-em-3-carboxylic Acid Ultraviolet Absorption Spectrum (H$_2$O), $\lambda_{max}$ nm: 300.

EXAMPLE 64

(1R,5S,6S)-2-[(2S,4S)-1-Methyl-2-(4-formimidoylpiperazin-1-ylcarbonyl)pyrrolidin-4-ylthio]-6-[(1R)-1-hydroxyethyl]-1-methyl-1-carbapen-2-em-3-carboxylic Acid Ultraviolet Absorption Spectrum (H$_2$O), $\lambda_{max}$ nm: 300.

Infrared Absorption Spectrum (KBr), $v_{max}$ cm$^{-1}$: 1754, 1707, 1651, 1595, 1450, 1385, 1285.

Nuclear Magnetic Resonance Spectrum (270 MHz, D$_2$O, using sodium tetradeuterated trimethylsilylpropionate as an internal standard), δ ppm: 1.21 (3H, doublet, J=7.3 Hz); 1.30 (3H, doublet, J=6.4 Hz); 1.68 (1H, doubled doublet of doublets, J=13.7, 8.8 & 5.4 Hz); 2.34 (3H, singlet); 2.78–2.95 (2H, multiplet); 3.14 (1H, doublet of doublets, J=12.2 & 1.4 Hz); 3.30–3.45 (2H, multiplet); 3.53–3.95 (10H, multiplet); 4.18–4.30 (2H, multiplet); 7.92 (1H, singlet).

EXAMPLE 65

(1R,5S,6S)-2-{(2S,4S)-1-Methyl-2-[(2S)-4-acetimidoyl-2-methylpiperazin-1-ylcarbonyl]pyrrolidin-4-ylthio}-6-[(1R)-1-hydroxyethyl]-1-methyl-1-carbapen-2-em-3-carboxylic Acid Ultraviolet Absorption Spectrum (H$_2$O), $\lambda_{max}$ nm: 299.

EXAMPLE 66

(1R,5S,6S)-2-[(2S,4S)-1-Acetimidoyl-2-(1piperazinylcarbonyl)pyrrolidin-4-ylthio]-6-[(1R)-1-hydroxyethyl]-1-methyl-1-carbapen-2-em-3-carboxylic Acid Ultraviolet Absorption Spectrum (H$_2$O), $\lambda_{max}$ nm: 297.

Infrared Absorption Spectrum (KBr), $v_{max}$ cm$^{-1}$: 1754, 1663, 1594, 1489, 1455, 1384, 1252, 1209.

Nuclear Magnetic Resonance Spectrum (270 MHz, D$_2$O, using sodium tetradeuterated trimethylsilylpropionate as an internal standard), δ ppm: 1.21 (3H, doublet, J=7.32 Hz); 1.30 (3H, doublet, J=6.35 Hz); 2.09–2.24 (1H, multiplet); 2.16 & 2.38 (together 3H, two singlets); 2.80–3.95 (13H, multiplet); 3.96–4.33 (3H, multiplet); 5.04–5.11 & 5.24–5.32 (together 1H, two multiplets).

EXAMPLE 67

(1R,5S,6S)-2-[(2S,4S)-1-Formimidoyl-2-(1-piperazinylcarbonyl)pyrrolidin-4-ylthio]-6-[(1R)-1-hydroxyethyl]-1-methyl-1-carbapen-2-em-3-carboxylic Acid Ultraviolet Absorption Spectrum (H$_2$O), $\lambda_{max}$ nm: 297.

Infrared Absorption Spectrum (KBr), $\nu_{max}$ cm$^{-1}$: 1754, 1708, 1660, 1594, 1489, 1455, 1395, 1251, 1209.

Nuclear Magnetic Resonance Spectrum (400 MHz, D$_2$O, using sodium tetradeuterated trimethylsilylpropionate as an internal standard), δ ppm: 1.22 (3H, doublet, J=7.32 Hz); 1.29 (3H, doublet, J=6.40 Hz); 2.08–2.19 (1H, multiplet); 2.98–4.33 (16H, multiplet); 5.06–5.10 & 5.19–5.23 (together 1H, two multiplets); 7.86 & 8.11 (together 1H, two singlets).

EXAMPLE 68

(1R,5S,6S)-2-[(2S,4S)-1-Acetimidoyl-2-(4-acetimidoylpiperazin-1-ylcarbonyl)pyrrolidin-4-ylthio]-6-[(1R)-1-hydroxyethyl]-1-methyl-1carbapen-2-em-3-carboxylic Acid Ultraviolet Absorption Spectrum (H$_2$O), $\lambda_{max}$ nm: 300.

EXAMPLE 69

(1R,5S,6S)-2-[(2S,4S)-1-Acetimidoyl-2-(4-formimidoylpiperazin-1-ylcarbonyl)pyrrolidin-4-ylthio]-6-[(1R)-1-hydroxyethyl]-1-methyl-1-carbapen-2-em-3-carboxylic Acid Ultraviolet Absorption Spectrum (H$_2$O), $\lambda_{max}$ nm: 300.

EXAMPLE 70

(1R,5S,6S)-2-[(2S,4S)-1-Formimidoyl-2-(4-formimidoylpiperazin-1-ylcarbonyl)pyrrolidin-4-ylthio]-6-[(1R)-1-hydroxyethyl]-1-methyl-1-carbapen-2-em-3-carboxylic Acid Ultraviolet Absorption Spectrum (H$_2$O), $\lambda_{max}$ nm: 300.

EXAMPLE 71

(1R,5S,6S)-2-[(2S,4S)-1-Formimidoyl-2-(4-acetimidoylpiperazin-1-ylcarbonyl)pyrrolidin-4-ylthio]-6-[(1R)-1-hydroxyethyl]-1-methyl-1-carbapen-2-em-3-carboxylic Acid Ultraviolet Absorption Spectrum (H$_2$O), $\lambda_{max}$ nm: 300.

EXAMPLE 72

(1R,5S,6S)-2-[(2S,4S)-1-Acetimidoyl-2-[(3S)-3-acetimidoylaminopyrrolidin-1-ylcarbonyl]pyrrolidin-4-ylthio]-6-[(1R)-1-hydroxyethyl]-1-methylcarbapen-2-em-3-carboxylic Acid Ultraviolet Absorption Spectrum (H$_2$O), $\lambda_{max}$ nm: 301.

Infrared Absorption Spectrum (KBr), $\nu_{max}$ cm$^{-1}$: 1756, 1633, 1594, 1452, 1385.

EXAMPLE 73

(1R,5S,6S)-2-{(2S,4S)-1-Acetimidoyl-2-[(3S)-3-formimidoylaminopyrrolidin-1-ylcarbonyl]pyrrolidin-4-ylthio}-6-[(1R)-1-hydroxyethyl]-1-methylcarbapen-2-em-3-carboxylic Acid Ultraviolet Absorption Spectrum (H$_2$O), $\lambda_{max}$ nm: 301.

EXAMPLE 74

(1R,5S,6S)-2-{(2S,4S)-1-Acetimidoyl-2-[(3S)-3-aminopyrrolidin-1-ylcarbonyl]pyrrolidin-4-ylthio}-6-[(1R)-1-hydroxyethyl]-1-methylcarbapen-2-em-3-carboxylic Acid Ultraviolet Absorption Spectrum (H$_2$O), $\lambda_{max}$ nm: 297.

EXAMPLE 75

(1R,5S,6S)-2-{(2S,4S)-1-Formimidoyl-2-[(3S)-3-acetimidoylaminopyrrolidin-1-ylcarbonyl]pyrrolidin-4-ylthio}-6-[(1R)-1-hydroxyethyl]-1-methylcarbapen-2-em-3-carboxylic Acid Ultraviolet Absorption Spectrum (H$_2$O), $\lambda_{max}$ nm: 301.

EXAMPLE 76

(1R,5S,6S)-2-{(2S,4S)-1-Formimidoyl-2-[(3S)-3-formimidoylaminopyrrolidin-1-ylcarbonyl]pyrrolidin-4-ylthio}-6-[(1R)-1-hydroxyethyl]-1-methylcarbapen-2-em-3-carboxylic Acid Ultraviolet Absorption Spectrum (H$_2$O), $\lambda_{max}$ nm: 301.

EXAMPLE 77

(1R,5S,6S)-2-{(2S,4S)-1-formimidoyl-2-[(3S)-3-aminopyrrolidin-1-ylcarbonyl]pyrrolidin-4-ylthio}-6-[(1R)-1-hydroxyethyl]-1-methylcarbapen-2em-3-carboxylic Acid Ultraviolet Absorption Spectrum (H$_2$O), $\lambda_{max}$ nm: 297.

EXAMPLE 78

(1R,5S,6S)-2-[(2S,4S)-1-Acetimidoyl-2-(homopiperazin-1-ylcarbonyl)pyrrolidin-4-ylthio]-6-[(1R)-1-hydroxyethyl]-1-methyl-1-carbapen-2-em-3-carboxylic Acid Ultraviolet Absorption Spectrum (H$_2$O), $\lambda_{max}$ nm: 297.

EXAMPLE 79

(1R,5S,6S)-2-[(2S,4S)-1-Acetimidoyl-2-(4-formimidoylhomopiperazin-1-ylcarbonyl}pyrrolidin-4-ylthio]-6-[(1R)-1-hydroxyethyl]-1-methyl-1carbapen-2-em-3-carboxylic Acid Ultraviolet Absorption Spectrum (H$_2$O), $\lambda_{max}$ nm: 300.

EXAMPLE 80

(1R,5S,6S)-2-[(2S,4S)-1-Formimidoyl-1-(homopiperazin-1-ylcarbonyl)pyrrolidin-4-ylthio]-6-[(1R)-1-hydroxyethyl]-1-methyl-1-carbapen-2-em-3-carboxylic Acid Ultraviolet Absorption Spectrum (H$_2$O), $\lambda_{max}$ nm: 297.

EXAMPLE 81

(1R,5S,6S)-2-[(2S,4S)-1-Formimidoyl-2-(4-formimidoylhomopiperazin-1-ylcarbonyl)pyrrolidin-4ylthio]-6-[(1R)-1-hydroxyethyl]-1-methyl-1-carbapen-2-em-3-carboxylic Acid Ultraviolet Absorption Spectrum (H$_2$O), $\lambda_{max}$ nm: 300.

EXAMPLE 82

(1R,5S,6S)-2-}(2S,4S)-2-[(3S)-3-(N-Methyl-N-acetimidoylaminopyrrolidin-1-ylcarbonyl]pyrrolidin-4-ylthio}-6-[(1R)-1-hydroxyethyl]-1-methylcarbapen-2-em-3-carboxylic Acid Ultraviolet Absorption Spectrum (H$_2$O), $\lambda_{max}$ nm: 300.

EXAMPLE 83

(1R,5S,6S)-2-[(2S,4S)-2-(2-Hydroxymethylpiperazin-1-ylcarbonyl)pyrrolidin-4-ylthio]-6-[(1R)-1-hydroxyethyl]-1-methyl-1-carbapen-2-em-3-carboxylic Acid Hydrochloride Ultraviolet Absorption Spectrum (H$_2$O), $\lambda_{max}$ nm: 297.

EXAMPLE 84

(1R,5S,6S)-2-[(2S,4S)-2-(4-Acetimidoyl-2-hydroxymethylpiperazin-1-ylcarbonyl)pyrrolidin-4-ylthio]-6-[(1R)-1-hydroxyethyl]-1-methyl-1-carbapen-2-em-3-carboxylic Acid Ultraviolet Absorption Spectrum (H$_2$O), $\lambda_{max}$ nm: 301.

EXAMPLE 85

(1R,5S,6S)-2-[(2S,4S)-2-(6-Hydroxyhomopiperazin-1-ylcarbonyl)pyrrolidin-4-ylthio]-6-[(1R)-1-hydroxyethyl]-1-methyl-1-carbapen-2-em-3-carboxylic Acid Hydrochloride Ultraviolet Absorption Spectrum (H$_2$O), $\lambda_{max}$ nm: 296.

EXAMPLE 86

(1R,5S,6S)-2-[(2S,4S)-2-(4-Formimidoyl-6-hydroxyhomopiperazin-1-ylcarbonyl)pyrrolidin-4-ylthio]-6-[(1R)-1-hydroxyethyl]-1-methyl-1-carbapen-2-em-3-carboxylic Acid Ultraviolet Absorption Spectrum (H$_2$O), $\lambda_{max}$ nm: 300.

EXAMPLE 87

(1R,5S,6S)-2-[(2S,4S)-1-Acetimidoyl-2-(4-acetimidoylaminopiperidin-1-ylcarbonyl)pyrrolidin-4-ylthio]-6-[(1R)-1-hydroxyethyl]-1-methyl-1-carbapen-2-em-3-carboxylic Acid Ultraviolet Absorption Spectrum (H$_2$O), $\lambda_{max}$ nm: 300.

EXAMPLE 88

(1R,5S,6S)-2-[(2S,4S)-1-methyl-2-(4-formimidoylhomopiperazin-1-ylcarbonyl)pyrrolidin-4-ylthio]-6-[(1R)-1-hydroxyethyl]-1-methyl-1-carbapen-2-em-3-carboxylic Acid Ultraviolet Absorption Spectrum (H$_2$O), $\lambda_{max}$ nm: 300.

PREPARATION 1

(2S,4S)-4-Mercapto-2-[4-(N-4-nitrobenzyloxycarbonylacetimidoyl)piperazin-1-ylcarbonyl]-1-(4-nitrobenzyloxycarbonyl)pyrrolidine Trifluoromethanesulfonate

1(i) (2S,4S)-4-(4-Methoxybenzylthio)-2-(4-t-butoxycarbonylpiperazin-1-ylcarbonyl)-1-(4-nitrobenzyloxycarbonyl)pyrrolidine 1.78 g of N,N'-carbonyldiimidazole was added to a solution of 4.46 g of (2S,4S)-4-(4- methoxybenzylthio)-1-(4-nitrobenzyloxycarbonyl)-2-pyrrolidinecarboxylic acid in 45 ml of dry acetonitrile, and the resulting mixture was stirred at room temperature for 1 hour. The reaction mixture was then cooled with ice, and a solution of 2.05 g of 1-t-butoxycarbonylpiperazine in 45 ml of dry acetonitrile was added to the mixture, which was then allowed to stand overnight at room temperature. At the end of this time, the reaction mixture was concentrated by evaporation under reduced pressure, and the concentrate was diluted with ethyl acetate. The ethyl acetate solution was washed with water and with an aqueous solution of sodium chloride and was then dried over anhydrous magnesium sulfate. The solvent was removed by distillation under reduced pressure, and the resulting residue was purified by column chromatography through silica gel, using a 3:2 by volume mixture of ethyl acetate and cyclohexane as the eluent, to give 5.4 g of the title compound, as a powder.

Infrared Absorption Spectrum (KBr), $v_{max}$ cm$^{-1}$: 1699, 1658, 1609, 1585, 1512, 1456, 1377, 1366, 1344, 1286, 1237, 1205.

Nuclear Magnetic Resonance Spectrum (CDCl$_3$, 270 MHz), δ ppm: 1.47 (9H, singlet); 1.73–1.87 (1H, multiplet); 2.40–2.52 (1H, multiplet); 3.03–3.17 (1H, multiplet); 3.25–4.09 (10H, multiplet); 3.73 (2H, singlet); 3.79 & 3.80 (together 3H, two singlets); 4.57 & 4.61 (together 1H, two triplets, J=8.30 Hz); 5.01–5.32 (2H, multiplet); 6.85 (2H, doublet, J=8.79 Hz); 7.23 (2H, doublet, J=8.79 Hz); 7.41 & 7.47 (together 2H, two doublets, J=8.79 Hz); 8.18 & 8.22 (together 2H, two doublets, J=8.79 Hz).

1(ii) (2S,4S)-4-(4-Methoxybenzylthio)-2-(1-piperazinylcarbonyl)-1-(4-nitrobenzyloxycarbonyl)pyrrolidine Hydrochloride 27 ml of a 4N ethyl acetate solution of hydrogen chloride were added to a solution of 5.2 g of (2S,4S)-4-(4-methoxybenzylthio)-2-(4-t-butoxycarbonylpiperazin-1-ylcarbonyl)-1-(4-nitrobenzyloxycarbonyl)pyrrolidine [prepared as described in step (i) above] in 27 ml of ethyl acetate, and the resulting mixture was heated under reflux for 2 hours. At the end of this time, the reaction mixture was concentrated to dryness by evaporation under reduced pressure, and the resulting concentrate was triturated with diethyl ether. The powder thus obtained was collected by filtration and dried to give 4.2 g of the title compound.

Infrared Absorption Spectrum (KBr), $v_{max}$ cm$^{-1}$: 1708, 1662, 1609, 1585, 1512, 1434, 1404, 1346, 1319, 1301, 1246, 1209.

Nuclear Magnetic Resonance Spectrum (hexadeuterated dimethyl sulfoxide+D$_2$O, 270 MHz), δ ppm: 1.53–1.68 (1H, multiplet); 2.58–2.75 (1H, multiplet); 2.90–3.94 (11H, multiplet); 3.71 & 3.74 (together 3H, two singlets); 3.78 (2H, singlet); 4.70 & 4.80 (together 1H, two triplets, J=8.06 Hz); 5.03–5.23 (2H, multiplet); 6.89 (2H, doublet, J=8.30 Hz); 7.27 (2H, doublet, J=8.30 Hz); 7.51 & 7.60 (together 2H, two doublets, J=8.79 Hz); 8.23 & 8.25 (together 2H, two doublets, J=8.79 Hz).

1(iii) (2S,4S)-4-(4-Methoxybenzylthio)-2-[4-(N-4-nitrobenzyloxycarbonylacetimidoyl)piperazin-1-ylcarbonyl]-1-(4-nitrobenzyloxycarbonyl)pyrrolidine 11 ml of methylene chloride, followed by 452 mg of N-(4-nitrobenzyloxycarbonyl)acetamidine, were added to a solution of 1.1 g of (2S,4S)-4- (4-methoxybenzylthio)-2-(1-piperazinylcarbonyl)-1-(4-nitrobenzyloxycarbonyl) pyrrolidine hydrochloride [prepared as described in step (ii) above] in 22 ml of methanol, whilst heating the solution under reflux. The resulting mixture was then heated under reflux for a further 4 hours. At the end of this time, the reaction mixture was freed from the solvent by distillation under reduced pressure, and the resulting residue was purified by column chromatography through silica gel, using a 20:1 by volume mixture of ethyl acetate and methanol as the eluent to give 466 mg of the title compound, as a powder.

Infrared Absorption Spectrum (KBr), $v_{max}$ cm$^{-1}$: 1709, 1662, 1608, 1570, 1520, 1430, 1405, 1346, 1291, 1254.

Nuclear Magnetic Resonance Spectrum (CDCl$_3$, 270 MHz), δ ppm: 1.73–1.94 (1H, multiplet); 2.30 & 2.40 (together 3H, two singlets); 2.38–2.52 (1H, multiplet); 3.03–3.18 (1H, multiplet); 3.11–4.05 (10H, multiplet); 3.73 (2H, singlet); 3.79 & 3.80 (together 3H, two singlets); 4.52–4.63 (1H, multiplet); 4.98–5.35 (4H, multiplet); 6.85 (2H, doublet, J=8.30 Hz); 7.23 (2H, doublet, J=8.30 Hz); 7.40–7.63 (4H, multiplet); 8.16–8.25 (4H, multiplet).

1(iv) (2S,4S)-4-Mercapto-2-[4-(N-4-nitrobenzyloxycarbonylacetimidoyl)piperazin-1-ylcarbonyl]-1-(4-nitrobenzyloxycarbonyl)pyrrolidine Trifluoromethanesulfonate 3.2 ml of trifluoroacetic acid and 103 μl of trifluoromethanesulfonic acid were added to a solution of 430 mg of (2S,4S)-4-(4-methoxybenzylthio)-2-[4-(N-4-nitrobenzyloxycarbonylacetimidoyl)piperazin-1-ylcarbonyl]-1-(4-nitrobenzyloxycarbonyl)pyrrolidine [prepared as described in step (iii) above] in 636 μl of anisole, and the resulting mixture was stirred for 1 hour, whilst ice-cooling. An the end of this time, the reaction mixture was freed from the solvent by distillation under reduced pressure, and the residue was repeatedly washed with diethyl ether by decantation, to give 450 mg of the title compound, as a powder.

Infrared Absorption Spectrum (KBr), $v_{max}$ cm$^{-1}$: 1782, 1705, 1634, 1610, 1522, 1441, 1406, 1348, 1277, 1249, 1224.

Nuclear Magnetic Resonance Spectrum (hexadeuterated dimethyl sulfoxide+D$_2$O, 270 MHz), δ ppm: 1.52–1.78 (1H, multiplet); 2.57–4.08 (15H, multiplet); 4.65–4.84 (1H, multiplet); 5.04–5.28 (4H, multiplet); 7.49–7.69 (4H, multiplet); 8.20–8.28 (4H, multiplet).

PREPARATION 2

(2S,4S)-4-Mercapto-2-[4-(N-4-nitrobenzyloxycarbonylacetimidoyl)homopiperazin-1-ylcarbonyl]-1-(4-nitrobenzyloxycarbonyl]pyrrolidine trifluoromethanesulfonate 2(i) (2S,4S)-4-(4-Methoxybenzylthio)-2-1-homopiperazinylcarbonyl)-1-(4-nitrobenzyloxycarbonyl)pyrrolidine Hydrochloride 1.95 g of N,N'-carbonyldiimidazole were added to a solution of 4.5 g of (2S,4S)-4-(4- methoxybenzylthio)-1-(4-nitrobenzyloxycarbonyl)-2-pyrrolidinecarboxylic acid in 45 ml of dry acetonitrile, and the resulting mixture was stirred at room temperature for 1 hour. A solution of 2.0 g of homopiperazine in 10 ml of dry acetonitrile was then added to the reaction mixture, and the mixture thus obtained was stirred at room temperature for 2 hours and at 35° C. for 30 minutes. At the end of this time, the reaction mixture was concentrated by evaporation under reduced pressure, and the resulting concentrate was diluted with ethyl acetate. The diluted solution was washed with water and with an aqueous solution of sodium chloride. The ethyl acetate solution was then dried over anhydrous magnesium sulfate and concentrated by evaporation under reduced pressure. The concentrate was dissolved in 44 ml of ethyl acetate, and the solution thus obtained was mixed with 2.5 ml of a 4N solution of hydrogen chloride in ethyl acetate; the mixture was then concentrated by evaporation under reduced pressure. The residue was triturated with diethyl ether, and the resulting powder was collected by filtration and then dried, to give 4.6 g of the title compound.

Infrared Absorption Spectrum (KBr), $v_{max}$ cm$^{-1}$: 1706, 1656, 1609, 1585, 1512, 1431, 1405, 1346, 1320, 1301, 1246, 1210.

Nuclear Magnetic Resonance Spectrum (hexadeuterated dimethyl sulfoxide+D$_2$O, 270 MHz), δ ppm: 1.54–1.72 (1H, multiplet); 1.86–2.14 (2H, multiplet); 2.60–2.72 (1H, multiplet); 2.94–3.96 (11H, multiplet); 3.72 & 3.74 (together 3H, two singlets); 3.79 (2H, singlet); 4.62–4.82 (1H, multiplet); 5.05–5.26 (2H, multiplet); 6.87 (2H, doublet, J=8.30 Hz); 7.27 (2H, doublet, J=8.30 Hz); 7.52 & 7.60 (together 2H, two doublets, J=8.79 Hz); 8.22 & 8.25 (together 2H, two doublets, J=8.79 Hz).

2(ii) (2S,4S)-4-(4-Methoxybenzylthio)-2-[4-(N-4-nitrobenzyloxycarbonylacetimidoyl)homopiperazin-1-ylcarbonyl]-1-(4-nitrobenzyloxycarbonyl)pyrrolidine 25 ml of methylene chloride were added to a solution of 2.5 g of (2S,4S)-4-(4-methoxybenzylthio)-2-(1-homopiperazinylcarbonyl)-1-(4-nitrobenzyloxycarbonyl)pyrrolidine hydrochloride [prepared as described in step (i) above] in 25 ml of methanol, which was being heated under reflux, and then 904 mg of N-(4-nitrobenzyloxycarbonyl)acetamidine were added to the resulting mixture. The reaction mixture was heated under reflux for a further 5 hours, after which it was worked up and purified by the same procedure as described in Preparation 1(iii), to give 415 mg of the title compound, as a powder.

Infrared Absorption Spectrum (KBr), $v_{max}$ cm$^{-1}$: 1753, 1708, 1657, 1608, 1564, 1520, 1429, 1404, 1346, 1319, 1301, 1274, 1250, 1229.

Nuclear Magnetic Resonance Spectrum (CDCl$_3$, 270 MHz), δ ppm: 1.70–2.60 (7H, multiplet); 3.02–3.17 (1H, multiplet); 3.22–4.60 (11H, multiplet); 3.716 & 3.723 (together 2H, two singlets); 3.781 & 3.786 (together 3H, two singlets); 4.93–5.44 (4H, multiplet); 6.83 & 6.85 (together 2H, two doublets, J=8.79 Hz); 7.22 (2H, doublet, J=8.79 Hz); 7.41–7.58 (4H, multiplet); 8.16–8.26 (4H, multiplet).

2(iii) (2S,4S)-4-Mercapto-2-[4-(N-4-nitrobenzyloxycarbonylacetimidoyl)homopiperazin-1-ylcarbonyl]-1-(4-nitrobenzyloxycarbonyl)pyrrolidine Trifluoromethanesulfonate 2.1 ml of trifluoroacetic acid and 67 μl of trifluoromethanesulfonic acid were added to a solution of 285 mg of (2S,4S)-4-(4-methoxybenzylthio)-2-[4-(N-4-nitrobenzyloxycarbonylacetimidoyl)homopiperazin-1-ylcarbonyl]-1-(4-nitrobenzyloxycarbonyl)pyrrolidine [prepared as described in step (ii) above] in 414 μl of anisole, and the resulting mixture was stirred for 1 hour, whilst ice-cooling. At the end of this time, the reaction mixture was worked up by the same procedure as described in Preparation 1(iv), to give 296 mg of the title compound, as a powder.

Infrared Absorption Spectrum (KBr), $v_{max}$ cm$^{-1}$: 1781, 1701, 1632, 1609, 1523, 1495, 1437, 1406, 1348, 1279, 1258, 1225, 1213.

Nuclear Magnetic Resonance Spectrum (hexadeuterated dimethyl sulfoxide+D$_2$O, 270 MHz), δ ppm: 1.55–4.12 (18H, multiplet); 4.56–4.83 (1H, multiplet); 5.03–5.31 (4H, multiplet); 7.48–7.68 (4H, multiplet); 8.17–8.27 (4H, multiplet).

PREPARATION 3

(2S,4S)-4-Mercapto-2-[(3S)-4-(N-4-
nitrobenzyloxycarbonylacetimidoyl)-3-
methylpiperazin-1-ylcarbonyl]-1-(4-
nitrobenzyloxycarbonyl)pyrrolidine
Trifluoromethanesulfonate

3(i) (2S,4S)-4-(4-Methoxybenzylthio)-2-[(3S)-3-methylpiperazin-1-ylcarbonyl]-1-(4-nitrobenzyloxycarbonyl)pyrrolidine Hydrochloride Following a procedure similar to that described in. Preparation 2(i), but using 4.5 g of (2S,4S)-4-(4-methoxybenzylthio)-1-(4-nitrobenzyloxycarbonyl)-2-pyrrolidinecarboxylic acid, 1.78 g of N,N'-carbonyldiimidazole and 1.4 g of (2S)-2-methylpiperazine, 5.3 g of the title compound were obtained, as a powder.

3(ii) (2S,4S)-4-(4-Methoxybenzylthio)-2-[(3S)-4-(N-4-nitrobenzyloxycarbonylacetimidoyl)-3-methylpiperazin-1-ylcarbonyl]-1-(4-nitrobenzyloxycarbonyl)pyrrolidine 2.26 g of (2S,4S)-4-(4-methoxybenzylthio)-2-[(3S)-3-methylpiperazin-1-ylcarbonyl]-1-(4-nitrobenzyloxycarbonyl)pyrrolidine hydrochloride [prepared as described in step (i) above] were mixed with 1.14 g of N-(4-nitrobenzyloxycarbonyl)acetamidine and 45 ml of acetonitrile, and the mixture was heated under reflux for 16 hours. At the end of this time, the reaction mixture was worked up and purified by the same procedure as described in Preparation 1(ii), to give 922 mg of the title compound, as a powder.

3(iii) (2S,4S)-4-Mercapto-2-[(3S)-4-(N-4-nitrobenzyloxycarbonylacetimidoyl)-3-methylpiperazin-1-ylcarbonyl]-1-(4-nitrobenzyloxycarbonyl)pyrrolidine Trifluoromethanesulfonate Following a procedure similar to that described in Preparation 2(iii), but using 458 mg of (2S,4S)-4-(4-methoxybenzylthio)-2-[(3S)-4-(N-4-nitrobenzyloxycarbonylacetimidoyl)-3-methylpiperazin-1-ylcarbonyl]-1-(4-nitrobenzyloxycarbonyl)pyrrolidine [prepared as described in step (ii) above], 475 mg of the title compound were obtained as a powder.

Infrared Absorption Spectrum (KBr), $v_{max}$ cm$^{-1}$: 1782, 1704, 1623, 1523, 1441, 1407, 1348, 1280, 1252, 1225.

Nuclear Magnetic Resonance Spectrum (hexadeuterated dimethyl sulfoxide+D$_2$O, 270 MHz), δ ppm: 1.09–1.28 (3H, multiplet); 1.53–1.78 (1H, multiplet); 2.22–2.42 (1H, multiplet); 2.67–3.46 (10H, multiplet); 3.90–4.31 (3H, multiplet); 4.63–4.90 (1H, multiplet); 5.02–5.28 (4H, multiplet); 7.46–7.70 (4H, multiplet); 8.19–8.28 (4H, multiplet).

PREPARATION 4

(2S,4S)-4-Mercapto-2-[4-(N-4-
nitrobenzyloxycarbonylformimidoyl)piperazin-1-
ylcarbonyl)-1-(4-nitrobenzyloxycarbonyl)pyrrolidine

4(i) (2S,4S)-4-(4-Methoxybenzylthio)-2-[4-(N-4-nitrobenzyloxycarbonylformimidoyl)piperazin-1-ylcarbonyl]-1-(4-nitrobenzyloxycarbonyl)pyrrolidine A suspension of 5.51 g of (2S,4S)-4-(4-methoxybenzylthio)-2-(1-piperazinylcarbonyl)-1-(4-nitrobenzyloxycarbonyl)pyrrolidine hydrochloride [prepared as described in Preparation 1(ii)] and 2.45 g of N-(4-nitrobenzyloxycarbonyl)formamidine in 10 ml of dry acetonitrile was stirred for 2 hours on a water-bath kept at 50° C. At the end of this time, the reaction mixture was freed from impurities by filtration, and the filtrate was concentrated by evaporation under reduced pressure. The resulting residue was purified by column chromatography through silica gel, using a 6:4 by volume mixture of ethyl acetate and acetonitrile as the eluent, to give 5.48 g of the title compound, as a powder.

Infrared Absorption Spectrum (KBr), $v_{max}$ cm$^{-1}$: 1716, 1652, 1598, 1516, 1346, 1162, 1007.

Nuclear Magnetic Resonance Spectrum (CDCl$_3$: 270 MHz), δ ppm: 1.75–1.95 (1H, multiplet); 2.35–2.53 (1H, multiplet); 3.05–3.19 (1H, multiplet); 3.73 (2H, singlet); 3.79 (3H, singlet); 3.30–4.13 (9H, multiplet); 4.53–4.66 (1H, multiplet); 5.15 & 5.18 (2H, AB-quartet, J=13.7 Hz); 5.29 (2H, singlet); 6.85 (2H, doublet, J=8.3 Hz); 7.23 (2H, doublet, J=8.3 Hz); 7.46 (2H, doublet, J=8.3 Hz); 7.58 (2H, doublet, J=8.3 Hz); 8.21 (2H, doublet, J=8.3 Hz); 8.23 (2H, doublet, J=8.3 Hz); 8.52 (1H, singlet).

4(ii) (2S,4S)-4-Mercapto-2-[4-(N-4-nitrobenzyloxycarbonylformimidoyl)piperazin-1-ylcarbonyl)-1-(4-nitrobenzyloxycarbonyl)pyrrolidine 15 ml of trifluoroacetic acid and 460 μl of trifluoromethanesulfonic acid were added to a solution of 2.50 g of (2S,4S)-4-(4-methoxybenzylthio)-2-[4-(N-4-nitrobenzyloxycarbonylformimidoyl)piperazin-1-ylcarbonyl]-1-(4-nitrobenzyloxycarbonyl)pyrrolidine [prepared as described in step (i) above] in 3 ml of anisole, and the resulting mixture was stirred for 1 hour, whilst ice-cooling. The solvent was removed by distillation under reduced pressure, and the resulting residue was washed with diethyl ether, to give 2.55 g of (2S,4S)-4- mercapto-2-[4-(N-4-nitrobenzyloxycarbonylformimidoyl)piperazin-1-ylcarbonyl]-1-(4-nitrobenzyloxycarbonyl)pyrrolidine trifluoromethanesulfonate as a powder. The whole of this product was dissolved in a mixture of ethyl acetate and water, and the solution was made alkaline by adding an aqueous solution of sodium hydrogencarbonate. The ethyl acetate layer was separated and washed with water and with an aqueous solution of sodium chloride, in that order. The solution was dried over anhydrous sodium sulfate, and then the solvent was removed by distillation under reduced pressure, to give 2.0 g of the title compound, as a powder.

Infrared Absorption Spectrum (KBr), $v_{max}$ cm$^{-1}$: 1709, 1660, 1603, 1521, 1440, 1346.

Nuclear Magnetic Resonance Spectrum (CDCl$_3$: 270 MHz), δ ppm: 1.89 (1H, doublet, J=8.8 Hz); 1.85–2.02 (1H, multiplet); 2.63–2.83 (1H, multiplet); 3.22–4.17 (11H, multiplet); 4.71 (1H, triplet, J=8.3 Hz); 5.19 & 5.22 (together 2H, AB-quartet, J=13.7 Hz); 5.27 (2H, singlet); 7.50 (2H, doublet, J=8.8 Hz); 7.57 (2H, doublet, J=8.8 Hz); 8.20 (2H, doublet, J=8.8 Hz); 8.22 (2H, doublet, J=8.8 Hz); 8.54 (1H, singlet).

PREPARATION 5

(2S,4S)-4-Mercapto-2-[4-(N-4-
nitrobenzyloxycarbonylformimidoyl)homopiperazin-
1-ylcarbonyl]-1-(4-nitrobenzyloxycarbonyl)
pyrrolidine Following a procedure similar to that described in Preparation 4, but using 2.10 g of (2S,4S)-4-(4- methoxybenzylthio)-2-(1-homopiperazinylcarbonyl)-1-(4-nitrobenzyloxycarbonyl)pyrrolidine hydrochloride [prepared as described in Preparation 2(i)] and 0.93 g of the N-(4-nitrobenzyloxycarbonyl)formamidine, 2.38 g of the trifluoromethanesulfonate of the title compound were obtained. The salt was treated by the same procedure as described in Preparation 4(ii), to give 1.90 g of the title compound.

Infrared Absorption Spectrum (KBr), $v_{max}$ cm$^{-1}$: 1709, 1679, 1653, 1600, 1519, 1345, 1159.

Nuclear Magnetic Resonance Spectrum (CDCl$_3$, 270 MHz), δ ppm: 1.80–1.92 (2H, multiplet); 2.00–2.15 (1H, multiplet); 2.63–2.80 (1H, multiplet); 3.18–4.35 (11H, multiplet); 4.55–4.67 (1H, multiplet); 5.10–5.30 (4H, multiplet); 7.40–7.60 (4H, multiplet); 8.15–8.26 (4H, multiplet); 8.42–8.56 (1H, multiplet).

PREPARATION 6

(2S,4S)-4-Mercapto-2-[(3S)-4-(N-4-nitrobenzyloxycarbonylformimidoyl)-3-methylpiperazin-1-ylcarbonyl]-1-(4-nitrobenzyloxycarbonyl)pyrrolidine Trifluoromethanesulfonate Following a procedure similar to that described in Preparation 4, but using 1.13 g of (2S,4S)-4-(4-methoxybenzylthio)-2-[(3S)-3-methylpiperazin-1-ylcarbonyl]-1-(4-nitrobenzyloxycarbonyl)pyrrolidine hydrochloride and 491 mg of N-(4-nitrobenzyloxycarbonyl)formamidine, 1.0 g of the title compound was obtained.

Infrared Absorption Spectrum (KBr), $v_{max}$ cm$^{-1}$: 1785, 1688, 1608, 1523, 1444, 1408, 1349, 1248, 1223.

Nuclear Magnetic Resonance Spectrum (hexadeuterated dimethyl sulfoxide+D$_2$O, 270 MHz), δ ppm: 1.10–1.28 (3H, multiplet); 1.60–1.78 (1H, multiplet); 2.65–3.45 (8H, multiplet); 3.88–4.30 (3H, multiplet); 3.65–3.89 (1H, multiplet); 5.02–5.27 (2H, multiplet); 5.36 (2H, singlet); 7.49–7.70 (4H, multiplet); 8.20–8.28 (4H, multiplet); 8.89 (1H, singlet).

PREPARATION 7

(2S,4S)-4-Mercapto-2-[2-methyl-4-(4-nitrobenzyloxycarbonyl)piperazin-1-ylcarbonyl]-1-(4-nitrobenzyloxycarbonyl)pyrrolidine 7(i) (2S,4S)-4-(4-Methyoxybenzylthio)-2-(4-t-butoxycarbonyl-2-methylpiperazin-1-ylcarbonyl)-1-(4-nitrobenzyloxycarbonyl)pyrrolidine 3.41 ml of triethylamine and 3.03 ml of pivaloyl chloride were added dropwise to a solution of 9.99 g of (2S,4S)-4-(4-methoxybenzylthio)-1-(4-nitrobenzyloxycarbonyl)-2-pyrrolidinecarboxylic acid in 100 ml of dry acetonitrile, whilst ice-cooling, and the resulting mixture was stirred at the same temperature for 20 minutes. A solution of 5.38 g of 1-t-butoxycarbonyl-3-methylpiperazine in 50 ml of dry tetrahydrofuran was then added dropwise to the mixture, and the mixture was stirred at the same temperature for 30 minutes and then at room temperature for 2 hours. At the end of this time, the reaction mixture was concentrated by evaporation under reduced pressure, and the residue was diluted with ethyl acetate. The diluted solution was washed, in turn, with a 1N aqueous solution of oxalic acid, with water and with an aqueous solution of sodium chloride. The ethyl acetate solution was dried over anhydrous magnesium sulfate, and the solvent was removed by distillation under reduced pressure. The residue was purified by column chromatography through silica gel, using a gradient elution method, with mixtures of ethyl acetate and cyclohexane ranging from 1:1 to 3:2 by volume as the eluent, to give 8.56 g of the title compound, as an amorphous solid.

Infrared Absorption Spectrum (KBr), $v_{max}$ cm$^{-1}$: 1701, 1655, 1609, 1523, 1513, 1426, 1405, 1345, 1251, 1168.

Nuclear Magnetic Resonance Spectrum (CDCl$_3$, 270 MHz), δ ppm: 0.97–1.43 (3H, multiplet); 1.47 (9H, singlet); 1.46–1.89 (3H, multiplet); 2.47–2.50 (1H, multiplet); 2.71–3.67 (4H, multiplet); 3.73 (2H, singlet); 3.79 & 3.80 (together 3H, two singlets); 3.76–4.82 (5H, multiplet); 5.02–5.29 (2H, multiplet); 6.85 (2H, doublet, J=8.79 Hz); 7.23 (2H, doublet, J=8.79 Hz); 7.41 & 7.46 (together 2H, two doublets, J=8.79 Hz); 8.17 & 8.23 (together 2H, two doublets, J=8.79 Hz).

(7(ii) (2S,4S)-4-(4-Methoxybenzylthio)-2-(2-methylpiperazin-1-ylcarbonyl)-2-(4-nitrobenzyloxycarbonyl)pyrrolidine 31.6 ml of a 4N solution of hydrogen chloride in ethyl acetate were added dropwise to a solution of 9.55 g of (2S,4S)-4-(4-methoxybenzylthio)-2-(4-t-butoxycarbonyl-2-methylpiperazin-1-ylcarbonyl)-1-(4-nitrobenzyloxycarbonyl)pyrrolidine [prepared as described in step (i) above] in 31.6 ml of ethyl acetate, and the resulting mixture was stirred at the same temperature for 90 minutes. At the end of this time, the reaction mixture was diluted with ethyl acetate, after which it was neutralized by adding an aqueous solution of sodium hydrogencarbonate. The ethyl acetate layer was separated, washed with an aqueous solution of sodium chloride and dried over anhydrous magnesium sulfate. The solvent was then removed by distillation under reduced pressure, and the resulting residue was purified by column chromatography through silica gel using a gradient elution method, with mixtures of ethyl acetate and methanol ranging from a 4:1 to 7:3 by volume as the eluent, to give 7.0 g of the title compound, as an amorphous solid.

Infrared Absorption Spectrum (KBr), $v_{max}$ cm$^{-1}$: 1709, 1648, 1513, 1432, 1404, 1345, 1249.

Nuclear Magnetic Resonance Spectrum (CDCl$_3$, 270 MHz), δ ppm: 1.10–1.46 (3H, multiplet); 1.70–1.87 (1H, multiplet); 2.18–3.15 (8H, multiplet); 3.30–3.58 (2H, multiplet); 3.73 (2H, singlet); 3.79 & 3.80 (together 3H, two singlets); 3.67–4.64 (3H, multiplet); 4.97–5.34 (2H, multiplet); 6.85 (2H, doublet, J=8.30 Hz); 7.23 (2H, doublet, J=8.30 Hz); 7.42 & 7.47 (together 2H, two doublets, J=8.30 Hz); 8.18 & 8.23 (together 2H, two doublets, J=8.30 Hz).

(7(iii) (2S,4S)-4-(4-Methoxybenzylthio)-2-[2-methyl-4-(4-nitrobenzyloxycarbonyl)piperazin-1-ylcarbonyl]-1(4-nitrobenzyloxycarbonyl)pyrrolidine 0.51 g of 4-dimethylaminopyridine was added dropwise at room temperature to a solution of 1.83 g of (2S,4S)-4-(4-methoxybenzylthio)-2-(2-methylpiperazin-1-ylcarbonyl)-2-(4-nitrobenzyloxycarbonyl)pyrrolidine [prepared as described in step (ii) above] in 25 ml of dry acetonitrile, and then a solution of 0.90 g of 4-nitrobenzyl chloroformate in 15 ml of dry acetonitrile was added dropwise to the resulting mixture, whilst ice-cooling. The reaction mixture was stirred at room temperature for 30 minutes, after which it was concentrated by evaporation under reduced pressure, and the residue was diluted with ethyl acetate. The diluted solution was washed with water and with an aqueous solution of sodium chloride, in that order, after which it was dried over anhydrous magnesium sulfate. The solvent was removed by distillation under reduced pressure, and the resulting residue was purified by column chromatography through silica gel, using a 7:3 by volume mixture of ethyl acetate and cyclohexane as the eluent, to give 2.28 g of the title compound, as an amorphous solid.

Infrared Absorption Spectrum (KBr), $v_{max}$ cm$^{-1}$: 1708, 1656, 1608, 1521, 1433, 1346, 1252.

Nuclear Magnetic Resonance Spectrum (CDCl$_3$, 270 MHz), δ ppm: 1.02–1.36 (3H, multiplet); 1.59–1.80 (3H, multiplet); 2.30–2.58 (1H, multiplet); 2.61–3.59 (5H, multiplet); 3.73 (2H, singlet); 3.78 & 3.79 (together 3H, two singlets); 3.62–4.92 (4H, multiplet); 4.97–5.30 (4H, multiplet); 6.85 (2H, doublet, J=8.79 Hz); 7.23 (2H, doublet, J=8.79 Hz); 7.41–7.52 (4H, multiplet); 8.17 & 8.23 (together 4H, two doublets, J=8.79 Hz).

7(iv) (2S,4S)-4-Mercapto-2-[2-methyl-4-(4-nitrobenzyloxycarbonyl)piperazin-1-ylcarbonyl]-1-(4-nitrobenzyloxycarbonyl)pyrrolidine 23 ml of trifluoroacetic acid, followed by 0.57 ml of trifluoromethanesulfonic acid, were added dropwise to a solution of 2.26 g of (2S,4S)-4-(4- methoxybenzylthio)-2-[2-methyl-4-(4-nitrobenzyloxycarbonyl)piperazin-1-ylcarbonyl]-1-(4-nitrobenzyloxycarbonyl)pyrrolidine prepared as described in step (iii) above] in 3.48 ml of anisole, and the resulting mixture was worked up and purified by the same procedure as described in Preparation 4(ii), to give 1.88 g of the title compound, as an amorphous solid.

Infrared Absorption Spectrum (KBr), $v_{max}$ cm$^{-1}$: 1707, 1654, 1607, 1521, 1433, 1346.

Nuclear Magnetic Resonance Spectrum (CDCl$_3$, 270 MHz), δ ppm: 1.05–1.40 (3H, multiplet); 1.59 (1H, singlet); 1.85–2.00 (2H, multiplet); 2.71–3.73 (6H, multiplet); 3.78–5.08 (5H, multiplet); 5.15–5.31 (4H, multiplet); 7.40–7.52 (4H, multiplet); 8.17–8.25 (4H, multiplet).

PREPARATION 8

(2S,4S)-4-Mercapto-2-[3-methyl-4-(4-nitrobenzyloxycarbonyl)piperazin-1-ylcarbonyl]-1-(4-nitrobenzyloxycarbonyl)pyrrolidine 7(i) (2S,4S)-4-(4-Methoxybenzylthio)-2-[3-methyl-4-(4-nitrobenzyloxycarbonyl)piperazin-1-ylcarbonyl]-1-(4-nitrobenzyloxycarbonyl)pyrrolidine Following a procedure similar to that described in Preparation 1(i), but using 3.06 g of (2S,4S)-4-(4-methoxybenzylthio)-1-(4-nitrobenzyloxycarbonyl)-2-pyrrolidinecarboxylic acid, 1.34 g of N,N-carbonyldiimidazole and 2.30 g of 2-methyl-1-(4-nitrobenzyloxycarbonyl)piperazine, 4.07 g of the title compound were obtained.

8(ii) (2S,4S)-4-Mercapto-2-[3-methyl-4-(4-nitrobenzyloxycarbonyl)piperazin-1-ylcarbonyl]-1-(4-nitrobenzyloxycarbonyl)pyrrolidine 20 ml of trifluoroacetic acid and subsequently 0.50 ml of trifluoromethanesulfonic acid were added dropwise, whilst ice-cooling, to a solution of 2.0 g of (2S,4S)-4-(4-methoxybenzylthio)-2-[3-methyl-4-(4-nitrobenzyloxycarbonyl)piperazin-1-ylcarbonyl]-1-(4-nitrobenzyloxycarbonyl)pyrrolidine [prepared as described in step (i) above] in 3.08 ml of anisole, and the resulting mixture was stirred at the same temperature for 50 minutes. At the end of this time, the reaction mixture was worked up by the same procedure as described in Preparation 4(ii), to give 1.56 g of the title compound as an amorphous solid.

Infrared Absorption Spectrum (KBr), $v_{max}$ cm$^{-1}$: 1705, 1657, 1607, 1521, 1429, 1405, 1346.

Nuclear Magnetic Resonance Spectrum (CDCl$_3$, 270 MHz), δ ppm: 1.16–1.36 (3H, multiplet); 1.63–2.40 (3H, multiplet); 2.66–3.66 (6H, multiplet); 3.71–4.78 (5H, multiplet); 5.06–5.30 (4H, multiplet); 7.39–7.53 (4H, multiplet); 8.17–8.25 (4H, multiplet).

PREPARATION 9

(2S,4S)-4-Mercapto-2-[(2S)-2-methyl-4-(4-nitrobenzyloxycarbonyl)piperazin-1-ylcarbonyl]-1-(4-nitrobenzyloxycarbonyl)pyrrolidine Following a procedure similar to that described in Preparation 7, but using 13.2 g of (2S,4S)-4-(4-methoxybenzylthio)-1-(4-nitrobenzyloxycarbonyl)-2-pyrrolidinecarboxylic acid, 4.0 ml of pivaloyl chloride, 4.5 ml of triethylamine and 6.5 g of (3 S)-1-t-butoxycarbonyl-3-methylpiperazine, 1.9 g of the title compound was obtained as an amorphous solid.

Infrared Absorption Spectrum (KBr), $v_{max}$ cm$^{-1}$: 1706, 1653, 1607, 1521, 1434, 1406, 1346.

Nuclear Magnetic Resonance Spectrum (CDCl$_3$, 270 MHz), δ ppm: 1.19–1.30 (3H, multiplet); 1.62 (1H, singlet); 1.85–2.04 (2H, multiplet); 2.68–3.59 (6H, multiplet); 3.78–4.77 (5H, multiplet); 5.08–5.31 (4H, multiplet); 7.42–7.52 (4H, multiplet); 8.17–8.25 (4H, multiplet).

PREPARATION 10

(2S,4S)-4-Mercapto-2-[(2R)-2-methyl-4-(4-nitrobenzyloxycarbonyl)piperazin-1-ylcarbonyl]-1-(4-nitrobenzyloxycarbonyl)pyrrolidine Following a procedure similar to that described in Preparation 7, but using 1.3 g of (2S,4S)-4-(4-methoxybenzylthio)-1-(4-nitrobenzyloxycarbonyl)-2-pyrrolidinecarboxylic acid, 0.40 ml of pivaloyl chloride, 0.45 ml of triethylamine and 0.65 g of (3 R)-1-t-butoxycarbonyl-3-methylpiperazine, 0.17 g of the title compound was obtained as an amorphous solid.

Infrared Absorption Spectrum (KBr), $v_{max}$cm$^{-1}$: 1708, 1655, 1607, 1521, 1432, 1435.

PREPARATION 11

(2S,4S)-4-Mercapto-2-[(3S)-3-methyl-4-(N-4-nitrobenzyloxycarbonyl)piperazin-1-ylcarbonyl]-1-(4-nitrobenzyloxycarbonyl)pyrrolidine Following a procedure similar to that described in Preparation 8, but using 4.5 g of (2S,4S)-4-(4-methoxybenzylthio)-1-(4-nitrobenzyloxycarbonyl)-2-pyrrolidinecarboxylic acid, 1.95 g of N,N'-carbonyldiimidazole and 3.34 g of (2 S)-2-methyl-1-(4-nitrobenzyloxycarbonyl)piperazine, 4.32 g of the title compound were obtained as an amorphous solid.

Infrared Absorption Spectrum (KBr), $v_{max}$ cm$^{-1}$: 1705, 1657, 1607, 1522, 1429, 1405, 1346.

Nuclear Magnetic Resonance Spectrum (CDCl$_3$, 270 MHz), δ ppm: 1.16–1.36 (3H, multiplet); 1.62 (1H, singlet); 1.70–2.04 (2H, multiplet); 2.69–2.86 (2H, multiplet); 2.98–4.18 (6H, multiplet); 4.23–4.74 (3H, multiplet);

5.02–5.33 (4H, multiplet); 7.40–7.53 (4H, multiplet); 8.17–8.26 (4H, multiplet).

PREPARATION 12

(2S,4S)-4-Mercapto-2-[(3R)-3-methyl-4-(4-nitrobenzyloxycarbonyl)piperazin-1-ylcarbonyl]-1-(4-nitrobenzyloxycarbonyl)pyrrolidine Following a procedure similar to that described in Preparation 8, but using 0.23 g of (2S,4S)-4-(4-methoxybenzylthio)-1-(4-nitrobenzyloxycarbonyl)-2-pyrrolidinecarboxylic acid, 0.10 g of N,N'-carbonyldiimidazole and 0.17 g of (2R)-2-methyl-1-(4-nitrobenzyloxycarbonyl)piperazine, 0.21 g of the title compound was obtained as an amorphous solid.

Infrared Absorption Spectrum (KBr), $v_{max}$ cm$^{-1}$: 1708, 1652, 1607, 1523, 1427, 1346.

PREPARATION 13

(2S,4S)-2-[trans-2,5-Dimethyl-4-(4-nitrobenzyloxycarbonyl)piperazin-1-ylcarbonyl]-4-mercapto-1-(4-nitrobenzyloxycarbonyl)pyrrolidine Following a procedure similar to that described in Preparation 8, but using 1.79 g of (2S,4S)-4-(4-methoxybenzylthio)-1-(4-nitrobenzyloxycarbonyl)-2-pyrrolidinecarboxylic acid, 0.54 ml of pivaloyl chloride, 0.61 ml of triethylamine and 1.29 g of trans-2,5-dimethyl-1-(4-nitrobenzyloxycarbonyl)piperazine, 577 mg of the title compound were obtained as an amorphous solid.

Infrared Absorption Spectrum (KBr), $v_{max}$ cm$^{-1}$: 1707, 1653, 1608, 1522, 1425, 1347.

Nuclear Magnetic Resonance Spectrum (CDCl$_3$, 270 MHz), δ ppm: 0.87–1.39 (6H, multiplet); 1.61 (1H, singlet); 1.68–2.04 (1H, multiplet); 2.60–2.88 (1H, multiplet); 2.95–3.59 (5H, multiplet); 4.07–4.95 (5H, multiplet); 4.97–5.36 (4H, multiplet); 7.40–7.53 (4H, multiplet); 8.16–8.25 (4H, multiplet).

PREPARATION 14

(2S,4S)-2-[cis-3,5-Dimethylpiperazin-1-ylcarbonyl)-4-mercapto-1-(4-nitrobenzyloxycarbonyl)pyrrolidine Following a procedure similar to that described in Preparation 8, but using 3.3 g of (2S,4S)-4-(4-methoxybenzylthio)-1-(4-nitrobenzyloxycarbonyl)-2-pyrrolidinecarboxylic acid, 1.4 g of N,N'-carbonyldiimidazole and 1.0 g of cis-2,6-dimethylpiperazine, 1.56 g of the title compound was obtained as an amorphous solid.

Infrared Absorption Spectrum (KBr), $v_{max}$ cm$^{-1}$: 1709, 1651, 1608, 1522, 1439, 1405, 1346.

Nuclear Magnetic Resonance Spectrum (CDCl$_3$, 270 MHz), δ ppm: 1.05–1.29 (6H, multiplet); 1.85–1.96 (2H, multiplet); 2.12–3.72 (9H, multiplet); 4.04–4.17 (1H, multiplet); 4.40–4.74 (2H, multiplet); 5.03–5.36 (2H, multiplet); 7.40–7.52 (2H, multiplet); 8.17–8.23 (2H, multiplet).

PREPARATION 15

(2S,4S)-4-Mercapto-2-[4-[2-(4-nitrobenzyloxycarbonyl)oxyethyl]-1-homopiperazinylcarbonyl]-1(4-nitrobenzyloxycarbonyl)pyrrolidine Trifluoromethanesulfonate Following a procedure similar to that described in Preparation 8, but using 5.0 g of (2S,4S)-4-(4-methoxybenzylthio)-1-(4-nitrobenzyloxycarbonyl)-2-pyrrolidinecarboxylic acid, 2.2 g of N,N'-carbonyldiimidazole and 6.81 g of N-[2-(4-nitrobenzyloxycarbonyl)oxyethyl]homopiperazine bis (trifluoroacetate), 6.50 g of the title compound were obtained.

Nuclear Magnetic Resonance Spectrum (hexadeuterated dimethyl sulfoxide, 270 MHz), δ ppm: 1.60–1.83 (1H, multiplet); 1.94–2.25 (2H, multiplet); 2.65–2.90 (1H, multiplet); 3.00–4.85 (18H, multiplet); 5.02–5.40 (4H, multiplet); 7.49–7.71 (4H, multiplet); 8.18–8.30 (4H, multiplet).

PREPARATION 16

(2S,4S)-4-Mercapto-2-(4-carbamoylmethyl-1-homopiperazinylcarbonyl)-1-(4-nitrobenzyloxycarbonyl)pyrrolidine Following a procedure similar to that described in Preparation 8, but using 5.69 g of (2S,4S)-4-(4-methoxybenzylthio)-1-(4-nitrobenzyloxycarbonyl)-2-pyrrolidinecarboxylic acid, 2.48 g of N,N'-carbonyldiimidazole and 5.89 g of N-carbamoylmethylhomopiperazine bis(trifluoroacetate), 4.88 g of the title compound were obtained.

Infrared Absorption Spectrum (KBr), $v_{max}$ cm$^{-1}$: 1707, 1680, 1647, 1520, 1432, 1404, 1344.

Nuclear Magnetic Resonance Spectrum (hexadeuterated dimethyl sulfoxide+D$_2$O, 270 MHz), δ ppm: 1.75–2.15 (3H, multiplet); 2.55–2.92 (4H, multiplet); 2.95–3.07 (1H, multiplet); 3.20–3.60 (6H, multiplet); 3.70–3.85 (1H, multiplet); 3.93–4.18 (2H, multiplet); 4.60–4.71 (1H, multiplet); 5.03–5.42 (2H, multiplet); 7.42–7.52 (2H, multiplet); 8.18–8.25 (2H, multiplet).

PREPARATION 17

(2S,4S)-4-Mercapto-2-[4-(N-4-nitrobenzyloxycarbonylacetimidoyl)piperazin-1-ylcarbonyl]-1-(4-nitrobenzyloxycarbonyl)pyrrolidine 17(i) (2S,4S)-4-(4-Methoxybenzlthio)-2-(1-piperazinylcarbonyl)-1-(4-nitrobenzyloxycarbonyl) pyrrolidine Hydrochloride 3.57 g of N,N'-carbonyldiimidazole were added to a solution of 8.93 g of (2S,4S)-4-(4- methoxybenzylthio)-1-(4-nitrobenzyloxycarbonyl)-2-pyrrolidinecarboxylic acid in 89 ml of dry acetonitrile, and the resulting mixture was stirred at room temperature for 30 minutes. The reaction mixture thus obtained was then added to a solution of 5.17 g of dry piperazine in 178 ml of dry acetonitrile, whilst ice-cooling, and the mixture was stirred for 4 hours under the same conditions, after which it was concentrated by evaporation under reduced pressure. The resulting residue was dissolved in 500 ml of ethyl acetate, and the solution was washed four times, each time with 300 ml of water, and then once with 300 ml of an aqueous solution of sodium chloride. The ethyl acetate layer was separated and dried over anhydrous sodium sulfate, after which 6 ml of a 4N solution of hydrogen chloride in ethyl acetate were added dropwise to the mixture, whilst stirring, and then 500 ml of diethyl ether were added. The powder thus produced was collected by filtration and dried to give 11.49 g of the title compound.

The spectral data of this product are completely identical with those of the compound prepared as described in Preparation 1(ii).

17(ii) (2S,4S)-4-(4-Methoxybenzylthio)-2-[4-(N-4-nitrobenzyloxycarbonyl)pyrrolidine A suspension of 5.0 g of (2S,4S)-4-(4-methoxybenzylthio)-2-(1-piperazinylcarbonyl)-1-(4-nitrobenzyloxycarbonyl)pyrrolidine hydrochloride [prepared as described in step (i) above] and 2.35 g of N-(4-nitrobenzyloxycarbonyl)acetamidine in 73 ml of dry acetonitrile was stirred on a water-bath kept at 48° C. for 3 hours. At the end of this time, the reaction mixture was freed from impurities by filtration, and the filtrate was concentrated by evaporation under reduced pressure. The resulting residue was purified by column chromatography through silica gel, using a 6:4 by volume mixture of ethyl acetate and acetonitrile as the eluent, to give 5.41 g of the title compound, as a powder.

The spectral data of this product are completely identical with those of the compound prepared as described in Preparation 1(iii).

17(iii) (2S,4S)-4-Mercapto-2-[4-(N-4-nitrobenzyloxycarbonylacetimidoyl)piperazin-1-ylcarbonyl]-1-(4-nitrobenzyloxycarbonyl)pyrrolidine 25 ml of trifluoroacetic acid and 1000 µl of trifluoromethanesulfonic acid were added to a solution of 4.90 g of (2S,4S)-4-(4-methoxybenzylthio)-2-[4-(N-4-nitrobenzyloxycarbonyl)pyrrolidine [prepared as described in step (ii) above] in 4.9 ml of anisole, and the resulting mixture was stirred for 1 hour, whilst ice-cooling, after which the solvent was removed by distillation under reduced pressure. The resulting residue was washed with diethyl ether, to produce a powder. This powder was dissolved in a mixture of ethyl acetate and water, and the resulting solution was made alkaline by the addition of an aqueous solution of sodium hydrogencarbonate. The ethyl acetate layer was separated, washed with water and with an aqueous solution of sodium chloride, in that order, and dried over anhydrous sodium sulfate. The solvent was removed by distillation under reduced pressure, to give 4.0 g of the title compound, as a powder.

Infrared Absorption Spectrum (KBr), $v_{max}$ cm$^{-1}$: 1709, 1660, 1607, 1570, 1520, 1431, 1346, 1210, 1198, 1162.

Nuclear Magnetic Resonance Spectrum (CDCl$_3$, 270 MHz), δ ppm: 1.90 (1H, doublet, J=8.8 Hz); 1.85–2.01 (1H, multiplet); 2.25 & 2.30 (together 3H, two singlets); 2.65–2.81 (1H, multiplet); 3.21–3.38 (1H, multiplet); 3.40–4.00 (8H, multiplet); 4.03–4.19 (2H, multiplet); 4.65 & 4.70 (together 1H, two triplets, J=7.8 Hz); 5.02–5.35 (4H, multiplet); 7.41–7.60 (4H, multiplet); 8.16–8.26 (4H, multiplet).

PREPARATION 18

(2S,4S)-4-mercapto-2-[(3S)-3-(4-nitrobenzyloxycarbonyl)aminopyrrolidin-1-ylcarbonyl]-1-(4-nitrobenzyloxycarbonyl)pyrrolidine

18(i) (2S,4S)-4-(4-Methoxybenzylthio)-2-[(3S)-3-(4-nitrobenzyloxycarbonyl)aminopyrrolidin-1-ylcarbonyl]-1-(4-nitrobenzyloxycarbonyl)pyrrolidine A solution of 1.43 g of (2S,4S)-4-(4-methoxybenzylthio)-1-(4-nitrobenzyloxycarbonyl)-2-pyrrolidinecarboxylic acid dissolved in 10 ml of dry tetrahydrofuran was cooled to 0° C. 356 mg of triethylamine, followed by 405 mg of pivaloyl chloride, were added to the cooled solution, and the resulting mixture was stirred at the same temperature for 30 minutes. At the end of this time, a mixture of 1.5 g of (3S)-3-(4-nitrobenzyloxycarbonyl)aminopyridine trifluoroacetate, 830 mg of diisopropylethylamine and 7 ml of dry acetonitrile was added to the solution, and then the temperature was allowed to rise. The reaction mixture was stirred at room temperature for 2.5 hours, after which it was filtered, and the filtrate was freed from the solvent by distillation under reduced pressure. The resulting residue was diluted with ethyl acetate, and the diluted solution was washed with an aqueous solution of sodium hydrogencarbonate and with a saturated aqueous solution of sodium chloride, in that order. The solution was dried over anhydrous magnesium sulfate, and then the solvent was removed by distillation under reduced pressure, and the residue was purified by column chromatography through silica gel, using a 4:4:1 by volume mixture of ethyl acetate, methylene chloride and acetonitrile as the eluent, to give 1.47 g of the title compound, as a powder.

Infrared Absorption Spectrum (KBr), $v_{max}$ cm$^{-1}$: 1716, 1625, 1609, 1519, 1346, 737.

Nuclear Magnetic Resonance Spectrum (hexadeuterated dimethyl sulfoxide, 270 MHz), δ ppm: 1.54–1.65 (1H, multiplet); 1.72–1.86 (1H, multiplet); 2.57–2.69 (1H, multiplet); 2.99–3.13 (1H, multiplet); 3.72 (3H, doublet, J=5.37 Hz); 3.15–4.15 (12H, multiplet); 4.36–4.58 (1H, multiplet); 5.00–5.23 (4H, multiplet); 6.87 (1H, doublet, J=8.3 Hz); 7.26 (1H, doublet, J=8.79 Hz); 7.46–7.62 (4H, multiplet); 7.70–7.80 (1H, multiplet); 8.15–8.25 (4H, multiplet).

18(ii) (2S,4S)-4-mercapto-2-[(3S)-3-(4-nitrobenzyloxycarbonyl)aminopyrrolidin-1-ylcarbonyl]-1-(4-nitrobenzyloxycarbonyl)pyrrolidine 12 ml of trifluoroacetic acid and 0.38 ml of trifluoromethanesulfonic acid were added to a suspension of 1.47 g of (2S,4S)-4-(4-methoxybenzylthio)-2-[(3S)-3-(4-nitrobenzyloxycarbonyl)aminopyrrolidin-1-ylcarbonyl]-1-(4-nitrobenzyloxycarbonyl)pyrrolidine [prepared as described in step (i) above] in 2.3 ml of anisole, and the resulting mixture was stirred at room temperature for 2 hours. At the end of this time, the solvent was removed by distillation under reduced pressure, and the residue was washed with hexane to remove the anisole, and then diethyl ether was added. The mixture was then cooled to −78° C., and the solidified product was broken up and separated by decantation. Several repetitions of this procedure yielded a powder and oily materials, which were dissolved in 100 ml of ethyl acetate to give a solution. The resulting solution was washed with an aqueous solution of sodium hydrogencarbonate, and the aqueous washings were extracted with 30 ml of ethyl acetate. The washings were combined with the ethyl acetate solution, and the combined organic phase was washed with an aqueous solution of sodium chloride and dried over anhydrous magnesium sulfate. The solvent was then removed by distillation under reduced pressure, to give 1.26 g of the title compound, as a powder.

Infrared Absorption Spectrum (KBr), $v_{max}$ cm$^{-1}$: 1710, 1522, 1347, 854, 738.

Nuclear Magnetic Resonance Spectrum (hexadeuterated dimethyl sulfoxide, 270 MHz), δ ppm: 1.60–2.20 (2H, multiplet); 2.62–2.75 (1H, multiplet); 3.08–4.13 (11H, multiplet); 4.37–4.59 (1H, multiplet); 5.02–5.26 (4H, multiplet); 7.47–7.81 (4H, multiplet); 8.16–8.26 (4H, multiplet).

PREPARATION 19

(2S,4S)-4-Mercapto-2-[(3S)-1-(4-nitrobenzyloxycarbonyl)pyrrolidin-3-ylaminocarbonyl]-1-(4-nitrobenzyloxycarbonyl) pyrrolidine

19(i) (2S,4S)-4-(4-Methoxybenzylthio)-2-[(3S)-1-(t-butoxycarbonyl)pyrrolidin-3-ylaminocarbonyl]-1-(4-nitrobenzyloxycarbonyl)pyrrolidine 3.05 g of N,N'-carbonyldiimidazole were added to a solution of 7.99 g of (2S,4S)-4-(4- methoxybenzylthio)-1-(4-nitrobenzyloxycarbonyl)-2-pyrrolidinecarboxylic acid in 80 ml of dry acetonitrile, and the resulting mixture was stirred at room temperature for 2 hours. At the end of this time, the reaction mixture was cooled to 0° C., after which a solution of 3.34 g of (3 S)-3-amino-1-t-butoxycarbonylpyrrolidine in 30 ml of dry acetonitrile was added, and the mixture was stirred an the same temperature for 20 minutes; it was then stirred at room temperature for a further 1.4 hours and at 32° C. for 45 minutes. The reaction mixture was then concentrated by evaporation under reduced pressure, and the concentrate was diluted with 200 ml of ethyl acetate. The resulting ethyl acetate solution was washed twice with water and then once with a saturated aqueous solution of sodium chloride. The solution was then dried over anhydrous magnesium sulfate, after which the solvent was removed by distillation under reduced pressure. The residue was recrystallized from diethyl ether, to give 9.11 g of the title compound, as a powder.

19(ii) (2S,4S)-4-(4-Methoxybenzylthio)-2-[(3S)-pyrrolidin-3-ylaminocarbonyl]-1-(4-nitrobenzyloxycarbonyl)pyrrolidine Hydrochloride A mixture of 1.00 g of (2S,4S)-4- (4-methoxybenzylthio)-2-[(3S)-1-(t-butoxycarbonyl) pyrrolidin-3-ylaminocarbonyl]-1-(4-nitrobenzyloxycarbonyl)pyrrolidine [prepared as described in step (i) above] and 10 ml of ethyl acetate was heated to form a solution. 2.5 ml of a 4N solution of hydrogen chloride in ethyl acetate were then added to this solution, and the resulting mixture was heated under reflux for 30 minutes. At the end of this time, the solvent was removed by distillation under reduced pressure, and then, in order to remove the acid, ethyl acetate was added to the residue and the solvent was again removed by distillation under reduced pressure. The residue was triturated with diethyl ether and washed by decantation to give 630 mg of the title compound, as a powder.

19(iii) (2S,4S)-4-(4-Methoxybenzylthio)-2-[(3S)-1-(4-nitrobenzyloxycarbonyl)pyrrolidin-3-ylaminocarbonyl]-1-(4-nitrobenzyloxycarbonyl) pyrrolidine 230 mg of diisopropylethylamine were added to a suspension of 1.0 g of (2S,4S)-4-(4-methoxybenzylthio)-2-[(3 S)-pyrrolidin-3-ylaminocarbonyl]-1-(4-nitrobenzyloxycarbonyl)pyrrolidine hydrochloride [prepared as described in step (ii) above] and 240 mg of 4-dimethylaminopyridine in 10 ml of dry acetonitrile, and the resulting mixture was cooled to 0° C. A solution of 430 mg of 4-nitrobenzyl chloroformate in 4 ml of dry acetonitrile was then added to the mixture. The mixture was then stirred at room temperature for 3 hours, after which a solution of 117 mg of 4-nitrobenzyl chloroformate in 2 ml of dry acetonitrile was added and the mixture was stirred at the same temperature for 1 hour. At the end of this time, the reaction mixture was freed from the solvent by distillation under reduced pressure, and the residue was diluted with 50 ml of methylene chloride. The diluted solution was washed with a saturated aqueous solution of sodium chloride. The aqueous washings were extracted with methylene chloride. The organic extract and the methylene chloride solution were combined and dried over anhydrous magnesium sulfate, and then the solvent was removed by distillation under reduced pressure. The resulting residue was purified by column chromatography through silica gel, using a 4:1 by volume mixture of methylene chloride and acetonitrile as the eluent, to give 862 mg of the title compound as a powder.

Infrared Absorption Spectrum (KBr), $\nu_{max}$ cm$^{-1}$: 1709, 1521, 1345, 1109, 854, 738.

Nuclear Magnetic Resonance Spectrum (CDCl$_3$, 270 MHz), δ ppm: 1.80–1.98 (1H, multiplet); 2.05–2.25 (1H, multiplet); 2.30–2.50 (1H, multiplet); 3.10–3.20 (1H, multiplet); 3.40–3.55 (2H, multiplet); 3.79 (3H, singlet); 3.20–3.90 (8H, multiplet); 4.20–4.30 (1H, multiplet); 4.42–4.48 (1H, multiplet); 5.13–5.26 (4H, multiplet); 6.82–6.87 (2H, multiplet); 7.19–7.26 (2H, multiplet); 7.45–7.53 (4H, multiplet); 8.19–8.24 (4H, multiplet).

19(iv) (2S,4S)-4-Mercapto-2-[(3S)-1-(4-nitrobenzyloxycarbonyl)pyrrolidin-3-ylaminocarbonyl]-1-(4-nitrobenzyloxycarbonyl) pyrrolidine 6.5 ml of trifluoroacetic acid and 0.21 ml of trifluoromethanesulfonic acid were added to a suspension of 835 mg of (2S,4S)-4-(4-methoxybenzylthio)-2-[(3S)-1-(4-nitrobenzyloxycarbonyl)pyrrolidin-3-ylaminocarbonyl]-1-(4-nitrobenzyloxycarbonyl)pyrrolidine [prepared as described in step (iii) above] in 1.3 ml of anisole, whilst ice-cooling, and the resulting mixture was stirred at room temperature for 1 hour. At the end of this time, the solvent was removed by distillation under reduced pressure, and the resulting residue was first washed with hexane to remove the anisole and then mixed with diethyl ether. The mixture was cooled to −78° C., and the solidified product was broken up and separated by decantation. Several repetitions of this procedure yielded 940 mg of the title compound as a powder.

Infrared Absorption Spectrum (KBr), $\nu_{max}$ cm$^{-1}$: 1702, 1523, 1347, 856, 739.

Nuclear Magnetic Resonance Spectrum (hexadeuterated dimethyl sulfoxide+D$_2$O, 270 MHz), δ ppm: 1.55–2.15 (2H, multiplet); 2.55–2.65 (1H, multiplet); 3.05–3.61 (7H, multiplet); 3.87–4.02 (1H, multiplet); 4.10–4.26 (2H, multiplet); 5.06–5.20 (4H, multiplet); 7.55–7.65 (4H, multiplet); 8.18–8.25 (4H, multiplet).

PREPARATION 20

(2S,4S)-4-Mercapto-2-[(3R)-1-(4-nitrobenzyloxycarbonyl)pyrrolidin-3-ylaminocarbonyl]-1-(4-nitrobenzyloxycarbonyl) pyrrolidine Following a procedure similar to that described in Preparation 19, but using 6.4 g of (2S,4S)-4-(4-methoxybenzylthio)-1-(4-nitrobenzyloxycarbonyl)-2-pyrrolidinecarboxylic acid, 2.40 g of N,N'-carbonyldiimidazole and 2.7 g of (3 R)-3-amino-1-t-butoxycarbonylpyrrolidine, 750 mg of the title compound were obtained as a powder.

Infrared Absorption Spectrum (KBr), $\nu_{max}$ cm$^{-1}$: 1705, 1522, 1347, 855, 735.

PREPARATION 21

(2S,4S)-4-Mercapto-2-[(3S)-3-dimethylaminopyrrolidin-1-ylcarbonyl]-1-(4-nitrobenzyloxycarbonyl)pyrrolidine Trifluoromethanesulfonate

21(i) (2S,4S)-4-(4-Methoxybenzylthio)-2-[(3S)-3-dimethylaminopyrrolidin-1-ylcarbonyl]-1-(4-nitrobenzyloxycarbonyl)pyrrolidine A solution of 924 mg of (2S,4S)-4-(4-methoxybenzylthio)-1-(4-nitrobenzyloxycarbonyl)-2-pyrrolidinecarboxylic acid in 10 ml of tetrahydrofuran was cooled to −20° C., and 209 mg of triethylamine were added, followed by 250 mg of pivaloyl chloride. The resulting mixture was stirred at the same temperature for 5 minutes, and then a mixture of 651 mg of (3 S)-3-dimethylaminopyrrolidine trifluoroacetate, 560 ml of diisopropylethylamine and 7 ml of dry acetonitrile was added to the mixture. The temperature of the reaction mixture was allowed to rise gradually, and the mixture was stirred at 0° C. for 1 hour. The solvent was then removed by distillation under reduced pressure. The resulting residue was diluted with ethyl acetate and the solution was washed with an aqueous solution of sodium hydrogencarbonate and with a saturated aqueous solution of sodium chloride, in that order. The organic solution was dried over anhydrous magnesium sulfate, and the solvent was removed by distillation under reduced pressure. The residue was purified by column chromatography through silica gel, using a 3:1 by volume mixture of acetonitrile and methanol as the eluent to give 884 mg of the title compound, as a powder.

Infrared Absorption Spectrum (KBr), $v_{max}$ cm$^{-1}$: 1710, 1654, 1512, 1345, 1109, 857, 738.

Nuclear Magnetic Resonance Spectrum (hexadeuterated dimethyl sulfoxide, 270 MHz), δ ppm: 1.49–3.31 (15H, multiplet); 3.35–3.57 (2H, multiplet); 3.71–4.00 (6H, multiplet); 4.44–4.56 (1H, multiplet); 5.00–5.21 (2H, multiplet); 6.88 (2H, doublet, J=8.79 Hz); 7.27 (2H, doublet, J=8.31 Hz); 7.51–7.61 (2H, multiplet); 8.19–8.26 (2H, multiplet).

21(ii) (2S,4S)-4-Mercapto-2-[(3S)-3-dimethylaminopyrrolidin-1-ylcarbonyl]-1-(4-nitrobenzyloxycarbonyl)pyrrolidine Trifluoromethanesulfonate 8.5 ml of trifluoroacetic acid and 0.28 ml of trifluoromethanesulfonic acid were added, whilst ice-cooling, to a suspension of 845 mg of (2S,4S)-4-(4- methoxybenzylthio)-2-[(3S)-3-dimethylaminopyrrolidin-1-ylcarbonyl- 1-(4-nitrobenzyloxycarbonyl)pyrrolidine [prepared as described in step (i) above] in 1.7 ml of anisole, and the resulting mixture was stirred at room temperature for 1 hour. At the end of this time, the solvent was removed by distillation under reduced pressure, and the resulting residue was first washed with hexane to remove the anisole and then mixed with diethyl ether. The mixture was cooled to −78° C., and the solidified product was broken up and separated by decantation. Several repetitions of this procedure yielded 1.14 g of the title compound as a powder.

Infrared Absorption Spectrum (KBr), $v_{max}$cm$^{-1}$: 1705, 1656, 1523, 1348, 857.

Nuclear Magnetic Resonance Spectrum (hexadeuterated dimethyl sulfoxide+D$_2$O, 270 MHz), δ ppm: 1.70–4.10 (18H, multiplet); 4.47–4.66 (1H, multiplet); 5.04–5.27 (2H, multiplet); 7.51–7.65 (2H, multiplet).

PREPARATION 22

(2S,4S)-4-Mercapto-2-{(3S)-3-[N-methyl-N,(4-nitrobenzyloxycarbonyl)amino]pyrrolidin-1-ylcarbonyl}-1-(4-nitrobenzyloxycarbonyl)pyrrolidine Following a procedure similar to that described in Preparation 18, but using 1.21 g of (2S,4S)-4-(4-methoxybenzylthio)-1-(4-nitrobenzyloxycarbonyl)-2-pyrrolidinecarboxylic acid, 343 mg of pivaloyl chloride and 1.27 g of (3S)-3-[N-methyl-N-(4- nitrobenzyloxycarbonyl)amino]pyrrolidine trifluoroacetate, 1.21 g of the title compound were obtained as a powder.

Infrared Absorption Spectrum (KBr), $v_{max}$ cm$^{-1}$: 1709, 1651, 1522, 1346, 856, 737.

PREPARATION 23

(2S,4S)-4-Mercapto-2-[(3S)-3-(N-4-nitrobenzyloxycarbonylacetimidoylamino)pyrrolidin-1-ylcarbonyl]-1-(4-nitrobenzyloxycarbonyl)pyrrolidine

23(i) (2S,4S)-4-(4-Methoxybenzylthio)-2-[(3S)-3-aminopyrrolidin-1-ylcarbonyl]-1-(4-nitrobenzyloxycarbonyl)pyrrolidine 2.92 g of N,N'-carbonyldiimidazole were added to a solution of 6.70 g of (2S,4S)-4-(4- methoxybenzylthio)-1-(4-nitrobenzyloxycarbonyl)-2-pyrrolidinecarboxylic acid in 50 ml of dry acetonitrile, and the resulting mixture was stirred at room temperature for 1 hour. A solution of 1.55 g of (3S)-3-aminopyrrolidine in 10 ml of dry acetonitrile was then added to the mixture, whilst ice-cooling, and the mixture was stirred at room temperature for 1 hour. At the end of this time, the reaction mixture was freed from the solvent by distillation under reduced pressure, and the residue was diluted with ethyl acetate. The diluted solution was washed with water and with an aqueous solution of sodium chloride, in that order, after which it was dried over anhydrous magnesium sulfate. The solvent was then removed by distillation under reduced pressure, and the resulting residue was purified by column chromatography through silica gel, using a 1:1 by volume mixture of ethyl acetate and methanol as the eluent, to give 4.10 g of the title compound, as a powder.

Infrared Absorption Spectrum (KBr), $v_{max}$ cm$^{-1}$: 1708, 1651, 1609, 1512, 1440, 1404, 1346, 1248, 1174.

Nuclear Magnetic Resonance Spectrum (hexadeuterated dimethyl sulfoxide, 270 MHz), δ ppm: 1.40–2.04 (3H, multiplet); 2.57–2.77 (1H, multiplet); 2.90–3.93 (10H, multiplet); 3.72 & 3.74 (together 3H, two singlets); 3.78 (2H, singlet); 4.33–4.58 (1H, multiplet); 4.99–5.26 (2H, multiplet); 6.88 (2H, doublet, J=8.79 Hz); 7.27 (2H, doublet, J=8.79 Hz); 7.48–7.67 (2H, multiplet); 8.14–8.29 (2H, multiplet).

23(ii) (2S,4S)-4-(4-Methoxybenzylthio)-2-[(3S)-3-aminopyrrolidin-1-ylcarbonyl]-1-(4-nitrobenzyloxycarbonyl)pyrrolidine Hydrochloride 4.37 ml of a 4N solution of hydrogen chloride in ethyl acetate were added, whilst ice-cooling, to a solution of 3.00 g of (2S,4S)-4-(4-methoxybenzylthio)-2-[(3S)-3-aminopyrrolidin-1-ylcarbonyl]-1-(4-nitrobenzyloxycarbonyl)pyrrolidine [prepared as described in step (i) above] in 30 ml of ethyl acetate, and the resulting mixture was stirred at the same temperature for 30 minutes. At the end of this time, it was diluted with ethyl acetate, and the powder which precipitated was collected by filtration and dried, to give 3.20 g of the title compound, as a powder.

Infrared Absorption Spectrum (KBr), $v_{max}$ cm$^{-1}$: 1707, 1656, 1609, 1585, 1512, 1440, 1405, 1346, 1249, 1175.

Nuclear Magnetic Resonance Spectrum (hexadeuterated dimethyl sulfoxide, 270 MHz), δ ppm: 1.49–1.78 (1H, multiplet); 1.88–2.33 (2H, multiplet); 2.59–2.75 (1H, multiplet); 2.96–3.12 (1H, multiplet); 3.12–3.97 (7H, multiplet); 3.72 & 3.74 (together 3H, two singlets); 3.78 & 3.79 (together 2H, two singlets); 4.36–4.61 (1H, multiplet); 5.00–5.28 (2H, multiplet); 6.88 (2H, doublet, J=8.79 Hz); 7.20–7.31 (2H, multiplet); 7.46–7.65 (2H, multiplet); 8.19–8.28 (2H, multiplet); 8.30–8.60 (3H, multiplet).

23(iii) (2S,4S)-4-(4-Methoxybenzylthio)-2-[(3S)-3-(N-4-nitrobenzyloxycarbonylacetimidoylamino)pyrrolidin-1ylcarbonyl]-1-(4-nitrobenzyloxycarbonyl)pyrrolidine A suspension of 1.00 g of (2S,4S)-4-(4-methoxybenzylthio)-2-[(3S)-3-aminopyrrolidin-1-ylcarbonyl]-1-(4-nitrobenzyloxycarbonyl)pyrrolidine hydrochloride [prepared as described in step (ii) above] and 0.47 g of N-(4-nitrobenzyloxycarbonyl)acetamidine in 20 ml of dry acetonitrile was stirred at 53° C. for 2 hours. The reaction mixture was then freed from impurities by filtration, and the filtrate was concentrated by evaporation under reduced pressure. The concentrate was purified by column chromatography through silica gel, using a 45:45:5 by volume mixture of methylene chloride, ethyl acetate and methanol as the eluent, to give 0.89 g of the title compound, as a powder.

Infrared Absorption Spectrum (KBr), $v_{max}$ cm$^{-1}$: 1709, 1643, 1619, 1609, 1557, 1521, 1441, 1402, 1346, 1247, 1226, 1199, 1175.

Nuclear Magnetic Resonance Spectrum (hexadeuterated dimethyl sulfoxide+D$_2$O, 270 MHz), δ ppm: 1.49–2.25 (3H, multiplet); 2.09 & 2.10 (together 3H, two singlets); 2.50–2.74 (1H, multiplet); 3.00–3.92 (7H, multiplet); 3.71 & 3.73 (together 3H, two singlets); 3.77 (2H, singlet); 4.15–4.63 (2H, multiplet); 5.00–5.31 (4H, multiplet); 6.87 (1H, doublet, J=8.79 Hz); 6.88 (1H, doublet, J=8.30 Hz); 7.25 (1H, doublet, J=8.30 Hz); 7.27 (1H, doublet, J=8.79 Hz); 7.43–7.70 (4H, multiplet); 8.13–8.29 (4H, multiplet).

23(iv) (2S,4S)-4-Mercapto-2-[(3S)-3-(N-4-nitrobenzyloxycarbonylacetimidoylamino)pyrrolidin-1-ylcarbonyl]-1-(4-nitrobenzyloxycarbonyl)pyrrolidine 4.56 ml of trifluoroacetic acid and 208 μl of trifluoromethanesulfonic acid were added, whilst ice-cooling, to a solution of 0.87 g of (2S,4S)-4-(4-methoxybenzylthio)-2-[(3S)-3-(N-4-nitrobenzyloxycarbonylacetimidoylamino)pyrrolidin-1-ylcarbonyl]-1-(4-nitrobenzyloxycarbonyl)pyrrolidine [prepared as described in step (iii) above] in 1.29 ml of anisole, and the resulting mixture was stirred under the same conditions for 1.5 hours. At the end of this time, the solvent was removed by distillation under reduced pressure, and the resulting residue was washed with diethyl ether and dried in vacuo, to give 1.10 g of the trifluoromethanesulfonate of the title compound as a powder. The whole of this salt was dissolved in a mixture of ethyl acetate and water and the solution was made alkaline by adding a 1N aqueous solution of sodium hydroxide. The ethyl acetate layer was separated, washed with water and with an aqueous solution of sodium chloride, in that order, and dried over anhydrous magnesium sulfate. The solvent was removed by distillation under reduced pressure, to give 662 mg of the title compound, as a powder.

Infrared Absorption Spectrum (KBr), $v_{max}$ cm$^{-1}$: 1708, 1650, 1607, 1553, 1520, 1440, 1404, 1346, 1217, 1170.

Nuclear Magnetic Resonance Spectrum (hexadeuterated dimethyl sulfoxide+D$_2$O, 270 MHz), δ ppm: 1.59–2.28 (2H, multiplet); 2.10 & 2.11 (together 3H, two singlets); 2.60–2.83 (1H, multiplet); 3.08–4.64 (10H, multiplet); 5.01–5.42 (4H, multiplet); 7.45–7.73 (4H, multiplet); 8.14–8.31 (4H, multiplet).

PREPARATION 24

(2S,4S)-4-Mercapto-2-[(3S)-3-(N-4-nitrobenzyloxycarbonylformimidoylamino)pyrrolidin-1-ylcarbonyl]-1-(4-nitrobenzyloxycarbonyl)pyrrolidine Following a procedure similar to that described in Preparations 23(iii) and 23(iv), but using 1.00 g of (2S,4S)-4-(4-methoxybenzylthio)-2-[(3S)-3- aminopyrrolidin-1-ylcarbonyl]-1-(4-nitrobenzyloxycarbonyl)pyrrolidine hydrochloride [prepared as described in Preparation 23(ii)] and 410 mg of N-(4-nitrobenzyloxycarbonyl)formamidine, 670 mg of the title compound were obtained as a powder.

Infrared Absorption Spectrum (KBr), $v_{max}$ cm$^{-1}$: 1707, 1645, 1604, 1520, 1441, 1404, 1346, 1188, 1111.

Nuclear Magnetic Resonance Spectrum (CDCl$_3$+D$_2$O, 270 MHz), δ ppm: 1.71–2.32 (3H, multiplet); 2.60–2.84 (1H, multiplet); 3.19–4.18 (8H, multiplet); 4.36–4.57 (1H, multiplet); 4.93–5.40 (4H, multiplet); 7.40–7.61 (4H, multiplet); 8.12–8.30 (4H, multiplet); 8.42 (1H, singlet).

PREPARATION 25

(2S,4S)-4-Mercapto-2-[(3S)-1-(N-4-nitrobenzyloxycarbonylformimidoyl)pyrrolidin-3-ylaminocarbonyl]-1-(4-nitrobenzyloxycarbonyl)pyrrolidine Following a procedure similar to that described in Preparations 23(iii) and 23(iv), but using 1.20 g of (2S,4S)-4-(4-methoxybenzylthio)-1-(4-nitrobenzyloxycarbonyl)-2-[(3S)-pyrrolidin-3-ylaminocarbonyl]pyrrolidine hydrochloride and 490 mg of N-(4-nitrobenzyloxycarbonyl)formamidine, 750 mg of the title compound were obtained as a powder.

Infrared Absorption Spectrum (KBr), $v_{max}$ cm$^{-1}$: 1721, 1678, 1664, 1602, 1520, 1449, 1439, 1403, 1346, 1234, 1222.

Nuclear Magnetic Resonance Spectrum (CDCl$_3$+D$_2$O, 270 MHz), δ ppm: 1.87–2.83 (4H, multiplet); 3.24–4.08 (7H, multiplet); 4.20–4.63 (2H, multiplet); 5.14–5.38 (4H, multiplet); 7.45–7.60 (4H, multiplet); 8.15–8.29 (4H, multiplet); 8.60 (1H, singlet).

PREPARATION 26

(2S,4S)-4-Mercapto-2[(3S)-1-(N-4-nitrobenzyloxycarbonylacetimidoyl)pyrrolidin-3-ylaminocarbonyl]-1-(4-nitrobenzyloxycarbonyl)pyrrolidine Following a procedure similar to that described in Preparations 23(iii) and 23(iv), but using 1.08 g of (2S,4S)-4-

(4-methoxybenzylthio)-1-(4-nitrobenzyloxycarbonyl)-2-[(3S)-pyrrolidin-3-ylaminocarbonyl)pyrrolidine hydrochloride and 440 mg of N-(4-nitrobenzyloxycarbonyl)acetamidine, 608 mg of the title compound were obtained as a powder.

Infrared Absorption Spectrum (KBr), $v_{max}$ cm$^{-1}$: 1701, 1655, 1609, 1555.

PREPARATION 27

(2S,4S)-4-Mercapto-2-[(3R)-1-(N-4-nitrobenzyloxycarbonylformimidoyl)pyrrolidin-3-ylaminocarbonyl]-1-(4-nitrobenzyloxycarbonyl)pyrrolidine Following a procedure similar to that described in Preparations 23(iii) and 23(iv), but using 1.38 g of (2S,4S)-4-(4-methoxybenzylthio)-1-(4-nitrobenzyloxycarbonyl)-2-[(3R)-pyrrolidin-3-ylaminocarbonyl]pyrrolidine hydrochloride and 564 mg of N-(4-nitrobenzyloxycarbonyl)formamidine, 795 mg of the title compound were obtained as a powder.

Infrared Absorption Spectrum (KBr), $v_{max}$ cm$^{-1}$: 1710, 1650, 1587, 1518, 1442, 1346, 1170.

PREPARATION 28

(2S,4S)-4-Mercapto-2-{N-methyl-N-[(3S)-1(N-4-nitrobenzyloxycarbonyl)pyrrolidin-3-yl]carbamoyl}-1-(4-nitrobenzyloxycarbonyl)pyrrolidine Following a procedure similar to that described in Preparation 19, but using 8.0 g of (2S,4S)-4-(4-methoxybenzylthio)-1-(4-nitrobenzyloxycarbonyl)-2-pyrrolidinecarboxylic acid, 3.05 g of N,N'-carbonyldiimidazole and 3.37 g of (3S)-3-methylamino-1-t-butoxycarbonylpyrrolidine, 504 mg of the title compound were obtained as a powder.

Infrared Absorption Spectrum (KBr), $v_{max}$ cm$^{-1}$: 1704, 1522, 1346, 854, 736.

PREPARATION 29

(2S,4S)-4-Mercapto-2-{N-methyl-N-[(3S)-1-(N-4-nitrobenzyloxycarbonylformimidoyl)pyrrolidin-3-yl]carbamoyl}-1-(4-nitrobenzyloxycarbonyl)pyrrolidine Following a procedure similar to that described in Preparations 23(iii) and 23(iv), but using 1.00 g of (2S,4S)-4-(4-methoxybenzylthio)-1-(4-nitrobenzyloxycarbonyl)-2-[N-methyl-N-[(3S)-pyrrolidin-3-yl]carbamoyl]pyrrolidine hydrochloride and 405 mg of N-(4-nitrobenzyloxycarbonyl)formamidine, 620 mg of the title compound were obtained as a powder.

Infrared Absorption Spectrum (KBr), $v_{max}$ cm$^{-1}$: 1707, 1648, 1514, 1404, 1347, 1173.

PREPARATION 30

(2S,4S)-2-[3-Carbamoyl-4-(4-nitrobenzyloxycarbonyl)-1-piperazinylcarbonyl]-4-mercapto-1-(4nitrobenzyloxycarbonyl)pyrrolidine Following a procedure similar to that described in Preparation 8, but using 2.18 g of (2S,4S)-4-(4-methoxybenzylthio)-1-(4-nitrobenzyloxycarbonyl)-2-pyrrolidinecarboxylic acid, 0.79 g of N,N'-carbonyldiimidazole and 1.81 g of 2-carbamoyl-1-(4-nitrobenzyloxycarbonyl)piperazine, 2.13 g of the title compound were obtained as an amorphous solid.

Infrared Absorption Spectrum (KBr), $v_{max}$ cm$^{-1}$: 1706, 1607, 1521, 1432, 1405, 1346.

Nuclear Magnetic Resonance Spectrum (CDCl$_3$, 270 MHz), δ ppm: 1.71–2.04 (3H, multiplet); 2.42–3.46 (5H, multiplet); 3.90–4.93 (6H, multiplet); 5.02–5.36 (4H, multiplet); 5.45–6.77 (2H, multiplet); 7.42–7.54 (4H, multiplet); 8.14–8.26 (4H, multiplet).

PREPARATION 31

(2S,4S)-4-Mercapto-2-[4-(2-fluoroethyl)-1-homopiperazinylcarbonyl]-1-(4-nitrobenzyloxycarbonyl)pyrrolidine Trifluoromethanesulfonate Following a procedure similar to that described in Preparation 8, but using 3.5 g of (2S,4S)-4-(4-methoxybenzylthio)-1-(4-nitrobenzyloxycarbonyl)-2-pyrrolidinecarboxylic acid, 1.53 g of N,N'-carbonyldiimidazole and 5.83 g of N-(2-fluoroethyl)homopiperazine bis(trifluoroacetate), 4.0 g of the title compound were obtained as a powder.

Infrared Absorption Spectrum (KBr), $v_{max}$ cm$^{-1}$: 1784, 1698, 1662, 1524, 1441, 1348, 1286, 1225, 1170, 1030.

Nuclear Magnetic Resonance Spectrum (CDCl$_3$, 270 MHz), δ ppm: 1.62–1.83 (1H, multiplet); 1.96–2.25 (2H, multiplet); 2.65–2.90 (1H, multiplet); 2.95–4.20 (14H, multiplet); 4.60–4.95 (2H, multiplet); 5.00–5.30 (2H, multiplet); 7.50–7.70 (2H, multiplet); 8.19–8.26 (2H, multiplet).

PREPARATION 32

(2S,4S)-4-Mercapto-2-[(3S)-3-(imidazol-1-yl)pyrrolidin-1-ylcarbonyl]-1-(4-nitrobenzyloxycarbonyl)pyrrolidine 32(i) (2S,4S)-4-(4-Methoxybenzylthio)-2-[(3S)-3-(imidazol-1-yl)pyrrolidin-1-ylcarbonyl]-1-(4-nitrobenzyloxycarbonyl)pyrrolidine 1.09 g of N,N'-carbonyldiimidazole were added to a solution of 2.5 g of (2S,4S)-4-(4-methoxybenzylthio)-1-(4-nitrobenzyloxycarbonyl)-2-pyrrolidinecarboxylic acid in 25 ml of dry acetonitrile, and the resulting mixture stirred at room temperature for 30 minutes. A solution of 850 mg of (3S)-3-(imidazol-1-yl)pyrrolidine in 5 ml of dry acetonitrile was then added, and the mixture was stirred at room temperature for 2 hours and then at 40° C. for a further 4 hours. At the end of this time, the reaction mixture was concentrated by evaporation under reduced pressure, and the resulting residue was purified by reverse phase column chromatography through 200 ml of Cosmo Sil 75C$_{18}$-PREP (a trade mark for a product of Nacalai Tesque), using a gradient elution method, with mixtures of acetonitrile and water ranging from 50:50 to 55:45 by volume as the eluent. Those fractions containing the title compound were combined and concentrated by evaporation under reduced pressure, to give 2.54 g of the title compound, as a powder.

Infrared Absorption Spectrum (KBr), $v_{max}$ cm$^{-1}$: 1708, 1656, 1609, 1512, 1438, 1404, 1345, 1246, 1173, 1110.

Nuclear Magnetic Resonance Spectrum (CDCl$_3$, 270 MHz), δ ppm: 1.88–2.05 (1H, multiplet); 2.15–2.31 (1H, multiplet); 2.36–2.57 (2H, multiplet); 3.02–3.18 (1H, multiplet); 3.31–3.40 (1H, multiplet); 3.49–3.63 (1H, multiplet); 3.73 & 3.74 (together 2H, two singlets); 3.78 & 3.79 (together 3H, two singlets); 3.80–4.08 (3H, multiplet); 4.26–4.48 (2H, multiplet); 4.71–4.89 (1H, multiplet);

5.00–5.34 (2H, multiplet); 6.76–7.60 (9H, multiplet); 8.15–8.27 (2H, multiplet).

32(ii) (2S,4S)-4-Mercapto-2-[(3S)-3-(imidazol-1-yl)pyrrolidin-1-ylcarbonyl]-1-(4-nitrobenzyloxycarbonyl)pyrrolidine 585 μl of trifluoromethanesulfonic acid were added, whilst ice-cooling, to a solution of 2.5 g of (2S,4S)-4-(4-methoxybenzylthio)-2-[(3S)-3-(imidazol-1-yl)pyrrolidin-1-ylcarbonyl]-1-(4-nitrobenzyloxycarbonyl)pyrrolidine [prepared as described in step (i) above] in a mixture of 5 ml of anisole and 15 ml of trifluoroacetic acid, and the resulting mixture was stirred at room temperature for 1 hour and then at 35° C. for a further 30 minutes. At the end of this time, the mixture was concentrated by evaporation under reduced pressure, and the resulting residue was washed four times with diethyl ether, to give a colorless powder. This powder was suspended in ethyl acetate, and the suspension was made alkaline by the addition of an aqueous solution of sodium hydrogencarbonate. The ethyl acetate layer was separated and washed with an aqueous solution of sodium chloride, after which it was dried over anhydrous sodium sulfate. The solvent was then removed by distillation under reduced pressure, to give 1.9 g of the title compound, as a colorless powder.

Infrared Absorption Spectrum (KBr), $v_{max}$ cm$^{-1}$: 1706, 1655, 1521, 1440, 1405, 1346.

Nuclear Magnetic Resonance Spectrum (CDCl$_3$+D$_2$O, 270 MHz), δ ppm: 1.90–2.09 (1H, multiplet); 2.15–2.37 (1H, multiplet); 2.42–2.83 (2H, multiplet); 3.20–3.35 (1H, multiplet); 3.41–4.93 (8H, multiplet); 5.02–5.37 (2H, multiplet); 6.79–8.26 (7H, multiplet).

PREPARATION 33

(2S,4S)-4-Mercapto-2-[(3S)-3-(1,2,4-triazol-1-yl)pyrrolidin-1-yl-1(4-nitrobenzyloxycarbonyl)pyrrolidine

33(i) (2S,4S)-4-(4-Methoxybenzylthio)-2-[(3S)-3-(1,2,4-triazol-1-yl)pyrrolidin-1-ylcarbonyl]-1-(4-nitrobenzyloxycarbonyl)pyrrolidine Following a procedure similar to that described in Preparation 18(a), but using 768 mg of (2S,4S)-4-(4-methoxybenzylthio)-1-(4-nitrobenzyloxycarbonyl)-2-pyrrolidinecarboxylic acid, 218 mg of pivaloyl chloride and 238 mg of (3S)-3-(1,2,4-triazol-1-yl)pyrrolidine trifluoroacetate, 803 mg of the title compound were obtained as a powder.

Infrared Absorption Spectrum (KBr), $v_{max}$ cm$^{-1}$: 1709, 1656, 1521, 1346, 857, 738.

Nuclear Magnetic Resonance Spectrum (hexadeuterated dimethyl sulfoxide, 270 MHz), δ ppm: 1.40–1.70 (1H, multiplet); 2.18–2.75 (2H, multiplet); 3.00–3.15 (1H, multiplet); 3.15–4.10 (13H, multiplet); 5.00–5.24 (3H, multiplet); 6.85–6.90 (2H, multiplet); 7.24–7.29 (2H, multiplet); 7.45–7.61 (2H, multiplet); 8.14–8.25 (2H, multiplet); 8.50–8.62 (1H, multiplet).

33(ii) (2S,4S)-4-Mercapto-2-[(3S)-3-(1,2,4-triazol-1-yl)pyrrolidin-1-yl-1-(4-nitrobenzyloxycarbonyl)pyrrolidine Following a procedure similar to that described in Preparation 18(b), but using the whole of the (2S,4S)-4-(4-methoxybenzylthio)-2-[(3S)-3-(1,2,4-triazol-1-yl)pyrrolidin-1-ylcarbonyl]-1-(4-nitrobenzyloxycarbonyl)pyrrolidine [prepared as described in seep (i) above], 803 mg of the title compound were obtained as a powder.

Infrared Absorption Spectrum (KBr), $v_{max}$ cm$^{-1}$: 1706, 1652, 1522, 1346, 857, 739.

Nuclear Magnetic Resonance Spectrum (hexadeuterated dimethyl sulfoxide, 270 MHz), δ ppm: 1.56–1.78 (1H, multiplet); 2.20–2.55 (2H, multiplet); 2.61–2.82 (1H, multiplet); 3.09–4.09 (9H, multiplet); 4.41–4.64 (1H, multiplet); 5.01–5.26 (3H, multiplet); 7.47–7.65 (2H, multiplet); 8.14–8.26 (2H, multiplet); 8.51–8.62 (1H, multiplet).

PREPARATION 34

(2S,4S)-4-Mercapto-2-[(3R)-3-(4-nitrobenzyloxycarbonyl)aminopyrrolidin-1-ylcarbonyl]-1-(4-nitrobenzyloxycarbonyl)pyrrolidine Following a procedure similar to that described in Preparation 18, but using 1.29 g of (2S,4S)-4-(4-methoxybenzylthio)-1-(4-nitrobenzyloxycarbonyl)-2-pyrrolidinecarboxylic acid, 365 mg of pivaloyl chloride and 1.14 g of (3R)-3-(4-nitrobenzyloxycarbonyl)aminopyrrolidine trifluoroacetate, 1.09 g of the title compound were obtained as a powder.

Infrared Absorption Spectrum (KBr), $v_{max}$ cm$^{-1}$: 1707, 1653, 1523, 1347, 855.

PREPARATION 35

(2S,4S)-4-Mercapto-2-[(3R)-3-(N-4-nitrobenzyloxycarbonylacetimidoylamino)pyrrolidin-1-ylcarbonyl]-1-(4-nitrobenzyloxycarbonyl)pyrrolidine Following a procedure similar to that described in Preparation 23, but using 3.00 g of (2S,4S)-4-(4-methoxybenzylthio)-1-(4-nitrobenzyloxycarbonyl)-2-pyrrolidinecarboxylic acid, 0.70 g of (3R)-3-aminopyrrolidine, 1.31 g of the title compound were obtained as a powder.

Infrared Absorption Spectrum (KBr), $v_{max}$ cm$^{-1}$: 1706, 1651, 1552, 1441, 1345, 1171.

Nuclear Magnetic Resonance Spectrum (hexadeuterated dimethyl sulfoxide+D$_2$O, 270 MHz), δ ppm: 1.56–2.25 (2H, multiplet); 2.09 & 2.11 (together 3H, two singlets); 2.62–2.83 (1H, multiplet); 3.04–4.09 (8H, multiplet); 4.14–4.62 (2H, multiplet); 4.98–5.37 (4H, multiplet); 7.43–7.70 (4H, multiplet); 8.15–8.30 (4H, multiplet).

PREPARATION 36

(2S,4S)-4-mercapto,2-[(3R)-3-(N-4-nitrobenzyloxycarbonylformimidoylamino)pyrrolidin-1-ylcarbonyl]-1-(4-nitrobenzyloxycarbonyl)pyrrolidine Following a procedure similar to that described in Preparations 23(iii) and 23(iv), but using 0.75 g of (2S,4S)-4-(4-methoxybenzylthio)-2-[(3R)-3-aminopyrrolidin-1-ylcarbonyl]-1-(4-nitrobenzyloxycarbonyl)pyrrolidine hydrochloride and 0.31 g of N-(4-nitrobenzyloxycarbonyl)formamidine, 0.51 g of the title compound were obtained as a powder.

Infrared Absorption Spectrum (KBr), $v_{max}$ cm$^{-1}$: 1706, 1644, 1521, 1405, 1345, 1186.

PREPARATION 37

(2S,4S)-4-Mercapto-2-[3-(4-
nitrobenzyloxycarbonyloxymethyl)-4-(4-
nitrobenzyloxycarbonyl)-1-piperazinylcarbonyl]-1-
(4-nitrobenzyloxycarbonyl)pyrrolidine

37(i) (2S,4S)-2-(3-Hydroxymethyl-1-piperazinylcarbonyl)-4-(4-methoxybenzylthio)-1-(4-nitrobenzyloxycarbonyl)pyrrolidine Following a procedure similar to that described in Preparation 8, but using 10.0 g of (2S,4S)-4-(4-methoxybenzylthio)-1-(4-nitrobenzyloxycarbonyl)-2-pyrrolidinecarboxylic acid, 4.4 g of N,N'-carbonyldiimidazole and 4.0 g of 2-hydroxymethylpiperazine, 6.9 g of the title compound were obtained, as a powder.

37(ii) (2S,4S)-4-(4-Methoxybenzylthio)-2-[3-(4-nitrobenzyloxycarbonyloxymethyl)-4-(nitrobenzyloxycarbonyl)-1-piperazinylcarbonyl]-1-(4-nitrobenzyloxycarbonyl)pyrrolidine Following a procedure similar to that described in Preparation 7(iii), but using 3.5 g of (2S,4S)-2-(3-hydroxymethyl-1-piperazinylcarbonyl)-4-(4-methoxybenzylthio)-1-(4-nitrobenzyloxycarbonyl)pyrrolidine [prepared as described in step (i) above], 4.2 g of 4-nitrobenzyl chloroformate and 2.4 g of 4-dimethylaminopyridine, 4.9 g of the title compound were obtained, as an amorphous solid.

37(iii) (2S,4S)-4-Mercapto-2-[3-(4-nitrobenzyloxycarbonyloxymethyl)-4-(4-nitrobenzyloxycarbonyl)-1-piperazinylcarbonyl]-1-(4-nitrobenzyloxycarbonyl)pyrrolidine Following a procedure similar to that described in Preparation 4(b), but using 0.23 g of (2S,4S)-4-(4-methoxybenzylthio)-2-[3-(4-nitrobenzyloxycarbonyloxymethyl)-4-(nitrobenzyloxycarbonyl)-1-piperazinylcarbonyl]-1-(4-nitrobenzyloxycarbonyl)pyrrolidine [prepared as described in step (ii) above], 0.28 ml of anisole, 2.3 ml of trifluoroacetic acid and 45 µl of trifluoromethanesulfonic acid, 190 mg of the title compound were obtained, as an amorphous solid.

Infrared Absorption Spectrum (KBr), $v_{max}$ cm$^{-1}$: 1707, 1608, 1521, 1430, 1406, 1345.

Nuclear Magnetic Resonance Spectrum (CDCl$_3$, 270 MHz), δ ppm: 1.68 (1H, singlet); 1.86–1.99 (1H, multiplet); 2.62–2.69 (1H, multiplet); 2.93 (1H, doublet of doublets, J=13.67 & 3.91 Hz); 3.10–3.63 (4H, multiplet); 3.91–4.75 (8H, multiplet); 5.11–5.30 (6H, multiplet); 7.47 (6H, doublet, J=8.30 Hz); 8.14–8.26 (6H, multiplet).

PREPARATION 38

(2S,4S)-4-Mercapto-2-[3-(4-
nitrobenzyloxycarbonyl)-4-(4-
nitrobenzyloxycarbonyl)-1-piperazinylcarbonyl]-1-
(4-nitrobenzyloxycarbonyl)pyrrolidine Following a procedure similar to that described in Preparation 8, but using 0.47 g of (2S,4S)-4-(4-methoxybenzylthio)-1-(4-nitrobenzyloxycarbonyl)-2-pyrrolidinecarboxylic acid, 0.20 g of N,N'-carbonyldiimidazole and 0.70 g of 2-(4-nitrobenzyloxycarbonyl)-1-(4-nitrobenzyloxycarbonyl)piperazine, 270 mg of the title compound were obtained as an amorphous solid.

Infrared Absorption Spectrum (KBr), $v_{max}$ cm$^{-1}$: 1707, 1653, 1607, 1522, 1430, 1346.

PREPARATION 39

(2S,4S)-4-Mercapto-2-[(3R)-1-(N-4-
nitrobenzyloxycarbonylacetimidoyl)pyrrolidin-3-
ylaminocarbonyl]-1-(4-nitrobenzyloxycarbonyl)
pyrrolidine Following a procedure similar to that described in Preparation 23(iii) and 23(iv), but using 0.76 g of (2S,4S)-4-(4-methoxybenzylthio)-1-(4-nitrobenzyloxycarbonyl)-2-[(3R)-pyrrolidin-3-ylaminocarbonyl]pyrrolidine hydrochloride and 0.33 g of N-(4-nitrobenzyloxycarbonyl)acetamidine, 0.45 g of the title compound was obtained as a powder.

Infrared Absorption Spectrum (KBr), $v_{max}$ cm$^{-1}$: 1720, 1665, 1520, 1437, 1345, 1234.

PREPARATION 40

(2S,4S)-4-Mercapto-2-{N-[2-(N-4-
nitrobenzyloxycarbonylacetimidoyl)aminoethyl]
carbamoyl}-1-(4-nitrobenzyloxycarbonyl)
pyrrolidine Following a procedure similar to that described in Preparation 17, but using 850 mg of (2S,4S)-4-(4-methoxybenzylthio)-1-(4-nitrobenzyloxycarbonyl)-2-pyrrolidinecarboxylic acid, 450 mg of ethylenediamine and 430 mg of N-(4-nitrobenzyloxycarbonyl)acetamidine, 295 mg of the title compound were obtained as a powder.

Infrared Absorption Spectrum (KBr), $v_{max}$ cm$^{-1}$: 1705, 1665, 1568, 1517, 1346, 1225.

Nuclear Magnetic Resonance Spectrum (CDCl$_3$+D$_2$O, 270 MHz), δ ppm: 2.23 (3H, singlet); 2.1–2.4 (1H, broad); 2.5–2.8 (1H, broad); 3.3–3.65 (6H, multiplet); 3.95–4.45 (2H, multiplet); 5.15–5.30 (4H, multiplet); 7.45–7.60 (4H, multiplet); 8.17–8.27 (4H, multiplet).

PREPARATION 41

(2S,4S)-4-Mercapto-2-{N-[2-(N-4-
nitrobenzyloxycarbonylformimidoyl)aminoethyl]
carbamoyl}-1-(4-nitrobenzyloxycarbonyl)
pyrrolidine Following a procedure similar to that described in Preparation 17, but using 850 mg of (2S,4S)-4-(4-methoxybenzylthio)-1-(4-nitrobenzyloxycarbonyl)-2-pyrrolidinecarboxylic acid, 450 mg of ethylenediamine and 400 mg of N-(4-nitrobenzyloxycarbonyl)formamidine, 280 mg of the title compound were obtained as a powder.

Infrared Absorption Spectrum (KBr), $v_{max}$ cm$^{-1}$: 1705, 1665, 1568, 1517, 1346, 1225.

Nuclear Magnetic Resonance Spectrum (CDCl$_3$, 270 MHz), δ ppm: 2.11–2.30 (1H, multiplet); 2.55–2.80 (1H, multiplet); 3.30–3.48 (3H, multiplet); 3.52–3.75 (3H, multiplet); 3.93–4.06 (1H, multiplet); 4.18–4.32 (1H, multiplet); 5.13–5.36 (4H, multiplet); 7.43–7.60 (4H, multiplet); 8.15–8.27 (4H, multiplet); 8.47 & 8.97 (1H, two singlets).

PREPARATION 42

(2S,4S)-4-Mercapto-2-(3-dimethylamino-1,2,5,6-
tetrahydropyrazin-1-ylcarbonyl)-1-(4-
nitrobenzyloxycarbonyl)pyrrolidine
Trifluoromethanesulfonate

42(i) (2S,4S)-4-(4-Methoxybenzylthio)-2-(3-dimethylamino-1,2,5,6-tetrahydropyrazin-1-ylcarbonyl)-1-(4-nitrobenzyloxycarbonyl)pyrrolidine Following a procedure similar to that described in Preparation 1(i), but using 446 mg of (2S,4S)-4-(4-methoxybenzylthio)-1-(4-nitrobenzyloxycarbonyl)-2-pyrrolidinecarboxylic acid, 178 mg of N,N'-carbonyldiimidazole, 289 mg of 3-dimethylamino-1,2,5,6-tetrahydropyrazine bis(trifluoroacetate) and 289 μl of diisopropylethylamine, 460 mg of the title compound were obtained, as a powder.

42(ii) (2S,4S)-4-Mercapto-2-(3-dimethylamino-1,2,5,6-tetrahydropyrazin-1-ylcarbonyl)-1-(4-nitrobenzyloxycarbonyl)pyrrolidine Trifluoromethanesulfonate Following a procedure similar to than described in Preparation 1(iv), but using the whole of the (2S,4S)-4-(4-methoxybenzylthio)-2-(3-dimethylamino-1,2,5,6-tetrahydropyrazin-1-ylcarbonyl)-1-(4-nitrobenzyloxycarbonyl)pyrrolidine [prepared as described in step (i) above], 451 mg of the title compound were obtained as a viscous oil.

Infrared Absorption Spectrum (liquid film), $v_{max}$ cm$^{-1}$: 1705, 1670, 1610, 1525, 1445, 1409, 1348, 1287, 1228.

Nuclear Magnetic Resonance Spectrum (hexadeuterated dimethyl sulfoxide+D$_2$O, 270 MHz), δ ppm: 1.58–1.78 (1H, multiplet); 2.71–2.86 (1H, multiplet); 2.88–3.86 (12H, multiplet); 3.90–4.10 (1H, multiplet); 4.48–4.68 (2H, multiplet); 4.75–4.92 (1H, multiplet); 5.02–5.23 (2H, multiplet); 7.52 & 7.63 (together 2H, two doublets, J=8.79 Hz); 8.21 & 8.23 (together 2H, two doublets, J=8.79 Hz).

PREPARATION 43

(2S,4S)-4-Mercapto-2-[4-(N-4-nitrobenzyloxycarbonyl-acetimidoyl) aminopiperidin-1-ylcarbonyl]-1-(4-nitrobenzyloxycarbonyl)pyrrolidine Following a procedure similar to that described in Preparation 1, but using 446 mg of (2S,4S)-4-(4-methoxybenzylthio)-1-(4-nitrobenzyloxycarbonyl)-2-pyrrolidinecarboxylic acid, 220 mg of 4-t-butoxycarbonylaminopiperidine and 119 mg of N-(4-nitrobenzyloxycarbonyl)-acetamidine, 307 mg of the title compound were obtained as a powder.

Infrared Absorption Spectrum (KBr), $v_{max}$ cm$^{-1}$: 1781, 1703, 1633, 1610, 1345.

Nuclear Magnetic Resonance Spectrum (CDCl$_3$, 270 MHz), δ ppm:

1.40–2.15 (7H, multiplet);
2.21 & 2.32 (together 3H, two singlets);
2.65–2.80 (1H, multiplet);
3.10–3.50 (3H, multiplet);
3.65–4.75 (6H, multiplet);
5.23 (4H, singlet);
7.48–7.60 (4H, multiplet);
8.18–8.26 (4H, multiplet).

PREPARATION 44

(2S,4S)-4-Mercapto-2-[4-(N-4-nitrobenzyloxycarbonyl-acetimidoyl) piperazin-1-ylcarbonyl)-1-methylpyrrolidine Following a procedure similar to that described in Preparation 1, but using 282 mg of (2S,4S)-4-(4-methoxybenzylthio)-1-methyl-2-pyrrolidinecarboxylic acid, 203 mg of 1-t-butoxycarbonylpiperazine and 258 mg of N-(4-nitrobenzyloxycarbonyl)acetamidine, 225 mg of the title compound were obtained as a viscous oil.

The title compound was also prepared by acylating 1-(N-4-nitrobenzyloxycarbonylacetimidoyl)piperazine with 4-(4-methoxybenzylthio)-1-methylpyrrolidine-2-carboxylic acid and then deprotecting the product.

Infrared Absorption Spectrum (liquid film), $v_{max}$ cm$^{-1}$: 1780, 1705, 1635, 1610, 1346.

Nuclear Magnetic Resonance Spectrum (hexadeuterated dimethyl sulfoxide+D$_2$O, 270 MHz), δ ppm:

1.77–1.90 (1H, multiplet);
2.14 (3H, singlet);
2.82 (3H, singlet);
2.95–3.05 (1H, multiplet);
3.10–3.28 (3H, multiplet);
3.45–3.80 (8H, multiplet);
4.60 (1H, doublet of doublets, J=9.3 & 8.3 Hz);
5.28 (2H, singlet);
7.66 (2H, doublet, J=8.8 Hz);
8.25 (2H, doublet, J=8.8 Hz).

PREPARATION 45

(2S,4S)-4-Mercapto-2-[(3S)-3-(4-nitrobenzyloxycarbonyl)aminopyrrolidin-1-ylcarbonyl]carbonyl]-1-methylpyrrolidine Following a procedure similar to that described in Preparation 18, but using 1.03 g of (2S,4S)-4-(4-methoxybenzylthio)-1-methyl-2-pyrrolidinecarboxylic acid, 463 mg of pivaloyl chloride and 1.45 g of (3S)-3-(4-nitrobenzyloxycarbonyl)aminopyrrolidine trifluoroacetate, 1.07 g of the title compound were obtained as a powder.

Infrared Absorption Spectrum (KBr), $v_{max}$ cm$^{-1}$: 1703, 1655, 1522, 1347, 854, 737.

Nuclear Magnetic Resonance Spectrum (hexadeuterated dimethyl sulfoxide, 270 MHz), δ ppm:

1.65–3.85 (15H, multiplet);
3.85–4.20 (2H, multiplet);
5.19 (2H, singlet);
7.62 (2H, doublet, J=8.30 Hz);
7.70–7.90 (1H, multiplet);
8.20–8.30 (2H, multiplet).

PREPARATION 46

(2S,4S)-4-Mercapto-2-[(3S)-3-(N-4-nitrobenzyloxycarbonylformimidoylamino) pyrrolidin-1-ylcarbonyl]-1-methylpyrrolidine 46(i) (2S,4S)-4-(4-Methoxybenzylthio)-2-[(3S)-3-aminopyrrolidin-1-ylcarbonyl]-1-(4-nitrobenzyloxycarbonyl)-1-methylpyrrolidine hydrochloride Following a procedure similar to that described in Preparations 23(i) and 23(ii), but using 2.55 g of (2S,4S)-4-(4-methoxybenzylthio)-1-methyl-2-pyrrolidine-carboxylic acid and 0.94 g of (3S)-3-aminopyrrolidine, 2.91 g of the title compound were obtained as a powder.

46(ii) (2S,4S)-4-Mercapto-2-[(3S)-3-(N-4-nitrobenzyl-oxycarbonylformimidoylamino) pyrrolidin-1-yl)carbonyl]-1-methylpyrrolidine Following a procedure similar to that described in Preparations 23(iii) and 23(iv), but using N-(4- nitrobenzyloxycarbonyl )formamidine instead of the N-(4-nitrobenzyloxycarbonyl)acetamidine used in Preparation 23(iii), 1.02 g of the title compound was obtained as a powder.

Infrared Absorption Spectrum (liquid film), $v_{max}$ cm$^{-1}$: 1705, 1650, 1510, 1440, 1345, 1173.

Nuclear Magnetic Resonance Spectrum (hexadeuterated dimethyl sulfoxide, 270 MHz), δ ppm:

1.60–4.60 (19H, multiplet);

5.10–5.30 (2H, multiplet);

7.55–7.75 (2H, multiplet);

8.25–8.28 (2H, multiplet).

PREPARATION 47

(2S,4S)-4-Mercapto-2-[4-(imidazol-1-yl)piperadin-1-ylcarbonyl]-1-(4-nitrobenzyloxycarbonyl) pyrrolidine 47(i) (2S,4S)-4-(4-Methoxybenzylthio)-2-[4-(imidazol-1-yl)piperidin-1-ylcarbonyl]-1-(4-nitrobenzyloxycarbonyl)-pyrrolidine 660 mg of N,N'-carbonyldiimidazole were added to a solution of 1.52 g of (2S,4S)-4-(4-methoxybenzylthio)-1-(4-nitrobenzyloxycarbonyl)-2-pyrrolidinecarboxylic acid in 15 ml of dry acetonitrile, and the resulting mixture was stirred at room temperature for 30 minutes. A solution of 538 mg of 4-(imidazol-1-yl)piperidine in 5 ml of dry acetonitrile was then added to the solution, and the mixture was stirred at room temperature for 30 minutes and then at 40° C. for a further 7 hours. At the end of this time, the reaction mixture was concentrated by evaporation under reduced pressure, and the residue was dissolved in ethyl acetate. The resulting solution was washed with an aqueous solution of sodium hydrogen-carbonate, with water and with an aqueous solution of sodium chloride, in that order. The organic solution was then dried over anhydrous sodium sulfate, and the solvent was removed by distillation under reduced pressure. The residue was purified by reverse phase column chromatography through 200 ml of Cosmo Sil 75C$_{18}$-PREP (a trade mark for a product of Nacalai Tesque), using a gradient elution method, with mixtures of acetonitrile and water ranging from 50:50 to 45 by volume as the eluent. Those fractions containing the title compound were combined and concentrated by evaporation under reduced pressure, to give 1.45 g of the title compound, as a powder.

Infrared Absorption Spectrum (liquid film), $v_{max}$ cm$^{-1}$: 1709, 1655, 1609, 1512, 1345, 1246, 1110.

Nuclear Magnetic Resonance Spectrum (CDCl$_3$, 270 MHz), δ ppm:

1.70–1.95 (2H, multiplet);

2.05–2.23 (3H, multiplet);

2.40–2.55 (1H, multiplet);

2.60–2.85 (1H, multiplet);

3.03–3.43 (3H, multiplet);

3.73 (3H, singlet);

3.77–4.25 (5H, multiplet);

4.59–4.84 (2H, multiplet);

5.02–5.35 (2H, multiplet);

6.85 (2H, doublet, J=8.8 Hz);

6.96 (1H, singlet);

7.07 & 7.09 (together 1H, two singlets);

7.23 (2H, doublet, J=8.8 Hz);

7.47 (2H, doublet, J=8.8 Hz);

7.56 (1H, singlet);

8.23 (2H, doublet, J=8.8 Hz).

47(ii) (2S,4S)-4-Mercapto-N-[4-(imidazol-1-yl)-piperidin-1-ylcarbonyl]-1-(4-nitrobenzyloxycarbonyl)-pyrrolidine 350 μl of trifluoromethanesulfonic acid were added, whilst ice-cooling, to a solution of 1.44 g of (2S,4S)-4-(4-methoxybenzylthio)-2-[4-(imidazol-N-yl)-piperidin-1-ylcarbonyl]-1-(4-nitrobenzyloxycarbonyl)-pyrrolidine [prepared as described in step (i) above] in a mixture of 1.5 ml of anisole and 7.5 ml of trifluoroacetic acid, and the resulting mixture was stirred at room temperature for 1 hour and then at 35° C. for a further 30 minutes. At the end of this time, the reaction mixture was concentrated by evaporation under reduced pressure, and the residue was washed four times with diethyl ether to give a colorless powder. The whole of this powder was suspended in ethyl acetate and the suspension was made alkaline by the addition of an aqueous solution of sodium hydrogencarbonate. The ethyl acetate layer was separated, washed with an aqueous solution of sodium chloride and dried over anhydrous sodium sulfate. The solvent was removed by distillation under reduced pressure, to give, 1.15 g of the title compound, as a colorless powder.

Nuclear Magnetic Resonance Spectrum (hexadeuterated dimethyl sulfoxide, 270 MHz), δ ppm:

1.55–1.85 (3H, multiplet);

2.00–2.11 (2H, multiplet);

2.63–2.89 (2H, multiplet);

3.05–3.30 (4H, multiplet);

3.92–4.15 (2H, multiplet);

4.25–4.59 (2H, multiplet);

4.71–4.92 (1H, multiplet);

5.03–5.27 (2H, multiplet);

6.92–8.28 (7H, multiplet).

Infrared Absorption Spectrum (liquid film), $v_{max}$ cm$^{-1}$: 1705, 1652, 1523, 1442, 1347, 1268, 1170, 1035.

PREPARATION 48

(2S,4S)-2-[3,3-Dimethyl-4-(4-nitrobenzyloxycarbonyl)-1-piperazinylcarbonyl]-4-mercapto-1-(4-nitrobenzyl-oxycarbonyl)pyrrolidine Following a procedure similar to that described in Preparation 38, but using 0.35 g of methoxybenzylthio)-1-(4-nitrobenzyloxycarbonyl)-2-pyrrolidinecarboxylic acid, 0.15 g of N,N'-carbonyl-diimidazole and 0.13 g of 2,2-dimethylpiperazine, 250 mg of the title compound were obtained as an amorphous solid.

Infrared Absorption Spectrum (KBr), $v_{max}$ cm$^{-1}$: 1707, 1652, 1607, 1521, 1431, 1347.

PREPARATION 49

(2S,4S)-4-Mercapto-1-methyl-2-[4-(4-nitrobenzyloxy-carbonyl)-1-homopiperazinylcarbonyl]pyrrolidine trifluoromethanesulfonate 49(i) [2S,4S)-2-Carbamoyl-4-(4-methoxybenzylthio) -1-methylpyrrolidine 10.86 ml of dimethyl sulfate were added to a solution of 30 g of (2S,4S)-2-carbamoyl-4-(4-methoxybenzylthio)

pyrrolidine hydrochloride in a mixture of 36 ml of a 20% w/v aqueous solution of sodium hydroxide and 470 ml of dioxane, and the resulting mixture was stirred at a temperature of between 22° C. and 23° C. for 1 hour. At the end of this time, the reaction mixture was concentrated by evaporation under reduced pressure, and the resulting residue was extracted with 2 liters of ethyl acetate. The extract was washed with an aqueous solution of sodium chloride and dried over anhydrous magnesium sulfate. The solution was then concentrated by evaporation under reduced pressure, until crystals emerged, and then 400 ml of diisopropyl ether were added to the mixture and the crystals which precipitated were collected by filtration, to give 23 g of the title compound as crystals, melting at 113°–114° C.

Infrared Absorption Spectrum (KBr), $v_{max}$ cm$^{-1}$: 1636, 1609, 1512.

Nuclear Magnetic Resonance Spectrum (60 MHz, CDCl$_3$) δ ppm:

1.58–3.36 (6H, multiplet);
2.35 (3H, singlet);
3.68 (2H, singlet);
3.78 (3H, singlet);
5.95 (1H, broad singlet);
6.84 & 7.23 (4H, A$_2$B$_2$, J=9.0 Hz);
7.20 (1H, broad singlet).

49(ii) (2S,4S)-2-Carboxy-4-(4-methoxybenzylthio)-1-methylpyrrolidine 15.16 g of (2S,4S)-2-carbamoyl-4-(4-methoxybenzylthio)-1-methylpyrrolidine [prepared as described in step (i) above] were dissolved in 170 ml of 2N aqueous hydrochloric acid, and the solution was stirred in a bath kept at 110° C. for 3.5 hours. At the end of this time, the reaction mixture was cooled to room temperature, and its pH was adjusted to a value of by the addition of sodium carbonate. The mixture was then concentrated by evaporation under reduced pressure, after which it was allowed to stand in a refrigerator precipitate crystals. The precipitated crystals were collected by filtration and washed with a small amount of cold water. They were then dried, to give 10.4 g of the title compound. The mother liquor was then concentrated by evaporation under reduced pressure, and the residue was subjected to column chromatography through CHP20P (75–150μ, Mitsubishi Chemical Industries, Ltd.), using 50% v/v aqueous methanol as the eluent, to afford a further 3.7 g of the title compound, as crystals melting an 185°–187.5° C.

Infrared Absorption Spectrum (KBr), $v_{max}$ cm$^{-1}$: 1641, 1623, 1512, 1373, 1311, 1253.

Nuclear Magnetic Resonance Spectrum (270 MHz, D$_2$O) δ ppm:

1.83–1.93 (1H, multiplet);
2.59–2.75 (1H, multiplet);
2.72 (3H, singlet);
3.16–3.23 (1H, multiplet);
3.03–3.43 (2H, multiplet);
3.62 (2H, singlet);
3.64 (3H, singlet);
3.74 (1H, doublet of doublets, J=9.53 & 6.96 Hz);
6.80 (2H, doublet, J=8.60 Hz);
7.15 (2H, doublet, J=8.60 Hz).

49(iii) (2S, 4S) -4-(4-Methoxybenzylthio)-1-methyl-2-[4-(4-nitrobenzyloxycarbonyl)-1-homopiperazinylcarbonyl]-pyrrolidine A suspension of 1.8 g of (2S,4S)-2-carboxy-4-(4-methoxybenzylthio)-1-methylpyrrolidine [prepared as described in step (ii) above] and 1.26 g of N,N'-carbonyldiimidazole in 18 ml of dry acetonitrile was stirred at 35° C. for 25 minutes. A solution of 3.7 g of 1-(4-nitrobenzyloxycarbonyl)homopiperazine trifluoroacetate in 20 ml of dry acetonitrile and 2.0 ml of N,N-diisopropylethylamine were then simultaneously added dropwise, whilst ice-cooling, to the reaction mixture, and the resulting mixture was stirred at room temperature for 8 hours, after which it was allowed to stand overnight at room temperature. At the end of this time, the reaction mixture was concentrated by evaporation under reduced pressure, and the residue was dissolved in ethyl acetate. The solution was washed with an aqueous solution of sodium hydrogencarbonate, with a phosphate buffer solution (pH 6.86), with water and with an aqueous solution of sodium chloride, in that order. The ethyl acetate layer was then dried over anhydrous magnesium sulfate, and the solvent was removed by distillation under reduced pressure. The resulting residue was purified by column chromatography through silica gel (Merck Art 9385), using a 95:5 by volume mixture of acetonitrile and water, to give 2.5 g of the title compound.

Infrared Absorption Spectrum (liquid film), $v_{max}$ cm$^{-1}$: 1701, 1646, 1513, 1426, 1346, 1246.

Nuclear Magnetic Resonance Spectrum (CDCl$_3$, 270 MHz), δ ppm:

1.66–1.95 (4H, multiplet);
2.26 & 2.29 (together 3H, two singlets);
2.42–2.63 (2H, multiplet);
3.07–3.23 (3H, multiplet);
3.44–3.82 (7H, multiplet);
3.70 (2H, singlet);
3.79 (3H, singlet);
5.15 5.30 (2H, multiplet);
6.83 (2H, doublet, J=8.30 Hz);
7.21 (2H, doublet, J=8.30 Hz);
7.49 & 7.50 (together 2H, two doublets, 8.30 Hz).

49(iv) (2S,4S)-4-Mercapto-1-methyl-2-[4-(4-nitrobenzyloxycarbonyl)-1-homopiperazinylcarbonyl]pyrrolidine trifluoromethanesulfonate 25 ml of trifluoroacetic acid and 0.83 ml of trifluoromethanesulfonic acid were added dropwise, whilst ice-cooling, to a solution of 2.5 g of (2S,4S)-4-(4-methoxybenzylthio)-1-methyl-2-[4-(4-nitrobenzyloxycarbonyl)-1-homopiperazinylcarbonyl]-pyrrolidine [prepared as described in step (iii) above] in 5.2 ml of anisole, and the resulting mixture was stirred at the same temperature for 50 minutes. At the end of this time, the reaction mixture was concentrated by evaporation under reduced pressure, and the residue was decanted, in turn, with hexane and with diethyl ether, to give 2.7 g of the title compound as an amorphous solid.

Infrared Absorption Spectrum (liquid film), $v_{max}$ cm$^{-1}$: 1688, 1650, 1522, 1483, 1434, 1349.

Nuclear Magnetic Resonance Spectrum (270 MHz, hexa-deuterated dimethyl sulfoxide) δ ppm:

1.58–1.92 (2H, multiplet);
2.67–3.08 (3H, multiplet);
3.28–3.82 (13H, multiplet);
4.20–4.85 (2H, multiplet);
5.16–5.28 (2H, multiplet);
7.53–7.67 (2H, multiplet);

PREPARATION 50

(2S,4S)-4-(4-Mercapto)-2-[4-(4-nitrobenzyloxycarbonylmethyl)-1-homopiperazinylcarbonyl]-1-(4-nitrobenzyloxycarbonyl)pyrrolidine bis (trifluoromethanesulfonate)

50(i) (2S,4S)-4-(4-Methoxybenzylthio)-2-[4-(4-nitrobenzyloxycarbonylmethyl)-1-homopiperazinylcarbonyl]-1-(4-nitrobenzyloxycarbonyl)pyrrolidine 3.5 g of N,N'-carbonyldiimidazole were added to a solution of 8.0 g of (2S,4S)-4-(4-methoxybenzylthio)-1-(4-nitrobenzyloxycarbonyl)-2-pyrrolidinecarboxylic acid in 80 ml of dry acetonitrile, and the resulting mixture was stirred at room temperature for 30 minutes. A solution of 14.0 g of 1-(4-nitrobenzyloxycarbonylmethyl)homopiperazine bis (trifluoroacetate) in 80 ml of dry acetonitrile and 14.1 ml of diisopropylethylamine were added, whilst ice-cooling, to the mixture, and the resulting mixture was stirred at room temperature for 1.5 hours and then at 30° C. for a further 1.5 hours, after which it was allowed to stand overnight at room temperature. At the end of this time, the reaction mixture was concentrated by evaporation under reduced pressure, and the resulting residue was diluted with ethyl acetate. The dilute solution was washed with water and with an aqueous solution of sodium chloride, in that order, and it was then dried over anhydrous magnesium sulfate. The solvent was then removed by distillation under reduced pressure, and the resulting residue was purified by column chromatography through silica gel (Merck Art 9385), using ethyl acetate as the eluent, to give 7.6 g of the title compound as an amorphous solid.

Infrared Absorption Spectrum (liquid film), $v_{max}$ cm$^{-1}$: 1748, 1709, 1650, 1608, 1520, 1429, 1404, 1346.

Nuclear Magnetic Resonance Spectrum (CDCl$_3$, 270 MHz), δ ppm:

1.71–2.03 (3H, multiplet);
2.42–3.17 (6H, multiplet);
3.32–4.08 (8H, multiplet);
3.73 (2H, multiplet);
3.80 & 3.82 (together 3H, two singlets)
4.49–4.63 (1H, multiplet);
5.02–5.35 (4H, multiplet);
6.85 (2H, doublet, J=8.30 Hz);
7.23 (2H, doublet, J=8.30 Hz);
7.43–7.52 (4H, multiplet);
8.15–8.25 (4H, multiplet).

50(ii) (2S, 4S)-4-Mercapto-2-[4-(4-nitrobenzyloxycarbonylmethyl)-1-homopiperazinylcarbonyl]-1-(4-nitrobenzyloxycarbonyl)pyrrolidine bis (trifluoromethanesulfonate)

15 ml of trifluoroacetic acid and 0.36 ml of trifluoromethanesulfonic acid were added, whilst ice-cooling, to a solution of 1.47 g of (2S,4S)-4-(4-methoxybenzylthio)-2-[4-(4-nitrobenzyloxycarbonylmethyl)-1-homopiperazinylcarbonyl]-1-(4-nitrobenzyloxycarbonyl)-pyrrolidine [prepared as described in step (i) above] in 2.2 ml of anisole, and the resulting mixture was stirred at room temperature for 1 hour. The solvent was then removed by distillation under reduced pressure, and the resulting residue was repeatedly washed with diethyl ether by decantation and dried in vacuo to give 1.8 g of the title compound, as a powder.

Infrared Absorption Spectrum (KBr), $v_{max}$ cm$^{-1}$: 1757, 1700, 1608, 1523, 1441, 1408, 1348.

Nuclear Magnetic Resonance Spectrum (270 MHz, hexadeuterated dimethyl sulfoxide) δ ppm:

1.61–1.80 (1H, multiplet);
2.00–2.28 (2H, multiplet);
2.65–2.86 (1H, multiplet);
3.08–4.24 (13H, multiplet);
4.31–4.48 (2H, multiplet);
5.02–5.37 (2H, multiplet);
5.42 (2H, singlet);
7.52 & 7.62 (together 2H, two doublets, 8.79 Hz);
8.23 (2H, doublet, J=8.79 Hz);
8.27 (2H, doublet, J=8.30 Hz).

PREPARATION 51

(2S,4S)-4-Mercapto-2-(4-methyl-1-piperazinylcarbonyl)-1-methylpyrrolidine difluoromethanesulfonate

51(1) (2S,4S)-4-(4-Methoxybenzylthio)-2-(N-methyl-1-piperazinylcarbonyl)-1-methylpyrrolidine 700 mg of N,N'-carbonyldiimidazole were added to a suspension of 1.0 g of (2S,4S)-2-carboxy-4-(4-methoxybenzylthio)-1-methylpyrrolidine in 15 ml of dry acetonitrile, and the resulting mixture was stirred at 40° C. for 30 minutes. At the end of this time, the reaction mixture was ice-cooled, and 440 μl of N-methylpiperazine were added to the mixture. The temperature was then allowed to rise to room temperature over a period of 30 minutes. At the end of this time, the reaction mixture was concentrated by evaporation under reduced pressure, and the residue was purified by reverse phase column chromatography using LiChroprep RP-8 (trade mark) as stationary phase and 70% v/v aqueous methanol as the eluent, to give 1060 mg of the title compound as an oil.

Nuclear Magnetic Resonance Spectrum (CDCl$_3$, 270 MHz), δ ppm:

1.77–1.85 (1H, multiplet);
2.30 (3H, singlet);
2.32 (3H, multiplet);
2.35–2.56 (5H, multiplet);
3.05–3.17 (3H, multiplet);
3.70 (2H, singlet);
3.80 (3H, singlet);
3.53–3.95 (5H, multiplet);
6.84 (2H, doublet, J=8.8 Hz);
7.21 (2H, doublet, J=8.8 Hz).

Infrared Absorption Spectrum (liquid film), $v_{max}$ cm$^{-1}$: 635, 1611, 1511, 1460, 1445, 1292, 1248, 1033, 833.

51(ii) (2S,4S)-4-Mercapto-2-(4-methyl-1-piperazinylcarbonyl)-1-methylpyrrolidine bis (trifluoromethane-sulfonate)

10 ml of trifluoroacetic acid, followed by liters of trifluoromethanesulfonic acid were added, whilst ice-cooling, to a solution of 1050 mg of (2S,4S)-4-(4-methoxybenzylthio)-2-(4-methyl-1-piperazinylcarbonyl)-1-methylpyrrolidine [prepared as described in step (i) above] in 3 ml of anisole, and the resulting mixture was stirred at room temperature for 1 hour. At the end of this time, the reaction mixture was concentrated by evaporation under reduced pressure, and the residue was triturated with diethyl ether to cause solidification. The solid was washed with diethyl ether five times and dried, to give 1350 mg of the title compound as a powder.

Nuclear Magnetic Resonance Spectrum (270 MHz, hexadeuterated dimethyl sulfoxide) δ ppm:

1.74–1.86 (1H, multiplet);
2.81 (3H, singlet);
2.84 (3H, singlet);
2.94–3.20 (4H, multiplet);
3.28–3.87 (12H, multiplet).

Infrared Absorption Spectrum (KBr), $v_{max}$ cm$^{-1}$: 1665, 1480, 1272, 1240, 1226, 1163, 1030, 640.

PREPARATION 52

(2S,4S)-2-[4-(2-Hydroxyethyl)-1-piperazinylcarbonyl)-4-mercapto-1-methylpyrrolidine bis(trifluoromethanesulfonate)

52(i) (2S,4S)-2-[4-(2-Hydroxyethyl)-1-piperazinylcarbonyl) -4-(4-methoxybenzylthio)-1-methylpyrrolidine 800 mg of N,N'-carbonyldiimidazole were added to a suspension of 1.13 g of (2S,4S)-2-carboxy-4-(4-methoxybenzylthio)-1-methylpyrrolidine in 20 ml of dry acetonitrile, and the resulting mixture was stirred at 40° C. for 30 minutes. At the end of this time, the reaction mixture was ice-cooled, and 600 mg of N-hydroxyethylpiperazine were added to the mixture. The temperature was allowed to rise to room temperature over a period of 30 minutes. The reaction mixture was then concentrated by evaporation under reduced pressure, and the residue was purified by reverse phase column chromatography using LiChroprep RP-8 (trade mark) as the stationary phase and 70% v/v aqueous methanol as the eluent, to give 1160 mg of the title compound as a colorless oil.

Nuclear Magnetic Resonance Spectrum (CDCl$_3$, 270 MHz), δ ppm:

1.76–1.87 (1H, multiplet);
2.32 (3H, singlet);
2.43–2.58 (9H, multiplet);
3.06–3.18 (3H, multiplet);
3.64 (2H, triplet, J=5.4 Hz);
3.70 (2H, singlet);
3.80 (3H, singlet);
3.52–4.08 (4H, multiplet);
6.84 (2H, doublet, J=8.8 Hz);
7.21 (2H, doublet, J=8.8 Hz).

Infrared Absorption Spectrum (liquid film), $v_{max}$ cm$^{-1}$: 1637, 1611, 1511, 1461, 1444, 1247, 1034, 834.

52(ii) (2S,4S)-4-Mercapto-2-[4-(2-hydroxyethyl) -1-piperazinylcarbonyl-1-methylpyrrolidine bis (trifluoromethanesulfonate)

10 ml of trifluoroacetic acid and 520 μl of trifluoromethanesulfonic acid were added; whilst ice-cooling, to a solution of 1150 mg of (2S,4S)-2-[4-(2-hydroxyethyl)-1-piperazinylcarbonyl)-4-(4-methoxy-benzylthio)-1-methylpyrrolidine [prepared as described in step (i) above] in 3 ml of anisole, and the resulting mixture was stirred at room temperature for 1 hour. At the end of this time, the reaction mixture was concentrated by evaporation under reduced pressure, to give 1680 mg of the title compound as an oil.

Nuclear Magnetic Resonance Spectrum (270 MHz, D$_2$O, using sodium tetradeuterated trimethylsilylpropionate as an internal standard), δ ppm:

1.99–2.09 (1H, multiplet);
2.98 (3H, singlet);
3.11–3.40 (8H, multiplet);
3.60–3.85 (3H, multiplet);
3.90–3.99 (6H, multiplet).

PREPARATION 53

(2S,4S)-4-Mercapto-2-[4-(2-carbamoyloxyethyl) -1-piperazinylcarbonyl]-1-(4-nitrobenzyloxycarbonyl)-pyrrolidine trifluoromethanesulfonate 53(i) (2S,4S)-2-[4-(2-Hydroxyethyl)-1-piperazinylcarbonyl]-4-(4-methoxybenzylthio)-1-(4-nitrobenzyloxy-carbonyl)pyrrolidine 10.9 g of N,N'-carbonyldiimidazole were added to a solution of 25.0 g of (2S,4S)-4-(4-methoxybenzylthio)-1-(4-nitrobenzyloxycarbonyl)-2-pyrrolidinecarboxylic acid in 200 ml of dry acetonitrile, and the resulting mixture was stirred at room temperature for 1 hour. A solution of 10.9 g of 1-(2-hydroxyethyl)piperazine in 50 ml of dry acetonitrile was added to the reaction mixture, and the resulting mixture was stirred at room temperature for 45 minutes. An the end of this time, the reaction mixture was concentrated by evaporation under reduced pressure, after which it was diluted with 800 ml of ethyl acetate. The dilute solution was washed, in turn, with water (200 ml, three times) and an aqueous solution of sodium chloride (150 ml, once). The resulting ethyl acetate solution was concentrated by evaporation under reduced pressure to a volume of 100 ml, and the crystals which precipitated were collected by filtration, to give 28.6 g of the title compound as colorless crystals, melting at 140°–141° C.

Infrared Absorption Spectrum (KBr), $v_{max}$ cm$^{-1}$: 1710, 1653, 1670, 1512, 1439, 1404, 1344.

Nuclear Magnetic Resonance Spectrum (CDCl$_3$, 270 MHz), δ ppm:

1.48–1.85 (2H, multiplet);
2.32–2.64 (6H, multiplet);
2.59 (2H, triplet, J=5.37 Hz);
3.03–3.16 (1H, multiplet);
3.30–3.71 (5H, multiplet);
3.65 (2H, triplet, J=5.37 Hz);
3.73 (2H, singlet);
3.79 & 3.80 (together 3H, two singlets);
3.82–4.07 (1H, multiplet);
4.56 & 4.61 (together 1H, two triplets, J=8.30 Hz);
5.02–5.31 (2H, multiplet);
6.85 (2H, doublet, J=8.79 Hz);
7.23 (2H, doublet, J=8.79 Hz);
7.43 & 7.47 (together 2H, two doublets, J=8.79 Hz);
8.18 & 8.23 (together 2H, two doublets, J=8.79 Hz).

53(ii) (2S,4S)-2-[4-(2-Carbamoyloxyethyl)-1-piperazinylcarbonyl]-N-(4-methoxybenzylthio)-1-(4-nitrobenzyloxycarbonyl)pyrrolidine 1.43 ml of trichloroacetyl isocyanate were added, whilst ice-cooling, to a solution of 5.59 g of (2S,4S)-[4-(2- hydroxyethyl)-1-piperazinylcarbonyl]-4-(4-methoxybenzylthio)-1-(4-nitrobenzyloxycarbonyl)-pyrrolidine [prepared as described in step (i) above] in 50 ml of dry methylene chloride, and the resulting mixture was stirred at the same temperature for 30 minutes. At the end of this time, the solvent was removed by distillation under reduced pressure, and the resulting residue was dissolved in 120 ml of methanol. This solution was then stirred at room temperature for 4.5 hours in the presence of 35 g of silica gel (Merck, silica gel 60, 230 400 mesh). The silica gel was removed by filtration and the filtrate was freed from the solvent. The residue was purified by column chromatography through silica gel, using a 8:1 by volume mixture of ethyl acetate and methanol as the eluent, to give 5.76 g of the title compound as a colorless powder.

Infrared Absorption Spectrum (KBr), $v_{max}$ cm$^{-1}$: 3353, 1711, 1652, 1608, 1513, 1344, 1242.

Nuclear Magnetic Resonance Spectrum (270 MHz, hexa-deuterated dimethyl sulfoxide) δ ppm:
1.38–1.57 (1H, multiplet);
2.14–2.70 (7H, multiplet);
2.98–4.08 (9H, multiplet);
3.72 & 3.74 (together 3H, two singlets);
3.77 (2H, singlet);
4.66 & 4.77 (together 1H, two triplets, J=7.81 Hz);
5.02–5.25 (2H, multiplet);
6.45 (2H, broad singlet);
6.88 (2H, doublet, J=8.79 Hz);
7.26 (2H, doublet, J=8.79 Hz);
7.52 & 7.60 (together 2H, two doublets, J=8.79 Hz);
8.20 &.8.24 (together 2H, two doublets, J=8.79 Hz).

53(iii) (2S,4S)-4-Mercapto-2-[4-(2-carbamoyloxyethyl) -1-piperazinylcarbonyl]yl-(4-nitrobenzyloxy-carbonyl)pyrrolidine trifluoromethanesulfonate 2.67 ml of trifluoroacetic acid and 122 μl of trifluoromethanesulfonic acid were added, whilst ice-cooling, to a solution of 417 mg of (2S,4S)-4-(4-methoxybenzylthio)-2-[4-(2-carbamoyloxyethyl) -1-piperazinylcarbonyl]-1-(4-nitrobenzyloxycarbonyl)-pyrrolidine [prepared as described in step (ii) above] in 753 μl of anisole, and the resulting mixture was stirred at the same temperature for 1 hour. An the end of this time, the solvent was removed by distillation under reduced pressure, and the residue was repeatedly washed with diethyl ether by decantation. After the residue had been dried in vacuo, 325 mg of the title compound were obtained, as a powder.

Infrared Absorption Spectrum (KBr), $v_{max}$ cm$^{-1}$: 1707, 1608, 1524, 1438, 1347, 1280, 1169, 1030.

Nuclear Magnetic Resonance Spectrum (270 MHz. hexa-deuterated dimethyl sulfoxide+$D_2O$) δ ppm:
1.60–1.84 (1H, multiplet);
2.65–2.90 (1H, multiplet);
2.85–4.60 (14H, multiplet);
4.63–5.30 (4H, multiplet);
7.52 & 7.64 (together 2H, two doublets, J=8.79 Hz);
8.23 & 8.24 (together 2H, two doublets, J=8.79 Hz).

PREPARATION 54

(2S,4S)-2-[4-(2-Hydroxyethyl)-1-piperazinylcarbonyl]-4-mercapto -1-(4-nitrobenzyloxycarbonyl)pyrrolidine 54(a)(i) trans-4-Methanesulfonyloxy-1-(4-nitrobenzyl-oxycarbonyl)-L-proline 12.20 ml of triethylamine and 6.81 ml of methanesulfonyl chloride were added, whilst ice-cooling, to a solution of 12.41 g of trans-4-hydroxy-1-(4-nitro-benzyloxycarbonyl)-L-proline in 100 ml of dry tetrahydrofuran, and the resulting mixture was stirred at the same temperature for 40 minutes. At the end of this time, the reaction mixture was concentrated by evaporation under reduced pressure, and the residue was mixed with 350 ml of ethyl acetate and 50 ml of 1N aqueous hydrochloric acid. The mixture was then stirred at room temperature for 2.5 hours, after which the organic layer was separated and washed three times with an aqueous solution of sodium chloride; it was then dried over anhydrous magnesium sulfate. The solvent was removed by distillation under reduced pressure, to give 12.57 g of the title compound, as a powder.

Infrared Absorption Spectrum (KBr), $v_{max}$ cm$^{-1}$: 1834, 1753, 1713, 1524, 1346, 1173.

Nuclear Magnetic Resonance Spectrum (CDCl$_3$, 270 MHz), δ ppm:
2.31–2.88 (2H, multiplet);
3.08 (3H, singlet);
3.76–4.07 (2H, multiplet);
4.58 (1H, triplet, J=7.81 Hz);
5.05–5.41 (3H, multiplet);
7.46 & 7.52 (together 2H, two doublets, J=8.79 Hz);
7.50 (1H, broad singlet);
8.19 & 8.22 (together 2H, two doublets, J=8.79 Hz).

54(a)(ii) (2S,4R)-2-[4-(2-Hydroxyethyl)-1-piperazinylcarbonyl]-4-methanesulfonyloxy -1-(4-nitrobenzyloxy-carbonyl)pyrrolidine 1.11 g of 1-(2-hydroxyethyl)piperazine, 1.29 ml of diethyl cyanophosphonate and 1.18 ml of triethylamine were added, in that order, whilst ice-cooling, to a solution of 3.00 g of trans-4-methanesulfonyloxy-1-(4-nitrobenzyloxycarbonyl)-L-proline [prepared as described in step 54(a)(i) above] in 35 ml of dry acetonitrile, and the resulting mixture was stirred at room temperature for 30 minutes. At the end of this time, the reaction mixture was concentrated by evaporation under reduced pressure, and the residue was purified by column chromatography through silica gel, using a 5:1 by volume mixture of ethyl acetate and methanol as the eluent, to give 2.60 g of the title compound, as a powder.

Infrared Absorption Spectrum (KBr), $v_{max}$ cm$^{-1}$: 1712, 1652, 1523, 1345, 1171.

Nuclear Magnetic Resonance Spectrum (CDCl$_3$, 270 MHz), δ ppm:
2.23–2.80 (9H, multiplet);
3.06 & 3.07 (together 3H, two singlets);
3.44–4.06 (8H, multiplet);
4.81–4.95 (1H, multiplet);
5.04–5.41 (3H, multiplet);
7.46 & 7.51 (together 2H, two doublets, J=8.79 Hz);
8.21 & 8.22 (together 2S, two doublets, J=8.79 Hz).

54(a)(ii') (2S,4R)-2-[4-(2-Hydroxylethyl) -1-piperazinylcarbonyl]-4-methanesulfonyloxy-1-(4-nitrobenzyloxy-carbonyl)pyrrolidine 584 mg of N,N'-carbonyldiimidazole were added to a solution of 1.16 g of trans-4-methanesulfonyloxy-1-(4-nitrobenzyloxycarbonyl)-L-proline in 10 ml of dry acetonitrile, and the resulting mixture was stirred at 40° C. for 1 hour. 586 mg of 1-(2-Hydroxyethyl)piperazine were then added to the mixture, whilst ice-cooling, and the resulting mixture was stirred at the same temperature for 35 minutes. The solvent was then removed by distillation under reduced pressure, and the residue was purified in a similar manner so that described in step 54(a)(ii), to give 930 mg of the title compound, as a powder. The infrared absorption spectrum and nuclear magnetic resonance spectrum of the product were identical with those of the compound obtained as described in step 54(a)(ii) above.

54(a)(ii") (2S,4R)-2-[4-(2-Hydroxyethyl)-1-piperazinylcarbonyl]-4-methanesulfonyloxy-1-(4-nitrobenzyloxy-carbonyl)pyrrolidine 0.21 ml of triethylamine, followed by 0.19 ml of pivaloyl chloride, were added dropwise at −20° C. to a solution of 0.5 g of trans-4-methanesulfonyloxy-1-(4-nitrobenzyloxycarbonyl)-L-proline in 5 ml of dry tetrahydrofuran, and the resulting mixture was stirred at the same temperature for 5 minutes. A solution of 0.25 g of N-(2-hydroxyethyl)piperazine in 3 ml of dry tetrahydrofuran was then added, and the reaction mixture was stirred at the same temperature for 30 minutes, after which the solvent was removed by distillation under reduced pressure. The resulting residue was worked up and purified in a similar manner to that described in step 54(a)(ii), to give 0.42 g of the title compound, as a powder. The infrared absorption spectrum and nuclear magnetic resonance spectrum of the product were identical with those of the compound obtained as described in step 54(a)(ii) above.

54(a)(iii) (2S,4S)-4-Acetylthio-2-[4-(2-hydroxyethyl)-1-piperazinylcarbonyl]-1-(4-nitrobenzyloxycarbonyl)-pyrrolidine 685 mg of potassium thioacetate were added to a solution of 2.0 g of (2S,4R)-2-[4-(2-hydroxyethyl)-1-piperazinylcarbonyl]-4-methanesulfonyloxy-1-(4-nitrobenzyloxycarbonyl)pyrrolidine [prepared as described step 54(a)(ii), 54(a)(ii') and 54(a)(ii") above] in 20 ml of dry acetonitrile, and the resulting mixture was stirred at 80° C. for 5 hours. At the end of this time, the reaction mixture was concentrated by evaporation under reduced pressure, the residue was diluted with 200 ml of ethyl acetate, and the dilute solution was washed with an aqueous solution of sodium chloride; was then dried over anhydrous magnesium sulfate. The solvent was removed by distillation under reduced pressure, and the residue was purified by column chromatography through silica gel, using a gradient elution method with mixtures of ethyl acetate and methanol ranging from 9:1 to 4:1 by volume as the eluent, to give 1.35 g of the title compound, as a powder.

Infrared Absorption Spectrum (KBr), $v_{max}$ cm$^{-1}$: 3437, 1710, 1652, 1522, 1345, 1113.

Nuclear Magnetic Resonance Spectrum (CDCl$_3$, 270 MHz), δ ppm:

1.82–1.98 (1H, multiplet);
2.34 (3H, singlet);
2.31–2.88 (8H, multiplet);
3.40–4.21 (9H, multiplet);
4.65–4.78 (1H, multiplet);
5.03–5.36 (2H, multiplet);
7.45 & 7.51 (together 2H, two doublets, J=8.79 Hz);
8.17–8.24 (2H, multiplet).

54(a)(iv) (2S,4S)-2-[4-(2-Hydroxyethyl)-1-piperazinylcarbonyl]-4-mercapto-1-(4-nitrobenzyloxycarbonyl)-pyrrolidine A sodium methoxide solution (prepared by adding 56 mg of metallic sodium to 2.4 ml of methanol) was added to a solution of 1.06 g of (2S,4S)-4-acetylthio-2-[4-(2-hydroxyethyl)-1-piperazinyl]-1-(4-nitrobenzyloxycarbonyl)pyrrolidine [prepared as described in step 54(a)(iii) above] in 10 ml of methanol, and the resulting mixture was stirred at 15° C. for 30 minutes. 610 μl of a 4N solution of hydrogen chloride in ethyl acetate were then added to the mixture at the same temperature, after which the mixture was stirred for 10 minutes. The reaction mixture was then concentrated by evaporation under reduced pressure, and the residue was purified by column chromatography through silica gel, using a 4:1 by volume mixture of ethyl acetate and methanol as the eluent, to give 710 mg of the title compound, as a powder.

Infrared Absorption Spectrum (KBr), $v_{max}$ cm$^{-1}$: 3430, 2944, 1700, 1647, 1521, 1439, 1350.

Nuclear Magnetic Resonance Spectrum (CDCl$_3$, 270 MHz), δ ppm:

1.81–1.98 (2H, multiplet);
2.28–2.84 (8H, multiplet);
3.20–3.82 (8H, multiplet);
4.04–4.20 (1H, multiplet);
4.60–4.77 (1H, multiplet);
5.01–5.38 (2H, multiplet);
7.45 & 7.51 (together 2H, two doublets, J=8.79 Hz);
8.15–8.25 (2H, multiplet).

54(a)(iv') (2S,4S)-2-[4-(2-Hydroxyethyl)-1-piperazinyl-carbonyl]-4-mercapto-1-(4-nitrobenzyloxycarbonyl)-pyrrolidine 40 ml of a 10% w/v methanolic solution of hydrogen chloride were added to a solution of 1.0 g of (2S,4S)-4-acetylthio-2-[4-(2-hydroxyethyl)-1-piperazinyl]-1-(4-nitrobenzyloxycarbonyl)pyrrolidine in 10 ml of 1,4-dioxane, and the resulting mixture was stirred at 50° C. for 1 hour. At the end of this time, the solvent was removed by distillation under reduced pressure, and the residue was mixed with 40 ml of tetrahydrofuran and 2 ml of a saturated aqueous solution of sodium hydrogencarbonate; it was then dried over anhydrous sodium sulfate. The solvent was removed by distillation under reduced pressure, and the residue was purified by column chromatography through silica gel in a similar manner to that described in step 54(a)(iv) above, to give 712 mg of the title compound, as a powder. The infrared absorption spectrum and nuclear magnetic resonance spectrum of the product were identical with those of the compound obtained as described in step 54(a)(iv) above.

54(b)(i) (2S,4S)-2-[4-(2-Hydroxyethyl)-1-piperazinyl-carbonyl]-4-mercaptoyl-(4-nitrobenzyloxycarbonyl)-pyrrolidine bis (trifluoromethanesulfonate)

2.8 ml of trifluoroacetic acid and 91 μl of trifluoromethanesulfonic acid were added, whilst ice-cooling, to a solution of 288 mg of (2S,4S)-2-[4-(2-hydroxyethyl)-1-piperazinylcarbonyl]-4-(4-methoxybenzyl-thio)-1-(4-nitrobenzyloxycarbonyl)pyrrolidine in 580 μl of anisole, and the resulting mixture was stirred at room temperature for 1 hour. At the end of this time, the solvent was removed by distillation under reduced pressure, and the resulting residue was washed with diethyl ether by decantation and dried in vacuo, to give 380 mg of the title compound, as a powder.

Infrared Absorption Spectrum (KBr), $v_{max}$ cm$^{-1}$: 1795, 1705, 1666, 1609, 1525, 1442, 1408, 1348, 1281, 1226, 1169.

Nuclear Magnetic Resonance Spectrum (270 MHz, D$_2$O) δ ppm:

1.54–1.63 (1H, multiplet);
2.61–2.72 (1H, multiplet);
2.90–4.46 (14H, multiplet);
4.64–4.96 (2H, multiplet);
5.08 (2H, singlet);
7.42 (2H, doublet, J=8.79 Hz);
8.08 & 8.10 (together 2H, two doublets, J=8.79 Hz).

54(b)(ii) (2S,4S)-2-[N-(2-Hydroxyethyl)-1-piperazinylcarbonyl]-4-mercapto-1-(4-nitrobenzyloxycarbonyl)-pyrrolidine A solution of 266 mg of (2S,4S)-2-[4-(2-hydroxyethyl)-1-piperazinylcarbonyl]-4-mercapto-1-(4-nitrobenzyloxycarbonyl)pyrrolidine bis (trifluoromethanesulfonate) [prepared as described in step 54(b)(i) above] in a mixture of 5 ml of tetrahydrofuran and 0.2 ml of water was neutralized by adding 76 mg of sodium hydrogencarbonate, after which it was dried over anhydrous magnesium sulfate. The solvent was then removed by distillation under reduced pressure, and the resulting residue was purified by column chromatography through silica gel, using a 4:1 by volume mixture of ethyl acetate and methanol as the eluent, to give 188 mg of the title compound, as a powder. The infrared absorption spectrum and nuclear magnetic resonance spectrum of the product were identical with those of the compound obtained as described in step 54(a)(iv) above.

PREPARATION 55

(2S,4S)-4-Mercapto-2-(4-nitrobenzyloxycarbonyl-1-piperazinylcarbonyl) -1-methylpyrrolidinetrifluoromethanesulfonate

55(i) (2S,4S)-4-(4-Methoxybenzylthio)-2-(4-nitrobenzyloxycarbonyl -1-piperazinylcarbonyl)-1-methylpyrrolidine 16.6 g of N,N'-carbonyldiimidazole were added to a suspension of 24 g of (2S,4S)-2-carboxy-4-(4-methoxybenzylthio) -1-methylpyrrolidine in 200 ml of dry acetonitrile, and the resulting mixture was stirred at 35° C. for 40 minutes. A solution of 14.7 g of dry piperazine was then added dropwise to the mixture at a temperature of between 30° C. and 35° C., after which the mixture was stirred at room temperature for 30 minutes. A solution of 36.8 g of 4-nitrobenzyloxycarbonyl chloride in 100 ml of acetonitrile was then added, whilst ice-cooling, to the reaction mixture, and the mixture thus obtained was stirred at room temperature for 1 hour. At the end of this time, the mixture was concentrated by evaporation under reduced pressure, and the residue was mixed with an aqueous solution of sodium chloride and a 10% aqueous solution of sodium carbonate. The resulting mixture was extracted with ethyl acetate. The extract was washed with an aqueous solution of sodium chloride and dried over anhydrous magnesium sulfate. The solvent was removed by distillation under reduced pressure, and the residue was purified by column chromatography through silica gel, using a 9:1 by volume mixture of ethyl acetate and methanol as the eluent, to afford 27.7 g of the title compound.

Infrared Absorption Spectrum (liquid film), ν$_{max}$ cm$^{-1}$: 1706, 1648, 1513, 1435, 1347, 1248, 1232.

Nuclear Magnetic Resonance Spectrum (CDCl$_3$, 270 MHz), δ ppm:

1.74–1.89 (1H, multiplet);
2.32 (3H, multiplet);
2.40–2.62 (2H, multiplet);
2.99–3.21 (3H, multiplet);
3.31–4.20 (8H, multiplet);
3.70 (2S, singlet);
3.80 (3H, singlet);
5.24 (2H, singlet);
6.84 (2H, doublet, J=8.79 Hz);
7.20 (2H, doublet, J=8.79 Hz);
7.52 (2H, doublet, J=8.79 Hz);
8.23 (2H, doublet, J=8.79 Hz).

55(ii) (2S,4S)-4-Mercapto-2-(4-nitrobenzyloxycarbonyl-1-piperazinylcarbonyl)-1-methylpyrrolidine trifluoromethanesulfonate 130 ml of trifluoroacetic acid and 4.6 ml of trifluoromethanesulfonic acid were added dropwise to a solution of 13.8 g of (2S,4S)-4-(4-methoxybenzylthio)-2-(4-nitrobenzyloxycarbonyl -1-piperazinylcarbonyl)-1-methylpyrrolidine [prepared as described in step (i) above] in 28.3 ml of anisole, and the resulting mixture was stirred for 30 minutes, whilst ice-cooling. At the end of this time, the reaction mixture was concentrated by evaporation under reduced pressure, and the resulting residue was washed with hexane and ether, in that order, by decantation to give 13.9 g of the title compound as a powder.

Infrared Absorption Spectrum (KBr), ν$_{max}$ cm$^{-1}$: 1695, 1643, 1518, 1446, 1345, 1251.

Nuclear Magnetic Resonance Spectrum (270 MHz, hexadeuterated dimethyl sulfoxide) δ ppm:

1.74–1.89 (1H, multiplet);
2.81 & 2.82 (together 3H, two singlets);
2.92–3.08 (1H, multiplet);
3.17 (1H, singlet);
3.31–3.80 (12H, multiplet);
4.58–4.72 (1H, multiplet);
5.26 (2H, singlet);
7.65 (2H, doublet, J=8.79 Hz);
8.24 (2H, doublet, J=8.79 Hz).

PREPARATION 56

(2S,4S)-4-Mercapto-N-[4-(4-nitrobenzyloxycarbonyl-methyl) -1-piperazinylcarbonyl]-1-(4-nitrobenzyloxy-carbonyl) pyrrolidine bis(trifluoromethanesulfonate)

8.0 ml of trifluoroacetic acid and 160 μl of trifluoromethanesulfonic acid were added, whilst ice-cooling, to a suspension of 1120 mg of (2S,4S)-4-(4-methoxybenzylthio) -2-[4-(4-nitrobenzyloxycarbonylmethyl) -1-piperazinecarbonyl]-1-(4-nitrobenzyloxycarbonyl)-pyrrolidine in 1.75 ml of anisole, and the resulting mixture was stirred at room temperature for 1.5 hours. At the end of this time, the solvent was removed by distillation under reduced pressure, and the resulting residue was repeatedly washed with diethyl ether by decantation and dried in vacuo, to afford 1.58 g of the title compound, as a powder.

Infrared Absorption Spectrum (KBr), ν$_{max}$ cm$^{-1}$: 1756, 1704, 1667, 1523, 1441, 1348.

Nuclear Magnetic Resonance Spectrum (270 MHz, hexadeuterated dimethyl sulfoxide) δ ppm:

1.60–1.76 (1H, multiplet);
2.70–2.85 (1H, multiplet);
3.08–3.42 (9H, multiplet);
3.65–3.83 (3H, multiplet);
3.94 & 4.05 (together 1H, two doublets of doublets, J=9.8 & 6.8 Hz);
4.72 & 4.81 (1H, two triplets, J=8.1 Hz);
5.05–5.26 (2H, multiplet);
5.42 & 5.43 (2H, two singlets);
7.52, 7.64, 7.69 & 7.70 (together 4H, four doublets, J=8.8 Hz);
8.23, 8.24 & 8.28 (together 4H, 3 doublets, J=8.8 Hz).

PREPARATION 57

(2R,4S)-4-Mercapto-2-{4-[2-(4-nitrobenzyloxycarbonyl) oxyethyl]-1-piperazinylcarbonyl}-1-(4-nitrobenzyloxycarbonyl) pyrrolidine 57(i) (2R,4R)-4-Hydroxy-2-{4-[2-(4-nitrobenzyloxycarbonyl)oxyethyl]-1-piperazinylcarbonyl}-1-(4-nitrobenzyloxycarbonyl) pyrrolidine 3.34 ml of diethyl cyanophosphate and 8.92 ml of triethylamine were added, whilst ice-cooling, to a suspension of 6.2 g of cis-4-hydroxy-1-(4-nitrobenzyloxycarbonyl)-D-proline and 8.41 g of 1-[2-(4-nitrobenzyloxycarbonyloxy)ethyl]piperazine dihydrochloride in 62 ml of dry dimethylformamide, and the resulting mixture was stirred at the same temperature for 30 minutes. At the end of this time, the reaction mixture was diluted with 250 ml of ethyl acetate, and the dilute solution was washed with water and then dried over anhydrous magnesium sulfate. The mixture was concentrated by evaporation under reduced pressure, and the resulting residue was purified by column chromatography through silica gel, using a 4:1 by volume mixture of ethyl acetate and methanol as the eluent, to give 7.84 g of the title compound, as an oil.

Infrared Absorption Spectrum (liquid film), $v_{max}$ cm$^{-1}$: 1748, 1710, 1658, 1624, 1608, 1522, 1439, 1403, 1347, 1262.

Nuclear Magnetic Resonance Spectrum (CDCl$_3$, 270 MHz), δ ppm:
1.98–2.80 (9H, multiplet);
3.37–3.90 (6H, multiplet);
4.22–4.46 (3H, multiplet);
4.60–5.60 (5H, multiplet);
7.42–7.57 (4H, multiplet);
8.17–8.23 (4H, multiplet).

57(ii) (2R,4S)-4-Acetylthio-2-{4-[2-(4-nitrobenzyloxycarbonyl) oxyethyl]-1-piperazinylcarbonyl}-1-(4-nitrobenzyloxycarbonyl) pyrrolidine A solution of 0.73 g of diethyl azodicarboxylate in 2 ml of tetrahydrofuran was added dropwise, whilst ice-cooling, to a solution of 2.1 g of (2R,4R)-4-hydroxy-2-{4-[2-(4-nitrobenzyloxycarbonyl)oxyethyl]-1-piperazinylcarbonyl}-[-(4-nitrobenzyloxycarbonyl)-pyrrolidine [prepared as described in step (i) above] and 1.1 g of triphenylphosphine in 14 ml of tetrahydrofuran, and the resulting mixture was stirred at the same temperature for 10 minutes. A solution of 0.32 g of mercaptoacetic acid in 2 ml of tetrahydrofuran was then added dropwise to the mixture, and the mixture was stirred at room temperature for 1 hour. At the end of this time, the solvent was removed by distillation under reduced pressure, and the resulting residue was purified by column chromatography through silica gel, using a 20:1 by volume mixture of ethyl acetate and methanol as the eluent, to give 1.2 g of (2R,4S)-4-acetylthio-2-{4-[2-(4-nitrobenzyloxycarbonyl)oxyethyl]-1-piperazinylcarbonyl}-1-(4-nitrobenzyloxycarbonyl)-pyrrolidine as a colorless powder.

Infrared Absorption Spectrum (liquid film), $v_{max}$ cm$^{-1}$: 1748, 1709, 1654, 1607, 1522, 1439, 1404, 1347, 1263, 1122.

Nuclear Magnetic Resonance Spectrum (CDCl$_3$, 270 MHz), δ ppm:
2.15–2.80 (8H, multiplet);
2.34 (3H, singlet);
3.35–3.76 (5H, multiplet);
3.91–4.40 (4H, multiplet);
4.68–4.81 (1H, multiplet);
5.03–5.35 (4H, multiplet);
7.26–7.57 (4H, multiplet);
8.19–8.26 (4H, multiplet).

57(iii) (2R,4S)-4-Mercapto-2-[4-[2-(4-nitrobenzyloxycarbonyl) oxyethyl]-1-piperazinylcarbonyl]-1-(4-nitrobenzyloxycarbonyl) pyrrolidine 40 ml of a 10% w/v methanolic solution of hydrogen chloride were added to a solution of 1.0 g of (2S,4S)-4-acetylthio-2-(4-[2-(4-nitrobenzyloxycarbonyl)oxyethyl]-1-piperazinylcarbonyl)-1-(4-nitrobenzyloxycarbonyl)-pyrrolidine [prepared as described in step (ii) above] in 10 ml of 1,4-dioxane, and the resulting mixture was stirred at 50° C. to 52° C. for 1 hour. At the end of this time, the reaction mixture was concentrated by evaporation under reduced pressure, and the concentrate was diluted with 100 ml of ethyl acetate. The dilute solution was neutralized with a saturated aqueous solution of sodium hydrogencarbonate and washed, in turn, with 30 ml of water and with 30 ml of an aqueous solution of sodium chloride. The solvent was removed by distillation under reduced pressure, and the resulting residue was purified by colorful chromatography through silica gel, using a 20:1 by volume mixture of ethyl acetate and methanol as the eluent, to give 566 mg of the title compound, as a colorless powder.

Infrared Absorption Spectrum (liquid film), $v_{max}$ cm$^{-1}$: 1748, 1709, 1653, 1607, 1521, 1439, 1404, 1346, 1263.

Nuclear Magnetic Resonance Spectrum (CDCl$_3$, 270 MHz), δ ppm:
1.74 (1H, doublet, J=7.32 Hz);
2.07–2.86 (8H, multiplet);
3.39–3.80 (6H, multiplet);
4.04–4.46 (3H, multiplet);
4.75–4.85 (1H, multiplet);
5.03–5.35 (4H, multiplet);
7.42–7.58 (4H, multiplet);
8.17–8.26 (4H, multiplet).

PREPARATION 58

(2R,4R)-1-Mercapto-2-{4-[2-(4-nitrobenzyloxycarbonyl) oxyethyl]-1-piperazinylcarbonyl}-1-(4-nitrobenzyloxycarbonyl) pyrrolidine 58(i) (2R,4S)-4-Formyloxy-2-{4-[2-(4-nitrobenzyloxycarbonyl) oxyethyl]-1-piperazinylcarbonyl}-1-(4-nitrobenzyloxycarbonyl) pyrrolidine A solution of 1.31 g of diethyl azodicarboxylate in 5 ml of tetrahydrofuran was added dropwise, whilst ice-cooling, to a solution of 3.0 g of (2R,4R)-4-hydroxy-2-{4-[2-(4-nitrobenzyloxycarbonyl)oxyethyl]-1-piperazinylcarbonyl}-1-(4-nitrobenzyloxycarbonyl)-pyrrolidine [prepared as described in Preparation 57(i)] and 1.97 g of triphenylphosphine in 25 ml of tetrahydrofuran, and the resulting mixture was stirred at the same temperature for 10 minutes. 283 μl of formic acid were then added dropwise to the mixture, and the mixture was stirred at the same temperature for 5 minutes and at room temperature for 1 hour. At the end of this time, the solvent was removed by distillation under reduced pressure, and the resulting residue was purified by column chromatography through silica gel, using a 20:1 by volume mixture of ethyl acetate and methanol as the eluent, to give 1.42 g of the title compound, as a colorless powder.

Infrared Absorption Spectrum (KBr), $v_{max}$ cm$^{-1}$: 1749, 1720, 1654, 1606, 1522, 1439, 1405, 1347, 1262.

Nuclear Magnetic Resonance Spectrum (CDCl$_3$, 270 MHz), δ ppm:

2.20–2.95 (8H, multiplet);
3.35–3.95 (6H, multiplet);
4.15–4.55 (2H, multiplet);
4.79 & 4.85 (together 1H, two triplets, J=7.81 Hz);
5.05–5.37 (4H, multiplet);
5.43–5.50 (1H, multiplet);
7.44–7.57 (4H, multiplet);
8.02 (1H, singlet);
8.19–8.26 (4H, multiplet).

58(ii) (2R,4S)-4-Hydroxy-2-{4-[2-(4-nitrobenzyloxycarbonyl) oxyethyl]-1-piperazinylcarbonyl}-1-(4-nitrobenzyloxycarbonyl) pyrrolidine 28 ml of a 10% w/v methanolic solution of hydrogen chloride were added dropwise to a solution of 1.42 g of (2R,4S)-4-formyloxy-2-{4-[2-(4-nitrobenzyloxycarbonyl)-oxyethyl]-1-piperazinylcarbonyl}-1-(4-nitrobenzyloxycarbonyl)pyrrolidine [prepared as described in step (i) above] in 14 ml of 1,4-dioxane, and the resulting mixture was stirred at room temperature for 1 hour. At the end of this time, the solvent was removed by distillation under reduced pressure, and the resulting residue was mixed with water. The aqueous mixture thus obtained was made alkaline by the addition of a saturated aqueous solution of sodium hydrogencarbonate, and then the mixture was extracted with ethyl acetate. The extract was washed with an aqueous solution of sodium chloride and dried over anhydrous magnesium sulfate. The solvent was removed by distillation under reduced pressure, and the residue was purified by column chromatography through silica gel using a 9:1 by volume mixture of ethyl acetate and methanol as the eluent to give 1.33 g of the title compound, as a colorless powder.

Infrared Absorption Spectrum (KBr), $v_{max}$ cm$^{-1}$: 1750, 1709, 1648, 1608, 1522, 1439, 1406, 1347, 1263.

Nuclear Magnetic Resonance Spectrum (270 MHz, CDCl$_3$+D$_2$O) δ ppm:

2.04–2.80 (8H, multiplet);
3.38–3.82 (6H, multiplet);
4.24–4.38 (2H, multiplet);
4.50–4.64 (1H, multiplet);
4.70–4.90 (1H, multiplet);
5.30–5.34 (4H, multiplet);
7.43–7.57 (4H, multiplet);
8.17–8.25 (4H, multiplet).

58(iii) (2R,4R)-4-Acetylthio-2-{4-[2-(4-nitrobenzyloxycarbonyl oxyethyl]-1-piperazinylcarbonyl}-1-(4-nitrobenzyloxycarbonylpyrrolidine A solution of 421 mg of diethyl azodicarboxylate in 1.2 ml of tetrahydrofuran was added dropwise, whilst ice-cooling, to a solution of 1.21 g of (2R,4S)-4-4-hydroxy-2-{4-[2-(4-nitrobenzyloxycarbonyl) oxyethyl]-1-piperazinylcarbonyl}-1-(4-nitrobenzyloxycarbonyl)-pyrrolidine and 634 mg of triphenylphosphine in 8 ml of tetrahydrofuran, and the resulting mixture was stirred at the same temperature for 10 minutes. 171 μl of mercaptoacetic acid were then added dropwise to the mixture, and the mixture was stirred at room temperature for 1 hour. Following the same procedure as described in Preparation 57(ii), the reaction mixture was worked up and purified, to give 1.04 g of the title compound, as a colorless powder.

Infrared Absorption Spectrum (KBr), $v_{max}$ cm$^{-1}$: 1750, 1712, 1656, 1607, 1522, 1496, 1438, 1404, 1347, 1263, 1207.

Nuclear Magnetic Resonance Spectrum (CDCl$_3$, 270 MHz), δ ppm:

1.82–1.93 (1H, multiplet);
2.34 (3H, singlet);
2.30–2.82 (7H, multiplet);
3.36–3.72 (8H, multiplet);
3.90–4.16 (2H, multiplet);
4.24–4.31 (1H, multiplet);
4.67 & 4.74 (together 1H, two triplets, J=7.81 Hz);
5.03–5.35 (4H, multiplet);
7.43–7.57 (4H, multiplet);
8.17–8.25 (4H, multiplet).

58(iv) (2R,4R)-1-Mercapto-2-{4-[2-(4-nitrobenzyloxycarbonyl) oxyethyl]-1-piperazinylcarbonyl}-1-(4-nitrobenzyloxycarbonyl) pyrrolidine 40 ml of a 10% w/v methanolic solution of hydrogen chloride were added to a solution of 1.0 g of (2R,4R)-4-acetylthio-2-{4-[2-(4-nitrobenzyloxycarbonyl)oxyethyl]-1-piperazinylcarbonyl}-1-(4-nitrobenzyloxycarbonyl)-pyrrolidine [prepared as described in step (iii) above] in 10 ml of 1,4-dioxane, and the resulting mixture was stirred at between 50° C. and 52° C. for 1 hour. Following the same procedure as described in Preparation 57(iii), the reaction mixture was worked up and purified, to afford 648 mg of the title compound, as a colorless powder.

Infrared Absorption Spectrum (KBr), $v_{max}$ cm$^{-1}$: 1749, 1710, 1653, 1607, 1522, 1496, 1439, 1404, 1346, 1263, 1206.

Nuclear Magnetic Resonance Spectrum (CDCl$_3$, 270 MHz), δ ppm:

1.82–1.96 (2H, multiplet);
2.30–2.91 (7H, multiplet);
3.18–3.78 (6H, multiplet);
4.05–4.46 (3H, multiplet);
4.63 & 4.68 (together 1H, two triplets, J=7.81 Hz);
5.03–5.33 (4H, multiplet);
7.43–7.57 (4H, multiplet);
8.17–8.26 (4H, multiplet).

PREPARATIONS 59 TO 88

The mercaptans shown in Preparations 59 to 88 were prepared in a similar manner to that described in Preparations 1, 49 and 66, but using (2S,4S)-4-(4-methoxybenzylthio)-1-(4-nitrobenzyloxycarbonyl)-2-pyrrolidinecarboxylic acid, (2S,4S)-2-carboxy-4-(4-methoxybenzylthio)-1-methylpyrrolidine and (2S,4S)-1-(t-butoxycarbonyl)-4-(4-methoxybenzylthio)-2-pyrrolidine-carboxylic acid as starting materials.

PREPARATION 59

(2S,4S)-4-Mercapto-2-[(2S)-4-(N-4-nitrobenzyloxycarbonyl-acetimidoyl) -2-methylpiperazin-1-ylcarbonyl-1-(4-nitrobenzyloxycarbonyl)pyrrolidine Infrared Absorption Spectrum (Liquid film), $v_{max}$ cm$^{-1}$: 1709, 1656, 1606, 1569, 1520, 1430, 1346, 1252.

Nuclear Magnetic Resonance Spectrum (CDCl$_3$, 270 MHz), δ ppm:

1.12–1.38 (3H, multiplet);
1.75–2.10 (2H, multiplet);
2.12–2.38 (3H, multiplet);
2.55–3.93 (8H, multiplet);
4.01–4.89 (4H, multiplet);
5.04–5.30 (4H, multiplet);
7.42–7.59 (4H, multiplet);
8.17–8.23 (4H, multiplet).

PREPARATION 60

(2S,4S)-4-Mercapto-2-[(2S)-4-(N-4-nitrobenzyloxycarbonyl-formimidoyl) -2-methylpiperazin-1-ylcarbonyl]-1-(4-nitrobenzyloxycarbonyl)pyrrolidine trifluoromethanesulfonate Nuclear Magnetic Resonance Spectrum (hexadeuterated dimethyl sulfoxide+D$_2$O, 270 MHz), δ ppm:

1.10–1.40 (3H, multiplet);
1.62–1.78 (1H, multiplet);
2.60–3.40 (8H, multiplet);
3.91–4.08 (2H, multiplet);
4.58–4.81 (1H, multiplet);
5.06–5.27 (2H, multiplet);
5.36 (2H, singlet);
7.53–7.70 (4H, multiplet);
8.19–8.28 (4H, multiplet);
8.89 (1H, singlet).

Infrared Absorption Spectrum (KBr), $v_{max}$ cm$^{-1}$: 1785, 1695, 1609, 1523, 1442, 1349, 1283, 1246, 1031.

PREPARATION 61

(2S,4S)-4-Mercapto-1-methyl-2-[(3S) -3-(N-4-nitrobenzyloxycarbonylacetimidoylamino) pyrrolidin-1-ylcarbonyl]-pyrrolidine Infrared Absorption Spectrum (KBr), $v_{max}$ cm$^{-1}$: 1522, 1348, 858, 740.

Nuclear Magnetic Resonance Spectrum (270 MHz, D$_2$O, using sodium tetradeuterated trimethylsilylpropionate as an internal standard), δ ppm:

1.70–2.00 (3H, multiplet);
2.00–2.25 (3H, multiplet);
2.30–3.95 (13H, multiplet);
3.95–4.07 (1H, multiplet);
4.30–4.50 (1H, multiplet);
7.62 (2H, doublet, J=8.79 Hz);
8.23 (2H, doublet, J=8.79 Hz).

PREPARATION 62

(2S,4S)-4-Mercapto-2-[3-(N-4-nitrobenzyloxycarbonyl -acetimidoylamino) piperidin-1-ylcarbonyl]-1-(4-nitrobenzyloxycarbonyl)pyrrolidine Infrared Absorption Spectrum (KBr), $v_{max}$ cm$^{-1}$: 1705, 1650, 1600, 1550, 1520, 1440, 1340, 1205.

PREPARATION 63

(2S,4S)-4-Mercapto-1-methyl-2-[4-(N-4-nitrobenzyloxycarbonylacetimidoylamino) piperidin-1-ylcarbonyl]-pyrrolidine Infrared Absorption Spectrum (KBr), $v_{max}$ cm$^{-1}$: 1710, 1520, 1345, 1210.

PREPARATION 64

(2S,4S)-4-Mercapto-1-methyl-2-[4-(N-4-nitrobenzyloxycarbonylformimidoyl) piperazin-1-ylcarbonyl]pyrrolidine bis (trifluoromethanesulfonate)

Nuclear Magnetic Resonance Spectrum (hexadeuterated dimethyl sulfoxide+D$_2$O, 270 MHz), δ ppm:

1.79–1.91 (1H, multiplet);
2.83 (3H, singlet);
2.96–3.07 (1H, multiplet);
3.10–3.28 (4H, multiplet);
3.47–3.85 (7H, multiplet);
4.61 (1H, triplet, J=9.4 Hz);
5.36 (2H, singlet);
7.68 (2H, doublet, J=8.8 Hz);
8.26 (2H, doublet, J=8.8 Hz);
8.89 (1H, singlet).

PREPARATION 65

(3S,4S)-4-Mercapto-2-[(2S)-4-(N-4-nitrobenzyloxycarbonyl-acetimidoyl) -2-methylpiperazin-1-ylcarbonyl]-[-methyl-pyrrolidine

PREPARATION 66

(2S,4S)-4-Mercapto-2-[4-(4-nitrobenzyloxycarbonyl) -piperazin-1-ylcarbonyl]-1-(N-4-nitrobenzyloxycarbonylacetimidoyl)pyrrolidine (2S,4S)-1-(N-Butoxycarbonyl)-4-(N-methoxybenzylthio) -2-[4-(4-nitrobenzyloxycarbonyl) piperazin-1-yl-carbonyl] pyrrolidine was prepared from (2S,4S)-1-(t-butoxycarbonyl) -4-(4-methoxybenzylthio)pyrrolidine-2-carboxylic acid, N,N'-carbonyldiimidazole and 4-(4-nitrobenzyloxycarbonyl)piperazine. This compound was then treated with a 4N solution of hydrogen chloride in ethyl acetate and the product was then subjected to similar reactions to those described in Preparations 1 and 17(iii), to give the title compound, melting at 181.5° C.

Nuclear Magnetic Resonance Spectrum (CDCl$_3$, 270 MHz), δ ppm:

1.93 (1H, doublet, J=9.2 Hz);
1.90–2.02 (1H, multiplet);
2.33 (3H, singlet);
2.61–2.72 (1H, multiplet);
3.08–3.88 (9H, multiplet);
4.03 (2H, doublet of doublets, J=10.6 & 7.3 Hz);
4.89 (1H, triplet, J=7.3 Hz);
5.06–5.31 (4H, multiplet);
7.43–7.52 (4H, multiplet);
8.12–8.26 (4H, multiplet).

PREPARATION 67

(2S,4S)-4-mercapto-2-[4-(4-nitrobenzyloxycarbonyl) -piperazin-1-ylcarbonyl]-1-(N-4- nitrobenzyloxycarbonyl-formimidoyl)pyrrolidine trifluoromethanesulfonate Infrared Absorption Spectrum (KBr), $v_{max}$ cm$^{-1}$: 1783, 1693, 1660, 1608, 1523, 1465, 1441, 1349, 1256, 1228.

Nuclear Magnetic Resonance Spectrum (hexadeuterated dimethyl sulfoxide+D$_2$O, 270 MHz), δ ppm:
1.67–1.79 (1H, multiplet);
2.82–2.92 (1H, multiplet);
3.02–3.10 (1H, multiplet);
3.40–3.80 (10H, multiplet);
4.62 (1H, triplet, J=8.30 Hz);
5.26 (2H, singlet);
5.36 (2H, singlet);
7.65 (2H, doublet, J=8.79 Hz);
7.68 (2H, doublet, 8.79 Hz);
8.25 (2H, doublet, 8.79 Hz);
8.26 (2H, doublet, 8.79 Hz);
8.89 (1H, singlet).

PREPARATION 68

(2S,4S)-4-Mercapto-1-(N-4- nitrobenzyloxycarbonylacetimidoyl) -2-[4-(N-4- nitrobenzyloxycarbonylacetimidoyl)-piperazin-1- ylcarbonyl]pyrrolidine Infrared Absorption Spectrum (KBr), $v_{max}$ cm$^{-1}$: 1782, 1705, 1635, 1522, 1440, 1348, 1280, 1225.

PREPARATION 69

(2S,4S)-4-Mercapto-1-(N-4- nitrobenzyloxycarbonylacetimidoyl) -2-[4-(N-4- nitrobenzyloxycarbonylformimidoyl)-piperazin-1- ylcarbonyl]pyrrolidine

PREPARATION 70

(2S,2S)-4-Mercapto-1-(N-4- nitrobenzyloxycarbonylformimidoyl) -2-[4-(N- nitrobenzyloxycarbonylformimidoyl)-piperazin-1- ylcarbonyl]pyrrolidine

PREPARATION 71

(2S,4S)-4-Mercapto-1-(N-4- nitrobenzyloxycarbonylformimidoyl) -2-[4-(N-4- nitrobenzyloxycarbonylacetimidoyl)-piperazin-1- ylcarbonyl]pyrrolidine

PREPARATION 72

(2S,4S)-4-Mercapto-1-(N-4- nitrobenzyloxycarbonylacetimidoyl) -2-[(3S)-3-(N- 4-nitrobenzyloxycarbonylacetimidoylamino) pyrrolidin-1-ylcarbonyl]pyrrolidine Infrared Absorption Spectrum (KBr), $v_{max}$ cm$^{-1}$: 1710, 1645, 1522, 1445, 1347.

PREPARATION 73

(2S,4S)-4-Mercapto-1-(N-4- nitrobenzyloxycarbonylacetimidoyl) -2-[(3S)-3-(N- 4-nitrobenzyloxycarbonylformimidoylamino) pyrrolidin-1-ylcarbonyl]pyrrolidine

PREPARATION 74

(2S,4S)-4-Mercapto-1-(N-4- nitrobenzyloxycarbonylacetimidoyl) -2-[(3S)-3-(N- 4-nitrobenzyloxycarbonylamino)pyrrolidin-1- ylcarbonyl]pyrrolidine Infrared Absorption Spectrum (KBr), $v_{max}$ cm$^{-1}$: 1708, 1646, 1525, 1442, 1348.

PREPARATION 75

(2S,4S)-4-Mercapto-1-(N-4- nitrobenzyloxycarbonylformimidoyl) -2-[(3S)-3-(N- 4-nitrobenzyloxycarbonylacetimidoylamino) pyrrolidin-1-ylcarbonyl]pyrrolidine

PREPARATION 76

(2S,4S)-N-Mercapto-1)N-4- nitrobenzyloxycarbonylformimidoyl) -2-[(3S)-3-(N- 4-nitrobenzyloxycarbonylformimidoylamino) pyrrolidinyl-1-ylcarbonyl]pyrrolidine

PREPARATION 77

(2S,4S)-4-Mercapto-1-(N-4- nitrobenzyloxycarbonylformimidoyl) -2-[(3S)-3-(N- 4-nitrobenzyloxycarbonylamino)pyrrolidin-1- ylcarbonyl]pyrrolidine

PREPARATION 77

(2S,4S)-4-Mercapto-1-(N-4- nitrobenzyloxycarbonylacetimidoyl) -2-[4-(4- nitrobenzyloxycarbonyl)homopiperazin-1-yl- carbonyl]pyrrolidine

PREPARATION 79

(2S,4S)-4-Mercapto-1-(N-4- nitrobenzyloxycarbonylacetimidoyl) -2-[4-(N-4- nitrobenzyloxycarbonylformimidoyl)homopiperazin- 1-ylcarbonyl]pyrrolidine

PREPARATION 80

(2S,4S)-4-Mercapto-1-(N-4- nitrobenzyloxycarbonylformimidoyl) -2-[4-(4- nitrobenzyloxycarbonyl)homopiperazin-1-yl- carbonyl]pyrrolidine

PREPARATION 81

(2S,4S)-4-Mercapto-1-(N-4- nitrobenzyloxycarbonylformimidoyl) -2-[4-(N-4- nitrobenzyloxycarbonylformimidoyl)homopiperazin- 1-ylcarbonyl]pyrrolidine

PREPARATION 82

(2S,4S)-4-Mercapto-2-{(3S)-3-[N-methyl-N-(N-4- nitrobenzyloxycarbonylacetimidoyl) amino] pyrrolidin-1yl-carbonyl}-1-(4- nitrobenzyloxycarbonyl)pyrrolidine

PREPARATION 83

(2S,4S)-4-Mercapto-2-[2-(4-nitrobenzyloxycarbonyloxymethyl) -4-(4-nitrobenzyloxycarbonyl)piperazin-1-yl-carbonyl]-1-(4-nitrobenzyloxycarbonyl) pyrrolidine

PREPARATION 84

(2S,4S)-4-Mercapto-2-[4-(N-4-nitrobenzyloxycarbonylacetimidoyl) -2-(4-nitrobenzyloxycarbonyloxymethyl)-piperazin-1-ylcarbonyl]-1-(4-nitrobenzyloxycarbonyl)-pyrrolidine

PREPARATION 85

(2S,4S)-4-Mercapto-2-[4-(4-nitrobenzyloxycarbonyl)-6-(4-nitrobenzyloxycarbonyloxy) homopiperazin-N-ylcarbonyl]-1-(4-nitrobenzyloxycarbonyl)pyrrolidine

PREPARATION 86

(2S,4S)-4-Mercapto-1-[4-(N-4-nitrobenzyloxycarbonylformimidoyl) -6-(4-nitrobenzyloxycarbonyloxy)homopiperazin-1-ylcarbonyl]-1-(4-nitrobenzyloxycarbonyl)-pyrrolidine

PREPARATION 87

(2S,4S)-4-Mercapto-1-(N-4-nitrobenzyloxycarbonylacetimidoyl) -2-[4-(N-4-nitrobenzyloxycarbonylacetimidoylamino)-piperidin-1-ylcarbonyl]pyrrolidine

PREPARATION 88

(2S,4S)-4-Mercapto-1-methyl-2-[N-(N-4-nitrobenzyloxycarbonylformimidoyl) homopiperazin-1-ylcarbonyl]-pyrrolidine

PREPARATION 89

(2S,4S)-4-(Methoxybenzylthio)-1-(4-nitrobenzyloxycarbonyl) -2-pyrrolidinecarboxylic acid

89(i) (2S,4S)-4-(4-Methoxybenzylthio)-2-pyrrolidinecarboxylic acid

A solution of 4.0 g of (2S,4S)-2-carbamoyl-4-(4-methoxybenzylthio)-2-pyrrolidine hydrochloride dissolved in 40 ml of 2N aqueous hydrochloric acid was stirred in an oil bath kept at 95°–110° C. for 1.5 hours. At the end of this time, the reaction mixture was cooled to room temperature, and its pH was adjusted to a value of from 4 to 6 by the addition of about 40 ml of a 2N aqueous solution of sodium hydroxide, whilst stirring. The crystals which precipitated were collected by filtration, washed with water and subjected to air-drying, to give 3.25 g of the title compound, melting at 198°–200° C.

Nuclear Magnetic Resonance Spectrum (270 MHz, hexadeuterated dimethyl sulfoxide) δ ppm:

1.69 (1H, doublet of triplets, J=13.2 & 8.3 Hz);
2.44 (1H, doublet of triplets, J=13.2 & 6.8 Hz);
2.90 (1H, doublet of doublets, J=11.2 & 7.8 Hz);
3.15–3.60 (4H, multiplet);
3.66 (1H, triplet, J=8.3 Hz);
3.73 (3H, singlet);
3.74 (2H, singlet);
6.88 (2H, doublet, J=8.8 Hz);
7.25 (2H, doublet, J=8.8 Hz).

Infrared Absorption Spectrum (KBr), $v_{max}$ cm$^{-1}$: 1610, 1576, 1511, 1445, 1376, 1243.

89(ii) (2S,4S)-4-(4-Methoxybenzylthio)-1-(4-nitrobenzyloxycarbonyl) -2-pyrrolidinecarboxylic acid A suspension of 1.87 g of (2S,4S)-4-(4-methoxybenzylthio)-2-pyrrolidinecarboxylic acid [prepared as described in step (i) above] in 80 ml of a 1:1 by volume mixture of tetrahydrofuran and water was transformed to a homogeneous solution by adding 7 ml of a 1N aqueous solution of sodium hydroxide. The solution was ice-cooled and stirred, and, little by little, a solution of 1510 mg of 4-nitrobenzyloxycarbonyl chloride in 10 ml of tetrahydrofuran and 7 ml of a 1N aqueous solution of sodium hydroxide were simultaneously added dropwise. The resulting mixture was stirred at the same temperature for 10 minutes. At the end of this time, the reaction mixture was freed from tetrahydrofuran by distillation under reduced pressure, and its pH was adjusted to a value of between 2 and 3 by the addition of 1N aqueous hydrochloric acid. The crystals which precipitated were collected by filtration, washed well with water and subjected to air-drying. The crystals were further washed with a small amount of diethyl ether and dried, to give 2.42 g of the title compound, melting at 96°–98° C.

Infrared Absorption Spectrum (KBr), $v_{max}$ cm$^{-1}$: 3000, 1746, 1673, 1511, 1341, 1178.

Nuclear Magnetic Resonance Spectrum (CDCl$_3$, 270 MHz), δ ppm:

2.03–2.18 (1H, multiplet);
2.52–2.68 (1H, multiplet);
3.08–3.22 (1H, multiplet);
3.27–3.42 (1H, multiplet);
3.72 (2H, singlet);
3.79 (3H, singlet);
3.77–3.98 (1H, multiplet);
4.38 (1H, triplet, J=7.3 Hz);
5.03–5.35 (2H, multiplet);
6.85 (2H, doublet, J=8.8 Hz);
7.22 (2H, doublet, J=8.8 Hz);
7.42 & 7.48 (together 2H, two doublets, J=8.3 Hz);
8.16 & 8.22 (together 2H, two doublets, J=8.3 Hz);
5.4–6.6 (1H, broad doublet).

PREPARATION 90

(2S,4S)-4-Mercapto-2-[4-[N-(4-nitrobenzyloxycarbonyl) oxyethyl]-1-piperazinylcarbonyl-1-(4-nitrobenzyloxycarbonyl) pyrrolidine

90(a)(i) (2S,4S)-2-{4-[2-(4-Nitrobenzyloxycarbonyl) -oxyethyl]-1-piperazinylcarbonyl}-4-(4-methoxybenzylthio) -1-(4-nitrobenzylcarbonyl) pyrrolidine A solution of 5.86 g of 4-dimethylaminopyridine and 10.35 g of p-nitrobenzyl chloroformate in 40 ml of dry methylene chloride was added, whilst ice-cooling, to a solution of 22.35 g of (2S,4S)-2-[4-(2-hydroxyethyl)-1-piperazinylcarbonyl]-4-(4-methoxybenzylthio)-1-(4-nitrobenzyloxycarbonyl)pyrrolidine in 160 ml of dry methylene chloride, and the resulting mixture was stirred at room temperature for 1 hour. The reaction mixture was then diluted with 300 ml of ethyl acetate and the dilute solution was washed, in turn, with water (100 ml, once), with an aqueous solution of sodium hydrogencarbonate (100 ml, once) and with an aqueous solution of sodium chloride (100 ml, once). The solvent was then removed by distillation under reduced pressure, and the resulting residue was purified by column chromatography through silica gel, using ethyl acetate as the eluent, to give 26.35 of the title compound, as a colorless powder.

Infrared Absorption Spectrum (KBr), $v_{max}$ cm$^{-1}$: 1748, 1710, 1655, 1608, 1521, 1346, 1251.

Nuclear Magnetic Resonance Spectrum (CDCl$_3$, 270 MHz), δ ppm:
1.72–1.84 (1H, multiplet);
2.26–2.73 (6H, multiplet);
2.97–3.16 (1H, multiplet);
3.29–4.10 (7H, multiplet);
3.72 (2H, singlet);
3.79 & 3.80 (together 3H, two singlets);
4.24–4.31 (2H, multiplet);
4.52–4.63 (1H, multiplet);
5.00–5.35 (4H, multiplet);
6.85 (2H, doublet, J=8.79 Hz);
7.23 (2H, doublet, J=8.79 Hz);
7.41–7.57 (4H, multiplet);
8.16–8.25 (4H, multiplet).

90(a)(ii) (2S,4S)-4-Mercapto-2-{4-[2-(4-nitrobenzyloxycarbonyl) oxyethyl]-1-piperazinylcarbonyl}-1-(4-nitrobenzyloxycarbonyl) pyrrolidine bis(trifluoromethanesulfonate)

135.75 mg of trifluoroacetic acid and 6.18 ml of trifluoromethanesulfonic acid were added, whilst ice-cooling to a solution of 26.00 g of (2S,4S)-2-{4-[2-(4-nitrobenzyloxycarbonyl)oxyethyl]-1-piperazinylcarbonyl}-4-(4-methoxybenzylthio-1-(4-nitrobenzyloxycarbonyl) pyrrolidine in 38.3 ml of anisole, and the resulting mixture was stirred at the same temperature for 1.5 hours. At the end of this time, the solvent was removed by distillation under reduced pressure, and the resulting residue was repeatedly washed with diethyl ether by decantation and dried in vacuo, to afford 32.5 g of the title compound, as a powder.

90(a)(iii) (2S,4)-4-Mercapto-2-{4-[2-(4-nitrobenzyloxycarbonyl)oxyethyl]-1-piperazinylcarbonyl}-1-(4-nitrobenzyloxycarbonyl) pyrrolidine 20 ml of a 5% w/v aqueous solution of sodium hydrogencarbonate was added to 862 mg of (2S,4S)-4-mercapto-2-{4-[2-(4-nitrobenzyloxycarbonyl)oxyethyl]-1-piperazinylcarbonyl}-1-(4-nitrobenzyloxycarbonyl)-pyrrolidine bis(trifluoromethanesulfonate), and the mixture was extracted with 50 ml of ethyl acetate. The extract was washed with water and dried over anhydrous magnesium sulfate. The solvent was removed by distillation under reduced pressure, and the resulting residue was purified by column chromatography through silica gel, using a 20:1 by volume mixture of ethyl acetate and methanol as the eluent, to afford 514 mg of the title compound, as a powder.

Infrared Absorption Spectrum (KBr), $v_{max}$ cm$^{-1}$: 2530, 1748, 1710, 1653, 1521, 1347.

Nuclear Magnetic Resonance Spectrum (CDCl$_3$, 270 MHz), δ ppm:
1.83 (1H, multiplet);
2.44–2.79 (7H, multiplet);
3.22–3.64 (6H, multiplet);
4.06–4.17 (1H, multiplet);
4.26–4.36 (2H, multiplet);
4.60–4.71 (1H, multiplet);
5.02–5.33 (4H, multiplet);
7.42–7.58 (4H, multiplet);
8.17–8.26 (4H, multiplet).

90(b)(i) (2S,4R)-4Hydroxy-2-{4-[2-(4-nitrobenzyloxycarbonyl) oxyethyl]-1-piperazinylcarbonyl)-1-(4-nitrobenzyloxycarbonyl}pyrrolidine 25.7 ml of diethyl cyanophosphonate and 68.7 ml of triethylamine were added dropwise, whilst ice-cooling, to a suspension of 47.8 g of trans-4-hydroxy-1-(4-nitrobenzyloxycarbonyl)-L-proline and 64.8 g of 1-[2-(4-nitrobenzyloxycarbonyloxy)ethyl]piperazine dihydrochloride in 400 ml of dry dimethylformamide, and the resulting mixture was stirred at the same temperature for 30 minutes. At the end of this time, the reaction mixture was diluted with 1.5 liters of ethyl acetate, and the dilute solution was washed with water and dried over anhydrous magnesium sulfate. The solvent was removed by distillation under reduced pressure, to give 87.6 g of the title compound, as a powder.

Infrared Absorption Spectrum (KBr), $v_{max}$ cm$^{-1}$: 1749, 1709, 1650, 1607, 1522, 1499, 1347, 1263.

Nuclear Magnetic Resonance Spectrum (CDCl$_3$, 270 MHz), δ ppm:
1.63 (1H, singlet);
1.92–2.38 (8H, multiplet);
3.41–3.83 (6H, multiplet);
4.24–4.32 (2H, multiplet);
4.55–4.60 (1H, multiplet);
4.79–4.90 (1H, multiplet);
5.03–5.35 (4H, multiplet);
7.44–7.57 (4H, multiplet);
8.17–8.25 (4H, multiplet).

90(b)(i') (2S,4R)-4-Hydroxy-2-{4-[2-(4-nitrobenzyloxycarbonyl) oxyethyl]-1-piperazinylcarbonyl}-1-(4-nitrobenzyloxycarbonyl) pyrrolidine 608 μl of chlorotrimethylsilane and 670 μl of triethylamine, whilst ice-cooling, were added to a solution of 620 mg of trans-4-hydroxy-1-(4-nitrobenzyloxycarbonyl)-L-proline in 20 ml of dry acetonitrile, and the resulting mixture was stirred at room temperature for 1 hour. At the end of this time, the solvent was removed by distillation under reduced pressure, and the resulting residue was mixed with an aqueous solution of sodium chloride. The mixture was then extracted with ethyl acetate. The extract was washed with an aqueous solution of sodium chloride and dried over anhydrous magnesium sulfate. The solvent was then removed by distillation under reduced pressure, to give 648 mg of trans-1-(4-nitrobenzyloxycarbonyl)-4-trimethylsilyloxy-L-proline as a powder. The whole of this was dissolved in 14 ml of dry acetonitrile, and then 330 mg of N,N'-carbonyldiimidazole were added. The mixture thus obtained was stirred at room temperature for 1 hour. At the end of this time, a solution of 630 mg of 1-[2-(4-nitrobenzyloxycarbonyl)oxyethyl]piperazine in 2 ml of dry acetonitrile was added to the reaction mixture, and the resulting mixture was stirred overnight an room temperature and then at 40° C. for a further 1 hour. The reaction mixture was then mixed with 14 ml of 1N aqueous hydrochloric acid and stirred at room temperature for 1 hour. At the end of this time, the mixture was concentrated by evaporation under reduced pressure, and the concentrate was made slightly alkaline by the addition of an aqueous solution of sodium hydrogencarbonate; it was then extracted with ethyl acetate. The extract was washed with water and dried over anhydrous magnesium sulfate. The solvent was removed by distillation under reduced pressure, and the resulting residue was purified by column chromatography through silica gel, using a 9:1 by volume mixture of ethyl acetate and methanol as the eluent, to give 589 mg of the title compound, as a powder. The infrared absorption spectrum and nuclear magnetic resonance spectrum of the compound thus obtained were identical with those of the compound prepared as described in step 90(b)(i) above.

90(b)(ii") (2S,4R)-4-Hydroxy-2-{4-[2-(4-nitrobenzyloxycarbonyl) oxyethyl]-1-piperazinylcarbonyl}-1-(4-nitrobenzyloxycarbonyl) pyrrolidine 343 mg of N,N'-carbonyldiimidazole were added to a solution of 674 mg of trans-1-(4-nitrobenzyloxycarbonyl)-4-trimethylsilyloxy-L-proline in 14 ml of dry acetonitrile, and the resulting mixture was stirred room temperature for 1 hour. A solution of 275 mg of 1-(2-hydroxyethyl) piperazine in 1 ml of dry acetonitrile was then added to the mixture, and the mixture was stirred overnight at room temperature. At the end this time, the mixture was concentrated by evaporation under reduced pressure, and the concentrate was mixed with an aqueous solution of sodium chloride. The mixture was then extracted with ethyl acetate. The extract was washed with water and dried over anhydrous magnesium sulfate. The solvent was then removed by distillation under reduced pressure, to give 574 mg (2S,4R)-2-[4-(2-hydroxyethyl)-1-piperazinylcarbonyl]-4-trimethylsilyloxy-1-(4-nitrobenzyloxycarbonyl)pyrrolidine as an oil. The whole of the compound thus obtained was dissolved in 5.7 ml of methylene chloride, and 170 mg 4-dimethylaminopyridine and 300 mg of 4-nitrobenzyl chloroformate were added to the solution, whilst ice-cooling. The resulting mixture was stirred at room temperature for 1hour and then the solvent was removed by distillation under reduced pressure. 15 ml of 1N aqueous hydrochloric acid were added to the residue, and the mixture was stirred at room temperature for 1 hour. The reaction mixture was then made slightly alkaline by the addition of an aqueous solution of sodium hydrogencarbonate, after which it was extracted with ethyl acetate. The extract was washed with water and dried over anhydrous magnesium sulfate. The solvent was then removed by distillation under reduced pressure. Following the procedure described in step 90(b)(i') above, the residue was purified to give 348 mg of the title compound, as a powder. The infrared absorption spectrum and nuclear magnetic resonance spectrum of the compound thus obtained were identical with those of the compound prepared as described in step 90(b)(i) above.

90(b) (ii) (2S,4S)-4-Acetylthio-2-{2-[2-(4-nitrobenzyloxycarbonyl)oxyethyl]-1-piperazinylcarbonyl}-1-(4-nitrobenzyloxycarbonyl) pyrrolidine A solution of 36.5 g of diethyl azodicarboxylate in 100 ml of tetrahydrofuran was added dropwise, whilst ice-cooling, to a solution of 105 g of (2S,4S)-4-hydroxy-2-{4-[2-(4-nitrobenzyloxycarbonyl)oxyethyl]-1-piperazinylcarbonyl}-N-(4-nitrobenzyloxycarbonyl)-pyrrolidine [prepared as described in steps 90(b)(i), 90(b)(i') and 90(b)(i") above] and 55 g of triphenylphosphine in 700 ml of tetrahydrofuran, and the resulting mixture was stirred at the same temperature for 10 minutes. A solution of 15.9 g of mercaptoacetic acid in 100 ml of tetrahydrofuran was then added dropwise to the mixture, and the mixture was stirred at room temperature for 1 hour. At the end of this time, the reaction mixture was concentrated by evaporation under reduced pressure, and the concentrate was dissolved in 1.5 liters of ethyl acetate. The resulting solution was then washed with water and with an aqueous solution of sodium chloride, in that order, after which it was dried over anhydrous sodium sulfate. The solvent was removed by distillation under reduced pressure, and then the residue was mixed with 400 ml of diisopropyl ether. The diisopropyl ether-soluble materials were extracted and discarded. The same extraction operations were repeated four times, and then the resulting residue was purified by column chromatography through 3 kg of silica gel, using a gradient elution method, with mixtures of ethyl acetate and methanol ranging from 1:0 to 20:1 by volume as the eluent, to give 88.4 g of the title compound, as a colorless powder.

Infrared Absorption Spectrum (KBr), $v_{max}$ cm$^{-1}$: 1749, 1711, 1655, 1522, 1347, 1262, 1110.

Nuclear Magnetic Resonance Spectrum (CDCl$_3$, 270 MHz), δ ppm:

1.82–1.93 (1H, multiplet);

2.34 (3H, singlet);

2.35–2.82 (7H, multiplet);

3.37–3.70 (5H, multiplet);

3.91 4.05 (1H, multiplet);

4.07–4.17 (1H, multiplet);

4.23 & 4.36 (together 2H, multiplet);

4.64–4.77 (1H, multiplet);

5.02–5.35 (4H, multiplet);

7.43–7.57 (4H, multiplet);

8.18–8.26 (4H, multiplet).

90(c)(i) (2S,4R)-4-Methanesulfonyloxy-2-{4-[2-(4-nitrobenzyloxycarbonyl) oxyethyl]-1-piperazinylcarbonyl}-1-(4-nitrobenzyloxycarbonyl) pyrrolidine 89 μl of triethylamine and 50 μl of methanesulfonyl chloride were added, whilst ice-cooling, to a solution of 321 mg of (2S,4R)-4-hydroxy-2-{4-[2-(4-nitrobenzyloxycarbonyl)oxyethyl]-1-piperazinyl carbonyl}-1-(4-nitrobenzyloxycarbonyl)pyrrolidine in 3.2 ml of dry tetrahydrofuran, and the resulting mixture was stirred at between 0° C. and 5° C. for 30 minutes and then at room temperature for a further 1 hour. At the end of this time, the reaction mixture was concentrated by evaporation under reduced pressure, and the resulting residue was mixed with an aqueous solution of sodium hydrogencarbonate; the mixture was then extracted with ethyl acetate. The extract was washed with an aqueous solution of sodium chloride and dried over anhydrous magnesium sulfate. The solvent was removed by distillation under reduced pressure, to give 345 mg of the title compound as a powder.

Infrared Absorption Spectrum (KBr), $v_{max}$ cm$^{-1}$: 1751, 1710, 1654, 1607, 1523, 1436, 1406.

Nuclear Magnetic Resonance Spectrum (CDCl$_3$, 270 MHz), δ ppm:

2.22–3.01 (8H, multiplet);
3.06 (3H, singlet);
3.40–4.03 (6H, multiplet);
4.25–4.47 (2H, multiplet);
4.84 & 4.89 (together 1H, two triplets, J=7.33 Hz);
5.04–5.37 (5H, multiplet);
7.46 & 7.50 (together 2H, two doublets, J=8.79 Hz);
7.56 (2H, doublet, J=8.79 Hz);
8.19–8.26 (4H, multiplet).

90(c)(ii) (2S,4S)-4-Acetylthio-2-{4-[2-(4-nitrobenzyloxycarbonyl) oxyethyl]-1-piperazinylcarbonyl}-1-(4-nitrobenzyloxycarbonyl) pyrrolidine 51 μl of thioacetic acid were added, whilst ice-cooling, to a suspension of 26 mg of sodium hydride (as a 55% w/w dispersion in mineral oil) in 1.4 ml of dry N,N-dimethylformamide, and the resulting mixture was stirred at room temperature for 30 minutes. A solution of 340 mg of (2S,4R)-4-methanesulfonyloxy-2-{4-[2-(4-nitrobenzyloxycarbonyl)oxyethyl]-1-piperazinylcarbonyl}-1-(4-nitrobenzyloxycarbonyl)pyrrolidine [prepared as described in step 90(c)(i) above] in 2 ml of dry N,N-dimethylformamide was then added to the mixture, and the mixture was stirred at between 8° C. and 90° C. for 4 hours. At the end of this time, the temperature of the reaction mixture was allowed to reduce to room temperature, after which the mixture was poured into an aqueous solution of sodium chloride and extracted with ethyl acetate. The extract was washed with water and dried over anhydrous magnesium sulfate. The solvent was removed by distillation under reduced pressure, and the resulting residue was worked up and purified according to the procedure described in step 90(b)(i) above, to give 166 mg of the title compound, as a powder. The infrared absorption spectrum and nuclear magnetic resonance spectrum of the compound thus obtained were identical with those of the compound prepared as described in step 90(b)(ii) above.

90(c)(ii') (2S,4S)-4-Acetylthio-2-{4-[2-(4-nitrobenzyloxycarbonyl) oxyethyl]-1-piperazinylcarbonyl}-1-(4-nitrobenzyloxycarbonyl) pyrrolidine A solution of 1.10 g of N-nitrobenzyl chloroformate in 10 ml of methylene chloride was added, whilst ice-cooling, to a solution of 1.63 g of (2S,4S)-4-acetylthio-2-[4-(2-hydroxyethyl)-1-piperazinylcarbonyl]-1-(4-nitrobenzyloxycarbonyl)pyrrolidine and 0.62 g of 4-dimethylaminopyridine in 15 ml of methylene chloride and the resulting mixture was stirred at the same temperature for 2 hours. At the end of this time, the reaction mixture was diluted with 100 ml of ethyl acetate, and the dilute solution was washed, in turn, with 100 ml of an aqueous solution of sodium hydrogencarbonate, with 100 ml of water and with 100 ml of an aqueous solution of sodium chloride. The solvent was removed by distillation under reduced pressure, and the resulting residue was purified by column chromatography through silica gel, using a gradient elution method, with mixtures of ethyl acetate and methanol ranging from 30:1 to 25:1 by volume as the eluent to give 1.86 g of the title compound, as a powder. The infrared absorption spectrum and nuclear magnetic resonance spectrum of the compound thus obtained were identical with those of the compound prepared as described in step 90(b)(ii) above.

90(c)(iii) (2S,4S)-4-Mercapto-2-{4-[2-(4-nitrobenzyloxycarbonyl) oxyethyl]-1-piperazinylcarbonyl}-1-(4-nitrobenzyloxycarbonyl) pyrrolidine 600 ml of a 10% w/v methanolic solution of hydrogen chloride were added to a solution of 140 g of (2S,4S)-4-acetylthio-2-{4-[2-(4-nitrobenzyloxycarbonyl)oxyethyl]-1-piperazinylcarbonyl}-1-(4-nitrobenzyloxycarbonyl)-pyrrolidine [prepared as described in step 90(b)(ii) or 90(c)(ii) above] in 150 ml of 1,4-dioxane, and the resulting mixture was stirred at 50° C. for 1 hour. At the end of this time, the reaction mixture was concentrated by evaporation under reduced pressure, and the concentrate was diluted with 1500 ml of ethyl acetate. The dilute solution was neutralized with an aqueous solution of sodium hydrogencarbonate and washed, in turn, with 300 ml of water and with 300 ml of an aqueous solution of sodium chloride. The solvent was removed by distillation under reduced pressure, and the resulting residue was purified by column chromatography through silica gel, using a gradient elution method, with mixtures of ethyl acetate and methanol ranging from 30:1 to 20:1 by volume as the eluent, to give 96.44 g of the title compound, as a colorless powder.

The infrared absorption spectrum and nuclear magnetic resonance spectrum of the compound thus obtained were identical with those of the compound prepared as described in step 90(a)(iii) above.

PREPARATION 91

(2S,4S)-1-(t-Butoxycarbonyl)-4-(4-methoxybenzylthio)-2-pyrrolidinecarboxylic acid A solution of 0.95 g of di-t-butyldicarbonate in 4 ml of tetrahydrofuran and 4:4 ml of a 1N aqueous solution of sodium hydroxide were simultaneously added dropwise, whilst ice-cooling, to a solution of 0.97 g of (2S,4S)-4-(4-methoxybenzylthio)-2-pyrrolidinecarboxylic acid in 18 ml of tetrahydrofuran and 3.6 ml of a 1N aqueous solution of sodium hydroxide. The mixture was then stirred at room temperature for 1 hour, after which the tetrahydrofuran was removed by evaporation under reduced pressure, and the residue was acidified to a pH value of 2–3 by the addition of 1N aqueous hydrochloric acid, and the resulting mixture was extracted with ethyl acetate. The ethyl acetate solution was washed with water and with an aqueous solution of sodium chloride, after which in was dried over anhydrous magnesium sulfate. The solvent was Then removed by distillation under reduced pressure, to give 1.33 g of the title compound.

Infrared Absorption Spectrum (Liquid film), $v_{max}$ cm$^{-1}$: 1808, 1732, 1626, 1586, 1552, 1509, 1482, 1436, 1367, 1325, 1315, 1299, 1286, 1246, 1221.

Nuclear Magnetic Resonance Spectrum (CDCl$_3$+D$_2$O, 270 MHz), δ ppm:

1.45 (9H, singlet);
1.88–2.61 (3H, multiplet);
3.03–3.34 (2H, multiplet);
3.64–3.95 (1H, multiplet);

3.72 (2H, singlet);
3.80 (3H, singlet);
4.15–4.35 (1H, multiplet);
6.85 (2H, doublet, J=8.79 Hz);
7.23 (2H, doublet, J=8.79 Hz).

The preparation of certain of the compounds of the invention is further illustrated by the following Examples, and the preparation of certain starting materials is illustrated by the subsequent Preparations. All mesh sizes used herein are Tyler standard mesh.

EXAMPLE 89

(1R,5S,6S)-6-[(1R)-1-Hydroxyethyl]-1-methyl-2-{ (2S,4S) -2-[(3S)-3-trimethylammoniopyrrolidin-1-ylcarbonyl]-pyrrolidin-4-ylthio}-1-carbapen-2-em-carboxylate

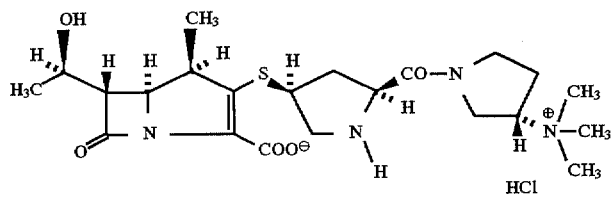

89(1) (2S,4S)-2-[(3S)-3-Dimethylamino-1-pyrrolidinylcarbonyl]-4-(4-methoxybenzylthio)-1-(4-nitrobenzyloxycarbonyl)pyrrolidine 924 mg of (2S,4S)-4-(4-methoxybenzylthio)-1-(4-nitrobenzyloxycarbonyl)-2-pyrrolidinecarboxylic acid were dissolved in 10 ml of dry tetrahydrofuran, and the resulting solution was cooled to −20° C. 209 mg of triethylamine, followed by 250 mg of pivaloyl chloride, were then added to the solution, after which the mixture was stirred at the same temperature for 5 minutes. At the end of this time, a mixture of 651 mg of (3S)-3-dimethylaminopyrrolidine trifluoroacetate, 560 mg of diisopropylethylamine and 7 ml of dry acetonitrile was added to the mixture, and the mixture was gradually heated and then stirred at 0° C. for 1 hour. After this, the reaction mixture was filtered, and the solvent was removed by evaporation under reduced pressure. The resulting residue was diluted with ethyl acetate, and the diluted solution was washed with an aqueous solution of sodium hydrogencarbonate and with a saturated aqueous solution of sodium chloride, in that order, after which it was dried over anhydrous magnesium sulfate. The solvent was then removed by distillation under reduced pressure, and the resulting residue was purified by silica gel column chromatography, using a 3:1 by volume mixture of acetonitrile and methanol as the eluent, to obtain 884 mg of the title compound as a powder.

Infrared Absorption Spectrum (KBr) $v_{max}$ cm$^{-1}$: 1710, 1654, 1512, 1345, 1109, 857, 738

Nuclear Magnetic Resonance Spectrum (hexadeuterated dimethyl sulfoxide, 270 MHz) δ ppm:

1.49–3.31 (15H, multiplet);
3.35–3.57 (2H, multiplet);
3.71–4.00 (6H, multiplet);
4.44–4.56 (1H, multiplet);
5.00–5.21 (2H, multiplet);
6.88 (2H, doublet, J=8.79 Hz);
7.27 (2H, doublet, J=8.31 Hz).
7.51–7.61 (2H, multiplet);
8.19–8.26 (2H, multiplet).

89(2) (2S,4S)2-[(3S)-3-Dimethylamino-1-pyrrolidinylcarbonyl]-4-mercapto-1-(4-nitrobenzyloxycarbonyl)-pyrrolidine trifluoromethanesulfonate 845 mg of (2S,4S)-2-[(3S)-3-dimethylamino-1-pyrrolidinylcarbonyl]-4-(4-methoxybenzylthio)-1-(4-nitrobenzyloxycarbonyl)pyrrolidine [prepared as described in step (1) above] were suspended in 1.7 ml of anisole, and 8.5 ml of trifluoroacetic acid and 0.28 ml of trifluoromethanesulfonic acid were added to the resulting suspension, whilst ice-cooling, after which the mixture was stirred at room temperature for 1 hour. The cycle comprising removing the solvent by evaporation under reduced pressure, washing the residue with hexane to remove anisole, adding diethyl ether to the mixture, cooling the mixture to −78° C. to solidify the product and milling the product, followed by decantation, was repeated several times to obtain 1.14 g of the title compound as a powder.

Infrared Absorption Spectrum (KBr) $v_{max}$ cm$^{-1}$: 1705, 1656, 1523, 1348, 857.

Nuclear Magnetic Resonance Spectrum (hexadeuterated dimethyl sulfoxide+D$_2$O, 270 MHz) δ ppm:

1.70–4.10 (18H, multiplet);
4.47–4.66 (1H, multiplet);
5.04–5.27 (2H, multiplet);
7.51–7.6B (2H, multiplet).

89(3) 4-Nitrobenzyl (1R,5S,6S)-2-{(2S,4S)-2-[(3S) -3-dimethylamino-1-pyrrolidinylcarbonyl]-6-[(1R)-1-hydroxyethyl]-1-methyl-1-(4-nitrobenzyloxycarbonyl]pyrrolidin-4-ylthio}-1-carbapen-2-em-3-carboxylate 544 mg of 4-nitrobenzyl (1R,5R,6S)-6-[(1R)-1-hydroxyethyl]-1-methyl-2-oxo-1-carbapenam-3-carboxylate were dissolved in 5.4 ml of dry acetonitrile, and 424 mg of diphenyl phosphorylchloride and 204 mg of diisopropylethylamine were added dropwise to the resulting solution, whilst ice-cooling, after which the mixture was stirred at the same temperature for 1 hour. A solution of 582 mg of diisopropylethylamine and 1.10 g of (2S,4S)-2-[(3S) -3-dimethylamino-1-pyrrolidinylcarbonyl]-4-mercapto-1-[4-nitrobenzyloxycarbonyl) -pyrrolidine trifluoromethanesulfonate [prepared as described in step (2) above] in 4 ml of dry acetonitrile was then added dropwise, whilst ice-cooling, to the mixture, after which the mixture was stirred at the same temperature for 6 hours. At the end of this time, the solvent was removed by distillation under reduced pressure, and the resulting residue was dissolved in methylene chloride and washed with water, with an aqueous solution of sodium hydrogencarbonate, again with water, and then with a saturated aqueous solution of sodium chloride. The aqueous washings were extracted with methylene chloride, and the organic phase was combined with the methylene chloride extract. The resulting mixture was dried over anhydrous magnesium sulfate. The solvent was removed from the mixture by distillation under reduced pressure, and the residue was purified by silica gel column chromatography, using a 14:1 by volume mixture of methylene chloride and methanol as the eluent, to obtain 814 mg of the title compound, as a powder.

Infrared Absorption Spectrum (KBr) $v_{max}$ cm$^{-1}$: 1773, 1711, 1650, 1607, 1522, 1346, 854, 738.

Nuclear Magnetic Resonance Spectrum (hexadeuterated dimethyl sulfoxide, 270 MHz) δ ppm:

1.15 (3H, doublet, J=3.42 Hz);
1.18 (3H, doublet, J=3.90 Hz);
2.09 (2H, doublet, J=8.3 Hz);
2.17 (1H, singlet);
2.49–2.51 (1H, multiplet);
2.70–3.93 (16H, multiplet);
3.95–4.08 (1H, multiplet);
4.11–4.20 (1H, multiplet);
4.23–4.29 (1H, multiplet);
4.55–4.66 (1H, multiplet);
5.06–5.75 (4H, multiplet);
7.53–7.74 (4H, multiplet);
8.21–8.25 (4H, multiplet).

89(4) (1R,5S,6S)-6-[(1R)-1-Hydroxyethyl]-1-methyl-2-{(2S,4S)-2-[(3S)-3-trimethylammoniopyrrolidin-1-ylcarbonyl]pyrrolidin-4-ylthio}-1-carbapen-2-em-3-carboxylate hydrochloride 771 mg of 4-nitrobenzyl (1R,5S,6S)-2-{(2S,4S)-2-[(3S)-3-dimethylamino-1-pyrrolidinylcarbonyl]-6-[(1R)-1-hydroxyethyl]-1-methyl-1-(4-nitrobenzyloxycarbonyl)-pyrrolidin-4-ylthio}-1-carbapen-2-em-3-carboxylate [prepared as described in step (3) above] were dissolved in 8 ml of dry acetonitrile, and 182 mg of methyl trifluoromethanesulfonate were added to the solution, whilst ice-cooling, after which the mixture was stirred at the same temperature for 1 hour. The powdery product obtained by evaporating off the solvent under reduced pressure was dissolved in a mixture of 7 ml of tetrahydrofuran and 3 ml of water, after which the mixture was hydrogenated at room temperature for 1 hour in the presence of a 10% w/w palladium-on-carbon catalyst. At the end of this time, the catalyst was removed by filtration, and the tetrahydrofuran was removed by distillation under reduced pressure; the aqueous phase was then washed with diethyl ether, after which it was concentrated by evaporation under reduced pressure. The resulting residue was then subjected to ion-exchange chromatography (Dowex 1-X4, 50 to 100 mesh, Cl FORM, manufactured by Dow Chemical; "Dowex" is a trade mark), using water as the eluent. The fractions containing the desired compound were collected and freeze-dried to obtain 460 mg of a crude product as a powder.

The whole of this crude product was applied to a column (Cosmosil 75C$_{18}$-prep, manufactured by Nacalai; "Cosmosil" is a trade mark) and eluted with water. The fractions containing the desired compound were combined, concentrated by evaporation under reduced pressure, and freeze-dried to obtain 182 mg of the title compound as a colorless powder.

Infrared Absorption Spectrum (KBr) $v_{max}$ cm$^{-1}$: 1756, 1656, 1599, 1479, 1373.

Nuclear Magnetic Resonance Spectrum (270 MHz, D$_2$O, internal standard: tetradeuterated sodium trimethylsilylpropionate) δ ppm:

1.21 (3H, doublet, J=6.83 Hz);
1.28 (3H, doublet, J=6.35 Hz);
1.95–2.10 (1H, multiplet);
2.40–2.65 (2H, multiplet);
3.00–3.15 (1H, multiplet);
3.21 (6H, singlet);
3.23 (3H, singlet);
3.37 (1H, doublet of doublets, J=7.32 & 9.28 Hz);
4.20–4.30 (2H, multiplet);
3.40–4.20 (9H, multiplet);
4.65–4.75 (1H, multiplet).

EXAMPLE 90

(1R,5S,6S)-6-[(1R)-1-Hydroxyethyl]-1-methyl-2-{(2S,4S) -2-[(3R)-3-trimethylammoniopyrrolidin-1-ylcarbonyl]-pyrrolidin-4-ylthio}-1-carbapen-2-em-3-carboxylate hydrochloride

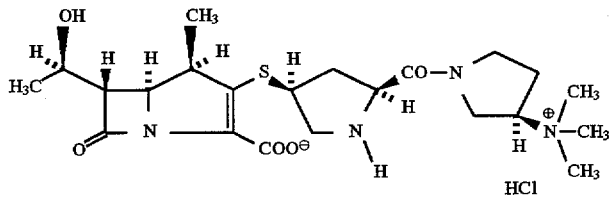

90(1) (2S,4S)-2-[(3R)-3-Dimethylamino-1-pyrrolidinylcarbonyl]-4-(4-methoxybenzylthio)-1-(4-nitrobenzyloxycarbonyl)pyrrolidine 2.60 g of (2S,4S)-4-(4-methoxybenzylthio)-1-(4-nitrobenzyloxycarbonyl)-2-pyrrolidinecarboxylic acid were dissolved in 20 ml of dry tetrahydrofuran, and the resulting solution was cooled to −20° C. 590 mg of triethylamine and then 704 mg of pivaloyl chloride were added to the solution, after which the resulting mixture was stirred at the same temperature for 5 minutes. 2100 g of (3R)-3-dimethylaminopyrrolidine trifluoroacetate, 788 mg of diisopropylethylamine and 20 ml of dry acetonitrile were then added, in that order, to the mixture, and the mixture was gradually heated and then stirred at 0° C. for 1 hour. The reaction mixture was then filtered, and the solvent was removed by evaporation under reduced pressure. The residue was diluted with ethyl acetate, and the diluted solution was washed with an aqueous solution of sodium hydrogencarbonate and with a saturated aqueous solution of sodium chloride, in that order. It was then dried over anhydrous magnesium sulfate. The solvent was removed by distillation under reduced pressure, and the resulting residue was purified by silica gel column chromatography, using a 3:1 by volume mixture of acetonitrile and methanol as the eluent, to obtain 2.56 g of the title compound as a powder.

Infrared Absorption Spectrum (KBr) $v_{max}$ cm$^{-1}$: 1710, 1655, 1512, 1344, 1110, 857, 738.

Nuclear Magnetic Resonance Spectrum (hexadeuterated dimethyl sulfoxide, 270 MHz) δ ppm:

1.28–3.31 (15H, multiplet);
3.40–3.63 (2H, multiplet);
3.72–3.92 (6H, multiplet);
4.36–4.53 (1H, multiplet);
4.95–5.22 (2H, multiplet);
6.88 (2H, doublet, J=8.79 Hz);
7.27 (2H, doublet, J=8.31 Hz);
7.51–7.61 (2H, multiplet);
8.18–8.26 (2H, multiplet).

90(2) (2S,4S)-2-[(3R)-3-Dimethylamino-1-pyrrolidinylcarbonyl]-4-mercapto-1-(4-nitrobenzyloxycarbonyl)-pyrrolidine trifluoromethanesulfonate 2.56 g of (2S,4S)-2-[(3R)-3-dimethylamino-1-pyrrolidinylcarbonyl]-4-(4-methoxybenzylthio)-1-(4-nitrobenzyloxycarbonyl)pyrrolidine [prepared as described in step (1) above] were suspended in 5.1 ml of anisole, and 25.5 ml of trifluoroacetic acid and 0.83 ml of trifluoromethanesulfonic acid were added, whilst ice-cooling, to the resulting suspension. The mixture was then stirred at room temperature for 3 hours. At the end of this time, the solvent was removed by distillation under reduced pressure, 1,2-dichloroethane was added to the residue, and excess acid was removed by azeotropic distillation. The residue was decanted using hexane and then triturated with diethyl ether, after which the mixture was decanted and dried by evaporation under reduced pressure to give 3.65 g of the title compound as a powdery product.

90(3) 4-Nitrobenzyl (1R,5S,6S)-2-[(2S,4S) -2-[(3R) -3-dimethylamino-1-pyrrolidinylcarbonyl]-6-[(1R)-1-hydroxyethyl]-1-methyl-1-(4-nitrobenzyloxycarbonyl)pyrrolidin-4-ylthio]-1-carbapen-2-em-3-carboxylate 1.71 g of 4-nitrobenzyl (1R, 5R,6S)-6-[(1R)-1-hydroxyethyl]-1-methyl-2-oxoyl-carbapenam-3-carboxylate were dissolved in 17 ml of dry acetonitrile, and 1.34 mg of diphenyl phosphorylchloride and 646 mg of diisopropylethylamine were added dropwise, whilst ice-cooling, to the resulting solution, after which the mixture was stirred at the same temperature for 1 hour. At the end of this time, a solution of 1.84 g of diisopropylethylamine and 3.65 g of (2S,4S)-2-[(3R)-3-dimethylamino-1-pyrrolidinylcarbonyl]-4-mercapto-1-(4-nitrobenzyloxycarbonyl)pyrrolidine trifluoromethane-sulfonate [prepared as described in step (2) above] in 35 ml of dry acetonitrile was added dropwise to the resulting mixture, after which the mixture was stirred at the same temperature for 7 hours. At the end of this time, the solvent was removed by distillation under reduced pressure, and the resulting residue was dissolved in methylene chloride. The resulting solution was washed with water, with an aqueous solution of sodium hydrogencarbonate, again with water and then with a saturated aqueous solution of sodium chloride, in that order. The aqueous washings were then extracted with methylene chloride and the organic phase was combined with the extract and dried over anhydrous magnesium sulfate. The solvent was removed by distillation under reduced pressure, and the resulting residue was purified by silica gel column chromatography, using a 12:1 by volume mixture of methylene chloride and methanol as the eluent, to obtain 2.60 g of the title compound, as a powder.

Infrared Absorption Spectrum (KBr) $v_{max}$ cm$^{-1}$: 1773, 1712, 1652, 1608, 1523, 1346, 855, 738.

Nuclear Magnetic Resonance Spectrum (hexadeuterated dimethyl sulfoxide, 270 MHz) δ ppm:

1.15 (3H, doublet, J=3.91 Hz);
1.18 (3H, doublet, J=4.39 Hz);
2.07 (2H, singlet);
2.16 (2H, doublet, J=4.88 Hz);
2.49–2.51 (1H, multiplet);
2.7–4.2 (16H, multiplet);
3.9–4.0 (1H, multiplet);
4.2–4.3 (1H, multiplet);
4.4–4.6 (1H, multiplet);
5.0–5.5 (4H, multiplet);
7.5–7.8 (4H, multiplet);
8.2–8.3 (4H, multiplet).

90(4) (1R,5S,6S)-6-[(1R)-1-Hydroxyethyl]-1-methyl-2-{(2S,4S)-2-[(3R)-3-trimethylammoniopyrrolidin-1-ylcarbonyl]pyrrolidin-4-ylthio}-1-carbapen-2-em-3-carboxylate hydrochloride 1.30 g of 4-nitrobenzyl (1R,5S,6S)-2-[(2S,4S)-2-[(3R)-3-dimethylamino-1-pyrrolidinylcarbonyl]-6-[(1R)-1-hydroxyethyl]-1-methyl-1-(4-nitrobenzyloxycarbonyl)-pyrrolidin-4-ylthio]-1-carbapen-2-em-3-carboxylate [prepared as described in step (3) above] were dissolved in 13 ml of dry acetonitrile, and 307 mg of methyl trifluoromethanesulfonate were added to the resulting solution, whilst ice-cooling, after which the mixture was stirred at the same temperature for 1 hour. The powdery product obtained by evaporating off the solvent under reduced pressure was dissolved in a mixture of 12 ml of tetrahydrofuran and 5 ml of water, after which the mixture was hydrogenated at room temperature for 1.5 hours in the presence of 3 g of a 10% w/w palladium-on-carbon catalyst. At the end of this time, the catalyst was removed by filtration, and the tetrahydrofuran was distilled off under reduced pressure. The aqueous phase was then washed with diethyl ether and concentrated by evaporation under reduced pressure. It was then subjected to ion-exchange chromatography (Dowex 1-X4, 50 to 100 mesh, Cl FORM, manufactured by Dow Chemical), using water as the eluent. The fractions containing the desired compound were collected and freeze-dried to obtain a crude product as a powder.

This crude product was applied to a column (Cosmosil 75C$_{18}$-prep, manufactured by Nacalai) and eluted with water. The fractions containing the desired compound were combined, concentrated by evaporation under reduced pressure, and freeze-dried to obtain 173 mg of the title compound as a colorless powder.

Infrared Absorption Spectrum (KBr) $v_{max}$ cm$^{-1}$: 1758, 1656, 1600, 1479, 1374.

Nuclear Magnetic Resonance Spectrum (270 MHz, D$_2$O, internal standard: tetradeuterated sodium trimethylsilylpropionate) δ ppm:

1.21 (3H, doublet, J=7.32 Hz);
1.28 (3H, doublet, J=6.35 Hz);
1.95–2.10 (1H, multiplet);
2.45–2.60 (2H, multiplet);
3.05–3.25 (1H, multiplet);
3.20 (6H, singlet);
3.21 (3H, singlet);
3.37 (1H, doublet of doublets, J=7.32 & 9.27 Hz);
3.45–3.55 (2H, multiplet);
3.60–4.20 (9H, multiplet);
4.20–4.35 (2H, multiplet);
4.63–4.72 (1H, multiplet).

EXAMPLE 91

(1R,5S,6S)-2-{(2S,4S)-2-[(3S) -1,1-Dimethyl-3-pyrrolidinioaminocarbonyl]pyrrolidin-4-ylthio}-6-[(1R)-1-hydroxyethyl]-1-methyl-1-carbapen-2-em-3-carboxylate hydrochloride

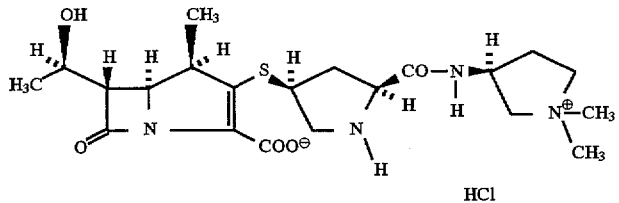

HCl

91(1) (2S,4S)-4-(4-Methoxybenzylthio)-2-](3S)-1-methyl -3-pyrrolidinylaminocarbonyl]-1-(4-nitrobenzyloxycarbonyl)-pyrrolidine 7.99 g of (2S,4S)-4-(4-methoxybenzylthio)-1-(4-nitrobenzyloxycarbonyl)-2-pyrrolidinecarboxylic acid were dissolved in 80 ml of dry acetonitrile, and 3.05 g of N,N'-carbodiimidazole were added to the resulting solution, after which the mixture was stirred at room temperature for 2 hours. At the end of this time, the reaction mixture was cooled to 0° C., and then a solution of 3.34 g of (3S)-3-amino-1-t-butoxycarbonylpyrrolidine in 30 ml of dry acetonitrile was added thereto. The mixture was then stirred at the same temperature for 20 minutes, at room temperature for 1.4 hours and then at 32° C. for 45 minutes. At the end of this time, the reaction mixture was concentrated by evaporation under reduced pressure, diluted with 200 ml of ethyl acetate and then washed twice with water and twice with a saturated aqueous solution of sodium chloride. The organic phase was then dried over anhydrous magnesium sulfate, and the solvent was removed by distillation under reduced pressure. The residue was recrystallized from diethyl ether to obtain 9.11 g of a powder.

1.00 g of the powder thus obtained was mixed with 10 ml of ethyl acetate and dissolved by heating. 2.5 ml of a 4N solution of hydrogen chloride in ethyl acetate were then added to the solution, after which the mixture was heated under reflux for 30 minutes. The solvent was then removed by distillation under reduced pressure, after which ethyl acetate was added to the residue, and the solvent was again removed by distillation under reduced pressure, so as to remove the acid. The resulting residue was triturated with diethyl ether, after which the mixture was decanted. The solvent was removed by distillation under reduced pressure to obtain 30 mg of a hygroscopic powder. This procedure was repeated to obtain further quantities of the powder.

2.5 g of the powder thus obtained were mixed with 25 ml of dioxane, and a 2.00 ml of a 5N aqueous solution of sodium hydroxide were added to the mixture at 10° C., followed by 0.47 ml of dimethyl sulfate, after which the mixture was stirred at the same temperature for 50 minutes and then at room temperature for 40 minutes. At the end of this time, the solvent was removed by distillation under reduced pressure, and the resulting residue was diluted with ethyl acetate. The resulting organic phase was washed with a saturated aqueous solution of sodium chloride. The aqueous phase was extracted with ethyl acetate, and the organic phases were combined and dried over anhydrous magnesium sulfate. The solvent was removed by distillation under reduced pressure, and the residue obtained was subjected to silica gel chromatography, using a gradient elution method, with mixtures of ethyl acetate and methanol ranging from 1:1 to 1:5 by volume as the eluent, to obtain 850 mg of the title compound, as a powder.

Infrared Absorption Spectrum (KBr) $v_{max}$ cm$^{-1}$: 1713, 1648, 1523, 1346, 1244, 1030, 850, 738.

Nuclear Magnetic Resonance spectrum (270 MHz, CDCl$_3$) δ ppm:

1.87–3.71 (16H, multiplet);
3.79 (3H, singlet);
4.15–4.50 (2H, multiplet);
5.10–5.30 (2H, multiplet);
6.82–6.87 (2H, multiplet);
7.19–7.23 (2H, multiplet);
7.49 (2H, doublet, J=8.79 Hz);
8.22 (2H, doublet, J=8.30 Hz).

(91)2 4-Nitrobenzyl (1R,5S,6S)-2-{(2S,4S)-2-[(3S) -1-methyl-3-pyrrolidinylaminocarbonyl]-1-(4-nitrobenzyloxycarbonyl)pyrrolidin -4-ylthio}-6-[(1R)-1-hydroxyethyl]-1-methyl-1-carbapen-2-em-3-carboxylate 834 mg of (2S,4S)-4-(4-methoxybenzylthio)-2-[(3S) -1-methyl-3-pyrrolidinylaminocarbonyl]-1-(4-nitrobenzyloxycarbonyl)pyrrolidine [prepared at described in step (1) above] were suspended in 1.7 ml of anisole, and 8.6 ml of trifluoroacetic acid and 0.28 ml of trifluoromethanesulfonic acid were added, whilst ice-cooling, to the resulting suspension, after which the mixture was stirred at room temperature for 1 hour. At the end of this time, the solvent was removed by distillation under reduced pressure, 1,2-dichloroethane was added to the residue, and the acid was removed by azeotropic distillation. The resulting residue was decanted with hexane and was then triturated with diethyl ether, after which the mixture was decanted and dried by evaporation under reduced pressure to give a salt as a powdery product.

572 mg of 4-nitrobenzyl (1R, 5R,6S)-6-[(1R)-1-hydroxyethyl]-1-methyl-2-oxo-1-carbapenam-3-carboxylate were dissolved in 5.7 ml of dry acetonitrile, and 445 mg of diphenylphosphoryl chloride and 214 mg of diisopropylethylamine were added dropwise, whilst ice-cooling, to the resulting solution. The mixture was then stirred at the same temperature for 1 hour. At the end of this time, a solution of 613 mg of diisopropylethylamine and the whole of the salt obtained in the above step in 6.1 ml of dry acetonitrile was added dropwise, whilst ice-cooling, to the resulting mixture and the mixture was stirred at the same temperature for 6 hours. The solvent was then removed by distillation under reduced pressure, and the residue was dissolved ethyl acetate. The resulting solution was then washed with water, with an aqueous solution of sodium hydrogencarbonate, again with water and finally with a saturated aqueous solution of sodium chloride. The aqueous washings were combined and extracted with ethyl acetate, and all the organic phases, including this extract, were combined and dried over anhydrous magnesium sulfate. The solvent was then removed by distillation under reduced pressure, and the resulting residue was purified by silica gel column chromatography, using a 6:1 by volume mixture of methylene chloride and methanol as the eluent, to obtain 566 mg of the title compound, as a powder.

Infrared Absorption Spectrum (KBr) $v_{max}$ cm$^{-1}$: 1775, 1712, 1670, 1606, 1522, 1346, 852, 737.

Nuclear Magnetic Resonance Spectrum (hexadeuterated dimethyl sulfoxide+D$_2$O, 270 MHz) δ ppm:

1.15 (3H, doublet, J=1.47 Hz);

1.17 (3H, doublet, J=2.44 Hz);

1.39–3.35 (12H, multiplet);

3.29 (1H, doublet of doublets, J=2.44 & 6.35 Hz);

3.54–3.66 (1H, multiplet);

3.79–4.32 (6H, multiplet);

5.09–5.48 (4H, multiplet);

7.57–7.74 (4H, multiplet);

8.19–8.25 (4H, multiplet).

91(3) (1R,5S,6S)-2-{(2S,4S)-2-[(3S)-1,1-Dimethyl-3-pyrrolidinioaminocarbonyl]pyrrolidine4-ylthio}-6-[(1R)-1-hydroxyethyl]-1-methyl-1-carbapen-2-em-3-carboxylate hydrochloride 552 mg of 4-nitrobenzyl (1R,5S,6S)-2-{(2S,4S)-2-[(3S)-1-methyl-3-pyrrolidinylaminocarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (2) above] were dissolved in 5 ml of dry acetonitrile, and 132 mg of methyl trifluoromethanesulfonate were added to the solution, whilst ice-cooling. The mixture was then stirred at the same temperature for 30 minutes. The powdery product obtained by evaporation of the solvent was dissolved in a mixture of 14 ml of tetrahydrofuran and 7 ml of water, after which the mixture was hydrogenated at room temperature for 1 hour in an atmosphere of hydrogen and in the presence of 1.2 g of a 10% w/w palladium-on-carbon catalyst. At the end of this time, the catalyst was removed by filtration and the tetrahydrofuran was distilled off under reduced pressure. The aqueous phase was then washed with diethyl ether. The aqueous phase was concentrated by evaporation under reduced pressure and then subjected to ion-exchange chromatography (Dowex 1-X4, 50 to 100 mesh, Cl FORM, manufactured by Dow Chemical), using water as the eluent. The fractions containing the desired compound were collected, and freeze-dried to obtain a crude product as a powder.

This crude product was applied to a column (Cosmosil 75C$_{18}$-prep, manufactured by Nacalai) and eluted with water. The fractions containing the desired compound were combined, concentrated and freeze-dried to obtain 187 mg of the title compound as a colorless powder.

Infrared Absorption Spectrum (KBr) $v_{max}$ cm$^{-1}$: 1758, 1683, 1595, 1562, 1452, 1384.

Nuclear Magnetic Resonance Spectrum (270 MHz, D$_2$O, internal standard: tetradeuterated sodium trimethylsilylpropionate) δ ppm:

1.21 (3H, doublet, J=7.32 Hz);

1.29 (3H, doublet, J=6.35 Hz);

2.10–2.20 (1H, multiplet);

2.25–2.40 (1H, multiplet);

2.70–2.85 (1H, multiplet);

2.85–3.00 (1H, multiplet);

3.24 (3H, singlet);

3.28 (3H, singlet);

3.35 (1H, doublet of doublets, J=7.33 & 9.28 Hz);

3.40–4.10 (9H, multiplet);

4.20–4.30 (2H, multiplet);

4.48 (1H, doublet of doublets, J=5.86 & 9.28 Hz).

EXAMPLE 92

(1R,5S,6S)-2-{(2S,4S)-2-[(3R)-1,1-Dimethyl-3-pyrrolidinioaminocarbonyl]pyrrolidin-4ylthio}-6-[(1R)-1-hydroxyethyl]-1-methyl-1-carbapen-2-em-3-carboxylate hydrochloride

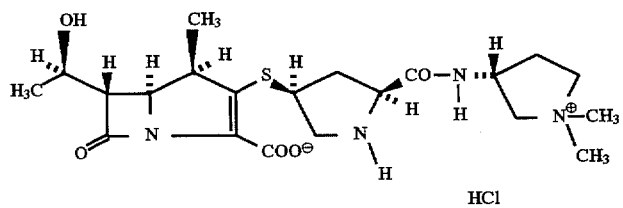

92(1) (2S,4S)-4-(4-Methoxybenzylthio)-2-[(3R)-1-methyl-3-pyrrolidinylaminocarbonyl]-1-(4-nitrobenzyloxycarbonyl)-pyrrolidine 8.00 g of (2S,4S)-4-(4-methoxybenzylthio)-1-(4-nitrobenzyloxycarbonyl)-2-pyrrolidinecarboxylic acid were dissolved in 80 ml of dry acetonitrile, and 3.05 g of N,N'-carbodiimidazole were added to the resulting solution, after which the mixture was stirred at room temperature for 2 hours. At the end of this time, the reaction mixture was cooled to 0° C., and then a solution of 3.67 g of (3R)-3-amino-1-t-butoxycarbonylpyrrolidine in 7 ml of dry acetonitrile was added to the mixture, which was then stirred at the same temperature for 10 minutes and then at room temperature for 2 hours. At the end of this time, the reaction mixture was concentrated by evaporation under reduced pressure. The resulting residue was diluted with 200 ml of ethyl acetate and then washed twice, each time with 100 ml of water, and once with 100 ml of a saturated aqueous solution of sodium chloride. The organic phase was dried over anhydrous magnesium sulfate, the solvent was removed by distillation under reduced pressure, and the residue was purified by silica gel column chromatography, using a 3:1 by volume mixture of ethyl acetate and cyclohexane as the eluent, to obtain 9.26 g of a white powder.

4.80 g of this powder were dissolved in 45 ml of ethyl acetate, and 15.6 ml of a 4N solution of hydrogen chloride in ethyl acetate were added to the resulting solution. The mixture was then heated under reflux for 30 minutes, after which the solvent was removed by distillation under reduced pressure. Ethyl acetate was added to the residue, and then the solvent was distilled off, so as to remove the acid. The residue thus obtained was triturated with diethyl ether after which the mixture was decanted. The solvent was then removed by distillation under reduced pressure to obtain 4.47 g of a white powder.

1.98 g of this powder were mixed with 20 ml of dioxane, and 1.58 ml of a 5N aqueous solution of sodium hydroxide and 0.41 ml of dimethyl sulfate were added at 10° C. to the mixture, after which the mixture was stirred at the same temperature for 30 minutes. At the end of this time, the solvent was removed by distillation under reduced pressure, the residue was diluted with ethyl acetate, and the resulting organic phase was washed with a saturated aqueous solution of sodium chloride. The aqueous washings were extracted with ethyl acetate. The organic phase was combined with the resulting extract, and the mixture was dried over anhydrous magnesium sulfate. The solvent was removed by distillation under reduced pressure, and the resulting residue was subjected to silica gel chromatography, using a 1:5 by volume mixture of ethyl acetate and methanol as the eluent, to obtain 550 mg of the title compound as a powder.

92(2) 4-Nitrobenzyl (1R,5S,6S)-6-[(1R)-1-hydroxyethyl]-1-methyl-2-{(2S,4S)-2-[(3R)-1-methyl-3-pyrrolidinyl -aminocarbonyl]-1-(4-nitrobenzyloxycarbonyl)pyrrolidin-4-ylthio}-1-carbapen-2-em-3-carboxylate 550 mg of (2S,4S)-4-(4-methoxybenzylthio)-2-[(3R)-1-methyl-3-pyrrolidinylaminocarbonyl]-1-(4-nitrobenzyloxycarbonyl)pyrrolidine [prepared as described in step (1) above] were suspended in 1.1 ml of anisole, and 5.5 ml of trifluoroacetic acid and 0.18 ml of trifluoromethanesulfonic acid were added to the resulting suspension, whilst ice-cooling, after which the mixture was stirred at room temperature for 1 hour. At the end of this time, the solvent was removed by distillation under reduced pressure, 1,2-dichloroethane was added to the residue, and the acid was removed by azeotropic distillation. The residue was decanted with hexane and then triturated with diethyl ether, after which the mixture was decanted and dried by evaporation under reduced pressure, to give a salt as a powdery product.

377 mg of 4-nitrobenzyl (1R, 5R,6S)-6-[(1R)-1-hydroxyethyl]-1-methyl-2-oxo-1-carbapenam-3-carboxylate was dissolved in 3.7 ml of dry acetonitrile, and 293 mg of diphenylphosphoryl chloride and 141 mg of diisopropylethylamine were added dropwise to the resulting solution, whilst ice-cooling, after which the mixture was stirred at the same temperature for 1 hour. At the end of this time, a solution of 403 mg of diisopropylethylamine and the whole of the salt obtained in the above step in 4 ml of dry acetonitrile was added dropwise to the resulting mixture, whilst ice-cooling. The resulting mixture was stirred at the same temperature for 1 hour and then left to stand in a refrigerator overnight. At the end of this time, the mixture was stirred at room temperature for 1.5 hours and the solvent was removed by distillation under reduced pressure. The resulting residue was dissolved in 10 ml of methylene chloride, after which the mixture was washed with water, with an aqueous solution of sodium hydrogencarbonate, again with water and finally with a saturated aqueous solution of sodium chloride, in that order. The aqueous washings were dried over anhydrous magnesium sulfate and the solvent was removed by distillation under reduced pressure. The resulting residue was purified by silica gel column chromatography, using a 3:1:3 by volume mixture of ethyl acetate, methylene chloride and methanol as the eluent, to obtain 230 mg of the title compound as a powder.

Infrared Absorption Spectrum (KBr) $v_{max}$ cm$^{-1}$: 1775, 1712, 1670, 1617, 1522, 1345, 853, 738.

Nuclear Magnetic Resonance Spectrum (hexadeuterated dimethyl sulfoxide+D$_2$O, 270 MHz) δ ppm:

1.15 (3H, doublet, J=1.15 Hz);
1.17 (3H, doublet, J=1.95 Hz);
1.47–1.56 (1H, multiplet);
1.72–1.75 (1H, multiplet);
1.98–3.39 (17H, multiplet);
3.54–3.62 (1H, multiplet);
3.84–4.34 (6H, multiplet);
5.08–5.49 (4H, multiplet);
7.57–7.74 (4H, multiplet);
8.19–8.25 (4H, multiplet).

92(3) (1R,5S,6S)-2-{(2S,4S)-2-[(3R)-1,1-Dimethyl-3pyrrolidinioaminocarbonyl]pyrrolidin-4-ylthio}-6-[(1R)-1-hydroxyethyl]-1-methyl-1-carbapen-2-em-3-carboxylate hydrochloride 230 mg of 4-nitrobenzyl (1R,5S,6S)-6-[(1R)-1-hydroxyethyl]-1-methyl-2-{(2S,4S)-2-[(3R)-1-methyl-3-pyrrolidinylaminocarbonyl]-1-(4-nitrobenzyloxycarbonyl)pyrrolidin-4-ylthio}-1-carbapen-2-em-3-carboxylate [prepared as described in step (2) above] were dissolved in 2 ml of dry acetonitrile, and 55.3 mg of methyl trifluoromethanesulfonate were added to the solution, whilst ice-cooling, after which the mixture was stirred at the same temperature for 30 minutes. The powdery product obtained by evaporation of the solvent was dissolved in a mixture of 7 ml of tetrahydrofuran and 3 ml of water, after which the mixture was hydrogenated at room temperature for 0.5 hour in an atmosphere of hydrogen and in the presence of 0.6 g of a 10% w/w palladium-on-carbon catalyst. At the end of this time, the catalyst was removed by filtration and the tetrahydrofuran was removed by distillation under reduced pressure. The aqueous residue was then washed with diethyl ether, concentrated by evaporation under reduced pressure and then subjected to ion-exchange chromatography (Dowex 1-X4, 50 to 100 mesh, Cl FORM, manufactured by Dow Chemical), using water as the eluent. Those fractions containing the desired compound were collected and freeze-dried to give a crude product as a powder.

This crude product was applied to a column (Cosmosil 75C$_{18}$-prep, manufactured by Nacalai) and eluted with water. Those fractions containing the desired compound were combined, concentrated by evaporation under reduced pressure, and freeze-dried to obtain 42 mg of the title compound as a colorless powder.

Infrared Absorption Spectrum (KBr) $v_{max}$ cm$^{-1}$: 1758, 1683, 1593, 1559, 1458, 1386.

Nuclear Magnetic Resonance Spectrum (270 MHz, D$_2$O, internal standard: tetradeuterated sodium trimethylsilylpropionate) δ ppm:

1.20 (3H, doublet, J=6.83 Hz);
1.28 (3H, doublet, J=6.35 Hz);
2.11–2.35 (2H, multiplet);
2.71–3.02 (2H, multiplet);
3.20 (3H, singlet);
3.27 (3H, singlet);
3.34 (1H, doublet of doublets, J=7.33 & 9.28 Hz);
3.45–4.09 (9H, multiplet);
4.21–4.27 (2H, multiplet);
4.51 (1H, doublet of doublets, J=6.84 & 9.28 Hz).

EXAMPLE 93

(1R,5S,6S)-2-[(2S,4S)-2-[(2S,4S) -2-Carbamoyl-4-trimethylammoniopyrrolidin-1-ylcarbonyl]pyrrolidin -4-ylthio]-6-[(1R)]-1-hydroxyethyl]-1-methyl-1-carbapen-2-em-3-carboxylate

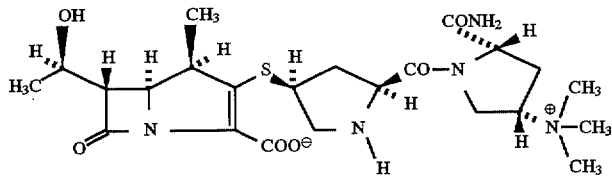

866 mg of 4-nitrobenzyl (1R,5R,6R)-6-[(1R)-1-hydroxyethyl]-1-methyl-2-oxo-1-carbapenam-3-carboxylate were dissolved in 8 ml of dry acetonitrile, and 520 µl of diphenylphosphoryl chloride and 437 µl of diisopropylethylamine were added dropwise to the resulting solution, whilst ice-cooling. The mixture was then stirred at the same temperature for 45 minutes. At the end of this time, a solution of 895 µl of diisopropylethylamine and 1.62 g of (2S,4S)-2-[(2S,4S)-2-carbamoyl-4-dimethylaminopyrrolidin -1-ylcarbonyl]-4-mercapto-1-(4-nitrobenzyloxycarbonyl)pyrrolidine trifluoromethanesulfonate in 7 ml of dry acetonitrile was added dropwise, whilst ice-cooling, to the mixture. The resulting mixture was then stirred at the same temperature for 30 minutes, after which it was left to stand overnight, whilst ice-cooling. The mixture was then treated in the same manner as described in Example 89(2), and was subjected to silica gel column chromatography. The fractions obtained by a gradient elution method, using mixtures of ethyl acetate and methanol ranging from 80:20 to 70:30 by volume as the eluent, were combined and concentrated by evaporation under reduced pressure, to obtain 521 mg of 4-nitrobenzyl (1R,5R,6R)-2-{(2S,4S)-2-[(2S,4S) -2-carbamoyl-4-dimethylaminopyrrolidin-1-ylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate as a pale brown powder. 505 mg of this compound were dissolved in 6 ml of dry acetonitrile, and 81 µl of methyl fluorosulfonate were added dropwise, whilst ice-cooling, to the resulting solution, after which the mixture was stirred at the same temperature for 1 hour. At the end of this time, the solvent was removed by distillation under reduced pressure, and the resulting crude product was hydrogenated, treated and purified in the same manner as described in Example 89(4), to obtain 161 mg of the title compound as a colorless powder.

Infrared Absorption Spectrum (KBr) $v_{max}$ cm$^{-1}$: 1754, 1668, 1600, 1436, 1382, 1288, 1264, 1225.

Ultraviolet Absorption Spectrum (HO), $\lambda_{max}$ nm: 298.0.

Nuclear Magnetic Resonance Spectrum (hexadeuterated dimethyl sulfoxide+D$_2$O, 270 MHz) δ ppm:

1.04 (3H, doublet, J=6.84 Hz);
1.15 (3H, doublet, J=6.35 Hz);
2.05–2.17 (1H, multiplet);
2.47–2.65 (3H, multiplet);
2.96–3.19 (2H, multiplet);
3.07 (9H, singlet);
3.52–3.78 (4H, multiplet);
3.84–4.07 (3H, multiplet);
4.21–4.34 (1H, multiplet);
4.40 4.56 (2H, multiplet).

EXAMPLE 94

(1R,5S, 6S)-2-{(2S,4S)-2-](3S)-3-(Carbamoylmethyldimethylammonio) pyrrolidin-1-ylcarbonyl]pyrrolidin-4-ylthio}-6-](1R)-1-hydroxyethyl]-1-methyl-1-carbapen-2-em-3-carboxylate hydrochloride

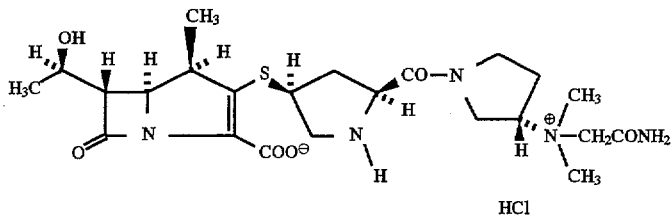

1.00 g of 4-nitrobenzyl (1R, 5S,6S)-2-{(2S,4S)-2-(3S)-3-dimethylamino-1-pyrrolidinylcarbonyl]-6-[(1R)-hydroxyethyl]-1-methyl-1-(4-nitrobenzyloxycarbonyl)-pyrrolidin-4-ylthio}-1-carbapen-2-em-3-carboxylate [prepared as described in Example 89(3)] was dissolved in 10 ml of dry acetonitrile, and 1.21 g of 2-iodoacetamide were added to the resulting solution, after which the mixture was stirred at 70° C. for 1.5 hours. At the end of this time, the solvent was removed by distillation under reduced pressure, and the residue was washed by decantation with diethyl ether and dried by evaporation under reduced pressure to obtain 1.28 g of a powder. The whole of this compound was dissolved in a mixture of 12 ml of tetrahydrofuran and 12 ml of water, and 1.00 g of a 10% w/w palladium-on-carbon catalyst was added to the solution. The mixture was then hydrogenated at room temperature for 2 hours. At the end of this time, the reaction mixture was treated, purified and freeze-dried in the same manner as described in Example 89(4), to obtain 155 mg of the title compound as a colorless powder.

Infrared Absorption Spectrum (KBr) $v_{max}$ cm$^{-1}$: 1758, 1695, 1656, 1600, 1469, 1375, 1286, 1226, 1182.

Ultraviolet Absorption Spectrum (H$_2$O), $\lambda_{max}$ nm:

296.9

Nuclear Magnetic Resonance Spectrum (hexadeuterated dimethyl sulfoxide, 270 MHz) δ ppm:

1.14 (3H, doublet, J=6.84 Hz);

1.15 (3H, doublet, J=6.34 Hz);

1.52–1.74 (1H, multiplet);

2.18–2.94 (4H, multiplet);

3.19 (1H, doublet of doublets, J=6.35 & 2.44 Hz);

3.25 (3H, singlet);

3.26 (3H, singlet);

3.25–4.25 (15H, multiplet);

4.44–4.63 (1H, multiplier);

5.08 (1H, broad singlet).

EXAMPLE 95

(1R,5S,6)-[(2S,4S)-2-{(3S)-3-[(2-Hydroxyethyl)-dimethylammonio]pyrrolidin-1-ylcarbonyl)pyrrolidin-4-ylthio}-6-[(1R)-1-hydroxyethyl]-1-methyl-1-carbapen-2-em-3-carboxylate hydrochloride

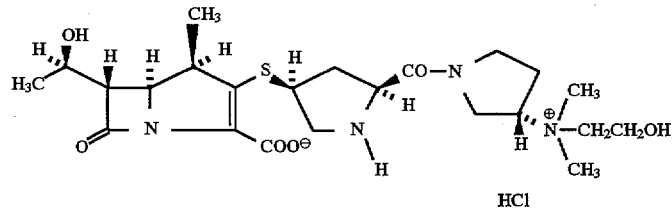

1.68 g of 4-nitrobenzyl (1R,5S,6S)-2-{(2S,4S) -2-[(3S)-3-dimethylamino-1-pyrrolidinylcarbonyl]-6-[(1R)-1-hydroxyethyl]-1-methyl-1-(4-nitrobenzyloxycarbonyl)-pyrrolidin-4-ylthio}-1-carbapen-2-em-3-carboxylate [prepared as described in Example 89(3)] were dissolved in 12 ml of dry acetonitrile and 1.68 g of 2-iodoethanol were added to the resulting solution, after which the mixture was stirred at 70° C. to 75° C. for 6.5 hours. The solvent was then removed by distillation under reduced pressure, and the residue was washed by decantation with diethyl ether and dried by evaporation under reduced pressure to obtain 1.66 g of a powdery product. The whole of this compound was dissolved in a mixture of 15 ml of tetrahydrofuran and 15 ml of water, and 1.20 g of a 10% w/w palladium-on-carbon catalyst were added to the solution, after which the mixture was hydrogenated at room temperature for 2 hours. At the end of this time, the reaction mixture was treated, purified and freeze-dried in the same manner as described in Example 89(4), to obtain 250 mg of the title compound as a colorless powder.

Infrared Absorption Spectrum (KBr) $v_{max}$ cm$^{-1}$: 1758, 1656, 1599, 1469, 1374, 1286, 1258, 1227, 1148.

Ultraviolet Absorption Spectrum (H$_2$O), $\lambda_{max}$ nm: 296.2

Nuclear Magnetic Resonance Spectrum (270 MHz, D$_2$O, internal standard: tetradeuterated sodium trimethylsilylpropionate) δ ppm:

1.21 (3H, doublet, J=6.84 Hz);

1.29 (3H, doublet, J=6.34 Hz);
1.96–2.13 (1H, multiplet);
2.30–2.64 (2H, multiplet);
2.94–3.16 (1H, multiplet);
3.22 & 3.25 (together 6H, two singlets);
3.25–3.70 (6H, multiplet);
3.72–4.84 (1H, multiplet).

EXAMPLE 96

(1R,5S,6S)-2-[(2S,4S)-2-[(3S)-3-[N -(N,N-Dimethylcarbamoylmethyl)-N,N-dimethylaminopyrrolidin-1-ylcarbonyl]pyrrolidin-4-ylthio]-6-[(1R)-1-hydroxyethyl]-1-methyl-1-carbapen-2-em-3-carboxylate hydrochloride 2.49–2.56 (2H, multiplet);
2.97 (3H, singlet);
3.03 (3H, singlet);
2.95–3.13 (1), multiplet);
3.37 (6H, singlet);
3.31–3.51 (3H, multiplet);
3.54–3.66 (1H, multiplet);
3.75–3.89 (2H, multiplet);
3.92–3.97 (2H, multiplet);
4.02–4.17 (1H, multiplet);
4.20–4.29 (2H, multiplet);
4.47 (2H, singlet);
4.69–4.81 (1H, multiplet);
4.86–4.98 (1H, multiplet).

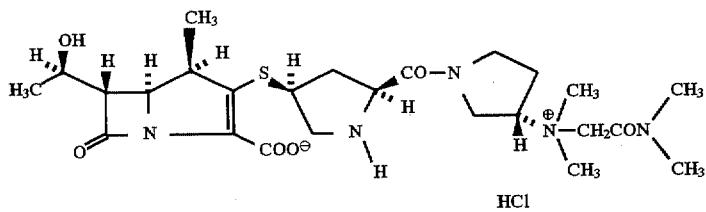

HCl 500 mg of 4-nitrobenzyl (1R,5S,6S)-2-{(2S,4S) -2-(3S)-3-dimethylamino-1-pyrrolidinylcarbonyl]-6-[(1R)-1-hydroxyethyl]-1-methyl-1-(4-nitrobenzyloxycarbonyl)-pyrrolidin-4-ylthio}-1-carbapen-2-em-3-carboxylate prepared as described in Example 89(3)] were dissolved in 5 ml of dry acetonitrile, and 700 mg of 2-iodo-N,N-dimethylacetamide were added to the resulting solution, after which the mixture was stirred at 80° C. for 4 hours. At the end of this time, the solvent was removed by distillation under reduced pressure, and the residue was washed with diethyl ether and dried by evaporation under reduced pressure to obtain 670 mg of a powdery product. The whole of this compound was dissolved in a mixture of 10 ml of tetrahydrofuran and 8 ml of water, and 2.0 g of a 10% w/w palladium-on-carbon catalyst were added to the resulting solution. The mixture was then hydrogenated at 28° to 30° C. for 2 hours. At the end of this time, the reaction mixture was treated, purified and freeze-dried in the same manner as described in Example 89(4), to obtain 82 mg of the title compound as a colorless powder.

Infrared Absorption Spectrum (KBr) $v_{max}$ cm$^{-1}$: 1759, 1657, 1603, 1461, 1370, 1147.

Nuclear Magnetic Resonance Spectrum (270 MHz, $D_2O$, internal standard: tetradeuterated sodium trimethylsilylpropionate) δ ppm:
1.21 (3H, doublet, J=6.8 Hz);
1.28 (3H, doublet, J=6.4 Hz);
1.98–2.07 (1H, multiplet);

EXAMPLE 97

(1R,5S,6S)-2-[(2S,4S)-2-{(3S)-3-[N-(2-Fluoroethyl)-N,N-dimethylammonio]pyrrolidin-1-ylcarbonyl}-pyrrolidin-4-ylthiol -6-[(1R)-1-hydroxyethyl]-1-methyl-1-carbapen-2-em-3-carboxylate hydrochloride

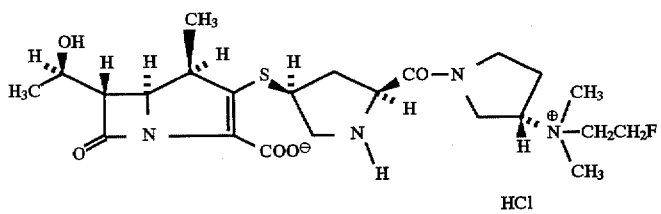

HCl 501 mg of 4-nitrobenzyl (1R, 5S,6S)-2-{(2S,4S) -2-[(3S) -3-dimethylamino-1-pyrrolidinylcarbonyl]-6-[(1R)-1-hydroxyethyl]-1-methyl-1-(4-nitrobenzyloxycarbonyl)-pyrrolidin-4-ylthio}-1-carbapen-2-em-3-carboxylate [prepared as described in Example 89(3)] were dissolved in 3 ml of dry acetonitrile, and 495 mg of sodium iodide and 419 mg of 1-bromo-2-fluoroethane were added to the resulting solution, after which the mixture was heated under reflux for 13 hours. At the end of this time, the reaction mixture was filtered, and the solvent was removed from the filtrate by distillation under reduced pressure, to obtain 631 mg of a powdery product. The whole of this compound was dissolved in a mixture of 10 ml of tetrahydrofuran and 6 ml of water, and the resulting solution was subjected to hydrogenation at room temperature for 1.5 hours in the presence of 1.2 g of a 10% w/w palladium-on-carbon catalyst. The reaction mixture was then treated, purified and freeze-dried in the same manner as described in Example 89(4), to obtain 36.0 mg of the title compound as a colorless powder.

Infrared Absorption Spectrum (KBr) $v_{max}$ cm$^{-1}$: 1758, 1656, 1599, 1470, 1375.

Ultraviolet Absorption Spectrum (H$_2$O), $\lambda_{max}$ nm: 296.8.

Nuclear Magnetic Resonance Spectrum (270 MHz, D$_2$O, internal standard: tetradeuterated sodium trimethylsilylpropionate) δ ppm:

1.22 (3H, doublet, J=7.26 Hz);
1.30 (3H, doublet, J=6.59 Hz);
1.97–2.10 (1H, multiplet);
2.40–2.65 (2H, multiplet);
3.00–3.15 (1H, multiplet);
3.26 (4S, singlet);
3.28 (2H, singlet);
3.30–5.20 (17H, multiplet).

EXAMPLE 98

(1R,5S,6S)-6-[(1R)-1-Hydroxyethyl]-1-methyl-2-{(2S,4S)-2-[4-[3-methylimidazolio)piperidin-1-yl-carbonyl]pyrrolidin-4-ylthiol}-1-carbapen-2-em-3-carboxylate hydrochloride

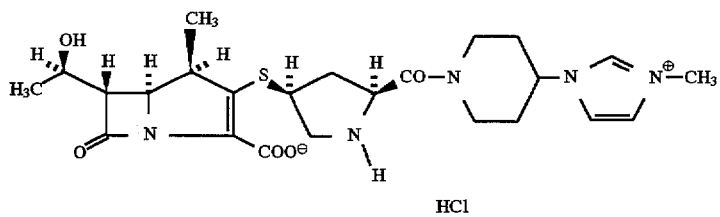

HCl

98(1) (2S,4S)-2-[4-(Imidazol-1-yl)piperidin-1-ylcarbonyl]-4-(4-methoxybenzylthio)-1-(4-nitrobenzyloxycarbonyl)pyrrolidine 1520 mg of (2S,4S)-4-(4-methoxybenzylthio)-1-(4-nitrobenzyloxycarbonyl)-2-pyrrolidinecarboxylic acid were dissolved in 15 ml of dry acetonitrile, and 660 mg of N,N'-carbonyldiimidazole were added to the resulting solution, after which the mixture was stirred at room temperature for 30 minutes. At the end of this time, a solution of 538 mg of 4-(imidazol-1-yl)piperidine in 5 ml of dry acetonitrile was added to the resulting mixture, and the solution was stirred at room temperature for 30 minutes and then at 40° C. for 7 hours. The reaction mixture was then concentrated by evaporation under reduced pressure. The resulting residue was dissolved in ethyl acetate, washed with an aqueous solution of sodium hydrogencarbonate, with water and with an aqueous solution of sodium chloride, in that order, after which the mixture was dried over anhydrous sodium sulfate. The solvent was then removed by distillation under reduced pressure, and the resulting residue was subjected to column chromatography using a reverse phase silica gel column (Cosmosil 75C$_{18}$-PREP, 200 ml, manufactured by Nacalai Kagaku), eluted with mixtures of acetonitrile and water ranging from 50:50 to 55:45 by volume. The fractions containing the title compound were collected and concentrated by evaporation under reduced pressure, to obtain 1450 mg of the title compound as a powder.

Infrared Absorption Spectrum (KBr) $v_{max}$ cm$^{-1}$: 1709, 1655, 1609, 1512, 1345, 1246, 1110.

Nuclear Magnetic Resonance Spectrum (270 MHz, CDCl$_3$) δ ppm:

1.70–1.95 (2H, multiplet);
2.05–2.23 (3H, multiplet);
2.40–2.55 (1H, multiplet);
2.60–2.85 (1H, multiplet);
3.03–3.43 (3H, multiplet);
3.73 (3H, singlet);
3.77–4.25 (8H, multiplet);
4.59–4.84 (2H, multiplet);
5.02–5.35 (2H, multiplet);
6.85 (2H, doublet, J=8.8 Hz);
6.96 (1H, singlet);
7.07 & 7.09. (together 1H, two singlets);
7.23 (2H, doublet, J=8.8 Hz);
7.47 (2H, doublet, J=8.8 Hz);
7.56 (1H, singlet);
8.23 (2H, doublet, J=8.8 Hz).

98(2) (2S,4S)-2-[4-(Imidazol-1-yl)piperidin-1-ylcarbonyl]-4-mercaptopyrrolidine 1.44 g of (2S,4S)-2-[4-(imidazol-1-yl)piperidin-1-ylcarbonyl]-4-(4-methoxybenzylthio)-1-(4-nitrobenzyloxycarbonyl)pyrrolidine [prepared as described in step (1) above] were dissolved in a mixture of 1.5 ml of anisole and 7.5 ml of trifluoroacetic acid, and 350 μl of trifluoromethanesulfonic acid were added to the resulting solution, whilst ice-cooling. The resulting mixture was then stirred at room temperature for 1 hour and then at 35° C. for 30 minutes, after which it was concentrated by evaporation under reduced pressure. The resulting residue was washed with diethyl ether four times to give a colorless powder. The whole of this powder was suspended in ethyl acetate, and the suspension was made alkaline by the addition of an aqueous solution of sodium hydrogencarbonate. The ethyl acetate phase was separated and washed with an aqueous solution of sodium chloride, after which this phase was dehydrated over anhydrous sodium sulfate. The solvent was then removed by distillation under reduced pressure, to give 1150 mg of the title compound, as a colorless powder.

Nuclear Magnetic Resonance Spectrum (hexadeuterated dimethyl sulfoxide, 270 MHz) δ ppm:

1.55–1.85 (3H, multiplet);
2.00–2.11 (2H, multiplet);
2.63–2.89 (2H, multiplet);
3.05–3.30 (4H, multiplet);
3.92–4.15 (2H, multiplet);
4.25–4.59 (2H, multiplet);
4.71–4.92 (1H, multiplet);
5.03–5.27 (2H, multiplet);
6.92–8.28 (7H, multiplet).

Infrared Absorption Spectrum (KBr), $v_{max}$ cm$^{-1}$: 1705, 1652, 1523, 1442, 1347, 1268, 1170, 1035.

98(3) 4-Nitrobenzyl (1R,5S,6S)-6-[(1R)-1-hydroxyethyl]-2-[(2S,4S)-2-[4-(imidazol-1-yl)piperidin-1-ylcarbonyl]-1-(4-nitrobenzyloxycarbonyl]pyrrolidin-4-ylthio]-1-methyl-1-carbapen-2-em-3-carboxylate 910 mg of 4-nitrobenzyl (1R,5R, 6S)-6-[(1R)-1-hydroxyethyl]-1-methyl-2-oxo-1-carbapenam-3-carboxylate were dissolved in 10 ml of dry acetonitrile, and 560 μl of diphenylphosphoryl chloride and 470 μl of diisopropylethylamine were added dropwise, whilst ice-cooling, to the resulting solution, after which the mixture was stirred at the same temperature for 30 minutes. A solution of 1140 mg of (2S,4S)-2-[4-(imidazol-1-yl)piperidin-1-ylcarbonyl]-4-mercaptopyrrolidine [prepared as described in step (2) above] in 10 ml of acetonitrile and 435 μl of diisopropylethylamine were then added dropwise to the resulting mixture. The mixture was then stirred, whilst ice-cooling for 2 hours, after which it was left to stand at 4° C. overnight. At the end of this time, the reaction mixture was diluted with an equivalent amount of water, and then 800 mg of sodium hydrogencarbonate were added thereto. The mixture was then subjected to column chromatography using a reverse phase silica gel column (Cosmosil 75$C_{18}$-PREP, 200 ml, manufactured by Nacalai), eluted with a 1:1 by volume mixture of acetonitrile and water. The desired fractions were collected and concentrated by evaporation under reduced pressure, to obtain 1.40 g of the title compound as a powder.

Nuclear Magnetic Resonance Spectrum (hexadeuterated dimethyl sulfoxide, 270 MHz) δ ppm:

1.12–1.20 (6H, multiplet);
1.58–1.90 (3H, multiplet);
1.91–2.06 (2H, multiplet);
2.62–2.79 (1H, multiplet);
2.80–2.97 (1H, multiplet);
3.06–3.37 (4H, multiplet);
3.55–3.70 (1H, multiplet);
3.71–3.93 (1H, multiplet);
3.94–4.56 (5H, multiplet);
4.74–4.97 (1H, multiplet);
5.04–5.49 (8H, multiplet);
6.81–8.28 (11H, multiplet).

Infrared Absorption Spectrum (KBr) $v_{max}$ cm$^{-1}$: 1773, 1710, 1656, 1522, 1346, 1208.

98(4) (1R,5S,6S)-6-[(1R)-1-Hydroxyethyl]-1-methyl-2-{(2S,4S)-2-[4-(3-methylimidazolio)piperidin-1-ylcarbonyl]pyrrolidin-4-ylthio}-1-carbapen-2-em-3-carboxylate hydrochloride 1000 mg of 4-nitrobenzyl (1R,5S,6S)-6-[(1R)-1-hydroxyethyl]-2-[(2S,4S) -2-[4-(imidazol-1-yl)piperidin-1-ylcarbonyl]-1-(4-nitrobenzyloxycarbonyl)pyrrolidin-4-ylthio]-1-methyl-1-carbapen-2-em-3-carboxylate [prepared as described in step (3) above] were dissolved in 10 ml of dry acetonitrile, and 150 μl of methyl trifluoromethanesulfonate were added dropwise, whilst ice-cooling, to the resulting solution, after which the mixture was stirred at the same temperature for 10 minutes and then at room temperature for 30 minutes. The reaction mixture was then concentrated by distillation under reduced pressure, and the resulting residue (1213 mg) was dissolved in a mixture of 20 ml of tetrahydrofuran and 15 ml of water. 1.3 g of a 10% w/w palladium-on-carbon catalyst were added to the resulting solution, after which the mixture was vigorously stirred at 28° C. to 30° C. for 1.7 hours in an atmosphere of hydrogen gas. At the end of this time, the catalyst was removed by filtration, and the filtrate was washed with diethyl ether (three times, each time with 100 ml). The aqueous phase was concentrated by evaporation under reduced pressure and then subjected to ion-exchange column chromatography (Dowex 1-X4, Model-C1, 30 ml), eluted with water. The fraction containing the title compound was concentrated by evaporation under reduced pressure, and subjected to column chromatography using a reverse phase silica gel column (Cosmosil 75$C_{18}$-PREP, 50 ml), eluted with water. The active fractions were collected and freeze-dried, to obtain 260 mg of the title compound as a colorless powder.

Ultraviolet Absorption Spectrum (H$_2$O), $\lambda_{max}$ nm: 297.

Nuclear Magnetic Resonance Spectrum (270 MHz, D$_2$O, internal standard: tetradeuterated sodium trimethylsilylpropionate) δ ppm:

1.22 (3H, doublet, J=7.3 Hz);
1.29 (3H, doublet, J=6.0 Hz);
1.88–2.09 (3H, multiplet);
2.28–2.43 (2H, multiplet);
2.96–3.16 (2H, multiplet);
3.33–3.55 (4H, multiplet);
3.73–3.84 (1H, multiplet);
3.90 (3H, singlet);
3.91–4.12 (2H, multiplet);
4.20 4.31 (2H, multiplet);
4.55–4.73 (2H, multiplet);
4.83–4.93 (1H, multiplet);
7.47 (1H, singlet);
7.57–7.60 (1H, multiplet);
8.85 (1H, doublet, J=7.9 Hz).

Infrared Absorption Spectrum (KBr) $v_{max}$ cm$^{-1}$: 1758, 1652, 1599, 1374, 1271, 1233, 1166.

EXAMPLE 99

(1R,5S,6S)-6-[(1R)-1-Hydroxyethyl]-1-methyl -2-{(2S,4S)-2-[(3S)-3-(3-methylimidazolio)pyrrolidin-1-ylcarbonyl]pyrrolidin-4-ylthio}-1-carbapen-2-em-3-carboxylate hydrochloride

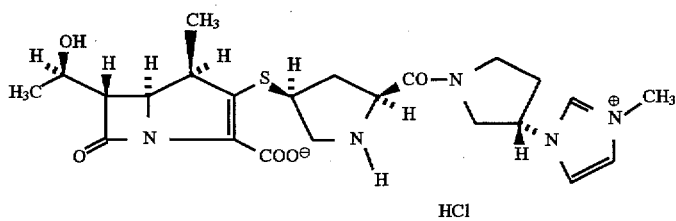

99(1) (2S,4S)-2-[(3R)-3-(Imidazol-1-yl)pyrrolidin-1-yl -carbonyl]-4-(4-methoxybenzylthio)-1-(4-nitrobenzyloxycarbonyl)pyrrolidine A procedure similar to that described in Example 98(1) was repeated, except that 2500 mg of (2S,4S)-4-(4-methoxybenzylthio)-1-(4-nitrobenzyloxycarbonyl)-2-pyrrolidinecarboxylic acid and 805 mg of (3R)-3-(imidazolyl-1-yl)pyrrolidine were used, to obtain 2540 mg of the title compound.

Infrared Absorption Spectrum (KBr) $v_{max}$ cm$^{-1}$: 1708, 1656, 1609, 1512, 1438, 1404, 1345, 1246, 1173, 1110.

Nuclear Magnetic Resonance Spectrum (270 MHz, CDCl$_3$) δ ppm:
1.88–2.05 (1H, multiplet);
2.15–2.31 (1H, multiplet);
2.36–2.57 (2H, multiplet);
3.02–3.18 (1H, multiplet);
3.31–3.40 (1H, multiplet);
3.49–3.63 (1H, multiplet);
3.73 & 3.74 (together 2H, two singlets);
3.78 & 3.79 (together 3H, two singlets);
3.80–4.08 (3H, multiplet);
4.26–4.48 (2H, multiplet);
4.71–4.89 (1H, multiplet);
5.00–5.34 (2H, multiplet);
6.76–7.60 (9H, multiplet);
8.15–8.27 (2H, multiplet).

99(2) 4-Nitrobenzyl (1R,5S,6S)-6-[(1R)-1-hydroxyethyl ]-2-{(2S,4S)-2-[(3R)-3-(imidazolyl-1-yl)pyrrolidin-1-ylcarbonyl]-1-(4-nitrobenzyloxycarbonyl)pyrrolidin-4-yl-thio}-1-methyl-1-carbapen-2-em-3-carboxylate 2.5 g of (2S,4S)-2-[(3R)-3-(imidazol-1-yl)-pyrrolidin-1-ylcarbonyl]-4-(4-methoxybenzylthio) -1-(4-nitrobenzyloxycarbonyl)pyrrolidine [prepared as described in step (1) above] were reacted and treated in the same manner as described in Example 98(2) and 98(3), to obtain 2.31 g of the title compound, as a powder.

Nuclear Magnetic Resonance Spectrum (270 MHz, CDCl$_3$) δ ppm:
1.25–1.39 (6H, multiplet);
2.00–2.80 (4H, multiplet);
3.25–4.96 (13H, multiplet);
5.05–5.53 (4H, multiplet);
6.82–8.29 (11H, multiplet).

99(3) (1R,5S,6S)-6-[(1R)-1-Hydroxyethyl]-1-methyl -2-{(2S,4S)-2-[(3S)-3-(3-methylimidazolio) pyrrolidin -1-ylcarbonyl]pyrrolidin-4-ylthio}-1-carbapen-2-em-3-carboxylate hydrochloride 1.2 g of 4-nitrobenzyl (1R,5S,6S)-6-[(1R)-1-hydroxyethyl]-2-{(2S,4S)-2-[(3R)-3-(imidazolyl-1-yl)pyrrolidin -1-ylcarbonyl]-1-(4-nitrobenzyloxycarbonyl)pyrrolidin-4-ylthio}-1-methyl-1-carbapen-2-em-3-carboxylate [prepared as described in step (2) above] were reacted and treated in the same manner as described in Example 98(4), to obtain 340 mg of the title compound as a colorless powder.

Nuclear Magnetic Resonance Spectrum (270 MHz, D$_2$O, internal standard: tetradeuterated sodium trimethylsilylpropionate) δ ppm:
1.19–1.31 (6H, multiplet);
1.82–2.07 (1H, multiplet);
2.40–2.58 (1H, multiplet);
2.60–2.80 (1H, multiplet);
2.92 (1H, multiplet);
3.32–3.51 (3H, multiplet);
3.71–4.31 (11H, multiplet);
3.60–3.75 (1H, multiplet);
5.17–5.27 (1H, multiplet);
7.50 & 7.54 (together 1H, two singlets);
7.60 (1H, singlet);
8.90 & 8.92 (together 1H, two singlets).
Ultraviolet Absorption Spectrum (H$_2$O), $\lambda_{max}$ nm: 297.

EXAMPLE 100

(1R,5S,6S)-2-[(2S,4S)-2-(4-Amidinopiperazin-1-yl -carbonyl)pyrrolidin-4-ylthio]-6-[(1R)-1-hydroxyethyl]-1-methyl-1-carbapen-2-em-3-carboxylic acid

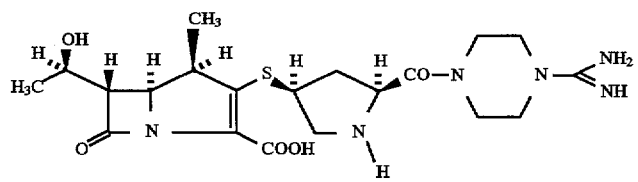

100(1) 4-Nitrobenzyl (1R,5S,6S)-6-[(1R)-1-hydroxyethyl]-1-methyl-2-[(2S,4S)-2-[4-(4-nitrobenzyloxycarbonylamidino)piperazin-1-ylcarbonyl]-1-(4-nitrobenzyloxycarbonyl)pyrrolidin-4-ylthio]-1-carbapen-2-em-3-carboxylate 290 μl of diphenylphosphoric acid chloride and 44 μl of diisopropylethylamine were added dropwise, whilst ice-cooling, to a solution of 471 mg of 4-nitrobenzyl (1R,5S,6S)-6-[(1R)-1-hydroxyethyl]-1-methyl-2-oxo-1-carbapenam-3-carboxylate in 5 ml of dry acetonitrile, and the resulting mixture was stirred at the same temperature for 1 hour. At the end of this time, a solution of 910 mg of (2S,4S)-4-mercapto-2-[4-(4-nitrobenzyloxycarbonylamidino)piperazin-1-ylcarbonyl]-1-(4-nitrobenzyloxycarbonyl)pyrrolidine trifluoromethanesulfonate (prepared as described in Preparation 92) in 7 ml of dry acetonitrile and 500 μl of diisopropylethylamine were added dropwise, whilst ice-cooling, to the mixture, and the resulting mixture was left to stand overnight at the same temperature. At the end of this time, the reaction mixture was concentrated by evaporation under reduced pressure, and the resulting residue was diluted with ethyl acetate, after which the mixture was washed with an aqueous solution of sodium hydrogencarbonate, with water and with an aqueous solution of sodium chloride. The ethyl acetate layer was dehydrated over anhydrous sodium sulfate and concentrated by evaporation under reduced pressure. The resulting residue was subjected to silica gel column chromatography [silica gel 60 (Art. 9385), manufactured by Merck, 150 ml], eluted with mixtures of ethyl acetate and acetonitrile in proportions of 8:2, 7:3 and 6:4, in that order. The fractions containing the desired compound were collected and concentrated by evaporation under reduced pressure, to obtain 691 mg of the title compound, as an amorphous powder.

Infrared Absorption Spectrum (KBr), $v_{max}$ cm$^{-1}$: 1773, 1710, 1652, 1607, 1552, 1441, 1347.

Nuclear Magnetic Resonance Spectrum (hexadeuterated dimethyl sulfoxide+D$_2$O, 270 MHz) δ ppm:

1.12–1.21 (6H, multiplet);
1.62–1.78 (1H, multiplet);
2.77–2.93 (1H, multiplet);
3.11–4.30 (15H, multiplet);
4.79 & 4.88 (together 1H, two triplets, J=7.8 Hz);
5.07–5.49 (6H, multiplet);
7.52–7.73 (6H, multiplet);
8.19–8.25 (6H, multiplet).

100(2) (1R,5S,6S)-2-[(2S,4S)-2-(4-Amidinopiperazin-1-yl-carbonyl)pyrrolidin-4-ylthio]-6-[(1R)-1-hydroxyethyl]-1-methyl-1-carbapen-2-em-3-carboxylic acid 680 mg of 4-nitrobenzyl (1R,5S,6S)-6-[(1R)-1-hydroxyethyl]-1-methyl-2-[(2S,4S)-2-[4-(4-nitrobenzyloxycarbonylamidino)piperazin-1-ylcarbonyl]-1-(4-nitrobenzyloxycarbonyl)pyrrolidin-4-ylthio]-1-carbapen-2-em-3-carboxylate [prepared as described in step (1) above] were dissolved in 40 ml of a 1:1 by volume mixture of tetrahydrofuran and water, and 950 mg of a 10% w/w palladium-on-carbon catalyst were added to the resulting solution. The mixture was then hydrogenated in an atmosphere of hydrogen at 28° C. for 1 hour. At the end of this time, the catalyst was removed by filtration, and the filtrate was washed with diethyl ether. The aqueous layer was then concentrated by evaporation under reduced pressure, to 10 ml. The resulting solution was subjected to reverse phase silica gel column chromatography (Cosmosil 75C$_{18}$-prep, manufactured by Nacalai Tesque, 30 ml), eluted with mixtures of acetonitrile and water in proportions of 0:100, 2:98, 4:96 and 6:94, in that order. The fractions containing the desired compound were collected, concentrated by evaporation under reduced pressure, and freeze-dried to obtain 211 mg of the title compound as a powder.

Ultraviolet Absorption Spectrum (H$_2$O), $\lambda_{max}$ nm: 299.

Infrared Absorption Spectrum (KBr), $v_{max}$ cm$^{-1}$: 1754, 1649, 1605, 1450, 1389, 1251.

Nuclear Magnetic Resonance Spectrum (270 MHz, D$_2$O, internal standard: tetradeuterated sodium trimethylsilylpropionate) δ ppm:

1.22 (3H, doublet, J=7.3 Hz);
1.30 (3H, doublet, J=6.4 Hz);
1.64 (1H, doubled doublet of doublets, J=13.7, 6.8 & 5.4 Hz);
2.74 (1H, doublet of triplets, J=13.7 & 8.8 Hz);
3.07 (1H, doublet of doublets, J=12.2 & 3.4 Hz);
3.17 (1H, doublet of doublets, J=12.2 & 5.4 Hz);
3.34–3.47 (2H, multiplet);
3.54–3.90 (9H, multiplet);
4.13 (1H, doublet of doublets, J=8.8 & 6.8 Hz);
4.19–4.13 (2H, multiplet).

Nuclear Magnetic Resonance Spectrum ($^{13}$C, D$_2$O, external standard: tetramethylsilane) δ ppm:

16.0, 20.2, 35.5, 41.3, 42.6, 42.8, 43.5, 44.2, 44.7, 53.9, 56.0, 57.4, 58.4, 65.2, 132.0, 140.9, 156.6, 167.8, 172.5, 176.4.

EXAMPLE 101

(1R,5S,6S)-2-[(2S,4S)-2-(4-Amidinopiperazin-1-ylcarbonyl)-1-methylpyrrolidin-4-ylthio]-6-[(1R)-1-hydroxyethyl]-1-methyl-1-carbapen-2-em-3-carboxylic acid

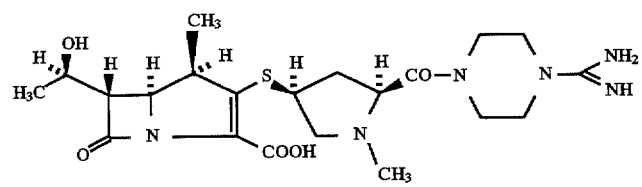

101(1) 4-Nitrobenzyl (1R,5S,6S)-6-[(1R)-1-hydroxyethyl]-1-methyl-2-{(2S,4S)-1-methyl-2-[4-[4-nitrobenzyloxycarbonylamidino) piperazin-1-ylcarbonyl]pyrrolidin-4-yl-thio}-1-carbapen-2-em-3-carboxylate 1600 mg of 4-nitrobenzyl (1R, 5R,6S)-2-(diphenylphosphoryloxy)-6-[(1R) -1-hydroxyethyl]-1-methyl-1-carbapen-2-em-3-carboxylate (prepared as described in Preparation 123) were dissolved in 16 ml of dry acetonitrile, and a solution of 1120 mg of (2S,4S)-4-mercapto-1-methyl-2-[4-(4-nitrobenzyloxycarbonylamidino) piperazin-1-ylcarbonyl] pyrrolidine (prepared as described in Preparation 93) in 11 ml of dry acetonitrile and 430 μl of diisopropylethylamine were added dropwise to the resulting solution, whilst ice-cooling. The resulting mixture was stirred at the same temperature overnight, after which it was concentrated by evaporation under reduced pressure. The resulting residue was diluted with ethyl acetate, and the mixture was washed with an aqueous solution of sodium hydrogencarbonate, with water and with an aqueous solution of sodium chloride, in that order. The ethyl acetate layer was dehydrated over anhydrous sodium sulfate and then concentrated by evaporation under reduced pressure. The resulting residue was subjected to reverse phase silica gel column chromatography (Cosmosil 75C$_{18}$-prep, manufactured by Nacalai Tesque, 300 ml), eluted with a 1 by volume mixture of acetonitrile and water. The fractions containing the desired compound were collected and concentrated by evaporation under reduced pressure, to obtain 1520 mg of the title compound, as a powder.

Infrared Absorption Spectrum (KBr), $v_{max}$ cm$^{-1}$: 771, 1708, 1648, 1606, 1544, 1521, 1448, 1347.

Nuclear Magnetic Resonance Spectrum (hexadeuterated dimethyl sulfoxide, 270 MHz) δ ppm:

1.10–1.20 (6H, multiplet);
1.58–1.69 (1H, multiplet);
2.24 (3H, singlet);
2.60–2.80 (2H, multiplet);
2.95–3.02 (1H, multiplet);
3.20–3.88 (12H, multiplet);
3.90–4.05 (1H, multiplet);
4.21 (1H, doublet of doublets, J=9.3 & 2.4 Hz);
5.05 (1H, doublet, J=5.4 Hz);
5.13 (2H, singlet);
5.29 (2H, doublet, J=13.7 Hz);
5.45 (2H, doublet, J=13.7 Hz);
7.59 (2H, doublet, J=8.8 Hz);
7.73 (2H, doublet, J=8.8 Hz);
7.90–8.20 (2H, broad);
8.21 (2H, doublet, J=8.8 Hz);
8.23 (2H, doublet, J=8.8 Hz).

101(2) (1R,5S,6S)-2-[(2S,4S)-2-(4-Amidinopiperazin-1-ylcarbonyl)-1-methylpyrrolidin-4-ylthio]-6-[(1R)-1-hydroxyethyl]-1-methyl-1-carbapen-2-em-3-carboxylic acid 500 ml of 4-nitrobenzyl (1R,5S,6S)-6-[(1R)-1-hydroxyethyl]-1-methyl-2-{(2S,4S) -1-methyl-2-[4-(4-nitrobenzyloxycarbonylamidino)piperazin-1-ylcarbonyl]-pyrrolidin-4-yl-thio}-1-carbapen-2-em-3-carboxylate [prepared as described in step (1) above] were dissolved in 75 ml of a 1:1 by volume mixture of tetrahydrofuran and water, and 2400 mg of a 10% w/w palladium-on-carbon catalyst were added to the resulting solution. The mixture was then hydrogenated in an atmosphere of hydrogen at 28° C. for 1 hour. At the end of this time, the catalyst was removed by filtration, and the filtrate was washed with diethyl ether. The filtrate was then concentrated to 20 ml by evaporation under reduced pressure. The solution was then subjected to reverse phase silica gel column chromatography (Cosmosil 75C$_{18}$-prep, manufactured by Nacalai Tesque, 100 ml), eluted with mixtures of acetonitrile and water in proportions of 0:100, 2:98, 4:96, 6:94 and 8:92 by volume, in that order. The fractions containing the desired compound were collected, concentrated to 3 ml by evaporation under reduced pressure, and cooled to precipitate colorless needle-like crystals. The crystals were filtered off and dried to obtain 435 mg of the title compound as crystals, melting at 218°–220° C. (with decomposition).

Ultraviolet Absorption Spectrum (H$_2$O), $\lambda_{max}$ nm:

298.

Infrared Absorption Spectrum (KBr), $v_{max}$ cm$^{-1}$: 1755, 1632, 1606, 1449, 1386, 1246.

Nuclear Magnetic Resonance Spectrum (270Hz, D$_2$O, internal standard: tetradeuterated sodium trimethylsilylpropionate) δ ppm:

1.20 (3H, doublet, J=6.8 Hz);
1.30 (3H, doublet, J=6.3 Hz);
1.66 (1H, doubled doublet of doublets, J=13.7, 8.8 & 5.4 Hz);
2.28 (3H, singlet);
2.74–2.87 (2H, multiplet);
3.09 (1H, doublet of doublets, J=10.8 & 1.5 Hz);
3.30–3.90 (12H, multiplet);
4.16–4.31 (2H, multiplet).

Nuclear Magnetic Resonance Spectrum ($^{13}$C, D$_2$O, external standard: tetramethylsilane) δ ppm: 15.7, 19.9, 34.9, 39.1, 39.3, 40.9, 42.4, 43.3, 43.9, 44.5, 55.7, 58.0, 62.2, 64.9, 65.0, 131.2, 141.6, 156.3, 167.5, 171.1, 175.9.

EXAMPLE 102

(1R,5S,6S)-2-[(2S,4S)-2-(4-Amidinohomopiperazin-1-ylcarbonyl)pyrrolidin-4-ylthio]-6-[(1R)-1-hydroxyethyl]-1-methyl-1-carbapen-2-em-3-carboxylic acid

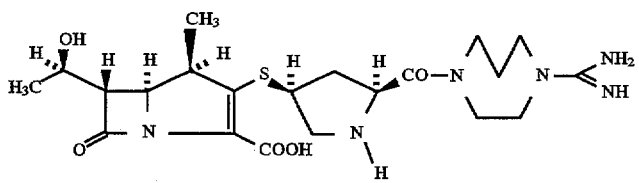

A procedure similar to that described in Example 101 was repeated, but using 4-nitrobenzyl (1R,5S,6S)-2-(diphenylphosphoryloxy)-6-[(1R)-1-hydroxyethyl]-1-methyl -1-carbapen-2-em-3-carboxylate (prepared as described in Preparation 123) and (2S,4S)-4-mercapto-1-(4-nitrobenzyl-oxycarbonyl)-2-[4-(4-nitrobenzyloxycarbonylamidino)homopiperazin-1-ylcarbonyl]pyrrolidine (prepared as described in Preparation 94) as starting materials, in relative proportions similar to those used in that Example, to obtain the title compound.

Ultraviolet Absorption Spectrum (H$_2$O), $\lambda_{max}$ nm: 299.

Infrared Absorption Spectrum (KBr), $v_{max}$ cm$^{-1}$: 1754, 1608, 1580, 1456, 1387, 1262.

Nuclear Magnetic Resonance Spectrum (1H, 270 MHz, D$_2$O, internal standard: tetradeuterated sodium trimethylsilylpropionate) δ ppm:

1.21 (3H, doublet, J=7.2 Hz);
1.30 (3H, doublet, J=6.3 Hz);
1.46–1.54 (1H, multiplet);
1.84–1.96 (2H, multiplet);
2.70–2.80 (1H, multiplet);
3.08 (1H, doublet of doublets, J=12.4 & 3.3 Hz);
3.14 (13H, doublet of doublets, J=12.4 & 5.4 Hz);
3.37–3.45 (2H, multiplet);
3.52–3.95 (9H, multiplet);
4.04–4.14 (1H, multiplet);
4.20–4.29 (2H, multiplet).

EXAMPLE 106

(1R,5S,6S)-2-((2S,4S)-2-(4-Amidinohomopiperazin-1-yl -carbonyl)-1-methylpyrrolidin-4-ylthiol-6-[(1R) -1-hydroxyethyl]-1-methyl-1-carbapen-2-em-3-carboxylic acid

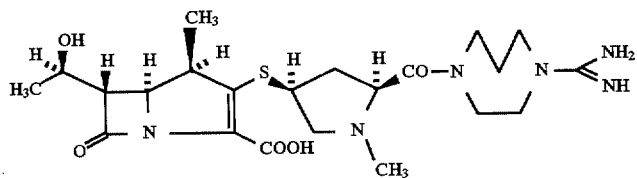

A procedure similar to that described in Example 101 was repeated, but using 4-nitrobenzyl (diphenylphosphoryloxy) -6-[(1R)-1-hydroxyethyl]-1-methyl -1-carbapen-2-em-3-carboxylate (prepared as described Preparation 123) and (2S,4S)-4-mercapto-1-methyl-2-[4-(4-nitrobenzyloxycarbonylamidino)homopiperazin-1-ylcarbonyl]-pyrrolidine (prepared as described in Preparation 95) as starting materials, in relative proportions similar to those used in that Example, to obtain the title compound.

Ultraviolet Absorption Spectrum (H$_2$O), $\lambda_{max}$ nm: 298.

Infrared Absorption Spectrum (KBr), $v_{max}$ cm$^{-1}$: 755, 1650, 1607, 1455, 1385, 1258.

Nuclear Magnetic Resonance Spectrum (270 MHz, D$_2$O, internal standard: tetradeuterated sodium trimethylsilylpropionate) δ ppm:

1.20 (3H, doublet, J=7.2 Hz);
1.30 (3H, doublet, J=6.3 Hz);
1.60 (1H, doubled doublet of doublets, J=13.5, 9.0 & 5.5 Hz);
1.80–1.95 (2H, multiplet);
2.24 & 2.25 (together 3H, two singlets);
2.74–2.87 (2H, multiplet);
3.09 (1H, doublet, J=9.0 Hz);
3.33–3.95 (12H, multiplet);
4.19 (1H, doublet of doublets, J=9.0 & 2.4 Hz);
4.22–4.28 (1H, multiplet).

EXAMPLE 107

(1R,5S, 6S)-2-[(2S,4S)-2-(4-Guanidinopiperidin-1-ylcarbonyl)pyrrolidin-4-ylthio]-6-[(1R)-1-hydroxyethyl]-1-methyl-1-carbapen-2-em-3-carboxylic acid A procedure similar to that described in Example 101 was repeated, but using 4-nitrobenzyl (1R,5R,6S)-2-(diphenylphosphoryloxy)-6-[(1R)-1-hydroxyethyl]-1-methyl -1-carbapen-2-em-3-carboxylate (prepared as described in Preparation 123) and (2S,4S)-4-mercapto-1-(4-nitrobenzyloxycarbonyl)-2-[4-(4-nitrobenzyloxycarbonylguanidino)piperidin-1-ylcarbonyl] pyrrolidine (prepared as described in Preparation 5) as starting materials, in relative proportions similar to those used in that Example, to obtain the title compound.

Ultraviolet Absorption Spectrum (H$_2$O), $\lambda_{max}$ nm: 299.

EXAMPLE 105

(1R,5S,6S)-2-[(2S,4S)-2-(4-Guanidinopiperidin-1-ylcarbonyl)-1-methylpyrrolidin-4-ylthiol-6-[(1R)-1-hydroxyethyl]-1-methyl-1-carbapen-2-em-3-carboxylic acid

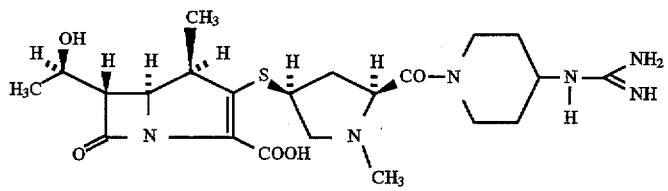

A procedure similar to that described in Example 13 was repeated, but using 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 32) and (2S,4S)-4-mercapto-1-methyl-2-[4-(4-nitrobenzyloxycarbonylguanidino)piperidin-1-ylcarbonyl]pyrrolidine (prepared as described in Preparation 97) as starting materials, in relative proportions similar to those used in that Example, to obtain the title compound.

Ultraviolet Absorption Spectrum (H₂O), λ$_{max}$ nm: 298.

EXAMPLE 106

(1R,5S,6S)-2-[(2S,4S)-2-[(3S)-3-Guanidinopyrrolidin-1-ylcarbonyl)pyrrolidin-4-ylthio-6-[(1R)-1-hydroxyethyl]-1-methyl-1-carbapen-2-em-3-carboxylic acid

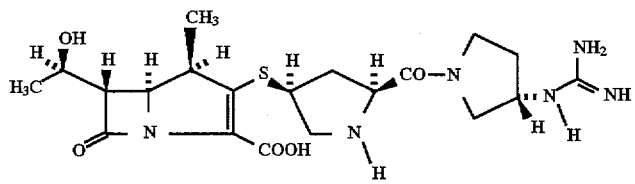

A procedure similar to that described in Example 101 was repeated, but using 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 32) and (2S,4S)-4-mercapto-1-(4-nitrobenzyloxycarbonyl)-2-[(3S)-3-(4-nitrobenzyloxycarbonylguanidino)pyrrolidin-1-ylcarbonyl]pyrrolidine (prepared as described in Preparation 98) as starting materials, in relative proportions similar to those used in that Example, to obtain the title compound.

Ultraviolet Absorption Spectrum (H₂O), λ$_{max}$ nm: 299.

EXAMPLE 107

(1R,5S,6S)-2-[(2S,4S)-2-[(3S)-3-Guanidinopyrrolidin-1-ylcarbonyl)-1-methylpyrrolidin-4-ylthio]-6-[(1R)-1-hydroxyethyl]-1-methyl-1-carbapen-2em-3-carboxylic acid

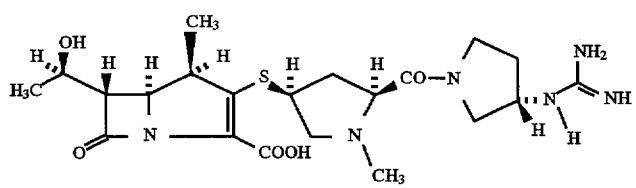

A procedure similar to that described in Example 101 was repeated, but using 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in preparation 123) and (2S,4S)-4-mercapto-1-methyl-2-[(3S)-3-(4-nitrobenzyloxycarbonylguanidino)pyrrolidin-1-ylcarbonyl]pyrrolidine (prepared as described in Preparation 99) as starting materials, in relative proportions similar to those used in that Example, to obtain the title compound.

Ultraviolet Absorption Spectrum (H₂O) λ$_{max}$ nm: 298.

EXAMPLE 108

(1R,5S,6S)-2-[(2S,4S)-2-(3-Guanidinoazetidin-1-ylcarbonyl)pyrrolidin-4-ylthio]-6-[(1R)-1-hydroxyethyl-1-methyl-1-carbapen-2-em-3-carboxylic acid

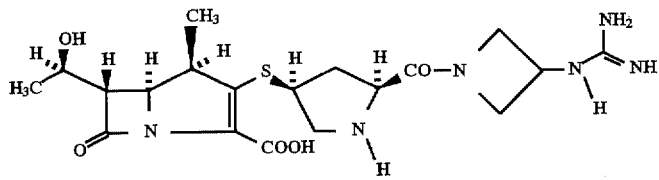

A procedure similar to that described in Example 101 was repeated, but using 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 32) and (2S,4S)-4-mercapto-1-(4-nitrobenzyloxycarbonyl)-2-[3-(4-nitrobenzyloxycarbonylguanidino)azetidin-1-ylcarbonyl]pyrrolidine (prepared as described in Preparation 100) as starting materials, in relative proportions similar to those used in that Example, to obtain the title compound.

Ultraviolet Absorption Spectrum (H$_2$O), $\lambda_{max}$ nm: 299.

EXAMPLE 109

(1R,5S,6S)-2-[(2S,4S)-2-(3-Guanidinoazetidin-1-ylcarboxyl)-1-methylpyrrolidin-4-ylthio]-6-[(1R)-1-hydroxyethyl]-1-methyl-1-carbapen-2-em-3-carboxylic acid

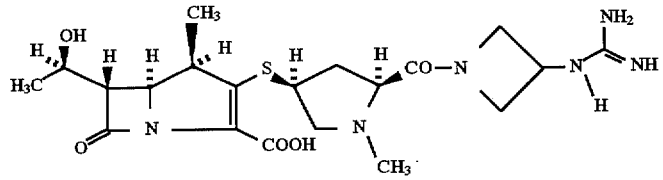

A procedure similar to that described in Example 101 was repeated, but using 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 32) and (2S,4S)-4-mercapto-1-methyl-2-[3-(4-nitrobenzyloxycarbonylguanidino)azetidin-1-ylcarbonyl]pyrrolidine (prepared as described in Preparation 101) as starting materials, in relative proportions similar to those used in that Example, to obtain the title compound.

Ultraviolet Absorption Spectrum (H$_2$O), $\lambda_{max}$ nm: 298.

EXAMPLE 110

(1R,5S,6S)-2-[(2S,4S)-2-(2-Guanidinoethylcarbamoyl)pyrrolidin-4-ylthio]-6-[(1R)-1-hydroxyethyl]-1-methyl-1-carbapen-2-em-3-carboxylic acid

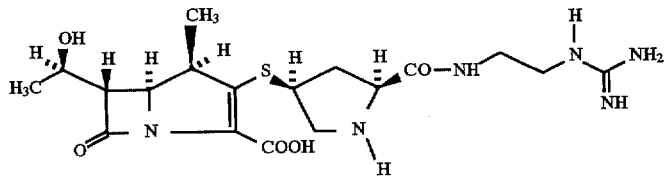

A procedure similar to that described in Example 101 was repeated, but using 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 32) and (2S,4S)-4-mercapto-1-(4-nitrobenzyloxycarbonyl)-2-[2-(4-nitrobenzyloxycarbonylguanidino)ethylcarbamoyl]pyrrolidine (prepared as described in Preparation 102) as starting materials, in relative proportions similar to those used in that Example, to obtain the title compound.

Ultraviolet Absorption Spectrum (H$_2$O), $\lambda_{max}$ nm: 299.

EXAMPLE 111

(1R,5S,6S)-2-[(2S,4S)-2-(2-Guanidinoethylcarbamoyl)-1-methylpyrrolidin-4-ylthio]-6-[(1R)-1-hydroxyethyl]-1-methyl-1-carbapen-2-em-3-carboxylic acid

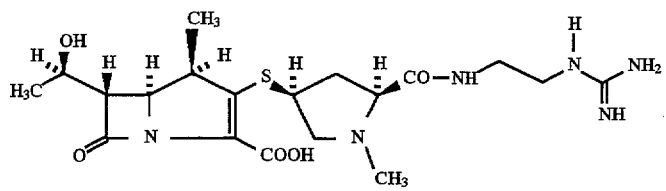

A procedure similar to that described in Example 101 was repeated, but using 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 123) and (2S,4S)-4-mercapto-1-methyl-2-[2-(4-nitrobenzyloxycarbonylguanidino) ethylcarbamoyl]pyrrolidine (prepared as described in Preparation 103) as starting materials, in relative proportions similar to those used in that Example, to obtain the title compound.

Ultraviolet Absorption Spectrum (H$_2$O), $\lambda_{max}$ nm: 298.

EXAMPLE 112

(1R,5S,6S)-6-[(1R)-1-Hydroxyethyl]-1-methyl-2-((2S,4S)-2-[4-(methylamidino)piperazin-1-ylcarbonyl]pyrrolidin-4-ylthio]-1-carbapen-2-em-3-carboxylic acid

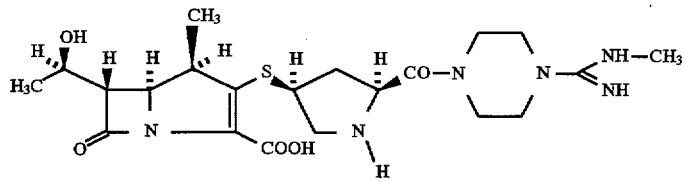

A procedure similar to that described in Example 101 was repeated, but using 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 123) and (2S,4S)-4-mercapto-2-[4-(methyl-4-nitrobenzyloxycarbonylamidino)piperazin-1-ylcarbonyl]-1-(4-nitrobenzyloxycarbonyl)pyrrolidine (prepared as described in Preparation 104 as starting materials, in relative proportions similar to those used in that Example, to obtain the title compound.

Ultraviolet Absorption Spectrum (H$_2$O), $\lambda_{max}$ nm: 299.

EXAMPLE 113

(1R,5S,6S)-6-[(1R)-1-Hydroxyethyl]-1-methyl-2-((2S,4S)-1-methyl-2-[4-(methylamidino)piperazin-1-ylcarbonyl]pyrrolidin-4-ylthio]-1-carbapen-2-em-3-carboxylic acid

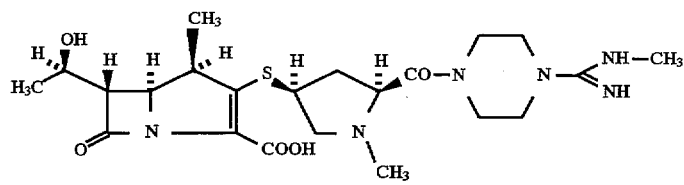

A procedure similar to that described in Example 101 was repeated, but using 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 123) and (2S,4S)-4-mercapto-1-methyl-2-[4-(methyl-4-nitrobenzyloxycarbonylamidino) piperazin-1-yl-carbonyl]pyrrolidine (prepared as described in Preparation 105) as starting materials, in relative proportions similar to those used in that Example, to obtain the title compound.

Ultraviolet Absorption Spectrum (H$_2$O), $\lambda_{max}$ nm: 298.

EXAMPLE 114

(1R,5S,6S)-2-(2S,4S)-2-[(3R)-3-Guanidinopyrrolidin-1-ylcarbonyl]pyrrolidin-4-ylthio]-6-[(1R)-1-hydroxyethyl]-1-methyl-1-carbapen-2-em-3-carboxylic acid

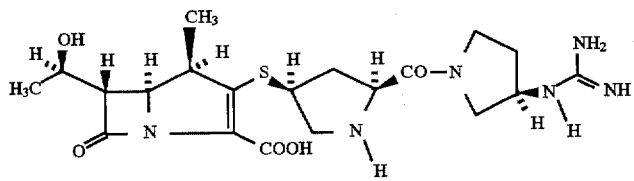

A procedure similar to that described in Example 101 was repeated, but using 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 123) and (2S,4S)-4-mercapto-1-(4-nitrobenzyloxycarbonyl)-2-[(3R)-3-(4-nitrobenzyloxycarbonylguanidino)pyrrolidin-1-ylcarbonyl] pyrrolidine (prepared as described in Preparation 106) as starting materials, in relative proportions similar to those used in that Example, to obtain the title compound.

Ultraviolet Absorption Spectrum (H$_2$O), $\lambda_{max}$ nm: 299.

EXAMPLE 115

(1R,5S,6S)-2-[(3R)-3-Guanidinopyrrolidin-1-ylcarbonyl]-1-methylpyrrolidin-4-ylthio-6-[(1R)-1-hydroxyethyl]-1-methyl-1-carbapen-2-em-)-3-carboxylic acid

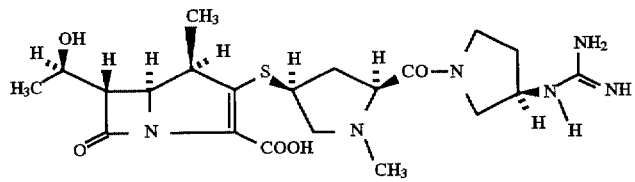

A procedure similar to that described in Example 101 was repeated, but using 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 123) and (2S,4S)-4-mercapto-1-methyl-2-[(3R)-3-(4-nitrobenzyloxycarbonylguanidino) pyrrolidin-1-yl-carbonyl]pyrrolidine (prepared as described in Preparation 107) as starting materials, in relative proportions similar to those used in that Example, to obtain the title compound.

Ultraviolet Absorption Spectrum (H$_2$O), $\lambda_{max}$ nm: 298.

EXAMPLE 116

(1R,5S,6S)-2-((2S,4S)-2-[(3R)-4-Amidino-3-methylpiperazin-1-ylcarbonyl]pyrrolidin-4-ylthio-6-[(1R)-1-hydroxythyl]-1-methyl-1-carbapen-2-em-3-carboxylic acid

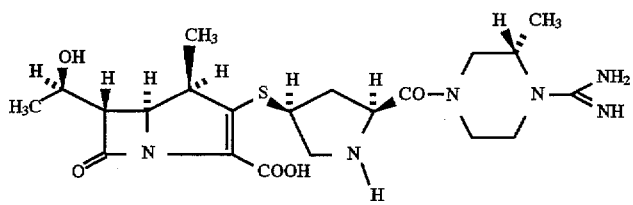

A procedure similar to that described in Example 101 was repeated, but using 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 123) and (2S,4S)-4-mercapto-1-(4-nitrobenzyloxycarbonyl)-2-[(3R)-4-(4-nitrobenzyloxycarbonylamidino)-3-methylpiperazin-1-ylcarbonyl]pyrrolidine (prepared as described in Preparation 108) as starting materials, in relative proportions similar to those used in that Example, to obtain the title compound.

Ultraviolet Absorption Spectrum (H$_2$O), $\lambda_{max}$ nm: 299.

EXAMPLE 117

(1R,5S,6S)-2-(2S,4S)-2-[(3R]-4-Amidino-3-methylpiperazin-1ylcarbonyl -1-methylpyrrolidin-4-ylthio)-6-[(1R)-1-hydroxyethyl]-1-methyl-1-carbapen-2-em-3-carboxylic acid

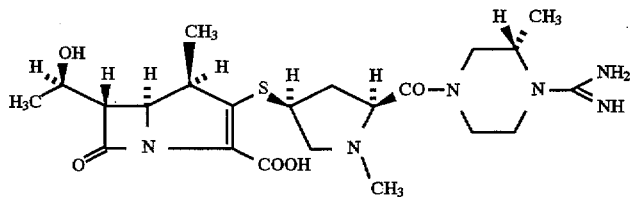

A procedure similar to that described in Example 101 was repeated, but using 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 123) and (2S,4S)-4-mercapto-1-methyl-2-[(3R)-4-(4-nitrobenzyloxycarbonylamidino)-3-methylpiperazin-1-ylcarbonyl]pyrrolidine (prepared as described in Preparation 109) as starting materials, in relative proportions similar to those used in that Example, to obtain the title compound.

Ultraviolet Absorption Spectrum (H$_2$O), $\lambda_{max}$ nm: 298.

EXAMPLE 118

(1R,5S,6S)-2-[(2S,4S)-2-[1-Amidinopiperidin-4-yl-carbamoyl]pyrrolidin-4-ylthio]-6-[(1R)-1-hydroxyethyl]-1-methyl-1-carbapen-2-em-3-carboxylic acid

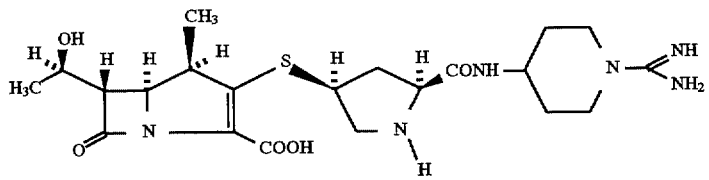

A procedure similar to that described in Example 101 was repeated, but using 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 32) and (2S,4S)-4-mercapto-1-(4-nitrobenzyloxycarbonyl)-2-[1-(4-nitrobenzyloxycarbonylamidino)piperidin-4-ylcarbamoyl]pyrrolidine (prepared as described in Preparation 110) as starting materials, in relative proportions similar to those used in that Example, to obtain the title compound.

Ultraviolet Absorption Spectrum (H$_2$O) $\lambda_{max}$ nm: 299.

EXAMPLE 119

(1R,5S,6S)-2-((2S,4S)-2-[(3S)-1-Amidinopyrrolidin-3-ylcarbamoyl]pyrrolidin-4-ylthio-6-[(1R)-1-hydroxyethyl]-1-methyl-1-carbapen-2-em-3-carboxylic acid

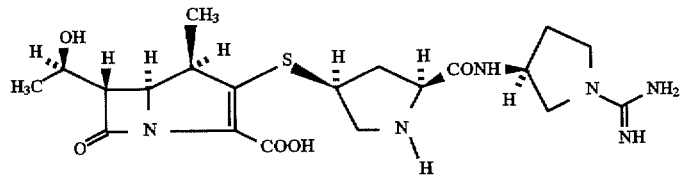

A procedure similar to that described in Example 101 was repeated, but using 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 32) and (2S,4S)-4-mercapto-1-(4-nitrobenzyloxycarbonyl)-2-[(3S)-1-(4-nitrobenzyloxycarbonylamidino)pyrrolidin-3-ylcarbamoyl]pyrrolidine (prepared as described in Preparation 20) as starting materials, in relative proportions similar to those used in that Example, to obtain the title compound.

Ultraviolet Absorption Spectrum (H$_2$O) $\lambda_{max}$ nm: 299.

EXAMPLE 120

(1R,5S,6S)-2-[(2S,4S)-2-[1-Amidinoazetidin-3-ylcarbamoyl]pyrrolidin-4-ylthio]-6-[(1R)-1-hydroxyethyl]-1-methyl-1-carbapen-2-em-3-carboxylic acid

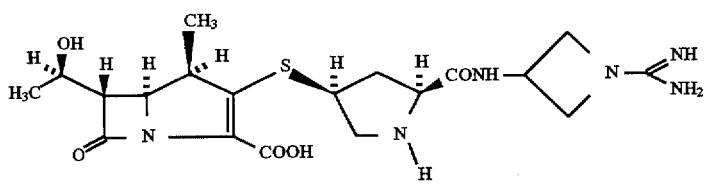

A procedure similar to that described in Example 101 was repeated, but using 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 32) and (2S,4S)-4-mercapto-1-(4-nitrobenzyloxycarbonyl)-2-[1-(4-nitrobenzyloxycarbonylamidino)azetidin-3-ylcarbamoyl]pyrrolidine (prepared as described in Preparation 112) as starting materials, in relative proportions similar to those used in that Example, to obtain the title compound.

Ultraviolet Absorption Spectrum (H$_2$O) $\lambda_{max}$ nm: 299.

EXAMPLE 121

(1R,5S,6S)-2-[(2S,4S)-2-(3-Aminoazetidin-1-ylcarbonyl)pyrrolidin-4-ylthio]-6-[(1R)-1-hydroxythyl]-1-methyl-1-carbapen-2-em-3-carboxylic acid hydrochloride

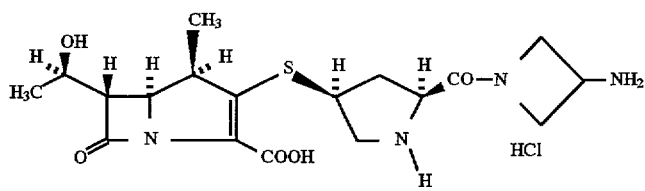

121(1) 4-Nitrobenzyl (1R,5S,6S)-2-((2S,4S)-2-[3-(4-nitrobenzyloxycarbonylamino)azetidin-1-ylcarbonyl]-1-(4-nitrobenzyloxycarbonyl)pyrrolidin-4-ylthio)-6-[(1R)-1-hydroxyethyl]-1-methyl-1-carbapen-2-em-3-carboxylate 167 μl of diphenylphosphoric acid chloride and 140 μl of ditsopropylethylamine were added dropwise at the same time, whilst ice-cooling, to a solution of 278 mg of 4-nitrobenzyl (1R,5R,6S)-6-[(1R)-1-hydroxyethyl]-1-methyl-2-oxo-1-carbapenam-3-carboxylate in 4 ml of dry acetonitrile, and the resulting mixture was stirred at the same temperature for 1 hour. At the end of this time, a solution of 430 mg of (2S,4S)-4-mercapto-2-[3-(4-nitrobenzyloxycarbonylamino)azetidin-1-ylcarbonyl]-1-(4-nitrobenzyloxycarbonyl)pyrrolidine (prepared as described in Preparation 113) in 4 ml of dry acetonitrile and 134 μl of ditsopropylethylamine were added dropwise at the same time to the mixture, whilst ice-cooling. The resulting mixture was then stirred at the same temperature for 2 hours, after which it was left to stand overnight whilst ice-cooling. The reaction mixture was then diluted with ethyl acetate and washed with water and with an aqueous solution of sodium chloride. The ethyl acetate layer was dehydrated over anhydrous magnesium sulfate and then concentrated by evaporation under reduced pressure. The resulting residue was subjected to silica gel column chromatography, and the fractions obtained by elution with a 98:2 by volume mixture of ethyl acetate and methanol were combined and concentrated by evaporation under reduced pressure, to give 224 mg of the title compound, as a powder.

Infrared Absorption Spectrum (KBr), $\upsilon_{max}$ cm$^{-1}$: 1772, 1713, 1659, 1608, 1522, 1453, 1403, 1347.

Nuclear Magnetic Resonance Spectrum (hexadeuterated dimethyl sulfoxide+D$_2$O, 270 MHz) δppm:
1.06–1.27 (6H, multiplet);
1.66–1.89 (1H, multiplet);
2.64–2.85 (1H, multiplet);
3.08–3.37 (2H, multiplet);
3.41–4.59 (11H, multiplet);
5.07–5.52 (6H, multiplet);.
7.51–7.78 (6H, multiplet);
8.23 (6H, doublet, J=8.79 Hz).

121(2) (1R,5S,6S)-2-[(2S,4S)-2-(3-Aminoazetidin-1-yl-carbonyl)pyrrolidin-4-ylthio]-6-[(1R)-1-hydroxyethyl]-1-methyl-1-carbapen-2-em-3-carboxylic acid hydrochloride 216 mg of 4-nitrobenzyl (1R,5S,6S)-2-((2S,4S)-2-[3-(4-nitrobenzyloxycarbonylamino)azetidin-1-ylcarbonyl]-1-(4-nitrobenzyloxycarbonyl)pyrrolidin-4-ylthio)-6-[(1R)-1-hydroxyethyl]-1-methyl-1-carbapen-2-em-3 -carboxylate [prepared as described in step (1) above] were dissolved in 10 ml of a 3:2 by volume mixture of tetrahydrofuran and water. 250 mg of a 10% w/w palladium-on-carbon catalyst and 239 μl of 1N aqueous hydrochloric acid were then added to the resulting solution, after which the mixture was hydrogenated at room temperature for 1.5 hours in an atmosphere of hydrogen. At the end of this time, the catalyst was removed by filtration, and the filtrate was washed with diethyl ether. The aqueous phase was then concentrated by evaporation under reduced pressure. The resulting residue was subjected to column chromatography (Cosmosil 75C$_{18}$-prep, manufactured by Nacalai Tesque, 18 ml). Of the fractions obtained by elution with water, the one containing the title compound was concentrated by evaporation under reduced pressure and freeze-dried to give 46 mg of the title compound as a powder.

Ultraviolet Absorption Spectrum (H$_2$O), $\lambda_{max}$ nm: 297.

Infrared Absorption Spectrum (KBr), $\lambda_{max}$ cm$^{-1}$: 1756, 1661, 1596, 1486, 1462, 1391, 1287, 1180.

Nuclear Magnetic Resonance Spectrum (270 MHz, D$_2$O, internal standard: tetradeuterated sodium trimethylsilylpropionate) δ ppm:
1.21 (3H, doublet, J=7.32 Hz);
1.29 (3H, doublet, J=6.35 Hz);
1.95–2.12 (1H, multiplet);
2.90–3.05 (1H, multiplet);
3.29–3.51 (3H, multiplet);
3.72–3.83 (1H, multiplet);
3.97–4.10 (1H, multiplet);
4.13–4.86 (8H, multiplet).

EXAMPLE 122

(1R,5S,6S)-2-[(2S,4S)-2-(3-Acetimidoylaminoazetidin-1-ylcarbonyl)pyrrolidin-4-ylthio]-6-[(1R)-1-hydroxyethyl]-1-methyl-1-carbapen-2-em-3-carboxylic acid

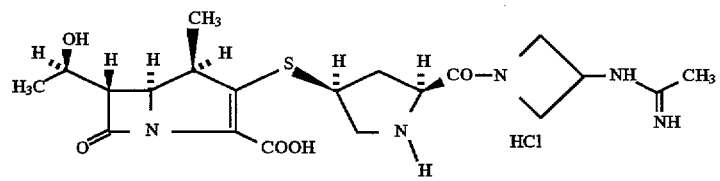

122(1) 4-Nitrobenzyl (1R,5S,6S)-6-[(1R)-1-hydroxyethyl]-1-methyl-2-[(2S,4S)-2-{3-[N-(4-nitrobenzyloxycarbonyl)-N-acetimidoylamino]azetidin-1-ylcarbonyl}-1-(4-nitrobenzyloxycarbonyl)pyrrolidin-4-ylthiol-1-carbapen-2-em-3-carboxylate 0.35 ml of diphenylphosphoric acid chloride and 0.29 ml of diisopropylethylamine were added dropwise at the same time to a solution of 0.55 g of 4-nitrobenzyl (1R,5R,6S)-6-[(1R)-1-hydroxyethyl]-1-methyl-2-oxo-1-carbapenam-3-carboxylate in 10 ml of dry acetonitrile, whilst ice-cooling, and the resulting mixture was stirred at the same temperature for 50 minutes. At the end of this time, a solution of 0.82 g of (2S,4S)-4-mercapto-2-{3-[N-(4-nitrobenzyloxycarbonyl)-N-acetimidoylamino]azetidin-1-ylcarbonyl}-1-(4-nitrobenzyloxycarbonyl)pyrrolidine (prepared as described in Preparation 114) in 10 ml of dry acetonitrile and 0.24 ml of diisopropylethylamine were added dropwise at the same time to the mixture, whilst ice-cooling. The resulting mixture was then stirred at the same temperature for 2 hours and then at room temperature for 1 hour. At the end of this time, the reaction mixture was concentrated by evaporation under reduced pressure and the resulting residue was diluted with ethyl acetate and washed with water and with an aqueous solution of sodium chloride, in that order. The ethyl acetate layer was dried over anhydrous magnesium sulfate and concentrated by evaporation under reduced pressure. The resulting residue was subjected to silica gel column chromatography (Silica gel 60 9385, manufactured by Merck, 200 ml), to give 0.77 g of the title compound, in the form of an amorphous powder from the fraction obtained by elution with a 95:5 by volume mixture of ethyl acetate and methanol.

Infrared Absorption Spectrum (KBr), $v_{max}$ cm$^{-1}$: 1773, 1709, 1607, 1549, 1522, 1448, 1346, 1225.

Nuclear Magnetic Resonance Spectrum (270 MHz, CDCl$_3$) δ ppm:
1.27 & 1.28 (together 3H, two doublets, J=7.33 Hz);
1.36 (3H, doublet, J=6.35 Hz);
1.47–2.28 (3H, multiplet);
2.19 & 2.22 (together 3H, two singlets);
2.50–2.83 (1H, multiplet);
3.26–3.52 (3H, multiplet);
3.59–3.78 (1H, multiplet);
3.70–4.84 (9H, multiplet);
5.06–5.51 (6H, multiplet);
7.48–7.66 (6H, multiplet);
8.19–8.23 (6H, multiplet).

122(2) (1R,5S,6S)-2-[(2S,4S)-2-(3-Acetimidoylaminoazetidin-1-ylcarbonyl)pyrrolidin-4-ylthio]-6-[(1R)-1-hydroxyethyl]-1-methyl-1-carbapen-2-em-3-carboxylic acid 0.77 g of 4-nitrobenzyl (1R,5S,6S)-6-[(1R)-1-hydroxyethyl]-1-methyl-2-[(2S,4S)-2-{3-[N(4-nitrobenzyloxycarbonyl)-N-acetimidoylamino]azetidin-1-ylcarbonyl}-1-(4-nitrobenzyloxycarbonyl)pyrrolidin-4-ylthio]-1-carbapen-2-em-3-carboxylate [prepared as described in step (1) above] was dissolved in 15 ml of a 2:1 by volume mixture of tetrahydrofuran and water. 0.77 g of a 10% w/w palladium-on-carbon catalyst was then added to the resulting solution, after which the mixture was hydrogenated at room temperature for 2 hours in a hydrogen atmosphere. At the end of this time, the catalyst was removed by filtration, and the filtrate was washed with diethyl ether. The aqueous layer was then concentrated by evaporation under reduced pressure, and the resulting residue was subjected to reverse phase column chromatography (Cosmosil 75C$_{18}$-prep, manufactured by Nacalai Tesque, 100 ml). The fraction containing the title compound and obtained by elution with 4% by volume aqueous acetonitrile was concentrated by evaporation under reduced pressure and freeze-dried, to give 0.13 g of the title compound as a powder.

Ultraviolet Absorption Spectrum (H$_2$O), $\lambda_{max}$ nm: 300.

Infrared Absorption Spectrum (KBr), $v_{max}$ cm$^{-1}$: 1755, 1633, 1591, 1463, 1389, 1286, 1262.

Nuclear Magnetic Resonance Spectrum (270 MHz, D$_2$O, internal standard: tetradeuterated sodium trimethylsilylpropionate) δ ppm:
1.22 (3H, doublet, J=6.84 Hz);
1.30 (3H, doublet, J=6.35 Hz);
1.64–1.74 (1H, multiplet);
2.25–2.35 (3H, multiplet);
2.58–2.70 (1H, multiplet);
2.98–3.04 (1H, multiplet);
3.20 (1H, doubled doublet of doublets, J=12.21, 5.86 & 2.44 Hz);
3.34–3.45 (1H, multiplet);
3.44 (1H, doublet of doublets, J=6.35 & 2.44 Hz);
3.73–3.88 (2H, multiplet);
4.03–4.10 (1H, multiplet);
4.19–4.37 (3H, multiplet);
4.41–4.90 (3H, multiplet).

EXAMPLE 123

(1R,5S,6S)-2-[(2S,4S)-2-(3-Formimidoylaminoazetidin-1-ylcarbonyl)pyrrolidin-4-ylthiol-6-[(1R)-1-hydroxyethyl]-1-methyl-1-carbapen-2-em-3-carboxylic acid

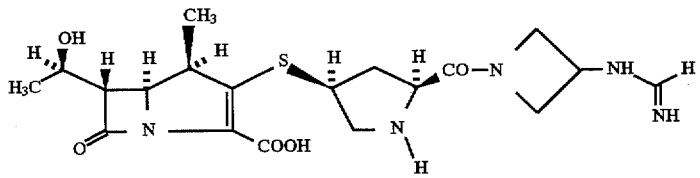

A procedure similar to that described in Example 122 was repeated, but using 0.12 g of 4-nitrobenzyl (1R,5R,6S)-6-[(1R)-1-hydroxyethyl]-1-methyl-2-oxo-1-carbapenam-3-carboxylate and 0.17 g of (2S,4S)-4-mercapto-2-[3-(N-4-nitrobenzyloxycarbonylformimdoylamino)azetidin-1-ylcarbonyl]-1-(4-nitrobenzyloxycarbonyl)pyrrolidine (prepared as described in Preparation 115), to give 19 mg of the title compound as a powder.

Ultraviolet Absorption Spectrum (H$_2$O), $\lambda_{max}$ nm: 301.

Infrared Absorption Spectrum (KBr), $v_{max}$ cm$^{-1}$: 1754, 1645, 1592, 1463, 1388, 1319, 1289, 1262.

Nuclear Magnetic Resonance Spectrum (270 MHz, D₂O, internal standard: tetradeuterated sodium trimethylsilylpropionate) δ ppm:
1.22 (3H, doublet, J=7.22 Hz);
1.30 (3H, doublet, J=6.33 Hz);
1.66–1.76 (1H, multiplet);
2.61–2.75 (1H, multiplet);
3.01–3.13 (1H, multiplet);
3.20–3.30 (1H, multiplet);
3.35–3.48 (2H, multiplet);
3.76–3.98 (2H, multiplet);
4.04–4.13 (1H, multiplet);
4.20–4.56 (4H, multiplet);
4.61–4.88 (25H, multiplet);
7.87 & 7.88 (1H, two singlets).

EXAMPLE 124

(1R,5S,6S)-2-[(2S,4S)-2-(3-Aminoazetidin-1-ylcarbonyl)-1-methylpyrrolidin-4-ylthio]-6-[(1R)-1-hydroxythyl]-1-methyl-1-carbapen-2-em-3-carboxylic acid

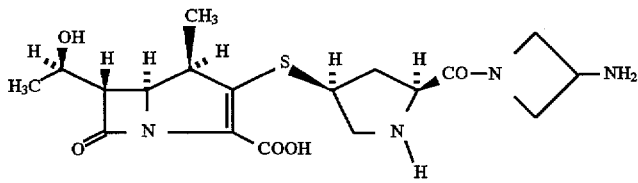

124(1) 4-Nitrobenzyl (1R,5S,6S)-6-[(1R)-1-hydroxyethyl]-1-methyl-2-[(2S,4S)-1-methyl-2-3-(4-nitrobenzyloxycarbonylamino)azetidin-1-ylcarbonyl) pyrrolidin-4-ylthio]-1-carbapen-2-em-3-carboxylate A solution of 0.42 g of (2S,4S)-4-mercapto-1-methyl-2-[3-(4-nitrobenzyloxycarbonylamino)azetidin-1-yl-carbonyl]pyrrolidine (prepared as described in Preparation 116) in 10 ml of dry acetonitrile and 0.18 ml of diisopropylethylamine were added dropwise at the same time to a solution of 0.70 g of 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 32) in 14 ml of dry acetonitrile, whilst ice-cooling, and the resulting mixture was left to stand at the same temperature for 2 days. At the end of this time, the reaction mixture was concentrated by evaporation under reduced pressure and the residue was diluted with ethyl acetate and washed with water and with an aqueous solution of sodium chloride, in that order. The ethyl acetate layer was dried over anhydrous magnesium sulfate and then concentrated by evaporation under reduced pressure. The resulting residue was subjected to silica gel column chromatography (silica gel 60 9385, manufactured by Merck, 100 ml) to give 0.25 g of the title compound, in the form of an amorphous powder, from the fractions obtained by elution with a 95:5 by volume mixture of acetonitrile and methanol.

Infrared Absorption Spectrum (KBr), $\upsilon_{max}$ cm⁻¹: 1771, 1723, 1641, 1608, 1522, 1455, 1347.

Nuclear Magnetic Resonance Spectrum (270 MHz, CDCl₃+D₂O) δ ppm:
1.27 & 1.28 (together 3H, two doublets, J=7.33 & 6.84 Hz);
1.36 (3H, doublet, J=5.86 Hz);
1.85–2.04 (1H, multiplet);
2.33 & 2.37 (3H, two singlets);
2.67–2.80 (2H, multiplet);
3.03–3.39 (4H, multiplet);
3.65–3.73 (1H, multiplet);
3.90–3.95 (1H, multiplet);
4.10–4.83 (6H, multiplet);
5.09–5.52 (4H, multiplet);
7.47–7.67 (4H, multiplet);
8.15–8.26 (4H, multiplet).

124(2) (1R,5S,6S)-2-[(2S,4S)-2-(3-Aminoazetidinyl-ylcarbonyl)-1-methylpyrrolidin-4-ylthio]-6-[(1R)-1-hydroxyethyl]-1-methyl-1-carbapen-2-em-3-carboxylic acid 0.25 g of 4-nitrobenzyl (1R,5S,6S)-6-[(1R)-1-hydroxyethyl]-1-methyl-2-[(2S,4S)-1-methyl-2-[3-(4-nitrobenzyloxycarbonylamino)azetidin-1-ylcarbonyl) pyrrolidin-4-ylthio]-1-carbapen-2-em-3-carboxylate [prepared as described in step (1) above] was dissolved in 5.5 ml of a 6:5 by volume mixture of tetrahydrofuran and water, and 0.25 g of a 10% w/w palladium-on-carbon catalyst was added to the resulting solution. The mixture was then hydrogenated at room temperature for 90 minutes in an atmosphere of hydrogen. At the end of this time, the catalyst was removed by filtration, and the filtrate was washed with diethyl ether. The aqueous layer was then concentrated by evaporation under reduced pressure. The resulting residue was subjected to reverse phase column chromatography (Cosmosil 75C₁₈-prep, manufactured by Nacalai Tesque, 25 ml). Of the fractions obtained by elution with 5% by volume aqueous acetonitrile, the one containing the title compound was concentrated by evaporation under reduced pressure and freeze-dried, to give 0.05 g of the title compound as a powder.

Ultraviolet Absorption Spectrum (H₂O), $\lambda_{max}$ nm: 301.

Infrared Absorption Spectrum (KBr) $\upsilon_{max}$ cm⁻¹: 1755, 1641, 1598, 1462, 1386, 1284, 1255.

Nuclear Magnetic Resonance Spectrum (270 MHz, D₂O, internal standard; tetradeuterated sodium trimethylsilylpropionate)

1.21 (3H, doublet, J=7.33 Hz);
1.30 (3H, doublet, J=6.35 Hz);
1.75–1.85 (1H, multiplet);
2.46 & 2.47 (together 3H, two singlets);
2.79–2.89 (1H, multiplet);
2.97–3.07 (1H, multiplet);
3.22–3.53 (4H, multiplet);
3.90–4.06 (2H, multiplet);
4.13–4.29 (4H, multiplet);
4.35–4.44 (1H, multiplet);
4.54–4.84 (1H, multiplet).

EXAMPLE 125

(1R,5S,6S)-2-[(2S,4S)-2-(3-Acetimidoylaminoazetidin-1-ylcarbonyl)-1-methylpyrrolidin-4-ylthio]-6-[(1R)-1-hydroxyethyl]-1-methyl-1-carbapen-2-em-3-carboxylic acid

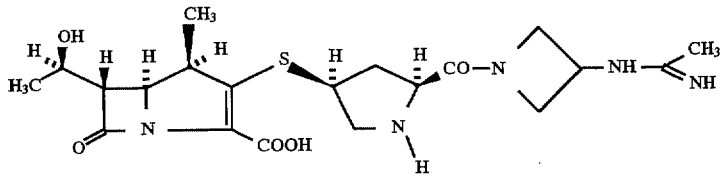

125(1) 4-Nitrobenzyl (1R,5S,6S)-6-[(1R)-1-hydroxyethyl]-1-methyl-2-[(2S,4S)-1-methyl-2-3-[N-(4-nitrobenzyloxycarbonyl)-N-acetimidoylamino]azetidin-1-ylcarbonylpyrrolidin-4-ylthio]-1-carbapen-2-em-3-carboxylate A solution of 435 mg of (2S,4S)-4-mercapto-1-methyl-2-{3-[-N-(4-nitrobenzyloxycarbonyl)-N-acetimidoylamino]azetidin-1-ylcarbonyl}pyrrolidine (prepared as described in Preparation 117) in 4 ml of dry acetonitrile and 174 μl of diisopropylethylamine were added dropwise at the same time to a solution of 595 mg of 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 123) in 10 ml of dry acetonitrile, whilst ice-cooling, and the resulting mixture was allowed to react at the same temperature for 20 minutes. It was then left to stand at room temperature for 3 hours and then in a refrigerator overnight. At the end of this time, the reaction mixture was diluted with ethyl acetate and washed with water and with an aqueous solution of sodium chloride, in that order. The ethyl acetate layer was then dried over anhydrous magnesium sulfate and concentrated by evaporation under reduced pressure. The resulting residue was subjected to silica gel column chromatography and the fractions obtained by solution with a 2:2:1 by volume mixture of methylene chloride, ethyl acetate and methanol were combined and concentrated by evaporation under reduced pressure, to give 464 mg of the title compound, as a powder.

Infrared Absorption Spectrum (KBr), $\upsilon_{max}$ cm$^{-1}$: 1771, 1690, 1607, 1549, 1521, 1455, 1378, 1346.

Nuclear Magnetic Resonance Spectrum (270 MHz, DMSO-d$_6$+D$_2$O) δ ppm:

1.16 (6H, doublet, J=6.83 Hz);
1.59–1.74 (1H, multiplet);
2.11 (3H, singlet);
2.29 (3H, broad singlet);
2.54–3.19 (3H, multiplet);
3.27 (1H, doublet of doublets, J=6.35 & 2.44 Hz);
3.32–4.27 (8H, multiplet);
4.42–4.60 (2H, multiplet);
5.11–5.49 (4H, multiplet);
7.60 & 7.61 (together 2H, two doublets, J=8.79 Hz);
7.70 & 7.72 (together 2H, two doublets, J=8.79 Hz);
8.16–8.28 (4H, multiplet).

125(2) (1R,5S,6S)-2-[(2S,4S)-2-(3-Acetimidoylaminoazetidin-1-ylcarbonyl)-1-methylpyrrolidin-4-ylthio]-6-[(1R)-1-hydroxyethyl]-1-methyl-1-carbapen-2-em-3-carboxylic acid 453 mg of 4-nitrobenzyl (1R,5S,6S)-6-[(1R)-1-hydroxyethyl]-1-methyl-2-[(2S,4S)-1-methyl-2-[3-[N-(4-nitrobenzyloxycarbonyl)-N-acetimidoylamino]azetidin-1-ylcarbonyl)pyrrolidin-4-ylthio]-1-carbapen-2-em-3-carboxylate [prepared as described in step (1) above] were dissolved in 21 ml of a 2:1 by volume mixture of tetrahydrofuran and water, and 500 mg of a 10% w/w palladium-on-carbon catalyst were added to the resulting solution. The mixture was then hydrogenated at room temperature for 1.5 hours in an atmosphere of hydrogen. The catalyst was then removed by filtration, and the filtrate was washed with diethyl ether. The aqueous layer was concentrated by evaporation under reduced pressure. The residue was subjected to reverse phase column chromatography (Cosmosil 75C$_{18}$-prep, manufactured by Nacalai Tesque, 40 ml). Of the fractions obtained by solution with 8% by volume aqueous acetonitrile, the one containing the title compound was concentrated by evaporation under reduced pressure and freeze-dried, to give 166 mg of the title compound as a powder.

Ultraviolet Absorption Spectrum (H$_2$O), $\lambda_{max}$ nm: 301.

Infrared Absorption Spectrum (KBr), $\upsilon_{max}$ cm$^{-1}$: 1757, 1633, 1592, 1462, 1386, 1335, 1284, 1256.

Nuclear Magnetic Resonance Spectrum (270 MHz, D$_2$O, internal standard: tetradeuterated sodium trimethylsilylpropionate) δ ppm:

1.21 (3H, doublet, J=6.83 Hz);
1.30 (3H, doublet, J=6.35 Hz);
1.64–1.78 (1H, multiplet);
2.27 (3H, singlet);
2.29 (3H, singlet);
2.63–2.85 (2H, multiplet);
3.01–3.21 (2H, multiplet);
3.27–3.46 (2H, multiplet);
3.75–3.88 (1H, multiplet);
4.00–4.10 (1H, multiplet);
4.15–4.96 (6H, multiplet).

EXAMPLE 126

(1R,5S,6S)-2-[(2S,4S)-2-(3-Formimidoylaminoazetidin-1-ylcarbonyl)-1-methylpyrrolidin-4-ylthio]-6-[(1R)-1-hydroxyethyl]-1-methyl-1-carbapen-2-em-3-carboxylic acid

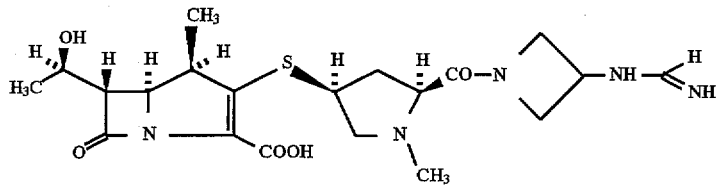

A procedure similar to that described in Example 125 was repeated, but using 0.35 g of 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 123) and 0.22 g of (2S,4S)-4-mercapto-1-methyl-2-(3-[N-(4-nitrobenzyloxycarbonyl)-N-formimidoylamino]azetidin-1-ylcarbonyl)pyrrolidine (prepared as described in Preparation 118), to give 17 mg of the title compound as a powder.

Ultraviolet Absorption Spectrum (H₂O), $\lambda_{max}$ nm: 302.

EXAMPLE 127

(1R,5S,6S)-6-[(1R)-1-Hydroxyethyl]-1-methyl-2-{(2S,4S)-2-[(3S)-3-(4-methyl-1-1,2,4-triazolio)pyrrolidin-1-ylcarbonyl]pyrrolidin-4-ylthio}-1-carbapen-2-em-3-carboxylate hydrochloride using a 5:1 by volume mixture of ethyl acetate and methanol as the eluent, to obtain 744 mg of the title compound, as a powder.

Infrared Absorption Spectrum (KBr), $v_{max}$ cm⁻¹: 1772, 1709, 1655, 1607, 1522, 1346, 854, 738.

Nuclear Magnetic Resonance Spectrum (270 MHz, hexadeuterated dimethyl sulfoxide+D₂O) δ ppm:
1.50–1.80 (1H, multiplet);
2.20–2.50 (2H, multiplet);
2.70–2.98 (2H, multiplet);
3.10–4.30 (12H, multiplet);
4.45–4.75 (1H, multiplet);
5.00–5.50 (4H, multiplet);
7.45–7.78 (4H, multiplet);
7.80–8.00 (1H, multiplet);
8.15–8.28 (4H, multiplet);
8.50–8.60 (1H, multiplet).

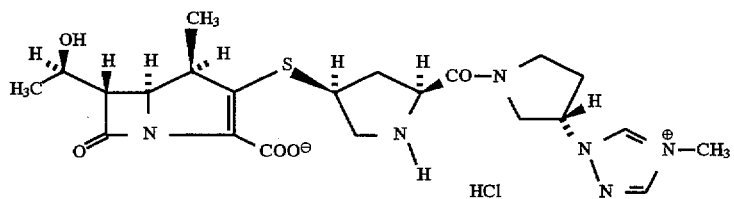

127(1) 4-Nitrobenzyl (1R,5S,6S)-6-[(1R)-1-hydroxythyl]-1-methyl-2-[(2S,4S)-1-(4-nitrobenzyloxycarbonyl)-2-[(3S)-3-(1-1,2,4-triazolyl)-1-pyrrolidinylcarbonyl]pyrrolidin-4-ylthio]-1-carbapen-2-em-3-carboxylate 486 mg of 4-nitrobenzyl (1R,5R,6S)-6-[(1R)-1-hydroxyethyl]-1-methyl-2-oxo-1-carbapenam-3-carboxylate were dissolved in 5 ml of dry acetonitrile, and 379 mg of diphenylphosphoryl chloride and 182 mg of diisopropylethylamine were added dropwise, with ice-cooling, to the resulting solution. The mixture was then stirred at the same temperature for 1 hour. At the end of this time, a solution of 173 mg of diisoproyl-ethylamine and 690 mg of (2S,4S)-4-mercapto-2-[(3S)-3-(1-1,2,4-triazolyl)-1-pyrrolidinylcarbonyl]-1-[4-nitrobenzyloxycarbonyl)pyrrolidine (prepared as described in Preparation 119) in 4 ml of dry acetonitrile was added dropwise with ice-cooling, to the resulting mixture, and the mixture was stirred at the same temperature for 6 hours. The solvent was then removed by distillation under reduced pressure, and the resulting residue was dissolved in ethyl acetate. The resulting solution was then washed with water, with an aqueous solution of sodium hydrogencarbonate, again with water and finally with a saturated aqueous solution of sodium chloride. The aqueous layer was extracted with methylene chloride, and the aqueous layer was combined with the washings and dried over anhydrous magnesium sulfate. The solvent was removed by distillation under reduced pressure, and the residue was purified by silica gel column chromatography, 127(2) (1R,5S,6S)-6-[(1R)-1-Hydroxythyl]-1-methyl-2-((2S,4S)-2-[[3S)-3-(4-methyl-1-1,2,4-triazolio)-pyrrolidin-1-ylcarbonyl]pyrrolidin-4-ylthio-1-carbapen-2-em-3-carboxylate hydrochloride 528 mg of 4-nitrobenzyl (1R,5S,6S)-6-[(1R)-1-hydroxyethyl]-1-methyl-2-[(2S,4S)-1-(4-nitrobenzyloxycarbonyl)-2-[(3S)-3-(1-1,2,4-triazolyl)-1-pyrrolidinylcarbonyl]pyrrolidin-4-ylthio]-1-carbapen-2-em-3-carboxylate [prepared as described in step (1) above] were dissolved in 6 ml of dry acetonitrile, and 121 mg of methyl trifluoromethanesulfonate were added to the resulting solution, whilst ice-cooling, after which the mixture was stirred at the same temperature for 30 minutes. The powdery product obtained by evaporation of the solvent was dissolved in a mixture of 7 ml of tetrahydrofuran and 5 ml of water, after which the mixture was hydrogenated at room temperature for 1 hour in the presence of 1 g of a 10% w/w palladium-on-carbon catalyst. At the end of this time, the catalyst was removed by filtration and the tetrahydrofuran was distilled off under reduced pressure. The aqueous layer was then washed with diethyl ether and concentrated by evaporation under reduced pressure after which it was subjected to ion exchange column chromatography (Dowex 1-X4, 50 to 100 mesh, Cl FORM, manufactured by Dow Chemical), using water as the eluent. The fractions containing the title compound were collected and concentrated to 1.5 ml by evaporation under reduced pressure.

The concentrated aqueous solution was applied to a colunm (Cosmosil 75C₁₈-prep, manufactured by Nacalai)

and eluted with water. The fractions containing the title compound were combined, concentrated by evaporation under reduced pressure and freeze-dried, to obtain 85 mg of the title compound as a colorless powder.

Ultraviolet Absorption Spectrum ($H_2O$), $\lambda_{max}$ nm: 296.7.

Infrared Absorption Spectrum (KBr), $v_{max}$ cm$^{-1}$: 3394, 1758, 1655, 1586, 1460, 1373.

Nuclear Magnetic Resonance Spectrum (270 MHz, $D_2O$, internal standard: tetradeuterated sodium trimethylsilylpropionate) δ ppm:
1.18–1.23 (3H,m), 1.27–1.30 (3H, multiplet);
1.95–2.11 (1H, multiplet);
2.40–2.80 (2H, multiplet);
2.95–3.20 (1H, multiplet);
3.30–3.40 (1H, multiplet);
3.40–3.54 (2H, multiplet);
3.70–3.85 (2H, multiplet);
3.85–4.05 (3H, multiplet);
4.05–4.15 (3H, multiplet);
4.15–4.30 (2H, multiplet);
4.70–4.85 (2H, , multiplet);
5.45–5.60 (1H, multiplet);
8.84 & 8.87 (together 1H, two singlets)

EXAMPLE 128

(1R,5S,6S)-6-[(1R)-1-Hydroxyethyl]-1-methyl-2-{(2S,4S)-2-3-(4-methyl-1-1,2,4-triazolio)azetidin-1-ylcarbonyl]pyrrolidin-4-ylthio}-1-carbapen-2-em-3-carboxylate hydrochloride 128(1) 4-Nitrobenzyl (1R,5S,6S)-6-[(1R)-1-hydroxyethyl]-1-methyl-2-[(2S,4S)-2-[3-(1-1,2,4-triazolyl)-1-azetidinylcarbonyl]-1-(4-nitrobenzyloxycarbonyl)pyrrolidin-4-ylthio]-1-carbapen-2-em-3-carboxylate 886 mg of 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 123) was dissolved in 10 ml of dry acetonitrile, and 0.26 ml of diisopropylethylamine and 873 mg of (2S,4S)-4-mercapto-2-[3-(1-1,2,4-triazolyl)-1-azetidinylcarbonyl]-1-(4-nitrobenzyloxycarbonyl)pyrrolidine (prepared as described in Preparation 120) dissolved in 5 ml of acetonitrile were added dropwise at the same time to the resulting solution, whilst ice-cooling. The mixture was then stirred at the same temperature for 3 hours. At the end of this time, the solvent was removed by distillation under reduced pressure, and the residue was diluted with ethyl acetate. The resulting mixture was washed with water, with an aqueous solution of sodium hydrogencarbonate, with water and with a saturated aqueous solution of sodium chloride. The aqueous layer was dried over anhydrous magnesium sulfate and then concentrated by evaporation under reduced pressure. The residue was purified by silica gel column chromatography, using a gradient solution method, with mixtures of ethyl acetate and methanol ranging from 6:1 to 4:1 by volume as the eluent, to obtain 661 mg of the title compound, as a powder.

Infrared Absorption Spectrum (KBr), $v_{max}$ cm$^{-1}$: 3402, 1709, 1665, 1608, 854, 738.

Nuclear Magnetic Resonance Spectrum (270 MHz, hexadeuterated dimethyl sulfoxide) δ ppm:
1.10–1.30 (6H, multiplet);
1.75–1.90 (1H, multiplet);
2.70–2.85 (1H, multiplet);
3.55–3.65 (1H, multiplet);
3.20–5.10 (12H, multiplet);
5.15–5.55 (5H, multiplet);
7.55–7.80 (4H, multiplet);
7.95–8.10 (1H, multiplet);
8.20–8.30 (4H, multiplet);
8.55–8.75 (1H, multiplet).

128(2) (1R,5S,6S)-6-[(1R)-1-Hydroxyethyl]-1-methyl-2-{(2S,4S-2-[3-(4-methyl-1-1,2,4-triazolio)azetidin-1-ylcarbonyl]pyrrolidin-4-ylthio}-1-carbapen-2-em-3-carboxylate hydrochloride 660 mg of 4-nitrobenzyl (1R,5S,6S)-6-[(1R)-1-hydroxyethyl]-1-methyl-2-[(2S,4S)-2-[3-(1-1,2,4-triazolyl)-1-azetidinylcarbonyl]-1-(4-nitrobenzyloxycarbonyl)pyrrolidin-4-ylthio]-1-carbapen-2-em-3-carboxylate [prepared as described in step (1) above] were dissolved in 7 ml of dry acetonitrile, and 154 mg of methyl trifluoromethanesulfonate were added to the resulting solution, whilst ice-cooling. The mixture was then stirred at the same temperature for 30 minutes. At the end of this time, the powdery product obtained by evaporation of the solvent under reduced pressure was dissolved in a mixture of 14 ml of tetrahydrofuran and 14 ml of water, and the mixture was hydrogenated at room temperature for 1 hour in the presence of 1.6 g of a 10% w/w palladium-on-carbon catalyst and in an atmosphere of hydrogen. The catalyst was removed by filtration and the tetrahydrofuran was removed by distillation under reduced pressure, after which the aqueous layer was washed with diethyl ether. The aqueous layer was then concentrated by evaporation under reduced pressure, and then subjected to ion exchange column chromatography (Dowex 1-X4, 50 to 100 mesh, Cl FORM, manufactured by Dow Chemical) using water as the eluent. The fractions containing the title compound were collected and concentrated by evaporation under reduced pressure.

The aqueous solution was applied to a column (Cosmosil 75$C_{18}$-prep, manufactured by Nacalai) and eluted with water. The fractions containing the title compound were combined, concentrated by evaporation under reduced pressure and freeze-dried, to obtain 139 mg of the title compound as a colorless powder.

Infrared Absorption Spectrum (KBr), $v_{max}$ cm$^{-1}$: 3390, 1759, 1664, 1586, 1455, 1369.

Nuclear Magnetic Resonance Spectrum (270 MHz, $D_2O$, internal standard: tetradeuterated sodium trimethylsilylpropionate) δ ppm:

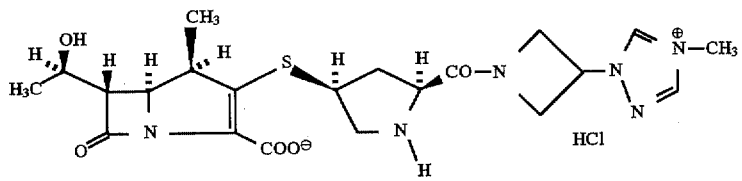

1.21 (3H, doublet, J=5.99 Hz);
1.29 (3H, doublet, J=6.29 Hz);
1.80–2.20 (2H, multiplet);
2.90–3.10 (1H, multiplet);
3.30–3.40 (1H, multiplet);
3.40–3.50 (1H, multiplet);
3.75–3.80 (1H, multiplet);
4.20–4.30 (2H, multiplet);
3.90–5.20 (8H, multiplet);
5.45–5.65 (1H, multiplet);
5.70–5.80 (1H, multiplet);
8.96 & 8.97 (together 1H, two singlets).

EXAMPLE 129

(1R,5S,6S)-6-[(1R)-1-Hydroxythyl]-1-methyl-2-[(2S,4S)-2-(3-trimethylammonioazetidin-1-ylcarbonyl)pyrrolidin-4-ylthio-1-carbapen-2-em-3-carboxylate hydrochloride

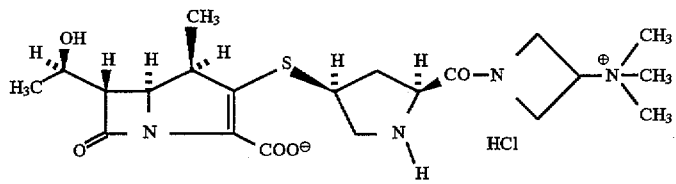

129(1) 4-Nitrobenzyl (1R,5S,6S)-2-[(2S,4S)-2-(3-dimethylaminoazetidin-1-ylcarbonyl)-1-(4-nitrobenzyloxycarbonyl)pyrrolidin-4-ylthio]-6-[(1R)-1-hydroxyethyl]-1-methyl-1-carbapen-2-em-3-carboxylate A solution of 0.98 g of (2S,4S)-2-(3-dimethylaminoazetidin-1-ylcarbonyl)-4-mercapto-1-(4-nitrobenzyloxycarbonyl)pyrrolidine (prepared as described in Preparation 121) dissolved in 20 ml of dry acetonitrile and 0.418 ml of diisopropylethylamine were added dropwise at the same time, whilst ice-cooling, to a solution of 1.43 g of 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 123) in 25 ml of dry acetonitrile. The mixture was then stirred at the same temperature for 2 hours, after which it was left to stand in a refrigerator overnight. The reaction mixture was then concentrated by evaporation under reduced pressure, and the resulting residue was diluted with ethyl acetate; the resulting mixture was washed with water and then with an aqueous solution of sodium chloride. The ethyl acetate layer was dried over anhydrous magnesium sulfate and then concentrated by evaporation under reduced pressure. The residue was purified by silica gel column chromatography and the fractions obtained by elution with a 75:25 by volume mixture of ethyl acetate and methanol were combined and concentrated by evaporation under reduced pressure, to obtain 1.16 g of the title compound, as a powder.

Infrared Absorption Spectrum (KBr), $\upsilon_{max}$ cm⁻: 1774, 1712, 1663, 1607, 1522, 1456, 1404, 1346.

Nuclear Magnetic Resonance Spectrum (270 MHz, $CDCl_3+D_2O$) δ ppm:
1.26 (3H, doublet, J=7.11 Hz);
1.36 (3H, doublet, J=6.13 Hz);
2.00–2.18 (1H, multiplet);
2.10, 2.14, 2.25 & 2.28 (together 6H, four singlets);
2.51–2.73 (1H, multiplet);
2.86–4.56 (13H, multiplet);
5.08–5.54 (4H, multiplet);
7.50 (2H, doublet, J=8.57 Hz);
7.65 (2H, doublet, J=8.57 Hz);
8.23 (4H, doublet, J=8.57 Hz).

129)2) (1R,5S,6S)-6-[(1R)-1-Hydroxyethyl]-1-methyl-2-[(2S,4S)-2-(3-trimethylammonioazetidin-1-ylcarbonyl)pyrrolidin-4-ylthio]-1-carbapen-2-em-3-carboxylate hydrochloride 1.00 g of 4-nitrobenzyl (1R,5S,6S)-2-[(2S,4S)-2-(3-dimethylaminoazetidin-1-ylcarbonyl)-1-(4-nitrobenzyloxycarbonyl)pyrrolidin-4-ylthio]-6-[(1R)-1-hydroxyethyl]-1-methyl-1-carbapen-2-em-3-carboxylate [prepared as described in step (1) above] was dissolved in 12 ml of dry acetonitrile, and 243 mg of methyl trifluoromethanesulfonate were added to the resulting solution, whilst ice-cooling, after which the mixture was stirred at the same temperature for 1 hour. At the end of this time, the solvent was removed by distillation under reduced pressure, and the resulting powdery product was dissolved in a mixture of 20 ml of tetrahydrofuran and 20 ml of water. The mixture was then hydrogenated at room temperature for 2 hours in the presence of 1.00 g of a 10% w/w palladium-on-carbon catalyst and in an atmosphere of hydrogen. The catalyst was then removed by filtration, the filtrate was washed with diethyl ether. The resulting aqueous phase was concentrated by evaporation under reduced pressure. The residue was subjected to ion exchange column chromatography (Dowex 1-X4, 50 to 100 mesh, Cl⁻ model, manufactured by Dow Chemical) using water as the eluent. The fraction containing the title compound was concentrated by evaporation under reduced pressure and subjected to reverse phase column chromatography (Cosmosil $75C_{18}$-prep, manufactured by Nacalai Tesque) and eluted with water. The fractions containing the title compound were concentrated by evaporation under reduced pressure and freeze-dried, to obtain 265 mg of the title compound as a powder.

Ultraviolet Absorption Spectrum ($H_2O$), $\lambda_{max}$ nm: 296.

Infrared Absorption Spectrum (KBr), $\upsilon_{max}$ cm⁻¹: 1758, 1665, 1594, 1482, 1373, 1285, 1255, 1145.

Nuclear Magnetic Resonance Spectrum (270 MHz, $D_2O$, internal standard: tetradeuterated sodium trimethylsilylpropionate) δ ppm:
1.21 (3H, doublet, J=7.17 Hz);
1.28 (3H, doublet, J=6.29 Hz);
1.98–2.09 (1H, multiplet);
2.93–3.05 (1H, multiplet);
3.21 & 3.22 (together 9H, two singlets);
3.32–3.50 (3H, multiplet);
3.78 (1H, doublet of doublets, J=12.26 & 6.60 Hz);
4.01–4.12 (1H, multiplet);
4.20–4.29 (2H, multiplet);
4.43–4.85 (6H, multiplet).

EXAMPLE 130

(1R,5S,6S)-6-[(1R)-1-Hydroxyethyl]-2-[(2S,4S)-2-[3-(1-imidazolyl)azetidin-1-ylcarbonyl]pyrrolidin-4-ylthio)-1-methyl-1-carbapen-2-em-3-carboxylic acid

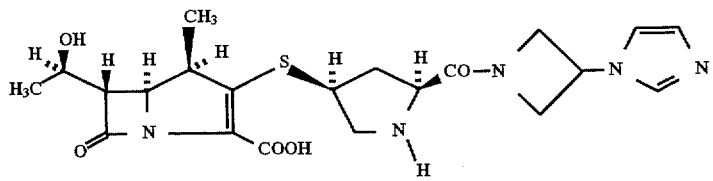

130(1) 4-Nitrobenzyl (1R,5S,6S)-6-[(1R)-1-hydroxyethyl]-2-[(2S,4S)-2-[3-(1-imidazolyl)azetidin-1-ylcarbonyl-1-(4-nitrobenzyloxycarbonyl)pyrrolidin-4-ylthio]-1-methyl-1-carbapen-2-em-3-carboxylate A solution of 3.10 g of (2S,4S)-2-[3-(1-imidzolyl)azetidin-1-ylcarbonyl}-4-mercapto-1-(4-nitrobenzyloxycarbonyl)pyrrolidine (prepared as described in Preparation 122) dissolved in 25 ml of dry acetonitrile and 1.25 ml of diisopropylethylamine were added dropwise at the same time, whilst ice-cooling, to a solution of 4.27 g of 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 123) in 55 ml of dry acetonitrile. The resulting mixture was left to stand at the same temperature for 1 hour and then in a refrigerator overnight. At the end of this time, the reaction mixture was concentrated by evaporation under reduced pressure, and the resulting residue was diluted with ethyl acetate. The mixture thus obtained was washed with water and then with an aqueous solution of sodium chloride. The resulting ethyl acetate solution was dried over anhydrous magnesium sulfate and then concentrated by evaporation under reduced pressure. The residue was applied to a silica gel chromatography column, and the fractions obtained by elution with a 7:7:6 by volume mixture of methylene chloride, ethyl acetate and methanol were combined and concentrated by evaporation under reduced pressure, to obtain 2.94 g of the title compound, as a powder.

Infrared Absorption Spectrum (KBr), $\upsilon_{max}$ cm$^{-1}$: 1772, 1708, 1667, 1607, 1522, 1449, 1403, 1346, 1209.

Nuclear Magnetic Resonance Spectrum (270 MHz, CDCl$_3$+D$_2$O) δ ppm:
1.27 (3H, doublet, J=7.19 Hz);
1.36 (3H, doublet, J=6.14 Hz);
2.15–5.55 (19H, multiplet);
7.10–8.28 (11H, multiplet).

130(2) (1R,5S,6S)-6-[(1R)-1-Hydroxyethyl]-2-(2S,4S)-2-[3-(1-imidazolyl)azetidin-1-ylcarbonyl]pyrrolidin-4-ylthio]-1-methyl-1-carbapen-2-em-3-carboxylic acid 0.25 g of 4-nitrobenzyl (1R,5S,6S)-6-[(1R)-1-hydroxyethyl]-2-[(2S,4S)-2-[3-(1-imidazolyl)azetidin-1-ylcarbonyl]-1-(4-nitrobenzyloxycarbonyl)pyrrolidin-4-ylthio]-1-methyl-1-carbapen-2-em-3-carboxylate [prepared as described in step (1) above] was dissolved in a mixture of 7.5 ml of tetrahydrofuran and 7.5 ml of water, and 0.25 g of a 10% w/w palladium-on-carbon catalyst was added to the resulting solution, after which the mixture was hydrogenated at room temperature for 1.5 hours in an atmosphere of hydrogen. At the end of this time, the catalyst was removed by filtration and the filtrate was washed with diethyl ether. The resulting aqueous layer was then concentrated by evaporation under reduced pressure, and the residue was subjected to reverse phase column chromatography (Cosmosil 75C$_{18}$-prep, 30 g, manufactured by Nacalai Tesque). Of the fractions obtained by elution with 7% by volume aqueous acetonitrile, the fraction containing the title compound was concentrated by evaporation under reduced pressure and freeze-dried, to obtain 70 mg of the title compound as a powder.

Ultraviolet Absorption Spectrum (H$_2$O), $\lambda_{max}$ nm: 297.

Infrared Absorption Spectrum (KBr), $\upsilon_{max}$ cm$^{-1}$: 1757, 1660, 1598, 1466, 1383, 1285, 1255, 1181, 1149.

Nuclear Magnetic Resonance Spectrum (270 MHz, D$_2$O, internal standard: tetradeuterated sodium trimethylsilylpropionate) δ ppm:
1.22 (3H, doublet, J=7.12 Hz);
1.30 (3H, doublet, J=6.27 Hz);
1.90–2.02 (1H, multiplet);
2.84–2.93 (1H, multiplet);
3.29–3.50 (3H, multiplet);
3.56–3.63 (1H, multiplet);
3.91–4.03 (1H, multiplet);
4.20–4.43 (4H, multiplet);
4.50–5.43 (4H, multiplet);
7.22 & 7.23 (together 1H, two singlets);
7.54 (1H, singlet);
8.12 (1H, singlet).

EXAMPLE 121

(1R,5S,6S)-6-[(1R)-1-Hydroxyethyl]-1-methyl-2-((2S,4S)-2-[3-(3-methyl-1-imidazolyl)azetidin-1-ylcarbonyl]pyrrolidin-4-ylthio-1-carbapen-2-em-3-carboxylate hydrochloride

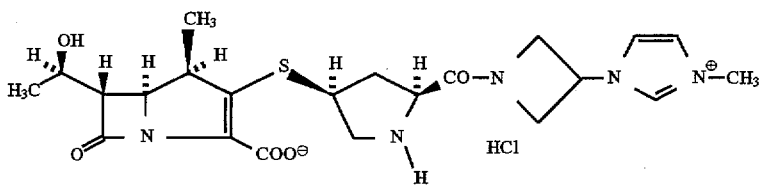

1.72 g of 4-nitrobenzyl (1R,5S,6S)-6-[(1R)-1-hydroxyethyl]-2-[(2S,4S)-2-[3-(1-imidazolyl)azetidin-1-ylcarbonyl]-1-(4-nitrobenzyloxycarbonyl)pyrrolidin-4-ylthio]-1-methyl-1-carbapen-2-em-3-carboxylate [prepared as described in Example 120(1)] were dissolved in 18 ml of dry acetonitrile, and 0.28 ml of methyl trifluoromethanesulfonate was added to the resulting solution, whilst ice-cooling. The mixture was then stirred at the same temperature for 1 hour. At the end of this time, the solvent was removed by distillation under reduced pressure, and the powdery product thus obtained was dissolved in a mixture of 30 ml of tetrahydrofuran and 30 ml of water. The mixture was then hydrogenated at room temperature for 2 hours in the presence of 2.10 g of a 10% w/w palladium-on-carbon catalyst and in an atmosphere of hydrogen. The reaction mixture was then treated, purified and freeze-dried in the same manner as described in Example 128(2), to obtain 383 mg of the title compound as a colorless powder.

Ultraviolet Absorption Spectrum (H$_2$O), $\lambda_{max}$ nm: 296.

Infrared Absorption Spectrum (KBr), $v_{max}$ cm$^{-1}$: 1759, 1664, 1597, 1561, 1466, 1373, 1284, 1184, 1147.

Nuclear Magnetic Resonance Spectrum (270 MHz, D$_2$O, internal standard: tetradeuterated sodium trimethylsilylpropionate) δ ppm:
1.21 (3H, doublet, J=7.21 Hz);
1.29 (3H, doublet, J=6.38 Hz);
2.00–2.14 (1H, multiplet);
2.93–3.05 (1H, multiplet);
3.30–3.51 (3H, multiplet);
3.73–3.82 (1H, multiplet);
3.92 (3H, singlet);
4.01–4.10 (1H, multiplet);
4.20–4.30 (2H, multiplet);
4.38–4.47 (1H, multiplet);
4.55–4.96 (4H, multiplet);
5.45–5.55 (1H, multiplet);
7.55 (1H, singlet);
7.80 (1H, singlet);
9.00, 9.02 (1H, two singlets).

EXAMPLE 132

(1R,5S,6S)-2-[(2S,4S)-2-(3-[3-(2-Fluoroethyl)-1-imidazolio]azetidin-1-ylcarbonyl]pyrrolidin-4-ylthio]-6-[(1R)-1-hydroxyethyl]-1-methyl-1-carbapen-2-em-3-carboxylate hydrochloride 0.87 g of 4-nitrobenzyl (1R,5S,6S)-6-[(1R)-1-hydroxyethyl]-2-[(2S,4S)-2-[3-(1-imidazolyl)azetidin-1-ylcarbonyl]-1-(4-nitrobenzyloxycarbonyl)pyrrolidin-4-ylthio]-1-methyl-1-carbapen-2-em-3-carboxylate [prepared as described in Example 130(1)] were dissolved in 10 ml of dry acetonitrile, and 0.63 ml of 1-bromo-2-fluoroethane, 0.84 g of sodium iodide and 80 ml of sodium carbonate were added to the resulting solution, after which the mixture was heated under reflux for 14 hours. At the end of this time, insolubles were filtered off and the filtrate was concentrated by evaporation under reduced pressure. The resulting residue was washed by repeated decantation with, in turn, methylene chloride and diethyl ether. It was then dried by evaporation under reduced pressure to obtain 0.494 g of a powder. The whole of this compound was dissolved in a mixture of 12.5 ml of tetrahydrofuran and 12.5 ml of water. 0.48 g of a 10% w/w palladium-on-carbon catalyst was then added to the solution, after which the mixture was hydrogenated at room temperature for 1 hour. At the end of this time, the reaction mixture was treated, purified and freeze-dried in the same manner as described in Example 40(2) to obtain 42 mg of the title compound as a colorless powder.

Ultraviolet Absorption Spectrum (H$_2$O), $\lambda_{max}$ nm: 297.

Infrared Absorption Spectrum (KBr), $v_{max}$ cm$^{-1}$: 1759, 1664, 1597, 1563, 1467, 1374, 1284, 1222, 1183.

Nuclear Magnetic Resonance Spectrum (270 MHz, D$_2$O, internal standard: tetradeuterated sodium trimethylsilylpropionate) δ ppm:
1.21 (3H, doublet, J=6.97 Hz);
1.28 (3H, doublet, J=6.28 Hz);
2.02–2.14 (1H, multiplet);
2.93–3.07 (1H, multiplet);
3.31–3.51 (3H, multiplet);
3.74–3.83 (1H, multiplet);
4.02–4.10 (1H, multiplet);
4.20–4.30 (2H, multiplet);
4.41–4.49 (1H, multiplet);
4.54–4.98 (9H, multiplet);
5.48–5.59 (1H, multiplet);
7.68 (1H, singlet);
7.88 (1H, singlet);
9.15 & 9.17 (1H, two singlets).

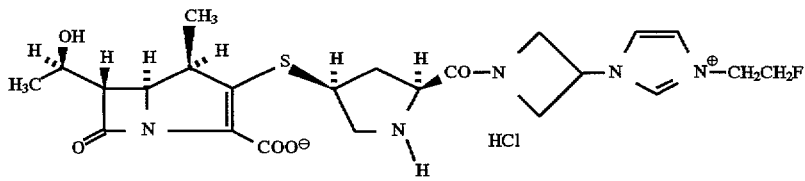

EXAMPLE 133

(1R,5S,6S)-2-[(2S,4S)-2-(3-Dimethylaminoazetidin-1-ylcarbonyl)pyrrolidin-4-ylthio]-6-[(1R)-1-hydroxyethyl]-1-methyl-1-carbapen-2-em-3-carboxylic acid

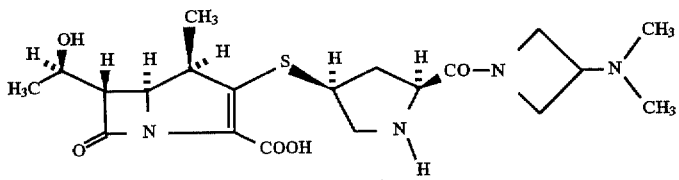

0.75 g of 4-nitrobenzyl (1R,5S,6S)-2-[(2S,4S)-2-(3-dimethylaminoazetidin-1-ylcarbonyl)-1-(4-nitrobenzyloxycarbonyl)pyrrolidin-4-ylthio]-6-[(1R)-1-hydroxyethyl]-1-methyl-1-carbapen-2-em-3-carboxylate [prepared as described in Example 129(1)] was dissolved in a mixture of 21 ml of tetrahydrofuran and 14 ml of water, and 0.75 g of a 10% w/w palladium-on-carbon catalyst was added to the resulting solution, after which the mixture was hydrogenated at room temperature for 1.5 hours in an atmosphere of hydrogen. At the end of this time, the catalyst was removed by filtration and the filtrate was washed with diethyl ether. The resulting aqueous solution was then concentrated by evaporation under reduced pressure, after which the residue was subjected to reverse phase column chromatography [Cosmosil 75C$_{18}$-prep, 25 g, manufactured by Nacalai Tesque). Of the fractions obtained by elution with 7% by volume aqueous acetonitrile, the fraction containing the title compound was concentrated by evaporation under reduced pressure and freeze-dried, to obtain 171 mg of the title compound as a powder.

Ultraviolet Absorption Spectrum (H$_2$O), $\lambda_{max}$ nm: 299.

Infrared Absorption Spectrum (KBr), $\upsilon_{max}$ cm$^{-1}$: 1757, 1653, 1599, 1462, 1385, 1284, 1259, 1150.

Nuclear Magnetic Resonance Spectrum (270 MHz, D$_2$O, internal standard: tetradeuterated sodium trimethylsilylpropionate) δ ppm:

1.22 (3H, doublet, J=7.22 Hz);
1.30 (3H, doublet, J=6.40 Hz);
1.83–1.92 (1H, multiplet);
2.41 (3H, singlet);
2.45 (3H, singlet);
2.78–2.89 (1H, multiplet);
3.26 (1H, doublet of doublets, J=12.14 & 4.90 Hz);
3.34–3.73 (4H, multiplet);
3.89–4.66 (2H, multiplet);
4.19–4.33 (5H, multiplet);
4.43–4.54 (1H, multiplet).

EXAMPLE 134

(1R,5S,6S)-2-[(2S,4S)-2-(3-[N-(Carbamoylmethyl)-N,N-dimethylammonio]azetidin-1-ylcarbonyl]pyrrolidin-4-ylthio]-6-[(1R)-1-hydroxyethyl]-1-methyl-1-carbapen-2-em-3-carboxylate hydrochloride

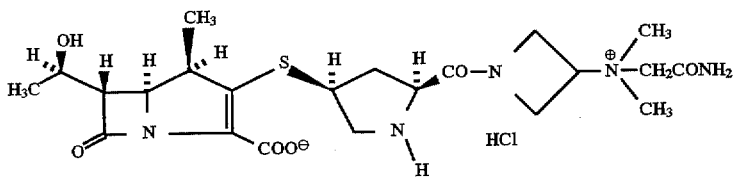

0.60 g of 4-nitrobenzyl (1R,5S,6S)-2-[(2S,4S)-2-(3-dimethylaminoazetidin-1-ylcarbonyl)-1-(4-nitrobenzyloxycarbonyl)pyrrolidin-4-ylthio]-6-[(1R)-1-hydroxyethyl]-1-methyl-1-carbapen-2-em-3-carboxylate [prepared as described in Example 129(1)] was dissolved in 8 ml of dry acetonitrile, and 0.74 g of 2-iodoacetamide was added to the resulting solution, after which the mixture was stirred at 70° C. for 2 hours. At the end of this time, the solvent was removed by distillation under reduced pressure, and the resulting residue was washed by repeated decantation, in turn, with methylene chloride and with diethyl ether. It was then dried by evaporation under reduced pressure to obtain 0.90 g of a powder. The whole of this compound was dissolved in a mixture of 24 ml of tetrahydrofuran and 16 ml of water. 0.95 g of a 10% w/w palladium-on-carbon catalyst was then added to the solution, after which the mixture was hydrogenated at room temperature for 1.5 hours in an atmosphere of hydrogen.

The reaction mixture was then treated, purified and freeze-dried in the same manner as described in Example 40(2), to obtain 156 mg of the title compound as a colorless powder.

Ultraviolet Absorption Spectrum (H$_2$O), $\lambda_{max}$ nm: 297.

Infrared Absorption Spectrum (KBr), $\upsilon_{max}$ cm$^{-1}$: 1767, 1701, 1607, 1521, 1445, 1404, 1346, 1170.

Nuclear Magnetic Resonance Spectrum (270 MHz, D$_2$O, internal standard: tetradeuterated sodium trimethylsilylpropionate) δ ppm:

1.21 (3H, doublet, J=7.18 Hz);
1.29 (3H, doublet, J=6.37 Hz);
1.98–2.10 (1H, multiplet);
2.93–3.04 (1H, multiplet);
3.38 & 3.40 (together 6H, two singlets);
3.30–3.50 (3H, multiplet);
3.74–3.80 (1H, multiplet);
4.01–4.10 (1H, multiplet);
4.15–4.30 (4H, multiplet);
4.43–4.88 (5H, multiplet);
4.94–5.03 (1H, multiplet).

EXAMPLE 135

(1R,5S,6S)-2-[(2S,4S)-2-[3-[(2-Fluoroethyl) dimethylammonio]azetidin-1-ylcarbonylpyrrolidin-4-ylthio-6-[(1R)-1-hydroxyethyl]-1-methyl-1-carbapen-2-em-3-carboxylate hydrochloride

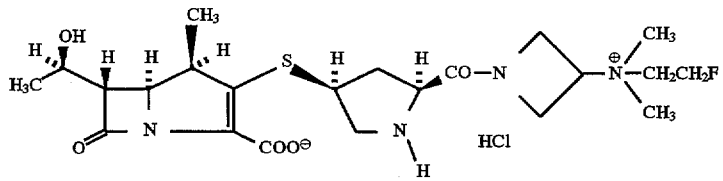

715 mg of 4-nitrobenzyl (1R,5S,6S)-2-[(2S,4S)-2-(3-dimethylaminoazetidin-1-ylcarbonyl)-1-(4-nitrobenzyloxycarbonyl)pyrrolidin-4-ylthio]-6-[(1R)-1-hydroxyethyl]-1-methyl-1-carbapen-2-em-3-carboxylate [prepared as described in Example 129(1)] were dissolved in 7 ml of dry acetonitrile, and 1.22 g of 1-bromo-2-fluoroethane, 721 mg of sodium iodide and 67 mg of sodium carbonate were added to the resulting solution, after which the mixture was heated under reflux for 23 hours. At the end of this time, insolubles were filtered off and the filtrate was concentrated by evaporation under reduced pressure. The resulting residue was washed by repeated decantation, in turn, with methylene chloride and with diethyl ether, and the mixture was dried by evaporation under reduced pressure to obtain 400 mg of a powder. The whole of this compound was dissolved in a mixture of 8 ml of tetrahydrofuran and 8 ml of water. 0.40 g of a 10% w/w palladium-on-carbon catalyst was added to the solution, after which the mixture was hydrogenated at room temperature for 1.5 hours in an atmosphere of hydrogen. The reaction mixture was then treated, purified and freeze-dried in the same manner as described in Example 128(2), to obtain 39 mg of the title compound as a colorless powder.

Ultraviolet Absorption Spectrum (H$_2$O), $\lambda_{max}$ nm: 296.

Infrared Absorption Spectrum (KBr), $\upsilon_{max}$ cm$^{-1}$: 1759, 1668, 1598, 1476, 1374, 1285, 1226, 1180.

Nuclear Magnetic Resonance Spectrum (270 MHz, D$_2$O, internal standard: tetradeuterated sodium trimethylsilylpropionate) δ ppm:

1.21 (3H, doublet, J=7.18 Hz);
1.28 (3H, doublet, J=6.26 Hz);
1.98–2.10 (1H, multiplet);
2.93–3.04 (1H, multiplet);
3.27 & 3.29 (together 6H, two singlets);
3.33–3.51 (3H, multiplet);
3.75–3.92 (3H, multiplet);
4.02–4.11 (1H, multiplet);
4.20–4.28 (2H, multiplet);
4.43–4.85 (6H, multiplet);
4.90–5.06 (2H, multiplet).

EXAMPLE 136

(1R,5S,6S)-2-[(2S,4S)-2-(3-[(2-Hydroxythyl) dimethylammonio]azetidin-1-ylcarbonyl]pyrrolidin-4-ylthio-6-[(1R)-1-hydroxyethyl]-1-methyl-1-carbapen-2-em-3-carboxylate hydrochloride

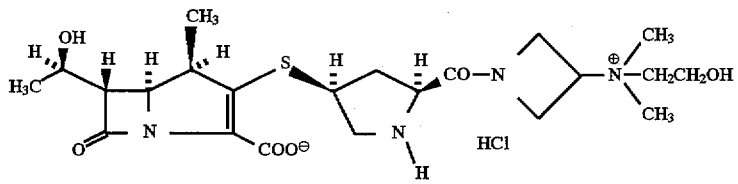

0.65 g of 4-nitrobenzyl (1R,5S,6S)-2-[(2S,4S)-2-(3-dimethylaminoazetidin-1-ylcarbonyl)-1-(4-nitrobenzyloxycarbonyl)pyrrolidin-4-ylthio]-6-[(1R)-1-hydroxyethyl]-1-methyl-1-carbapen-2-em-3-carboxylate [prepared as described in Example 129(1)] was dissolved in 7 ml of dry acetonitrile, and 1.05 g of 2-iodoethanol were added to the resulting solution. The mixture was then heated under reflux for 5 hours. At the end of this time, the solvent was removed by distillation under reduced pressure, and the residue was washed by repeated decantation, in turn, with methylene chloride and with diethyl ether. The mixture was then dried by evaporation under reduced pressure to obtain 0.84 g of a powder. The whole of this compound was dissolved in a mixture of 21 ml of tetrahydrofuran and 14 ml of water. 0.90 g of a 10% w/w palladium-on-carbon catalyst was then added to the solution, after which the mixture was hydrogenated at room temperature for 1.5 hours in an atmosphere of hydrogen. The reaction mixture was then treated, purified and freeze-dried in the same manner as described in Example 128(2), to obtain 55 mg of the title compound as a colorless powder.

Ultraviolet Absorption Spectrum (H$_2$O), $\lambda_{max}$ nm: 297.

Infrared Absorption Spectrum (KBr), $\upsilon_{max}$ cm$^{-1}$: 1758, 1665, 1595, 1477, 1374, 1261, 1227, 1149.

Nuclear Magnetic Resonance Spectrum (270 MHz, D$_2$O, internal standard: tetradeuterated sodium trimethylsilylpropionate) δ ppm:
1.21 (3H, doublet, J=7.20 Hz);
1.28 (3H, doublet, J=6.36 Hz);
1.98–2.10 (1H, multiplet);
2.93–3.04 (1H, multiplet);
3.25 & 3.26 (together 6H, two singlets);
3.31–3.60 (5H, multiplet);
3.77 (1H, doublet of doublets, J=12.23 & 6.63 Hz);
4.00–4.10 (3H, multiplet);
4.21–4.29 (2H, multiplet);
4.42–4.86 (6H, multiplet).

EXAMPLE 137

(1R,5S,6S)-2-[(2S,4S-2-(3-Aminoazetidin-1-ylcarbonyl)-pyrrolidin-4-ylthio-6-[(1R]-1-hydroxyethyl]-1-methyl-1-carbapen-2-em-3-carboxylic acid

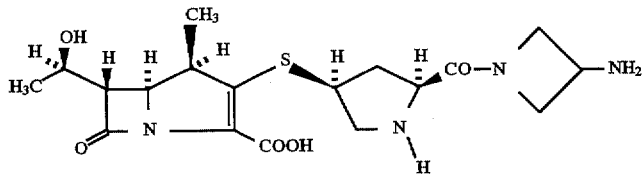

3630 mg of 4-nitrobenzyl (1R,5S,6S)-2-((2S,4S)-2-[3-(4-nitrobenzyloxycarbonylamino)azetidin-1-ylcarbonyl]-1-(4-nitrobenzyloxycarbonyl)pyrrolidin-4-ylthio)-6-[(1R)-1-hydroxyethyl]-1-methyl-1-carbapen-2-em-3-carboxylate [prepared as described in Example 121(1)] were dissolved in 190 ml of a 3:2 by volume mixture of tetrahydrofuran and water, and 5500 mg of a 10% w/w palladium-on-carbon catalyst were added to the resulting solution. The mixture was then hydrogenated at 30° C. for 1.5 hours in an atmosphere of hydrogen. At the end of this time, the catalyst was removed by filtration, the filtrate was washed with diethyl ether and the resulting aqueous solution was concentrated to 10 ml by evaporation under reduced pressure. The resulting solution was subjected to reverse phase silica gel column chromatography (Cosmosil 75C$_{18}$-prep, 250 ml, manufactured by Nacalai Tesque), eluted with mixtures of acetonitrile and water in proportions of 0:100, 2:98, 4:96, 6:94 by volume, in that order. The fractions containing the title compound were collected, concentrated by evaporation under reduced pressure and freeze-dried, to obtain 901 mg of the title compound as a powder.

Ultraviolet Absorption Spectrum (H$_2$O), $\lambda_{max}$ nm: 298.5.

Infrared Absorption Spectrum (KBr), $\upsilon_{max}$ cm$^{-1}$: 1755, 1642, 1594, 1464, 1387.

Nuclear Magnetic Resonance Spectrum (270 MHz, D$_2$O, internal standard: tetradeuterated sodium trimethylsilylpropionate) δ ppm:

1.22 (3H, doublet, J=7.2 Hz);
1.29 (3H, doublet, J=5.3 Hz);
1.75–1.85 (1H, multiplet);
2.70–2.83 (1H, multiplet);
3.14–3.21 (1H, multiplet);
3.35–3.47 (3H, multiplet);
3.82–3.92 (1H, multiplet);
3.96–4.03 (1H, multiplet);
4.05–4.18 (2H, multiplet);
4.19–4.28 (3H, multiplet);
4.34–4.43 (1H, multiplet);
4.56–4.65 (1H, multiplet).

EXAMPLE 138

(1R,5S,6S]-2-[(2S,4S)-2-(3-Acetimidoylaminoazetidin-1-ylcarbonyl]pyrrolidin-4-ylthio]-6-[(1R)-1-hydroxyethyl]-1-methyl-1-carbapen-2-em-3-carboxylic acid hydrochloride

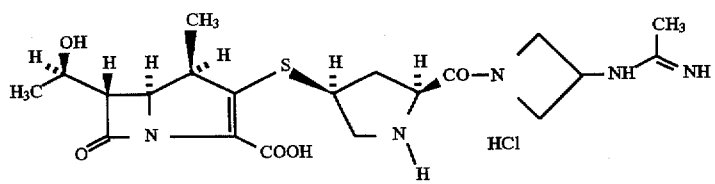

0.40 g of (1R,5S,6S)-2-[(2S,4S)-2-(3-Acetimidoylaminoazetidin-1-ylcarbonyl)pyrrolidin-4-ylthio]-6-[(1R)-1-hydroxyethyl]-1-methyl-1-carbapen-2-em-3-carboxylic acid (prepared as described in Example 122) was dissolved in 20 ml of cold water. 0.88 ml of 1N aqueous hydrochloric acid was added to the resulting solution, and the mixture was freeze-dried, to obtain 400 mg of the title compound as a colorless powder.

Ultraviolet Absorption Spectrum (H$_2$O), $\lambda_{max}$ nm: 296.

Infrared Absorption Spectrum (KBr), $\upsilon_{max}$ cm$^{-1}$: 1760, 1664, 1630, 1585, 1463, 1378, 1286, 1148.

Nuclear Magnetic Resonance Spectrum (270 MHz, D₂O, internal standard: tetradeuterated sodium trimethylsilylpropionate) δ ppm:
1.01 (3H, doublet, J=7.17 Hz);
1.09 (3H, doublet, J=6.37 Hz);
1.76–1.86 (1H, multiplet);
2.07 (3H, singlet);
2.70–2.82 (1H, multiplet);
3.10–3.30 (3H, multiplet);
3.55 (1H, doublet of doublets, J=12.9 & 6.54 Hz);
3.78–3.96 (2H, multiplet);
4.00–4.17 (3H, multiplet);
4.26–4.67 (4H, multiplet).

EXAMPLE 139

(1R,5S,6S)-2-[2S,4S)-2-(Azetidin-3-ylcarbamoyl)pyrrolidin-4-ylthio]-6-[(1R)-1-hydroxythyl]-1-methyl-1-carbapen-2-em-3-carboxylic acid

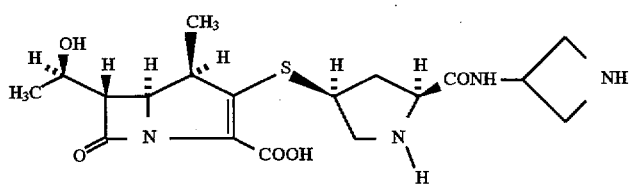

Following a procedure similar to that described in Example 121(1), followed by a procedure similar to that described in Example 49, but using 0.80 g of 4-nitrobenzyl (1R,5R,6S)-2-(diphenylphosphoryloxy)-6-[(1R)-1-hydroxyethyl]-1-methyl-1-carbapen-2-em-3-carboxylate (prepared as described in Preparation 123) and 0.95 g of (2S,4S)-4-mercapto-2-[1-(4-nitrobenzyloxycarbonyl)azetidin-3-ylaminocarbonyl]-1-(4-nitrobenzyloxycarbonyl)pyrrolidine (prepared as described in Preparation 33), 86 mg of the title compound was obtained.

Ultraviolet Absorption Spectrum (H₂O), λ$_{max}$ nm: 301.

Infrared Absorption Spectrum (KBr) υ$_{max}$ cm⁻¹: 1754, 1590, 1450, 1389, 1287, 1264.

Nuclear Magnetic Resonance Spectrum (270 MHz, D₂O, internal standards tetradeuterated sodium trimethylsilylpropionate) δ ppm:
1.22 (3H, doublet, J=7.25 Hz);
1.30 (3H, doublet, J=6.36 Hz);
1.83–1.93 (1H, multiplet);
2.72–2.82 (1H, multiplet);
2.88 (1H, doublet of doublets, J=11.64 & 5.19 Hz);
3.34–3.48 (3H, multiplet);
3.65–3.82 (4H, multiplet);
4.04 (1H, triplet, J=11.67 Hz);
4.19–4.29 (2H, multiplet);
4.34 (1H, doublet of doublets, J=9.02 & 5.98 Hz);
4.40–4.48 (1H, multiplet).

PREPARATION 92

(2S,4S)-4-Mercapto-2-[4-(4-nitrobenzyloxycarbonylamidino)piperazin-1-ylcarbonyl]-1-(4-nitrobenzyloxycarbonyl)pyrrolidine trifluoromethanesulfonate 92(a) 1-Amidino-4-t-butoxvcarbonylpiperazine hemisulfate 2.50 g of 1-amidinopiperazine hemisulfate were dissolved in 60 ml of a 1:1 by volume mixture of tetrahydrofuran and water, and a solution of 3.40 g of di-t-butyl dicarbonate in 10 ml of tetrahydrofuran was added to the resulting solution, after which the mixture was stirred at room temperature for 2.5 hours. At the end of this time, the tetrahydrofuran was removed from the reaction mixture by distillation under reduced pressure, the insolubles were filtered off and the filtrate was evaporated to dryness under reduced pressure. The resulting residue was extracted with ethanol (twice, each time with 50 ml), and methanol (twice, each time with 50 ml). The extract was evaporated to dryness to obtain 2.48 g of the title compound, as crystals, melting at 278° C. (with decomposition).

Nuclear Magnetic Resonance Spectrum (270 MHz, D₂O, internal standard substance: tetradeuterated sodium trimethylsilylpropionate) δ ppm:
1.47 (9H, singlet);
3.49–3.64 (8H, multiplet).

Infrared Absorption Spectrum (KBr), υ$_{max}$ cm⁻¹: 1696, 1656, 1616, 1416, 1169, 1121.

92(b) 4-t-Butoxycarbonyl-1-(4-nitrobenzyloxycarbonylamidino)piperazine 2.22 g of 1-amidino-4-t-butoxycarbonylpiperazine hemisulfate [prepared as described in step (a) above] were dissolved in 90 ml of a 1:1 by volume mixture of tetrahydrofuran and water, and a solution of 1.89 g of 4-nitrobenzyloxycarbonyl chloride in 16 ml of tetrahydrofuran and 16 ml of a 1N aqueous solution of sodium hydroxide were added thereto at the same time, whilst stirring and ice-cooling. The resulting mixture was stirred for 30 minutes under the same conditions, and then the organic solvent was removed from the reaction mixture by distillation under reduced pressure. The residual aqueous solution was extracted with ethyl acetate, and the ethyl acetate extract was washed with an aqueous solution of sodium chloride and dried over anhydrous sodium sulfate. The mixture was then concentrated by evaporation under reduced pressure. The resulting residue was subjected to silica gel column chromatography, eluted with a 4:1 by volume mixture of ethyl acetate and hexane. The fraction containing the desired compound was concentrated by evaporation under reduced pressure, to obtain 2.32 g of the title compound, as an amorphous powder.

Nuclear Magnetic Resonance Spectrum (270 MHz, CDCl₃) δ ppm:
1.47 (9H, singlet);
3.45–3.61 (8H, multiplet);
5.21 (2H, singlet);
6.90–7.20 (2H, broad);
7.56 (2H, doublet, J=8.6 Hz);
8.20 (2H, doublet, J=8.6 Hz).

Infrared Absorption Spectrum (KBr), υ$_{max}$ cm⁻¹: 1698, 1652, 1601, 1547, 1523, 1279.

92(c) 1-(4-Nitrobenzyloxycarbonylamidino)piperazine 750 mg of 4-t-butoxycarbonyl-1-(4-nitrobenzyloxycarbonylamidino)piperazine [prepared as described in step (b) above] were dissolved in 10 ml of trifluoroacetic acid, and the resulting solution was stirred at room temperature for 30 minutes. At the end of this time, the reaction mixture was concentrated by evaporation under reduced pressure, and the resulting residue was dissolved in a mixture of ethyl acetate and water, and an aqueous solution of sodium hydrogen-carbonate was added thereto to make the mixture alkaline. The ethyl acetate layer was separated and the aqueous layer was extracted with ethyl acetate three times. The ethyl acetate layer and all of the ethyl acetate washings were combined and concentrated by evaporation under reduced pressure, to obtain 530 mg of the title compound, as a powder.

Nuclear Magnetic Resonance Spectrum (270 MHz, D$_2$O, internal standard: tetradeuterated sodium trimethylsilylpropionate) δ ppm:
3.27 (4H, triplet, J=5.3 Hz);
3.80 (4H, triplet, J=5.3 Hz);
3.25 (2H, singlet);
7.61 (2H, doublet, J=8.6 Hz);
8.2 (2H, doublet, J=8.6 Hz).

92 (d) (2S,4S) -4-(4-Methoxybenzylthio)-2-[4-(4-nitro; benzyloxycarbonylamidino)piperazin-1-ylcarbonyl]-1-(4-nitrobenzlyoxycarbonyl) pyrrolidine 740 mg of (2S,4S)-4-(4-methoxybenzylthio)-1-(4-nitrobenzyloxy)pyrrolidine-2-carboxylic acid was dissolved in 7.4 ml of dry acetonitrile, and 330 mg of N,N'-carbonyldiimidazole were added to the resulting solution, after which the mixture was stirred at room temperature for 30 minutes. At the end of this time, a solution of 525 mg of 1-(4-nitrobenzyloxycarbonylamidino)piperazine [prepared as described in step (c) above] dissolved in 10 ml of acetonitrile was added to the resulting mixture, and the mixture was left to stand overnight under the same conditions. The reaction mixture was then diluted with ethyl acetate, after which it was washed with an aqueous solution of sodium hydrogencarbonate, with water and with an aqueous solution of sodium chloride, in that order, dried over anhydrous sodium sulfate and concentrated by evaporation under reduced pressure. The resulting residue was subjected to silica gel column chromatography, eluted first with ethyl acetate alone and then with a 4:1 by volume mixture of ethyl acetate and acetonitrile, in that order. The fractions containing the desired compound were concentrated by evaporation under reduced pressure, to obtain 890 mg of the title compound, as a powder.

Infrared Absorption Spectrum (KBr), $v_{max}$ cm$^{-1}$: 1709, 1652, 1608, 1520, 1439, 1346.

Nuclear Magnetic Resonance Spectrum (270 MHz, CDCl$_3$+D$_2$O) δ ppm.
1.72–1.89 (1H, multiplet);
2.39–2.52 (1H, multiplet);
3.03–3.18 (1H, multiplet);
3.30–4.10 (15H, multiplet);
4.51–4.62 (1H, multiplet);
4.98–5.32 (4H, multiplet);
6.85 (2H, doublet, J=8.8 Hz);
7.23 (2H, doublet, J=8.8 Hz);
7.40–7.58 (4H, multiplet);
8.15–8.25 (4H, multiplet).

92(e) (2S,4S)-4-Mercapto-2-[4-(4-nitrobenzyloxycarbonylamidino)piperazin-1-ylcarbonyl]-1-(4-nitrobenzyloxycarbonylpyrrolidine trifluoromethanesulfonate 880 mg of (2S,4S)-4-(4-methoxybenzylthio)-2-[4-(4-nitrobenzyloxycarbonylamidino)piperazin-1-ylcarbonyl]-1-(4-nitrobenzyloxycarbonyl)pyrrolidine [prepared as described in step (d) above] were dissolved in a mixture of 4.4 ml of trifluoroacetic acid and 0.88 ml of anisole, and then 160 μl of trifluoromethanesulfonic acid were added dropwise to this solution, whilst stirring and ice-cooling. The resulting mixture was then stirred at room temperature for 3 hours, after which it was concentrated by evaporation under reduced pressure. The resulting residue was washed three times with diethyl ether, and the powder thus formed was dried to obtain 918 mg of the title compound, as a powder.

Infrared Absorption Spectrum (KBr), $v_{max}$ cm$^{-1}$: 1761, 1671, 1618, 1523, 1443, 1348, 1285, 1246, 1225, 1169.

Nuclear Magnetic Resonance Spectrum (hexadeuterated dimethyl sulfoxide+D$_2$O, 270 MHz) δ ppm:
1.60–1.76 (1H, multiplet);
2.65–2.82 (1H, multiplet);
3.05–3.80 (10H, multiplet);
3.94 & 4.05 (together 1H, two doublets of doublets, J=9.8 and 6.8 Hz);
4.74 & 4.83 (together 1H, two triplets, J=7.8 Hz);
5.05–5.25 (2H, multiplet);
5.40 (2H, singlet);
7.53 & 7.63 (together 2H, two doublets, J=8.8 Hz);
7.72 (2H, doublet, J=8.8 Hz);
8.21 & 8.23 (together 2H, two doublets, J=8.8 Hz);
8.28 (2H, doublet, J=8.8 Hz).

PREPARATION 93

(2S,4S)-4-Mercapto-1-methyl-2-[4-[4-nitrobenzyloxycarbonylamidino)piperazin-1-ylcarbonyl]pyrrolidine 93(a) 1-(4-Nitrobenzyloxycarbonylamidino) piperazine bis(trifluoroacetate)

750 mg of 4-t-butoxycarbonyl-1-(4-nitrobenzyloxycarbonylamidino)piperazine [prepared as described in Preparation 92(b)] were dissolved in 12 ml of trifluoroacetic acid, and the resulting solution was stirred at room temperature for 30 minutes. At the end of this time, the reaction mixture was concentrated by evaporation under reduced pressure, and diethyl ether was added to the residue. The powder thus formed was washed three times with diethyl ether and then dried to obtain 1010 mg of the title compound, as a colorless powder.

Infrared Absorption Spectrum (KBr), $v_{max}$ cm$^{-1}$: 1771, 1698, 1665, 1623, 1518, 1353, 1221, 1197.

Nuclear Magnetic Resonance Spectrura (hexadeuterated diraethyl sulfoxide+D$_2$O, 270 MHz) δ ppm:
3.21 (4H, triplet, J=5.4 Hz);
3.73 (4H, triplet, J=5.4 Hz);
5.31 (2H, singlet);
7.68 (2H, doublet, J=8.8 Hz);
8.26 (2H, doublet, J=8.8 Hz).

93(b) (2S,4S)-4-(4-Methoxybenzylthio)-1-methyl-2-[4-(4-nitrobenzyloxycarbonylamidino)piperazin-1-ylcarbonyl]pyrrolidine 480 mg of (2S,4S)-4-(4-methoxybenzylthio)-1-methylpyrrolidine-2-carboxylic acid were suspended in 20 ml of dry acetonitrile, and 325 mg of N,N'-carbonyldiimidazole were added to this suspension, after which the mixture was stirred at 40° C. for 1 hour. At the end of this time, the reaction mixture was cooled with ice, and 980 mg of 1-(4-nitrobenzyloxycarbonylamidino)piperazine bis(trifluoroacetate) [prepared as described in step (a) above]

and 320 μl of diisopropylethylamine were added to the mixture, which was then stirred at room temperature overnight. At the end of this time, the reaction mixture was diluted with ethyl acetate and washed with an aqueous solution of sodium hydrogen-carbonate, with water (4 times) and with an aqueous solution of sodium chloride, in that order. The ethyl acetate solution was dried over anhydrous sodium sulfate and then concentrated by evaporation under reduced pressure. The resulting residue was subjected to silica gel column chromatography, eluted with a 4:1 by volume mixture of ethyl acetate and methanol. The fraction containing the desired compound was concentrated by evaporation under reduced pressure, to obtain 860 mg of the title compound, as a powder.

Infrared Absorption Spectrum (KBr), $\upsilon_{max}$ cm$^{-1}$: 1648, 1609, 1542, 1513, 1440, 1346, 1303, 1273, 1239.

Nuclear Magnetic Resonance Spectrum (270 MHz, CDCl$_3$+D$_2$O) δ ppm:
1.78 (1H, doubled doublet of doublets, J=13.7, 9.3 & 5.4 Hz);
2.33 (3H, singlet);
2.48–2.60 (2H, multiplet);
3.03–3.24 (3H, multiplet);
3.70 (2H, singlet);
3.80 (3H, singlet);
3.45–4.15 (8H, multiplet);
5.21 (2H, singlet);
6.84 (2H, doublet, J=8.8 Hz);
7.20 (2H, doublet, J=8.8 Hz);
7.56 (2H, doublet, J=8.8 Hz);
8.20 (2H, doublet, J=8.8 Hz).

93(c) (2S,4S)-4-Mercaptool-methyl-2-[4-(4-nitrobenzyloxycarbonylamidino)piperazin-1-ylcarbonyl]pyrrolidine 1450 mg of (2S,4S)-4-(4-methoxybenzylthio)-1-methyl-2-[4-(4-nitrobenzyloxycarbonylamidino)piperazin-1-ylcarbonyl]pyrrolidine [prepared as described in step (b) above] were dissolved in a mixture of 7.25 ml of trifluoroacetic acid and 1.45 ml of anisole, and then 562 μl of trifluoromethanesulfonic acid were added dropwise, whilst stirring and ice-cooling, to the resulting solution. The reaction mixture was stirred for 60 minutes under the same conditions and then at room temperature for 30 minutes, after which it was concentrated by evaporation under reduced pressure. The resulting residue was washed three times with diethyl ether, and the powder thus formed was dried to obtain 1940 mg of the bis(trifluoromethanesulfonate) of the title compound as a powder.

Nuclear Magnetic Resonance Spectrum (hexadeuterated dimethyl sulfoxide+D$_2$O, 270 MHz) δ ppm:
1.81 (1H, doubled doublet of doublets, J=13.2, 9.3 & 8.8 Hz);
2.82 (3H, singlet);
2.98 (1H, doublet of triplets, J=13.2 & 7.8 Hz);
3.28–3.81 (1H, multiplet);
4.63 (1H, triplet, J=8.8 Hz);
5.40 (2H, singlet);
7.72 (2H, doublet, J=8.8 Hz);
8.28 (2H, doublet, J=8.8 Hz).

The whole of this salt was dissolved in aqueous ethyl acetate, and an aqueous solution of sodium hydrogencarbonate was added to the resulting solution to make it alkaline. The ethyl acetate layer was separated, washed with an aqueous solution of sodium chloride, dried over anhydrous sodium sulfate and concentrated by evaporation under reduced pressure, to obtain 1.21 g of the title compound, in the form of an amorphous powder.

Infrared Absorption Spectrum (KBr), $\upsilon_{max}$ cm$^{-1}$: 1648, 1605, 1544, 1520, 1440, 1346, 1304, 1273, 1232.

Nuclear Magnetic Resonance Spectrum (270 MHz, CDCl$_3$+D$_2$O) δ ppm:
1.91 (1H, doubled doublet of doublets, J=13.7, 8.3 & 4.9 Hz);
2.36 (3H, singlet);
2.65–2.80 (2H, multiplet);
3.08 (1H, doublet of doublets, J=10.2 & 2.9 Hz);
3.24 (1H, triplet, J=8.3 Hz);
3.32–3.44 (1H, multiplet);
3.46–4.00 (8H, multiplet);
5.21 (2H, singlet);
7.56 (2H, doublet, J=8.8 Hz);
8.19 (2H, doublet, J=8.8 Hz).

PREPARATIONS 94 TO 112

The Compounds of Preparations 94 to 112 were synthesized in the same manner as described in Preparations 92 and 93.

Preparation 94

(2S,4S)-4-Mercapto-1-(4-nitrobenzyloxycarbonyl)-2-[4-(4-nitrobenzyloxycarbonylamidino)homopiperazin-1-ylcarbonyl]pyrrolidine Infrared Absorption Spectrum (KBr), $\upsilon_{max}$ cm$^{-1}$: 1708, 1651, 1605, 1551, 1520, 1441, 1346, 1284.

Nuclear Magnetic Resonance Spectrum (270 MHz, CDCl$_3$+D$_2$O) δ ppm:
1.75–1.98 (3H, multiplet);
2.00–2.20 (1H, multiplet);
2.66–2.82 (1H, multiplet);
3.13–3.96 (8H, multiplet);
4.06–4.15 (2H, multiplet);
4.61 (1H, triplet, J=8.0 Hz);
5.10–5.25 (4H, multiplet);
7.42–7.58 (4H, multiplet);
8.16–8.23 (4H, multiplet).

Preparation 95

(2S,4S)-4-Mercapto-1-methyl-2-[4-(4-nitrobenzyloxycarbonylamidino)homopiperazin-1-ylcarbonyl]pyrrolidine Infrared Absorption Spectrum (KBr), $\upsilon_{max}$ cm$^{-1}$: 1641, 1607, 1552, 1520, 1486, 1444, 1347, 1285.

Nuclear Magnetics Resonance Spectrum (270 MHz, CDCl$_3$+D$_2$O) δ ppm:
1.81–2.01 (3H, multiplet);
2.63–2.75.(1H, multiplet);
2.80–2.88 (1H, multiplet);
3.07–3.15 (1H, multiplet);
3.23–3.93 (10H, multiplet);
5.21 (2H, singlet);
7.54–7.57 (2H, multiplet);
8.17–8.22 (2H, multiplet).

Preparation 96

(2S,4S)-4-Mercapto-1-(4-nitrobenzyloxycarbonyl)-2-[4-(4-nitrobenzyloxycarbonylguanidino)piperidin-1-ylcarbonyl]pyrrolidine

Preparation 97

(2S,4S)-4-Mercapto-1-methyl-2-[4-(4-nitrobenzyloxycarbonylguanidino)piperidino-1-ylcarbonyl]pyrrolidine

Preparation 98

(2S,4S)-4-Mercapto-1-(4-nitrobenzyloxycarbonyl)-2-[(3S)-3-(4-nitrobenzyloxycarbonylguanidino)pyrrolidin-1-ylcarbonyl]pyrrolidine

Preparation 99

(2S,4S)-4-Mercapto-1-methyl-2-[(3S)-3-(4-nitrobenzyloxycarbonylguanidino)pyrrolidin-1-ylcarbonyl]pyrrolidine

Preparation 100

(2S,4S)-4-Mercapto-1-(4-nitrobenzyloxycarbonyl)-2-[3-(4-nitrobenzyloxycarbonylguanidino)azetidin-1-ylcarbonyl]pyrrolidine

Preparation 101

(2S,4S)-4-Mercapto-1-methyl-2-[3-(4-nitrobenzyloxycarbonylguanidino)azetidin-1-ylcarbonyl]pyrrolidine

Preparation 102

(2S,4S)-4-Mercapto-1-(4-nitrobenzyloxycarbonyl)-2-[2-(4-nitrobenzyloxydarbonylguanidino)ethylcarbamoyl]pyrrolidine

Preparation 103

(2S,4S)-4-Mercapto-1-methyl-2-[2-(4-nitrobenzyloxycarbonylguanidino)ethylcarbamoyl]pyrrolidine

Preparation 104

(2S,4S)-4-Mercapto-1-(4-nitrobenzyloxycarbonyl)-2-[4-(methyl-4-nitrobenzyloxycarbonylamidino)piperazin-1-ylcarbonyl]pyrrolidine

Preparation 105

(2S,4S)-4-Mercapto-1-methyl-2-[4-(methyl-4-nitrobenzyloxycarbonylamidino)piperazin-1-ylcarbonyl]pyrrolidine

Preparation 106

(2S,4S)-4-Mercapto-1-(4-nitrobenzyloxycarbonyl)-2-[(3R)-3-(4-nitrobenzyloxycarbonylguanidino)pyrrolidin-1-ylcarbonyl]pyrrolidine

Preparation 107

(2S,4S)-4-Mercapto-1-methyl-2-[(3R)-3-(4-nitrobenzyloxycarbonylguanidino)pyrrolidin-1-ylcarbonyl]pyrrolidine

Preparation 108

(2S,4S)-4-Mercapto-1-(4-nitrobenzyloxycarbonyl)-2-[(3S)-4-(4-nitrobenzyloxycarbonylamidino)3-methylpiperazin-1-ylcarbonyl]pyrrolidine

Preparation 109

(2S,4S)-4-Mercapto-1-methyl-2-[(3R)-4-(4-nitrobenzyloxycarbonylamidino)-3-methylpiperazin-1-ylcarbonyl]pyrrolidine

Preparation 110

(2S,4S)-4-Mercapto-1-(4-nitrobenzyloxycarbonyl)-2-[1-(4-nitrobenzyloxycarbonylamidino)piperidin-4-ylcarbamoyl]pyrrolidine

Preparation 111

(2S,4S)-4-Mercapto-1-[1-(4-nitrobenzyloxycarbonyl)-2-[(3S)-1-(4-nitrobenzyloxycarbonylamidino)pyrrolidin-3-ylcarbamoyl]pyrrolidine

Preparation 112

(2S,4S)-4-Mercapto-1-(4-nitrobenzyloxycarbonyl)-2-[1-(4-nitrobenzyloxycarbonylamidino)azetidin-3-ylcarbamoyl]pyrrolidine

PREPARATION 113

(2S,4S)-4-Mercapto-2-[3-(4-nitrobenzyloxycarbonylamino)azetidin-1-ylcarbonyl]-1-(4-nitrobenzyloxycarbonyl)pyrrolidine 113(a) (2S,4S)-2-(3-Aminoazetidin-1-ylcarbonyl)-4-(4-methoxybenzylthio)-1-(4-nitrobenzyloxycarbonyl)pyrrolidine 2.05 g of (2S,4S)-4-(4-methoxybenzylthio)-1-(4-nitrobenzyloxycarbonyl)-2-pyrrolidine carboxylic acid were dissolved in 20 ml of dry acetonitrile, and 0.78 g of N,N'-carbonyldiimidazole was added to the resulting solution, after which the mixture was stirred at for 1 hour. The resulting mixture was then added dropwise to a solution of 1.00 g of 3-aminoazetidine dihydrochloride and 2.40 ml of diisopropylethylamine in 10 ml of methanol, whilst ice-cooling, and the mixture was stirred at the same temperature for 1 hour. At the end of this time, the reaction mixture was filtered, and the filtrate was concentrated by evaporation under reduced pressure. The resulting residue was diluted with ethyl acetate and washed with water and with an aqueous solution of sodium chloride, in that order. The ethyl acetate layer was dried over anhydrous magnesium sulfate and concentrated by evaporation under reduced pressure. The residue was subjected to silica gel column chromatography (silica gel 60 9383, manufactured by Merck, 100 g) to give 2.56 g of the title compound, in the form of an amorphous powder, from the fraction obtained by elution with a 65:35 by volume mixture of ethyl acetate and methanol.

Infrared Absorption Spectrum (KBr), $v_{max}$ cm$^{-1}$: 1708, 1660, 1609, 1513, 1442, 1404, 1346, 1248.

Nuclear Magnetic Resonance Spectrum (270 MHz, CDCl$_3$) δ ppm:
1.88–2.04 (1H, multiplet);
2.38 3.20 (4H, multiplet);
3.23–3.34 (1H, multiplet);
3.67–4.62 (6H, multiplet);
3.72 (2H, singlet);
3.78 & 3.79 (together 3H, two singlets);
5.09–5.37 (2H, multiplet);
6.84 (2H, doublet, J=8.78 Hz);
7.22 (2H, doublet, J=8.78 Hz);
7.45 (2H, doublet, J=8.78 Hz);
8.21 (2H, doublet, J=8.78 Hz).

113(b) (2S,4S)-4-(4-Methoxybenzylthio)-2-[3-[4-nitrobenzyloxycarbonylamino)azetidin-1-ylcarbonyl]-1-(4-nitrobenzyloxycarbonyl)pyrrolidine 0.81 g of (2S,4S)-2-(3-aminoazetidin-1-ylcarbonyl)-4-(4-methoxybenzylthio)-1-(4-nitrobenzyloxycarbonyl) pyrrolidine [prepared as described in step (a) above] was dissolved in 20 ml of methylene chloride, and 0.32 g of diisopropylethylamine and 0.40 g of p-nitrobenzyl chloroformate were added to the resulting solution, whilst ice-cooling. The resulting mixture was then stirred at the same temperature for 40 minutes. At the end of this time, the reaction mixture was diluted with ethyl acetate and washed with water and with an aqueous solution of sodium chloride, in that order. The ethyl acetate layer was dried over anhydrous magnesium sulfate and concentrated by evaporation under reduced pressure. The residue was subjected to silica gel column chromatography (silica gel 60 9385, manufactured by Merck, 40 g) to give 0.64 g of the title compound, in the form of an amorphous powder, from the fraction obtained by solution with a 99:1 by volume mixture of ethyl acetate and methanol.

Infrared Absorption Spectrum (CHCl$_3$), $\upsilon_{max}$ cm$^{-1}$: 1725, 1662, 1608, 1521, 1440, 1347, 1250.

Nuclear Magnetic Resonance Spectrum (270 MHz, CDCl$_3$) δ ppm:
1.94–2.04 (1H, multiplet);
2.31–2.48 (1H, multiplet);
3.04–3.12 (1H, multiplet);
3.26–3.34 (1H, multiplet);
3.72 (2H, singlet);
3.79 (3H, singlet);
3.81–3.99 (1H, multiplet);
4.08–4.87 (6H, multiplet);
5.09–5.72 (5H, multiplet);
6.82–6.87 (2H, multiplet);
7.23 (2H, doublet, J=8.30 Hz);
7.45 & 7.50 (together 4H, two doublets, J=8.79 Hz);
8.22 & 8.23 (together 4H, two doublets, J=8.79 Hz).

113(c) [2S, 4S] -4-Mercapto-2-[3-(4-nitrobenzyloxycarbonylamino)azetidin-1-ylcarbonyl-1-(4-nitrobenzyloxycarbonyl)pyrrolidine 0.59 g of (2S,4S)-4-(4-methoxybenzylthio)-2-[3-(4-nitrobenzyloxycarbonylamino)azetidin-1-ylcarbonyl]-1-(4-nitrobenzyloxycarbonyl)pyrrolidine [prepared as described in step (b) above] was suspended in 0.94 ml of anisole, and 3.32 ml of trifluoroacetic acid and 0.15 ml of trifluoromethanesulfonic acid were added dropwise to the suspension, whilst ice-cooling, after which the mixture was stirred at the same temperature for 1 hour. At the end of this time, 1,2-dichloroethane was added to the reaction mixture, and the solvent was removed by distillation under reduced pressure. The residue was then washed by repeated decantation, in turn, with hexane and with diethyl ether. The residue was diluted with ethyl acetate and made alkaline by the addition of an aqueous solution of sodium hydrogencarbonate. The ethyl acetate layer was separated and washed with water and with an aqueous solution of sodium chloride; in that order, after which it was dried over anhydrous magnesium sulfate and concentrated by evaporation under reduced pressure to give 0.44 g of the title compound, in the form of an amorphous powder.

Infrared Absorption Spectrum (KBr), $\upsilon_{max}$ cm$^{-1}$: 1709, 1656, 1521, 1440, 1405, 1347, 1257.

Nuclear Magnetic Resonance Spectrum (hexadeuterated dimethyl sulfoxide, 270 MHz) δ ppm:
1.62–1.85 (1H, multiplet);
2.56–2.69 (1H, multiplet);
3.05–3.25 (2H, multiplet);
3.70–4.55 (8H, multiplet);
5.08–5.28 (4H, multiplet);
7.55–7.65 (4H, multiplet);
8.11–8.25 (5H, multiplet).

PREPARATION 114

(2S,4S)-4-Mercapto-2-[3-(N-4-nitrobenzyloxycarbonylacetimidoylamino)azetidin-1-ylcarbonyl]-1-(4-nitrobenzyloxycarbonyl)pyrrolidine 114(a) [2S,4S]-4-(4-Methoxybenzylthiol-2-[3-(N-4-nitrobenzyloxycarbonylacetimidoylamino)azetidin-1-ylcarbonyl]-1-(4-nitrobenzyloxycarbonyl)pyrrolidine 0.78 g of (2S,4S)-2-(3-amtnoazetidin-1-ylcarbonyl)-4-(4-methoxybenzylthio)-1-(4-nitrobenzyloxycarbonyl)pyrrolidine [prepared as described in Preparation 113(a)] was dissolved in 15 ml of ethyl acetate, and 0.78 ml of a 4N solution of hydrogen chloride in ethyl acetate was added to the resulting solution, whilst ice-cooling. Diethyl ether was added to the reaction mixture, and the resulting powder was filtered off and dried, to give 0.79 g of (2S,4S)-2-(3-aminoazetidin-1-ylcarbonyl)-4-(4-methoxybenzylthio)-1-(4-nitrobenzyloxycarbonyl)pyrrolidine hydrochloride.

0.78 g of this compound was suspended in 20 ml of dry acetonitrile, and 0.51 g of N-(4-nitrobenzyloxycarbonyl) acetamidine was added to the suspension, after which the mixture was stirred at 50° C. for 80 minutes. At the end of this time, the reaction mixture was concentrated by evaporation under reduced pressure, and the residue was diluted with ethyl acetate, washed with water and with an aqueous solution of sodium chloride, in that order, dried over anhydrous magnesium sulfate and concentrated by evaporation under reduced pressure. The resulting residue was subjected to silica gel column chromatography (silica gel 60 9385, manufactured by Merck, 150 ml) to give 0.99 g of the title compound, in the form of an amorphous powder, from the fraction obtained by solution with a 95:5 by volume mixture of ethyl acetate and methanol.

Infrared Absorption Spectrum (KBr), $\upsilon_{max}$ cm$^{-1}$: 1707, 1667, 1608, 1551, 1520, 1442, 1346, 1238.

Nuclear Magnetic Resonance Spectrum (270 MHz, CDCl$_3$) δ ppm:
1.29–2.59 (7H, multiplet);
3.05–3.14 (1H, multiplet);
3.26–3.34 (1H, multiplet);
3.67–4.86 (6H, multiplet);
3.73 (2H, singlet);
3.79 (3H, singlet);
5.09–5.33 (4H, multiplet);
6.85 (2H, doublet, J=8.79 Hz);
7.23 (2H, doublet, J=8.79 Hz);
7.44–7.65 (4H, multiplet);
8.19–8.25 (4H, multiplet).

114(b) (2S,4S)-4-Mercapto-2-[3-(N-4-nitrobenzyloxycarbonylacetimidoylamino)azetidin-1-ylcarbonyl-1(4-nitrobenzyloxycarbonyl)pyrrolidine 0.99 g of (2S,4S)-4-(4-methoxybenzylthio)-2-[3-(N-4-nitrobenzyloxycarbonylacetimidoylamino)azetidin-1-ylcarbonyl]-1-(4-nitrobenzyloxycarbonyl)pyrrolidine [prepared as described in step (a) above] was dissolved in 1.49 ml of anisole, and 10 ml of trifluoroacetic acid and 0.24 ml of trifluoromethanesulfonic acid were added dropwise to the resulting solution. The resulting mixture was stirred at the same temperature for 40 minutes and then at room temperature for 50 minutes, after which 1,2-dichloroethane was added to the reaction mixture. The mixture was then concentrated by evaporation under reduced pressure. The resulting residue was washed by repeated decantation, in turn, with hexane and diethyl ether, and the mixture was then diluted with ethyl acetate, and made alkaline by the addition of an aqueous solution of sodium hydrogen-carbonate. The ethyl acetate layer was washed with water and with an aqueous solution of sodium chloride, in that order, dried over anhydrous magnesium sulfate and concentrated by evaporation under reduced pressure, to give 0.82 g of the title compound, in the form of an amorphous powder.

Infrared Absorption Spectrum (KBr), $\nu_{max}$ cm$^{-1}$: 1706, 1664, 1607, 1551, 1521, 1442, 1346, 1228.

Nuclear Magnetic Resonance Spectrum (270 MHz, CDCl$_3$) δ ppm:
1.73–2.65 (4H, multiplet);
2.23 (3H, singlet);
3.23–3.54 (2H, multiplet);
3.78–4.94 (7H, multiplet);
5.11–5.37 (4H, multiplet);
7.48–7.59 (4H, multiplet);
8.22 & 8.23 (together 4H, two doublets, J=8.79 Hz).

PREPARATION 115

[2S,4S)-4-Mercapto-2-[3-(N-4-nitrobenzyloxycarbonylformimidoylamino)azetidin-1-ylcarbonyl]-1-(4-nitrobenzyloxycarbonyl)pyrrolidine Following a procedure similar to that described in Preparation 114, but using (2S,4S)-2-(3-aminoazetidin-1-ylcarbonyl)-4-(4-methoxybenzylthio)-1-(4-nitrobenzyloxycarbonyl)pyrrolidine hydrochloride and N-(4-nitrobenzyloxycarbonyl)formamidine as starting materials, in relative proportions similar to those used in that Preparation, the title compound was obtained.

PREPARATION 116

(2S,4S)-4-Mercapto-1-methyl-2-[3-(4-nitrobenzyloxycarbonylamino)azetidin-1-ylcarbonyl]pyrrolidine 116(1) 2S,4S)-2-(3-Aminoazetidin-1-ylcarbonyl-4-(4-methoxybenzylthio)-1-methylpyrrolidine 1.62 g of (2S,4S)-4-(4-methoxybenzylthio)-1-methyl-2-pyrrolidinecarboxylic acid were suspended in 20 ml of dry acetonitrile, and 1.02 g of N,N'-carbonyldiimidazole were added to the suspension, after which the mixture was stirred at 40° C. for 45 minutes. A solution of 1.00 g of 3-aminoazetidine dihydrochloride and 2.40 ml of diisopropylethylamine in 10 ml of methanol was added dropwise to the mixture, whilst ice-cooling, and the mixture was stirred at the same temperature for 90 minutes. At the end of this time, the reaction mixture was concentrated by evaporation under reduced pressure. The resulting residue was subjected to reverse phase column chromatography (Cosmosil 75C$_{18}$-PREP, manufactured by Nacalai Tesque, 145 g) to give 1.21 g of the title compound, as a colorless oil, from the fraction obtained by solution with 30% by volume aqueous acetonitrile.

Infrared Absorption Spectrum (CHCl$_3$), $\nu_{max}$ cm$^{-1}$: 1618, 1510, 1465, 1246, 1176.

Nuclear Magnetic Resonance Spectrum (270 MHz, CDCl$_3$) δ ppm:
1.77–2.00 (3H, multiplet);
2.30 (3H, singlet);
2.45–2.56 (2H, multiplet);
2.88–2.95 (1H, multiplet);
3.00–3.16 (2H, multiplet);
3.70 (2H, multiplet—central value reported);
3.80 (3H, multiplet—central value reported);
3.65–4.06 (3H, multiplet);
4.23–4.33 (1H, multiplet);
4.50–4.68 (1H, multiplet);
6.81–6.87 (2H, multiplet);
7.18–7.24 (2H, multiplet).

116(b) (2S,4S)-4-(4-Methoxybenzylthio)-1-methyl-2-[3-(4-nitrobenzyloxycarbonylamino)azetidin-1-ylcarbonyl-pyrrolidine 0.60 g of (2S,4S)-2-(3-aminoazetidin-1-ylcarbonyl]-4-(4-methoxybenzylthio)-1-methylpyrrolidine [prepared as described in step (a) above] was dissolved in 18 ml of methylene chloride, and 0.38 ml of diisopropylethylamine and 0.46 g of p-nitrobenzyl chloroformate were added to the resulting solution, whilst ice-cooling, after which the mixture was stirred at the same temperature for 30 minutes. At the end of this time, the reaction mixture was diluted with ethyl acetate and washed with water and with an aqueous solution of sodium chloride, in that order. The ethyl acetate layer was dried over anhydrous magnesium sulfate and concentrated by evaporation under reduced pressure. The resulting residue was subjected to silica gel column chromatography (silica gel 60 9385, manufactured by Merck, 40 g), to give 0.85 g of the title compound, in the form of an amorphous powder, from the fraction obtained by elution with a 95:5 by volume mixture of ethyl acetate and methanol.

Infrared Absorption Spectrum .(KBr), $\nu_{max}$ cm$^{-1}$: 1725, 1637, 1610, 1512, 1463, 1346, 1251.

Nuclear Magnetic Resonance Spectrum (270 MHz, CDCl$_3$) δ ppm:
1.77–1.95 (1H, multiplet);
2.32 & 2.36 (together 3H, two singlets);
2.49–2.66 (2H, multiplet);
2.98–3.14 (3H, multiplet);
3.69 (2H, singlet);
3.80 (3H, singlet);
3.73–3.94 (1H, multiplet);
4.11–4.83 (4H, multiplet);
5.20 (2H, multiplet—central value reported);
5.40–5.51 (1H, multiplet);
6.81–6.87 (2H, multiplet);
7.18–7.22 (2H, multiplet);
7.51 (2H, doublet, J=8.79 Hz);
8.22 (2H, doublet, J=8.79 Hz).

116(c) (2S,4S)-4-Mercapto-1-methyl-2-[3-(4-nitrobenzyloxycarbonylamino)azetidin-1-ylcarbonyl]pyrrolidine 0.73 g of (2S,4S)-4-(4-methoxybenzylthio)-1-methyl-2-[3-(4-nitrobenzyloxycarbonylamino)azetidin-1-ylcarbonyl]pyrrolidine [prepared as described in step (b) above] was dissolved in 1.53 ml of anisole, and 7.25 ml of trifluoroacetic acid and 0.25 ml of trifluoromethanebulfonic acid were added dropwise, whilst ice-cooling, to the resulting solution. The mixture was then stirred at room temperature for 90 minutes, after which 1,2-dichloroethane was added to the reaction mixture and the solvent was removed by evaporation under reduced pressure. The resulting residue was washed by repeated decantation, in turn, with hexane and with diethyl ether. The residue was diluted with ethyl acetate and was made alkaline by the addition of an aqueous solution of sodium hydrogencarbonate. The ethyl acetate layer was washed with water and with an aqueous solution of sodium chloride, in that order, dried over anhydrous magnesium sulfate and concentrated by evaporation under reduced pressure, to give 420 mg of the title compound, in the form of an amorphous powder.

Infrared Absorption Spectrum (liquid film), $\upsilon_{max}$ cm$^{-1}$: 1721, 1638, 1609, 1522, 1460, 1347, 1258.

Nuclear Magnetic Resonance Spectrum (270 MHz, CDClO$_3$) δ ppm:
1.85–2.12 (2H, multiplet);
2.35 & 2.37 (together 3H, two singlets);
2.63–2.82 (2H, multiplet);
3.00–3.10 (2H, multiplet);
3.30 (1H, broad singlet);
3.86–3.96 (1H, multiplet);
4.08–4.79 (4H, multiplet);
5.21 (2H, singlet);
5.40–5.62 (1H, multiplet);
7.51 (2H, doublet, J=8.79 Hz);
8.22 (2H, doublet, J=8.79 Hz);

PREPARATION 117

(2S,4S)-4-Mercapto-1-methyl-2-[3-[N-4-nitrobenzyloxycarbonylacetimidoylamino)azetidin-1-ylcarbonyl]pyrrolidine 117(a) (2S,4S)-4-(4-Methoxybenzylthio)-1-methyl-2-[3-(N-4-nitrobenzyloxycarbonylacetimidoylamino)azetidin-1-ylcarbonyl]pyrrolidine 540 mg of (2S,4S)-2-(3-aminoazetidin-1-ylcarbonyl]-4-(4-methoxybenzylthio)-1-methylpyrrolidine [prepared as described in Preparation 116(a)] were dissolved in 15 ml of ethyl acetate and 5 ml of methylene chloride, and 1.61 ml of a 4N solution of hydrogen chloride in ethyl acetate were added to the resulting solution, whilst ice-cooling. The mixture was then stirred at the same temperature for 30 minutes, after which it was diluted with diethyl ether, and a powder was filtered off and dried to give 650 mg of a hydrochloride.

650 mg of this hydrochloride, 413 mg of N-(4-nitrobenzyloxycarbonyl)acetamidine and 277 µl of diisopropylethylamine were suspended in 10 ml of dry acetonitrile, after which the mixture was stirred at 55° C. for 1 hour. At the end of this time, insolubles were filtered from the reaction mixture and the filtrate was concentrated by evaporation under reduced pressure. The residue was subjected to silica gel column chromatography to give 622 mg of the title compound, as a powder, from the fraction obtained by solution with a 45:45:5 by volume mixture of methylene chloride, ethyl acetate and methanol.

Infrared Absorption Spectrum (KBr), $\upsilon_{max}$ cm$^{-1}$: 1682, 1638, 1609, 1353, 1512, 1454, 1346, 1225, 1190, 1080.

Nuclear Magnetic Resonance Spectrum (270 MHz, CDCl$_3$+D$_2$O) δ ppm:
1.60–2.38 (7H, multiplet);
2.43–2.68 (2H, multiplet);
2.83–3.20 (3H, multiplet);
3.69 (2H, singlet);
3.79 (3H, singlet);
3.84–5.02 (5H, multiplet);
5.22 (2H, singlet);
6.84 (2H, doublet, J=8.79 Hz);
7.20 (2H, doublet, J=8.79 Hz);
7.51–7.62 (2H, multiplet);
8.15–8.28 (2H, multiplet).

117(b) 2S, 4S)-4-Mercapto-1-methyl-2-[3-(N-4-nitrobenzyloxycarbonylacetimidoylamino)azetidin-1-ylcarbonyl]-pyrrolidine 610 mg of (2S,4S)-4-(4-methoxybenzylthio)-1-methyl-2-[3-(N-4-nitrobenzyloxycarbonylacetimidoylamino)azetidin-1-ylcarbonyl]pyrrolidine [prepared as described in step (a) above] were dissolved in 1.19 ml of anisole, and 4.23 ml of trifluoroacetic acid and 193 µl of trifluoromethanesulfonic acid were added to the resulting solution, whilst ice-cooling. The mixture was then stirred for 1 hour under the same conditions and then at room temperature for a further 1 hour. At the end of this time, the solvent was removed by distillation under reduced pressure, and the resulting residue was washed with hexane and with diethyl ether and dried by evaporation under reduced pressure, to convert it to the trifluoromethanesulfonate in the form of a powder. Ethyl acetate was added to the whole of this compound, followed by sufficient of a saturated aqueous solution of sodium hydrogencarbonate to make it alkaline. The ethyl acetate layer was separated, washed with an aqueous solution of sodium chloride and dried over anhydrous magnesium sulfate, and the solvent was removed by evaporation under reduced pressure, to give 448 mg of the title compound as a powder.

Infrared Absorption Spectrum (liquid film), $\upsilon_{max}$ cm$^{-1}$: 1642, 1608, 1554, 1522, 1465, 1347, 1237, 1193.

Nuclear Magnetic Resonance Spectrum (270 MHz, CDCl$_3$+D$_2$O) δ ppm:
1.81–1.98 (1H, multiplet);
2.07–3.50 (11H, multiplet);
3.83–5.02 (5H, multiplet);
5.22 & 5.28 (together 2H, two singlets);
7.50–7.62 (2H, multiplet);
8.15–8.28 (2H, multiplet).

PREPARATION 118

(2S,4S)-4-Mercapto-1-methyl-2-[3-(N-4-nitrobenzyloxycarbonylformimidoylamino)azetidin-1-ylcarbonyl]pyrrolidine A procedure similar to that described in Preparation 117 was repeated, but using (2S,4S)-2-(3-aminoazetidin-1-ylcarbonyl)-4-(4-methoxybenzylthio)-1-methylpyrrolidine hydrochloride and N-(4-nitrobenzyloxycarbonyl) formamidine as starting materials, in relative proportions similar to those used in that Preparation, to give the title compound.

PREPARATION 119

(2S,4S)-4-Mercapto-1-(4-nitrobenzyloxycarbonyl)-2-[(3S)-3-(1-1,2,4-triazolyl)-1-pyrrolidinylcarbonyl] pyrrolidine 119(1) [2S,4S)-4-(4-methoxybenzylthio)-2-[(3S)-3-(1-1,2,4-triazolyl)-1-pyrrolidinylcarbonyl)-1-(4-nitrobenzyloxycarbonyl]pyrrolidine 768 mg of (2S,4S)-4-(4-methoxybenzylthio)-1-(4-nitrobenzyloxycarbonyl)-2-pyrrolidinecarboxylic acid were dissolved in 8 ml of dry tetrahydrofuran, and the resulting solution was cooled to 0° C. 191 mg of triethylamine were added to the solution, followed by 218 mg of pivaloyl chloride, and then the mixture was stirred at the same temperature for 5 minutes. At the end of this time, a mixture of 238 mg of (3S)-3-(1-1,2,4-triazolyl)pyrrolidine trifluoroacetate, 440 mg of diisopropylethylamine and 7 ml of dry acetonitrile was added to the mixture, and the mixture was gradually heated and then stirred at 0° C. for 15 minutes and at room temperature for 2 hours. The solvent was then removed by evaporation under reduced pressure, and the residue was diluted with ethyl acetate, after which the diluted solution was washed with an aqueous solution of sodium hydrogencarbonate and with a saturated aqueous solution of sodium chloride, in that order, and dried over anhydrous magnesium sulfate. The solvent was then removed by distillation under reduced pressure, and the residue was purified by silica gel column chromatography, using a 7:1 by volume mixture of ethyl acetate and methanol as the eluent, to give 803 mg of the title compound, as a powder.

Infrared Absorption Spectrum (KBr), $\upsilon_{max}$ cm$^{-1}$: 1709, 1656, 1512, 1346, 857, 738.

Nuclear Magnetic Resonance Spectrum (270 MHz,. hexadeuterated dimethyl sulfoxide) δ ppm:
1.40–1.70 (1H, multiplet);
2.20–2.80 (2H, multiplet);
2.98–3.18 (1H, multiplet);
3.18–3.95 (11H, multiplet);
4.35–4.68 (1H, multiplet);
8.00–5.30 (4H, multiplet);
6.80–6.98 (2H, multiplet);
7.20–7.35 (2H, multiplet);
7.40–7.70 (2H, multiplet);
8.00 (1H, multiplet—central value reported);
8.13–8.26 (2H, multiplet);
8.49–8.61 (1H, multiplet).

119(b) (2S,4S)-4-Mercapto-1-[4-nitrobenzyloxycarbonyl)-2-[3S)-3-1-1,2,4-triazolyl)-1-pyrrolidinylcarbonyl]pyrrolidine 783 mg of (2S,4S)-4-(4-methoxybenzylthio)-2-[(3S)-3-(1-1,2,4-triazolyl)-1-pyrrolidinylcarbonyl)-1-(4-nitrobenzyloxycarbonyl)pyrrolidine [prepared as described step (a) above] were suspended in 1.8 ml of anisole, and 7.8 ml of trifluoroacetic acid and 0.24 ml of trifluoromethanesulfonic acid were added to the resulting suspension, whilst ice-cooling, after which the mixture was stirred at room temperature for 1.5 hours. A cycle consisting of removing the solvent by evaporation under reduced pressure, washing the residue with hexane to remove anisole, adding diethyl ether to the mixture to solidify the product and milling the product, after which the mixture was decanted was repeated several times to obtain a powder. The whole of this powder was mixed with 40 ml of ethyl acetate and with an aqueous solution of sodium hydrogencarbonate, and then the organic layer was separated. The organic layer was dried over anhydrous magnesium sulfate, filtered and concentrated by evaporation under reduced pressure, to give 713 mg of the title compound, as a powder.

Infrared Absorption Spectrum (KBr), $\upsilon_{max}$ cm$^{-1}$: 1706, 1652, 1522, 1346, 887, 739.

Nuclear Magnetic Resonance Spectrum (270 MHz, hexadeuterated dimethyl sulfoxide) δ ppm:
1.15–1.25 (1H, multiplet);
1.50–1.80 (1H, multiplet);
2.20–2.60 (2H, multiplet);
2.60–2.90 (1H, multiplet);
3.10–4.10 (8H, multiplet);
4.40–4.65 (1H, multiplet);
5.00–5.30 (2H, multiplet);
7.45–7.70 (2H, multiplet);
8.00–8.02 (1H, multiplet);
8.10–8.30 (2H, multiplet);
8.50–8.62 (1H, multiplet).

PREPARATION 120

(2S,4S)-4-Mercapto-1-(4-nitrobenzyloxycarbonyl)-2-[3-(1-1-1,2,4-triazolyl)-1-azetidinylcarbonyl]pyrrolidine

120(a) (2S,4S)-4-(4-Methoxybenzylthio)-2-3-(1-1,2,4-triazolyl)-1-azetidinylcarbonyl)-1-(4-nitrobenzyloxycarbonyl)pyrrolidine 1.13 g of (2S,4S)-4-(4-methoxybenzylthio)-1-(4-nitrobenzyloxycarbonyl)-2-pyrrolidinecarboxylic acid were dissolved in 11 ml of dry tetrahydrofuran, and the resulting solution was cooled to 0° C. 280 mg of triethylamine were added to the solution, followed by 320 mg of pivaloyl chloride, and the mixture was stirred at the same temperature for 5 minutes. At the end of this time, a mixture of 1.36 g of 3-(1-1,2,4-triazolyl)azetidine hydrochloride [prepared by a procedure similar to that described in Preparation 122(a) and (b), but using 1,2,4-triazole], 956 mg of diisopropylethylamine and 6 ml of dry acetonitrile was added to the mixture, after which the mixture was stirred at 0° C. for 30 minutes and at room temperature for 30 minutes. The reaction mixture was then filtered, and the solvent was removed by evaporation under reduced pressure. The resulting residue was diluted with ethyl acetate, and the diluted solution was washed with an aqueous solution of sodium hydrogencarbonate and with a saturated aqueous solution of sodium chloride, in that order, and dried over anhydrous magnesium sulfate. The solvent was then removed by distillation under reduced pressure, and the residue was purified by silica gel column chromatography, using a 10:1 by volume mixture of ethyl acetate and methanol as the eluent, to give 870 mg of the title compound, as a powder.

Infrared Absorption Spectrum (KBr), $\upsilon_{max}$ cm$^{-1}$: 1708, 1665, 1512, 1346, 854, 738.

Nuclear Magnetic Resonance Spectrum (270 MHz, hexadeuterated dimethyl sulfoxide) δ ppm:
1.60–1.80 (1H, multiplet);
2.50–2.70 (1H, multiplet);
3.00–3.15.(1H, multiplet);
3.15–3.25 (1H, multiplet);
3.65–3.90 (6H, multiplet);
4.05–4.80 (4H, multiplet);
5.10–5.50 (4H, multiplet);
6.88 (2H, doublet, J=8.50 Hz);
7.27 (2H, doublet, J=8.36 Hz);
7.59–7.62 (2H, multiplet);
7.90–8.10 (1H, multiplet);
8.21–8.28 (2H, multiplet);
8.57–8.66 (1H, multiplet).

120(b) (2S,4S)-4-Mercapto-1-(4-nitrobenzyloxycarbonyl)-2-[3-(1-1,2,4-triazolyl)-1-azetidinylcarbonyl]pyrrolidine 858 mg of (2S,4S)-4-(4-methoxybenzylthio)-2-[3-(1-1,2,4-triazolyl)-1-azetidinylcarbonyl)-1-(4-nitrobenzyloxycarbonyl)pyrrolidine [prepared as described in step (a) above] were suspended in 1.7 ml of anisole, and 8.4 ml of trifluoroacetic acid and 0.27 ml of trifluoromethanesulfonic acid were added to the resulting suspension, whilst ice-cooling, after which the mixture was stirred at 0° C. for 30 minutes and then at room temperature for 30 minutes. At the end of this time, the solvent was removed by evaporation under reduced pressure, and the residue was washed with hexane to remove anisole. The mixture was then mixed with diethyl ether to wash the mixture further. The resulting compound was mixed with 100 ml of ethyl acetate and with 30 ml of a saturated aqueous solution of sodium hydrogencarbonate, and the organic layer was separated. The organic layer was then dried over anhydrous magnesium sulfate, and the residue was filtered and concentrated by evaporation under reduced pressure, to give 873 mg of the title compound, as a white powder.

Infrared Absorption Spectrum (KBr), $v_{max}$ cm$^{-1}$, 1706, 1663, 1522, 1347, 854, 739.

Nuclear Magnetic Resonance Spectrum (270 MHz, hexadeuterated dimethyl sulfoxide+D$_2$O) δ ppm:
1.70–1.85 (1H, multiplet);
2.60–2.75 (1H, multiplet);
3.05–3.25 (1H, multiplet);
3.25–3.40 (1H, multiplet);
3.65–4.90 (7H, multiplet);
5.10–5.50 (4H, multiplet);
7.55–7.70 (2H, multiplet);
7.95–8.15 (1H, multiplet);
8.20–8.30 (2H, multiplet);
8.55–8.70 (1H, multiplet).

PREPARATION 121

(2S,4S)-2-3-Dimethylaminoazetidin-1-ylcarbonyl)-4-mercapto-1-(4-nitrobenzyloxycarbonyl)pyrrolidine 121(a) (2S,4S)-2-[3-Dimethylaminoazetidin-1-ylcarbonyl)-4-(4-methoxybenzylthio)-1-(4-nitrobenzyloxycarbonyl)pyrrolidine 644 mg of formic acid and 750 mg of a 35% by volume aqueous formaldehyde solution were added to 1.75 g of (2S,4S)-2-(3-aminoazetidin-1-ylcarbonyl)-4-(4-methoxybenzylthio)-1-(4-nitrobenzyloxycarbonyl) pyrrolidine [prepared as described in Preparation 113(a)], and the resulting mixture was stirred at 50° C. for 5 hours. The mixture was then diluted with ethyl acetate, and the diluted solution was washed with an aqueous solution of sodium hydrogencarbonate, with water and with an aqueous solution of sodium chloride, in that order. It was then dried over anhydrous magnesium sulfate. The solvent was removed by distillation under reduced pressure, and the resulting residue was subjected to silica gel column chromatography. 1.45 g of the title compound were obtained, as a colorless powder, from the fraction obtained by elution with a 45:45:10 by volume mixture of methylene chloride, ethyl acetate and methanol.

Infrared Absorption Spectrum (KBr), $v_{max}$ cm$^{-1}$: 1710, 1664, 1609, 1513, 1442, 1403, 1345, 1248, 1172.

Nuclear Magnetic Resonance Spectrum (270 MHz, CDCl$_3$) δ ppm:
1.86–2.05 (1H, multiplet);
2.11, 2.13 & 2.27 (together 6H, three singlets);
2.34–2.52 (1H, multiplet);
2.83–3.36 (3H, multiplet);
3.73 (2H, singlet);
3.79 & 3.80 (together 3H, two singlets);
3.68–4.51 (6H, multiplet);
5.05–5.36 (2H, multiplet);
6.85 (2H, doublet, J=8.52 Hz);
7.23 (2H, doublet, J=8.52 Hz);
7.46 & 7.50 (together 2H, two doublets, J=8.57 Hz);
8.23 (2H, doublet, J=8.57 Hz).

121(2) (2S,4S)-2-(3-Dimethylaminoazetidin-1-ylcarbonyl)-4-mercapto-1-(4-nitrobenzyloxycarbonyl)pyrrolidine 1.47 g of (2S,4S)-2-(3-dimethylaminoazetidin-1-ylcarbonyl)-4-(4-methoxybenzylthio)-1-(4-nitrobenzyloxycarbonyl)pyrrolidine [prepared as described in step (a) above] were dissolved in 3.02 ml of anisole, and 10.71 ml of trifluoroacetic acid and 0.488 ml of trifluoromethanesulfonic acid were added to the resulting solution, after which the mixture was stirred at the same temperature for 1 hour. The solvent was then removed by distillation under reduced pressure, and the residue was washed by repeated decantation, in turn, with hexane and with diethyl ether. Ethyl acetate was added to the residue and the mixture was made alkaline by the addition of a saturated aqueous solution of sodiumhydrogencarbonate. The ethyl acetate layer was separated, washed with an aqueous solution of sodium chloride and dried over anhydrous magnesium sulfate. The solvent was then removed by distillation under reduced pressure, to give 1.01 g of the title compound as a powder.

Infrared Absorption Spectrum (KBr), $v_{max}$ cm$^{-1}$: 1710, 1645, 1607, 1517, 1459, 1432, 1403, 1343, 1169.

Nuclear Magnetic Resonance Spectrum (270 MHz, CDCl$_3$) δ ppm.
1.87–2.05 (2H, multiplet);
2.11, 2.13 & 2.25 (6H, three singlets);
2.58–2.7t (1H, multiplet);
2.82–3.46 (3H, multiplet);
3.75–4.54 (6H, multiplet);
5.05–5.37 (2H, multiplet);
7.50 (2H, doublet, J=8.57 Hz);
8.22 (2H, doublet, J=8.57 Hz).

PREPARATION 122

(2S,4S)-2-[3-(1-Imidazolyl)azetidin-1-ylcarbonyl-4-mercapto-1-[4-nitrobenzyloxycarbonyl)pyrrolidine 122(a) 1-Benzhydryl-3-(1-imidazolyl)azetidine A solution of 3.20 g of imidazole in 25 ml of dimethylformamide was added to 2.10 g of a suspension of sodium hydride (as a 55% w/w dispersion in mineral oil) in 25 ml of dimethylformamide, whilst ice-cooling. The mixture was then stirred at room temperature for 1 hour. A solution of 5.00 g of 1-benzhydryl-3-methanesulfonyloxyazetidine in 50 ml of dimethylformamide was then added to the mixture, after which the mixture was stirred at 70° C. for 17 hours. At the end of this time, the reaction mixture was diluted with ethyl acetate and washed with water and with an aqueous solution of sodium chloride, in that order. The ethyl acetate layer was then dried over anhydrous magnesium sulfate and concentrated by evaporation under reduced pressure. The resulting residue was subjected to silica gel column chromatography to obtain 2.88 g of the title compound, as a powder, from the fraction obtained by elution with a 95:5 by volume mixture of ethyl acetate and methanol.

Infrared Absorption Spectrum (KBr), $v_{max}$ cm$^{-1}$: 1490, 1452, 1311, 1236, 1074, 905, 755, 707.

Nuclear Magnetic Resonance Spectrum (270 MHz, CDCl$_3$) δ ppm:
3.23–3.35 (2H, multiplet);

3.60–3.69 (2H, multiplet);
4.43 (1H, singlet);
4.67–4.79 (1H, multiplet);
7.08–7.69 (13H, multiplet).

122(b) 3-(1-Imidazolyl)azetidine dihydrochloride 3.20 g of 1-benzhydryl-3-(1-imidazolyl)azetidine [prepared as described in step (a) above] were dissolved in 30 ml of methanol, and 8.90 ml of a 10% w/v solution of hydrogen chloride in methanol were added to the resulting solution. 1.60 g of a 20% w/w palladium hydroxide-on-carbon catalyst were then added to the mixture, after which the mixture was hydrogenated at 50° C. for 40 minutes in an atmosphere of hydrogen. The catalyst was then removed by filtration and the filtrate was concentrated by evaporation under reduced pressure. The resulting residue was washed with diethyl ether and dried under reduced pressure, to obtain 2.03 mg of the title compound, as a powder.

Infrared Absorption Spectrum (KBr), $\upsilon_{max}$ cm$^{-1}$: 1581, 1554, 1509, 1435, 1303, 1092, 839, 637, 623.

Nuclear Magnetic Resonance Spectrum (270 MHz, hexadeuterated dimethyl sulfoxide) δ ppm:
4.27–4.35 (2H, multiplet);
4.39–4.46 (2H, multiplet);
5.40–5.50 (1H, multiplet);
7.48 (1H, singlet);
8.03 (1H, singlet);
8.85 (1H, singlet).

122(c) (2S,4S)-2-[3-[1-Imadazolyl)azetidin-1-ylcarbonyl]-4-(4-methoxybenzylthio-1-(4-nitrobenzyloxycarbonyl)pyrrolidine 3.80 g of (2S,4S)-4-(4-methoxybenzylthio)-1-(4-nitrobenzyloxycarbonyl)-2-pyrrolidinecarboxylic acid were dissolved in 40 ml of dry acetonitrile. 1.65 g of N,N'-carbonyldiimidazole were added to the resulting solution, and the mixture was stirred at 40° C. for 1 hour. A solution of 2.00 g of 3-(1-imidazolyl)azetidine dihydrochloride [prepared as described in step (b) above] and 2.90 g of diisopropylethylamine dissolved in a mixture of 30 ml of dry acetonitrile and 5 ml of methanol was then added at room temperature to the reaction mixture, after which the mixture was stirred at the same temperature for 1 hour. At the end of this time, the reaction mixture was concentrated by evaporation under reduced pressure, and the residue was diluted with ethyl acetate. The diluted solution was washed with water and with an aqueous solution of sodium chloride, in that order. The ethyl acetate layer was separated, dried over anhydrous magnesium sulfate and concentrated by evaporation under reduced pressure. The resulting residue was subjected to silica gel chromatography to obtain 4.00 g of the title compound, as a powder, from the fraction obtained by elution with an 85:15 by volume mixture of ethyl acetate and methanol.

Infrared Absorption Spectrum (KBr), $\upsilon_{max}$ cm$^{-1}$: 1706, 1667, 1609, 1512, 1442, 1403, 1346, 1245.

Nuclear Magnetic Resonance Spectrum (270 MHz, CDCl$_3$) δ ppm:
2.05–3.38 (4H, multiplet);
3.75 (2H, singlet);
3.79 (3H, singlet);
4.12–5.45 (9H, multiplet);
6.84–8.29 (11H, multiplet).

122(d) (2S,4S)-2-[3-(1-Imidazolyl)azetidin-1-ylcarbonyl]-4-mercapto-1-(4-nitrobenzyloxycarbonyl)pyrrolidine 4.00 g of (2S,4S)-2-[3-(1-imidazolyl)azetidin-1-ylcarbonyl]-4-(4-methoxybenzylthio)-1-[4-nitrobenzyloxycarbonyl)pyrrolidine [prepared as described in step (c) above] were dissolved in 7.88 ml of anisole, and 27.9 ml of trifluoroacetic acid and 1.27 ml of trifluoromethanesulfonic acid were added to the resulting solution, whilst ice-cooling, after which the mixture was stirred for 1 hour under the same conditions. At the end of this time, the solvent was removed by distillation under reduced pressure, and the residue was washed with hexane and diethyl ether and dried by evaporation under reduced pressure to give the trifluoromethanesulfonate of the title compound as a powder. Ethyl acetate was added to the whole of this compound and then sufficient of a saturated aqueous solution of sodiumhydrogencarbonate was added to make it alkaline. The ethyl acetate layer was separated, washed with an aqueous solution of sodium choloride and dried over anhydrous magnesium sulfate, after which the the solvent was removed by evaporation under reduced pressure, to obtain 3.10 g of the title compound as a powder.

Infrared Absorption Spectrum (KBr), $\upsilon_{max}$ cm$^{-1}$, 2606, 1746, 1722, 1623, 1569, 1468, 1419, 1378, 1344, 1250.

Nuclear Magnetic Resonance Spectrum (270 MHz, CDCl$_3$+D$_2$O) δ ppm:
2.01–3.50 (4H, multiplet);
4.00–5.35 (9H, multiplet);
7.10–8.30 (7H, multiplet).

PREPARATION 223

4-Nitrobenzyl (1R,5R,6S)-2-(diphenylphosphoryloxy)-6-[(1R)-1-hydroxyethyl]-1-methyl-1-carbapen-2-em-3-carboxylate 3.63 g of 4-nitrobenzyl (1R,5R,6S)-6-[(1R)-1-hydroxyethyl]-1-methyl-2-oxo-1-carbapenam-3-carboxylate were dissolved in 72 ml of dry acetonitrile, and then 2.28 ml of diphenylphosphoric acid chloride and 1.92 ml of diisopropylethylamine were added dropwise to the resulting solution, whilst stirring and ice-cooling. The resulting mixture was then stirred for a further 1 hour under the same conditions, after which it was concentrated by evaporation under reduced pressure. The resulting residue was dissolved in ethyl acetate and washed twice with water and then with an aqueous solution of sodium chloride after which it was dried over anhydrous sodium sulfate and again concentrated by evaporation under reduced pressure. The residue was dissolved in 10 ml of ethyl acetate, and the resulting solution was left to stand to precipitate crystals. The mixture was diluted with 500 ml of diisopropyl ether, and crystals formed were collected by filtration and dried to obtain 5.34 g of the title compound, as colorless needle-like crystals, melting at 123°–125° C.

Nuclear Magnetic Resonance Spectrum (270 MHz, CDCl$_3$) δ ppm:
1.22 (3H, doublet, J=7.2 Hz);
1.33 (3H, doublet, J=6.6 Hz);
3.32 (1H, doublet of doublets, J=6.6 & 2.6 Hz);
3.42–3.56 (1H, multiplet);
4.20–4.31 (2H, multiplet);
5.22 (1H, doublet, J=13.8 Hz);
5.35 (1H, doublet, J=13.8 Hz);
7.13–7.40 (10H, multiplet);
7.55 (1H, doublet, J=8.6 Hz);
8.13 (2H, doublet, J=8.6 Hz).

PREPARATION 124

[2S,4S)-4-Mercapto-2-[1-(4-nitrobenzyloxycarbonyl)azetidin-3-ylaminocarbonyl-1-(4-nitrobenzyloxycarbonyl)pyrrolidine Following a procedure similar to that described in Preparation 22, the title compound was prepared.

333

Infrared Absorption Spectrum (liquid film), $\nu_{max}$ cm$^{-1}$:
1709, 1662, 1609, 1523, 1435, 1406, 1348, 1287.

Nuclear Magnetic Resonance Spectrum (270 MHz, hexadeuterated dimethyl sulfoxide+D$_2$O) δ ppm:
1.86–2.04 (1H, multiplet);
2.65–2.80 (1H, multiplet);
2.98–3.61 (5H, multiplet);
3.87–4.53 (4H, multiplet);
5.08–5.27 (4H, multiplet);
7.51–7.67 (4H, multiplet);
8.14–8.26 (4H, multiplet).

We claim:
1. A compound of formula (I):

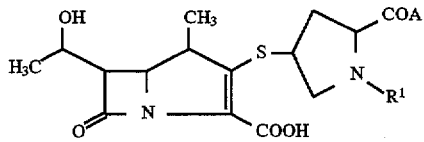

wherein:
$R^1$ represents:
  a hydrogen atom,
  an unsubstituted alkyl group having from 1 to 6 carbon atoms,
  a substituted alkyl group which has from 1 to 6 carbon atoms and which is substituted by at least one substituent selected from the group consisting of substituents (a), defined below,
  an alkenyl group having from 2 to 6 carbon atoms,
  an alkynyl group having from 2 to 6 carbon atoms, or
  a group of formula —C(=NH)R°, where R° represents a hydrogen atom or an alkyl group having from 1 to 6 carbon atoms; and A represents a group of formula (A2), (A7) or (Q—VIII):

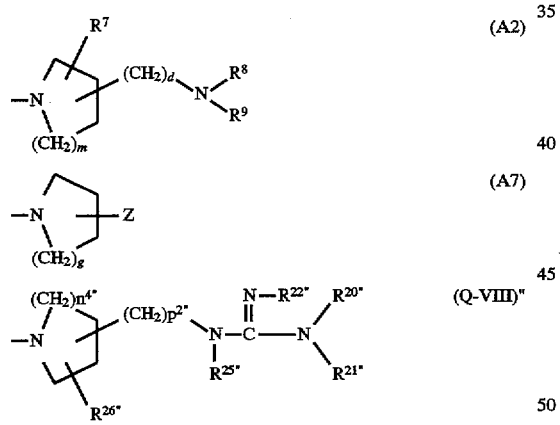

wherein:
$R^7$ is selected from the group consisting of a hydrogen atom, an unsubstituted alkyl group having from 1 to 6 carbon atoms, a substituted alkyl group which has from 1 to 6 carbon atoms and which is substituted by at least one substituent selected from the group consisting of substituents (d), defined below, a halogen atom, a hydroxy group, and a group of formula —CO.NR$^a$R$^b$, —OCO.NR$^a$R$^b$ or —NR$^a$R$^b$, wherein R$^a$ and R$^b$ are selected from the group consisting of a hydrogen atom, an alkyl group having from 1 to 4 carbon atoms, and a cyano group;

$R^8$ represents:
  a hydrogen atom,
  an unsubstituted alkyl group having from 1 to 6 carbon atoms,

334 a substituted alkyl group which has from 1 to 6 carbon atoms and which is substituted by at least one substituent selected from the group consisting of substituents (a), defined below,
  an alkenyl group having from 2 to 6 carbon atoms, or
  an alkynyl group having from 2 to 6 carbon atoms;

$R^9$ represents:
  a hydrogen atom,
  an unsubstituted alkyl group having from 1 to 6 carbon atoms,
  a substituted alkyl group which has from 1 to 6 carbon atoms and which is substituted by at least one substituent selected from the group consisting of substituents (a), defined below, or
  a group of formula —C(=NH)R$^{10}$, where R$^{10}$ represents a hydrogen atom, an unsubstituted alkyl group having from 1 to 6 carbon atoms, a substituted alkyl group which has from 1 to 6 carbon atoms and which is substituted by at least one substituent selected from the group consisting of substituents (c), defined below, or a cycloalkyl group having from 3 to 7 ring carbon atoms;

or $R^8$ and $R^9$ together represent a group of formula —(CH$_2$)$_s$—W—(CH$_2$)$_t$—
  wherein W represents a carbon-carbon single bond, an oxygen atom, a sulfur atom or a group of formula >NR$^{22}$, wherein R$^{22}$ represents a hydrogen atom or an alkyl group having from 1 to 6 carbon atoms, and
  s and t are independently 1, 2 or 3;

Z represents an imidazolyl, triazolyl or tetrazolyl group;

d is 0 or 1;
g and m are independently 0, 1 or 2;
$R^{20"}$, $R^{21"}$ and $R^{22"}$ are independently selected from the group consisting of a hydrogen atom and an unsubstituted alkyl group having from 1 to 6 carbon atoms;

or $R^{20"}$ and $R^{21"}$ or $R^{20"}$ and $R^{22"}$ together represent a group of formula —(CH$_2$)$_{s"}$—, —(W")$_{w"}$—(CH$_2$)$_{t"}$— where s" is 0, 1, 2 or 3, t" is 0, 1, 2 or 3, W" represents an oxygen or sulfur atom and w"' is 0 or 1;

$R^{25"}$ represents a hydrogen atom, an unsubstituted alkyl group having from 1 to 6 carbon atoms, a substituted alkyl group which has from 1 to 6 carbon atoms and which is substituted by at least one substituent selected from the group consisting of substituents C", defined below, an alkenyl group having from 2 to 6 carbon atoms, or an alkynyl group having from 2 to 6 carbon atoms;

$R^{26"}$ represents a hydrogen atom, a halogen atom, an unsubstituted alkyl group having from 1 to 6 carbon atoms, a substituted alkyl group which has from 1 to 6 carbon atoms and which is substituted by at least one substituent selected from the group consisting of substituents C", defined below, a hydroxy group, a carboxy group, a carbamoyl group, an amino group, a cyano group or a carbamoyloxy group;

$n^{4"}$ is 0, 1 or 2;
$p^{2"}$ is 0 or 1;

said substituents (a) are selected from the group consisting of a hydroxy group, a carboxy group, a cyano group, a halogen atom, an oxygen atom to form an oxo group, an alkoxy group having from 1 to 6 carbon atoms, and a group of formula —CO.NR$^a$R$^b$, —OCO.NR$^a$R$^b$ or —NR$^a$R$^b$, wherein R$^{a'}$ and R$^b$ are as defined above;

said substituents (c) are selected from the group consisting of a halogen atom, an alkoxy group having from 1 to 6 carbon atoms and a cycloalkyl group having from 3 to 7 ring carbon atoms;

said substituents (d) are selected from the group consisting of a hydroxy group, a cyano group, a group of the formula —CO.NR$^a$R$^b$, —OCO.NR$^a$R$^b$ or —NR$^a$R$^b$, wherein R$^a$ and R$^b$ are as defined above, a carboxy group, a halogen atom and an alkoxy group having from 1 to 6 carbon atoms; and said substituents C" are selected from the group consisting of a hydroxy group, a carboxy group, a carbamoyl group, a cyano group, a halogen atom, an alkoxy group having from 1 to 6 carbon atoms and an amino group, or a pharmaceutically acceptable salt thereof or a pharmaceutically acceptable ester thereof.

2. The compound of claim 1, wherein said compound is an ester of the compound of the formula (I) and has the formula (Ia):

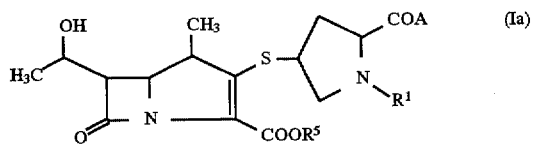

wherein R$^1$ and A are as defined in claim 1, and R$^5$ represents:

a C$_1$–C$_{20}$ alkyl group;

a C$_3$–C$_7$ cycloalkyl group, an aralkyl group, in which the alkyl part is a C$_1$–C$_3$ alkyl group and the aryl part is a C$_6$–C$_{14}$ carbocyclic aromatic group which may be substituted or unsubstituted and, if substituted, has at least one substituent selected from the group consisting of substituents (e) defined below, an alkenyl group, which is substituted or unsubstitued and, if substituted, has at least one substituent selected from the group consisting of substituents (a) defined in claim 1;

a halogenated C$_1$–C$_6$ alkyl group, a substituted silylalkyl group, in which the alkyl part has from 1 to 6 carbon atoms, and the silyl group has up to substituents selected from the group consisting of a C$_1$–C$_6$ alkyl group and a phenyl group which is unsubstituted or has at least one substituent selected from the group consisting of substituents (e) defined below;

a phenacyl group, which is unsubstituted or has at least one substituent selected from the group consisting of substituents (e) defined below;

a cyclic or acyclic terpenyl group;

an alkoxymethyl group, in which the alkoxy part is C$_1$–C$_6$;

an aliphatic acyloxyalkyl group, in which the acyl group is a C$_2$–C$_6$ alkanoyl group, and the alkyl part is a C$_2$–C$_6$ alkyl group;

a cycloalkyl-substituted aliphatic acyloxyalkyl group, in which the acyl group is a C$_2$–C$_6$ alkanoyl group, the cycloalkyl substituent is C$_3$–C$_7$, and the alkyl part is a C$_1$–C$_6$ alkyl group;

an alkoxycarbonyloxyalkl group, in which the alkoxy part is C$_1$–C$_{10}$, and the alkyl part is C$_1$–C$_6$;

a cycloalkylcarbonyloxyalkyl group or cycloalkyloxycarbonyloxyaalkyl group, in which the cycloalkyl group is C$_3$–C$_{10}$, is mono- or poly- cyclic and is unsubstituted or is substituted by at least one C$_1$–C$_4$ alkyl group, and the alkyl group is a C$_1$–C$_6$;

a cycloalkylalkoxycarbonyloxyalkyl group, in which the alkoxy group has a single cycloalkyl substituent, the cycloalkyl substituent being C$_3$–C$_{10}$ and mono- or poly- cyclic;

a terpenylcarbonyloxyalkyl or terpenyloxycarbonyloxyalkyl group, in which the alkyl group has from 1 to 6 carbon atoms;

a 5-alkyl or 5-phenyl (2-oxo-1,3-dioxolen-4-yl)alkyl group in which each alkyl group is C$_1$–C$_6$; or a phthalidyl, indanyl or 2-oxo-4,5,6,7-tetrahydro-1,3-benzodioxolen-4-yl group; and substituents (e) are selected from the group consisting of a C$_1$–C$_4$ alkyl group, a C$_1$–C$_4$ alkoxy group, a C$_1$–C$_4$ haloalkyl group, a C$_1$–C$_3$ alkylenedioxy group, a halogen atom, a cyano group and a nitro group.

3. The compound of claim 2, wherein R$^5$ represents a (5-substituted 2-oxo-1,3-dioxolen 4-yl)methyl group, a 1-methylcyclohexylcarbonyloxymethyl group, a 1-isopropoxycarbonyloxyethyl group or a 1-cyclohexylcarbonyloxyethyl group.

4. The compound of claim 1, wherein R$^1$ represents:

a hydrogen atom; an alkyl group having from 1 to 3 carbon atoms; a substituted alkyl group having from 1 to 3 carbon atoms; a substituted alkyl group having from 1 to 3 carbon atoms, in which the substituent is selected from the group consisting of substituents (a'), defined below; an alkenyl group having 3 or 4 carbon atoms; an alkynyl group having 3 or 4 carbon atoms; a formimidoyl group; or an acetimidoyl group; and substituents (a') are selected from the group consisting of a hydroxy group, a carboxy group, a carbamoyl group, a carbamoyloxy group, a cyano group, a halogen atom, an alkoxy group having from 1 to 3 carbon atoms, an amino group, a mono-alkylamino group in which the alkyl group has 1 to 3 carbon atoms and a di-alkylamino group in which each alkyl group has from 1 to 3 carbon atoms.

5. The compound of claim 1, wherein:

A represents a group of formula (A2), and R$^7$ represents: a hydrogen atom; a carboxy group; a carbamoyl group; an unsubstituted alkyl group having from 1 to 3 carbon atoms; or a substituted alkyl group having from 1 to 3 carbon atoms, in which the substituent is selected from the group consisting of a hydroxy group, an alkoxy group having from 1 to 3 carbon atoms, a carbamoyl group, a carboxy group and a cyano group.

6. The compound of claim 1, wherein A represents a group of formula (A2), and R$^8$ represents: a hydrogen atom; an unsubstituted alkyl group having from 1 to 3 carbon atoms; a substituted alkyl group having from 1 to 3 carbon atoms, in which the substituent is selected from the group consisting of a hydroxy group, an alkoxy group having from 1 to 3 carbon atoms, a carbamoyl group, a carbamoyloxy group, a carboxy group, a cyano group, an amino group and a halogen atom; an alkenyl group having 3 or 4 carbon atoms; or an alkynyl group having 3 or 4 carbon atoms.

7. The compound of claim 6, wherein R$^8$ is a substituted ethyl group or a substituted propyl group.

8. The compound of claim 1, wherein A represents a group of formula (A2), and R$^9$ represents: a hydrogen atom; an unsubstituted alkyl group having from 1 to 3 carbon atoms; a substituted alkyl group having from 1 to 3 carbon atoms, in which the substituent is selected from the group consisting of a hydroxy group, an alkoxy group having from 1 to 3 carbon atoms, a carbamoyl group, a carbamoyloxy group, a carboxy group, a cyano group, an amino group and a halogen atom; or a group of formula —C(=NH)R$^{10}$, in which R$^{10}$ represents:

a hydrogen atom;

an unsubstituted alkyl group having from 1 to 3 carbon atoms;

a substituted alkyl group having from 1 to 3 carbon atoms, in which the substituent is selected from the group consisting of an alkoxy group having from 1 to 3 carbon atoms and a halogen atom;

a cycloalkyl group having from 3 to 6 carbon atoms; or an alkyl group having from 1 to 3 carbon atoms, which is substituted by a single cycloalkyl group having from 3 to 6 carbon atoms.

9. The compound of claim 1, wherein A represents a group of formula (A2), and R$^8$ and R$^9$ together represent a group of formula —(CH$_2$)$_s$—W—(CH$_2$)$_t$—, wherein W represents a carbon-carbon single bond, an oxygen atom, a sulfur atom or a group of formula >NR$^{22}$ wherein R$^{22}$ represents a hydrogen atom or an alkyl group having from 1 to 3 carbon atoms, s is 1, 2 or 3 and t is 2.

10. The compound of claim 1, wherein:

A represents a group of formula (A2);

d is 0 or 1;

m is 0, 1 or 2;

R$^1$ represents a hydrogen atom, a methyl group, a fluoromethyl group, a formimidoyl group or an acetimidoyl group;

R$^7$ represents a hydrogen atom, an alkyl group having from 1 to 3 carbon atoms, a hydroxy group, an amino group, a cyano group, a halogen atom, a carboxy group, carbamoyl group or a hydroxymethyl group;

R$^8$ represents a hydrogen atom, an alkyl group having from 1 to 3 carbon atoms, a fluoromethyl group, a carbamoylmethyl group, a carboxymethyl group, an alkenyl group having 3 or 4 carbon atoms, an alkynyl group having 3 or 4 carbon atoms, a 2-haloethyl group, a 2-hydroxyethyl group, a 2-alkoxyethyl group, in which the alkoxy part has from 1 to 3 carbon atoms, or a 2-aminoethyl group;

R$^9$ represents a hydrogen atom, an alkyl group having from 1 to 3 carbon atoms, a fluoromethyl group, a carbamoylmethyl group, a carboxymethyl group, a formimidoyl group, an acetimidoyl group, a 2-haloethyl group, a 2-hydroxyethyl group, a 2-alkoxyethyl group, in which the alkoxy part has from 1 to 3 carbon atoms, or a 2-aminoethyl group;

or

R$^8$ and R$^9$ together represent a group of formula

—(CH$_2$)$_4$—,
—(CH$_2$)$_5$—,
—(CH$_2$)$_2$O(CH$_2$)$_2$—,
—(CH$_2$)$_2$S(CH$_2$)$_2$—,
—(CH$_2$)$_2$NH(CH$_2$)$_2$— or
—(CH$_2$)$_2$NCH$_3$(CH$_2$)$_2$—.

11. The compound of claim 1, wherein:

d is 0;

m is 1 or 2;

R$^1$ represents a hydrogen atom, a methyl group, a fluoromethyl group, a formimidoyl group or an acetimidoyl group;

R$^7$ represents a hydrogen atom;

R$^8$ represents a hydrogen atom, an alkyl group having from 1 to 3 carbon atoms, a carbamoylmethyl group, a carboxymethyl group, a 2-fluoroethyl group or a 2-hydroxyethyl group; and R$^9$ represents a hydrogen atom, an alkyl group having from 1 to 3 carbon atoms, a formimidoyl group, an acetimidoyl group or a 2-fluoroethyl group.

12. The compound of claim 1, wherein A is the group of formula (A2).

13. The compound of claim 1, wherein A is (A7).

14. The compound of claim 1, wherein A represents a group of formula (A7), and Z represents a 1-imidazolyl group, a 1,2,4-triazol-1-yl group or a 1,2,3-triazol-1-yl group.

15. The compound of claim 1, wherein:

A represents a group of formula (A7);

g is 0, 1 or 2;

R$^1$ represents a hydrogen atom or a methyl group; and

Z represents a 1-imidazolyl group, a 1,2,4-triazol-1-yl group or a 1,2,3-triazol-1-yl group.

16. The compound of claim 1, wherein:

A represents a group of formula (A7);

g is 1 or 2;

R$^1$ represents a hydrogen atom or a methyl group; and

Z represents a 1-imidazolyl group, a 1,2,4-triazol-1-yl group or a 1,2,3-triazol-1-yl group.

17. The compound of claim 1, wherein A is (Q-VIII).

18. The compound of claim 17, wherein R$^1$ represents a hydrogen atom, an unsubstituted alkyl group having from 1 to 3 carbon atoms, a substituted alkyl group which has from 1 to 3 carbon atoms and which is substituted by at least one substitutent selected from the group consisting of substituents A$^{1"}$, defined below, an alkenyl group having 3 or 4 carbon atoms, an alkynyl group having 3 or 4 carbon atoms, or a group of formula —C(=NH)R$^{0"}$, wherein R$^{0"}$ represents a hydrogen atom or an alkyl group having from 1 to 3 carbon atoms; said substituents A$^{1"}$ are selected from the group consisting of a hydroxy group, a carboxy group, a carbamoyl group, a carbamoyloxy group, a cyano group and a halogen atom;

R$^{20"}$, R$^{21"}$ and R$^{22"}$ are independently selected from the group consisting of a hydrogen atom and an unsubstituted alkyl group having from 1 to 3 carbon atoms;

R$^{20"}$ and R$^{21"}$ or R$^{20"}$ and R$^{22"}$ together represent a group of formula —(CH$_2$)$_{s"}$—(W")$_{w"}$(CH$_2$)$_{t"}$—, where s" is 1 or 2, t" is 1 or 2, w" represents an oxygen or sulfur atom and w'" is 0 or 1, provided that (s"+w'"+t") is 2, 3 or 4;

R$^{25"}$ represents a hydrogen atom, an unsubstituted alkyl group having from 1 to 3 carbon atoms, a substituted alkyl group which has from 1 to 3 carbon atoms and which is substituted by at least one substituent selected from the group consisting of substituents C$^{1"}$, defined below, an alkenyl group having 3 or 4 carbon atoms, or an alkynyl group having 3 or 4 carbon, atoms;

R$^{26"}$ represents a hydrogen atom, a halogen atom, an unsubstituted alkyl group having from 1 to 3 carbon atoms, a substituted alkyl group which has from 1 to 3 carbon atoms and which is substituted by at least one substituent selected from the group consisting of substituents C$^{1"}$, defined below, a hydroxy group, a carboxy group, a carbamoyl group, an amino group, a cyano group or a carbamoyloxy group; and substituents C$^{1"}$ are selected from the group consisting of a hydroxy group, a carboxy group, a carbamoyl group, a halogen atom and an amino group.

19. The compound of claim 17, wherein $R^1$ represents a hydrogen atom, an unsubstituted alkyl group having from 1 to 3 carbon atoms, a substituted alkyl group which has from 1 to 3 carbon atoms and which is substituted by at least one substitutent selected from the group consisting of substituents $A^{2''}$, defined below, or a group of formula —C(=NH)$R^{0''}$, wherein $R^{0''}$ represents a hydrogen atom or an alkyl group having from 1 to 3 carbon atoms;

said substituents $A^{2''}$ are selected from the group consisting of a hydroxy group, a carboxy group, a carbamoyl group, a carbamoyloxy group and a halogen atom;

$R^{20''}$, $R^{21''}$ and $R^{22''}$ are independently selected from the group consisting of a hydrogen atom and an unsubstituted alkyl group having from 1 to 3 carbon atoms; or $R^{20''}$ and $R^{21''}$ or $R^{20''}$ and $R^{22''}$ together represent a group of formula —(CH$_2$)$_{s''}$—(W'')$_{w'''}$—(CH$_2$)$_{t''}$—, where s'' is 1 or 2, t'' is 1 or 2, W'' represents an oxygen or sulfur atom and w''' is 0 or 1, provided that (s''+w'''+t'') is 2, 3 or 4;

$R^{25''}$ represents a hydrogen atom or a methyl group; and $R^{26''}$ represents a hydrogen atom.

20. The compound of claim 1, wherein $R^1$ represents a hydrogen atom, a methyl group, a fluoromethyl group, a formimidoyl group or an acetimidoyl group.

21. The compound of claim 1, in which the carbon atoms are in the same configurations as those of thienamycin.

22. The compound of claim 1, selected from the group consisting of 2-[2-(3-acetimidoylaminopyrrolidin-1-ylcarbonyl)pyrrolidin-4-ylthio]-6-(1-hydroxyethyl)-1-methyl-1-carbapen-2-em-3-carboxylic acid, a pharmaceutically acceptable salt thereof and a pharmaceutically acceptable esters thereof.

23. The compound of claim 1, selected from the group consisting of 2-[2-(3-formimidoylaminopyrrolidin-1-ylcarbonyl)pyrrolidin-4-ylthio]-6-(1-hydroxyethyl)-1-methyl-1-carbapen-2-em-3-carboxylic acid, a pharmaceutically acceptable salt thereof and a pharmaceutically acceptable ester thereof.

24. The compound of claim 1, selected from the group consisting of 2-[2-(3-aminopyrrolidin-1-ylcarbonyl)pyrrolidin-4-ylthio]-6-(1-hydroxyethyl)-1-methyl-1-carbapen-2-em-3-carboxylic acid, a pharmaceutically acceptable salts thereof and a pharmaceutically acceptable esters thereof.

25. The compound of claim 1, selected from the group consisting of 2-[2-(4-acetimidoylaminopiperidin-1-ylcarbonyl)pyrrolidin-4-ylthio]-6-(1-hydroxyethyl)-1-methyl-1-carbapen-2-em-3-carboxylic acid, a pharmaceutically acceptable salt thereof and a pharmaceutically acceptable esters thereof.

26. The compound of claim 1 selected from the group consisting of 2-[2-(3-aminopyrrolidin-1-ylcarbonyl)-1-methylpyrrolidin-4-ylthio]-6-(1-hydroxyethyl)-1-methyl-1-carbapen-2-em-3-carboxylic acid, a pharmaceutically acceptable salt thereof and a pharmaceutically acceptable esters thereof.

27. The compound of claim 1, selected from the group consisting of 2-[2-(3-acetimidoylaminopyrrolidin-1-ylcarbonyl)-1-methylpyrrolidin-4-ylthio -6-(1-hydroxyethyl)-1-methyl-1-carbapen-2-em-3-carboxylic acid, a pharmaceutically acceptable salt thereof and a pharmaceutically acceptable esters thereof.

28. The compound of claim 1, selected from the group consisting of 2-[2-(3-formimidoylaminopyrrolidin-1-ylcarbonyl)-1-methylpyrrolidin-4-ylthio]-6-(1-hydroxyethyl)-1-methyl-1-carbapen-2-em-3-carboxylic acid, a pharmaceutically acceptable salt thereof and a pharmaceutically acceptable esters thereof.

29. The compound of claim 1, selected from the group consisting of 2-[2-(4-acetimidoylaminopiperidin-1-ylcarbonyl)-1-methylpyrrolidin-4-ylthio]-6-(1-hydroxyethyl)-1-methyl-1-carbapen-2-em-3-carboxylic acid, a pharmaceutically acceptable salt thereof and a pharmaceutically acceptable esters thereof.

30. The compound of claim 1, selected from the group consisting of 2-[2-(3- acetimidoylamtnoazetidin-1-ylcarbonyl)pyrrolidin-4-ylthio]-6-(1-hydroethyl)-1-methyl-1-carbapen-2-em-3-carboylic acid and a pharmaceutically acceptable salt thereof.

31. The compound of claim 1, selected from the group consisting of 2-[2-(3-fomimidoylamoazetidin-1-ylcarbonyl) pyrrolidin-4-ylthio]-6-(1-hydroethyl)-1-methyl-1-carbapen-2-em-3-carbolic acid and a pharmaceutically acceptable salt thereof.

32. The compound of claim 1, selected from the group consisting of 2-[2-(3-formimidoylaminoazetidin-1-ylcarbonyl)pyrrolidin-4-ylthio]-6-(1-hydroxyethyl)-1-methyl-1-carbapen-2-em-3-carboxylic acid and a pharmaceutically acceptable salt thereof.

33. The compound of claim 1, selected from the group consisting of 2-[2-(3-aminoazetidin-1-methylpyrrolidin-4-ylthio]carbapen-2-em-3-carboxylic acid and a pharmaceutically acceptable salt thereof.

34. A pharmaceutical composition comprising an effective antibacterial amount of the compound of formula (I) of claim 1 or a pharmaceutically acceptable salt or ester thereof and a pharmaceutically acceptable carrier, diluent or adjuvant.

35. The composition of claim 34, wherein said antibiotic is selected from the group consisting of 2-[2-(3-acetimidoylaminopyrrolidin-1-ylcarbonyl) pyrrolidin-4-ylthio]-6-(1-hydroxyethyl)-1-methyl-1-carbapen-2-em-3-carboxylic acid;

2-[2-(3-formimidoylaminopyrrolidin-1-ylcarbonyl) pyrrolidin-4-ylthio]-6-(1-hydroxyethyl)-1-methyl-1-carbapen-2-em-3-carboxylic acid;

2-[2-(3-aminopyrrolidin-1-ylcarbonyl)pyrrolidin-4-ylthio]-6-(1-hydroxyethyl)-1-methyl-1-carbapen-2-em-3-carboxylic acid;

2-[2-(4-acetimidoylaminopiperidin-1-ylcarbonyl) pyrrolidin-4-ylthio]-6-(1-hydroxyethyl)-1-methyl-1-carbapen-2-em-3-carboxylic acid:

2-[2-(3-aminopyrrolidin-1-ylcarbonyl)-1-methylpyrrolidin-4-ylthio]-6-(1-hydroxyethyl)-1-methyl-1-carbapen-2-em-3-carboxylic acid;

2-[2-(3-acetimidoylaminopyrrolidin-1-ylcarbonyl)-1-methylpyrrolidin-4-ylthio]-6-(1-hydroxyethyl)-1-methyl-1-carbapen-2-em-3-carboxylic acid;

2-[2-(3-formimidoylaminopyrrolidin-1-ylcarbonyl)-1-methylpyrrolidin-4-ylthio]-6-(1-hydroxyethyl)-1-methyl-1-carbapen-2-em-3-carboxylic acid;

2-[2-(4-acetimidoylaminopiperidin-1-ylcarbonyl)-1-methylpyrrolidin-4-ylthio]-6-(1-hydroxyethyl)-1-methyl-1-carbapen-2-em-3-carboxylic acid;

2-[2-(3-aminoazetidin-1-ylcarbonyl)pyrrolidin-4-ylthio]-6-(1-hydroxyethyl)-1-methyl-1-carbapen-2-em-3-carboxylic acid;

2-[2-(3-acetimidoylaminoazetidin-1-ylcarbonyl) pyrrolidin-4-ylthio]-6-(1-hydroxyethyl)-1-methyl-1-carbapen-2-em-3-carboxylic acid;

2-[2-(3-formimidoylaminoazeridin-1-ylcarbonyl)
pyrrolidin-4-ylthio]-6-(1-hydroxyethyl)-1-methyl-1-
carbapen-2-em-3-carboxylic acid and;

2-[2-(3-aminoazetidin-1-ylcarbonyl)-1-methylpyrrolidin-
4-ylthio]-6-(1-hydroxyethyl)-1-methyl-1-carbapen-2-
em-3-carboxylic acid;

or a pharmaceutically acceptable salt thereof or a pharmaceutically acceptable ester thereof.

36. A method for the treatment or prophylaxis of a bacterial infection in an animal, which comprises administering to said animal an effective antibacterial amount of an antibiotic, wherein the antibiotic is selected from the group consisting of a compound of formula (I), a pharmaceutically acceptable salt thereof and a pharmaceutically acceptable ester thereof, as claimed in claim 1.

37. The method of claim 36, wherein said antibiotic is selected from the group consisting of 2-[2-(3-acetimidoylaminoazetidin-1-ylcarbonyl)
pyrrolidin-4-ylthio]-6-(1-hydroxyethyl)-1-methyl-1-
carbapen-2-em-3-carboxylic acid;

2-[2-(3-formimidoylaminopyrrolidin-1-ylcarbonyl)
pyrrolidin-4-ylthio]-6-(1-hydroxyethyl)-1-methyl-1-
carbapen-2-em-3-carboxylic acid;

2-[2-(3-aminopyrrolidin-1-ylcarbonyl)pyrrolidin-4-
ylthio]-6-(1-hydroxyethyl)-1-methyl-1-carbapen-2-
em-3-carboxylic acid;

2-[2-(3-acetimidoylaminoazetidin-1-ylcarbonyl)
pyrrolidin-4-ylthio]-6-(1-hydroxyethyl)-1-methyl-1-
carbapen-2-em-3-carboxylic acid;

2-[2-(3-aminopyrrolidin-1-ylcarbonyl)-1-
methylpyrrolidin-4-ylthio]-6-(1-hydroxyethyl)-1-
methyl-1-carbapen-2-em-3-carboxylic acid;

2-[2-(3-acetimidoylaminoazetidin-1-ylcarbonyl)-1-
methylpyrrolidin-4-ylthio]-6-(1-hydroxyethyl)-1-
methyl-1-carbapen-2-em-3-carboxylic acid;

2-[2-(3-formimidoylaminopyrrolidin-1-ylcarbonyl)-1-
methylpyrrolidin-4-ylthio]-6-(1-hydroxyethyl)-1-
methyl-1-carbapen-2-em-3-carboxylic acid;

2-[2-(3-acetimidoylaminoazetidin-1-ylcarbonyl)-1-
methylpyrrolidin-4-ylthio]-6-(1-hydroxyethyl)-1-
methyl-1-carbapen-2-em-3-carboxylic acid;

2-[2-(3-aminocazetidin-1-ylcarbonyl)pyrrolidin-4-ylthio]
-6-(1-hydroxyethyl)-1-methyl-1-carbapen-2-em-3-
carboxylic acid;

2-[2-(3-acetimidoylaminoazetidin-1-ylcarbonyl)-1-
ylcarbonyl)pyrrolidin-4-ylthio]-6-(1-hydroxyethyl)-1-
methyl-1-carbapen-2-em-3-carboxylic acid;

2-[2-(3-formimidoylaminopyrrolidin-1-ylcarbonyl)
pyrrolidin-4-ylthio]-6-(1-hydroxyethyl)-1-methyl-1-
carbapen-2-em-3-carboxylic acid and;

2-[2-(3-aminocazetidin-1-ylcarbonyl)-1-
methylpyrrolidin-4-ylthio]-6-(1-hydroxyethyl)-1-
methyl-1-carbapen-2-em-3-carboxylic acid;

or pharmaceutically acceptable salt therefor or a pharmaceutically acceptable ester thereof.

* * * * *

UNITED STATES PATENT AND TRADEMARK OFFICE
CERTIFICATE OF CORRECTION

PATENT NO. : 5,712,267
DATED : January 27, 1998
INVENTOR(S) : Kawamoto et al.

It is certified that error appears in the above-identified patent and that said Letters Patent is hereby corrected as shown below:

Column 2,
Line 16, delete "non" and insert -- not --.

Column 20,
Line 1, before "However" insert -- ion. --.

Column 23,
Line 11, "aralkyl groups," begins a new paragraph.

Column 35,
Line 35, delete "or".

Column 107,
Line 20, delete "anjou" and insert -- anion --.

Column 243,
Line 28, delete "(ii")" and insert -- (i") --.

Column 275,
Line 44, delete "EXAMPLE 106" and insert -- EXAMPLE 103 --.

Column 276,
Line 24, delete "EXAMPLE 107" and insert -- EXAMPLE 104 --.

Column 304,
Line 55, delete "EXAMPLE 121" and insert -- EXAMPLE 131 --.

Column 333, claim 1,
Line 61, before "selected" insert -- independently --.

Column 335, claim 2,
Line 45, before "substituents" insert -- 3 --.

Column 339, claim 24,
Line 45, delete "salts" and insert -- salt --.
Line 46, delete "esters" and insert -- ester --.

UNITED STATES PATENT AND TRADEMARK OFFICE
CERTIFICATE OF CORRECTION

PATENT NO. : 5,712,267
DATED : January 27, 1998
INVENTOR(S) : Kawamoto et al.

It is certified that error appears in the above-identified patent and that said Letters Patent is hereby corrected as shown below:

Column 339, claim 25,
Line 52, delete "esters" and insert -- ester --.

Column 339, claim 26,
Line 58, delete "esters" and insert -- ester --.

Column 339, claim 27,
Line 64, delete "esters" and insert -- ester --.

Column 340, claim 28,
Line 3, delete "esters" and insert -- ester --.

Column 340, claim 29,
Line 9, delete "esters" and insert -- ester --.

Signed and Sealed this

Sixteenth Day of April, 2002

*Attest:*

JAMES E. ROGAN
*Attesting Officer*     *Director of the United States Patent and Trademark Office*